US012054716B2

(12) United States Patent
Collin et al.

(10) Patent No.: US 12,054,716 B2
(45) Date of Patent: Aug. 6, 2024

(54) ANTISENSE OLIGONUCLEOTIDES FOR THE TREATMENT OF STARGARDT DISEASE

(71) Applicant: Stichting Katholieke Universiteit, Nijmegen (NL)

(72) Inventors: Robert Wilhelmus Johanna Collin, Venlo (NL); Alejandro Garanto Iglesias, Nijmegen (NL); Franciscus Peter Maria Cremers, Malden (NL); Silvia Albert, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 0 days.

(21) Appl. No.: 17/552,372

(22) Filed: Dec. 16, 2021

(65) Prior Publication Data

US 2022/0204972 A1 Jun. 30, 2022

Related U.S. Application Data

(62) Division of application No. 16/465,405, filed as application No. PCT/EP2017/082627 on Dec. 13, 2017, now Pat. No. 11,236,333.

(30) Foreign Application Priority Data

Dec. 13, 2016 (EP) .................................... 16203864
Sep. 5, 2017 (EP) .................................... 17189492

(51) Int. Cl.
*C07H 21/04* (2006.01)
*A61K 9/00* (2006.01)
*C12N 15/113* (2010.01)

(52) U.S. Cl.
CPC .......... *C12N 15/113* (2013.01); *A61K 9/0048* (2013.01); *C12N 2310/11* (2013.01); *C12N 2310/315* (2013.01); *C12N 2310/321* (2013.01); *C12N 2310/346* (2013.01); *C12N 2320/32* (2013.01); *C12N 2320/33* (2013.01)

(58) Field of Classification Search
None
See application file for complete search history.

(56) References Cited

U.S. PATENT DOCUMENTS 10,351,906 B2 * 7/2019 Zimmermann ........ C12Q 1/686

OTHER PUBLICATIONS

Cremers, Frans PM, et al. "Clinical spectrum, genetic complexity and therapeutic approaches for retinal disease caused by ABCA4 mutations." Progress in retinal and eye research 79 (2020): 100861.*

* cited by examiner

*Primary Examiner* — Kimberly Chong
(74) *Attorney, Agent, or Firm* — N.V. Nederlandsch Octrooibureau

(57) ABSTRACT

The present invention relates to the field of medicine. In particular, it relates to novel antisense oligonucleotides that may be used in the treatment, prevention and/or delay of Stargardt disease.

11 Claims, 20 Drawing Sheets

Specification includes a Sequence Listing.

Fig. 7A1
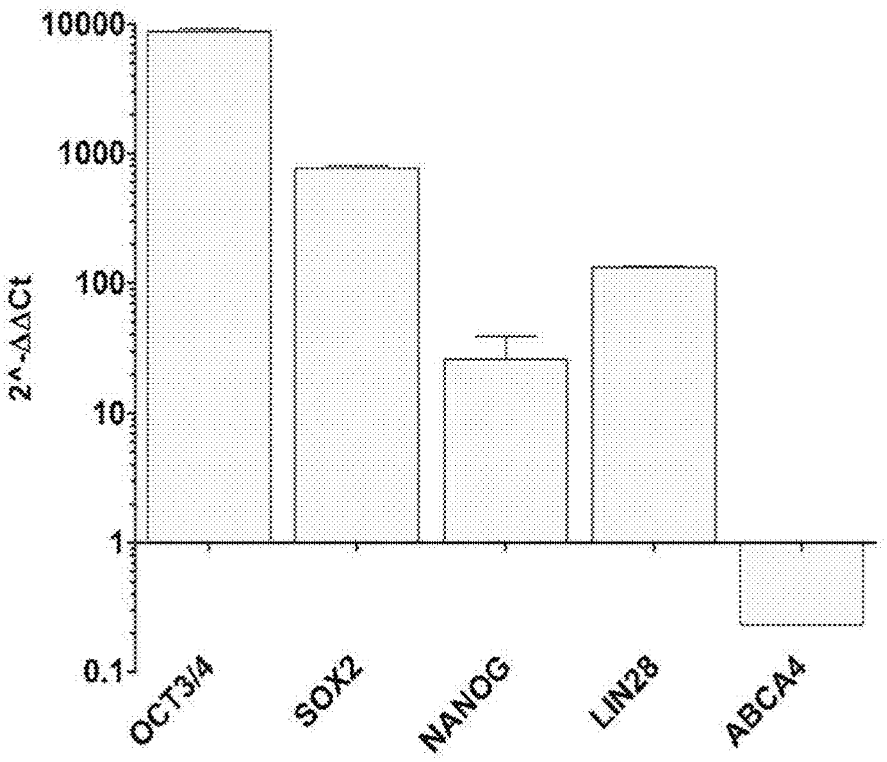
Fig. 7A2
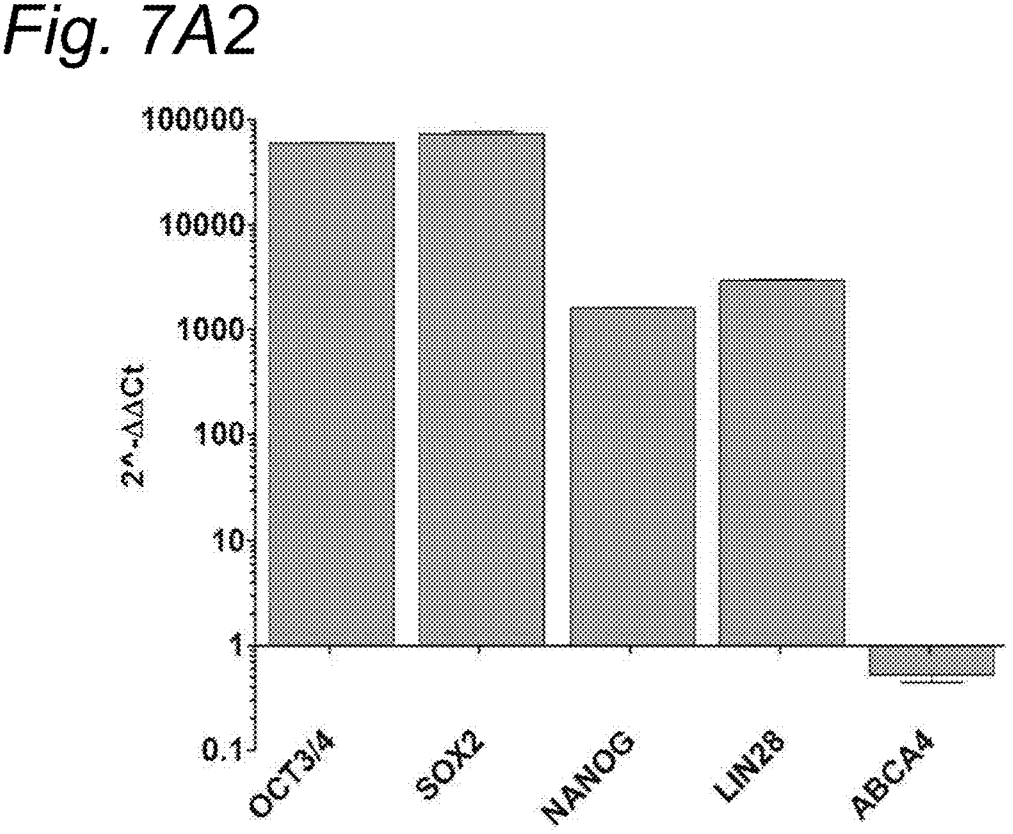

Fig. 7A3
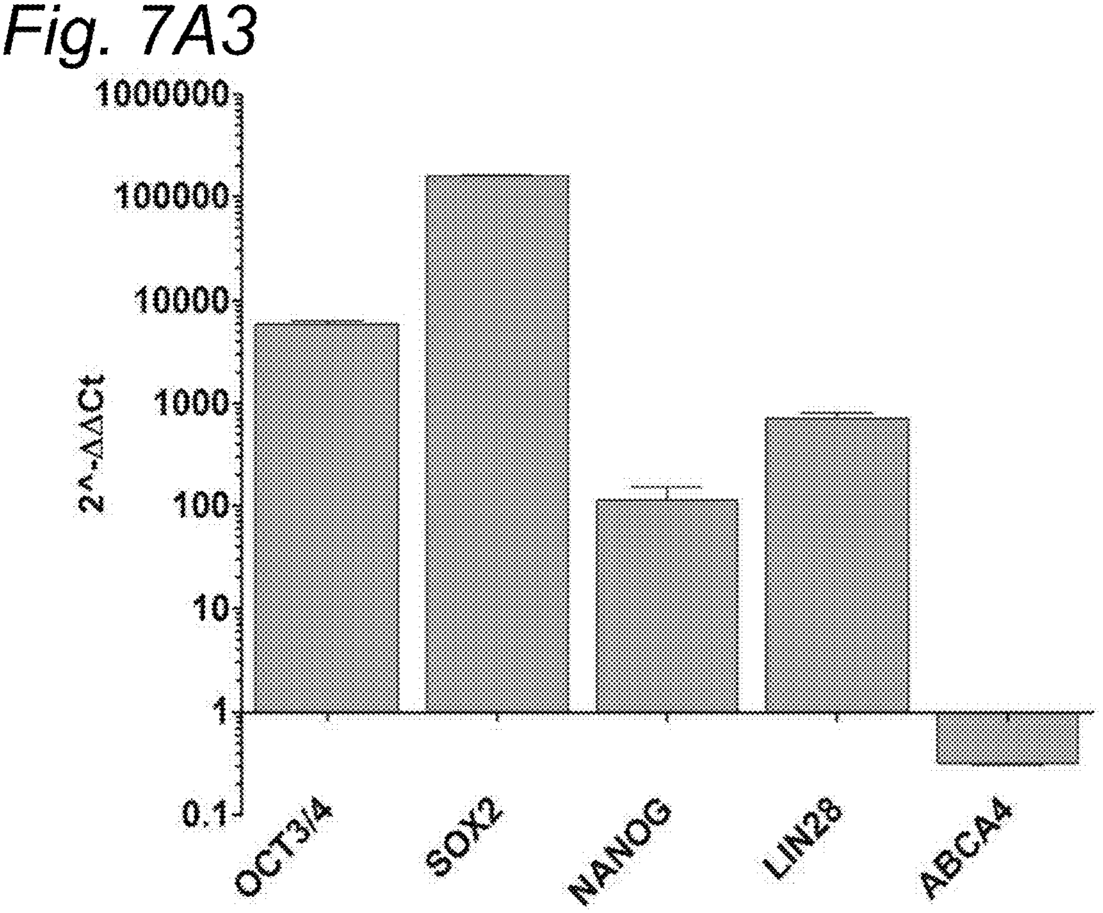
Fig. 7B1
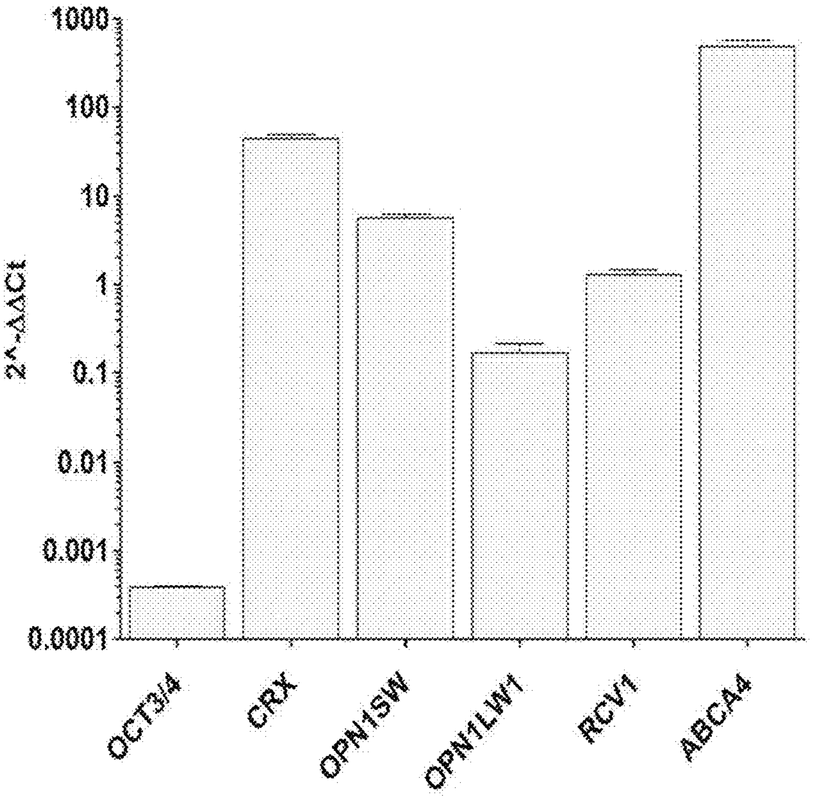

Fig. 7B2
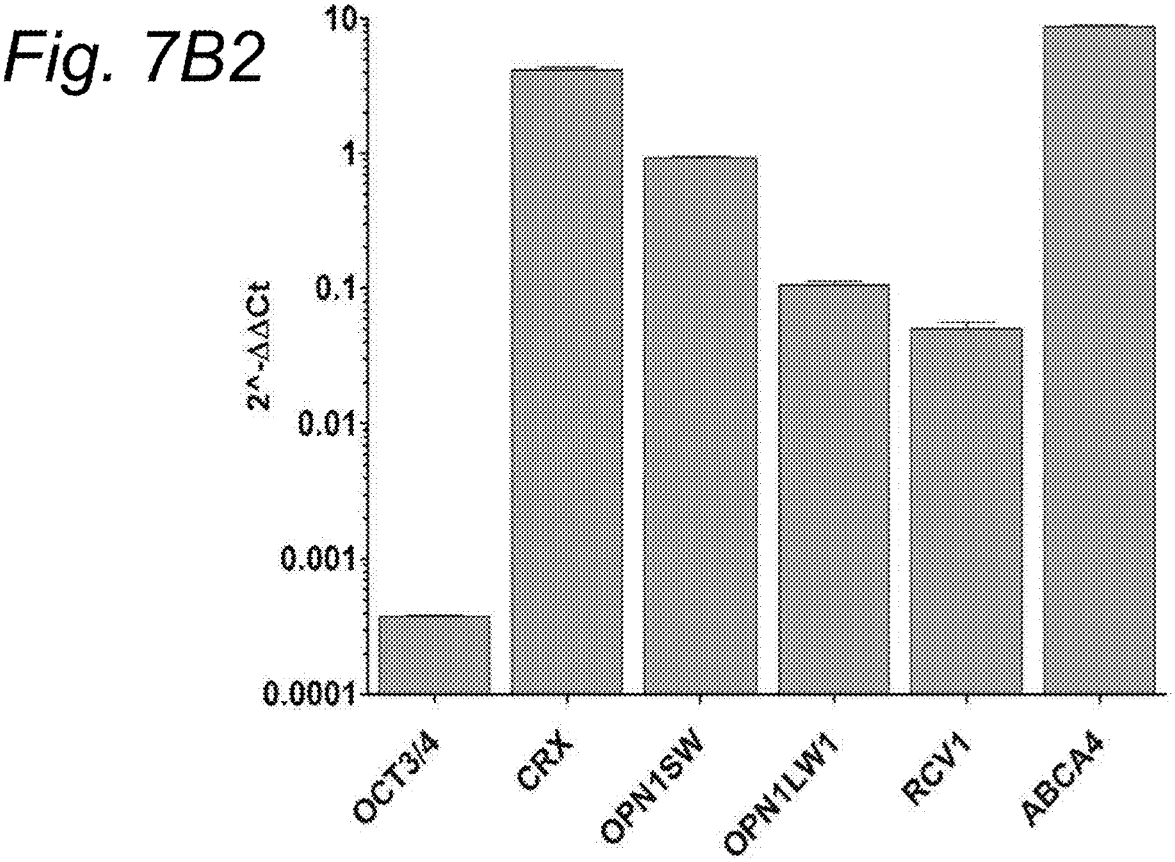
Fig. 7B3
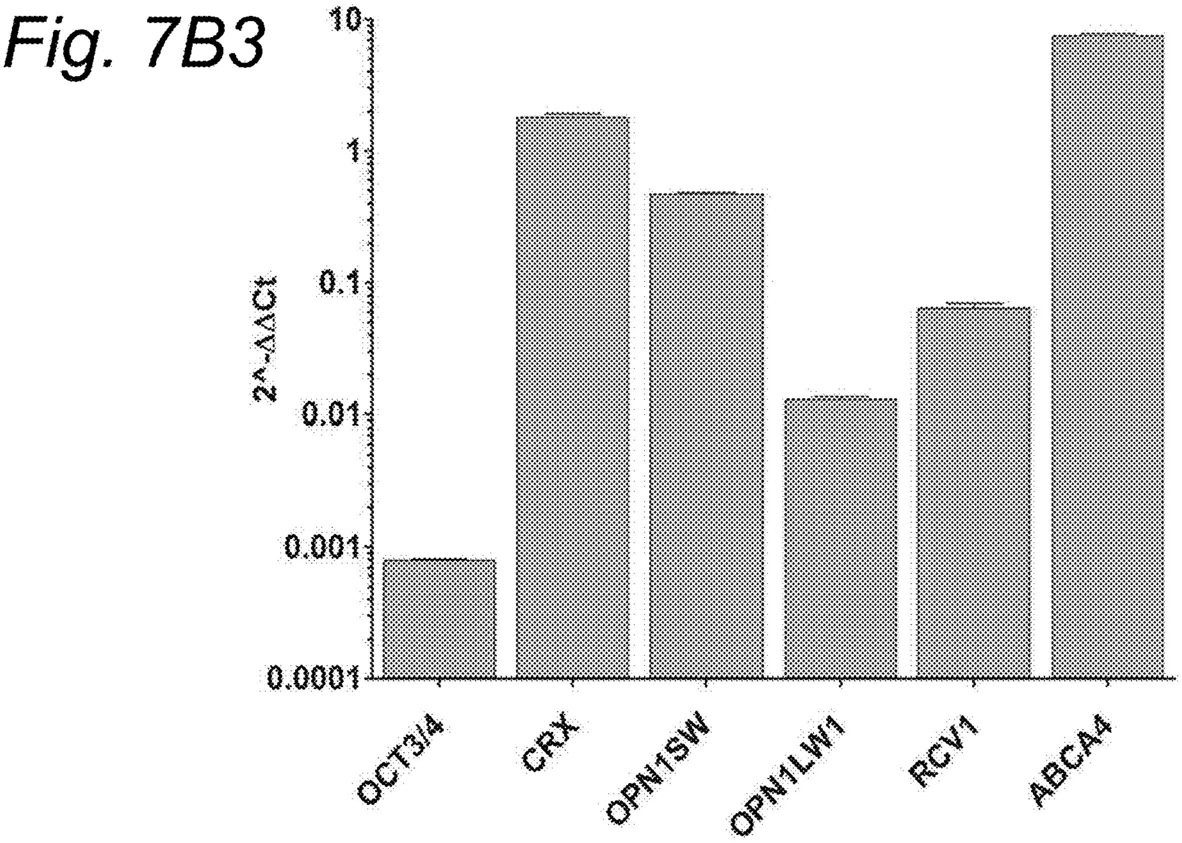

c.769-784C>T c.859-540C>G c.4539+1100A>G c.5197-557G>T c.4539+1106C>T

SEQUENCE LISTING

```
<160> NUMBER OF SEQ ID NOS: 311

<210> SEQ ID NO 1
<211> LENGTH: 128312
<212> TYPE: DNA
<213> ORGANISM: Homo sapiens

<400> SEQUENCE: 1

aggacacagc gtccggagcc agaggcgctc ttaacggcgt ttatgtcctt tgctgtctga      60

ggggcctcag ctctgaccaa tctggtcttc gtgtggtcat tagcatgggc ttcgtgagac     120

agatacagct tttgctctgg aagaactgga ccctgcggaa aaggcaaaag gtaacagtta     180
```

-continued

```
ctgtctgtgg tttaaaaatg aggtgtggag caaataaaca ggttggaagt gtggggtggg    240
gtggtggggt agggtggtgg ggcagggtgg ggggttgtga gcagtcagtg ggcttgtcgc    300
cgattagcac tgaagcagtg tttagctgga cggcctttct gtgggcccct ctgacagtgc    360
ccttcccagg aagatgtgtt tctctgtcct cagccacatg aaaatctttt gcctaccgtg    420
cctgtcaatc cattgcctgc ccgcccctcc cccaccccc gttttacacc tgcctgtcca     480
gtctaccgct ctctagggca tccacgctga gcagtgggaa gaactttaag ccctgaagag    540
caggccaaag gcaagcaaga accccctcga acagcttccc agcttagtga ggccttattt    600
cattgattct ctgaggcaca ttgtttttc acatgttagc atttctgaaa ttgggatgca     660
gctcacgatc aagtcacagt ttaactggac acattatttt tctttcttag tggtgcagaa    720
aagtaacagt gtgtcttaca attgactgcg tcctagattc tgtgagatgc aatacgttat    780
taaccatcac gcacatttcc tgaactcttt caatgagcag acaccagcct gggttagact    840
ggagccctaa aagcacgaca cagattccac cctggactgg cttctgttct gcctgggaaa    900
acccaaagta cgtttggaga ccaagagcaa cataaagtag cataggtgga atagtccatg    960
agaagtgcga gcaaaaggtg ccggagatca gagaacacca agactgtact tgtaaatgac   1020
aactggcttt gtgcaatttt ttctgggaaa ggataaggag tgactataga actgtaaaga   1080
aagaatgcac tttgctacag ccttgcagag ttgtgcaaat gccgatgact aaaggagctg   1140
aaagaggaag gaggggataa gggatggggg ctgggtaggg gtgagattag gaccctggga   1200
gctgcaagcc actggagaga tcaggaggaa agggagggag acctgcttta ggcgagaaga   1260
gaacagtatt tgttccaaat ctcggttcag aataagttca tgtaggtgat ggggccaact   1320
ggaacaggtg aaggcctatg aatgagtgtc tcagttaggg tctccttaga gtttaatatg   1380
aaaaggtgtt agctaagtac agagctggta cctgagagag taaaaggaaa ctctaaggta   1440
tcatggaggt agcaattgca ggacacagct cccaccccta gggctgagag aaccaaggga   1500
agagacagga attattaaga cttggagcat agatgagagg tctgtggagc tgacattagg   1560
acttgggagg aaggcgtgca tggaggctgc tgctggatct ctgaacctga cctcgggtct   1620
ggacccctga ggagaaagcc ctggcaggtt ggtgcatgtg gggccgaggg acaatagctt   1680
aacaaccagc ataaaagaga gcagcatggg acacgcttca accatgcgca tggatggctc   1740
caaaacctgt gtgtggctgg cccaggacgc agggaggctg caggggggaag agacaagtta   1800
aacctgactt gtctgggaag caccattgtc ctcaggtcac tttcctctgt caagcctggt   1860
gctgaagtta tctgttgtct ccagggggcca agtattaaga gtaatcagaa actcagtcct   1920
ttcttctagg agcttccctt cttgcatgaa aatcctgata aaactggaaa aaaaaacctc   1980
atgattaaat tttttcatgt attcattctt tccttctatc aaaaaaataat ctccaggcac   2040
cgtgctaggt tcattggtat acaatggcaa caagacctcc cagcccctgc ctatgtgagg   2100
catctgtgga ctgcggagga aaatccaata tgccattgtt ctctctttcc cataagaaat   2160
tacaattctc agttcatttt attctcactg tgctctttgt gaccctcaaa gggggtcaca   2220
tgataacagg actgtagctg ctggcctaaa atgagcccat tcctgtggcg ctcatgtcgc   2280
tgtgacagag aataaccctg ttttcagaat gctctggtgc cctccctctc aatctggcct   2340
ttcgctggca tgggtgggcg actcctgctc agggactctg ccttctccac agtgtgctcc   2400
cagggagatg gagccactcg ggctgagggc cttggccagg gcacctccca gggctgggcc   2460
tggtctgggc tggcgttcac tggatgccat cctgatggcc tggaaattga gatttctgtc   2520
```

-continued

```
tggcacgcct cccgatggct ccccacctgc taccacattc caggagcttc caggatgtct   2580
gggtaagaca gaggcacccc caacagattc agtagctctg agagggatct gtggctcctt   2640
cctaagcttg cggttcttct ggaaacttct gcctctagaa gatggtccct ctaagaaaag   2700
tacaaccacc cagcccataa ttcagctccc aggttttccc tcaaacctcc atgtctcctg   2760
taagcagagc aagagtaaaa tcagatacca aatttcctca ttcctcagct cccaatccct   2820
aagggcataa gatgaaaatc ttcagatctc tgctttcctc cctctttttt tcttcctctg   2880
ttaacatttg tcaagtgtta ctaagtgtct ggcactgtac taagtgcatc acctccctga   2940
actctccgaa cagttccacg agagaggcct ctctgtgatc cccccggtac tgatgaggtc   3000
actgaggctc cagagaagga ttagtaactg gtggggttgg acctgggatt cacacccatg   3060
ctgcgtgacc caggacaggc aggcatggcc gttacaccac actgaccccc gtggatcgag   3120
atctatccaa tagtctggtc actgatatca ctaagataga gtggccatat aatttatcat   3180
ccaatcaggg cagttttgca agtgaaaggg agcactatta ataattgcac tgggacaata   3240
aatgtaaacc aacactggac ctggaaaact gggacgtgtg tttgccctat accaaggtaa   3300
gctagacaca gccactgcct tcatggagtt cagaaccagg caggggcggc tcccacgtat   3360
aattactgtg cagcacaacg tggagaccgt ggagtagaag gaaacacgga tgggaggtga   3420
ggaggaggtc tgtgagctca gaggaggcac cggggctgga gagggtgaga gaagacttcc   3480
caaggagttc atcctgataa cgtgcattcc caatgacgag cgctctctcc actgcacaag   3540
acaagtatac atctgcccgt gttggctgtg gacctggcgc tgtgtcaggg agggtttatg   3600
aagatcacta ggtgggtctc ttggtgtcat cccttcatcc cagcttctgg gttaggatgg   3660
atatctgtgg gggggcctga ggactcatga aagtggggcg ctaatcatgt tttggacacc   3720
acaccctgga gcacctggga cagctgtggc ctttgtcctg ggttcagcat caagccgagg   3780
atgtggcaag taaagagagg ctgggcacca actccagtgt acccaggctc cgggtcatgt   3840
ttgtccaggc taagaattct gtcctggttc tcagtgcaga aggaagaatc atggggctca   3900
ttttaggcct tggctgcctt ctgttaaatt gaaaacagag caggaaggaa gaaaatttaa   3960
caggctcagt tctaaaacaa caagcacaac tgtgcccttg ccagaaaccc ctcctcccca   4020
tgttgattga atggtaaaga gaggagggga ggtgagaggg agagagagag agaggaagag   4080
agagagaaag gaaagaaagg aaagaagaag aaagaaagaa aaggaaagaa agaaagaaag   4140
aaagaaagaa agaaagaaag aaagaaagaa agaaagaaag agaaagaaag aaaggaggga   4200
gggagggaag gggaaaagaa aagaaaagaa aaagaaaaaa agaaggaaat accagtttgg   4260
gaaaaaagaa ttttccacca gcccttctga gccttggctg ggcttaatta aagttacaga   4320
catgtgtaaa gggcagggta gggggagtct gagctgctga gaaaacatgt ttttaattat   4380
actgtggaat ttctccctgg ggtatgcctg tacgcagtta agcgtcaagg acagggatgc   4440
cgctctgggg aggggaagct gagcatgatt ttggaagccg gcagaagagg ctattgtgaa   4500
aaccagacct gtcaggctag gaaaagaatg gctggtggtc tttgaccagg gagtgacgcg   4560
tgaaatgcag caaccgcccc cgccccccgc caaaaacaaa cacactctca cagagttaga   4620
acaacagtga cctctcaaca aatatttttc aaagattacc aaccaaccat tacctagagc   4680
agcggttctc aaccttggct gcacggtgga actacctgag acgtgttaaa aagaagaacc   4740
ctgatgtccc atgccccaag attctgatgt agttgatctg ggtatgatc tgagaccccg   4800
gcatgttttc agcctgcagc cacatgagaa gtgctgacct aatcaacagg ggtgatgatt   4860
tgaggggcgg ggactatagg caaaaaaaaa cagcctaatt caaggatgag aagagggcac   4920
```

-continued

```
aggtgaggtg ggaacagtcc tagggccaga caaagaagga agggagaaag gaggtgctga   4980
tccctcccct actcctgaga ggaggccttt aagtcaccgt gccttgtgga gaccagattc   5040
ttcaaaaata caagaatgag tgagtgaggg agtgggtgga tgccaggaga gtgcgtgaca   5100
agccttgcaa gggaggatga caatgcacta gcttggtttg gaaattttac ccctggaaca   5160
ggcaggccaa gctggctggt cccctccctg atacacagcc ctccctcttt atatatggag   5220
caggggacgg tgtgtggctg gtttcttagc aagcaccatg gttccaagtt ggcaactggg   5280
gagttctgaa tccaaaaagg agggagatga acgtaagtgg agggcaggcc tacaaggttg   5340
cagataagct taattctgtc tccttactct tctgcctttg caacaaccct gtgatcttgc   5400
gacaaccctg taaggcaata acaaatggct catgtttatt gagtgttacc tcatgccata   5460
ttgtgctttc gtgtttaaca caattgtctc atttcaccct cacgactgct ctgggaggta   5520
ggtcctggta tcacatccat ttcacagatg agaccatttg gcacggaaga gttgagtggg   5580
ctgcccaagg tcacatagct aagatggaac aggctggata ggaaccccag taacttgacc   5640
tcagagtaac cttctcttaa ccctgagtgt acactgtagg aaaaatgagc agtcccattt   5700
cagagaggac aaaactgaga ctcagaggtt aagcaagccc caaagtggtt gttaacccag   5760
atcttcccac taactcccaa atcagcatca gtgtttaacg taccagacct ctcccagata   5820
gatgttgccg catggaagac agccgatcta cgtgatagaa agccaatatt gcaagcagtc   5880
gtctaaagga gtcaaatgtg ttggatttga actggatgtc tcatttcttt ggtgaagaca   5940
ctggaaacaa cttccaggtt tcatcaattg ctcctatcac tcaacgttgc tatcttactg   6000
aacttgttcc ccagccttac ccactgatgg aatgatccag aatggaagac aagacaccaa   6060
tgtacatgac cctgggggag gctgtttctt aaatctacag actgttggtg acctgagccc   6120
catgtcacca aaggctttcc tggagaagcc tcctagacca gtcttgacaa aggctcactc   6180
attccgtgga tatttattgg gcacctatta tgagttctgc cccatgtggg gtgctggaat   6240
cacagtagtg acaacgacag atgaggttcc tgtcctcagg aagcttactg cccttgaggg   6300
cttcacttac ttggaggagt gatgaacctg aagtgcggtg tgtgttaaga agcggaagtc   6360
cagggccagg cgcggtggct cacgcctgta atcccagcac tttgggaggc tgaggcaggc   6420
ggatcaccag gtcaggagat cgagaccatc ctggctaaca tggtgaaacc ccgtctctac   6480
taaaaataca aaaaaattag ccgggcatgg tggtgggcac ctgcagtccc agctactcag   6540
gaggctgagg caggagagtg gcgtgaacct gggaggcaga gcttgcagtg agccaagatc   6600
gtgccactgc actccagcct gggcaacaga gtgagactcc gtctcaaaaa gaaaaaaaaa   6660
agtgcctcac ggagagtcta ttcttttctt cccatattgt gtgtgtgtgt gcgcgcttcc   6720
tccaacacat cctccctata tatattttga gtaaaacatc ttgtaaaaag ttacagctac   6780
ataatcacca cctgtcccta aatagttttt gctttttctt tcttcaatgc acgatcattt   6840
tcccccatca atttattttt tagtttctta taatcttgtt gccagtaggc tgttttttaa   6900
aaagcagaac atggtttgtt cttactagca ggaaaggagc atttattgag cctctgctat   6960
ggtgtctttt attttgctga gagcctattt acatttcttt gagaggaaaa caacaaaggg   7020
ttacatgaaa gaccatgtga atagccccta gctgatctat taaacttgct attccccggc   7080
cagctgcttc agatctcctt cagatcttat gtgtttcctt cctaaggtcc ctggagtaag   7140
ggttgcatag acctattcta ctctccaact cacatgtccc tctccctctt cctctccata   7200
attccacatc tccaaccccc accccctatgt gcaatgccac agggtgtgga ctgccacagc   7260
```

-continued

```
cactggatct gcttttggaa tcaagagtcc ttaagctcca aatggaaccg aaatttaaat   7320
accaactttc aaccatatgt taacatcagc agcctcttcc aatgtaaaaa cccatggcag   7380
tgtgccctgc tttgtttctt taagcaatag aaacttgaag gaagcatgtt ggtaggccag   7440
atttttgttg gctttgcaat ggatcacagt catttattca ctcattcatt cactgattca   7500
ttaaatgacc acatttgcaa gggcaaggta atggggaggg ccagaaagga cactggcccc   7560
agaaacagga ggctggattt tggttctgat gctgccactg ctgatgtgac actgcacagg   7620
tcacctgcct cctctgagcc tctttcctta actgcagagt gagtggctac agagaaatct   7680
ttactacctg ttagatcagc attacctggg agcttgttag aaatgcaagc tctggtgggg   7740
ccatactgaa cccaaatctg cattcatgtg catagtgaca gctaaaatgc actgaagcag   7800
atgatcttga tgatccttta tgaaagtctc atgctaatgc agttttctaa aatagaggca   7860
gagtggaacc cagatggaca caaaatctgg ttgatataat aaaacaaggt agagggtgta   7920
tggtggggag ggggtaaagg aaggaaactg tttaggtaaa gataccacaa ccaaagtcct   7980
actgcacaca tgggatctga ggagggctgt gtctgctctg gttacgtttt ctataatctc   8040
ttagcaccac tgaactttct ctctttttgt tttgttttc cagattcgct ttgtggtgga   8100
actcgtgtgg cctttatctt tatttctggt cttgatctgg ttaaggaatg ccaacccact   8160
ctacagccat catgaatgta agcatagcag ggtagcttgg gcaagccctg aagagacttt   8220
ggtctgggcc ttttgtctag aaagatcttg gggtgggagt gtggggatca gatctgctta   8280
tcatcatttc atgtctatga tgcatgtaac agatttatca atgttacaca aattataatt   8340
tttaaaaagt ctttagagac agggtctcac tctgttgccg aggctggagt acagtgttag   8400
gaccatggca cactgcagct tctatctctt gggctcaagt gatcctcctg cctgggcttc   8460
caaagtgctg gaattatagg catgagccac tgctcccagc taattttttt gtttttttgtg   8520
gagacagagt cactacattg cccgggctgg tcttgaactc ctggcctcaa gtgatcctcc   8580
cacctcagcg ttctaaagca ctgggattac aagcatgagc caccttgtcc agcccaaatt   8640
ttcatgtttt aatcctacac attctaagca aatacttgtg tgtagttact aagggactgt   8700
gcacttattt ttgtttgctt tgttgttgct agtttttatt tttttatacc taaactctct   8760
cgttttaaag agaacagatt tgtagatgag ttctcgaaaa tatttcagga atcaatatag   8820
agaatatgtt atacatggtg ccagagaaaa atgaggacaa gagatgctat acaatcgtac   8880
tgaagaaaaa ttttatttct tggacccctg aggtgtctgc agacctgaaa ggaacctagt   8940
gagagcctct tttacactct gcccctgtgg gaaagccttc acctggtttc cggccctcta   9000
tgtggtgaat gtggaagcct caagcgttat gcaaatctgc ccagtcctct attcttgatc   9060
ttcaccttct cgttcatgag tttcaggccc cagttctgaa tcagcctcct gtccatcaga   9120
ctcttcttta cctctccccg aggagcccat aacctgcagc cctactgcat gcttggggta   9180
ggtgctcagt tcaccgtggt tgaaggaata gacgagcgtc tgctcaagca gcagcagcaa   9240
ctgcgtggag tcttcttgaa ctaacactcc tatgcccctc tcggcacaaa atgacgtgtc   9300
ccccttgct tccccttcac atttccaccc atgcctatta caacatccgt ctgtctcccc   9360
actacaccgg gagcttgaga gaagaggcca tgtctctagc acccagcaca gggactggca   9420
cacatgagat gctcctgctt cttaaatgct gagaatgaag gaggacatca gaggggcccg   9480
ggccccttcc caaaaaggcc aactcctagg tctgcatcct gcttggtctc catgactaat   9540
cccgtcttgt cctcattttc tgttttaaag gccatttccc caacaaggcg atgccctcag   9600
caggaatgct gccgtggctc caggggatct tctgcaatgt gaacaatccc tgttttcaaa   9660
```

-continued gccccacccc aggagaatct cctggaattg tgtcaaacta taacaactcc atgtaagtgt 9720
tgagatccct accatgcagg ggaggaagtt gcacacccct tcacgtgctg aaatgcacac 9780
gtgcgtgcac ggagcatgga gcactgagtg ttcttgtggc tttgctgagc ccctaacctc 9840
ttaggagcag agcaggtttc ctctctggaa cattctgtta actgtcaggg cacttgggga 9900
gaaatctcca agctaaggcc acgtgcacaa aatttcttgg tccttatatc cccagaatgt 9960
gacctggagt ctgatggcag cccgctgcag agatgtgtcc actgccttct ggtcattgac 10020
ctgcttgggt ggagtgaatc attgtaggag aaaaactcag ttccctcacc ctgatcaacc 10080
tggacagatc tctcttcctt taaaagcttt cttggacatc taagggctag gaaaaatgtc 10140
agggagcatt gggaaggtaa atgaagtcag gtttacaaag tcaagtttac ttcttgggag 10200
aaaaatacaa tttccaaatc ctctgttata attgccatcg gccccctgga gtggtgagat 10260
ctcggaatat ggctcgggtg cagtggctct tcactgtggg cctgcaggct attctgaaaa 10320
gctgatgaaa accaatgacc cctcttccaa gaaaaatggc cacataccaa acattacact 10380
gtacatctga tttcagggaa ttgtagatgc caggttagta gcctcaggtc tagggtcaaa 10440
attcaagtcg aatcccacag gaagagggtc tgccttcgga attccctttc agagcattgg 10500
gagaacatca tgggagcata ttctagagac agaggcttag ggtgtggaca gggccatccc 10560
tcacccactg tgctgacctt aagcagcacc ttgtgcagcc catacctgaa ggccaccagc 10620
aaaggcctgt tggggagcag gctttacccg acctgtataa acaccaggct aggtgaaaac 10680
tgagatacct ggttacttta gtttttttcct tgggggagct cagtatgatt cttccaggag 10740
aagcctgctt ttagactaaa aagaaaaaaa gtttgatagg tcaacctaat gattggaggt 10800
ggccttcccc actgtgaaca aactatggct gcatgtgccc tacaatggca gagttgagta 10860
gttgtgatag agactgtatg atctgtaagc ctgtaatttt tatgtttgct gacccctgga 10920
ttaccagatg atagaagagg aaacatctgt cttcctagca aagtcaagga agtggcattt 10980
agcaggactc atattgctgc aagcactgcc ttgcagtttt agtttacaac tgcactttca 11040
gcttaagaaa cacctgccca tccagagaga tcgtgtgggg tcacatggtg ggatcaggga 11100
ggcctgaaga cagctcagtg gaggctgcat ggagctttgg tgggaacggc cctggcagtg 11160
tctatagatg ttattgcgga aaactgaggg gtgggagttg gagaaggggg ctccagactc 11220
tagctgtact tggcatttga acccggaaag ttgggtttca tgttttgcac tcacattatg 11280
agtgaaatat tggcttattc aaggttcttt tgcttgcaag gcacggaaac ccattcaagc 11340
aatcttaaac cccagaagga aatctatgat ttggatacta gacattctca cagagccaag 11400
ggcagcaagg cggggctcag gagaggcagg ccaagacctg gagagctgtc aggagctgct 11460
tcctcaactc tcttccatct gggcctgcca gccctggcct ctgtatctac tccattcacc 11520
tctctccatg gaccagtctc ccctgctcct caatgcctgg gctgccattg ttcatgcaat 11580
tcacaatacc tcggcctggg caatcagaag ctcatctctg aacaccatcc aaattcctgg 11640
gaacaaatcg ggttgaccca gctttattct ccctgtccca tcagccttgg cagaggcgtg 11700
catgtgcatg cgtgccaatg tgtgtgtgca gggaggtcct tgtggatgaa gcatggctgt 11760
cagagcctac ctgcgtgaat gggtggaagg gcaggtctca gagaattggg taaaaactgg 11820
ataaaccctc cagtgatatc caccaatgtc accctgttta aggcttctct gggcaagaga 11880
cacacagagc atgggaccga gaggcgagca gaccctgcca aaactgggag actgaataga 11940
tcgctcacca tccttgtcag ttagcctata tgtacaagga agtaaaatta tctctttctc 12000

-continued

```
ctgccttggc agtattgtaa ggatactcaa tgtagtagct aggccagaca catagtatct  12060
ttaaatatag catgagatgg ccaagcacgg tggctcatgc ctgtaatccc agcactttgg  12120
gaggctgagg cgggtggatc acgaggtcag gagatcgaga ccatcctggc taacacgatg  12180
aagccccgtc tctactaaaa atataaaaaa ttagctgggt gtggtggcgg gcgcctgtag  12240
tcccagctac tcgggaggct gaggcaggag aatagcgtga acccgggggg cagagcttgc  12300
agtgagccga gatcacgcca ctgcactcca gcctgggtga cagagcgaga taaaaaaaaa  12360
aaatagcatg agatattatt actgttataa aaataacagc tatttcctta ttaatgaggc  12420
tttgtcctta cagcttggca agggtatatc gagattttca agaactcctc atgaatgcac  12480
cagagagcca gcaccttggc cgtatttgga cagagctaca catcttgtcc caattcatgg  12540
acaccctccg gactcacccg gagagaattg caggtaagca tgactgcagt gctctcaagc  12600
atcatttccc tcacctatgg agagactgaa gatataggaa agaacaggga gagttggtga  12660
aaaatatact agcggaggca ggaagggatg gggtctggag gcggcttgaa catcaccttg  12720
gtgaagatgc ctcttcctcc acagaagcct ggaaggtagg aagttgggaa ggaaggcagg  12780
aaaggtctca tccacgttaa gtctagagac agaaagaatg ctaagagaga tggcactatg  12840
ggaagtatga ggctaggtca agggctagaa gcaggggaga cgagtttaca gagtttcgta  12900
aagatataga gcaactctca cagagttcta gagcgagagc taaccaggaa catgaagcag  12960
caaggccaac tatcattaag gagccaggga ggtcagagat catgtattat catgacataa  13020
atatgcataa ttgtactatt tctcccagta atatttagca cccaggcccc gaggcagagc  13080
aagtggagag tgggtgatgc agggctgggg gtgtgtatgg aggcaccaca gaaggtcaac  13140
aggcagcggg ctgaaggcag ggactggact acatgcatca agtccaggct gcacgaggaa  13200
ggatgagaag gcagatgagc acggaaatgg actgggggaa atgaagaggc aagggaatag  13260
aagtctcagt gggtgccatg accctgttta agtgattgag aaaatgaaca agatgaaaag  13320
gttaatggct gtggtcagaa agtgaaatat gtgaattcag gatttcgaag gtagggtggg  13380
tgatgactgg cccccagatg cggccatggt gaagtggggc aaaggtgcag gtgcatggtg  13440
aggggaagga ggaaatggga ggtgatgatg ttggccccac acggacacca cggttgtgca  13500
ggaagatggc aggagctggg caccagggtg ggagccacct ggagtcagga agagtgaaga  13560
gaaaggatga agaggctccc tctcctgtgt ctctcctccc caggagaaga acaagaaaca  13620
atccgaaagt aataacacca atgtgccttt acaaagtgtg agtgggtgtt gtgtgctgtc  13680
acgtgtgtag taggctcctc tgtggatggc tagagggact ggacatggcc actggatccc  13740
acttgcaaga gcagaggaaa agagtggtcg tgaggaagta aagccccccca aaatccaggg  13800
gttgctgcag ctttgggtgt ggagcgtgcc ctctgaggaa aggctgctct gggggagatt  13860
gcccaggaaa cggggctcag aggccacgaa agcagctgtt aggggcttct gggagatgtg  13920
tgctcctagg attagggagt tgactctaag gatgacctta gaggttaaca gggatgagaa  13980
aggggtcacc aaggggtcta ccaggggaat gggagaggct gtattgatag aacagcttct  14040
gctgcaggtt ccaaacaaga aatgtgggag aatggttgaa atcagccccg ggggcacctt  14100
cccgtgcatg cgtgcagctc cttcaacatt cagtcgacct tcagtgcctc ctgtgagcca  14160
ggcactgggc tagtctctgg gggtggagag atgagtcagg caaatgccag ccctcagagg  14220
gctcacaggg cagaaggtga gagatgagtg agcagaaaat gaccacagcg cgtgtggggc  14280
ccagtggagg gaaggagggg attcaggagc acaggagagt caacagggga aacttctccg  14340
aggagaatct gatcctcctc ccatctggcc accttctgaa gccctctctc cccatccaag  14400
```

-continued tgagaaagga caggcgtatg accagattgg tgtatgaaga tgctgaatta cgttctcatt 14460
gtttcaaact agtaaaccat agattttatg tagtaacttc tacaaactgc attacaaaca 14520
ctccattctt tgttgccctg ggtagaagtt tattttagtg agcccaagtt tgaggaacct 14580
tatatggtat gagtacaatt accattttaa tagtaagaaa tccccccttcc cctgtgtacc 14640 aaccagaagg tgttttttttc ctaatttaaa caaacagatg cagacgtggg ctgtccagct 14700
cctggcggga tgacatacct catgcatcca gtgggtttga tgatgaggca gacatttcac 14760
ttaagtgcct gatcatcaga ttgagtcctg ctgggaggaa gtgtgaagga agtaatttca 14820
aaccacagtt tctctgtggc ttttacaatg tggatatgag aaccaaaatc actacttctt 14880
aaccccagag caggactgat tttgaattgg tatgcaggcg gttccttctg caggcttcgg 14940
gctgtgagaa gtccctaaca gagcaaatct ggggacaagg gctcaggaaa ggttggccac 15000
ggccccctag gaatgggggc tctgcaagat ccctggcctt agaggctgtg agagggaaca 15060
ggggtccatc cccaagtaag ggacacggtc tttgaggaaa tcccaggcca gggcctgaag 15120
ggcactgtca ggaacacagg ctgtttcagt ctgttgagat tcaccggggc gctgctcact 15180
gtgagcacgg actcctcagg ccaatgtggc agaagagccc acctttgaaa gcgagcgggt 15240
gggggtggcg gggctggtgc tggtgcgtgc ttctgcacag ccacctggga aggtatgccg 15300
ctggttgacc caggcagagg ttttctttca tggcaaacct gcagtactgc attctcagca 15360
gggaggatta atggtaaaag accaggcatg gagccccctt ccctctccct cgaagcaagc 15420
tctgtggtct ctcaatcatc tttaaaacac cttcttcccg ggagcctcct acattctcct 15480
ggcttccctc ccaccccccac cctcagctcc tggggcctca gcagccccac ccccaagcct 15540
ctaatcttcc cagggaaggg aacaagaaga accacatttt aaacgaaatt tatttttctt 15600
tcctcaggct cccagttcac atttctccct caggagtcta gggaagcttc tgtctggtat 15660
cggcctcctc ttcacctggg cccccgccct cctcaggtgt accagaagcc agcacactcc 15720
cccttccccc ccagagccac agcagccctg tctcctgggt ggtcttgtgt gccaagcctg 15780
ggcaacatca ctcccagctt ttcttgtttt gccccttctc cccagcaaga tatttgtatg 15840
taaggtcagg tgagtgagtt aaagaataac gaagagataa acagtcaaat ggagtcctga 15900
ctgtcaggtc aagacaacag ttatttactg aatgcctcat gtcattcaac agacatttat 15960
tgagactctg attggatgtc agtctttaat gctgggtgtc agagagaggt gacttcaagg 16020
gcttgcatct gtgcacccag cattgctagg tacaatgagg agtataataa aagcaggagc 16080
catagccccc aactctcaag agatctccca tgtgtgtatg tctgcatatg cgtgcgtgtg 16140
catgtgtgcg catgtgtgca tgtgtgtgtg catgtgtgtg catgcgtgtg tgtgtgcgtg 16200
tgttggggat ggtgttggtg gagtgagagt gtacaaggct gtgtatgaag ggtaattgg 16260 gaaaagaaca atggagctgg cacccaggga caggaggaaa agcaggaggg ctgggtttgg 16320
aagacagccg gatttatgtt tttgaagagg gaagactaga atataaggga gcagcccttc 16380
tcagagccct cctcctccct tcgggccctg tgtccagctt tccccaaagt ccttggatct 16440
ttcctatgca aaggggagtg acagtgggca ccactctcag ggaacccatt actgtgagag 16500
aagccactgt gccactgtgt ggtcgaactt caagaccggc ttcccctgcc ccagctgcat 16560
ggacaggcct gtggggttgg cgcaagaccc ttccagagga aactagctgc aacataaatc 16620
cggatatggt gctgttcagg gaaaggcaca acctggggat gagaagggtg gctgtccagc 16680
acacaggggc aggcctcttg gccactgggg gaggggagaa tttggagagg aagaggatgg 16740

-continued

```
gatgccgtgg aattgggacc aggaaagaat ggggacatgt gatggttaaa gctagttaga  16800
gaagaactgg gagataaaca gtcacccatg cccctgaagc actcggggtg aagagattgg  16860
cattttcacg caccccagtg ctttcccttt gtgttgaagt cccttcgtag acatccaggc  16920
ccataaggct cttctctggc cagagcctca tgaactatag cactagcagg gttgaggcca  16980
agcattggcc ctggaagcca gccgaggagg agggtgcttg tgtgaatctc ccaggagggg  17040
taagaattat attaattcga tcataataag catttattga gtgctgtttt gaggcctggg  17100
agctaagcac ttcacattcc ttaccccgca tcaacaatcc tatgaggtag atgtggaaaa  17160
tgcagacacg gggacaggct caatcacttg ccccaaggtc accttaactg ttaggtgttc  17220
tttatgcctc cttataaaga aaccctgctt cccacaggtg ttgagaggag ctggagggag  17280
cttgactagg gctcatcagg caagccccgg catgtgcctg gctctcctct ttctacctgg  17340
agcttttcct gcccttaatg gccccaactc atttctctta gtccatgtca gtgccctgag  17400
catctcagcc caagctgaga tgatagaaac acccagaggg gtcctctacc ctgtgacagc  17460
tgcggtgtgg gaagagcacg tgtctcctcc aatcctagac cagagtttct cagcctcagc  17520
atcactgaca cttggggcta gataatcctt tgtgtggggg agggaggagt gtcttgggcc  17580
ttgcaggatg tttagcagca tctctggcct ctacccacca gcacctcccc agttgtgaca  17640
cccagaaatg tctttagatc ttgccaaata tttccaggag gatgaaattc ccctgtttca  17700
gttccccagc cccacctcaa tgagaagcac tgtcctagac caaccccaca aagcatctga  17760
cacccccatc cagccctggc taactttttc caccttctta ctaaattggg cccagctgct  17820
tcagcagtca atgtgttggg ggcagcccac tggcaagagc ctcacctcta ggggctccca  17880
gagaccccaa gaacagaacc ttcctctgag agttgagtta caagtgtttc caatcgactc  17940
tggctgtttt ccttttttttg acccatttcc ccttcaacac cctgttcttt ctcttattca  18000
tatgtaggaa gaggaatacg aataagggat atcttgaaag atgaagaaac actgacacta  18060
tttctcatta aaaacatcgg cctgtctgac tcagtggtct accttctgat caactctcaa  18120
gtccgtccag agcaggtagg gggatgtcac tggccagtgg tccctggagg ggagggaagc  18180
acccagcctg agaaaggcaa gaaatatatt ggctttttttc ttctttcttc cttgtgttca  18240
cattcagaat ccatcactta atgccttgta tttagaaaaa aaccggggga tcacttgaga  18300
tcgtgatcat tttcaacata ggattcgaag ctgtacacat cctggtgacc ttaaaacatc  18360
tcaggttttt ataactggaa ggaaccttag agatcatggg gcacaacctt ctctttatag  18420
atgaggaaac agaaatctat tcatttatta ctcaaatatt tagggacagt tgtaggtact  18480
agaacacagt gtgaaccaga caggcaaaac cccaggccag ggagcttcca ttccagtggg  18540
gccacaggcg atgctcaggt aagcagagac tccgctgtgt gacttctggc tgtgatgggt  18600
gctgcaagga aaatccggta gagtcgaggg ttagagaggg acggaggggc aggtttaagg  18660
gggatgctca ggaaggcctt cctgaggagg tggtatttga gcagagttgt ctgtcagcca  18720
cacagtaagt gagaggggag ttccgggctt ggaagctgcc agcacagtgc tggcaagtgc  18780
tggggtggcg tcccgaggct acagaacctg agatgctgca gaagagccca cttctgcttt  18840
cctggaccac ttccttctca gcaccaggca aactccttct tctatcccct ggcacatttc  18900
tgacctgtgt atacgccccc aatttatcta accccttttaa ataatctcct ctatttatgc  18960
agagcattct taccactaac tcacgacttg cacatccctt agctccctta ctcctcacaa  19020
caatcctgag atgggtcaga gaaggaggct tgcgcgtctg gtgatggggt gatttgtgca  19080
cagttacagg gctagaaatt gtcagagcca gatggaatcc aggtcctctc aatcctaatc  19140
```

cagtgtttct tacttcagtc ctgtggctct caaagcccag agaccagcag catcagcgat 19200
gcctgggagc ttgttaggaa tgcaaattat cagggcccac tccaggtgaa ctgggtccaa 19260
agccctggga taaggcctag caatctgtgc ttcacaagcc ctccaggtga ttccgcaggc 19320
tcaggtgtga gagctgcagc tgtcctctgg gccttctggg ctccccgccc agcttcttca 19380
gtgtgatgaa cacagcgaga atgctagatc tgcagcagct gatatcccag acaccctccc 19440
gactccctcc tggctgggtc tgatcctcct ccagactcca ggagagaacg agacataaac 19500
agaacttcag agcctgtgtt aaccctgaga tcaaggtctg cacagggtgc tgtctgagtc 19560
cagaggagtg agggacccca ccccacctgg tcagcaccag ctcctggaag caggttctca 19620
cactggttcc ctgcacaatg aaggagctca tacctgcttt tctggcttct cagaccctga 19680
ggttttcacc gaaactagac aaggggaacc tagggtcagc ctggaggcag ggtgagcttg 19740
gcgcctgcag tgcccaggcc ctgggtggtg cggctccggc caggccctgt ttagcttcct 19800
ctcccacccc cacagagggg gtgctgtcgg caccgattgc tcattttccc ctttgctttc 19860
tcttcagctc gtaaaactca agtcctgaca atgccttgat gacttccagt tggtaataaa 19920
agggagatga agataaggac aggaatttcg gggaaatttc tttccagttc cttactaatg 19980
tgacatttag atctctagta ctgtgcttct ggcatcagtg ccaaggcctt tcatgttgga 20040
gaatggaggc cggggtcacc aggttgtgcc tttatttcat gttgctggct ctgatgagct 20100
gatgctctgc tgattagcaa acgctgagcc atctgcgctt cgcagaggca cgttccagcc 20160
aacccggccc tccctgccca cttcccagga tgctttgcct tgtgggctca cctgtcttct 20220
agctcctgat ctgtatctcc acctccatcc agttccgggg ctccttatca gcactgttcc 20280
cagaactgtc catcacgatg gcaacgttct ctctgggcgc tgtccaacat gggagctcgc 20340
ctctgtgttg tcactcatgc tcattgaaca tggatttgtg tcctttacca tcaggactgg 20400
ataccccctcc tggtcctttc tgcctggggt cttagcacag ctcagaagga acctcaccat 20460
tccctctctc catctaggga attagaagat gacaggggca cagttctctg gctcaccccc 20520
agcccagtaa actcctggac atgcttcaag gcccagctca gatgttgcct cctcagtgaa 20580
ataatttata aacccaccct tctttgtcct gccttctccc tcttccctac tcactggaga 20640
gttaacaggt gatggttaag ctctgggttc aaatctcaca aggccacaca cttagctatg 20700
tgacttcagg caagttaatt aaccactctg tgcctctcgt ttcctcattt gtaaaatgga 20760
aatagtaaaa gtgcctacca gcatggcagt tgaagttaaa agaaataata tatgtgaaca 20820
cttggaaggg cgcctgacac atagtaaact ctcagtaaat actagctgct tttagtggct 20880
attcttaaca caccctcttc agtgctctgg tttcactatg ttttatgggt ccctgagatc 20940
gaaagtgtcc acaccgactc atggtcagct gtaacctgtg cctcgtgtgg ggaccaggct 21000
gccatgtgta gtctggacag tgtaggaggt ggcagagctc aggcctgttc tgccctccag 21060
cccagagagc cacgtcgtta gatgtcatgg gagactgtgg tgccccggga atctcacgaa 21120
tttgcccacg gtactcagtg tctgtccaat gctatgggag tccaggactc taggagccag 21180
ttaaggtgct gggtggccac aggtccctgg ccaaggtcca ggcctctccc ctgccacctg 21240
atcctcgaga ggccatcacg agggttgtac ttcaagaacc actatccttg agctacctag 21300
gagctgcaga atgtgcactc tgcagggctt agggcctgca gacaagatag atgcagggtg 21360
tctagttaaa ttcgaacttc agataaacaa caaataattt tttcaaataa ttgtgttcta 21420
ttcggtccct atttgggaca tatttgtact aaaaagtatt catttatctg aaattcagat 21480

-continued

```
tcgactgggc atctggtgct tttgtttgct aaatccaaga gcaaatttgt tctagctact  21540
tctcaacccc accttcagag aggaagcctt gatggtactg taacatcatg ctgtaagaag  21600
gggatccctt gaattgtaaa tggcactctg ataagatgag gtatggggat tgtattggtt  21660
tcctgttgct gctgtcataa attaccacaa acttagtggc ttcaaacaac acagatgcat  21720
tatcttacag ttctggaggt cacaagtctg aaagttaggg catcagcagg actgcattcc  21780
ttactgcgga gttctagaga aaaatccatt ttcctgcctc cttcagcctc cagagacacg  21840
ccacattctt tggctagtgg tctgcttcca tctccaaggc cagtgggggc ttatcaagtc  21900
tttctcacat cacatgactc tgtttcttct gcctccctct tctacattta agggaccctt  21960
gtgattacac aggggcccac ctagaaaagc caaaataatc tccttatttt aaaatcagct  22020
aatcagtggc tttaatccca tctgcgatct taattcctgt cgccatgtaa cacaaggtat  22080
tcccaggttc tgtgggttag gacgtgggtg tctttcctac cacagggcag tttctagtgt  22140
tgcctcttct ccctgcagtt cgctcatgga gtcccggacc tggcgctgaa ggacatcgcc  22200
tgcagcgagg ccctcctgga gcgcttcatc atcttcagcc agagacgcgg ggcaaagacg  22260
gtgcgctatg ccctgtgctc cctctcccag ggcaccctac agtggataga agacactctg  22320
tatgccaacg tggacttctt caagctcttc cgtgtggtaa gggaggggtt tggctgctcg  22380
ccaattgcaa ggtgattcct ggggtagcag agcctcacga attgaccttg gggagggcgt  22440
gagcctggtg ttctggacaa tccttgcaaa agctccaggc tcccagggct caaaaaatca  22500
caactgatag tatttctaga acagtggccc agggacccag aagtcactat gaggttcacc  22560
attaggtatg tggctgtggc atgtttgtgt ccactctaaa tgtggggata atcccccttta  22620
cctcctctaa cagagtggta aaggaaggag gaggcctggt ttgactccct gacctgctat  22680
ttcctagcca ggtgatcatg gtaagatatt gaaccttttc tggtcccagt actcatctat  22740
aaaacaaata taatacttta cagagtggta ggaattatac aagaaaagta tacgcaaaac  22800
atttcataaa ttttaataaa tgatggcccc atgcttcttc ctctggaaat ggtctcaacc  22860
tcaatggttg gtgtttctag agagaaaaaa cgacagagaa agtttcatag tctcaaaaat  22920
ttggaaagcc ctgatctagc tcaacccttt gttctagaac tgcatcccag acagactgct  22980
tgggacctga aaatatctcc tcctttgcta gaaggataag atgagaagga attagataaa  23040
ggaggtgtag agcagaggtt ttcacactgc aaagtgcata aaaaccatca gagggccggg  23100
cgcagtggct cacgcctgta atcccagcac tttgggaggc cgaggcgggc ggatcatgag  23160
gtcaggagat agagaccatc ctggctaaca cggtgaaacc ccgtctctac taaaaaacac  23220
acacacacaa aaattagcca ggtgtggtgg cgggcgcctg taatcccagc tactgaggag  23280
gctgaggccg gagaatggcg tgaacccggg aggcggagct tgcagtgagc cgagattgcg  23340
ccactgcact ccagcctggg tgacagagca agactccgtc tcaataaaaa caaacaaaca  23400
aacaaaccaa aaaaacccat cagagaagtt ggtaaaagat gcaagtgcta aatccccacc  23460
cccaatcact gtgattcaga agaaccaggc caggcccaga atctatcctg ttaccttagg  23520
cgattctgat gaagaccatt gtaggccaca ctttcagaaa cactcaaaat tagaatcctt  23580
cagagaaggt ggcatatata atatttctag catggaatta tgtttttttt cttttgccta  23640
cattttaatt tctagaactg tgttgtaggg aatgtcagtc actaagaact tgattgagga  23700
actgtgtttt gtctgtttca tgactgctct ctcaagtccc aggaaactca ctttcagctt  23760
gtcttaaaaa gcaagctgaa ggcttttaaa aatgaagcaa catgaaataa gacaccgcag  23820
tttctggcac ggtccacgct taatcccctt caatgtgtga ctttccgtgg aaagttactc  23880
```

```
tacgattttc ccagctcgtc agggtggggc cccagagtga gtatgaaggg tcagagccta  23940
gggatgccac catcagtgag agcccaggac cccagaaaag gtctcttggc tcaccacact  24000
gtaggaaaaa taaaaagcaa tgtagtccaa atgtctctat ccaaagtttc aaaaagaact  24060
tgattttaga cacgctcctt gacttgtttt cagaatcaga cagaagagtg aggcaacaaa  24120
ggtcccttat tccaggcagc tgaataccag cacagccagg agtccagtgc tggtgtttgc  24180
agagccacca gaggctccct ctcaggtgtc cagggcccgc atgctttgta gaatgggcag  24240
aatgagcaat gtctgtgcac ctgggctttg caggcagggc ctgggtaccc aggttcgtgc  24300
aatcctctcg tcaccatgaa gggagcagca tcattcttcc cttcttgaag caccttggcc  24360
accagtatag gtaaatttac ctcccaggac atgaccattg attctgggat gtcaatgcca  24420
gagatagtag ggtaaatcgg cacctgggta aaactttcca ttggagacta gaaccaaaac  24480
tcaggacact ggcttccaaa tgtttcttta tcagacaaga aagaccaagt ctttccttac  24540
gtcttcacat gctgccttgg caaatgctag cattcacaaa ccctgggcta ccttgacctg  24600
tcacccttgc agacctcaga cgggtcctgg gggcttgctt tctcggtttc tgtatgcagg  24660
cactcaaacc tgcatcaggc acctgtgaag ggccgggcac tgtgctgagg ccaaggctcc  24720
aaatgtgaac cttccaccct cactgaactc acagccagac cagagacaag caaacaggac  24780
atttcacagc agtgcagcct agaaagggcc aacaccagca gcatttgtcc ccccgagcgg  24840
tagcttttag aagcttcccc agtgattcaa tgtgtcctac aaatgcctgg cccccactcc  24900
cagagattct gagtcagctg gcctagggtg cagccttgac ttcactgtgt taaaaagctt  24960
cccagataag tccaatgtcc ggccaagatt gagaatcact gacctagagt ttaatttacc  25020
acctcagtct ctatagacca cgcataataa tagtacccca cacacctctg agggtccaaa  25080
gaactttcat ttgatcaccc atgagaccac cgtggtgtgg agatgctttc tctctcctgt  25140
tctcttaaca aagctggtga gcgacagagc ctgcagtgga ccgggagatg gcccagagga  25200
gaaagctctg ccgtagtcgg cctcagttaa ccacggagca ccacccctac ctgctctcct  25260
ctcactcctg cttccgtctc ggtggagaaa gatccaaccg aagcaggaca catctagtct  25320
tctggtgcct ttaaaatgta cttttccatt tgacaaatgg attacactaa aaacaaaaat  25380
ttacaaaaaa aaaaaaaaaa cctgaaagaa attgcaggca ttaaaatggg actttgcctt  25440
tattgctcct gggcccatcc tatttgggtt tttagaaaaa caagcctgag gcaggcccag  25500
aaaggctcag ggcagaccct ccgatcctct gaaaggagca tcaggcaggc aggggttgct  25560
ccggggccag ggaaggggcc ccgctgggac gcggctgtta ttgcagctgg ttggcgcgca  25620
gccatgctta gctgcagtgc gggaatgctg ggccttctgt tctgggctgt ttctcatacg  25680
cacgtaggcc agtgtataaa taaggtttta ttaaatgcca aatgagttct cattaacaaa  25740
gaaagaggga aaatctcagt aaaccaccgt gacggcatct acccactttg agtcaggagc  25800
tgggggtgtg agtgcaacct ccgagacaag ggaacctgtg gagcccagag aatcggaggg  25860
gggcgctggg gttagcaccg actgagacca gctgtgtttt ctctcggttc cttggagatc  25920
agaagtgagt gttgtcatct tcaaacaatc caaaggcagt acccatggcc ttactacatc  25980
cctcccacac catcccaccc atccccgcgc gtacactcac acgctcattt gcacactatc  26040
gcacacgctc acttgcgtgc gcacacacag attggtgacc taggtggact gggagagaaa  26100
taagagccaa atgactggat tttctccaag gaaatttatt aatagcccct cttggtttca  26160
cctgaaggag cttgtcttca cctgcggcct ttgcaggctt aacgcccccca gcttgaaacc  26220
```

-continued

```
cagaagctca gacttgggcc caaggtatta ttagtgccaa cactacctga aatgtttcgc  26280
acctcataaa aatggtgtgt cagtttcggg tgagaggttg ggacgcttcc catctgattt  26340
ggcccaaggc atgcatgccc ctccttctcc ttcccctcct cctccccctc ttccccctac  26400
catccttcct gttttctctc caactctggt gcacagcttt gaaatcttgc tgagaagcaa  26460
atctgtccct tctgctttga atgtttattt gtggaagttc ggcaggggaa ccgaggcggg  26520
tgccaagacc tgccatgctg ctgggaagtc tgagtctccc tcccttcccc ctcctaaatg  26580
cttgttgata gagaaaagtc agcctcctcg gcatttgggc tcacggtttt cctttgaaaa  26640
tgcttccagt gtggcatgat tcagctttct tttctgtccc ccaaccactg ctctgttgtc  26700
atttttactt ttctgattgc attttatccg tgtctctttg actacggggt ggctggacgt  26760
tgagttccag gaagaaaagg gcccaatctt ggggttctga ctacatgcgc ccatcaatgt  26820
cctgtttcat tcttggctct ggctccctga attcctgagt cactggggag aagcgtgggt  26880
ggaccgcccc ctacccagtg agagttgcca cagttgctgc tctcctgggt cattggttgc  26940
agattgttaa acttcaccta tgcatttcaa ctttcgggtg gatattgcta cgtcaagtgt  27000
ctgggaaagc cccacagct acaggatttt acagtgaggt cccactaatg acttgatgtc  27060
atgacttcct cattctttcc aatttctccc acttctccat aagggttttg ggaaggggag  27120
aagagaaagg agtgattcct gagtgccagt accagggaac agcagggctg ttgggaggaa  27180
acaaaactaa atcaggaagg tttttgttgt tgtttttggg gggttttatg aaaatattca  27240
agccacagca aatatatttg atttatagca ttagtatttt ttctgcctgc atctacaaaa  27300
atctttacct attaccatca aaatatcctc tgggtgaatg gatttcaaca aagaagaaat  27360
aaaaatgaaa tagaagagag gccccttcgt gcacattgag cctactggct ggattgtcac  27420
ttgcctgcct tgatgtcttt tcagctccag gcaggcagta ggccagggct tattttcatg  27480
acagatcaga tgttctttta tggatttaca aagaaagaaa tactgagaag tcaaaactga  27540
agtcacttaa gacaagagca ggcccctggg aaggctgcca ttgaggataa tgagtcctgg  27600
ggtcctggcc tttgttcagt aaatacgcac taggcgccta caatgtgtgc accaatgtgt  27660
gaggcgtcag gttctctcca gggtcagttg gttttaagaa aggttttggc ttctgatatg  27720
ttttatctct acagaacagt agctcttaac ctttcttatg ggttaggatt accttcgaga  27780
atctgactac agctctagac ctgttcccta aagaaaacta agttcacagg gacacacagg  27840
atggggctca tggagcagct gaagccagac cccaggttaa tagcctttac attaaaatgt  27900
ttttctacct accactaata tgcattcttt agtaagcggt ctcaatatac accgattctt  27960
ccttaactct gtttatgaag tattcagcat cctccctgcc cccttcagca tcctccctgc  28020
ccctgagcac aggatccaat ggcgtgagga ccacaggcct gggcagctgc tggggcatac  28080
aggcatctct tagtggctga gagactgggc cctggctcta tgttggctcc taacttgctg  28140
ccatttaaag gaaatcttag cctcccatcc gtaaaatcga gaaaataaga cttgtcctac  28200
acagctcatg aaatagtaat gaaattcaca ttagagaaga gatggaaaaa cactttgaac  28260
aaaaagcatt ttgctcttat aaaagcacag cctcttttga gaggcccttt gctccccatt  28320
tctccttctt cagacccccc cagactagga gaaggtctgt ctcatggagt gaccttttgg  28380
ctgcctctag attccaagct cagttttgct ttcattaacc acagatactg ggacggacag  28440
aaaaagacct agtttctgtt gagccaaaga gtctcataac ttgtctgttc acatacccaa  28500
gagcccaccc tctagttgag acactcagtt ccctctcatt ctgggagact gcatgtctct  28560
gtgacctcct ggtagagacc gtttgacatg tcccccaacc ccccagtgat tgagtctgaa  28620
```

ttctccactg atgacgcatt tcctagcact cagggtgtcc cctcctggtt gccccctcac 28680
cactgaagcc cgcttcctcc cttttcattt gatgcttaac aactgtcagt ttgcaagaaa 28740
catgcttcaa atccacattc tcccagttgc ctagcaacaa cttccctccc ggataaatgt 28800
gggtttcctg tagctcagcc caggactgaa cacagcagca cacacttctg tccactgctt 28860
caactgcttt tcacctctgg tctgcatgcc ttcaagactg cagctcatcc ctcccttcag 28920
aaccttccat agcctgcaga ggccatgtct gccccaaaaa gacacattga acctgaggct 28980
acttatttac ccttgtgtta ggtatatcct caacttagaa attaatactg tttccagatt 29040
gtcttctttg aatcacagaa agtaaaacaa caaaacattc aatgcttaag acatttcatg 29100
tgcggttggg tgacatctgt ttgatgaaca catttgatcc aaagcatcag aaatactatg 29160
ccaacaagac tttttaggag gtgataaaca tgtctgttct accttaagaa aaaaatatta 29220
cacagtccca agggagagac atggttttga tcccagacaa cccaagcaga gacctcttag 29280
ggccggaatc atcttggctg ctgcctagga ccttatatca atttcttaag cacaggatca 29340
aggcctaaag gccccttaga ctgacctcag ttagtagagg cagatccctt cacagcctta 29400
tcttccttag aggtctagtc tgaccttgaa cttcggctgg cagtgctgtc agttgtgatg 29460
tgtgacatgg aagagttatt tgttacttgg aaaattaaga gaacttattt ggcataggaa 29520
attgtgtgtg tgtgtgtgtg tgtgtgtgtg tgtgtgtgtg tgtgtgtgtg agatgatgtt 29580
tgccatttg atctgtgact tttttttcca gaaatagttt ctcagttcca ttccaactaa 29640
acttacagtc tcttccggtt ctttgacaga aacaattcat gtgaatttga acagataata 29700
gggaaggggg aaccaaaaga agaggagagc cctgggaaag ttattttata atttatggca 29760
acctcagtca ggcaactgtg aacaggtaca tatggagggc tccctcggga ctaggcagta 29820
ttcagagatg taaggtgtga ggaccggacc ctcatcattt accattccca ctaaaaagag 29880
ctgggaagga aattgtagct gtagcaccag gcacgtaact ggagcttagt aactatttgg 29940
tgaaggaata ttattaaatt attaacaaga tggaaaaaag ggtattaacc acacaaaaat 30000
acatctcaag ctattgtttc tctgttccct ttcccccaaa ttcctagtct tgctcttatc 30060
tggctgtctc tctagtcact ctttcttgct gactctcttc acgttccttt ctccacctgg 30120
aattcctggg ccctcccctt ttactgacag acactgtcct cactctcaca gtcatcagtt 30180
tgtctcttta caaacctcag ctcaagtgtc acttccccgt ccccaggtga aactgactgc 30240
tccctccctg taagtcacca tgatgactgc tatatatagc cctcatggaa cctaaaacct 30300
caacagacac agtctctttc ctactctgtt atagtttatt tactcattaa ttaccacaac 30360
acgtattatt gagcacctac tgtgtaccat gcccagaaga taaaagacaa acaaaataaa 30420
acctattcct atgcttaatg agtttacagt ctagtggaga gatagataca ttaaaaaata 30480
acagcaaacc aaaataaaag tggtaaataa atgcactgag aaagacagga atagctagga 30540
ggggcaccta atccctaggg aaggaaagct ggaagagcat ggtgatgggg gaagaaggct 30600
ttctggagaa ggtgaggtag tttgaaatga gttgactctg gccagtaggg gtagagtgag 30660
aatggggtga gacagggtgg gttggtcatt ttgatccatt agtcctcaaa gtgataggac 30720
tagtggctaa ggactgcagg ctttacagaa gcctacaaaa ctatttgaga tttgaagttt 30780
ttttttttt ttaattggct ccaaaagaaa atgaaaaaac tttagaatta taatgaatga 30840
atattaaatg aatatttaag gaaggtaatt ttattcaact tcattgttaa atttagttaa 30900
aacaagccct tgagtttcat tcaacactgt tttatcatac cgttgatgag agaaaacaaa 30960

-continued

```
actgattcct ggccagggcc actgtcagcg tggggtttgc acatctttcc catgtctgct  31020
tgggttagct ccaggtactc ctgtttcccc cacatcccca agatgtgccc attagtggaa  31080
acggtgtgtc tgcatgattc caacgtgagt gagtgtgggt gtgggagtga gtgcccctgc  31140
catgggaggg catcctgtcc aggttagatt cctaccttgt gccctgagct gctgggatgg  31200
aatccagcca cccatgactc tgaactgaaa taattgggtg aataattatc ttacttttta  31260
attaatcttt gaaaatgtat gtatagttca catgtatttc aatatttaat attagaagta  31320
ttttagtctt tattttgaag tttggtgatt tattgtaacc agaaacaagc tatagaaact  31380
taattttggg ccaagtgcag tggctcacac ctataatccc agcattttgg gaggccgagg  31440
cagacgcatc acttgaggtc cggagttcaa gatcagcctg gccaacatgg taaaaccctg  31500
tctctactaa aaaatacaaa aattagccag atgtggtggg cacctgtagt cccagctact  31560
tgggtggctg aagcaggaga atcacttgaa cccgggaggc ggagcagtga gcagagatcg  31620
tgccactgca ctcccaccta ggcgacagtg tgacactcca tctcaaaaaa aaaaaaaaat  31680
agaaaagaaa gaaacttaat tctggtttat atcaattagc ctgtggtaaa attggtttca  31740
ttatagccat ttcacttagt tgaagtttcc aataacctgt ggatgaatta agtgaggatt  31800
tactatattc ataaaatctt aaattccaaa gcctgtttgc agttcaggtt tttccacttt  31860
acaaacactt ctaagtattc acaatgattg cttaaaattc ataccagata aatcattaaa  31920
taagttgttc aaagtcaaat aatttcataa gtaaaaatta ggagctttta gaaaactata  31980
cctacataga cctagaccta tagatagaca gagatctgaa tagatatgga cacagatgct  32040
ttccaaagtg ttcatgtgat gtgtggtgga gtttcaagac cagagtgtgc ctggggcctg  32100
cagaagtaaa ggagagggga tggagagaag attgtccaca tggccatggg caatctccca  32160
cccacactca agtgaggaag acaggaaaca aattcagaaa gaagagaaaa taatcaaaac  32220
tgatgggagc ttgtgactga tttacttatg cgcagcctcc ctggagacat gagtgtggct  32280
gttccttagg ttgtgcctct gggctcctac cccctcttag atgccttcct attatctagg  32340
acctggttgc tttttgtctg catagcttct ttggattcca gtctttgatg ccagcttcct  32400
cctaaagtag cctttcagat gtcccttggt taccctctgc tatctaaggg ctcatcctac  32460
cccacactca ttcccagcac caatttctgg atctccaggc tggagattta gacaatggga  32520
tgggaagaac ccatgatggg tcccagacag aaagtggtgc cagccacaga aagggcacac  32580
aggcacagaa gttggtttgg ggtaagacga tgtggtcagt tcagaacacg ctggatctag  32640
gcagatgccc agcagacagt tggatatgta agtctgaagc tctggggaga ggtctaggtt  32700
ggaggtacag atttagaagt catcaacaaa aaggtagcag attaaatgat aaaggaaatg  32760
agactatccg gggagtgtgc agagtgagag gagcaaggga ggcccttggg aacctcagca  32820
cttcagggga aggtagaggt acagttgctg gtgggaaagg cagagaagta gcaaagcaaa  32880
ccaggcaaaa gcagtgtcac agacgaccag ggaggaaaag gacatgatca aaatgttgag  32940
aaaagcagag aggtttgaaa atacaagaag caaaaatgtc cactagactt aaaaaccagg  33000
agaaaactgg ggggttcttg ataaagcatc ttagtaggat ggtgagggta gaagccaggg  33060
aagtgttggt gaggaagtga agtcactgat tacggactat gcttaaaaga atgtgggaat  33120
gaagggtgga agagagaaat tagactgtag ctagggagac ataagcgatc agaggtagat  33180
tctttctctc ctgtgggaga atcttgcacg tatacacagc atgacgacag tgatggaagg  33240
gctggcgaag cctcagggag actcttggag gtaaacccca tgaagggagg actttgtttc  33300
attcactgcc gtgtccccag cacctggcac aatagcagac actcaataca tatttgtcaa  33360
```

-continued

```
atgtgggatt ttatcattta gaaactgcac ctggctgtga gtaacaaaag tcagagaaac  33420
cgtgggtttc atttttctcc ccaggcagag tctggagctg ggtcctccaa gaggggtttg  33480
gagcaccaca ggtttcctca agacccccag gctgccctgt gtttccctcc ttcatcccca  33540
gcatatgcct gtcatctggt gacctccaaa cacctgtgct gcctcctcca gcacatccat  33600
gttgcaggca gggaccaggc aaagggcaga ggggcctact tcaaaagacc atttccagaa  33660
accccatcct atgacttctc ctggtgtctt ggttaccatt gtgccatagg ctcaccctgt  33720
atgcatggga ggctgggcca ggcattatga cttttagcaa tattgcatag ataagcatca  33780
atctttgtca ctgtgacgaa gcctagtcac tcagtgctag gcaaggttaa tggaatgggt  33840
tggtgtgtgc attattcttg aggtctttct tatgcttcat gttatacatt tattaggacg  33900
tttaggcaac agggggataa aaatgaagag gagatgcatg ctatgatctg aatgtttgca  33960
tcctccccaa aattcatatg ttgaaatctt catccccaag atgatggcat taggaggtgg  34020
ggcctttcgg aggcaattag gtcatgactg ggattagtgc ccttgtaaaa ccccagaaag  34080
ccagcttgcc gcttccacca tatgaagaca cagagagaag atgccatcta cgaatcagga  34140
aatgagcccg caccatgcaa taaacctgct ggagccttga tcttagactt cccagctgcc  34200
agatctgtgg gaaatagatt tctgttgttt acccagctta tggtattttg ttgtagcagc  34260
cagagtgaac taagacagtg ctgatctcgt attcttggag ggaaccctta gtctttaggg  34320
aaagcaaagc caccatttgg ggcagggtgt tctccaagtg ctgccacata tgctgatgtg  34380
gttaaactgc aaactatggt aaaaatgtgg aggtctgtgg aattgtcaat caggaaaaag  34440
atataaaaag aagttaaagt cttcgtgctt ctggaaggat atgtgccaaa ttgttaacat  34500
tgattatcct tgggtagaga tgtggggaag tttgcagaga cagttttgcc ttgtacttta  34560
tataagtaaa cagctactac ttcgttgtct taaaaaaaaa aaacagccta tgtgctcttc  34620
atgtgactca gaactaccta ggcaatacga ttaattgaat tagtaaaatt gagtgattat  34680
gaattttcag gaagtcatta atttaccact tctttattac atccacttct aacaggactt  34740
caatataggg gaatttgact tcaagataaa aagaccaaat ttatttaccc ttttaaaaaa  34800
agacaactta aaagcagact tgtcttacag aaccttcctt agttggacat cgatgagtgt  34860
acagaaaatg caatggataa aaagcttggt gatacaaaga taaaaagtgg ggtcctgtcc  34920
ttaatgaaca taccatttca tggagtatca ggtgtataaa caattataat caatctgctt  34980
gttattctga taagatcatt tactcacaca tcaaatactg agtgcccacc acatgcccag  35040
catacctaga agtcatccag tatgatttct gtctacatgg agcatagagt cttacagggg  35100
agatagatga caagtaaaca ccagaataat taccaatggt gaagagcaca aggaaggaaa  35160
cagaactcct aaagagagcg tggctgggca ggggtgagca agaggcatag aaaaaggggc  35220
atctaaatct acttgggagg aagctgtttc tcacataggt catcatgtta ggaatgagac  35280
ttgagggatg agtagaagtt tgccaggcaa agaaggaatg ggggggaata gagagcagag  35340
ctaggggcag gagacagctg acgtgtgagc agacataaaa agaagtccac tgtggcagca  35400
gagaagcagg agagaaggca agtgagggag ccaggcacca gctcacagag gtcatgtgtg  35460
tcaaaacgta gtaatggcct tctcttctgg agacagtagg gagccatgga agatgtttga  35520
gcagggaaag cgacatgact ggattggcct gttgggtaac tcagaccaca atgcattgga  35580
agggaggggg ctagaggcaa ggggactggc aagaaggcca gtcctttttc tatgcctatt  35640
ttgatgaaat attctagaag ggaagtgaac aaaggtagtc ctagagagga agaacaaaac  35700
```

-continued

```
agataggata cttccttagt atttgctcat tcgacaattt atttttgcat atacactaaa  35760
acctttttta ttattaaaac gttttattgt aggaaaaaag tatgaaagta gagtgaataa  35820
taaaatgagc tcccatggat ctatcaccca gcttcaacta ttatcaatat ttggctgttc  35880
ttgttttaac tgttctccac cttttttttcc tgaagttttt ttgaagcaaa tcacagacaa  35940
catatcattt caccatatgt acttccctct gtatctctaa catgtaagaa cttgttttaa  36000
caaaatcacc atgctatgat catacccaac aaaatttatc ataatgtctt aataatacct  36060
aatacccatt tcatgtccac tttcccccaa ttgctacagc tggtttgttc agatcagaat  36120
caaaatccac ctgtggccat tttactgcta tgtctctcag gtctcttttc atctctaata  36180
atctcagggg agacaggagg gaggacgggc aggacttggg gctaacttgc ttatcgacac  36240
acagttttgc ctacttgctt cctcccttca cacccactct tcttctcagc cccacccttg  36300
tatggaaaaa acagaaatta aagtgctttg cccagcaccc actgaagcta tttcgaagga  36360
gtttgaagag tactcccggc aagacaaatg cctcggtcca gtgctcaggt caaagagggg  36420
agacgcttct cagtgatgtg gtgtcaatag cagcttagtt gttctttcct ctggaaaatt  36480
ctacccatct gctttgtaac tcccatacct aacaaggcct tttatttcac aattagaaaa  36540
taagcctgaa atatgaatgc tgcctgagtg tacctacatt tattctagag tttcagggtc  36600
aaaaagaata caaggacctc tgcatctaca gccaagagga gaggggcaaa gacacacagc  36660
tacaaatgag aacctggctg gtcaaagcct aactccacct gtttgtcagc actgatgcaa  36720
gttaggtcag cccaatgatc atttaggaga actgtgctgg caaataaaaa gcagaggctt  36780
ttggtcccca gatacttgga tgagaattac aagtccagct ggttaaaagg cacatgccca  36840
gtgctcactt cacacctact caggaagcac acttgagttg gaaaaccact gtctttacac  36900
ttagaactca gtcctacatg actcctctag gatcagtgat tccatcagtt ttgaaacatg  36960
aagcatgaag tcaaacagga catgaccttg gtttccagaa aaccagatgt tcacatcagt  37020
ctctggagct tggaggcagc acacctgggg acttccacat cccctgccga ggtggcaaaa  37080
gcaggagcag tggtgagttc acatgggctg gggtttcctg aacactgctg gcaattggag  37140
aatctgcaag ggaacttctc cgactcctac cagcagctgc tttaaaataa aggtgatgta  37200
gctggtcaaa tcctccatga gagagcagtg ttgaatggag gaagagacac aacctgtctg  37260
aaaatggcac aaaggaagaa agatgtaaac aatgacgaga agactgcagt gtctacaaag  37320
ctccgaggtg aacagatggg caccccaggc ccgcagcact tccttcagtc tctgccagct  37380
gcactctgtt ttccttcctc caggaatctt gtttggtgtc actaaaacag caattagaat  37440
cactttgaaa tagtgatagt atttaatata actatgaaac tatctgtgat tgacaagtgc  37500
agcaaggagt cttggaatga gagcctttat tttttcaatt aaataaaaga gttttttgtt  37560
tctaaaagta atcttgcaga aaagatcctg cgatcagaaa gaaggagggg gggagttttc  37620
aaacatatag gagatcagac tgtgcctatg tgtgtatata cctacaaaca tatatatatt  37680
taaaaaattg ttttactgtc aattacagct tcccacactc ctagacagcc gttctcaagg  37740
tatcaatctg agatcttggg gaggaatatt atctgatatg tcaccaagaa ttcaagaggt  37800
gagtagcctg atggtagtaa ttataatttc attatgtctt tccaccattt accccactta  37860
tgtcaaataa tttaattgta tttcaaacct gttcaaggaa aagtacattt gatctttcca  37920
tctagcaatt tcaaagcacc tgttcacatc ccaaattatc tgtgctctta agtaagaggc  37980
agaaagaaag gaaccaccct tctgatttca catcaaaaaa gaaatgccac tggcaataag  38040
caacttgcct ggtgtggcat aaatcatcag aagacttaca gttgaatcta agtcttttca  38100
```

gtactgaggt ggttcattat tctgttacag tcttaaaatt cacataaata tatactgcca 38160
ataataatag catacacctt tatagcttac aggcactctt cttctaagtg ttttacctat 38220
gttggcttat ttcatcataa agaaaacaat ggacttttgt gttgttttgt aaaaagatgc 38280
gcacatttta attaacatct gattgcacaa gtctcctccc atatagaaat ggattcttcc 38340
acgcaataga taagaggtgc tggggatatg atgatgaaca cacagatttg gtcatgaccc 38400
tgtgggaaag agagatggga aaaaaacaat tctcttcaag tgtgatgagt gttacgaaag 38460
ggagggaaaa gttgaaacag gtttttttcc aaacttttct ccctccatta ttcgcagctg 38520
acttgggctc caccaacctg gaaaactgca tggttggaat ctgtctttat aaaacgcatc 38580
tcaacctggg ccgagtatgc acactgatgt gggaaagtta gagaagagcc cattgtacta 38640
atgctcacct gctacagtgg gagtctctgt taaacagtct tttcttcata gcattaaaaa 38700
aatttatatc actacaataa ggttgaaatt gatagagaat gtacaaacaa tccccaaagt 38760
atatcaacac tcttagttct gagtagaagt tccagaaggc ttcttgactg tctagatagc 38820
aagtctaatc atttgtgaac taagttaaag cagaaggccc agtttatatg aattggtatt 38880
acaccatttg acctgagaac agccccttca tctctgagtg ctttgactaa atgagcaaca 38940
taataatagt aataacccct tacaagatgt cataagactc actgttgttg aagcaatttg 39000
agattttgac tttattgaag catagatggt gattataggc atgactcact gtgtggattc 39060
tccctgggct catcagtttc agagggcaag tgttggcatg tggacaaaga gagggatgac 39120
acgtaaacat ggcttattgc aatggggaaa tattttcagt ctcactgatt gaatcctaat 39180
ggttttataa attccccagt accactgaaa gcaaagcaag taatcaggtg tgttttagga 39240
ataaaagcag cattatttta atttcgtatt ttcccctaaa gcaaagccaa atggcattat 39300
gggagccaag ctactggcag ctccaccagc cttctcctga gttctcggca ttacagatct 39360
accctcaaag gatgaggcca gcaagcacca cagggtgccc acatggagaa gagaaggcca 39420
ccaacctcct cttagctggc acagaattga aaaagtgttt ttccaggaat ggatacttca 39480
tctgttctgt atttgctaga attttaaaac gcacacacag acacacacag gcgtgcacac 39540
acacacgcac acacacacga gaaaaccaca aaccacacat ttcaaggaaa tggaagaatt 39600
cattggtaaa attaagctaa taagattatt ttccaaatat aagaaactaa attttagact 39660
atttagccaa agaaatttgc tctgatcttg cttttctaca acagaatcat tccccaatca 39720
ttttatttcc ctctttttct ccccagtatc cccatcttgg tgggacaaca gaacccaaga 39780
actggcttaa cagtaaaata ttttctgcat ttgcccaagg acacattccc aacgaattca 39840
aataaaggag actagaagaa gagaggctat actacagtgc tctaggggtc actctgtgat 39900
ttgttgttgt tgttgttgtt gttttgagac ggagtattgc tcagtcgccc aggctggagt 39960
gcagtggcac gatgtctact cactgtaagc tctgcccccc aggttcacgc cattctcctg 40020
cctcagcctc ccgaatagct gggagtacag gggcccgcca ccatgtccgg ctaatttttt 40080
tgtattttta atagagacgg ggtttcacca tgttcgccag gatggtctcg atctcctgac 40140
ctcgtgatcc gcccgcctcg gcctcccaaa gtgctaggat tacaggcatg agccactgcg 40200
cccggccact ctgtgatttt ctttaaggct catcctagta ttctcctagt ccctaagtag 40260
atggcagtag gttttgtttt ttgtttttcg cagctggatt aaggattgct gagaatatat 40320
ggatgttttc ttttaaatgt ggaagtcaaa ccaaacgttg gagcattggc ctcacagcag 40380
attatgactc tagctgcctt aaaataacct gaagactttg ccttgcccta gtttatccat 40440

-continued

```
cggccgagta tgcaggactt gctgtgggtg accaggcccc tcatgcagaa tggtggtcca  40500
gagaccttta caaagctgat gggcatcctg tctgacctcc tgtgtggcta ccccgaggga  40560
ggtggctctc gggtgctctc cttcaactgg tatgaagaca ataactataa ggcctttctg  40620
gggattgact ccacaaggaa ggatcctatc tattcttatg acagaagaac aagtaagttt  40680
tctgagtcct gcttataaat tggcctctca tgttggttaa gttgatggtt taacacttct  40740
aggtgaaacc aaacctgggg ttgcatctgt cttgtcttgc tgagtggcct taggtaaaga  40800
gacttctccc agaaagtcca cttccccttg cagaaagggg gcattgctta taagcaattc  40860
tggacatgaa ccacagaaag aactgaggcc cacttggaaa gggaacagag gggccatttc  40920
ccactgatgt aattgaacta gggctaagtt caagaggaag agaatgatcc gcaaggaagc  40980
aacccagagt tccaggtgaa gctcaggtca gaagggccct ggcaagtaaa cacggctgtg  41040
ggatgctttt acaaacacaa tatcgtgaaa atctatgtgt gtagtactga attacattcc  41100
aaatggcaaa ttcctggcaa atcatcttcc ccacctttca ctattttttt ttttttggtc  41160
ttctatgggg taaaggagga tggggtgggg aagaaatgta actggctgcc cctctagtta  41220
aaaactgaaa agaggcagca agggacatgc caaaagtagt tggactctaa gatagctaca  41280
cacaacaaag cagctaagca gctaattgaa gggaaattac tgaggctcaa gctgagattc  41340
caagcggggg ccttgtttgg cctctcagtc cctttcatct gagaaaggcc tcagttccta  41400
gcagtaatca gaggcaggct tctcagcctc cttctcctaa agcagaataa accacagggc  41460
aagtcgcatc ctttgtttct ctgatgaggc cattactgag agtcactgtg gcattttgct  41520
actaatgatg agcttgttat tggtggggta cagcctatta atttaggtta ttcatcaaat  41580
cctccagcat ggagttgaat gagacatgtg atgtggatac actaatgact atattgagtt  41640
acaagcaatg gggagtttct gtaaaatctg tcccttgtct cctggcagca tccttttgta  41700
atgcattgat ccagagcctg gagtcaaatc ctttaaccaa aatcgcttgg agggcggcaa  41760
agcctttgct gatgggaaaa atcctgtaca ctcctgattc acctgcagca cgaaggatac  41820
tgaagaatgt aagatcccag ctgggcttgc cttgtgtacc ctggacctcc cagaagtgtg  41880
tgtgtgtgtg tgtgtgtgtg agagagatgt gccttcctgg tagcacatct catgtttgtt  41940
ttttgctaag tggactcttg cgtttcctcc cccatccaca gtcatcactg gaatgctttg  42000
cttcagtgcc cctgcctggg ccctcccctc tctactgcag cctacaatga ggttttcttt  42060
cccattgctt gaattatatc cctaatggaa gggttcacaa ttctctgaat cctggctact  42120
cagataaaga cagggaggaa gggaggaagg gtattttctc ccagggggtc caaatctagc  42180
tttaacgagg gaggttctga gaaaataata tcatcaatat tacatggact tctgagatac  42240
taagaaatta gattctgtca gcccaggaag ttgggagatg gtgaattgtt ctgggaaata  42300
gcaatagact gagaaaataa aaacacttcc ttgaaaagcc tttccctaac actaagtgat  42360
aggggcagaa aagacacaac caaaagttct ctctcacttt tctctctgtt cgtgtctctg  42420
tcttgatctc tgtctggttt taggccaact caacttttga agaactggaa cacgttagga  42480
agttggtcaa agcctgggaa gaagtagggc cccagatctg gtacttcttt gacaacagca  42540
cacagatgaa catgatcaga gtaagggggg ttggaggatg gggaggggag gggaggagga  42600
agcggtgggg gcaagaaagt tccacttgtt tccttttccc aggaaagagt taatcgctat  42660
tggagttaga tcaaaataca acaagcaggc cccaaaggcc ttcattccaa gcagtcacca  42720
agtggggtca ctgactttgg atgagaaata tgtttcttga attctgggag aagtctaaaa  42780
gctgccacaa gaccagtggc ttcctggagt ttcctacttt tatgaattca ctcaagggcc  42840
```

```
tcaaattcaa agaggcatct ccccaagggg ccagctctgt aactccaaag atggtggaat  42900
gtgtttgtct ggtctcattt tcagctttgc aaaatgaaga caagagttct atatatcagg  42960
gacactcaaa agaaaacaaa aatatccata agcaaaagaa agctttttat acaccatatt  43020
caatgacccc catctggccc ctcctttgcc cctacacatc ttccctctat tctagagacc  43080
catggacttg gggaaatggg atatagatag gtatgtttca tagtggaaca agctcaccag  43140
ctcttcaggg agccttagca tctctatcct caatcactaa aaattagaaa tggctgaaga  43200
acaagaccaa agatcctatg gaatttctaa gcagagcagt gactgtattt cttcttccca  43260
aggataccct ggggaaccca acagtaaaag actttttgaa taggcagctt ggtgaagaag  43320
gtattactgc tgaagccatc ctaaacttcc tctacaaggg ccctcgggaa agccaggctg  43380
acgacatggc caacttcgac tggagggaca tatttaacat cactgatcgc accctccgcc  43440
tggtcaatca atacctggag gtaaggggct gcaagcccca cagtgggccc cttgaagata  43500
gccccatgag tggggccaga gctcccttag caagtcaagt ggtcttgaat ttaagctttc  43560
attttcccca ctgaagaaac aagaatccct acatcccctg tacagttctc attctctaac  43620
agcttatcca tacttaaaac ttatctatgc tgaaaacggt ttcctcttca catctcctac  43680
ttctcatgct gggcacctcc tcctgtagcc ccctttaagc atctgtgtct gtcctcaacc  43740
ctcttctgtc tgacattgct tgagtggcca tctatggcca gtgtcccctc aaccccacag  43800
tccattgctt gctggacact cctgccctca agttctacaa gcacatcagc ctcaacatgt  43860
cccctccaaa aactgtatgt tctccttgcc catagaacat atccttctcc tatatttcct  43920
atcctaatta acgtcctcag catttgcccg aattctcaag tgagggattt cagggtcatc  43980
cctaattttc cttcttcacc ctccacacag tagctgtcac ttactgagtg ttactttatg  44040
ccaagtactg tgccaactgc ttttacacac atatgcttca tttaattctc acagctccat  44100
gaggcttgca ccattatcat tgccaatttg cagatgagaa gccagggctt aaagaggtta  44160
aataagatcc cacgcatgac cattaagagg agcgaacagg atccagctct gggggtgcct  44220
gagttcagag cctgcctttc tgatttctct taccaagctt tgtctcctct ccctcctaaa  44280
tatctctcaa ctctgcctct tgcattccag gctctctgag gactagaggc cttgtcatct  44340
ctgcgccagc ccattccaag ggcttccttc ctggaatcca gggtccagcc tctgttggcc  44400
caggcatttc tctacactgg caccagagtt acattccgca cacctgctta cgttgctctc  44460
tcacttaaaa tcttaatgac tcgaccccca aataacacag gtcccttcca aatctgtcct  44520
accccacctt cccagccctt gctcaactct gctacctggc cctttcacgc ctacaggcat  44580
tcccattcca tgacctcttg ggattctacc ctttgcaaat gctgttttca ttgcccattt  44640
attagagcgc ttttggtcac aagctttttg cttaaccaaa aagaaagcat ttattggtgg  44700
acataaataa tgaagttcag gaggatccaa gagttggaag ccaccatgag acccctgtgt  44760
ccttccacct cacttttcta ctcgcctctg ctcagcttca tctctggcca ggccctctcc  44820
tctgctgatg ccctagctgc ttacagccct tagcagtcat ctatacacca aaaatccctt  44880
tcccatagca gaagcaatgc tcctagagag tttccctgtt ggtctggctc ctgtacccac  44940
ccctgtgtac tctgattggg aggcctgggt cagctgccca ccatggggcc atttctatga  45000
gcaggattac tgtgaagtgg aggaagatgt ttccccaaaa gaagaaacac aaggtagaaa  45060
agtgtatgtc caccaatgcc tgaaatgact gtccctttcc tcatctgctg agcttctact  45120
cattcattct ttgagactca gcactcagct cttaaatgtc acttctgctt tgatggaggt  45180
```

-continued ttagtcattc actcctctgt gcttcctggc cctctcttca cacctctctc agacccctct 45240
cccagataga ttagagttgg ctgttgacat gtccatctct ggctgggcag ctaaactgga 45300
gttatttaga atcagggagc acatgtcagt cattttcaaa ttctcaacct catactccca 45360
gtaaatgact ccatctaagg gtggaccact cttgcccatg ggccaggtct gggtctgtgt 45420
catctagaac tgttggaagg taggggcttc tgtgagcagt aggagaggga ataaactcga 45480
gggccctcgg gagcatgccc tcttgtctca gacttgtgag tcctgaggat aacaaactag 45540
tgaagaaaag cctcgttcta tctgtcacct ggtgctcttg aggactttct gttgccctgg 45600
tgccaccaca attttccaga gtgtgtgacc ctcgctctcc aaactctgga agtggcagcc 45660
gaggctcccc agtggccttt cagaaggtgc cagtcatgac agcagcacca aactgcaggc 45720
aactactaag cgatcaccaa cttgtctgaa gataagaatg accttgaatg cattttataa 45780
aacaggattt ttttttaat ttttagattt tctttcttta ttttacctta agttctggga 45840
tacaagtgca gaatgtgtag gtttgttaca taggtatatg tgtgccatgg tggtttgctg 45900
cacttgtcaa cccatcatct aggttttaag ccccacatgc attagctatt tgtcctaatg 45960
ctctccctcg cctcgcccct accccacccc aacaggctcc ggtgtgtgat gttcccctcc 46020
ctgtgtccat gtgttctcat tgttcagctt ccacttacaa gtgagaacat gtggtgttta 46080
gttttctgtt cctgtgttag tttgctgagg atgatggctt ccagcttctt ccatgtccct 46140
gcaaaggaca tgatctcatt ccttttatg gctgcatagt attctatggt gtatatgtac 46200
catattttcc ttatccagcc tatcactgat gggcatttgg attggttcca tgtctttgca 46260
attgtaaaca tacatgtgca tgtattttta tagtagaatg atttatattc ctttggttat 46320
atacccagta atgggattgc ctggtcaaat tgtatttctg gttctagatc cttgaggaat 46380
cacactatct tccacaatgg ttgaactaat ttacattccc accaacagtg taaaagcctt 46440
cctatttctc aacagcctca ccagcatcta ttgtttcttg acattttaat aatcaccatt 46500
ctgactggca tgagatgata gatacccatt tgtcagatgg gtagattaca aaaattttct 46560
ctcattctgc aggttgcctg ttcacgctaa tgatagtttc ttttgctgtg cagaagctct 46620
ttagcctaat tagatccatt tttcaatttt ggcttttgtt gcaattgctt ttggtgtttt 46680
agtcatgaag tctttgccca tgcgtatgtc ctgagtggta ttgcctaggc tttcttctag 46740
ttttcatgat tttagatttt acatttaagt ctttaatcca gcttgagtta atttttgtat 46800
aaggtgtaag gaagggatcc agtttaagtt ttctacatat ggctagccag ttttcccaac 46860
accatttatt aaatagggaa tcctttcccc attgcttgtg tgtgtcaggt ttggcaaaga 46920
tcaggtggtt gtagatgtgt ggtgctattt ctgaagcctc tgttctgttc cattggtcta 46980
tgtgtctgtt tacaaaacag attcttaagc atcaacccag atcgactggc tcagaatttc 47040
cagggaagag gcctggttat ctgcatgttt acagacctat tagatttgtg ggacctgcag 47100
ttcccttgta cagttagtta ctcaattaac atctccctcc tctcatggtg cctctacctg 47160
ctaagccctt attcccagcc aggcccacca ccatccaccc actgctgtta taacataagc 47220
aggacctgtg cgaggggggtg tggacggagg agagaggctc tgttgcttca tttgtgcagc 47280
atggagttca gtggttctca caatgttttt gcaaagtata taaagaatac tccttgtcta 47340
cttgacattc gtatcgtgac ataaatgtct tgttttccag aaggattatt ttttccaagc 47400
agcttgttcc taatgcagcc ccaggcacca aacagatact taaaatatat taattgctta 47460
aatggttaag aattcagtct ctggacccac actgcctggg ttcaaattcc tattatctgt 47520
gcccagtttc caagtctata aaatagggat attaatagca cttacctaat aggctcgtta 47580

-continued

```
tgagaattaa atgagctaat tcatgcaaag cactgacata tagtaagcac ttaataaata  47640
ttagcttttt aacaaaatac aagccaaaaa acactgctta ggagaggaaa tgatgttagt  47700
gcctcctgta aataggccca gcctccaagc tggtgctcct ctaggaatca caacgctgca  47760
aatcacatcc tccggggccg ccaggacttc acgagggcct ctgagcagag gggtatgatg  47820
ggagcagaag cccagcagct gtgatgatgt ggtttctgat cttcctgccc ttggggtggg  47880
ggaggaggaa agcaaggggc aatgaacaga aaggagaaga tagcggggag gaaatgtgtg  47940
aggaagaaac acatcactgt ggcttgtcct ggatttttct gcttctgttc tcgtgttttg  48000
ggaagtctgg aggagacttg aaaatcattc atgtccccac cctgaggatg gcttagtagc  48060
agagaggcca tgaaaactct ttgctgatgg ctctgaaagc aaggatgttg cttcactggg  48120
ctgctgaagg cctgcctggg ggttctgagc agagagtaca ggcccctccc aggagggcgg  48180
cctaaccacc atgctggcat ttctgtggac catggtctgc tgtctcagac cccctccaca  48240
atagggtctg caatctcatt caccccataa atacattctg tctttcctct gatcccctcc  48300
cattagcagg gggaaataaa tggaagtcag acggcccagt tagaaggcag gcagtggagt  48360
aggaaaatag atgatggtgg tttggggagc ctcacatcac tcatggggag acattcattc  48420
ccatgggcct tccaatcacc cttttctcca aatctaagga cacaggacaa atgggtcctc  48480
atacaggcaa atatcttaaa ctggtatgtg tattcattta tagttctaat ttatatgtgt  48540
ctttattcac atatattttg cttctggaga aaagctcaat tagaaaaatt aatacattat  48600
tcttcttatt gcccttcagc taaaacaagc atacacaccc ctcccctttg gatttttttgt  48660
ttagcaaaag gttaggcctg gcacagatga aatactattc agagttcaca gtgtattttc  48720
atttcataat atatttgatt ttcaggtctt gaatttcaca tcaggaagct gatataggaa  48780
gctgaattca gccagatttt aatacgaaaa tacctctgat caaggcataa aattgtactt  48840
taaccagtaa ccactgtatt tctctaagct gtgaaaaaac atgcattcat taactgcttt  48900
ttcctctgct gtcaacacag tcaatacatg tgcataactc cttattgtct acatggtgat  48960
tatcttgctg atgaattctc aaaggccaga gatttggact attttttctc tgtaaccttg  49020
catgttcctg gccacatgcc accaccaccc aaacagaatg tacgcaggga atgtattttt  49080
caggataacc taagaaaaaa taggattaag aagataaagc tgctgatcat gtaatgtact  49140
ttagactcag atatataaat atttgtgaat tatctgtcct atttctttct tctattaatt  49200
cattgactct agatgtgcat tggaaggcta gggagaaatc aggggatcgt gagaaagagc  49260
acagaagtct gcatcacaca aacaatatta tttcaagagc catgaactag atcctaagca  49320
actcataggc aatgacctca tttcatacct ctagtctcta agaaacatat aactggcctg  49380
aggaaggaaa atgtgggcaa ggggtagacc ggggtcatgg gtggaggtcc aaatagtaat  49440
caatggagct catagggtgg actgatattg aagctgctat gagccagcca catgctgggc  49500
actgttacat gtcatctcat gcaatactcc caattacctg cctagtaagc ataattgtca  49560
ttttatagaa ttaaaaacag actcaaagag gttgacagtc taatgtaaca caacagctaa  49620
atgggggatc tggaattata atccagagct gcctggctct gatgagaaag ctctttctgc  49680
tgtcatatgc agcccacatt aatagggggc tcagaaagta ttctctggat aaattatata  49740
atgaatccaa tgaaggaaga cattatttta taatatgcag cataataggc actattatga  49800
ttggattttc ctgcttgaaa gtagctagat tagagtagga aaccaaaaag atgtgaattc  49860
attcagtcat tcatgcattt gcatggattg agctacctac atttgaataa atgctgttaa  49920
```

-continued

```
tccctgattc cttggaagct cacattggag agataagcat gtcattaaat aatgccataa  49980
tagtggtatc tcagaggact agcagaacat aattcaatct gacagagtag aaacagattg  50040
tacaaatcca attcaaaaca tcataaatcc tctaagcact gtcaattctt cctccaaatt  50100
atctctgaaa ttcctccttc tttcccattt atggcctcca tttacagaag cgtgtactgt  50160
ctctcttagc tgtttgccag gccgccagtc tcttgctgtt cagctctcaa ctgcttccag  50220
caagatcttt ctaaaatccc aggcttgcca agacttagcg cccacagctc cacagtgact  50280
cctcattgct gttaaggtaa aggccttccc agtctagccc ttcatgcttc ttccatgttc  50340
tatgggactg ccccaggctt cccacctggt accactgagc ctttccatcc ttcccccact  50400
cgactgccag gtcaacaccc acacccacgc ttcaggactc aggtcctatg tttcgggcct  50460
tcttctgtgc accattccct tccctgtagc ccttgatcat gatttgttta tacgcctccg  50520
caccttcatg gccctgaacc cctcaagggc cgaaactgcc ttacttttct ttttgacttc  50580
ccaacttacc ttagtggagc tgtagtcaca tagaatagac gctcataaat gcttctctgg  50640
gctgtaaagg ttgaattttc cagctaagca aggaagaaag acaatttcag gcaggaggaa  50700
gggcataagc aaagtgcaga gatgtgaagc tcaagagaaa tggatgggct gggcagaggt  50760
gtggctgcag catcagggga gaagaagtag tgcctggagt cagcaggcac ggcttgcaaa  50820
agcttcacct ataggtgaaa ggacaccatc tcttgcacca ataggctctg tgattggagg  50880
caactttgct gttttactgc cagaaaactg aggatgataa cccaaactgc agttcaagtg  50940
gcattcactg gtgtggctga aatgggtgtt tgtggccaga atgtggtctg attggtcagt  51000
gcccagctct gttgattagc agatgttttg aatatagtag catccatgtg cccaagttgt  51060
tgggatgatt caacaagaaa ctttaagagc tcaagtgccc tgcagttgtc agccaggtga  51120
ttctcttcct ttggacccag ttagacgcag gcattacctc gtggctttgc cccagtgtga  51180
atctttgtcc tccaacttga tctttttatt tgtttcatta ttgtatttaa gttgtttatt  51240
ttagagacag acatttttta acagctgtgc atttcctgtc cctttgtttt ccagtcgtca  51300
tgtgtttcct tactctctgt gggtgaacgt ttcagatgtc tgtttgcggt gcccagcgtg  51360
caagataaaa tttattgcag tgccttcggc ctctaactca ccattccaac caattcagat  51420
agcccaaggc tgttttatcc agtggatttt tccatgtagt gggaaataaa tcttgaatgt  51480
tactgtttag attagccagg aaactcattc tgggatgttt gcccacatcc attggcattt  51540
ctcaaaagga accccaggtg tctaccttga caccagcagg gccacttgag ccctccgctg  51600
gcattcatcg cccgctttgt tctcagcctg agtttaggag ttacagatgt gagaggcggg  51660
attatacagc caacatctct aagcgggcag tggctccctt accctcgaag acctcactcc  51720
tagcacgtcc tggatgtatt cgtcaaaata tgtcctctta tgccacgtca gcacagggtt  51780
gctccccact ttgatcatca agtttaaaca aaaggaaaga ttttctttct ttctctgcct  51840
ctactggaca tcatttccca cctaacagat aatttaatgt atctgttact gaatgtgttt  51900
gaattacaga cagagaggtc acagttaaag aaggaagcct gctgctactg cagcttgtcc  51960
tcccaaggag gtgtttgatt tagctgtgta aacaaatgac tgcattctcc agaggtcctg  52020
aacacagctg cctgcgctgg agagggctca aacctcttcc gccagggtga actctgcttc  52080
ctggtgagtg ccagcaaaac aaccaacaaa gagctgtagg acttgtgtgg acttcaaatg  52140
gtggtggtcc tgccacttgg gctcagccac agcagttagg aaactaaagg ggaggaggaa  52200
agccctttcc ttgctttatt gtcattggct gtcatagggc attacaatgg ttctctttga  52260
gattctgagc tccggctata acatttgccc agaatctgcc tctgaggcct taagacactg  52320
```

tgtttttatt cagcaaagat gccctttgac tccttttccc actagtggtg ctaggtttga 52380
gcaccttaca ctggcccctt acaatagcca gttcttgtct acctacattc ttccctaaca 52440
ttcatgattg catagttact cttagtgtag aagcagacag cttttacaca tagactccat 52500
ggccgtagcc tcatagaacc tactatattc taacttgcaa gctaatcaga ccaaatatat 52560
caaaatcaaa aacctctgct gagagtttat tcattcatct ctgtctccca aacgtactta 52620
tgtacatacg tgcactaata tacatgtcca ttagccaaga ttttgatttc agggatcaaa 52680
gcaagtacca atagggaatg aggtcacttg ctgcatggca ggtggcttcc ccatgagaat 52740
gcaaggccac ctcatgactc atacttcaga gggtgaccca ggaacttctg attcatgtcc 52800
aaagcagctt ctacaattgc tctaccttga tctagggaag atgtggggag gatgacattc 52860
gggattagct ttataaggcc ttcctgtggg cagagttgtc tgactttcac ctagtgatca 52920
acaagcagct agcaagcatc agtgtgtgag gccccacgcc ctctcagctc ccctactgcc 52980
cacctgggac atgggctttg gcatctgtcc atagcattgt tctaaccaaa tgaggtgtta 53040
tggatcagct caggatggga tatgttccca gacatattat ttaaagaaaa tagctccctt 53100
cctcccctga taaacagctg ccatggctaa aaggtaacct ggctggggct taaaagtctg 53160
ttgactttca agatattttg caaaaacagt cataaaaatg gtatttatca gatcctaact 53220
atttgtgaga cggtttggta taccatagtg gttaaaaaca caggctcttt ccagaggagg 53280
tttactttgc ttagtcgtgt ctcctaagtg aacttggacc tcataaggtt gttgtgagaa 53340
tgaaatgggt gaatatgagt aaagtccttg gaccagtttt ggccgtatag taagccttca 53400
gcaagcatct gcttttattc ctacagggag gcaattgtaa gcccttcaca aacagcgtct 53460
aatgtgatcc ttagaacaaa cctatgagat agggcatatc tcaattttgt aggtagggaa 53520
acagaagcca cacaattagg aaatggcaac agatctgtta gactcttaaa cactatgcta 53580
caccaatttg caaggcaagg aagacaaagc acctttgaaa atgggtcaga tgttttaggg 53640
taaatgaacg tttgagaatc ttttaagttt tttttccccc agagattatc aaggtatcat 53700
tgtaggggga tgcatcagga aacatgacta tgaatcagct gcctgataaa ccagccagga 53760
tggagcccac gtcatcacag cagtcagcaa tgccactgaa aaacatcagc tgcttattcc 53820
cgtatagatt tccccttaag acatgaaaag ggagttcaaa gagaatgggc cagatatctc 53880
tgagagtcat attactaaaa tatatttatt tttactagct tttttgtttt aagaggtata 53940
ctgtcattag cactgtagca aaaattcacg ttttattaat ttctcctagt ttatcatgtg 54000
attctagggt aggatgcaga gttatattca aaatacacaa atcaactcaa ctcagtaaac 54060
atatatcgag gccctatcat gacaaaatgc tattctagag accacggcga acaagccacg 54120
gccccagcct caaagaatgt actatctttg gaactgtgct ggccaataca gtaaccagca 54180
gccacgcagg gctatttaaa tttaaattaa ttaaaagtaa aaacacaatg cctcagatgc 54240
attagccaca ttttaagtgt tcaatagata tttgtggctc ctgcctgcca tattggacag 54300
ggcagatata gaacaattcc atcactgcag aaagttctac tgaacaatgc tgctctggag 54360
cagaagatct tcttgttcag ggatgttaca ccccccgcttg tggctagagt gtggcttatc 54420
ctcagagcaa ggatagggga accatggcac tctgcaggct cagcactgaa gacacggatg 54480
caggctctgc ttctgaccta gattgacctt gggcaaggcc ctttgctcct ctgatcccaa 54540
tttcttcacc agccaagtaa gaacatcaga ccacaagccc tctagggctc tgtccaaatg 54600
ccccatgact gagtgaactg gtagaacatt ctatgtgtgt gtcacaacat gaagagcaaa 54660
gactttcatc tccccaaata attttgtttt tcgttttagg aattaaattt cagattcact 54720
ctaattgcca atactaaaat tctctatatg cagttctaaa cttgacaaac caataaaaaa 54780
agattatttg actacttatc tttgtacaac attgaggtct ccctaaagca aatttaaatg 54840
catattttaa aaatgtattc tagcagttca gttcagaagc cccctggccc aagcatcaca 54900
ctgtcaatcc tttgtcctca agcagcatgg ttgggtgggt taagtactga caaacactgg 54960
gtgtcaggcc catggtcagg gactgtgcta acagtctaca tattagatgc cacctacccc 55020
caccctcaac agacccaaac tatttatcca atagcaaacc ttgcattatt tctgtccaga 55080
agaaacaaac atttattgac aacttttggt gtgtgacctg tttaagtcct acatctcatt 55140
taaggactgg tcaatgttag gctaggcaat gcctgtttgt gagagaatca ctgcctaaag 55200
aaaattctcc atttccctta gctctatggt gggtgactac acatactggt atttcttaaa 55260
gaaataccaa ttccatttcc ttttaacata attattaata tctcattagc atggtgtcac 55320
tgaagcctgg gcccaaagaa ataccaattc catatcattt taagatcatt attaatatct 55380
catcagcgtg gtgtcactta agcctgggcc ctttagaatt tttcatgtac ctgtgttcct 55440
ctgcccatat cagctggaac actaatagtt ttcttccttt ttatctagaa gactgagaac 55500
attacatggg acctgccccc agggcatgga ggctgaggtg ggacagttta gttcaggagg 55560
cccaagaagt gttgggtgtg cagccccttg ttcaaacaca gcctctgaat cgccagaggc 55620
ttccggtgca tactctgagg cgcaggtggg actcgggagt gagaggtttc ggcgaatgaa 55680
ttgggattgc ctacttcttc ccagtgcagt ggagcttggt tctgtggtca ggtccttacg 55740
ccctgtctgc ctttctcgtt tctttatttc tcgggtagta gttgtggaat caaatgacct 55800
ggggtttgat acctactcta ccacgcctct gggggagtca ctcagactcg ttgaacctaa 55860
gttccggggc tgccaagtga ggataagtag taattgctga tccacctact tgacaagata 55920
gtagtgaggg ccctgagcgc caggctgtgg atccagcctt tcccacggtt cctggtgtgg 55980
caggaagaac tctaggcctg aaggtgaaat tggggaggga gtcccagctc tgccactgtc 56040
tctctgggtg acctcaggca ggtctcctca aaaaaataag atactttata aagctcagtt 56100
tcctcttcag taaaatgagg attccaggta actcacagat agtttgtggg gatgaatctg 56160
ttccttaaag cctgcagtac atcaataacc cagtcttcct gcttgctttc ccccctctcc 56220
actaccagtg atcatagtct gatcccatag gtgatatccc agctcaaaac cctacattag 56280
cttctgtggc tgtttaaggc ctgcccagaa ctcccctggt cttagcactg aaagcacgtg 56340
tccggggaag ccctgcattg gtcgttcata ctactgagtc ccgcagggca aaccgtccgg 56400
tcccaccctc ctttctagtg ctgctgtcac actcacctcc cttcacccta cactcccttc 56460
tgtgccttgc aattacctag ggagtttttt acaagatatg gatgccctgg ccctgccact 56520
agagattctg atttaattgc ttggggtagg gcctggcata ggtatctttt aaagctccgc 56580
agtggttcta aagcacagcc acagatggga accactgatc tattcttgta ggtccccaga 56640
tacctcatgt gctgttccct gtgcctgagc tgacctttcc cccactttcc tctcctcggc 56700
taattcctgc ttatcctcct actcaggagg ctcttcctcc aggcagcctt ccctgatccc 56760
tccaggaaga cttagctgcg tccctccgct gggcttcccc aatacactgg gcttgctttc 56820
attagaacct gatccttcca cattatggtt gttggtttgc tccaatcctc tccctcatta 56880
gctctcaact ttctttcagg aagagatgtt tatctttcct tcttgtattc ctagagtcga 56940
ccaggctctg gcacattgca gattctcagt atgcattcag ggaacaactt aatcaagaca 57000
agaccatctg acttcttgtg agttacatgc taagaaagaa atgtcgacac caatagccct 57060

-continued

```
cacaatgata ggaacaggag gttaaagaaa aggaaataga tgcaaatagc aatataagtg  57120
ctttaacaaa tctatacagg aggacaacca tcatattcaa attttcaaac attcttagtt  57180
ctgctctttt gtgggtaatg gttttttttt ttcctcttcc aggagaagaa aagaggcata  57240
ttatagaaat tcctcctccc ccagcattac ttgtcacaga attgtaattg gaagtgattt  57300
ccctgactaa gttattttgg ctgtctgtta ttttctctct tcctccttgc tcttccctca  57360
gctggccatc ctgtgtgttt ggagagagcc agaaaggttc aaggctagga atgtttctct  57420
ctctctttaa agctctttaa tcgtcaggct ttctgatctt caaagcaggc tgtagccagt  57480
gtgaccccac tccctcgcct ccccatgctg gagagtaaaa gcctggagta tttttgtcat  57540
tttgaagact tgcatatttg gacagccttg gacatctgga aagtgtggtc ctcactagct  57600
ctgcagggat aagagcacgt cagcacttcc aagctctctg gcgcccctac atctggacac  57660
gttgaaaaat taacaccaga ctctggagtt aagcaaacat taagtttata ggcctccttg  57720
catttgacca tttcctggga cagcagccct tatcctgtga ctttctgtgt gtagagttga  57780
gtctttgcag ttggtcctcc tcacactctc tcaactttgt gactctctgc agtgcttggt  57840
cctggataag tttgaaagct acaatgatga aactcagctc acccaacgtg ccctctctct  57900
actggaggaa aacatgttct gggccggagt ggtattccct gacatgtatc cctggaccag  57960
ctctctacca ccccacgtga agtataagat ccgaatggac atagacgtgg tggagaaaac  58020
caataagatt aaagacaggt gatgtttcag gaagggctcg ctgcatttct ccaaagtcag  58080
tgggaaatta catttggtag agagaaaggg attgagactg gactcataaa tcaataaaat  58140
taagttaaat aagaaaaaat aagatatttt ataaagctca acaaagagtc cttgaatgaa  58200
agcaattaca gagtcacatt gtggctaata ttcaaaactg agatttaaac tgaggactag  58260
gaaatagaat tggatccttt tgaagcgttt aggagaaaga ttttaagaga atgagttccg  58320
agtcaccctg tggtcgggag gtgtgagtga gctatccaag cccgttccca tcctttgtcc  58380
ctctgtgtct tctcaggtat tgggattctg gtcccagagc tgatcccgtg gaagatttcc  58440
ggtacatctg gggcgggttt gcctatctgc aggacatggt tgaacagggg atcacaagga  58500
gccaggtgca ggcggaggct ccagttggaa tctacctcca gcagatgccc taccccctgct  58560
tcgtggacga ttcgtgagtc tgaagttcgc gatcctcctc catgacacgc taatgggggt  58620
gctggagtgg gctggggtgg gctgggggtg ccctcaaggc ttccatgtct ttagagagag  58680
ccccagggac cagagccaaa ttggagagca tggagctctg actgaggaac ctgcttctcc  58740
caagctccag gcaggcacag atgagtcagt gcagtggtgg gaaagggaaa agagttgatg  58800
ttgtagctgg aaaagggaag gggaaaatta aagcaaggaa agtgaggctg ggggagggga  58860
caaattcccc actatgtagt atgtttggta tgtggaaggg ttctggtcag aatgtttgcc  58920
caatgattgc cacatcagca ttcattttgg actctgtatg gccagtaggt ctggttcctg  58980
ggagccctgg aataatgcag ccccttccct aactaacatt tccatgatgt atgctcaatg  59040
acaaggcaga ggaatgtgtt ggatgagctc aggacctgcc tccctggaca ctcccatccc  59100
aggcctgtat atctgttgac caggaataag ccaagcaagc agcctactgt ttgactgaat  59160
atggatttgg ggggtggtag agaaagggcc ggggtggagg gttgggaggc tcatttgtca  59220
ttatagatgg ggtcagacac actaccaaaa cagcagcaga gatctacaat tgagttcacc  59280
taaaactcag tgtggacaca ggaaaccctc ttttaataac tgtccaatgg gttttccagc  59340
ctcagctcta cagaaaactt gagataacag tggccagtct gcagttagtt tgggttcgga  59400
```

-continued caataggcag agctgggaaa tggagccagg ggcgaaagcc caggtccact ttaggatcag 59460
gacgggagtg gctggtgggg aagtgaggtg ggtgtgggga ggcaataggg agctgggtca 59520
tttggtatgg gagagtcctc tggtggctag tcccagaagt gcatgcttta cgaacatatg 59580
cttctctccc tagggccacc ttgagtgaaa ccctcccatg ctggaattgg gccctttcag 59640
tgacaacaca caacagtttt caatagataa taatcccaag ggctttacta gcacatgaaa 59700
cacagggaaa acgtgtaaag ttcacaagaa agtcgttcca gtgtatcaaa tctatcctgt 59760
ttgccaggtg gatataccag ggtctcctcc acctgtgcat ggctggtggt gggtccagtg 59820
gctgttggat aactgatgta ttgatggatc attcgccttc tgaaagtgcc aaactgatta 59880
gttattttgt gtgtcttttt gtgtaactag ggtttgacct tccagggcag actgtgctgg 59940
ggcggctgac cccttgggga gccaagttat tgctcttacc accaccactt gcccttgtca 60000
gtcctccacc ctcttgggtt tcagtgtcag catgtagctg tctactcaga tcccatccac 60060
atcatcaagt ctgcagtttt ttccttgcaa ggccttacag ggaagatctt tgacatagag 60120
gatataattt tattgacaca ttttacttgc agagcattca cccgggctaa ccagaaagcc 60180
agcactctgc tataaacaaa aaataatgct tcagggctaa catggaatgt gttaaaagat 60240
tccagcccat taaatgtcca ggggaggttt tcctgttttc ctttccctcc atctgggctt 60300
tgttctcaac acattcattc aacaaacatt tattctgcct ctaccaggta cagagcactc 60360
tactattctg cttctctcct tttgctttag tttcatgatc atcctgaacc gctgtttccc 60420
tatcttcatg gtgctggcat ggatctactc tgtctccatg actgtgaaga gcatcgtctt 60480
ggagaaggag ttgcgactga aggagacctt gaaaaatcag ggtgtctcca atgcagtgat 60540
ttggtgtacc tggttcctgg acagcttctc catcatgtcg atgagcatct tcctcctgac 60600
gatattcatc atggtaagcc aaatggagaa ggcccagaaa atcttgaata ctttggttcc 60660
tttccccttt cctcctgttc atgtgcctgg attagtcatg tggccaccaa ggagagcgtg 60720
acatctagct tcccagccct tccttttagc caacgtggga gacactcaaa gagacgaaat 60780
ctcctgaagg agccactgta tcacagcatc ctcccatctc ccacttcctg cccaggggtc 60840
catggtccac acagacttcc cagtcccatt ccgtgaccat ctggagaagc tgctattagc 60900
agagccctgc acagggtgat agtgtaatta aagtggtctt ctctttccaa acacagaaaa 60960
aatcagttca gggagtgttt tcctgggctt acaattttaa ctactggcta gagttgaaat 61020
ggggaaagcc ttttgccttt tcagtagcag taggggagga gatctggatt atttacttat 61080
catcatcatg gtcacctcct acatggcttc accaaaaaac attctgctgc ctgaaaaagc 61140
tccaacacct ctctctcttt taaaggatgg aatttggagt ccatccttcc tcagtgataa 61200
ggagttttta tagccacagg cagcatctat tggtctgtcc tctgcaaact tgcaactcct 61260
ctgagagcta gacttggaaa tgaaacatta ttttgcaatg cgctgctatc cttcattttt 61320
agctcctcca ccgtagatga tagtttgtac ttgttaaatg ataaggatat aaatttaggt 61380 catttttat attttattgg gtggaatttg gtataatttt tagacttcag gctttacagg 61440
ctcctgagat ggactgattg agcttgttct acttcttccc catcatgata ggaagtgctg 61500
taccacacta ggcagtgtgt gtagtgacca cagactggct gagtgtctcc catcccatgc 61560
tggcccatat ctggtaccca cctgatccac aaatgttcca tcagatcctg ttcaaacaac 61620
acatctccag ttaagccaaa tcttgccctt tctccttacg gtaaaatgta ctaaatctga 61680
aggttttgtc tttttaatgt tgctccatga tccagtgatc tgtggccttg gttatgctct 61740
gtgctagagt cctaacaaga caaatgctaa ggtagaggtc attctgctca aacaacctga 61800
ccccacctgg atgtgggctt acatttgcaa agggcaccaa agttctaaga gatgagggga 61860
ggagctgagc cccttgtcct tatctaggtt tcccttgttc tttcccatcc ctcagtctgc 61920
ttcttttccc agtaccaaca tgtttgtgtc ctcagaatta aaggagtaaa aatgtgtaaa 61980
catctgacta gcaacagcca tgagattttg cctggcttgt tgataagcag cattgagatc 62040
tgccctccta agaatgggcc attaggtctt caaagctttt acgatgtgag gtaaagaatg 62100
ttcaccagga gtttcatgca caaaagggtt tctctttgtg ggaactagaa cattgttcca 62160
gtgatgacgg aaacagggct ttccatacca aaacagggtt ttcctttgaa tgactctccc 62220
acctttccct tgtctcttcc tccccacctc aacaacacag gaaagaagct ggaagcaggg 62280
acaatgggaa ggtccctttg ttactcgagc tattagaaac aaaaagaaaa gtggccatct 62340
gaggaagcca cagctggtga aactgtaggg tcacagagtg aattacacct ctggcttaag 62400
tcagtgaaaa gtcctagaag tttgtggtcc tagaagtcct aaaagtttat gggactttgt 62460
tttgagcaag gataagaaat tgatttcagg ctgggcgtgg tggctcacgc ctgtaaccct 62520
aatactttgg gagacagagg caggtggatc acttcaggtc aggagttcca gagcagtctg 62580
gccaacatgg cgaaaccctg cctctcctaa aaatacaaaa attagccagg tgcggtggca 62640
catgcctgta gtcccggcta ctcaggagac tgagcaagga gaatcccttg aacccaggag 62700
gtggaggtct cagtgagctg atatcatatc actgcactct agcctgggca acagagcaag 62760
actctgtcta aaaaaataaa taaataaaaa agaaattgat ttcattcttc tgagaactgc 62820
aacaactacc ttaaagtgat tccatccaaa acccacatgt tcagccatgg acttgctttt 62880
atggagctgc gtgtgggtga cacacaaaat caggagctct gagtcctaat ttagactttt 62940
atttagattt cctcaaattt gggttccagt taagcgtggg tctcttctgt gccccgctcc 63000
cctttgccat ttgttttatc tgttcttcag tctgttctgt cagtacccac aggcaggaga 63060
gcagaaagga gaaatggcag ccacagcaga caaatggcac attcgttcca ctcagctctc 63120
gcatgcccat cacagataca gctcattggt ctcttttcta tgagaggaag ccagagctcc 63180
agggaactac tgccaactga tcagaactca tttaggacat ggacctattt gttcctttat 63240
gttcctggga agagcacagg atgaattcta tgtactcatt tacgtgttca gagagtaaag 63300
tgcctcatag gatgcctcca gcaaaagata accaagaagg tctaatacct ttgacaatct 63360
cagtttatcc tatagtgtaa ttggatagca gttcccctag caaaagttgc tagtttggtc 63420
ctattttcta catagccaaa gtgattgatt cattggttaa tgtgaaagtt actgagtact 63480
gccagcaggt tctaggaaat atatttgtgt gatattcatg gatggggagg atcaatccac 63540
ttccaagtga tttggattaa ttactggtat tttcacctgt gtgggtagca aacctcagaa 63600
aatcaagtat agatgacggc ataggacagg ccaggcccca ggcaaaatgt tgaagctcct 63660
ctggagttcc ctcccatctc cctcttttgt tttccatata cctggtttat ccagggccct 63720
ggagatgctc caagaccccc tacccaggtc ttcctccctt gtcccagcta tatttctcca 63780
tattaccact cttctcaccg aggatttgct tacttaacac ataataaata ctattaaaag 63840
agaaacttag gcacattaaa atgttagagt tgattccagc aaacagtgat tcacaggagg 63900
ctccagatca caagtggttc agggccccac tgaggggtag ggaagcaaga caaagaaaaa 63960
caaagcaaat atttgattgg ttcaagtgga aagtccctga ttacaggtta gtgggcagtt 64020
tgtgattagt taagtttctc taagttgggt tttggtttgc tgatgtagga acacagaatg 64080
ctggggccgt ttcaacctaa tggtctccca attaattttt ttaacattac tgatgactgt 64140
taggagtcta atgtgctact cctcccaggg aaaatggcat tcctaggatt aaaggaactc 64200
agcacatgga gtgtgcgtag aaatttagac actaactgca ggctggtggg agagagccct 64260
ttagggcaga atgagaaggc gtccggccaa gggcaggagt tactgacgca tggcctcttg 64320
gtttcagcat ggaagaatcc tacattacag cgacccattc atcctcttcc tgttcttgtt 64380
ggctttctcc actgccacca tcatgctgtg ctttctgctc agcaccttct tctccaaggc 64440
cagtctggca gcagcctgta gtggtgtcat ctatttcacc ctctacctgc cacacatcct 64500
gtgcttcgcc tggcaggacc gcatgaccgc tgagctgaag aaggctgtgg tgaggcccctt 64560
gggctggccc ctgtcctaca acacgtttcc ttggaagggt ccgtagcagt cctggaggcc 64620
cagcctgccc tctgaggggg tccactttgc ctttgaccta aggttaaaaa gttcacgtga 64680
ggctaaaatg tacaggggca aaagtgggag cagtcctcac cccgagcgat gcaacagtga 64740
ctcctcacca cgcctgcttg attcatctgc cctggaaagt cattaaaaaa ccagttcaac 64800
tcatgggtcc ctttatttac tcacaagaga gagccagcag cccatttcac tagttttcct 64860
ttcctactct ttgagaagaa tcagaaggga gggagcttgc cactttacta tctgtctaaa 64920
gagatgtttc cattaattaa aggtttttgt tttgcttcaa aaaaacttga attggagtat 64980
ttccacaagt atctttaaca tgctctacca atgtttgcag aaagaagtgc agaaatgaga 65040
ctgtccacag agtcaggctc gctggccagg agaggactcc cgaagctgac ttctgatggc 65100
ctgagaaact tcctagttca caattcccag acccagacaa agagcactgt cttttctcta 65160
attgttttca aatgggccat ttccaccctc taatcagcct ctggccctgg agggtgcagt 65220
tccccttgtc ctccggagtc tccctgtctc tgtgctgtag agtcaagaag ggacaaccac 65280
ctgccctcac tgggaaaaga cagaaagtct gacttgttct cacgactcac acttattagg 65340
ctccagaggt gtcagggcat ctgcctttca tttcttaggt taaataagaa atcaattgct 65400
gccatttgta gtacccaatt ttctaaaatg atcacaatgg ataagtggca agaaatcctt 65460
atgactcatc tgtgggcaga gttgggctat tttggtaatc cttgagtagg cagatggaat 65520
ttgaggccat cttcttgggt acatagatca ctaggaagct ataggtctag caactgtgga 65580
ttagggctgg gctgagaatt gtttcatgtt ttttgtgact gtatagctag agactctctt 65640
gtttgcagag agacactctg aactccccct ggccgtcaag ggaaagactg ccttcaccct 65700
cctgagctga ccttacactg agagacaatg gggaccctct tttggccctc ccctctacct 65760
cgagggcatc tgggtgctgt tgcattggat aaaaggcact gctctttttc tgtgccctct 65820
ccgcctcact gcagagctta ctgtctccgg tggcatttgg atttggcact gagtacctgg 65880
ttcgctttga agagcaaggc ctggggctgc agtggagcaa catcgggaac agtcccacgg 65940
aaggggacga attcagcttc ctgctgtcca tgcagatgat gctccttgat gctgctgtct 66000
atggcttact cgcttggtac cttgatcagg tgtttccagg taagcatcct cctctatagg 66060
gtaaaggtaa ttgagttctt cagatcccca gccctctcca ttcatctagt ttaaatttca 66120
tttcttccaa gctctttgtc agaaccagca tttgaagttt aaatctagaa gttaaaaatc 66180
caccagcaaa tcctactggc tctacttgag aaacaaatcc agaatctgat ctcttgtcac 66240
cacctccacc acaaccttcc caatgccagt ctcttccttc cactaccacc tcccatcagt 66300
ccattctgca cactgtattc agggagatcc tttcagaatc aaggtcatgt ggtgtcagcc 66360
ctctctgtca aatgcttgca ctggcttttc ctctctttca gagtaaaacc cagtgtctca 66420
accctggcct ccaagctgct tcattatccg gcctccaact ctcttcttca tcttacgatt 66480
ttccctactc ctccatgttc ctctgctcca gccacgtcgg cctccttact gactgtttaa 66540
tacaccgagc gcatttcctc ttcagggcct ttccacctgc tgttctcatg ccagaagcac 66600
atttctctcc ccacaacctg caacccgccc ctcatatctg caggcttgct tccttacttt 66660
gttaaggtct ctgttcaaat gtcccattat cacagggatc tttccagact gaagagatct 66720
acataactat ggctctgtaa acaacattcc tccagggttc ctgtcccctt accctacttt 66780
attttgggga acattcttca ccatctgata caatgatgta tcttatgcat gtatttactg 66840
actctctgcc cttagtagaa tatgagccca gagagcatgc atgtggtcta ttttgttaac 66900
tgtgacagtc ccagtgccca gaatagtgcc tgacctttgg tgggcactga ataaatatct 66960
aagtaatctg tagcatggaa aatcagcttc tgaaaattgg ctgtttgcac ggtcgtgtat 67020
ttgcttggta gaaaatcaaa ttttccttca aattagcatt ttctggtaac tagagctgcc 67080
ccatcttcct ctgagtggtc tccaagtcag ccaatagcct tgtgctgtgg cagccatgcc 67140
tggctcttga tgctgtagcc aaaagcaggc aggggatggt gaggctggtc cagtccatgg 67200
ggagggacaa actcacagct ctcagatcat ctcagggcag cctttgttgg cagaaatagg 67260
taggcagcca ccctgaatag gaggaaggct tctagactgg gtcaggaggc ctgggtttgc 67320
atcctagtgg caagcgtgca ttcatttact agggctgcca taacaaaata ccactaactg 67380
ggcagcttag acaacagcca tttatatctc acagctctga aggctggaag tccaaaatca 67440
aggtgttggc agggccatgc tccctctgaa acctgtaggt gcttgggcac tccttgactt 67500
gtagatgctt cctgctgatc cttcgtctgc acatggcatt ctgcctgtct tacatggcca 67560
tcttataagg ataccaactg gattggatta ggtgcctacc ttgctcccat gtgacctcat 67620
ctcaactaat cacatctgca atgaccctgt tcctaaacaa ggccacatta tgaggtacct 67680
ggggttagca ctctggtatc ttttttcttg acagcacttc tgacaccaaa tgtgtgtttt 67740
ggttttttgt tgttgttgtt ttggcaccaa ccaattctcc tatattaatg ggttgtccaa 67800
gaattcaatt gaattctgac actatccaga attcacacag actccacggg ttcagtccca 67860
caaggcttcc ccgtcttcag atgccagctg gaaatgtggt gcccaggcta cccacacttt 67920
tgccaaaatc ctgtacttac aatcacagct ttaaaatgaa ggatgcagct caggaactgc 67980
cacatggaag agaagcacag tatggggtcg ggggaagagt ttctatgctc tctctagacg 68040
caccactctc ccagcacctc aaagtgttca gcaacccaaa agctctccaa atcttgttgt 68100
tcgagagttt ttataaccct atctccagct ccatactccc ccattggagg ttgagggttg 68160
ggactgaaag ttccattctt cacatgtgtg gtgtttctgg tgaccagtcc ccagaaactg 68220
cagctatctt ggggctctac cctgagtcac atcattagca taaactcaga tgtggtagag 68280
gaaggggctt attatgaata aaaaaagaca ctcctttctg ccaggaaatt ccaagggttt 68340
taggagatct gtgccctgca caggagctgg ggacaaagac caagtatatt ttgtgttatg 68400
ccacagaccc caacatgtct ttttggaggg agaccaaatt caacccatga cagtgacttt 68460
gaacaagaca tttgaactta gtctgttttt tctatcctac tagattgttg gaaacagata 68520
taatagatga aaattagttg attaaaattg aaatttgtgc ataattcaaa agttttattt 68580
tagccaagct aaagctttca tttattcaac agctatttac tgagcagcac ctgtgcatga 68640
ggctcagcag ggccaggttc tgggaacaga gcggtggaga taaagatcca gacctgcccc 68700
gaggaataga cagtccagtg gcagcaaagg ccatgaaaca tacggcaact cttaaaaaaa 68760
gccgagacca tgattttaca aaatcaacat tttgtaggga gcagaacttt caaagagaac 68820
tggactagaa atttgggagt ctttttcttg gaaccctggt agatccagta gaatgaggga 68880

```
tgggggtgta gggttaaaaa cactgacatt agaactggat tacctgtgtt ggaattccta  68940
catttctgtt tcactatctg tgacgggggg cagatggctg aatctcagtg tgcctctgtt  69000
tcctttctca caagaataat attactacct atctcctggg gttgttttga ggtttagatt  69060
atttaacaca tggaaagcac tcacagcaat gcctgccaca gaaagaatat ccagtacatc  69120
ttagtgatga tcaccattat tattatctga ctcctggaaa aggacttgat ttaattctct  69180
catgaaacgt tttcttggaa aactgatgtc aaccaagatt attggtcttg ctgttgctta  69240
taacacccca aaaacatgac tgtgtggata aaaatatgtt ggaaggggta gtctttctgg  69300
gagcctgaga atagccatgt aataataact gcaaatatct atagttacaa tttgaggttc  69360
aggtaaataa actctagatc ttatagaact gcggtaaggt aggataggga gactccttcg  69420
actttctctg tttatttgtc tctattttta ggagactatg gaaccccact tccttggtac  69480
tttcttctac aagagtcgta ttggcttggc ggtgaaggtg agtcctttaa aacacaaatc  69540
ttaatgtttg aaatcaactc cttgggctct gtgcaagatg tatatggatc acagaggtgg  69600
ccctctatgt aaacggtgtg attcctgatg agtcagctgc ctcctggggc tctgcccctt  69660
gatgggcatt gcagcgtctg gggaccaccc tttcacaagt tgctgggccc tgtgtgatca  69720
tgaatggctg atcatggatg aagccctggg tcctgtacac cttgtccagt agactaaatt  69780
gccctattta aaaaaggcca agccacttca gggttcaaag aacttttgca gcttttcagt  69840
ataaagcaga aatccaggga atcatgaagg aacctttgca ttcatctccc attgccttcc  69900
ttgtgccttt ttattcttct ctgccttttc aaaatataaa ttagtttatt ctcccaagat  69960
gaagactcct cctggggctg aggcagagct gttatcttca gggcaatacc tcagattctc  70020
ctggtgttga tctttcttag gggtggggaa aaaggctgaa agggcatttg cccacaacac  70080
atcttaggta aaaggcacct ttactactga accaaacagg aggcctagct agagaaagtt  70140
ctagaagcag ggaaaagcac agactctttt gtgaggtctg agaaagcaaa gaaattccag  70200
ggtgaaagcg ggggactccc ctagagctga agtactctcc catctgtttg ttgctcacct  70260
acctattctt tactttgtat tattgggcct gggccaggac ttatcctgca agcactgaga  70320
tggatgtttg ttttctctgg gggattagtc ttttttttc ttttttctt ttgtttttg  70380
cttttgtttt cactgggtca aacaaacaac actttaacag ctcaggattt tttcattgta  70440
ttgacttgtc tacctgtaaa cttgttaatt ttttactata ataaaattat catataataa  70500
atgaaaaatt tcaacacagg gcttgtgggc attttatttt tctctacaat cccaacagat  70560
actctgcctc ttaagaaaaa aagaaatcat aaggaaaata tgctccttca aaagtgaatc  70620
acaaatatgt ttgccaacgg aaggcaaata tttttcacct gtctcatagg ctggactgaa  70680
atggatttct aaaactctct aaaaccagaa aagagctgag tgtctccacc caacctccct  70740
cctttcacag attaaaaaat aaaaaatgga gcccaggaga catccagtat cttcccctat  70800
tggtcacctg ggacaaaatc tggaacatgc acatgcattg cctggcagga actcattcca  70860
gtgattaaac tcttcaggag gatgtttcct cttgctattt cattacctat ttgtgcagtt  70920
tgatagctag taaagtgatc aaaggaactg tggggcatag attcaaaagt ccttcaggaa  70980
gcagaaatag aagaacagta ctagaggcag caggtccctg accagcaggc ccactacctg  71040
ctgctccagc acacatcctg cacattttca gagggtgggg gacagagggg ccctgggtgg  71100
ctgttgcatt gagaaatctc gccctgctcc tgtatgtgca cttgaggccg agagcccttg  71160
gatgcctggt gacagtggtt tcctcctgcc cctgccttcc tctctggcag actgactggc  71220
ccttctgctc ctcttcccct tccaggatgt cctgatatct ttttaaacca aatgccaagt  71280
```

ttgccaaaaa gtgtctgttt gtgtgtgtgt gtgtgtgtgt gttcaatgcg tgtgtttata 71340
ccacacttca caatttgtcc aggcttgtat taataccatc accaggctca accctggtgt 71400
taattccaag atacttaaat gcccatctag gtgaatttct caggtaaacc atatattcaa 71460
gctgtagttt aagctggctg cccgtcatag cactttgaat agactttgtt tttgtttttg 71520
tttttgaga cagagtctca ctctgtcggc caggctggag tgcagtggca ctatctcggc 71580
tcactgcaac ctccgcctcc cgggttcaag cgattctcct gcctcagcct cctaagtagc 71640
tgggattaca ggtgagcgcc accccacccg gctaattttt gtatttttag tagatacggg 71700
gtttcaccat gttggtcaga ctggtctcga actcctgacc tcatgatacg cctacattgg 71760
cctcccaaag tgctgggatt acaggcgtga gccaccacat ccggcccctg aatagacttt 71820
tactcaaggt tcaccatgac tttcacatgt tttgtattgg agtaaaatgt gccagtggtg 71880
ggctaaagaa aattaactca tttcaaattc aaacctggtt ttcttaattt ttttaaaatc 71940
acagtttctg aaactgtggg ctcctcatgg cacattgaga ggaggaggtg aaactctcca 72000
agtctgaagc tcctgttata aatcttcctc tggcaaagat tgtgtgatca ggcttgagta 72060
cctcacagtc ctagagcagg tcaaaggctg gctaggaaac tcatttgctc cctgtacctc 72120
tcccctcctt tcctgccttt gctcgttctc agctcccggt ggtagagtaa cactggcttc 72180
tgattggtgc agggtgttca accagagaag aaagagccct ggaaaagacc gagcccctaa 72240
cagaggaaac ggaggatcca gagcacccag aaggaataca cggtaaaacc ccgataaaga 72300
atacacagca gaggcgagga aaaggctcta agcactgcag agggccagag caaaacatct 72360
catggcaagg gtggaaagaa gcctaggaaa ctgactctct ctgtggacaa gtgttaaacc 72420
agatcccttc tcagaggtcc atctgcatgt gtgtggaatg aatggttcag cccagacatt 72480
agcgcatatt tcctggagaa agcaaatacc aactatgtag tgtgcctgtg cccttgttag 72540
gcaaatccca agtgagttgc acaaatgtgc tgacttccga ggatttagca agaacaataa 72600
ctttggtcac tgggacttaa agcggatatg agctataagg aaagacaaaa ataaatgctt 72660
ctgtgtccag gggaaagag actccagggg agctgactac acttcactta cggcttacaa 72720
atctagaagg ccattcattg aaaccatcag aagcctttcc tgacagtgga agttacctaa 72780
taatccctaa actgacgacc cagatttaca agttttgttt tcctggcttt tgctgccctc 72840
atcttctctc ttaaactagt tctgtatttc tcccaaggct tttcattccc taagcatacg 72900
catttctctg tggccaaaat gctctgggtt tagacaggca gcacagcccc tgggctctgc 72960
ctgacagggc aggagagggt ctggccttta tccctccagc ccaccccagg ggccatttca 73020
taaaactaaa gccagagacc tgcagcccct cccagagtta gactgcagta caccatgcct 73080
ctggcaagat cctcctccca cagtggaaag tctaagccaa atcaggaggc tggggactgg 73140
ttccacctca gttgcaggca aggccaggag gcacggatag aagaaacagt ggactttttc 73200
cccctaggga aagaaatgct tagagctaca gtattaagat gacaaattaa gctgtgccat 73260
atagggtgaa atgaagcagg gatagatggg aggtcaggga gaagtgagag cactcggtga 73320
gggtctgcac tggagggggc atgggaggaa gaaggagggg agtggggttt gagggatggt 73380
gatgaggaag cgtggactgc cctacccacc tattggaaaa cctgggagtt ctgaggagca 73440
agaagcctta gtcaaagtca actcaaagat tcaagccaag gtgactaaga gaatggcggt 73500
ccagaaaagg tcatgggaga atctgaaggc agatgttgtt ttgggaagat gaagaaccta 73560
agccgcttcc agaaattcat gaggaaatgc cccgtggact gttggcaatg agggcctagg 73620

-continued

```
accaaggttg agcttggggc caactctccc tatagacagt gagtgcattc tgacaagcat  73680
gggctctggg ttcaaatccc aactctgcca ctcatgccta tgtgtcctta ataggacgct  73740
tgatgtctct gtgtctaagg tttcctggac tatggaaatg agcctaataa atgtctaccc  73800
cttaggacca ttgtaagagt acattgaggt aatttgtgta aagcagtcga agcagtgcct  73860
ggcatatagg aggtgctgta taaacgtttg atgctagtat tactattatt attctggagt  73920
cttccttgca acggtgatag ccgaagccac aggggcaggt gacgttatag gcagaataca  73980
agggcctgga gacagagccc tggggccatg taattaggca ttatgtttac atcatgttca  74040
ttttttttcc tccaagactc cttctttgaa cgtgagcatc cagggtgggt tcctggggta  74100
tgcgtgaaga atctggtaaa gatttttgag ccctgtggcc ggccagctgt ggaccgtctg  74160
aacatcacct tctacgagaa ccagatcacc gcattcctgg gccacaatgg agctgggaaa  74220
accaccacct tgtgagtctt ccagcagaga agctggctgc catgctagcc tgtcatttcc  74280
tggcttagtc tttccctatc agcggctgtc tactctttcc cacaaatttt agtgacaaat  74340
atttgcggcc ccaaaaatgt gtaaaagctt tctgcagtat tcaaagatca ctaatatgta  74400
ttctcttgat ggggaggtag aatacgttta ttgccccttt tgtgtgccgg ggaagtggac  74460
attcattcag agagttgaag tgactttcct gaagccacca agttgtcatg gctcagcggg  74520
ggcaaaagcc aggcaccaca gttgcctctt gtttctcaca ccttgagtct ttccccccat  74580
ctcaacagtc catggtggtg atcaagtcat ggccactgtc atcatgtgca tggaagctat  74640
agagtcctcc tatttccttt ctcttttctt ttcttttttt tttttttttt ttttgagata  74700
gtaaccatta cccatgctgg agggcagtgg tgcgatcttg gctcactgca acctccgcct  74760
cccaggatca agcgattctc ccacctcagc ctcccaagta ggtgggacta caggtgcata  74820
ccaccatgcc cagctaattt ttgtattttt tttttttttt ttttttttta gtacagacag  74880
ggtttcacca tgttggccag gctggtctcg aactcctgac ctcaggtgat ctgcccgcct  74940
cagcttccca aagtgctggg attacaggcg tgagcgaccg caccaggccg agtcctgcta  75000
ttttcaagga acattccttt tcctaccaat cattaggcag gcttcaacat cagctgatga  75060
gggttagtgg tcgttctgga gaaagtgaaa aaagaatcag tctctagagg ggcttgtgga  75120
gtaaccgcct ggtaacagaa ggtcagggca gggaaggcaa aggggctctg cgcggatctc  75180
tcagctccgc aggcgcccca ctctcctcca agggacccga gcgccatctg ctgagaggag  75240
aacacggccc gccatggttt cccaaggagc agcagacacg gacctcgcag ggggcagcga  75300
acccacgtga cacagtcttc aagtcctttg gagagcccca ggaaggaaca acagcgtgta  75360
caccctgtga tggaatgttc tctagggcgg ttcagtgtga atggaatgtg gggccggtgc  75420
cattctaatt ggttctgttt ccctctagtg gttgatcgcg gagatttcgg cttctccatc  75480
aggacaagtt cagatagcct gagatggtat cagaactcag ggacagagct gggtgtggcg  75540
gccctgcatc catctgcttt ctctccatgc taactgatat ggtcagagag ctggaagcaa  75600
attccaggac cccagggctc cgcaaaggca aacacattac ttcatcggct gctgacatgc  75660
aacttccccc aggggttaaa acaatgttta atactaacag taataatatt tttgagtttt  75720
actttatgct ggcgctgttc taatgttgta agtgtattaa ctcatttaag ccttacaaca  75780
acctaaggac atgggagtca tagttcccat ttaaaaaaaa aaaaaaaaaa agcccaccat  75840
tgctctgagg ctttttatgt tttggatcca aagctaatat tggtggtggt aattcccatg  75900
cctggcttcg atcaattaat cagcaaatgc ctaggactgc ttagggttct ggccttcatc  75960
aagaccttac ccgggcttta tgatgatgac acctggcttt tcaatagcca tgactgctca  76020
```

-continued

```
cccaggaggc aacgcctcga gtcatgcacc gaacaccttt tattgatcct ctccaacacc  76080
aggctccgtg atggctgagc tggggacacc tgtgactgca cgtgaacatt ttgaggctgg  76140
gaatcccaaa ggccctcggc gttggcctgg gagcaccatg aaacaagtag aagcagagaa  76200
ggatggcaga ggtggccctc tgcattaggg cctggatgta tacactggtg ctaagggggc  76260
cccacagcta ataggggttt gagtttgact gacagcccca ggcaggaatc tgtgagagtt  76320
ctcactgaac ctggtgtggg ggtggccctc ctaaggcatg ttgctaaagg ccatctcttc  76380
tgccactgac gcctgtgttc tgcaggtcca tcctgacggg tctgttgcca ccaacctctg  76440
ggactgtgct cgttggggga agggacattg aaaccagcct ggatgcagtc cggcagagcc  76500
ttggcatgtg tccacagcac aacatcctgt tccaccagta agcgacacag gaactgagac  76560
cgccccatcc cctctcctca cctctgcccc cagcacactt ctctagagcc cagctcaggg  76620
gtgccaggcc tgggcacagg cagagataca gactcttatt tggtttcccc tatgtttaaa  76680
gtcctttgtc ctacttgcag tgagaattgt ccctgagaat atgggactct gcctctgctg  76740
ctcagagctg agggctcctc cctcagaagg gtgaggctgc cttcgctctg acagagcagc  76800
tgatcgatcc ccgagcccct tgtgcagccc tgaagtactt cctctctggg accaaagaca  76860
ggagaaccat tgttcctttt tcctgttgaa gccacggcct gaaaggcaaa cttttcaggg  76920
ggcttttcag ttactttttt tccccaataa gatatctttt atttcttatc taagaagcta  76980
cgcatagtca ttgtgaaaga aaaaaaagga agggaggaag gaagggagga aggaaggaag  77040
gaaggaagga aggaaagaag ggagggaggg aggggagaag gaagcgaggg agggagggag  77100
gggagaagga agggaacagg agggaggaaa agggaagggg aaggaggaag gaaagggaag  77160
gagggaggaa gtaaatatag gtaaacaaaa aattgaaaat aaaagtcacc tgtaatttca  77220
ctactcagag ataaccgctg agttataaca ttggtatata attttttaga actttctcct  77280
atacatgtat agatagataa acacatatac ttcaaaatga taaagaatag taaaactatg  77340
catacaattt tataacctga cttttttttc aaaaaaaagg attgcttttt taaacataag  77400
atatcaggaa catctttcat gtcattacat attcttctat aaaataatat ttaatgttta  77460
cagattattc cattgtatgc atgaactatg taagccatcc tcttattaga tatttaagca  77520
gggtctgcta tttttgtatt gtatcataaa caccaccaca gtgagcatct tgattgccaa  77580
atcaagaata cttgtcctca attatttctg taagatcagc tgctggaagt ggaagtgcta  77640
agccactgct tttctcgttg tcccatcctc ctagcctcac ggtggctgag cacatgctgt  77700
tctatgccca gctgaaagga aagtcccagg aggaggccca gctggagatg gaagccatgt  77760
tggaggacac aggcctccac cacaagcgga atgaagaggc tcaggaccta tcaggtgctc  77820
agagctggat ggagacaggg ccacagatgg caaatccatg gctccccagt gcacccagga  77880
ggcaggggag gcttggagca ggagagcttc taagggtggg aacacctctg tgaagttaca  77940
ccaaaaatct aagagcagcc cccagatcat tttccctgca gagcactgtc tcacagcagc  78000
ctgggtttta tttgtcctga gattgatgtg cttgaacagt cttcaaaggg tctgatccga  78060
ggaggtgagg gttgcccttt ctgcatttac aaagcctgaa cagtattagg gctttgaacg  78120
ctataaacat ctaagaggca gcaccaaacc actgctgggt taaggtaccc ccacaatgcc  78180
acttgccctg ggcctttctc ttcctcaccc tccacagccc cttaactctc ccgtccttct  78240
tgtgcctcca ggtggcatgc agagaaagct gtcggttgcc attgcctttg tgggagatgc  78300
caaggtggtg attctggacg aacccacctc tggggtggac ccttactcga gacgctcaat  78360
```

-continued

```
ctgggatctg ctcctgaagt atcgctcagg taacagctgc tgctcagtct cctgggctgg  78420
gctctcactg cagccctagc tgtggtcccc actctctcac ctgccatttt gtagctgagt  78480
acaggaacca caatgactac actcagaagg gggtttatca gtgacttggt gaatctaagt  78540
tccagctaaa gcctcctgag gtttttacaa atataaacag agaatcactg atgatgcaac  78600
ctacttccca aaatatttta gaaaattctc ttgacctgca gcccttctgt ctggaataat  78660
ggatgctact ctaggtgaat gtcttctctg accatgggga cccaggtcac ctgcaaacat  78720
acctagaagc tccatagctg tcagatgacc actcaggacc agtgtgaggg tgacctgctg  78780
ggcattcagt gctccagagg gtggccacag atggaagtgg ctcctctgtc atggcacctc  78840
tcagacaagg ggctcagatc agaagagaca gcaagcagag ctgagtgccc atagaggtaa  78900
cagcacggtt caaccccgtg gtcaagccag agctttcccc cttgctctac tcacacagcg  78960
ttgccccgtg cctttctctg agggtttgtc atcctgaaat cctcattgct attttctttc  79020
tttcttttct ttttttttt ttttttttt tgagacagaa tctcgctctg tcgcgcaggc  79080
tggagtgcag tggcgcaatc tccactcact gcaagctccg cctcctgggt tcgagccatt  79140
ctcctgcctc agcctcctga gtagctggga ctacaggtgc ccgccaccac gcctagctaa  79200
ttgtttttgt atttttagta gagacggggt ttcaccgtgt tagccaggat ggtctcgatc  79260
tcccgacctc aggtgatcct cccgccttgt cctcccaaag tgctgggatt acaggcatga  79320
gccaccgtgc ccggcctgct gttttctgtt aatgacatct ccagttagtg agagtatgca  79380
cgtgtgtgtt ctttatgaag agtataaatc cagagcttaa tgatccagaa aatgtacata  79440
tgaaactccc tagatgctga ccataataca tgagccccta atatagagat ttatttgaat  79500
cagatcctat gctggataca gagacactgt gtgtggcaat gctttacagt atgtaggaag  79560
ctatgaaatg ttagttatta ttgtcctaat atgctggaat ttgctgctga attagttccc  79620
ttgggttttt ttttttagtt aactcctgat ttttgcaact atatagccag gaaattgctg  79680
tacacccttt accaacaatg cccaacccag ggcaggcctg gtgattgccc tggcccctac  79740
cttgcaggca gaaccatcat catgtccact caccacatgg acgaggccga cctccttggg  79800
gaccgcattg ccatcattgc ccagggaagg ctctactgct caggcacccc actcttcctg  79860
aagaactgct ttggcacagg cttgtactta accttggtgc gcaagatgaa aaacatccag  79920
agccaaagga aaggcagtga ggtaggtgtc tgcccaggga aggaccctgg cctgggtgag  79980
aaggagcaca cagcacgggg ctgccactcc agacatggct actcacacag gctctcgcca  80040
ccagaatcag tgtctttgtt ctgggaccat ttgcagaaga tttcgatgaa cacattctga  80100
agcctcctcc tacagagatg ctttagccaa aatgaaacaa ctagctttaa atggtctgca  80160
agtattacat gccagattac acaccagttt ggtgcggttt ggtgcaacat agaagtgagt  80220
gtcttattct gtaaggttag gctgttttaa gagcaattgg ttgagcttca tttcaacatt  80280
aatattccct aattaaacct gaatttcagt ggtaagtgaa aactaagaag aggcctcctt  80340
gggtgctata acataaaaat gatgaaggca aaaagtacca accagcagag accacttcag  80400
cacatcagga gacccagttt tatgtctgtg ctgcgaagtg aacaaactgt gtcatcctag  80460
gcaaattatt taattcctcc tttttttag tattttttc ttcttcacat ggaacatgaa  80520
gctaatgacc tctgcttcta tttcttaggg atgtgaagat aagtgagata aagtattata  80580
aatgtgctct gggcttctta agaacaggca ttgctcacat tcaaatggtc atgattatga  80640
tatggcagca ttatttatgc ctctggttta agtgtctggc tgccgctggg gtttcctatg  80700
tccatccacg gggagggagg cacagaatgt ctcccacagg cagaacctac agctgccaca  80760
```

-continued taattgatga caagccaaag ggacccttgg aggttctgct cctctctgtg tgtgactcac 80820
acactctcta ggataaaatc aagcgactac accctcaaaa tgctcagatg aattaacaga 80880
ttaaacagtg aagaaaaaaa tgtgttgact acacttggca gtgagaaata aataaagcgg 80940
gcggtgacag cagctggcat cagggagagg ctgtcatgga agggatgtgc atcttgtcag 81000
tcatcccatc catctgttgc aggggacctg cagctgctcg tctaagggtt tctccaccac 81060
gtgtccagcc cacgtcgatg acctaactcc agaacaagtc ctggatggta aggactggac 81120
gggccatact tgggttccgt ctggcagcca tctcccagta ttgctgggtg tgtcctgttg 81180
tgatgcattt taatgggagc aaagagaaca ctgggtactt ctgcaggtca cacagttgtt 81240
cttttgcttt gagcttcttt ctcctcttcc ttcttccttc attcccaaag ggattttaaa 81300
agtcatgcac ctaaaggccc tctcccttta atgaggaata cactctgtgc tcttaccctt 81360
agtaagccat cattcctggg gtccccctgc cctggctcca ggccacattc cttagtgtct 81420
ggggagagct tcttctacat gtgtgccgtg gcgccctcta gtggaagcat ggtgatgcac 81480
ggctcttcca gtgaattcgt ggagtcagag attgcacatg tggatggcaa gtctggaaat 81540
agcatacacc cctgttatac tcctgattct cccctcagct tcccaatttc ccagtgattc 81600
tccctttaat taggatgcac tgaagctctc aggggtgccc ccatctccaa ggagctgcag 81660
tggagaggct atcccctctc tatgtgagag aatgtgtgag aagcgtattc ccacacagga 81720
gcaaaactaa acttacgtac tgatgcaggt taatgaatgg ggaaagtatc tgcttatcaa 81780
agaaaaggca tatttttcta tttagcacaa actttttcaa atgttaagaa tttactaact 81840
gaaatctggt gaagcaagag aaccgggcaa tatttgcgtt gtctgatcat tacaactgga 81900
gggaacatgc tcagagaggc atcatcactg ttcatgcacc tgccctctct ttacactgag 81960
agaccctgtg atgaacagaa aacatctttt taggatgaca tctctgggtc tttctcctag 82020
cctgccttgc tgtgggtacc tatctccctg ctctctgaac cttggtcaag aagtttatat 82080
ttgttttaaa ttgatactaa tatgttaagt tactgtgatt tgccaaaatc agattggaaa 82140
cagggcctgc atggctgaat gattcttttt tttaaattac tttatttcta aataaaggtt 82200
ttctttgtat agaatcggga tgctgtgaat ggtgggaaat gcactaaata gttatgcccc 82260
aaataagaaa gggaaaatca tttgaatccc cagttagctc cttgaaagtc ttttcactta 82320
aacacaccca cataccacac acacactcac agacctccct cccagatgcc caaagccctg 82380
ctgacctaca gagctacttc tggaaaggct gacacatgcc taagacacaa ttcctgggaa 82440
tccagcagct ttgggttcaa tttccttcct aaaagaacaa tgaatatgac ccctggagag 82500
ctattagggc agagctgctt ccttaacgta aaggactctc cagcctccgt atgaagtcat 82560
ctcagagcta aagacaatca agtccaactt gcagatttga cataaagcaa gacttccaat 82620
ccggctaggc agaaggattt tggttgaaaa ccatgaaatc ccttcatatg gatcattttt 82680
taaacaacaa aaaaagaaaa gaacctactg ggtgtccaca actctgagag ctgctttctg 82740
aagagtcatg ttttgagtcc tggaatccct ctccctttga cctgcctctc aagacaatgt 82800
gcgagagaac tctctcttca agtgcatgca agtgaggttt tcacagttag atttttaatt 82860
ttaaagtaat acacatttgt acataaaatt caattctgac tgtatacatg tgtcagataa 82920
acagttgata cctgacactt gttcacagtc tatgatacgc accgcatatc ctaccctctc 82980
ccccagcctc tctccatggc ttctcaaccc cccctctgca tttcctgtga cctgaggatt 83040
cagttttgtt tgtggaggca ggtgcaatcc caagagaaac tgtgcaatct tctgagaagt 83100

```
tagagtaggc atgtgtgtgt gatttaggga aggtacttct cactcagctt ggtcaccggt  83160
tccaggtttg tgtcttgggc aagtccccca tagctggtga cagaccagaa aaatgaaaac  83220
aactttgact tagccctcaa gttttcagtg aatgagaatg aaaaacaacc atgagtaaga  83280
gatttcttac cgagatgatg taaaggataa taatagcagc cagcactcac ctatgtgcca  83340
ggtatttctc taactgcttt gtgtagtttg actcatccag tcctcaaaaa caacaatgaa  83400
gtggatacca gtattttccc cttttcacag atgaggaaag tctaatgtga cccacccaac  83460
ataacatagt ttgaggggac agagcatttc gttgaacaga ggaggaactg gcacaggaaa  83520
gttgcatgac ccccccacca acctccgccc ccaggttgca cagctagcta gtcgggagga  83580
ctttgcttcc gtttccctct gcctctcaat gatgatctca gggccaacta agctaaaagc  83640
agacttgatg gagcatcagt cctctgaaag agtcactgcc gagatacaaa atacctcttc  83700
ttcaaagggg aagtggagag aagtaggaaa tctgggtaac ctcacagtct tccagtttct  83760
ggaaaacaga gctggcatca gtcttttttc ttgtcctagg ggatgtaaat gagctgatgg  83820
atgtagttct ccaccatgtt ccagaggcaa agctggtgga gtgcattggt caagaactta  83880
tcttccttct tccaaataag aacttcaagc acagagcata tgccagcctt ttcagagagc  83940
tggaggagac gctggctgac cttggtctca gcagttttgg aatttctgac actcccctgg  84000
aagaggtaaa gtagagattc cagctggttt ctgtcaagtg ccagaagtgg cggttctttg  84060
aaaaagtcta acattagagc aaagttttgt aaaagcaaaa agccatcgtt ccccacccaa  84120
gcatagcaac tatctttatt tttggcatag ttcccccatc tctgcatgca tacaaatttt  84180
atgtacttgt ggttactgtg tgcttacgtt tttgtattta tagaagatga tgttctcaga  84240
tagagtcgta atggattttc ttcccattat gaagcaatac ccaacaaaac agagcttggg  84300
ttagattttt ctgagaataa gaatgactaa acaaaattct ctcttttttt cttcttgaca  84360
gatttttctg aaggtcacgg aggattctga ttcaggacct ctgtttgcgg gtatggtgct  84420
ggagccagtg gcttgttccc ttccttgcct ccctcccaag ttccatctcg aaagtctaag  84480
gggctgggca cagtggctca tgcctgtaat cccagcaatt tgggaggcca aggcagatgg  84540
accacctgag ttcgagacca gcctggccaa catggtgaaa ccccatctgt actaaaaata  84600
caaaaattag ctaggtgtgg tggcgcgcac ctgtaattcc agctactcgg gaggctgagg  84660
caggagaatc acttgaacct gggaggcaga ggttgcagtg agcagagatt gtgccactgc  84720
actgcagcct gagcgacaag agcaaaatcc atctcaaaaa aaaaaaaaag tctaaggaaa  84780
aagtcatgaa acaacaaagc aggcaaatac tcctccatag tatctgactc cccagtagta  84840
ggcattttgc atcctagatg gctttgagtg acaaaggaat aacagactga gttaggtcta  84900
gatggggaca ctttggatga atgaggattc ttacggaggt caggttggta gcttcatccc  84960
tcagctcctc atgctgtatc cccagtctct cggcctgcca tgtcatcatc ctcatctcct  85020
cctgtcatct ccaccaggcc tctgatccat ctctgtctgc atgagtgaca gctggcagag  85080
tccttaatgt ttatcaaata caactcagac gtcagtctcc tggccccttt gagatcaaca  85140
taaaatcatt ttgaaccctt atttagtggt ctatgggctt tgaaaacatg gggaccaaaa  85200
ttcctgtgga ttctagaagt ctctcttcta catgtgtcag cctgggcacc aactagctcc  85260
ttccatgaac ttttatcaaa ccccacagcca cacaaagcat gtgtgagtgt agcagagttt  85320
acagcagagg gtggagggtg gggagataga tgtgtggaag ggttacctgc cacacaaaca  85380
gaaaccactt ctgatagaac acgaggtgtc cacccacact gtaaaatcct ctcctggtac  85440
aggcaaagct ttgcagcgat tctcctttgc tgcccctggg ctcctaacac ctcctaaacc  85500
```

-continued

```
accagttacc tccttctttc cagtgtggca tatttcagtg ttttcctgtt ggagtgtttc  85560
ctttctatgt ggattctgga atcagctctt aagataactt ggttttcatc tttcttcata  85620
atgatcccaa acatctatct actatgccta gaactaccaa tggacacata taccagccca  85680
gatatgcttc agcccatccc agtacatcgc atggtgacca aaagatgtag tcgtcctggc  85740
acagtgggtg tggggcagga agcagtcctc tccaggggac agcagcaatt caccacagaa  85800
cccaagtttc tttcaagctc tgctgacaca gaaattgaat aatctcagct cacccaatgt  85860
caaagactca tattaaccaa gaccagaatg aaaatatgct aatttatatc agaagctttg  85920
ctggattcaa gagttagggc cttttacctg tgcagaatat tccttcttga taaataggcc  85980
ctctcaggag aataaattac acatcagagg actgtttagt cagcataggc atagaacagg  86040
atgttccaaa gatacagtca aggggagtgg gtaagagtgt agcctctgga gtgaggccga  86100
ccaaatatca aacctgagct tcataatttg caaactaact ggctttgggt aagtacatag  86160
cctctttgta cctgtttccc catctgcaaa atggagataa taatagcatc tacctgtagc  86220
attgttgaga gaattaagtg agttaatgct tgccgactta taacacagta tacgatcact  86280
gattaagact tagcaactct aaactaaatg tttacaaacc atctcttacc tcaaagcact  86340
taacatccat tgtcttattt gattatcact gtaatcttat gaagcaggca gggcaggggt  86400
ctgccccatc tggggggaac tgagctcaca gaggttggag ggtttgccta aagtcaccca  86460
ggccactggg tctcactctc tggtcttagc tctgtaatct aggatgctca atgccacact  86520
ctcagccact tttcagatgg ctaagtacat ttgttttgag ttagctcagt ctcagaggat  86580
gacattttct gatcttgtct ccagtgttta aatgaacctg tagctgtgca ttggggtcac  86640
acaatgcgtg gcatggagag ggtctgtggc tgactgccac ggttactacg tgaaaccatc  86700
attacagcag ttactactgt tactgcctga gaacatcatt acaagactga acgaagggat  86760
caacatggaa atgataacaa aaaaaccaaa gtaactgttt taaggaaagg ctagcatcgg  86820
gaagaagaag agagaagaag agaagaagaa aagggctccc tgcttctaat gagtaaaggc  86880
agctccctaa gcttctgcag cccttcatta tttattgggt aacaggagga aggagcagga  86940
ggtaatgatt gggtcagctg cttaaatgat cacgggttca tgttgttact gacagatttc  87000
aattatgcct aatcataaga aacatttgtg cagcctccaa caagggtcaa tgccacttct  87060
gaaggggtga ctcatagtca gtaactagaa agcagcagat agctagggac aaactggcga  87120
ttctgaatag gcctggaacc cttagctctg gccaggtcag tgggctccag tcaggatgga  87180
gccttcaggg agagatcaaa gctcagaggt ttgagatgat atcagccagc aaagaggagg  87240
ggcagtaggg atcctcccag agggagggcc agccatagaa gacatcaaat ctgagcccgg  87300
atcaggagaa ggagcctgca gaactggggc tctggcaccg agaacctgca gaacttcgcc  87360
cctctgagtg caggtgccag ggctggggct gccacccagc cttcgcatcc caggcctggc  87420
acgtcatagg taaatgtagt tgaaaggatg actgagctga tccaattccc tttacaactg  87480
tccttgtcct gggggacttg aggagggtta agaaagcagc tggggaccaa ccaacagtcc  87540
tctaggctct ccatgtccag caatagttgt tcagcaaatg agcattaatc agtgactata  87600
aactgtagct tcaacataac cgacaacttg caatggtttc tagagcatgc tcccatgtgt  87660
tatctcattt aaatttccaa accaatcctg tgaaatgttc ttttttttt tcttttttt  87720
ttttttgaga tagagttttg ctctgtcacc caggctggaa tacagcggct cgatcatagc  87780
tcactgcagc cttgacctcc tgggcccaag ggtcctccc acctcagcct cccaagtagc  87840
```

-continued

```
tgggactaca ggcacacgcc accgtgcctg gctaatttct tttctagttg tttgtagaga  87900
cagggtctcc ctatgttgta caggctgatc tgaaactcct ggggtcaatc aatcctcctg  87960
gcttggcctc ccaaagtgct gggattacag gcatgagcca ccatgccttc attttacaga  88020
taagaagtct gagaaaactc agatttaggc agattgagtc acttccccaa atttatgtat  88080
cttgtaagaa tccatattca aacctcagtc ccctaactct tagttcatta ctttttctac  88140
cacttctcag tatcctctaa gaattcagaa agaaccacat cgactctgat tttcatttg  88200
tttaagtaca caggtaatag gtgaatgtat tttgttgttt aaaaattcat ataatacaca  88260
aaaggctaaa gtctcgcttc ccacttcctc tcccctttct acccaactct gcctccccag  88320
ggagagcttc tgctgacagt cggtggacat tctttcagag ttttacaatt atgtgtgtgt  88380
gtgtacataa gatgtcagtt tttctttgtg taggatacat gaacatgaat tttaaacata  88440
aatgtgagtg tattacacat attgaccagc accttagttt ttttgtttgt ttgtttggtt  88500
ttctttgtgc tgtttgagaa ggagtcttgc tctgtcaccc aggctggagt gcagtcttgc  88560
aatctcggct tacgcaacct ccacctcctg ggttcaagtg attctcctgc ctcagcctcc  88620
cgagtagttg ggattacagg tgcctgccac catgcctggc taatttttgt atttttgtag  88680
agagggggtt tcactatgta ggtcaagctg gtctcaaact gctgacctca aatgatccat  88740
ccacctcagc ctcccaaagt gctgagatga caggcgtgag cctccgtgcc cagccagttt  88800
tgttttttta ttaaccaagt tacgtatttt aaacttctcc atgtcaatgc ttttagagct  88860
attttgttct ctttaatgtt aatagagaat tttaaggcaa tttcaggtga atctatacaa  88920
tttctctgta taagtaattt acactagaaa tagattttta taaagatgat taagctacca  88980
gcctggtatt tcattgctga cttaaatgaa gaggaaaatc aatgctgtaa gggaaaaaaa  89040
aaatggcatt agagatccag accttatagg cattttccaa attattaatt caatctctca  89100
aaacaggtgg cgctcagcag aaaagagaaa acgtcaaccc ccgacacccc tgcttgggtc  89160
ccagagagaa ggctggacag acaccccagg actccaatgt ctgctcccca ggggcgccgg  89220
ctgctcaccc agagggccag cctcccccag agccagagtg cccaggcccg cagctcaaca  89280
cggggacaca gctggtcctc cagcatgtgc aggcgctgct ggtcaagaga ttccaacaca  89340
ccatccgcag ccacaaggac ttcctggcgc aggtactatt gtcggtcggt gtttagctga  89400
gctcagtggc tcctctccca gccttcccct cctctcctga gtgttccttc aggcatgggt  89460
tataactcag caaggagcac cctctttaga ttctgctggt tttgtttcct gctttccaaa  89520
cccttatctt gattcttggt aacatgaatc ttctttgtaa gttggacctc ccctagcaaa  89580
gaaaatagaa taatagtgaa aatgttaata ttgtttttat ttttacagtg agggataaag  89640
tcatgttttc attcattttt gcagtgaccc tacatatcaa aatcattgcc ctcttttttc  89700
ttttaatgtt gtttaattta gaaaaagaag ctctggttta aagaacagtg agtcacgtga  89760
cttgctcttt gaaatgccct ttgaagtctg gctgaacact gggctgcatt cagattcttc  89820
agtggccacc agaacattct gttttcttct gcacatctta cctttgcaca ccctgcttat  89880
tatgttcccc cagaagccca accctctcca ccaggggctg attaggaggc tgcaggataa  89940
atgtttaaaa gaatgaagat gtgtgtgcac gcgcacgtgt gacatctcca tgccacagtc  90000
atgtttattc cacgtctatt ctcccacaga tcgtgctccc ggctaccttt gtgtttttgg  90060
ctctgatgct ttctattgtt atccctcctt ttggcgaata ccccgctttg acccttcacc  90120
cctggatata tgggcagcag tacaccttct tcaggtgcgc ggactcgggg tcaccattct  90180
cctctgtggg tttggggcac ctgggtcaca tgctgcttag aagggccctg accttcccac  90240
```

-continued

```
ttcactggga ccttcaccaa tgagagaggg gaggggtctt tgggctgcct gcagaaagga  90300
acttaatgta tctgccactg cttggaaagg cgatcctagt ggacaggcag gactgcttgg  90360
gaaggccgaa tggggaaagg aatgcaaagc ttaggtgaat gggttgaagc gccatctttt  90420
tgaggcatag gtgacatgcc atcagaccac tgcgagtgtt caggcagcct accgcactcc  90480
caggagagct agcgccatcc caaggcagca ttcggtgcct ccaatacata cctggcacac  90540
agcagctatc cagtaaaggc tctgagttgc atgatgttgg cacgcgcctg ctctgtccca  90600
gtcacatgtc tcactctgtc tagcatggat gaaccaggca gtgagcagtt cacggtactt  90660
gcagacgtcc tcctgaataa gccaggcttt ggcaaccgct gcctgaagga agggtggctt  90720
ccgtaagtgc ctacgcgccc ctgtcctaag aagactagct cccctgggag gacccaacgg  90780
tgggttcaag atggcaggcg ttggggaggc cccactcaat cctgctctgc tggtcacttc  90840
catgtctctg accagcactc ccccaacctc tccttccaca cttgtgtgca gggacattca  90900
ctacctccta ggaagccccc acaccactgg acagctctat atttctcagc atagaagttc  90960
tatgttgagt tgacagatga ttccccataa cttatttgaa aggcctctga gcagggaggg  91020
agggaaatag ggttatgcta ttgtgtgatt gggccttgaa tggcgtgagt gacacagtgg  91080
ccagtacttt gtgatagttg tgagtctgga gaagggagtt agcgaaggcc attgacatcc  91140
accaggaatc ctaaaagttc aatataattt taacttttct ccctcagtct ttttcaaagc  91200
tgtcaataag gaccaaaaca gactaatttc aaattcctct tctggttgct gtgtctctca  91260
acagctagag ctgctaggaa taaaaaggga gacaaaacga tccacaagct agagatggtt  91320
attccccagc cccacaccta gtcagtcaca aaaccctagt tttgatattg cttgagcaga  91380
aaccagcctc caagagaata agaagaaagg gcctgggtct aaagaggagg aggaaagggt  91440
tgggcacaat ttcttatgcc tagggatttg tcagcaactt tgaggctgat tatggaatat  91500
tttcttgtct tccatgaggg agtacccctg tggcaactca acaccctgga agactccttc  91560
tgtgtcccca aacatcaccc agctgttcca gaagcagaaa tggacacagg tcaacccttc  91620
accatcctgc aggtgcagca ccagggagaa gctcaccatg ctgccagagt gccccgaggg  91680
tgccgggggc ctcccgcccc cccaggtacc tgacctccaa acaacggggc cccaggtctg  91740
cctgccacag agggactagg ggagtccctg gtatctcctg agtctctcac aaactaacat  91800
ttcaaactgg cagttgagta ggggactaaa ccaaactccc tgcaccctct gggaggggct  91860
ccccacaggg cgctgtggct gccaactgga ggaagccact caccaaaagc ttcattttcc  91920
accagatact tcctatttga tctagtagaa aaaatgtgtt taagcactaa aaaaaattaa  91980
gtcatatgtg ctcattatag aaaaattaga aaacacaggt aagtcagaag gaaaaaaaat  92040
catcgcttgg atataaacac agataatgtt tggtttgcag ccacccaaac agattatatt  92100
ccaaatattg tcttaaaatc tgatttactg cataatttac taggaacatg catccatgtc  92160
aataaataga catctgcatc acttttaata tctgtatatt atcccattgt ttgaatttct  92220
tttttttttt tttttttttt tttgagacag agtctctctc tgtcacccag gttggagtgc  92280
agcggtgtga tctcggctca ctgcaacctc tgcctcccag gttcaattct tgtgcctcag  92340
cccccccgag tagtggggat tacaggcatg caccatcatg cccgcctaat ttttttggta  92400
gttttagtac agatggggtt ttaccatgtt ggccaggctg gtgttgaact cctggcctca  92460
agtgatctac ccacttctgc ctaccagagt gctaggatta caagcgtcag ccactgctcc  92520
tggcctaaag ttactttaaa ttaactgatc tcccattatt cgccacttag gtttttttagt  92580
```

```
tttcaccatt ataagcaatg ctatgatgta cattcaaatg gaaatgtgtt tacacactta  92640
ttaacagtct taattaagaa gctctccatg tgctgtgtct ctaacatctg caggtatgta  92700
cacaaataca tgcacagcca gcatccatct tttgcaggga cattaatgat cttggctctg  92760
agcagcaccc tgtcctggga gttctaaagt ccagaacaga ttacagtgag catctcctgg  92820
gggatttaga gacatcaaag aaggctgtgt ccgtggttga taatgggcct cccagctgac  92880
ttgccagggc tgggccttag acagccctgt ccaatgattt gtcaatgaat aaactgttcc  92940
caaacaggct atgcagttca gtgggaaagc acaggtatgg gacacggaga gccccaggtg  93000
gactacttga cctctctgag ccttaatttt atcacctgtg aattgggaat aactgcttat  93060
ttcataatat tattatgagg atttaatgaa atcatgtggg caaggaatta tttagaatta  93120
gattcaactc aagtgatgac aaccccaaac taacagcaga taaaacaaga cacaacttgt  93180
ttctcactca tctaaaagtc tacgtgggtg gtgcacgatg ttctattctc tttctcctcc  93240
acactaaaca ggcctcagcc tcatcagcca ataaggcagg agctgccttc caggcagcgg  93300
aatggaagaa ggatgaagca aaacagaggg cagagtgtgc acatgtgcta tgtttaggga  93360
aggttttctg aagttcccac atagtacttc cacttacaaa cccaacaaaa aaggctatgg  93420
ctaaggcagc agggaggagc aaataatggg agcaactaga ttttgccaca gcacctatca  93480
cagtctggtt tataaatggt tctaggccaa gaacacccga tccctgctct tttttatatt  93540
ctaaagcatg tatctttata tttctcaagc aatattttct ctctttgaat cacagctcat  93600
ctgctgcatc atagggatcc caaaagaagg acccaaggaa cttgtctcag tcctctgtgc  93660
cccaagagga agctttgctt gtttgctttg ctgtcaatgc tgagggctcc tgtggctgcc  93720
tccactcaaa accctccagc atcaggacgt caaggctgtg atactgtacc ctgagctctt  93780
ggccagggcg agggagggga ggccaagcct acctacatgg tgtttcattt cctaaacgaa  93840
cccttacttc cacgcggtct gtccagctta gaaacttatt ttcagtagtg ttggtccttg  93900
gtccctggac aaaatgtaac agccaaagtc ctagaaaaag gcaagccagt tcctgccatt  93960
ttctttcact tctgcatttc ctcactatta tacgtgcctt ccattggagc aaaactgaat  94020
gccacgcata tgcacaggag ctgtgcgcgc tctgtctctc tcactcactc tttttctctc  94080
tctctctttc tctctcaatc tctctgtctc tatctatctc ttactcttta tctctcactc  94140
tctcactctt tctcactctt tctctcaatc tctttctcat tctctctcta tctttctctc  94200
tctctctctt tctcacacac acacactcac aaacccacac tcttattcac atctgctcac  94260
cctagccact caaacacaat ccctcattca gcctggaata agtccagagg gcgtgggcct  94320
gattcagaga caatcagttg ttctcatctg ggaaatgggg caatgtggtc atctctaggg  94380
accctccctg ctctaacatt ctttgaatgt ggtgggtcct gaggtggaag cactctgtcc  94440
ctgacttcta gtatatgtgg agatagggtt acacaaatat tttattgggc agaactttta  94500
taaaacaatt tatcataagc tatcgcagcc agcagcaatt tttccaacct ggattccacc  94560
aggggagctt ggccggtgtc tgagtgccac tttcagcttg agaagcaggt gactcagtga  94620
aaagagcaag gaggagacag aggcagattc agttcctagg ccctgggcca cccacctgca  94680
agtttgcagc ccagtcagtg caagtcagct aactgttctg aacctcagtt tctctgtctg  94740
taaattaagc taaaaattct tctttcaaag agtgtcagga tgaagtgaga tcgtgtatgt  94800
agggcattta acatagtgcc cgacacacag ggagcattcg gtaggtgcca gctctcctcc  94860
tggcaggaga gagagaaaca aggtgaaaag agtgaattaa agaagaggaa agtcaaatgg  94920
gaaaacaggg ggaggagata gaaagtgtat gaaaaggaaa gaatggtgcg caataacggc  94980
```

```
ggtgtaatgc caccaaaatc ccctcaacta cttctgggca gcacccttga cagagtgaat  95040
gcttttatga gaatgtaagc ggaatgtgtt cccagatttg cagtaatatt gccacctggt  95100
ggacaaaccc atgcaccttt gaattttcca aaatatttcg atgaactagc ttccagtcct  95160
agatgtattt tgaaagtgat ttgtaaattg taaggaacta ttcaaattct ttcattaatg  95220
tcacaaatca actgtgtcat ctgtatgcca cccactattc tgggtgctgg ggacacaaca  95280
gctcacaaat caggcaaagt ccctgctctc accaaaatga tatcctacgg gggattacag  95340
atacaaatac gtaaacagat ccatcgggag gaaactctca gatggaaatg agagctatga  95400
agataacaca acagtacatg acaatacaga gtgactggaa ccaggaacat ttctccgagg  95460
aataaaattt gaagcgagcc atgagagggt ctacaggtag agttcccagg cagagtgaac  95520
agccaagcac aaagctgcac caggagagag aggtgctcgc cgagagacag ggaggggagt  95580
gtggcaggtg agctcagaga ggggcagggc cacacacatc ggccacatgg gccttggtag  95640
tgagtcgaga tttgatccca gggtttattg gagtggataa gtaagcaagg tgactgaggt  95700
gctcgggttt acatttttat agttcaagct ggctgctggg tggaaaacgg aagttggcag  95760
accaaggaca gaatcaggca gacccatgtg gaagtttctc tagtggtcta ggtggtggct  95820
tgggtagcgt ggcagtattg gagctggaga aacgcagatg gattggagat ttgttttgga  95880
gtgacgccat tctgtcttgt caatggattg gcgaaaaaag aggcatcaaa gatgagttac  95940
acatcattga agtgagaact agggagatgc cagtacttta tttagtattt tctcagcagc  96000
tcaatccata aataattttt ggaagacaac aagcagtttc acaaactact tataagtcct  96060
caagttccaa ggtaattaac gtgggtgtct cattgcctca gagaacacag cgcagcacgg  96120
aaattctaca agacctgacg gacaggaaca tctccgactt cttggtaaaa acgtatcctg  96180
ctcttataag aagcaggtaa gaagaaatcc ttttatgctt tttatcctgg ctccctgtag  96240
aagatattaa ctagggacag aagataattt tctctctcaa tttatgtatg atcagggcag  96300
tagatttttt tctttttat ctgatttgag ggccccattc aacataaaaa gcaattgagg  96360
cacatacaag taaaatgtaa cttaagatta attcttttt tgttgtttgt ttgtttgttt  96420
ttacatttag ggcaagcagt cttaaatttt aacccacgta ttattaaaag ttatatcaga  96480
agaccataga agttattcaa aaatgcagcc acatatttta actagttaaa agagagagta  96540
aaaatttgga gggaggtgga ggagtatagg ggaaaaggta gaagaaaaag agaaaataag  96600
taagtggcaa aaaagagaaa ggaaaaagat agggtgggaa agaggcagcg ggacagtgtc  96660
tgagtccagc acacgccagg gcgagccagg tcaactgcag ctgtcatatt ctaactgtga  96720
attatcatct ttgatcactg ccctttgaga tgccaatgaa cttttcaaga aatatctagt  96780
tctcttggct ctccagctgt tcttatcagc cccatccagg atggaacagc tttggcagcc  96840
cgtatcagaa caagcagctt gacaggggca tgccatgcca ggagagagga tcctaaggaa  96900
gcgtggtcca gtccgcacag gctctggggc tttaagataa aacctcctgt ctaactttag  96960
taggactttc tgttgcttca cctgccagag ccctgaacga gggataaatt gacttaatta  97020
actagaacac actgcaaatg gtgaaagcat ttagcaaaac aaagaatgcc atccaagccc  97080
caaaataaaa gcagaataaa tagaatgcaa taaacagcaa ccatcccaaa ctgagttctc  97140
agcagcaaat ctccagtatg aaattttgga ttttgtgcgt gtgtgcttaa aggtggatga  97200
caatgacagt tcatgggatt gagctctggg gtccagagtt ggcatctgtt catttcccat  97260
tttgtcattt tacccttgat tgactgaatg tcagtgcctt aactttgggc tgtggagtga  97320
```

-continued gtcggaactc ccccgaggtg tgcaggtggt tgttagagtc tcatttttgc agggtggaag 97380
acaggagggc tgcagccttc attccacact gacatggtca ttgccgtgtg ttctgggtcc 97440
agatcaggca tattgacctg acatatgacc tgacaacagg accactcaga aagtccagca 97500
tgcgggatat gatttggaga gccagtgggg gaaatcatag gtcctttctc tgcatgtgta 97560
ttcaggcaat gtcccagggc tgggcggctt ccgcattgct tggatatcgg aaaatgcaaa 97620
aatgcccctg aagactgaga cttcagtctt caaaatgaat gtttgggaaa gaaagttaac 97680
ggcactgctg tacttgtggt attcattgca ttattttatt ttggctttca gcttaaagag 97740
caaattctgg gtcaatgaac agaggtaaga aactattttt atcagaatta aaatctcaga 97800
ttgattcatt gttgaaataa ttgcacactt ttaaaaggca cacctcacag ccatgaggag 97860
gggctgttct gtaggtgctc aggaagtcac aagacacgtc ctgaagaata tgtggctagg 97920
gacatcccag actcagaaga cactcagtgg tgcctcttct tggaggacat aagtgggggt 97980
ggcattccct gatgtggcgt ttcagagcat tctcacccaa aaaaagcttc taaaacctcc 98040
aagtatataa cagtttataa tactccaaca agagggcctt gtagcctaaa cccgggacac 98100
tccttggccc attcctttta agcttcaggg agtgtgggcc agccccagac tcaccccatt 98160
cctgaggcat cctggaggtt gaaatatttc cagaggttta gaacctcacc aagtgggact 98220
ctaggagcct gctgcctccc agcctccctc aggaactgca cctccagaac aggtgcgggg 98280
ctgacatgta tgtgctttcc tgggcagatt ctagaccgta cacatgaaat ctggctttca 98340
ggattgctct ccagagggac ctgtggggcc tcggctgaga cagagagtag gagtgaggca 98400
gtgattcaag gccctgagaa agagctcctc ctctgcttgg tataaccagc taattcattc 98460
tgttctgttg actttggctt ctgccctgcc tttgaagggt ttgaggccag ggagtgatgc 98520
actcagactg gtgtttccac acagtcactt cagacttcca gggcagtaca ggagatagat 98580
cccagggcca gtgaagaagc agagcacaag tccaggcagg agaggctaag ggcctccctg 98640
aacaggtgtg aggcacagaa gccccgagag gtagggatga caggatgaag atgggtcctg 98700
tgctgctaga agtacctgca aagcacagag gtggcacaga aaaggagtcc ttggctggga 98760
tgggaggaga tgacatgtga catgtgaaag aggacctgga gttggctcga tgctcccaaa 98820
agggaaaggt gccgagggga gctagcagcc atgcaaaggc agagacatgc aggcagtctg 98880
ggccatgagg agctctggaa gtgactcgat atgtccagaa taggccactc cagggaaggg 98940
ctgaggaagg atgaagttgg agaggggcac agaccagatg cagaagggcc tcagaggcca 99000
ggatgagggt ttggactcct tcctggaggc agcagcagtg ggaaaagagt taaaagctgg 99060
tttgtaaagt ggagccatgt tgctcgctgg tccaggcaat tcccccgaaa gttcatgttt 99120
ccctacaaaa cccgagagag ctactagtag gcgtgaagtt cgtggccctg gtctgaggat 99180
ttcctgtttc cttgtcaggt atggaggaat ttccattgga ggaaagctcc cagtcgtccc 99240
catcacgggg gaagcacttg ttgggttttt aagcgacctt ggccggatca tgaatgtgag 99300
cggggtatgt aaacagactg gagatttgag taggattttt gacttgctta actaccatga 99360
atgagaaact ctcatgagtg ataacaggaa aaaaaaatta aaaccgtctt gtttgtttgt 99420
ttacatggtt tttagggccc tatcactaga gaggcctcta aagaaatacc tgatttcctt 99480
aaacatctag aaactgaaga caacattaag gtacttgacc tatgtataat ctgctctgga 99540
gctaaaaatt tacctgagct ggttatttta tttttacttt cctaccttca ttaaattcca 99600
tccctcctcc tgctgaaatc tagcaaggaa tgtcttccag ctaccaaacc cttcctgctt 99660
ctcaaatttc ctttccttca ctgatttctg ctttaactag ctgttagtgc agcgtctcag 99720
atgtcctctc caccctctag gtgtggttta ataacaaagg ctggcatgcc ctggtcagct 99780
ttctcaatgt ggcccacaac gccatcttac gggccagcct gcctaaggac aggagccccg 99840
aggagtatgg aatcaccgtc attagccaac ccctgaacct gaccaaggag cagctctcag 99900
agattacagt gtaagccacc acagccccag cctcaccact ttcttgtcac cttctccact 99960
ctttgaacat cctgagagga ttctcaccac cgcgaagtgc tgatttggat ggtaatgctg 100020
tttagtcagg cacatatgaa catccgactt tcaaataagt gcctcacact tcacatacca 100080
gacctcttgg tcattctttc tccccaacat ttatgtggca agtaagttta catttggttc 100140
cattcccttt tggcttttga tagcaagttg ctcctggagc ttatacaatt attatctttg 100200
ctatgtgcaa agcagctgcc aggaactggc aaagttcagt aaacctttca gctccctcgg 100260
agtaattatc ttagattcca ggaatttcct cagaagagca tactttggag atgtcgacag 100320
agctttgcta ccctcaagct gaggctcttc ttgcacagtt tcagccagtg gagacagtgg 100380
ccttgtgcgt tttgtagtat gttcactcta tttgaggcct acatggagga ggggttggta 100440
ggagcacctt tgttagtgca aacttcagca acgttgtggg gtcctgattt tactatccta 100500
gcacacgctg agtgccagtg aacatgccca gggtcatcca ctaaaacctg ggccttggct 100560
ccttggtgtc ttcctctgga caccctaggg ccctagactg tcctctgtta attctcactc 100620
agccacactt tcgtgtgtct ccttccagtc atttgttcta agcttactac gtgtatggat 100680
gatatgatct gtagttttat caaggtagtg actaccacat aggatacctt tgtggaaatt 100740
agtaaaaatg ctcttttctg caggtggaca ctgtcccatg ccaggggtta tggcttgtac 100800
ataaagttca ggctggcttt agccccaact tacccctcag ccagatgcct tctatttgtc 100860
cgaggaaaga ataaatagag ccaagtccct gtacaacttg cctgccctct tttcacttaa 100920
atttacatca tgaacatttc cttgtgttac gatgtacttc ttgaaaatgt gatttaacaa 100980
gatgattatt aacaaaagat aaatctcaca gaccgtatgt ctgtcaacat agaaaattca 101040
agagactcta tagacagatt attagagcta atgagagcat tgcagtacat aagattaata 101100
taaacatcta tttctataca ccataaaaat aattagagaa tataataaaa agaaaggttg 101160
tctagaaata ttcacatgaa atagaaaggc aacccgcaaa tacccattta accttggtcc 101220
atatggatta agacagttta gtggagtgac agcttcaagg tagagaagag gaacctggag 101280
gccacacctg ggcgggtgta aggccttccc aaagcctgac tttgtatctt ctcctccttc 101340
tgctcttccc tcttcatcgc cctctccctg tgtctctggc cctgctgcag gctgaccact 101400
tcagtggatg ctgtggttgc catctgcgtg attttctcca tgtccttcgt cccagccagc 101460
tttgtccttt atttgatcca ggagcgggtg aacaaatcca agcacctcca gtttatcagt 101520
ggagtgagcc ccaccaccta ctgggtgacc aacttcctct gggacatcgt aagtgtcagt 101580
ttacagcgcc tccctcccct ccgtgggccc aaggtggagc ttgtgtgtgc tctgaaggac 101640
cagaccaaga ggggaggggt tctcacggtg ccagggctgc tgaaaggcac tgggccaagg 101700
gccttgtgta tctgctgtcc cttgacatct tctcagaaag gcacagaact aggagcccga 101760
agctaggaaa ggctgtgggg tgcagcttaa caactggtga acgggggctc tctatgtcct 101820
gcactgaggg gtcttctgac ccatcaaata atcactgcac cgcaggcatg agtctggcct 101880
tcctggcatc agtctggcgc tgagaaggta atatgaaggg gtctttcacc ccaagtcccc 101940
ttctcaaatc ctgccccacc ttcaaaaggg taaaggtaaa actttccctg tggtagggtc 102000
accagataaa tacaggacac ccagttaaat ttaatttcag atgatgaata atttttagta 102060
taagcatatg ctacttcaaa tattgcacag gacatatcta cactaaaaaa aaaaaaaaaa 102120
aaaaaaaaaa cctggttgtt tatctgaaac tcaaatttca ctaggcatcc tagattttta 102180
tttgccaaat ctggcaaccc cagccagtgg ccaaaataat aagaccttca cttattagat 102240
taaccaccgc tacagggaaa aatgaagaaa aaatatttat taaatcaata gcacactacc 102300
accttcctga caaccaaggt tggtgggggt agggaggggt caggatagcg taccctatta 102360
caggctgcag ggtcaaagga attggtagta aaggcctagt tataatgtaa cagggatcat 102420
tatgacatca accccaattt attctaggtg tcttgagtag taaaatctca acattttaag 102480
accaacatga gcctccattt catgtgatga taagatatac caactgatgg agaccaacac 102540
aaatgacctt ctcatccatg gtttttaaa atgatggtga atattggaat tcctgaagat 102600
atgatttcta tcttactcag cttagtaagc agctatcact taacaataca aaaccagaga 102660
ttatcagtag caactaaatt atttcctctc tcttctgtct acacgaggaa acactcataa 102720
atgcacgggg aggaggtcag aacctgaaag cctttctttg gataagagca tcaactgcag 102780
gtaccacatt ggccctgtga tgctaatata aaaggagcta ggcccaccgg taccgaaaag 102840
ttacttagaa aagtgcggag gcttttaatt ttactttttt taaaagataa gaaatagaat 102900
ttacacactt ggggctggcc cacgtgtttc tgtgtgtgtg tatgtgtgca cgcacgcgcg 102960
tgtgcgctta cagggatctc tgagcctatg gagagagatg tagctaggat agagtggaca 103020
tctgaggtgg gaggtgatac tagctggcag tccaatgaag gggtagaaga tggtaggcat 103080
catgttagca ggctttctga tgctccagaa ttttaaagct ggcctggaat ctcacctccg 103140
cgatccatca ttttggaact taggaccacc attagccagt ggcaaaaaaa aagttgaatg 103200
aaggaacaaa caattattgc ttatgtaatt cacttagcac atatatgatg ttttaaattc 103260
ttatatgtgt catctatttt tctttacttt aaaattttgc aacagttaca gacttatgga 103320
aaagtcacaa gtacagttga aaccttttt tcttagtcat ttgaaagtaa cttctcagca 103380
agatgcccct tctcatttat ttctctcttc ctgtctctct ctctcacacc cctcagcacg 103440
tccgatgtat acttcctaca aacgaggata caccccatac aaccacaaca caaactgtca 103500
acatgaggaa accagcactg atgtgtcatc accacctaat cctcacaccc cactcctctt 103560
tcgcccattg ccccagtgat gtctttcaga aaaaaggatc tagctcagaa tcatgcatga 103620
catttgattg tgctgtttct ttagtctcgt tcagcctgga agagttccac agtcttttgt 103680
taacactcat ggtcttgaca ctttgaggac tgcaggctgg ttattttgca gaatgtccct 103740
tggtctgagc ttgtctgagg tttcctcttg cccaggttga gggtgtgcat cttggcagca 103800
gtatcagcaa acagatgctg tgttctcact gcatcctatc aggtggcttc tgatttcaat 103860
ttgctctgtt actgatgatg ttcaattcgg tcacttaaga aggtgtctgc tgagcttctt 103920
cactgtaaaa ttactctttt cccctttata ataaatacaa atttcaggta gaggcacttc 103980
aaagatatat aaatatccta ttcattatac aattttccat ttattcatcc atttatttat 104040
ctctgtatgc agtcatggtt catgtgttaa tcaatggact atgatccaag actatcatta 104100
tttattttga tattcacatt atccccactg tggtcagtgg ggggccgttg aagctggctt 104160
ctgtatcgtc ttgacttggg tcctcatgcc cctggacctc ctccatgctc aatggcacag 104220
caagatattc caggctcatc cttccattat ccccattcct accctctccc caagaagccc 104280
tggttcctgc cagtgggaag tggccctcag aagccaaggt ctgagtgcta gatatgttca 104340
ttgcctctgg agcaccattg gtcccaggcc ttctcagtga tagaactagg gaagatatgg 104400
atgtacacac acaggtatgc acacacctct atctatagtt ctctatctac ctatacagtg 104460
aacactatga gctctccaaa accaactcca cagggctcat tctagttttt tttctttcca 104520
catctgtaac tcccttctcc aacagtgaga cgctggcttc tctcactccc aactcattta 104580
tctaccggac ctatacacct gaacagtgcc caactctgcc accatcccct ccccatgtgg 104640
atgccgtcct ctccctgctc cagctgcctc tgctgcatgc aggtcctcct cgttctgctc 104700
tggctctgat accctgcacc agatcagcct cctgtaagga tatctttctc atcccgttga 104760
ggcctccaca ccccacggca ggttgccccc tgaggaagcc cgtctctggt tcttgccctg 104820
ctcctgatca ccatggctcc tcccctaacc ccactgttgc cgtccccttt ctgtgcccag 104880
tatagtggct gtaggactaa attgtttaaa aagggtatca ttatttattt gagctttgtg 104940
aagccaagaa ctaggcttta agtttttctg aattctgaag acatgcttag aaagaagaat 105000
caacaaaact ttatgaccaa atagaaagag tgagagacca ggcagaattt tgtaattgat 105060
cctttcaaaa gatacaaact aaaggttccc ttggcaggga ggtagggcat ggggtggggt 105120
aggaggacta gtgacagctt aacatatgtt tgccaaccaa gaactgttta aaaagcaagt 105180
cgaatcagaa tcccagaccc tacgagctgg aggagcctgg ccccacccct cattttgcag 105240
agctggcagc aggtctgaga ggttaagtga cttgctctcc tcttctcttt ccgagatgaa 105300
ttattccgtg agtgctgggc tggtggtggg catcttcatc gggtttcaga agaaagccta 105360
cacttctcca gaaaaccttc ctgcccttgt ggcactgctc ctgctgtatg ggtaagccgt 105420
ttgggccatt agctaatgcc tctgaagaga agcctggtgg tgggggtggg ggatcatctc 105480
ctgacagaaa acctgggctg tcctgtggtg gtagcaccca caagtttagc ttccggcccc 105540
aggtagggtc tgaagctgat aaccagggat ctgtctggct tctgattctg actccactga 105600
cagaggtatc tctgaggcct ggtcctgtca gtgacaatga gagaagtccc acatgatctg 105660
aatctcctac tcaaactgag gccttgacca aagcctgggg gcagccattc cccaacccct 105720
cacccagctc tgactctcac tcatctgtgg ccaatctgtc cacctcagtg tccccatgtg 105780
aactggccaa gagttaccgc ccacagtaga agactccggc caaaaagctc ctcctgagtc 105840
agggacagag gatgacacag gggttacatc agcagagtta cagggcccag catgcaactt 105900
tctttcccac gtgtgtaaat ttgaatgagt aattcatcca tctcggcctc agtttcctca 105960
tctgtaaaag aaaatagtga tcctggtcct tcctctgtgg gccagtagag ccttgccaaa 106020
gcattgttct ccacatcttt ctcttggaaa tagagaattt gggaaccaac ctgactataa 106080
gctgtgaaga tgagctcact gggctcatct gagatgacct cagctgggct ttgctgaccc 106140
aggctagagt gggaggtgtt gcaggctgga gaaccctcct atgaattgta cagggctttg 106200
tagtttacag agtatataca cagctagcag cccatttgct cctcacaaaa ccccatgaag 106260
tggtcaaggc aggcatcatt atctccattt aaagttgagg cacagagacc aacaaatgga 106320
gtatctctct ggtcccctgg gactctggcc agttcacaca catcacctca ggtgtaaggg 106380
gagtgcatta tatccagacg tattgtaggt ggaatggaat gtggaactcc atcactctga 106440
gttgtctcat ttcacacaga tgggcggtca ttcccatgat gtacccagca tccttcctgt 106500
ttgatgtccc cagcacagcc tatgtggctt tatcttgtgc taatctgttc atcggcatca 106560
acagcagtgc tattaccttc atcttggaat tatttgagaa taaccgggtg agcataactt 106620
tcttggcttt tttgtttgat tagtaggata gtagagtatg tgttggtcga gcagagccag 106680
gggcaagcat cgtacatgta gcagctgtat gcggatgagt gccactttct tcctccctac 106740
ccccgaccct gcctcctttc cttccttcct tcctcccatc cttccttcct ctttccttct 106800
tctcctccct cctccctcct tcccccgtcc ctccttcctt ccttttcat tgcttccttc 106860 cttccttcgt ccctccttcc cttcctcttt ccttctgccc tctctccctt tttcctttca 106920
tcctccctcc atccctccct ccatccttcc ttctttcttc cttctttcct tcctataagc 106980
acctttttca tttctgtgct ctgaatgaaa tggttttctg tgtttattct gcaagcaaaa 107040
cttgattctt gcaataaact ttaagctttg cttactcttt cagaaaggtt ttctcaggga 107100
ctttgggtgt tgggttttac acacacacac atcaatacat ttgggtaatt tcaaaatcta 107160
aaaggaacaa aaaggcatac aatgaaaaaa tctccttcct acccctgttt cccactcatg 107220
cagttctctt ctccagaggc aaactcttac ttgagtttcc tgtgtgctct ggagacacat 107280
cagcagatcc ctatacggtc tttctcccgc tttcttatgg aaattgtaac actctgacat 107340
atactattcc ttgggcaagt taatcttgat gaagagactg ggtgttctcc atgctgaatg 107400
cctcactttt atgagctgcc aagcccagtt gtcccttcca cctgacctcc ccctgtccag 107460
agacagatgg ccaaactgaa tcataaaaag agggggaaaa aaagaaggca gtcgctgcag 107520
ggctgtcttt actccacact ccacactccc agtccccacc gctgtgtctg agtcctggct 107580
gtggctgtcc ttggaacatt tgcctcacca cgtgcctgtg tccccaggcg cctcaacctt 107640
tcctctcctc attagctctt cccagttcag agggtgggac cggccagcac atctgcactg 107700
ctgccctgcc acacccacct ccacctgcct ctgggcccca ctggggaaca caggacaaat 107760
ctgtgcggag gccccaccat gaaccgccca gacccgtgga cccctgagac tgactctttc 107820
cagatcttgt tagggtttcg tggctgctag gcaagtaacg aagcctcatc tgtcccatga 107880
atgataagaa attcagcatg tcagagtcag actctggaaa ggcgggggga taagaacaca 107940
gccccagcag atggccagag cacccaggtg actgaaagtg ctgctttgca gagctgtgtt 108000
tgccacaggc tcacagccca ctaagtctta agacagtttt ccttcagaat aattaaatag 108060
ccagcttaaa gcaactcaga acattttccc ctctgaggct gcacccattt agccaacatt 108120
tgctaagcac ccgccttcaa aaacctggta ttttcatgta aattatccga tacacagctg 108180
ctatggaaac ccccagtatc ccacaggaag ctccccagct cccagcagct gccggcccgt 108240
gtgagatcag gaggtcttta ccagctgaac accacgtgcc gggtgtgtgc tgatataaac 108300
aagcgtggcc cactcgtcct gccctccaga ggctcccgtt ccagtcggaa aaggacctgc 108360
ccacgaagtt tgcaacgata taagccacag tgtatgatcc tccataatac agcgtgtgac 108420
agagcagcag aggagcgagg cagataacat gctgcaggcc agaggcagcg ggaagagcca 108480
ggctgcaggg gctgggggag ccgtggtgga ggaagttcaa tttcagcctg tagatttcta 108540
ttagcccatt taataaataa tgaagtgcct actctgagct aatcattgtg caggtattta 108600
ggaaggacaa aaaaataatt aggactcagt gcccaccctc caggggccca ctgactagta 108660
gagaaagtag gcagattttt aaaaaattaa tcatgggaat gtgataagtg ctgggagaga 108720
ggaatggata ctttctcatg ggaatcttgg aaggcttgta agggaaggca ctctctgagc 108780
cagctgtcta aagaagaaca ggaatcttta agaaagcaga agggaaaaga gcattctttc 108840
ctgcttggag caataggtaa cagcctgcac atgcccaggc ctagaggcca aagagcacag 108900
tgattccaga aagagtgggg agaaagggta ggcagggaag gatgaggtaa tgtgggcgca 108960
ggtgtggagg ctggagaggg aggaggttgt gggactggga ggagccagat ggaatggaca 109020
gcagtggccc agccaggagc tatgctggcc tcgtacgcct cgatgtccct tctattttct 109080
caggggaggc tctgcccaac atgccaagtc cgaccacttg aaaacaagtc cctggcttaa 109140
cacagacccc agagagagtc tccaaccctc ctctccctag acaatggtag ttgccctgtg 109200

-continued aggggctgaa aagcagagct ggagatggct cagggcctgg tgttaacaaa tgccttgagg 109260
gctcctgttg tttcaaagtg agtctgcagg gagagctccc taagtggaca gcaggagggc 109320
tgcagcttct ctgcacattc ctgctgtcac ccccagagtc acctagggga ggggtaagga 109380
cagtaatgca ggttcctcac agttagcctc ggtgcccaca tggtactgag catagtaaat 109440
gtttagaaga tgctgcctgg ctagacaaag ggaagctcc cgcccactag aaacttgcag 109500
ggagccccag tccttgattg gtcatttaat tgattagctc cttggcctgg ccttgaggca 109560
ctgcttgtaa gtacttcatg acctccattg caaacccatg atgctctgct ggacaaatcc 109620
ctccagtggc cagtctggct gcaaggactc tctgtctgca ggccttgccc tgtgctgtcc 109680
tgtgagagca tctgggcccc acctgctgaa gagagggggg gtggggtttg ccccgtttcc 109740
aacagtccta cttctctgtt tcagacgctg ctcaggttca acgccgtgct gaggaagctg 109800
ctcattgtct tcccccactt ctgcctgggc cggggcctca ttgaccttgc actgagccag 109860
gctgtgacag atgtctatgc ccggtttggt gggtggtagc cgaggcccat ggagcatggg 109920
ccctgggtcc aaagctggga gggttaccgg gggggctcct gcatcagact gtggcagggg 109980
ctggtgctag gaggggacct tgttgggctg gaggtgtcct gccagctgga gaggattagg 110040
gtgcctctgt ttccatggct ggggagccac aggagggatg gagggcagcc cttatgaggc 110100
gggtgtttgg ctcttgctca gttcccacat aaggcctggt ctagtgggcc ctgtgctgtg 110160
gccaggtctg tggggtgagc tggggcggct gaagtggact caattcctgt tgatgcccag 110220
gtgaggagca ctctgcaaat ccgttccact gggacctgat tgggaagaac ctgtttgcca 110280
tggtggtgga aggggtggtg tacttcctcc tgaccctgct ggtccagcgc cacttcttcc 110340
tctcccaatg gtacgtccat gccacaccct gggccagtgg gcagctcagg gcatccagaa 110400
ctggacctta tacccacatg gtcatttctt tcctcaggag ccccactcca caatgttttt 110460
tctacattct caaagcctgg cttttctcca ataatacaag tagaggatcg ggttaaaata 110520
ggcacattca aatatgtgaa gagcatccac tttaaaatat ttaaaatgca gtgctattaa 110580
tttcaattgc tgatatttaa tccttctcat ttaattacca aatgtgtatt ttgattagat 110640
gatagtattg caaataacaa tggttacagg gtatccaaag tactaggaaa tagactaatg 110700
tatttatgag agaaaggaca cagcaggccc ctttgctaat tagagatttg ggagcatggg 110760
agtaatatgg gagccatgtg gaggggtgcg ggcagtgatc acgacccccc actcctggag 110820
gaaggtgggt agctgccaac cctgactttt gaccagggct tctcaaatgc caggttagct 110880
ggcaattgcc attcttccgc aggctcttcc tgaagctggg tgggcccctg cctcactccc 110940
ctctgcaatc cagtcctacc tttattgtcc tcacccaggg gcctgaattg ccaagcagca 111000
gcccttccta gcaagctttc cccaatagtg ttttgtttct taacttttcc tcctctcagg 111060
ctgagtgtgg tcacctgtaa atagattcca aggacttggt tttatgtttt gatccacagg 111120
gaattgattt attggaaatg aatctgcctt tctactcaca ggactgtgag aggtgaatga 111180
gatcacaggt gtcaacacac gcctgatgaa acaggataca caagcagttc tagttatggg 111240
agacagtgtc aggaattgtt gtccttggca ccctcagccc ctgcagaccc tttctgcagc 111300
cttggccata ccttttagag gcttttgtgt gggagagagc aggtcaggag gttgactacc 111360
caaattgact cattagcttc aaactctgat gtcaacacat ttgaatgagt cctgcctgct 111420
ttagggccta aagaggacca gagaagtaca ccatagtccc tggcttccag aaggtcaggg 111480
agggtttcaa agaagaggct gtgtctttaa gaatggggaa gattccattt ggtggggcag 111540

-continued gaggaggaga acattgaggg actggaaaca catgcggagg ctgggagacg ggaatgacca 111600
ataggactgg gaaccagggg gagatgccaa ttgctgacag aggagttagt gcaagaggta 111660
agtgagaagg gtaggtgggg ctggattgca gggctgtaac tacagctgca gagggagggc 111720
ttcaacctac agctgatggg gaacaacaga aggttttgag gcatgaggtg gcctgatgac 111780
aactctgttt tggaaaggtg gagttggcag ggcagactgg aggaagtggg aggctcggag 111840
gttagtaact accccttact gagtgcttgc tgtagaggaa gcattttagt cctgacggtg 111900
atcccaggcc ctgagtcttt actctgtgcc aggcactgtg ctgagttcat cttcagcaca 111960
atcctatgag acaggtattg ttaccctcct cctcatcaca tggttgaagt aggcaaggtt 112020
cagagaggtc caatgcccaa gatcacacat gaggaggcca ggactggaac ccaaggctga 112080
ctctggacat gagcacctga cctctctacc taatgcctaa tgcctctcct gctgggagcc 112140
ctttttagaa tttaagtctt aaaggatgga agcccagaag gaagcagaag caaggaagtg 112200
gaagagaggt cccatggaaa ggacagtgcc aaggacactg tacagccagc ccaatcctga 112260
ccccttttct tcatctagga ttgccgagcc cactaaggag cccattgttg atgaagatga 112320
tgatgtggct gaagaaagac aaagaattat tactggtgga aataaaactg acatcttaag 112380
gctacatgaa ctaaccaagg taagggaatg ggtatgagtt tggaggtgct ggttagatcc 112440
acagttggca tgatgttgcc attttccttc tatagaacaa ttgatatgct tatgcaagca 112500
atttggttcc cagttttatg tagggtcatc atccctgtgt tataactcgt cttccaagag 112560
catctaattc caatgtgtgt tccctgctat tcatctcggg cactgacaca gggcctcagt 112620
gagaatcact ccagctgagc atcattccct tttctgtgtt ctgtttctgc agagcatggg 112680
tcagcctcga gatgtctcag tactcaccac acctctgtgc ctgcccatgt caatatgtaa 112740
cctcctagtg ctggtagttt tctcctaaac catcctttgc tctttgttcc ctcttcccct 112800
ccttgctctc accctgtctc agttctcagt ccggtttctt cgtatcttgc agatttatcc 112860
aggcacctcc agcccagcag tggacaggct gtgtgtcgga gttcgccctg gagaggtggg 112920
tactctgcag accacgtgtg aaaggcttcc gaacatcagc tcttgtgcct gcctctcctc 112980
cccataaggc agagctattc aataggaaca taatgccata atgcaagtca catatgtaat 113040
tttaaatctt ccactagcca catgagaaaa gtaaaaagaa aataggtaaa attaatttca 113100
ttagtatttt ttattttact caatataacc aaaatattat ttcaaaatgt aattaataga 113160
aaaccttatt aatgaaatat ttgacaattt ctcgttgttt ttaagtcttt gaatctttac 113220
actcagggcc cgtgtcaact gggacttaga tgtgtttcaa gtgcttagta gccacatatg 113280
gctcgtggcc tctgatggca gcccaggtct aaaattcctc ccccagctca cacacacact 113340
taccctgggg cctgacattt tagaccttct tgatctctag ggccaggcta gctctgtgtt 113400
ttctcctagt gctttggcct cctgggagtg aatggtgccg gcaaaacaac cacattcaag 113460
atgctcactg gggacaccac agtgacctca ggggatgcca ccgtagcagg caagaggtga 113520
gtatcctgct cctcctgtct cagggagtct ctcacaggtc ctgtgagaag aataggaagg 113580
gtgatcatca gaccctatag tagggtggct ctgaggccct gaaagatctg tacagagaag 113640
gaggcctccc agagagcatg gcccaaaaag cccaacacat agacccaatg gaaaagtgaa 113700
ctgaattgtg atagttaaga gattcctctg ttgggatgga ttcttggaaa gacctgggaa 113760
gcactaagtg tgtggttctt aatctcttag aggtcacgga acctttttaag catctgatga 113820
atatttgtag cctattccta taaaaatgca ccattgcttc ccattacctc cctccacaca 113880
tttttacaaa acgtttcagg gagtttactg agccccaggt cacatttatg atcctgcagg 113940
agctcttgaa tcccaggtta agaacccctg tgatgaatga agaatccttc ctctgggttg 114000
agtttctaga taggggctca tgcatgggcc tttggggtag cctaacctgc attggctatt 114060
tgtaggctga tatttggctt tgccagacca aggagcatag agggaaaact ggcgtgtgcc 114120
cttggattct ggagggtgac tgctgctctc tgtaataaaa tgtgtttaaa cagactggtc 114180
ccctatgggc aggacagaga ggatgagctc tcactcatct gcctctttcc tggctgcagg 114240
aaaagcttga acagtaaaac ttcagcacac acaatagagg tgcccagagg aagcctctgc 114300
cctggtttat aagtggagtt aggtgctgct gacatctgtc cagcatctgc ttgactgggg 114360
cctcttcctc tctcctgaaa gccatcctca gcatggccca atgcccagtg ggcaggacga 114420
gtcctgagca cgcttcactg gctcagacag gatgaatttg attctttggc ctccatagcc 114480
agccctactg ggtttacaga aaagggacag gcaggggtga agccaggtca tggctgagtc 114540
catctcaaca gatccagctt cacctgcaag tgaccacgca ggtgacttcc tcatggtgac 114600
aaaaggagtc atggcagggt agagatatca taccatggca ggggaaagat atcatagaat 114660
tttccatgag cacatttatg agacatcaag ttacaactgt gtccaagtga ggcacagtct 114720
gacatccaga aggtaaaact gagctggacg ctagaaagaa actataggct taagacacag 114780
aattgggatt atatggtagg gtagctccca ctaatttgga aacgtaccct acttgcttcc 114840
ctgagtagtt ttaattggcc cagccatgcc tttggtggct tttgtcattg tggggaactg 114900
taatggtctc tctgtaccat cctatatcat ccatccttta ttcatagacc ctaagctata 114960
agaagaaaag gatgagatta gactaaatgt ctatgtatag tttattttcc atcttggcaa 115020
tatatttttt agtgggggtg aatatattag ccaaagggag ttggtggaac ccaactcact 115080
ctacccctgc tccctgcagg cctctcgctg tgggtagtta tctgactggc tcctctttca 115140
ttgctatctt tgccaataaa tacagataga gaagtttact tccatcggga cacatgcatc 115200
ttttctagtt acttcccaaa tgtctgaaaa ttattgataa atcatgaatc attttcttaa 115260
acctgatctt ccctctgttt ttaaactcac atgtgaggtg atctgatcca aaatgaaagc 115320
tgacttttgg cgtaacaggg attcaattaa tcctagacat ggaaacatgg aagaatctga 115380
caggattcag tttctaaccg aagggcccct gttttgattc ccaaatatcc catgcatttc 115440
tgaagccaaa taggagaaga gaagaagcag cttccttttc ccgttggcag aagcttctcc 115500
agccctagct ctatggtcat ccctccactc cttgaaggat actcagtaat tgcttttttt 115560
cttgcagtat tttaaccaat atttctgaag tccatcaaaa tatgggctac tgtcctcagt 115620
ttgatgcaat tgatgagctg ctcacaggac gagaacatct ttacctttat gcccggcttc 115680
gaggtgtacc agcagaagaa atcgaaaagg tgaaaaatgt tttgttgtgg ccacatagga 115740
gtctggttaa ttacaagcct gtttcatgag agtgcattct cttggagatg agaaactgaa 115800
gcgtgctatt cattcattca ttccaacaaa tgtttactat gtgtctactg tgtgccaagt 115860
actgttctag aaaccaggag tatagcagtg aacaagacag acaaaaaaaa atccccactc 115920
tcatatctaa caaaatgttg tatgcattta tcctctgact cagcaatcac acgtctaaga 115980
gtttatcctg aagatgcatc tcccacagtg caaaatgaat atgtataagg tgatccattg 116040
catttgtaat tgcaaaatgc tggaagttac ctaaatgttt agtcattgta gattggctga 116100
ataatttatg gtacagacac acaataaagt cttacgcaac tataaaaaag aagaagaaaa 116160
gtctcagtaa actgatatgg agatatttcc agtaaatact gttaaatgat aaaaagcaaa 116220
gtggaaaaca gaacatagag aacgctactt tgtatgtaag aaagaaggaa aaacaagaaa 116280

-continued gtaaacgtat gtctgcttac ctttgcaaat agaacgtaga aaggataaac cagaaaacaa 116340
tgaatttggt gatcaacaag aagaaaatgg gaagaaagaa aaatgggagg aaacagtact 116400
tctggggata tatttttgta tagttttaat ttttggaagc atgttaatgt tccacatatt 116460
caaaaaaaat cagtaagaat gggaagtagg caaaaatgaa aacaaaaaga aaacctaaca 116520
ctgacagcaa actaaataaa gtaacccaat tttatttcaa ataaatatca taatcttgca 116580
aaagggggat agagctaaca caaacaactg ctgaacacag tgtttgactc tatatcctca 116640
ttcttgggca gggtggagcg ggggagaaga actacaaata atttctgagt tctttttagt 116700
ttgtttttta tagtggtata ggcaaagtga ttctgaaaat tttagatgtg ttacaggatt 116760
aaataaatta ataaatgttt tgatgttatt gggacccaga attctcaccg tggaagaagg 116820
gacttacaaa tatggaaaag ggaaaagcaa gaaagaactg tgaggtcatg gataggaacc 116880
ggaggtagca ctgggaattc aggaatattt atatgcttgt gtttgtgggt gcatgcagat 116940
gtgttcatgt ttcatgcaca taggcatgta tatatagaca tatatttgca tgtgtgtatc 117000
tgtcttccga aaggctcaag aagcaaaaac accccagtag ccatgagcac acttagcact 117060
caggcttttg tcttaataac attccccact aaaagtaacc ctgattcctc caataaatga 117120
taagttccag ggctggaatg gcataggtat aaaatgaacc tggaatatct tatgccagaa 117180
agtaaggaag tgcttttaaa aaaaaaataa ggggctgggc atggtggctc acacctgtaa 117240
tcgcagcact ttgggaggcc aaggtaggaa gatcgcttga gcccaggagt tccagattag 117300
cctgtgcaac atagggagac cctgtctcta caaaaaatta gcaaacaaat tagctgggcc 117360
tggtggtgca cgcctatagt cccagctact caggtggctg aggtgggagg aatgcttgag 117420
cccaggaggt tgaggctgca gtgagctgtg atcaagccac tgctctccag cctgggaaac 117480
agagcaagac tctgtctctt aaaataataa taatataatt ttaaagaaat aaaagtaact 117540
ctgtacagat tgcttattgg ttacatggga gaaacataat aattttacaa tggagaaatt 117600
agacagcacc ttaactgggt gatcaaaatt aaccataagg ggcagatgga catctcatgc 117660
cccgagatgt gataccctgt gaaggacaca atttcactta tgtagaatcc agattggaga 117720
tatgtaacct gaatcttatc atgaggaaac atctgacaag ctccaaagaa ggaatattcc 117780
ttaaaaaaaa aaaaaggaga ctgtattctt caaaaacata agagtcataa aagacaaaga 117840
aagagctatg gaaatatctc tgatcgcagg aggctaaaca ggcataatga ctgaatagca 117900
gacaatagac tacatcttgt gcagaagaga aaaaaaatga tagaaggata ttattggacc 117960
aactgacaaa actgaactat gaacagtaga ttaggtaaat gtatcataac attaagttta 118020
ctgacattga taatgtactg tggttatgta agagaagatc tctattctta ggaaatatgc 118080
cctgaagtat ttaggagtga agggctgtga tgagtaattt accctcaaat gggtcacaaa 118140
aaattgtgtg tgagagagag aagggtttta ttagttaata attctatgaa ctatttttat 118200
tcctatatgt ttgtgtgagt ttgaaactat ttccaaataa aaagttaaaa atggagatta 118260
cattctagtg ggagggatag acgatctgta gataaatagg taaaatatcc agtacattag 118320
agagtgaaaa gtcctcaggg aaaagtaacg cagggaggaa ctgctggggc agggtttgca 118380
ttttgaggta gggtggccca gggagagcct gcagaggaga gaacctgaat gaagaactag 118440
aggtgagaga aggagccacg tgcacaccta gggaggaaca ttccaggcac gggggactag 118500
tatagaaggc agaagcatgg tgagcttgtc tccagtggct tccctagatc ccctcctgcg 118560
catgtgcaca cacacctggt gtctctgtca tcgttccctc acagcactgt cacgatctgc 118620
cagtattctg tttattttga ctgccacctc cccgcagtct gaggatagca gcaatggctg 118680

-continued tgttcacatt gttctccagt gcctggttca gtgcctggcg tatggtcagt gctccatagg 118740
tatgtgtcgg atgcacaagg ctttgggtgt aaccctcttg acgggtggga tcaacaggtc 118800
tgggactcac catcttctca aacagagcct tcctcctcca ctgctagcca tggtccagga 118860
cgctgggcga gacccactgt cttgctcttt gtaaggctga agtccatttc ccaggcggct 118920
acacccaaca gatgctgagc aggctgggcc accctgggat ccaagacaca gagagaaaga 118980
gcccctgtct ggcgcctgaa gcacatgcca gaggacagga gccagcagga gcctgtttca 119040
gcctagctgg ggatttcatt ctggaggcgt gagatctggg agcccaaggc tttgaactgg 119100
gggaggtttg gggtgtttgc ttgtcttctc caaatggcat ttctttctct tccctaggtt 119160
gcaaactgga gtattaagag cctgggcctg actgtctacg ccgactgcct ggctggcacg 119220
tacagtgggg gcaacaagcg gaaactctcc acagccatcg cactcattgg ctgcccaccg 119280
ctggtgctgc tggtaactgc gggcttgggc cgcaccaagg gcttaaacca agtgctgggt 119340
ctcttgggtt ggggaaatag gttctgggtc ggcagattta gaaactgcag cagtttggct 119400
ttagtctgga ctgtttcctg tgttgctcat tttgagcgat cagcccagtg tttggttcac 119460
acagctccgg agaaaaacaa gtcacggcac agccttgact tgggactgcg cacatcctgc 119520
gttcccagga tgtctcctgt ggggccatcg gctcacagcc gggaagttca gcccactctg 119580
cggcctgtcg gtgtctggtc cccatacagg agcactgagc tgggtcaaag gctcctgagc 119640
tgagccaggc caggcctgag gccatgccca cgcagcccaa ggatcatgag ggcacaggac 119700
atagcgggaa ccaaggaagt gacctgagtg acctccctgc cttctgacaa atgtatttgc 119760
aggattttct ttttttgagg agaattctgt cattgcctta atccacttta atcccctcgt 119820
gggctgaaat gggcccagga tggacgccac gcttctttac tcttggatcc acctcctgcc 119880
ttccctaccc tacaccaggg taccccctgtc ttgctcaagt gaggggagtg actgtgtgcg 119940
ccttctgtca gctcatcctc cacaggggag ccagcccagg gggaagcagt aatcagaagg 120000
gccagctccc agcctgtgcc cccaaccttc tctccacccc ccaggatgag cccaccacag 120060
ggatggaccc ccaggcacgc cgcatgctgt ggaacgtcat cgtgagcatc atcagagaag 120120
ggagggctgt ggtcctcaca tcccacaggc aagagattcc cagggctggg gaaggtgggt 120180
gggaatcctc tcctgctcac ctcctctctc ctgccccaca gcatggaaga atgtgaggca 120240
ctgtgtaccc ggctggccat catggtaaag ggcgcctttc gatgtatggg caccattcag 120300
catctcaagt ccaagtaagc agatggtggg gcgtgcccct tgttgccttc tgtggatcca 120360
cctggatcct gtgttctcca ttgacacttg gaagagtcct gctgctccgt catcccctgg 120420
ggcagaggca ggtggtggct gggcctcatt ctccagcagc agatggagaa ggccatcatg 120480
ctgataagaa actcctctat attggcctaa tttcctgtgg tcgaagactc gcccaagtct 120540
ctggatgggg catctgatca ggatgcatgc agagcctggc tgggatgagg gagggctgct 120600
accactgcct caatatttca ccacttatct caacagatcc gggacctgtg gcctatttac 120660
taagagtcca ctccaatgta ggaatggtta ggagaccaac tgacttgagg acccatcttt 120720
gtttttagaa tattgtatgc ttttgagttt gaaaaaagac catatgttat atgacaaacc 120780
aacaatggca gtaatcttga ataggattat ccttatcctg tacccacaca ttgtaaacta 120840
ttgtagataa ttccttatta ttaagagttt gcatgccaaa gctaacagtt taagattatc 120900
agcatattgc cgtgctcatt cacgttctga tatgctttat aacctagaaa agagcagagt 120960
tacaattact catttattta acaaacactt attaagagct cagaatataa gtcactaagc 121020

-continued tggttggtgg gaggaacagc acataaccca ccttatctat gctgaggtgc ataatcctga 121080
tgcacccaca ggagggtgtt acacagaaga tgtcatcctt tcatatgtgt cagagcagat 121140
aaataattga gagaaaggtc taatagatta gctgcttgtg gcaagtggac gtttgaccca 121200
tgatttattg agcaactaca acttggacac tgcatagata tctatagaaa tagcagcatg 121260
tcaggtcacc agacctgtgt cagcaacttc ctgtgtccaa ctgctggaga aagggaagtc 121320
tcctattcct ttccctccag ctccttaata tctccatgat agagggggtg agaggggagt 121380
gttccctgtg tggagggatg gtgagttttc tggagctgaa aggtaaacag cctttctcct 121440
ctgcatctta ctgcagagga gaacagccct agactgtgga ggaagctttg gagtcagtta 121500
tgactgacac aggataccag ggcatagggt actgacaccc gctagccgtg cacacactct 121560
ctggtggacc atcactcatc caagagaggg taaccagcca tcctgctgaa ggagaaagaa 121620
agcaccaatg gcccaagccc tagcagctcc attgtttcag gaagcttcct cagggaagtg 121680
ctgccttccc gagcctttgc tcccacctgg cccatcagcc cttaccacca ctcagtatgc 121740
actggtccac gtgtctttat gggcagtctt gggatcccca cactgggcta aaactacctt 121800
tgacggccag gtgcagtggc ttacacctgt aatcctatca ctttgggaag ctgaggcagg 121860
tggatcactt gaggtcagga gttcgagacc agcctggcca acacggtgaa accctgtctc 121920
tactaaaaat acaaaaatta gatgggcatg gtggtatgca cctgtaatcc cacctactcg 121980
ggaaactgag gcacaagaat tgcttgaact cagaaggcag aggttgcagt gaatcgagat 122040
cacaccactg cactccagcc tgggtgaaac agcaagactc tgtctcaaaa aataaaatag 122100
gctgggcgtg gtggctcatg cctgtaatcc cagcactttg ggaggccaag gcgggcggat 122160
cacttgaggt caggagttta agaccagcct ggccaacata gtgaaaccct gtctctacta 122220
aaaatacaaa aaaaaaaaaa aaaattagcc gagtgtggtg gcaggtgcct gtagttccag 122280
cctctcagga gactgaggca ggagaattgc ttgaacccag gaggcggagg ttgcagtgag 122340
ccaagatcat gccactgtac tccagcctgg gcaacggtga gactgtctca aataaaataa 122400
aataaaataa aataaaataa aataaaataa aataaataaa ataaaataaa taaaactacc 122460
tttgacttca gcaagtacga ttatcccaca ttaccatgca gacatttgat ctctaaaaac 122520
tggtatcaaa tgatttctcc agggactacc atggtttttc tctcctagtt ttcagtatgt 122580
acacaggtct atggtatggg cctttaatcc ccagtatttc ttttttttgtt gttcttgttt 122640 gggtttgttt cttgttttc ggttttttttg agacagggtc tcactctgtc acccaggctg 122700
gagtgcagtg gcatgatcat ggctcactgt agccttgacc tcctatgctc aagtgatcct 122760
cccgcctcag cctcccaagt agctgggacc acaggcatgt gccaccatgc cctgctaatt 122820
ttcgtagaga cagggtcttt cttgttgccc aggcttatct tacattcctg agctcaagtg 122880
atcctcccac ctctacctcc caaattgctg ggatttcagg tgtgagccac caagctgagc 122940
ttaatcccca aaatttctga tgagtctact ccttattttg ggattacctt aggcccaacc 123000
actaacagag gcctgtcctg cactgtgtgc atcccctaga tttggagatg gctatatcgt 123060
cacaatgaag atcaaatccc cgaaggacga cctgcttcct gacctgaacc ctgtggagca 123120
gttcttccag gggaacttcc caggcagtgt gcagagggag aggcactaca acatgctcca 123180
gttccaggtc tcctcctcct ccctggcgag gatcttccag ctcctcctct cccacaagga 123240
cagcctgctc atcgaggagt actcagtcac acagaccaca ctggaccagg caagttggcc 123300
ctggggcacc gagagctgag caaagactgg tccagaacac ccagtgtggg ttggaattgc 123360
cataagaggg aggcataaca ttcccgattt ttaacaaact cttgccctct gtttattggg 123420
gtaaaagctg atatatcaga aattgttttc taacaatatt ttttagtcat caggaaactt 123480
cattgattct tttttttaca ttttccttcc ctgtgatgct atggtgtgtt atttcattct 123540
tgctcgtttg tggtggtggt ttttccttca aatcagcttt attgatgtgt aattaacata 123600
cgatgaaaca caggttcttt gggaggccaa ggcaggagga tcacttgagc ccaggagttt 123660
aagacaggcc catgtaacaa agtgagactt tgtctctaca gaaaaaaaaa aaaaaaatca 123720
gaaaattagc caggcgtggt ggtgcatgcc tgtggtccca tctacatggg aggttgagga 123780
aggaagattg ctggagccca ggaggtcaag gctgcaatga gctgtgttca taccactgca 123840
ctctagtctg ggtgacagag caagcccctg tctcaaaaaa gcaaaacaaa acaaaaacac 123900
ctattttaaa tgtacagttt agtgagtttt gataaacgtg cattccatgt gtggttttta 123960
aaaatgtaat cacatttttt attgcggtaa aatataataa cataaaattg accatgccaa 124020
ccatgtttaa gtgcacagtg cagtggcact aagtacattt acattgttgt gcaaccgtta 124080
ccaccatccc cgatagaact ctttcatctt gcttcagtga aaatctgtgc ccattaaaca 124140
ctaactcacc acttactgcc cccctcgccc ttggcaacta ctgttctact ttctgtctct 124200
aaggctctga ctactataga tacctcatat aagtggaatc atacagtgtt tgtccttttg 124260
tgtctggctt attatgcgag gacttagcat aatgtcctca aggttcatcc gtgttgtatc 124320
atgtgccaga atttccttcc tttttcaggc cgaataatat tcctttgtac gtatatgtgc 124380
tacattttgt tcatccatct attcattcat tgatagacat ttgggttgtt tctgggtttt 124440
gtgtttttat atatgttttt ttaaaaataa acatctttag agacagttca gtaaagcagt 124500
ggaaacaggg aagtctccat ttaacccctg aggatctggc tcacctgcac cttctcatca 124560
gcattaagca gagggaggca cgagcaggag ccacctgcac actcaatgag gagctgaaca 124620
gggatcaatt accttttttt ttagttatta ggatgctgct agctgagaat ctgccttgcc 124680
ttgattaccc caatgtctgg tgcccaagtc ccttgagtcc tccagcagga actcctgtgg 124740
catcactcag gagtctagtc taagaagcta gctctgacca gggcagtggt ggccaggctt 124800
ctgtgagtgg gccagcctcc cccgggtagg acacaagcca taccagcagg gctgtatgtg 124860
aactgtggaa aatagagagc aaagtgggta ggtgggtgta gggtgctgtt ttcctggaaa 124920
tatctaccta atctcgctct tctcttacct ctaggtgttt gtaaattttg ctaaacagca 124980
gactgaaagt catgacctcc ctctgcaccc tcgagctgct ggagccagtc gacaagccca 125040
ggtacccctg ctgcttatgc agtccacagc ttgaggcagt tccttggctc agagcccagc 125100
tggttcactg ggcttgagtt gctccaaggc tcagatatgc ctcctacaga gagccccacc 125160
cacaccacgg tccctaccaa gtccccacca catcctcatc acatccttgc taagtccctg 125220
ccactgtgtg ttctgtgctg aagaactttt cattcagtag ttgtaggggt tcctattgta 125280
atcaggaaac catctggata gcatgggaga gcatttttga aaagaacttt cccatgtttt 125340
tgcttacagc aaaaaagctt ggatttgggg aataaggagc agagaaggta atagagaata 125400
ttagaatgtt ttgggtgctt gacatctatg tctggacatg tgtttgagtt tcaagggaag 125460
ggacttaact ggcacatcat ttcagtgtca gacacatttg gttagatcaa ggaatagcat 125520
ctgttgtagg aagagggctc tttgttcttt ataaaaatta caagaagatg gagaaagaag 125580
caataggagg tatgtctcct ggcttgtgat aactcttgga ataggtgctt gtaggttcct 125640
gccctggcac agtgccccat gtaaggagca caccacccaa gaaggagaga gctagagcaa 125700
gtactggagg aggcaccagc atcccaatgc cttggcttaa gcctgggatt gtagagggat 125760

-continued gaattagcca ctctcttctg acttacctgg agagtaaatc aaatcaaatc aagaagcaag 125820
gatatgcaaa aaccttattt ccccataaag tttttattct gcccagtttc tggattgcaa 125880
gaaaaaccaa atacagctaa tgattgaaac actgctgtct aaagcagtgc ttgtgatgaa 125940
ttttttccct tcctcttgac cagcagagac ctaatggcta cttggcaaaa ctgactttgt 126000
cttcccaccc cttacctgcc agagggccca gaaatgccta aggctccttt agttacagaa 126060
agtttgcttt tactgagatc ttccagccac tgattcccat ttatagatct ggtgattgct 126120
gttgacatca gttgaaaatt atttttaaaa accacttgca gttgcaaatc ctttttataa 126180
ctctgtaact cagaatatag aattgggtag caaaattgtt tcccagaatt accaatggtc 126240
tccccacccc tgcctggcat gttccctctt aaaggactaa tcccaccaca tcacctctgg 126300
gccaggcaga acatcagggg tgctgatgtt ctgtgatcta cagcagttaa ttccaaactt 126360
ttctccctta ttggatgaga tcatttttct attgtgtttt ttacattttt gttcacaaag 126420
attagaaaac ctgcaacaca cttattggca tatttttctg ataattttca tccaaaacct 126480
aattctgact ttacaacata ctatctttac aaaggtttgc aaaaattctt tcatatagca 126540
ttgtatatgt ctgtcatgaa ataatagtaa gtatattatt gtttacatta taccacttca 126600
aaataatttc ctttaaagta ttcttcaaac aagaaaaagg caatttctct caagaagttt 126660
tagagagaat ttacaacttg ctcctaagca aatgtgagaa cttcaggagg ttcatctggc 126720
cattggcttt acaactccaa attgtgagcc aggaccacac agatatttct ctagaaatca 126780
gcgtttgctt accaagaaca tttttactct ccaaaggact ccatcctgga aaacatgttt 126840
tgggataagg tcttatgcaa tcttatactc tgttattaaa accagtgagg gtcaaggtgt 126900
taatagatta agtagtgaca gatgatcaga caacttagaa acatcctaaa taggttaata 126960
attatgtgac catcgcatgt gcattcccaa attaggaaca actcagatca atttctaatc 127020
cttattctta cactgttcca gttcccccat ataactcgta tctttgtgtt agtttcagaa 127080
gtttctgaag taccctcagc cttgatgggg atcctcgcac cacctcaaat cctgttctca 127140
gccctaagaa ctgtgttagt catcctctta agaggatgtg tgattttaaa tcagataatg 127200
ggataaacca catttcgtct agactggtca ggcctttgtc cagtcccctc ctcgcccaca 127260
ctaccccagc tccacagcgg gcattggttc aggaattcaa cccacacttt ataactggag 127320
acagtatctc tccagttaaa aaggtcacct tggtgtccgc ttctcaagga acatggacat 127380
ctttattaat caaagcccaa gctttgatct ggagcctaat atcctgcact ccagctctca 127440
tctctcccct cccccagtca cactttcatg cttcccagag ccacccctac aggaagtggt 127500
caagggaatt ctatacctca gggctgacct aaattaggat ttcttggctt ttaagataat 127560
ggtaactttc ttaagctaaa aaagccccaa aagaccctgt aagagccctt ggaaacagca 127620
ccatgggtgt agcttccccc caggatgtaa gcatgtatgc acacatctcg tatgtgtgtc 127680
tttgtaacaa atgcctggat cttagtacca gggagacctg attcatagat ttcatagaga 127740
aggagagaaa gatggcccat aacctgggtg atctgacaga atcacagtgc cctcagctga 127800
gtgcccttca gaaattgatt gacaactgtt tagcttttga aatctaaaag tagtacagca 127860
tctcagaaaa ccaagatgac gcgagtccat gtgatctcct tccacaggac tgatctttca 127920
caccgctcgt tcctgcagcc agaaaggaac tctgggcagc tggaggcgca ggagcctgtg 127980
cccatatggt catccaaatg gactggccag cgtaaatgac cccactgcag cagaaaacaa 128040
acacacgagg agcatgcagc gaattcagaa agaggtcttt cagaaggaaa ccgaaactga 128100
cttgctcacc tggaacacct gatggtgaaa ccaaacaaat acaaaatcct tctccagacc 128160
ccagaactag aaaccccggg ccatcccact agcagctttg gcctccatat tgctctcatt 128220
tcaagcagat ctgcttttct gcatgtttgt ctgtgtgtct gcgttgtgtg tgattttcat 128280
ggaaaaataa aatgcaaatg cactcatcac aa 128312

<210> SEQ ID NO 2
<211> LENGTH: 7326
<212> TYPE: RNA
<213> ORGANISM: Homo sapiens

<400> SEQUENCE: 2
aggacacagc guccggagcc agaggcgcuc uuaacggcgu uuauguccuu ugcugucuga 60
ggggccucag cucugaccaa ucuggucuuc guguggucau uagcaugggc uucgugagac 120
agauacagcu uuugcucugg aagaacugga cccugcggaa aaggcaaaag auucgcuuug 180
ugguggaacu cguguggccu uuaucuuuau uucuggucuu gaucugguua aggaaugcca 240
acccgcucua cagccaucau gaaugccauu uccccaacaa ggcgaugccc ucagcaggaa 300
ugcugccgug gcuccagggg aucuucugca augugaacaa ucccuguuuu caaagcccca 360
ccccaggaga aucuccugga auugugucaa acuauaacaa cuccaucuug gcaaggguau 420
aucgagauuu ucaagaacuc cucaugaaug caccagagag ccagcaccuu ggccguauuu 480
ggacagagcu acacaucuug ucccaauuca uggacacccu ccggacucac ccggagagaa 540
uugcaggaag aggaauacga auaagggaua ucuugaaaga ugaagaaaca cugacacuau 600
uucucauuaa aaacaucggc cugucugacu caguggucua ccuucugauc aacucucaag 660
uccguccaga gcaguucgcu cauggagucc cggaccuggc gcugaaggac aucgccugca 720
gcgaggcccu ccuggagcgc uucaucaucu ucagccagag acgcggggca aagacggugc 780
gcuaugcccu gugcucccuc ucccagggca cccuacagug gauagaagac acucuguaug 840
ccaacgugga cuucuucaag cucuuccgug ugcuucccac acuccuagac agccguucuc 900
aagguaucaa ucugagaucu uggggaggaa uauuaucuga uaugucacca agaauucaag 960
aguuuaucca ucggccgagu augcaggacu ugcugugggu gaccaggccc cucaugcaga 1020
augguggucc agagaccuuu acaaagcuga ugggcauccu gucugaccuc cugugugggcu 1080 accccgaggg agguggcucu cgggugcucu ccuucaacug guaugaagac aauaacuaua 1140
aggccuuucu ggggauugac uccacaagga aggauccuau cuauucuuau gacagaagaa 1200
caacauccuu uuguaaugca uugauccaga gccuggaguc aaauccuuua accaaaaucg 1260
cuuggagggc ggcaaagccu uugcugaugg gaaaaauccu guacacuccu gauucaccug 1320
cagcacgaag gauacugaag aaugccaacu caacuuuuga agaacuggaa cacguuagga 1380
aguuggucaa agccugggaa gaaguagggc cccagaucug guacuucuuu gacaacagca 1440
cacagaugaa caugaucaga gauacccugg ggaacccaac aguaaaagac uuuuugaaua 1500
ggcagcuugg ugaagaaggu auuacugcug aagccauccu aaacuuccuc uacaagggcc 1560
cucgggaaag ccaggcugac gacauggcca acuucgacug gagggacaua uuuaacauca 1620
cugaucgcac ccuccgccug gucaaucaau accuggagug cuugguccug gauaaguuug 1680
aaagcuacaa ugaugaaacu cagcucaccc aacgugcccu cucucuacug gaggaaaaca 1740
uguucugggc cggaguggua uucccugaca uguaucccug gaccagcucu cuaccacccc 1800
acgugaagua uaagauccga auggacauag acguggugga gaaaaccaau aagauuaaag 1860
acagguauug ggauucuggu cccagagcug aucccgugga agauuuccgg uacaucuggg 1920

-continued gcggguuugc cuaucugcag gacaugguug aacaggggau cacaaggagc caggugcagg 1980
cggaggcucc aguuggaauc uaccuccagc agaugcccua ccccugcuuc guggacgauu 2040
cuuucaugau cauccugaac cgcuguuucc cuaucuucau ggugcuggca uggaucuacu 2100
cugucuccau gacugugaag agcaucgucu uggagaagga guugcgacug aaggagaccu 2160
ugaaaaauca gggugucucc aaugcaguga uuugguguac cugguuccug gacagcuucu 2220
ccaucauguc gaugagcauc uuccuccuga cgauauucau caugcaugga agaauccuac 2280
auuacagcga cccauucauc cucuuccugu ucuuguuggc uuucuccacu gccaccauca 2340
ugcugugcuu ucugcucagc accuucuucu ccaaggccag ucuggcagca gccuguagug 2400
gugucaucua uuucacccuc uaccugccac acauccugug cuucgccugg caggaccgca 2460
ugaccgcuga gcugaagaag gcugugagcu uacugucucc gguggcauuu ggauuuggca 2520
cugaguaccu gguucgcuuu gaagagcaag gccuggggcu gcaguggagc aacaucggga 2580
acagucccac ggaaggggac gaauucagcu uccugcuguc caugcagaug augcuccuug 2640
augcugcugu cuauggcuua cucgcuuggu accuugauca gguguuucca ggagacuaug 2700
gaaccccacu uccuugguac uuucuucuac aagagucgua uuggcuuggc ggugaagggu 2760
guucaaccag agaagaaaga gcccuggaaa agaccgagcc ccuaacagag gaaacggagg 2820
auccagagca cccagaagga auacacgacu ccuucuuuga acgugagcau ccaggguggg 2880
uuccuggggu augcgugaag aaucugguaa agauuuuuga gcccuguggc cggccagcug 2940
uggaccgucu gaacaucacc uucuacgaga accagaucac cgcauuccug ggccacaaug 3000
gagcugggaa aaccaccacc uuguccaucc ugacgggucu guugccacca accucuggga 3060
cugugcucgu uggggggaagg gacauugaaa ccagccugga ugcaguccgg cagagccuug 3120
gcauguguccc acagcacaac auccuguucc accaccucac gguggcugag cacaugcugu 3180
ucuaugccca gcugaaagga aagucccagg aggaggccca gcuggagaug gaagccaugu 3240
uggaggacac aggccuccac cacaagcgga augaagaggc ucaggaccua ucagguggca 3300
ugcagagaaa gcugucgguu gccauugccu uugugggaga ugccaaggug gugauucugg 3360
acgaacccac cucuggggug gacccuuacu cgagacgcuc aaucugggau cugcuccuga 3420
aguaucgcuc aggcagaacc aucaucaugu ccacucacca cauggacgag gccgaccucc 3480
uuggggaccg cauugccauc auugcccagg gaaggcucua cugcucaggc accccacucu 3540
uccugaagaa cugcuuuggc acaggcuugu acuuaaccuu ggugcgcaag augaaaaaca 3600
uccagagcca aaggaaaggc agugagggga ccugcagcug cucgucuaag gguuucucca 3660
ccacgugucc agcccacguc gaugaccuaa cuccagaaca aguccuggau ggggauguaa 3720
augagcugau ggauguaguu cuccaccaug uuccagaggc aaagcuggug gagugcauug 3780
gucaagaacu uaucuuccuu cuuccaaaua agaacuucaa gcacagagca uaugccagcc 3840
uuuucagaga gcuggaggag acgcuggcug accuugcucu cagcaguuuu ggaauuucug 3900
acacuccccu ggaagagauu uuucugaagg ucacggagga uucugauuca ggaccucugu 3960
uugcgggugg cgcucagcag aaaagagaaa acgucaaccc ccgacacccc ugcuuggguc 4020
ccagagagaa ggcuggacag acaccccagg acuccaaugu cugcuccca ggggcgccgg 4080
cugcucaccc agagggccag ccucccccag agccagagug cccaggcccg cagcucaaca 4140
cggggacaca gcugguccuc cagcaugugc aggcgcugcu ggucaagaga uuccaacaca 4200
ccauccgcag ccacaaggac uuccuggcgc agaucgugcu cccggcuacc uuuguguuuu 4260
uggcucugau gcuuucuauu guuaucccuc cuuuuggcga auaccccgcu uugacccuuc 4320
accccuggau auaugggcag caguacaccu ucuucagcau ggaugaacca ggcagugagc 4380
aguucacggu acuugcagac guccuccuga auaagccagg cuuuggcaac cgcugccuga 4440
aggaagggug gcuuccggag uaccccugug gcaacucaac acccuggaag acuccuucug 4500
uguccccaaa caucacccag cuguuccaga agcagaaaug gacacagguc aacccuucac 4560
cauccugcag gugcagcacc agggagaagc ucaccaugcu gccagagugc cccgagggug 4620
ccgggggccu cccgcccccc cagagaacac agcgcagcac ggaaauucua caagaccuga 4680
cggacaggaa caucuccgac uucuugguaa aaacguaucc ugcucuuaua agaagcagcu 4740
uaaagagcaa auucuggguc aaugaacaga gguauggagg aauuuccauu ggaggaaagc 4800
ucccagucgu ccccaucacg ggggaagcac uuguuggguu uuuaagcgac cuuggccgga 4860
ucaugaaugu gagcgggggc ccuaucacua gagaggccuc uaaagaaaua ccugauuucc 4920
uuaaacaucu agaaacugaa gacaacauua aggugugguu uaauaacaaa ggcuggcaug 4980
cccuggucag cuuucucaau guggcccaca acgccaucuu acgggccagc cugccuaagg 5040
acaggagccc cgaggaguau ggaaucaccg ucauuagcca accccugaac cugaccaagg 5100
agcagcucuc agagauuaca gugcugacca cuucagugga ugcugugguu gccaucugcg 5160
ugauuuucuc cauguccuuc gucccagcca gcuuuguccu uuauuugauc caggagcggg 5220
ugaacaaauc caagcaccuc caguuuauca guggagugag ccccaccacc uacugggguga 5280 ccaacuuccu cugggacauc augaauuauu ccgugagugc ugggcuggug gugggcaucu 5340
ucaucggguu ucagaagaaa gccuacacuu cuccagaaaa ccuuccugcc cuuguggcac 5400
ugcuccugcu guauggaugg gcggucauuc ccaugaugua cccagcaucc uuccuguuug 5460
auguccccag cacagccuau guggcuuuau cuugugcuaa ucuguucauc ggcaucaaca 5520
gcagugcuau uaccuucauc uuggaauuau uugagaauaa ccggacgcug cucagguuca 5580
acgccgugcu gaggaagcug cucauugucu ucccccacuu cugccugggc cggggccuca 5640
uugaccuugc acugagccag gcugugacag augucuaugc ccgguuuggu gaggagcacu 5700
cugcaaaucc guuccacugg gaccugauug ggaagaaccu guuugccaug gugguggaag 5760 gggugguguaa cuuccuccug acccugcugg uccagcgcca cuucuuccuc ucccaaugga 5820
uugccgagcc cacuaaggag cccauuguug augaagauga ugauguggcu gaagaaagac 5880
aaagaauuau uacuggugga aauaaaaacug acaucuuaag gcuacaugaa cuaaccaaga 5940
uuuauccagg caccuccagc ccagcagugg acaggcugug ugucggaguu cgcccuggag 6000
agugcuuugg ccuccuggga gugaauggug ccggcaaaac aaccacauuc aagaugcuca 6060
cuggggacac cacagugacc ucaggggaug ccaccguagc aggcaagagu auuuuaacca 6120
auauuucuga aguccaucaa aauaugggcu acuguccuca guuugaugca auugaugagc 6180
ugcucacagg acgagaacau cuuuaccuuu augcccggcu ucgaggugua ccagcagaag 6240
aaaucgaaaa gguugcaaac uggaguauua agagccuggg ccugacuguc uacgccgacu 6300
gccuggcugg cacguacagu gggggcaaca agcggaaacu cuccacagcc aucgcacuca 6360
uuggcugccc accgcuggug cugcuggaug agcccaccac agggauggac ccccaggcac 6420
gccgcaugcu guggaacguc aucgugagca ucaucagaga agggagggcu gugguccuca 6480
caucccacag cauggaagaa ugugaggcac uguguacccg gcuggccauc augguaaagg 6540
gcgccuuucg auguaugggc accauucagc aucucaaguc caaauuugga gauggcuaua 6600
ucgucacaau gaagaucaaa uccccgaagg acgaccugcu uccugaccug aacccugugg 6660
agcaguucuu ccaggggaac uucccaggca gugugcagag ggagaggcac uacaacaugc 6720
uccaguucca ggucuccucc uccucccugg cgaggaucuu ccagcuccuc cucucccaca 6780
aggacagccu gcucaucgag gaguacucag ucacacagac cacacuggac cagguguuug 6840
uaaauuuugc uaaacagcag acugaaaguc augaccuccc ucugcacccu cgagcugcug 6900
gagccagucg acaagcccag gacugaucuu ucacaccgcu cguuccugca gccagaaagg 6960
aacucugggc agcuggaggc gcaggagccu gugcccauau ggucauccaa auggacuggc 7020
cagcguaaau gaccccacug cagcagaaaa caaacacacg aggagcaugc agcgaauuca 7080
gaaagagguc uuucagaagg aaaccgaaac ugacuugcuc accuggaaca ccugauggug 7140
aaaccaaaca aauacaaaau ccuucuccag accccagaac uagaaacccc gggccauccc 7200
acuagcagcu uuggccucca uauugcucuc auuucaagca gaucugcuuu ucugcauguu 7260
ugucugugug ucugcguugu gugugauuuu cauggaaaaa uaaaaugcaa augcacucau 7320
cacaaa 7326

<210> SEQ ID NO 3
<211> LENGTH: 2273
<212> TYPE: PRT
<213> ORGANISM: Homo sapiens

<400> SEQUENCE: 3

Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190

His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255

```
Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
        275                 280                 285

His Arg Pro Ser Met Gln Asp Leu Leu Trp Val Thr Arg Pro Leu Met
    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Gly Ser Arg Val Leu Ser
                325                 330                 335

Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
        355                 360                 365

Phe Cys Asn Ala Leu Ile Gln Ser Leu Glu Ser Asn Pro Leu Thr Lys
    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
        435                 440                 445

Asn Met Ile Arg Asp Thr Leu Gly Asn Pro Thr Val Lys Asp Phe Leu
    450                 455                 460

Asn Arg Gln Leu Gly Glu Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
        515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
    610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                645                 650                 655

Ile Phe Met Val Leu Ala Trp Ile Tyr Ser Val Ser Met Thr Val Lys
            660                 665                 670
```

```
Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
            725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
        755                 760                 765

Tyr Phe Thr Leu Tyr Leu Pro His Ile Leu Cys Phe Ala Trp Gln Asp
    770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
            805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
        835                 840                 845

Val Tyr Gly Leu Leu Ala Trp Tyr Leu Asp Gln Val Phe Pro Gly Asp
    850                 855                 860

Tyr Gly Thr Pro Leu Pro Trp Tyr Phe Leu Leu Gln Glu Ser Tyr Trp
865                 870                 875                 880

Leu Gly Gly Glu Gly Cys Ser Thr Arg Glu Glu Arg Ala Leu Glu Lys
            885                 890                 895

Thr Glu Pro Leu Thr Glu Glu Thr Glu Asp Pro Glu His Pro Glu Gly
            900                 905                 910

Ile His Asp Ser Phe Phe Glu Arg Glu His Pro Gly Trp Val Pro Gly
        915                 920                 925

Val Cys Val Lys Asn Leu Val Lys Ile Phe Glu Pro Cys Gly Arg Pro
    930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
            965                 970                 975

Thr Gly Leu Leu Pro Pro Thr Ser Gly Thr Val Leu Val Gly Gly Arg
            980                 985                 990

Asp Ile Glu Thr Ser Leu Asp Ala  Val Arg Gln Ser Leu  Gly Met Cys
        995                 1000                 1005

Pro Gln  His Asn Ile Leu Phe  His His Leu Thr Val  Ala Glu His
    1010                 1015                 1020

Met Leu  Phe Tyr Ala Gln Leu  Lys Gly Lys Ser Gln  Glu Glu Ala
    1025                 1030                 1035

Gln Leu  Glu Met Glu Ala Met  Leu Glu Asp Thr Gly  Leu His His
    1040                 1045                 1050

Lys Arg  Asn Glu Glu Ala Gln  Asp Leu Ser Gly Gly  Met Gln Arg
    1055                 1060                 1065

Lys Leu  Ser Val Ala Ile Ala  Phe Val Gly Asp Ala  Lys Val Val
    1070                 1075                 1080

Ile Leu  Asp Glu Pro Thr Ser  Gly Val Asp Pro Tyr  Ser Arg Arg
```

```
    1085                1090                1095

Ser Ile  Trp Asp Leu Leu Leu  Lys Tyr Arg Ser Gly  Arg Thr Ile
    1100                1105                1110

Ile Met  Ser Thr His His Met  Asp Glu Ala Asp Leu  Leu Gly Asp
    1115                1120                1125

Arg Ile  Ala Ile Ile Ala Gln  Gly Arg Leu Tyr Cys  Ser Gly Thr
    1130                1135                1140

Pro Leu  Phe Leu Lys Asn Cys  Phe Gly Thr Gly Leu  Tyr Leu Thr
    1145                1150                1155

Leu Val  Arg Lys Met Lys Asn  Ile Gln Ser Gln Arg  Lys Gly Ser
    1160                1165                1170

Glu Gly  Thr Cys Ser Cys Ser  Ser Lys Gly Phe Ser  Thr Thr Cys
    1175                1180                1185

Pro Ala  His Val Asp Asp Leu  Thr Pro Glu Gln Val  Leu Asp Gly
    1190                1195                1200

Asp Val  Asn Glu Leu Met Asp  Val Val Leu His His  Val Pro Glu
    1205                1210                1215

Ala Lys  Leu Val Glu Cys Ile  Gly Gln Glu Leu Ile  Phe Leu Leu
    1220                1225                1230

Pro Asn  Lys Asn Phe Lys His  Arg Ala Tyr Ala Ser  Leu Phe Arg
    1235                1240                1245

Glu Leu  Glu Glu Thr Leu Ala  Asp Leu Gly Leu Ser  Ser Phe Gly
    1250                1255                1260

Ile Ser  Asp Thr Pro Leu Glu  Glu Ile Phe Leu Lys  Val Thr Glu
    1265                1270                1275

Asp Ser  Asp Ser Gly Pro Leu  Phe Ala Gly Gly Ala  Gln Gln Lys
    1280                1285                1290

Arg Glu  Asn Val Asn Pro Arg  His Pro Cys Leu Gly  Pro Arg Glu
    1295                1300                1305

Lys Ala  Gly Gln Thr Pro Gln  Asp Ser Asn Val Cys  Ser Pro Gly
    1310                1315                1320

Ala Pro  Ala Ala His Pro Glu  Gly Gln Pro Pro Pro  Glu Pro Glu
    1325                1330                1335

Cys Pro  Gly Pro Gln Leu Asn  Thr Gly Thr Gln Leu  Val Leu Gln
    1340                1345                1350

His Val  Gln Ala Leu Leu Val  Lys Arg Phe Gln His  Thr Ile Arg
    1355                1360                1365

Ser His  Lys Asp Phe Leu Ala  Gln Ile Val Leu Pro  Ala Thr Phe
    1370                1375                1380

Val Phe  Leu Ala Leu Met Leu  Ser Ile Val Ile Pro  Pro Phe Gly
    1385                1390                1395

Glu Tyr  Pro Ala Leu Thr Leu  His Pro Trp Ile Tyr  Gly Gln Gln
    1400                1405                1410

Tyr Thr  Phe Phe Ser Met Asp  Glu Pro Gly Ser Glu  Gln Phe Thr
    1415                1420                1425

Val Leu  Ala Asp Val Leu Leu  Asn Lys Pro Gly Phe  Gly Asn Arg
    1430                1435                1440

Cys Leu  Lys Glu Gly Trp Leu  Pro Glu Tyr Pro Cys  Gly Asn Ser
    1445                1450                1455

Thr Pro  Trp Lys Thr Pro Ser  Val Ser Pro Asn Ile  Thr Gln Leu
    1460                1465                1470

Phe Gln  Lys Gln Lys Trp Thr  Gln Val Asn Pro Ser  Pro Ser Cys
    1475                1480                1485
```

```
Arg Cys  Ser Thr Arg Glu Lys  Leu Thr Met Leu Pro  Glu Cys Pro
    1490                 1495                 1500

Glu Gly  Ala Gly Gly Leu Pro  Pro Pro Gln Arg Thr  Gln Arg Ser
    1505                 1510                 1515

Thr Glu  Ile Leu Gln Asp Leu  Thr Asp Arg Asn Ile  Ser Asp Phe
    1520                 1525                 1530

Leu Val  Lys Thr Tyr Pro Ala  Leu Ile Arg Ser Ser  Leu Lys Ser
    1535                 1540                 1545

Lys Phe  Trp Val Asn Glu Gln  Arg Tyr Gly Gly Ile  Ser Ile Gly
    1550                 1555                 1560

Gly Lys  Leu Pro Val Val Pro  Ile Thr Gly Glu Ala  Leu Val Gly
    1565                 1570                 1575

Phe Leu  Ser Asp Leu Gly Arg  Ile Met Asn Val Ser  Gly Gly Pro
    1580                 1585                 1590

Ile Thr  Arg Glu Ala Ser Lys  Glu Ile Pro Asp Phe  Leu Lys His
    1595                 1600                 1605

Leu Glu  Thr Glu Asp Asn Ile  Lys Val Trp Phe Asn  Asn Lys Gly
    1610                 1615                 1620

Trp His  Ala Leu Val Ser Phe  Leu Asn Val Ala His  Asn Ala Ile
    1625                 1630                 1635

Leu Arg  Ala Ser Leu Pro Lys  Asp Arg Ser Pro Glu  Glu Tyr Gly
    1640                 1645                 1650

Ile Thr  Val Ile Ser Gln Pro  Leu Asn Leu Thr Lys  Glu Gln Leu
    1655                 1660                 1665

Ser Glu  Ile Thr Val Leu Thr  Thr Ser Val Asp Ala  Val Val Ala
    1670                 1675                 1680

Ile Cys  Val Ile Phe Ser Met  Ser Phe Val Pro Ala  Ser Phe Val
    1685                 1690                 1695

Leu Tyr  Leu Ile Gln Glu Arg  Val Asn Lys Ser Lys  His Leu Gln
    1700                 1705                 1710

Phe Ile  Ser Gly Val Ser Pro  Thr Thr Tyr Trp Val  Thr Asn Phe
    1715                 1720                 1725

Leu Trp  Asp Ile Met Asn Tyr  Ser Val Ser Ala Gly  Leu Val Val
    1730                 1735                 1740

Gly Ile  Phe Ile Gly Phe Gln  Lys Lys Ala Tyr Thr  Ser Pro Glu
    1745                 1750                 1755

Asn Leu  Pro Ala Leu Val Ala  Leu Leu Leu Leu Tyr  Gly Trp Ala
    1760                 1765                 1770

Val Ile  Pro Met Met Tyr Pro  Ala Ser Phe Leu Phe  Asp Val Pro
    1775                 1780                 1785

Ser Thr  Ala Tyr Val Ala Leu  Ser Cys Ala Asn Leu  Phe Ile Gly
    1790                 1795                 1800

Ile Asn  Ser Ser Ala Ile Thr  Phe Ile Leu Glu Leu  Phe Glu Asn
    1805                 1810                 1815

Asn Arg  Thr Leu Leu Arg Phe  Asn Ala Val Leu Arg  Lys Leu Leu
    1820                 1825                 1830

Ile Val  Phe Pro His Phe Cys  Leu Gly Arg Gly Leu  Ile Asp Leu
    1835                 1840                 1845

Ala Leu  Ser Gln Ala Val Thr  Asp Val Tyr Ala Arg  Phe Gly Glu
    1850                 1855                 1860

Glu His  Ser Ala Asn Pro Phe  His Trp Asp Leu Ile  Gly Lys Asn
    1865                 1870                 1875
```

-continued

Leu Phe Ala Met Val Val Glu Gly Val Val Tyr Phe Leu Leu Thr
1880 1885 1890

Leu Leu Val Gln Arg His Phe Phe Leu Ser Gln Trp Ile Ala Glu
1895 1900 1905

Pro Thr Lys Glu Pro Ile Val Asp Glu Asp Asp Asp Val Ala Glu
1910 1915 1920

Glu Arg Gln Arg Ile Ile Thr Gly Gly Asn Lys Thr Asp Ile Leu
1925 1930 1935

Arg Leu His Glu Leu Thr Lys Ile Tyr Pro Gly Thr Ser Ser Pro
1940 1945 1950

Ala Val Asp Arg Leu Cys Val Gly Val Arg Pro Gly Glu Cys Phe
1955 1960 1965

Gly Leu Leu Gly Val Asn Gly Ala Gly Lys Thr Thr Thr Phe Lys
1970 1975 1980

Met Leu Thr Gly Asp Thr Thr Val Thr Ser Gly Asp Ala Thr Val
1985 1990 1995

Ala Gly Lys Ser Ile Leu Thr Asn Ile Ser Glu Val His Gln Asn
2000 2005 2010

Met Gly Tyr Cys Pro Gln Phe Asp Ala Ile Asp Glu Leu Leu Thr
2015 2020 2025

Gly Arg Glu His Leu Tyr Leu Tyr Ala Arg Leu Arg Gly Val Pro
2030 2035 2040

Ala Glu Glu Ile Glu Lys Val Ala Asn Trp Ser Ile Lys Ser Leu
2045 2050 2055

Gly Leu Thr Val Tyr Ala Asp Cys Leu Ala Gly Thr Tyr Ser Gly
2060 2065 2070

Gly Asn Lys Arg Lys Leu Ser Thr Ala Ile Ala Leu Ile Gly Cys
2075 2080 2085

Pro Pro Leu Val Leu Leu Asp Glu Pro Thr Thr Gly Met Asp Pro
2090 2095 2100

Gln Ala Arg Arg Met Leu Trp Asn Val Ile Val Ser Ile Ile Arg
2105 2110 2115

Glu Gly Arg Ala Val Val Leu Thr Ser His Ser Met Glu Glu Cys
2120 2125 2130

Glu Ala Leu Cys Thr Arg Leu Ala Ile Met Val Lys Gly Ala Phe
2135 2140 2145

Arg Cys Met Gly Thr Ile Gln His Leu Lys Ser Lys Phe Gly Asp
2150 2155 2160

Gly Tyr Ile Val Thr Met Lys Ile Lys Ser Pro Lys Asp Asp Leu
2165 2170 2175

Leu Pro Asp Leu Asn Pro Val Glu Gln Phe Phe Gln Gly Asn Phe
2180 2185 2190

Pro Gly Ser Val Gln Arg Glu Arg His Tyr Asn Met Leu Gln Phe
2195 2200 2205

Gln Val Ser Ser Ser Ser Leu Ala Arg Ile Phe Gln Leu Leu Leu
2210 2215 2220

Ser His Lys Asp Ser Leu Leu Ile Glu Glu Tyr Ser Val Thr Gln
2225 2230 2235

Thr Thr Leu Asp Gln Val Phe Val Asn Phe Ala Lys Gln Gln Thr
2240 2245 2250

Glu Ser His Asp Leu Pro Leu His Pro Arg Ala Ala Gly Ala Ser
2255 2260 2265

Arg Gln Ala Gln Asp

2270

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 168
<212> TYPE: DNA
<213> ORGANISM: Artificial Sequence
<220> FEATURE:
<223> OTHER INFORMATION: Pseudoexon 30-31(86) RNA

<400> SEQUENCE: 10
cugcagguau guacacaaau acaugcacag ccagcaucca ucuuuugcag ggacauuaau 60
gaucuuggcu cugagcagca cccuguccug ggaguucuaa aguccagaac agauuacagu 120
gagcaucucc ugggggauuu agagacauca aagaaggcug uguccgug 168

<210> SEQ ID NO 11
<211> LENGTH: 112
<212> TYPE: RNA
<213> ORGANISM: Artificial Sequence
<220> FEATURE:
<223> OTHER INFORMATION: Pseudoexon 30-31(86) RNA; smaller target

<400> SEQUENCE: 11
ucuuuugcag ggacauuaau gaucuuggcu cugagcagca cccuguccug ggaguucuaa 60
aguccagaac agauuacagu gagcaucucc ugggggauuu agagacauca aa 112

<210> SEQ ID NO 12
<211> LENGTH: 81
<212> TYPE: RNA
<213> ORGANISM: Artificial Sequence
<220> FEATURE:
<223> OTHER INFORMATION: Pseudoexon 30-31 (86) RNA; smaller target (AON area +10)

<400> SEQUENCE: 12
ugagcagcac ccuguccugg gaguucuaaa guccagaaca gauuacagug agcaucuccu 60
gggggauuua gagacaucaa a 81

<210> SEQ ID NO 13
<211> LENGTH: 39
<212> TYPE: RNA
<213> ORGANISM: Artificial Sequence
<220> FEATURE:
<223> OTHER INFORMATION: AON-1 Pseudoexon 30-31 (86) target site and flanking sequences (+10nt)

<400> SEQUENCE: 13
gggaguucua aaguccagaa cagauuacag ugagcaucu 39

<210> SEQ ID NO 14
<211> LENGTH: 28
<212> TYPE: RNA
<213> ORGANISM: Artificial Sequence
<220> FEATURE:
<223> OTHER INFORMATION: AON-1 Pseudoexon 30-31 (86) target site and flanking sequences (+5nt)

<400> SEQUENCE: 14
uucuaguaau cuguucugga cuuaguga 28

<210> SEQ ID NO 15
<211> LENGTH: 18
<212> TYPE: RNA
<213> ORGANISM: Artificial Sequence
<220> FEATURE:
<223> OTHER INFORMATION: AON-1 Pseudoexon 30-31 (86)

<400> SEQUENCE: 15
guaaucuguu cuggacuu 18

<210> SEQ ID NO 16
<211> LENGTH: 38
<212> TYPE: RNA
<213> ORGANISM: Artificial Sequence
<220> FEATURE:
<223> OTHER INFORMATION: AON-2 Pseudoexon 30-31 (86) target site and flanking sequences (+10nt)

<400> SEQUENCE: 16
ugagcagcac ccuguccugg gaguucuaaa guccagaa 38

<210> SEQ ID NO 17
<211> LENGTH: 28
<212> TYPE: RNA
<213> ORGANISM: Artificial Sequence
<220> FEATURE:
<223> OTHER INFORMATION: AON-2 Pseudoexon 30-31 (86) target site and flanking sequences (+5nt)

<400> SEQUENCE: 17
agcacccugu ccugggaguu cuaaaguc 28

<210> SEQ ID NO 18
<211> LENGTH: 18
<212> TYPE: RNA
<213> ORGANISM: Artificial Sequence

```
<220> FEATURE:
<223> OTHER INFORMATION: AON-2 Pseudoexon 30-31 (86)

<400> SEQUENCE: 18

uagaacuccc aggacagg                                                18


<210> SEQ ID NO 19
<211> LENGTH: 38
<212> TYPE: RNA
<213> ORGANISM: Artificial Sequence
<220> FEATURE:
<223> OTHER INFORMATION: AON-3 Pseudoexon 30-31 (86) target site and
      flanking sequences (+10nt)

<400> SEQUENCE: 19

uacagugagc aucuccuggg ggauuuagag acaucaaa                          38


<210> SEQ ID NO 20
<211> LENGTH: 28
<212> TYPE: RNA
<213> ORGANISM: Artificial Sequence
<220> FEATURE:
<223> OTHER INFORMATION: AON-3 Pseudoexon 30-31 (86) target site and
      flanking sequences (+5nt)

<400> SEQUENCE: 20

ugagcaucuc cugggggauu uagagaca                                     28


<210> SEQ ID NO 21
<211> LENGTH: 18
<212> TYPE: RNA
<213> ORGANISM: Artificial Sequence
<220> FEATURE:
<223> OTHER INFORMATION: AON-3 Pseudoexon 30-31 (86)

<400> SEQUENCE: 21

cuaaaucccc caggagau                                                18


<210> SEQ ID NO 22

<400> SEQUENCE: 22

000


<210> SEQ ID NO 23

<400> SEQUENCE: 23

000


<210> SEQ ID NO 24

<400> SEQUENCE: 24

000


<210> SEQ ID NO 25

<400> SEQUENCE: 25

000


<210> SEQ ID NO 26

<400> SEQUENCE: 26

000
```

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
<211> LENGTH: 420
<212> TYPE: RNA
<213> ORGANISM: Artificial Sequence
<220> FEATURE:
<223> OTHER INFORMATION: Pseudoexon 30-31 (345) RNA

<400> SEQUENCE: 30
gcauguaucu uuauauuucu caagcaauau uuucucucuu ugaaucacag cucaucugcu 60
gcaucauagg gaucccaaaa gaaggaccca aggaacuugu cucaguccuc ugugccccaa 120
gaggaagcuu ugcuuguuug cuuugcuguc aaugcugagg gcuccugugg cugccuccac 180
ucaaaacccu ccagcaucag gacgucaagg cugugauacu guacccugag cucuuggcca 240
gggcgaggga ggggaggcca agccuaccua cauggugguuu cauuuccuaa acgaacccuu 300
acuuccacgc ggucugucca gcuuagaaac uuauuuucag uaguguuggu ccuuggucc 360 uggacaaaau guaacagcca aaguccuaga aaaaggcaag ccaguuccug ccauuuucuu 420

<210> SEQ ID NO 31
<211> LENGTH: 327
<212> TYPE: RNA
<213> ORGANISM: Artificial Sequence
<220> FEATURE:
<223> OTHER INFORMATION: Pseudoexon 30-31 (345) RNA; smaller target

<400> SEQUENCE: 31
aagaaggacc caaggaacuu gucucagucc ucugugcccc aagaggaagc uuugcuuguu 60
ugcuuugcug ucaaugcuga gggcuccugu ggcugccucc acucaaaacc cuccagcauc 120
aggacgucaa ggcugugaua cuguacccug agcucuuggc cagggcgagg gaggggaggc 180
caagccuacc uacauggugu uucauuuccu aaacgaaccc uuacuuccac gcggucuguc 240
cagcuuagaa acuuauuuuc aguaguguug guccuugguc ccuggacaaa auguaacagc 300
caaaguccua gaaaaaggca agccagu 327

<210> SEQ ID NO 32
<211> LENGTH: 298
<212> TYPE: RNA
<213> ORGANISM: Artificial Sequence
<220> FEATURE:
<223> OTHER INFORMATION: Pseudoexon 30-31 (345) RNA; smaller target (AON
area +10)

<400> SEQUENCE: 32

-continued

```
aaggaacuug ucucaguccu cugugcccca agaggaagcu uugcuuguuu gcuuugcugu      60

caaugcugag ggcuccugug gcugccucca cucaaaaccc uccagcauca ggacgucaag     120

gcugugauac uguacccuga gcucuuggcc agggcgaggg aggggaggcc aagccuaccu     180

acauggugu u ucauuuccua aacgaacccu uacuuccacg cggucugucc agcuuagaaa     240

cuuauuuuca guaguguugg uccuugguccc cuggacaaaa uguaacagcc aaaguccu      298
```

<210> SEQ ID NO 33
<211> LENGTH: 39
<212> TYPE: RNA
<213> ORGANISM: Artificial Sequence
<220> FEATURE:
<223> OTHER INFORMATION: AON-1 Pseudoexon 30-31 (345) target site and flanking sequences (+10nt)

<400> SEQUENCE: 33
gcuuugcugu caaugcugag ggcuccugug gcugccucc 39

<210> SEQ ID NO 34
<211> LENGTH: 29
<212> TYPE: RNA
<213> ORGANISM: Artificial Sequence
<220> FEATURE:
<223> OTHER INFORMATION: AON-1 Pseudoexon 30-31 (345) target site and flanking sequences (+5nt)

<400> SEQUENCE: 34
gcugucaaug cugagggcuc cuguggcug 29

<210> SEQ ID NO 35
<211> LENGTH: 19
<212> TYPE: RNA
<213> ORGANISM: Artificial Sequence
<220> FEATURE:
<223> OTHER INFORMATION: AON-1 Pseudoexon 30-31 (345)

<400> SEQUENCE: 35
acaggagucc ucagcauug 19

<210> SEQ ID NO 36
<211> LENGTH: 39
<212> TYPE: RNA
<213> ORGANISM: Artificial Sequence
<220> FEATURE:
<223> OTHER INFORMATION: AON-2 Pseudoexon 30-31 (345) target site and flanking sequences (+10nt)

<400> SEQUENCE: 36
uaguguuggu ccuuggucccc uggacaaaau guaacagcc 39

<210> SEQ ID NO 37
<211> LENGTH: 29
<212> TYPE: RNA
<213> ORGANISM: Artificial Sequence
<220> FEATURE:
<223> OTHER INFORMATION: AON-2 Pseudoexon 30-31 (345) target site and flanking sequences (+5nt)

<400> SEQUENCE: 37
uugguccuug gucccuggac aaaauguaa 29

<210> SEQ ID NO 38
<211> LENGTH: 19
<212> TYPE: RNA
<213> ORGANISM: Artificial Sequence

```
<220> FEATURE:
<223> OTHER INFORMATION: AON-2 Pseudoexon 30-31 (345)

<400> SEQUENCE: 38

uuuuguccag ggaccaagg                                            19

<210> SEQ ID NO 39
<211> LENGTH: 39
<212> TYPE: RNA
<213> ORGANISM: Artificial Sequence
<220> FEATURE:
<223> OTHER INFORMATION: AON-3 Pseudoexon 30-31 (345) target site and
      flanking sequences (+10nt)

<400> SEQUENCE: 39

guccuugguc ccuggacaaa auguaacagc aaaaguccu                      39

<210> SEQ ID NO 40
<211> LENGTH: 29
<212> TYPE: RNA
<213> ORGANISM: Artificial Sequence
<220> FEATURE:
<223> OTHER INFORMATION: AON-3 Pseudoexon 30-31 (345) target site and
      flanking sequences (+5nt)

<400> SEQUENCE: 40

uggucccugg acaaaaugua acagcaaaa                                 29

<210> SEQ ID NO 41
<211> LENGTH: 19
<212> TYPE: RNA
<213> ORGANISM: Artificial Sequence
<220> FEATURE:
<223> OTHER INFORMATION: AON-3 Pseudoexon 30-31 (345)

<400> SEQUENCE: 41

cuguuacauu uuguccagg                                            19

<210> SEQ ID NO 42
<211> LENGTH: 39
<212> TYPE: RNA
<213> ORGANISM: Artificial Sequence
<220> FEATURE:
<223> OTHER INFORMATION: AON-4 Pseudoexon 30-31 (345) target site and
      flanking sequences (+10nt)

<400> SEQUENCE: 42

aaggaacuug ucucaguccu cugugcccca agaggaagc                      39

<210> SEQ ID NO 43
<211> LENGTH: 29
<212> TYPE: RNA
<213> ORGANISM: Artificial Sequence
<220> FEATURE:
<223> OTHER INFORMATION: AON-4 Pseudoexon 30-31 (345) target site and
      flanking sequences (+5nt)

<400> SEQUENCE: 43

acuugucuca guccucugug ccccaagag                                 29

<210> SEQ ID NO 44
<211> LENGTH: 19
<212> TYPE: RNA
<213> ORGANISM: Artificial Sequence
<220> FEATURE:
<223> OTHER INFORMATION: AON-4 Pseudoexon 30-31 (345)
```

<400> SEQUENCE: 44
ggggcacaga ggacugaga 19

<210> SEQ ID NO 45
<211> LENGTH: 19
<212> TYPE: RNA
<213> ORGANISM: Artificial Sequence
<220> FEATURE:
<223> OTHER INFORMATION: SON-1 Pseudoexon 30-31 (345) sense version of SEQ ID NO: 35

<400> SEQUENCE: 45
caaugcugag gacuccugu 19

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 11486
<212> TYPE: DNA
<213> ORGANISM: Artificial Sequence
<220> FEATURE:
<223> OTHER INFORMATION: pCI-Neo-Rho-ABCA4-30-31 wild-type

<400> SEQUENCE: 50
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagcccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720

-continued

```
aactagaatg cagtgaaaaa aatgctttat ttgtgaaatt tgtgatgcta ttgctttatt    780
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta attttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
```

ttttataggt taatgtcatg ataataatgg tttcttagac gtcaggtggc acttttcggg 3180
gaaatgtgcg cggaacccct atttgtttat ttttctaaat acattcaaat atgtatccgc 3240
tcatgagaca ataaccctga taaatgcttc aataatattg aaaaaggaag agtatgagta 3300
ttcaacattt ccgtgtcgcc cttattccct tttttgcggc attttgcctt cctgtttttg 3360
ctcacccaga aacgctggtg aaagtaaaag atgctgaaga tcagttgggt gcacgagtgg 3420
gttacatcga actggatctc aacagcggta agatccttga gagttttcgc cccgaagaac 3480
gttttccaat gatgagcact tttaaagttc tgctatgtgg cgcggtatta tcccgtattg 3540
acgccgggca agagcaactc ggtcgccgca tacactattc tcagaatgac ttggttgagt 3600
actcaccagt cacagaaaag catcttacgg atggcatgac agtaagagaa ttatgcagtg 3660
ctgccataac catgagtgat aacactgcgg ccaacttact tctgacaacg atcggaggac 3720
cgaaggagct aaccgctttt ttgcacaaca tgggggatca tgtaactcgc cttgatcgtt 3780
gggaaccgga gctgaatgaa gccataccaa acgacgagcg tgacaccacg atgcctgtag 3840
caatggcaac aacgttgcgc aaactattaa ctggcgaact acttactcta gcttcccggc 3900
aacaattaat agactggatg gaggcggata aagttgcagg accacttctg cgctcggccc 3960
ttccggctgg ctggtttatt gctgataaat ctggagccgg tgagcgtggg tctcgcggta 4020
tcattgcagc actggggcca gatggtaagc cctcccgtat cgtagttatc tacacgacgg 4080
ggagtcaggc aactatggat gaacgaaata gacagatcgc tgagataggt gcctcactga 4140
ttaagcattg gtaactgtca gaccaagttt actcatatat actttagatt gatttaaaac 4200
ttcattttta atttaaaagg atctaggtga agatcctttt tgataatctc atgaccaaaa 4260
tcccttaacg tgagttttcg ttccactgag cgtcagaccc cgtagaaaag atcaaaggat 4320
cttcttgaga tccttttttt ctgcgcgtaa tctgctgctt gcaaacaaaa aaaccaccgc 4380
taccagcggt ggtttgtttg ccggatcaag agctaccaac tctttttccg aaggtaactg 4440
gcttcagcag agcgcagata ccaaatactg ttcttctagt gtagccgtag ttaggccacc 4500
acttcaagaa ctctgtagca ccgcctacat acctcgctct gctaatcctg ttaccagtgg 4560
ctgctgccag tggcgataag tcgtgtctta ccgggttgga ctcaagacga tagttaccgg 4620
ataaggcgca gcggtcgggc tgaacggggg gttcgtgcac acagcccagc ttggagcgaa 4680
cgacctacac cgaactgaga tacctacagc gtgagctatg agaaagcgcc acgcttcccg 4740
aagggagaaa ggcggacagg tatccggtaa gcggcagggt cggaacagga gagcgcacga 4800
gggagcttcc agggggaaac gcctggtatc tttatagtcc tgtcgggttt cgccacctct 4860
gacttgagcg tcgatttttg tgatgctcgt caggggggcg gagcctatgg aaaaacgcca 4920
gcaacgcggc ctttttacgg ttcctggcct tttgctggcc ttttgctcac atggctcgac 4980
agatcttcaa tattggccat tagccatatt attcattggt tatatagcat aaatcaatat 5040
tggctattgg ccattgcata cgttgtatct atatcataat atgtacattt atattggctc 5100
atgtccaata tgaccgccat gttggcattg attattgact agttattaat agtaatcaat 5160
tacggggtca ttagttcata gcccatatat ggagttccgc gttacataac ttacggtaaa 5220
tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460

```
tacttggcag tacatctacg tattagtcat cgctattacc atggtgatgc ggttttggca   5520
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttcaaaggg agacaaaacg atccacaagc tagagatggt tattccccag   6360
ccccacacct agtcagtcac aaaaccctag ttttgatatt gcttgagcag aaaccagcct   6420
ccaagagaat aagaagaaag ggcctgggtc taaagaggag gaggaaaggg ttgggcacaa   6480
tttcttatgc ctagggattt gtcagcaact ttgaggctga ttatggaata ttttcttgtc   6540
ttccatgagg gagtacccct gtggcaactc aacaccctgg aagactcctt ctgtgtcccc   6600
aaacatcacc cagctgttcc agaagcagaa atggacacag gtcaaccctt caccatcctg   6660
caggtgcagc accagggaga agctcaccat gctgccagag tgccccgagg gtgccggggg   6720
cctcccgccc ccccaggtac ctgacctcca aacaacgggg ccccaggtct gcctgccaca   6780
gagggactag gggagtccct ggtatctcct gagtctctca caaactaaca tttcaaactg   6840
gcagttgagt aggggactaa accaaactcc ctgcaccctc tgggaggggc tccccacagg   6900
gcgctgtggc tgccaactgg aggaagccac tcaccaaaag cttcattttc caccagatac   6960
ttcctatttg atctagtaga aaaaatgtgt ttaagcacta aaaaaaatta agtcatatgt   7020
gctcattata gaaaaattag aaaacacagg taagtcagaa ggaaaaaaaa tcatcgcttg   7080
gatataaaca cagataatgt ttggtttgca gccacccaaa cagattatat tccaaatatt   7140
gtcttaaaat ctgatttact gcataattta ctaggaacat gcatccatgt caataaatag   7200
acatctgcat cacttttaat atctgtatat tatcccattg tttgaatttc ttttttttt   7260
ttttttttt ttttgagaca gagtctctct ctgtcaccca ggttggagtg cagcggtgtg   7320
atctcggctc actgcaacct ctgcctccca ggttcaattc ttgtgcctca gcccccccga   7380
gtagtgggga ttacaggcat gcaccatcat gcccgcctaa tttttttggt agttttagta   7440
cagatggggt tttaccatgt tggccaggct ggtgttgaac tcctggcctc aagtgatcta   7500
cccacttctg cctaccagag tgctaggatt acaagcgtca gccactgctc ctggcctaaa   7560
gttactttaa attaactgat ctcccattat tcgccactta ggttttttag ttttcaccat   7620
tataagcaat gctatgatgt acattcaaat ggaaatgtgt ttacacactt attaacagtc   7680
ttaattaaga agctctccat gtgctgtgtc tctaacatct gcaggtatgt acacaaatac   7740
atgcacagcc agcatccatc ttttgcaggg acattaatga tcttggctct gagcagcacc   7800
ctgtcctggg agttctaaag tccagaacag attacagtga gcatctcctg ggggatttag   7860
```

agacatcaaa gaaggctgtg tccgtggttg ataatgggcc tcccagctga cttgccaggg 7920
ctgggcctta gacagccctg tccaatgatt tgtcaatgaa taaactgttc ccaaacaggc 7980
tatgcagttc agtgggaaag cacaggtatg ggacacggag agccccaggt ggactacttg 8040
acctctctga gccttaattt tatcacctgt gaattgggaa taactgctta tttcataata 8100
ttattatgag gatttaatga aatcatgtgg gcaaggaatt atttagaatt agattcaact 8160
caagtgatga caaccccaaa ctaacagcag ataaaacaag acacaacttg tttctcactc 8220
atctaaaagt ctacgtgggt ggtgcacgat gttctattct ctttctcctc cacactaaac 8280
aggcctcagc ctcatcagcc aataaggcag gagctgcctt ccaggcagcg gaatggaaga 8340
aggatgaagc aaaacagagg gcagagtgtg cacatgtgct atgtttaggg aaggttttct 8400
gaagttccca catagtactt ccacttacaa acccaacaaa aaaggctatg gctaaggcag 8460
cagggaggag caaataatgg gagcaactag attttgccac agcacctatc acagtctggt 8520
ttataaatgg ttctaggcca agaacacccg atccctgctc ttttttatat tctaaagcat 8580
gtatctttat atttctcaag caatattttc tctctttgaa tcacagctca tctgctgcat 8640
catagggatc ccaaaagaag gacccaagga acttgtctca gtcctctgtg ccccaagagg 8700
aagctttgct tgtttgcttt gctgtcaatg ctgagggctc ctgtggctgc ctccactcaa 8760
aaccctccag catcaggacg tcaaggctgt gatactgtac cctgagctct tggccagggc 8820
gagggagggg aggccaagcc tacctacatg gtgtttcatt tcctaaacga acccttactt 8880
ccacgcggtc tgtccagctt agaaacttat tttcagtagt gttggtcctt ggtccctgga 8940
caaaatgtaa cagccaaagt cctagaaaaa ggcaagccag ttcctgccat tttctttcac 9000
ttctgcattt cctcactatt atacgtgcct tccattggag caaaactgaa tgccacgcat 9060
atgcacagga gctgtgcgcg ctctgtctct ctcactcact ctttttctct ctctctcttt 9120
ctctctcaat ctctctgtct ctatctatct cttactcttt atctctcact ctctcactct 9180
ttctcactct ttctctcaat ctctttctca ttctctctct atctttctct ctctctctct 9240
ttctcacaca cacacactca caaacccaca ctcttattca catctgctca ccctagccac 9300
tcaaacacaa tccctcattc agcctggaat aagtccagag ggcgtgggcc tgattcagag 9360
acaatcagtt gttctcatct gggaaatggg gcaatgtggt catctctagg gaccctccct 9420
gctctaacat tctttgaatg tggtgggtcc tgaggtggaa gcactctgtc cctgacttct 9480
agtatatgtg gagatagggt tacacaaata ttttattggg cagaactttt ataaaacaat 9540
ttatcataag ctatcgcagc cagcagcaat ttttccaacc tggattccac caggggagct 9600
tggccggtgt ctgagtgcca ctttcagctt gagaagcagg tgactcagtg aaaagagcaa 9660
ggaggagaca gaggcagatt cagttcctag gccctgggcc acccacctgc aagtttgcag 9720
cccagtcagt gcaagtcagc taactgttct gaacctcagt ttctctgtct gtaaattaag 9780
ctaaaaattc ttctttcaaa gagtgtcagg atgaagtgag atcgtgtatg tagggcattt 9840
aacatagtgc ccgacacaca gggagcattc ggtaggtgcc agctctcctc ctggcaggag 9900
agagagaaac aaggtgaaaa gagtgaatta aagaagagga aagtcaaatg ggaaaacagg 9960
gggaggagat agaaagtgta tgaaaaggaa agaatggtgc gcaataacgg cggtgtaatg 10020
ccaccaaaat cccctcaact acttctgggc agcacccttg acagagtgaa tgcttttatg 10080
agaatgtaag cggaatgtgt tcccagattt gcagtaatat tgccacctgg tggacaaacc 10140
catgcacctt tgaattttcc aaaatatttc gatgaactag cttccagtcc tagatgtatt 10200

```
ttgaaagtga tttgtaaatt gtaaggaact attcaaattc tttcattaat gtcacaaatc  10260

aactgtgtca tctgtatgcc acccactatt ctgggtgctg gggacacaac agctcacaaa  10320

tcaggcaaag tccctgctct caccaaaatg atatcctacg ggggattaca gatacaaata  10380

cgtaaacaga tccatcggga ggaaactctc agatggaaat gagagctatg aagataacac  10440

aacagtacat gacaatacag agtgactgga accaggaaca tttctccgag gaataaaatt  10500

tgaagcgagc catgagaggg tctacaggta gagttcccag gcagagtgaa cagccaagca  10560

caaagctgca ccaggagaga gaggtgctcg ccgagagaca gggaggggag tgtggcaggt  10620

gagctcagag aggggcaggg ccacacacat cggccacatg ggccttggta gtgagtcgag  10680

atttgatccc agggtttatt ggagtggata agtaagcaag gtgactgagg tgctcgggtt  10740

tacattttta tagttcaagc tggctgctgg gtggaaaacg gaagttggca gaccaaggac  10800

agaatcaggc agacccatgt ggaagtttct ctagtggtct aggtggtggc ttgggtagcg  10860

tggcagtatt ggagctggag aaacgcagat ggattggaga tttgttttgg agtgacgcca  10920

ttctgtcttg tcaatggatt ggcgaaaaaa gaggcatcaa agatgagtta cacatcattg  10980

aagtgagaac tagggagatg ccagtacttt atttagtatt ttctcagcag ctcaatccat  11040

aaataatttt tggaagacaa caagcagttt cacaaactac ttataagtcc tcaagttcca  11100

aggtaattaa cgtgggtgtc tcattgcctc agagaacaca gcgcagcacg gaaattctac  11160

aagacctgac ggacaggaac atctccgact tcttggtaaa aacgtatcct gctcttataa  11220

gaagcaggta agaagaaatc cttttatgct ttttatcctg gctccctgta gaagatatta  11280

actagggaca gaagataatt ttctctctca atttatgtat gatcagggca gtagattttt  11340

ttcttttta tctgatttga gggccccatt caacataaaa agcaattgag gcacatacaa  11400

gtaaaatgta acttaagatt aattctttt ttgttgtttg tttgtttgtt tttacattta  11460

gggcaagcag tcttcaccca gctttc                                      11486
```

<210> SEQ ID NO 51
<211> LENGTH: 11486
<212> TYPE: DNA
<213> ORGANISM: Artificial Sequence
<220> FEATURE:
<223> OTHER INFORMATION: pCI-Neo-Rho-ABCA4-30-31 c.4539+1100G

<400> SEQUENCE: 51

```
ttgtacaaag tggtgatctt gtacaaagtg gtgatgagag gtacctccga ggggtaaaca     60

gttgggtaaa cagtctctga agtcagctct gccattttct agctgtatgg ccctgggcaa    120

gtcaatttcc ttctctgtgc tttggtttcc tcatccatag aaaggtagaa agggcaaaac    180

accaaactct tggattacaa gagataattt acagaacacc cttggcacac agagggcacc    240

atgaaatgtc acgggtgaca cagccccctt gtgctcagtc cctggcatct ctaggggtga    300

ggagcgtctg cctagcaggt tcccaccagg aagctggatt tgagtggatg ggcgctgga     360

atcgtgaggg gcagaagcag gcaaagggtc ggggcgaacc tcactaacgt gccagttcca    420

agcacactgt gggcagccct ggccctgact caagcctctt gccttccagt tccggaactg    480

catgctcacc accatctgct gcggcaagaa cccactgggt gacgatgagg cctctgctac    540

cgtgtccaag acggagacga gccaggtggc cccggcctaa gacctgccta ggactctgtg    600

gccgactata ggcgtctccc atcccctaca cctgtcgacc cgggcggccg cttcccttta    660

gtgagggtta atgcttcgag cagacatgat aagatacatt gatgagtttg gacaaaccac    720

aactagaatg cagtgaaaaa aatgctttat ttgtgaaatt tgtgatgcta ttgctttatt    780
```

-continued

```
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta atttttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
```

-continued

```
ttttataggt taatgtcatg ataataatgg tttcttagac gtcaggtggc acttttcggg   3180
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
```

```
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttcaaaggg agacaaaacg atccacaagc tagagatggt tattccccag   6360
ccccacacct agtcagtcac aaaaccctag ttttgatatt gcttgagcag aaaccagcct   6420
ccaagagaat aagaagaaag ggcctgggtc taaagaggag gaggaaaggg ttgggcacaa   6480
tttcttatgc ctagggattt gtcagcaact ttgaggctga ttatggaata ttttcttgtc   6540
ttccatgagg gagtacccct gtggcaactc aacaccctgg aagactcctt ctgtgtcccc   6600
aaacatcacc cagctgttcc agaagcagaa atggacacag gtcaaccctt caccatcctg   6660
caggtgcagc accagggaga agctcaccat gctgccagag tgccccgagg gtgccggggg   6720
cctcccgccc ccccaggtac ctgacctcca aacaacgggg ccccaggtct gcctgccaca   6780
gagggactag gggagtccct ggtatctcct gagtctctca caaactaaca tttcaaactg   6840
gcagttgagt aggggactaa accaaactcc ctgcaccctc tgggaggggc tccccacagg   6900
gcgctgtggc tgccaactgg aggaagccac tcaccaaaag cttcatttc caccagatac    6960
ttcctatttg atctagtaga aaaaatgtgt ttaagcacta aaaaaaatta agtcatatgt   7020
gctcattata gaaaaattag aaaacacagg taagtcagaa ggaaaaaaaa tcatcgcttg   7080
gatataaaca cagataatgt ttggtttgca gccacccaaa cagattatat tccaaatatt   7140
gtcttaaaat ctgatttact gcataattta ctaggaacat gcatccatgt caataaatag   7200
acatctgcat cacttttaat atctgtatat tatcccattg tttgaatttc ttttttttt    7260
ttttttttt ttttgagaca gagtctctct ctgtcaccca ggttggagtg cagcggtgtg    7320
atctcggctc actgcaacct ctgcctccca ggttcaattc ttgtgcctca gcccccccga   7380
gtagtgggga ttacaggcat gcaccatcat gcccgcctaa ttttttggt agttttagta    7440
cagatggggt tttaccatgt tggccaggct ggtgttgaac tcctggcctc aagtgatcta   7500
cccacttctg cctaccagag tgctaggatt acaagcgtca gccactgctc ctggcctaaa   7560
gttactttaa attaactgat ctcccattat tcgccactta ggttttttag ttttcaccat   7620
tataagcaat gctatgatgt acattcaaat ggaaatgtgt ttacacactt attaacagtc   7680
ttaattaaga agctctccat gtgctgtgtc tctaacatct gcaggtatgt acacaaatac   7740
atgcacagcc agcatccatc ttttgcaggg acattaatga tcttggctct gagcagcacc   7800
ctgtcctggg agttctaaag tccagaacag attacggtga gcatctcctg gggatttag    7860
```

agacatcaaa gaaggctgtg tccgtggttg ataatgggcc tcccagctga cttgccaggg 7920
ctgggcctta gacagccctg tccaatgatt tgtcaatgaa taaactgttc ccaaacaggc 7980
tatgcagttc agtgggaaag cacaggtatg ggacacggag agccccaggt ggactacttg 8040
acctctctga gccttaattt tatcacctgt gaattgggaa taactgctta tttcataata 8100
ttattatgag gatttaatga aatcatgtgg gcaaggaatt atttagaatt agattcaact 8160
caagtgatga caaccccaaa ctaacagcag ataaaacaag acacaacttg tttctcactc 8220
atctaaaagt ctacgtgggt ggtgcacgat gttctattct ctttctcctc cacactaaac 8280
aggcctcagc ctcatcagcc aataaggcag gagctgcctt ccaggcagcg gaatggaaga 8340
aggatgaagc aaaacagagg gcagagtgtg cacatgtgct atgtttaggg aaggttttct 8400
gaagttccca catagtactt ccacttacaa acccaacaaa aaaggctatg gctaaggcag 8460
cagggaggag caaataatgg gagcaactag attttgccac agcacctatc acagtctggt 8520
ttataaatgg ttctaggcca agaacacccg atccctgctc ttttttatat tctaaagcat 8580
gtatctttat atttctcaag caatattttc tctctttgaa tcacagctca tctgctgcat 8640
catagggatc ccaaaagaag gacccaagga acttgtctca gtcctctgtg ccccaagagg 8700
aagctttgct tgtttgcttt gctgtcaatg ctgagggctc ctgtggctgc ctccactcaa 8760
aaccctccag catcaggacg tcaaggctgt gatactgtac cctgagctct tggccagggc 8820
gagggagggg aggccaagcc tacctacatg gtgtttcatt tcctaaacga acccttactt 8880
ccacgcggtc tgtccagctt agaaacttat tttcagtagt gttggtcctt ggtccctgga 8940
caaaatgtaa cagccaaagt cctagaaaaa ggcaagccag ttcctgccat tttctttcac 9000
ttctgcattt cctcactatt atacgtgcct tccattggag caaaactgaa tgccacgcat 9060
atgcacagga gctgtgcgcg ctctgtctct ctcactcact ctttttctct ctctctcttt 9120
ctctctcaat ctctctgtct ctatctatct cttactcttt atctctcact ctctcactct 9180
ttctcactct ttctctcaat ctctttctca ttctctctct atctttctct ctctctctct 9240
ttctcacaca cacacactca caaacccaca ctcttattca catctgctca ccctagccac 9300
tcaaacacaa tccctcattc agcctggaat aagtccagag ggcgtgggcc tgattcagag 9360
acaatcagtt gttctcatct gggaaatggg gcaatgtggt catctctagg gaccctccct 9420
gctctaacat tctttgaatg tggtgggtcc tgaggtggaa gcactctgtc cctgacttct 9480
agtatatgtg gagatagggt tacacaaata ttttattggg cagaactttt ataaaacaat 9540
ttatcataag ctatcgcagc cagcagcaat ttttccaacc tggattccac caggggagct 9600
tggccggtgt ctgagtgcca ctttcagctt gagaagcagg tgactcagtg aaaagagcaa 9660
ggaggagaca gaggcagatt cagttcctag gccctgggcc acccacctgc aagtttgcag 9720
cccagtcagt gcaagtcagc taactgttct gaacctcagt ttctctgtct gtaaattaag 9780
ctaaaaattc ttctttcaaa gagtgtcagg atgaagtgag atcgtgtatg tagggcattt 9840
aacatagtgc ccgacacaca gggagcattc ggtaggtgcc agctctcctc ctggcaggag 9900
agagagaaac aaggtgaaaa gagtgaatta aagaagagga aagtcaaatg ggaaaacagg 9960
gggaggagat agaaagtgta tgaaaaggaa agaatggtgc gcaataacgg cggtgtaatg 10020
ccaccaaaat cccctcaact acttctgggc agcacccttg acagagtgaa tgcttttatg 10080
agaatgtaag cggaatgtgt tcccagattt gcagtaatat tgccacctgg tggacaaacc 10140
catgcacctt tgaattttcc aaaatatttc gatgaactag cttccagtcc tagatgtatt 10200
ttgaaagtga tttgtaaatt gtaaggaact attcaaattc tttcattaat gtcacaaatc 10260
aactgtgtca tctgtatgcc acccactatt ctgggtgctg gggacacaac agctcacaaa 10320
tcaggcaaag tccctgctct caccaaaatg atatcctacg gggattaca gatacaaata 10380 cgtaaacaga tccatcggga ggaaactctc agatggaaat gagagctatg aagataacac 10440
aacagtacat gacaatacag agtgactgga accaggaaca tttctccgag gaataaaatt 10500
tgaagcgagc catgagaggg tctacaggta gagttcccag gcagagtgaa cagccaagca 10560
caaagctgca ccaggagaga gaggtgctcg ccgagagaca gggaggggag tgtggcaggt 10620
gagctcagag aggggcaggg ccacacacat cggccacatg ggccttggta gtgagtcgag 10680
atttgatccc agggtttatt ggagtggata agtaagcaag gtgactgagg tgctcgggtt 10740
tacattttta tagttcaagc tggctgctgg gtggaaaacg gaagttggca gaccaaggac 10800
agaatcaggc agacccatgt ggaagtttct ctagtggtct aggtggtggc ttgggtagcg 10860
tggcagtatt ggagctggag aaacgcagat ggattggaga tttgttttgg agtgacgcca 10920
ttctgtcttg tcaatggatt ggcgaaaaaa gaggcatcaa agatgagtta cacatcattg 10980
aagtgagaac tagggagatg ccagtacttt atttagtatt ttctcagcag ctcaatccat 11040
aaataatttt tggaagacaa caagcagttt cacaaactac ttataagtcc tcaagttcca 11100
aggtaattaa cgtgggtgtc tcattgcctc agagaacaca gcgcagcacg gaaattctac 11160
aagacctgac ggacaggaac atctccgact tcttggtaaa aacgtatcct gctcttataa 11220
gaagcaggta agaagaaatc cttttatgct ttttatcctg gctccctgta gaagatatta 11280
actagggaca gaagataatt ttctctctca atttatgtat gatcagggca gtagattttt 11340 ttcttttta tctgatttga gggccccatt caacataaaa agcaattgag gcacatacaa 11400
gtaaaatgta acttaagatt aattcttttt ttgttgtttg tttgtttgtt tttacattta 11460
gggcaagcag tcttcaccca gctttc 11486

<210> SEQ ID NO 52
<211> LENGTH: 11486
<212> TYPE: DNA
<213> ORGANISM: Artificial Sequence
<220> FEATURE:
<223> OTHER INFORMATION: pCI-Neo-Rho-ABCA4-30-31 c.4539+1106T

<400> SEQUENCE: 52
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720
aactagaatg cagtgaaaaa aatgctttat ttgtgaaatt tgtgatgcta ttgctttatt 780

-continued tgtaaccatt ataagctgca ataaacaagt taacaacaac aattgcattc attttatgtt 840
tcaggttcag ggggagatgt gggaggtttt ttaaagcaag taaaacctct acaaatgtgg 900
taaaatccga taaggatcga tccgggctgg cgtaatagcg aagaggcccg caccgatcgc 960
ccttcccaac agttgcgcag cctgaatggc gaatggacgc gccctgtagc ggcgcattaa 1020
gcgcggcggg tgtggtggtt acgcgcagcg tgaccgctac acttgccagc gccctagcgc 1080
ccgctccttt cgctttcttc ccttcctttc tcgccacgtt cgccggcttt ccccgtcaag 1140
ctctaaatcg ggggctccct ttagggttcc gatttagtgc tttacggcac ctcgacccca 1200
aaaaacttga ttagggtgat ggttcacgta gtgggccatc gccctgatag acggtttttc 1260
gccctttgac gttggagtcc acgttcttta atagtggact cttgttccaa actggaacaa 1320
cactcaaccc tatctcggtc tattcttttg atttataagg gattttgccg atttcggcct 1380
attggttaaa aaatgagctg atttaacaaa aatttaacgc gaattttaac aaaatattaa 1440
cgcttacaat ttcctgatgc ggtattttct ccttacgcat ctgtgcggta tttcacaccg 1500
catacgcgga tctgcgcagc accatggcct gaaataacct ctgaaagagg aacttggtta 1560
ggtaccttct gaggcggaaa gaaccagctg tggaatgtgt gtcagttagg gtgtggaaag 1620
tccccaggct ccccagcagg cagaagtatg caaagcatgc atctcaatta gtcagcaacc 1680
aggtgtggaa agtccccagg ctccccagca ggcagaagta tgcaaagcat gcatctcaat 1740
tagtcagcaa ccatagtccc gcccctaact ccgcccatcc cgcccctaac tccgcccagt 1800
tccgcccatt ctccgcccca tggctgacta atttttttta tttatgcaga ggccgaggcc 1860
gcctcggcct ctgagctatt ccagaagtag tgaggaggct tttttggagg cctaggcttt 1920
tgcaaaaagc ttgattcttc tgacacaaca gtctcgaact taaggctaga gccaccatga 1980
ttgaacaaga tggattgcac gcaggttctc cggccgcttg ggtggagagg ctattcggct 2040
atgactgggc acaacagaca atcggctgct ctgatgccgc cgtgttccgg ctgtcagcgc 2100
aggggcgccc ggttcttttt gtcaagaccg acctgtccgg tgccctgaat gaactgcagg 2160
acgaggcagc gcggctatcg tggctggcca cgacgggcgt tccttgcgca gctgtgctcg 2220
acgttgtcac tgaagcggga agggactggc tgctattggg cgaagtgccg gggcaggatc 2280
tcctgtcatc tcaccttgct cctgccgaga aagtatccat catggctgat gcaatgcggc 2340
ggctgcatac gcttgatccg gctacctgcc cattcgacca ccaagcgaaa catcgcatcg 2400
agcgagcacg tactcggatg gaagccggtc ttgtcgatca ggatgatctg gacgaagagc 2460
atcaggggct cgcgccagcc gaactgttcg ccaggctcaa ggcgcgcatg cccgacggcg 2520
aggatctcgt cgtgacccat ggcgatgcct gcttgccgaa tatcatggtg gaaaatggcc 2580
gcttttctgg attcatcgac tgtggccggc tgggtgtggc ggaccgctat caggacatag 2640
cgttggctac ccgtgatatt gctgaagagc ttggcggcga atgggctgac cgcttcctcg 2700
tgctttacgg tatcgccgct cccgattcgc agcgcatcgc cttctatcgc cttcttgacg 2760
agttcttctg agcgggactc tggggttcga aatgaccgac caagcgacgc ccaacctgcc 2820
atcacgatgg ccgcaataaa atatctttat tttcattaca tctgtgtgtt ggttttttgt 2880
gtgaatcgat agcgataagg atccgcgtat ggtgcactct cagtacaatc tgctctgatg 2940
ccgcatagtt aagccagccc cgacacccgc caacacccgc tgacgcgccc tgacgggctt 3000
gtctgctccc ggcatccgct tacagacaag ctgtgaccgt ctccgggagc tgcatgtgtc 3060
agaggttttc accgtcatca ccgaaacgcg cgagacgaaa gggcctcgtg atacgcctat 3120
ttttataggt taatgtcatg ataataatgg tttcttagac gtcaggtggc acttttcggg 3180

```
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
```

-continued

```
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttcaaaggg agacaaaacg atccacaagc tagagatggt tattccccag   6360
ccccacacct agtcagtcac aaaaccctag ttttgatatt gcttgagcag aaaccagcct   6420
ccaagagaat aagaagaaag ggcctgggtc taaagaggag gaggaaaggg ttgggcacaa   6480
tttcttatgc ctagggattt gtcagcaact ttgaggctga ttatggaata ttttcttgtc   6540
ttccatgagg gagtacccct gtggcaactc aacaccctgg aagactcctt ctgtgtcccc   6600
aaacatcacc cagctgttcc agaagcagaa atggacacag gtcaaccctt caccatcctg   6660
caggtgcagc accagggaga agctcaccat gctgccagag tgccccgagg gtgccggggg   6720
cctcccgccc ccccaggtac ctgacctcca aacaacgggg ccccaggtct gcctgccaca   6780
gagggactag gggagtccct ggtatctcct gagtctctca caaactaaca tttcaaactg   6840
gcagttgagt aggggactaa accaaactcc ctgcaccctc tgggaggggc tccccacagg   6900
gcgctgtggc tgccaactgg aggaagccac tcaccaaaag cttcatttc caccagatac   6960
ttcctatttg atctagtaga aaaaatgtgt ttaagcacta aaaaaaatta agtcatatgt   7020
gctcattata gaaaaattag aaaacacagg taagtcagaa ggaaaaaaaa tcatcgcttg   7080
gatataaaca cagataatgt ttggtttgca gccacccaaa cagattatat tccaaatatt   7140
gtcttaaaat ctgatttact gcataattta ctaggaacat gcatccatgt caataaatag   7200
acatctgcat cacttttaat atctgtatat tatcccattg tttgaatttc ttttttttt   7260
ttttttttt ttttgagaca gagtctctct ctgtcaccca ggttggagtg cagcggtgtg   7320
atctcggctc actgcaacct ctgcctccca ggttcaattc ttgtgcctca gcccccccga   7380
gtagtgggga ttacaggcat gcaccatcat gcccgcctaa tttttttggt agttttagta   7440
cagatggggt tttaccatgt tggccaggct ggtgttgaac tcctggcctc aagtgatcta   7500
cccacttctg cctaccagag tgctaggatt acaagcgtca gccactgctc ctggcctaaa   7560
gttactttaa attaactgat ctcccattat tcgccactta ggttttttag ttttcaccat   7620
tataagcaat gctatgatgt acattcaaat ggaaatgtgt ttacacactt attaacagtc   7680
ttaattaaga agctctccat gtgctgtgtc tctaacatct gcaggtatgt acacaaatac   7740
atgcacagcc agcatccatc ttttgcaggg acattaatga tcttggctct gagcagcacc   7800
ctgtcctggg agttctaaag tccagaacag attacagtga gtatctcctg ggggatttag   7860
agacatcaaa gaaggctgtg tccgtggttg ataatgggcc tcccagctga cttgccaggg   7920
```

ctgggcctta gacagccctg tccaatgatt tgtcaatgaa taaactgttc ccaaacaggc 7980
tatgcagttc agtgggaaag cacaggtatg ggacacggag agccccaggt ggactacttg 8040
acctctctga gccttaattt tatcacctgt gaattgggaa taactgctta tttcataata 8100
ttattatgag gatttaatga aatcatgtgg gcaaggaatt atttagaatt agattcaact 8160
caagtgatga caaccccaaa ctaacagcag ataaaacaag acacaacttg tttctcactc 8220
atctaaaagt ctacgtgggt ggtgcacgat gttctattct ctttctcctc cacactaaac 8280
aggcctcagc ctcatcagcc aataaggcag gagctgcctt ccaggcagcg gaatggaaga 8340
aggatgaagc aaaacagagg gcagagtgtg cacatgtgct atgtttaggg aaggttttct 8400
gaagttccca catagtactt ccacttacaa acccaacaaa aaaggctatg gctaaggcag 8460
cagggaggag caaataatgg gagcaactag attttgccac agcacctatc acagtctggt 8520
ttataaatgg ttctaggcca agaacacccg atccctgctc ttttttatat tctaaagcat 8580
gtatctttat atttctcaag caatattttc tctctttgaa tcacagctca tctgctgcat 8640
catagggatc ccaaaagaag gacccaagga acttgtctca gtcctctgtg ccccaagagg 8700
aagctttgct tgtttgcttt gctgtcaatg ctgagggctc ctgtggctgc ctccactcaa 8760
aaccctccag catcaggacg tcaaggctgt gatactgtac cctgagctct tggccagggc 8820
gagggagggg aggccaagcc tacctacatg gtgtttcatt tcctaaacga acccttactt 8880
ccacgcggtc tgtccagctt agaaacttat tttcagtagt gttggtcctt ggtccctgga 8940
caaaatgtaa cagccaaagt cctagaaaaa ggcaagccag ttcctgccat tttctttcac 9000
ttctgcattt cctcactatt atacgtgcct tccattggag caaaactgaa tgccacgcat 9060
atgcacagga gctgtgcgcg ctctgtctct ctcactcact ctttttctct ctctctcttt 9120
ctctctcaat ctctctgtct ctatctatct cttactcttt atctctcact ctctcactct 9180
ttctcactct ttctctcaat ctctttctca ttctctctct atctttctct ctctctctct 9240
ttctcacaca cacacactca caaacccaca ctcttattca catctgctca ccctagccac 9300
tcaaacacaa tccctcattc agcctggaat aagtccagag ggcgtgggcc tgattcagag 9360
acaatcagtt gttctcatct gggaaatggg gcaatgtggt catctctagg gaccctccct 9420
gctctaacat tctttgaatg tggtgggtcc tgaggtggaa gcactctgtc cctgacttct 9480
agtatatgtg gagatagggt tacacaaata ttttattggg cagaactttt ataaaacaat 9540
ttatcataag ctatcgcagc cagcagcaat ttttccaacc tggattccac caggggagct 9600
tggccggtgt ctgagtgcca ctttcagctt gagaagcagg tgactcagtg aaaagagcaa 9660
ggaggagaca gaggcagatt cagttcctag gccctgggcc acccacctgc aagtttgcag 9720
cccagtcagt gcaagtcagc taactgttct gaacctcagt ttctctgtct gtaaattaag 9780
ctaaaaattc ttctttcaaa gagtgtcagg atgaagtgag atcgtgtatg tagggcattt 9840
aacatagtgc ccgacacaca gggagcattc ggtaggtgcc agctctcctc ctggcaggag 9900
agagagaaac aaggtgaaaa gagtgaatta aagaagagga aagtcaaatg ggaaaacagg 9960
gggaggagat agaaagtgta tgaaaaggaa agaatggtgc gcaataacgg cggtgtaatg 10020
ccaccaaaat cccctcaact acttctgggc agcacccttg acagagtgaa tgcttttatg 10080
agaatgtaag cggaatgtgt tcccagattt gcagtaatat tgccacctgg tggacaaacc 10140
catgcacctt tgaattttcc aaaatatttc gatgaactag cttccagtcc tagatgtatt 10200
ttgaaagtga tttgtaaatt gtaaggaact attcaaattc tttcattaat gtcacaaatc 10260
aactgtgtca tctgtatgcc acccactatt ctgggtgctg gggacacaac agctcacaaa 10320
tcaggcaaag tccctgctct caccaaaatg atatcctacg ggggattaca gatacaaata 10380
cgtaaacaga tccatcggga ggaaactctc agatggaaat gagagctatg aagataacac 10440
aacagtacat gacaatacag agtgactgga accaggaaca tttctccgag gaataaaatt 10500
tgaagcgagc catgagaggg tctacaggta gagttcccag gcagagtgaa cagccaagca 10560
caaagctgca ccaggagaga gaggtgctcg ccgagagaca gggaggggag tgtggcaggt 10620
gagctcagag aggggcaggg ccacacacat cggccacatg ggccttggta gtgagtcgag 10680
atttgatccc agggtttatt ggagtggata agtaagcaag gtgactgagg tgctcgggtt 10740
tacattttta tagttcaagc tggctgctgg gtggaaaacg gaagttggca gaccaaggac 10800
agaatcaggc agacccatgt ggaagtttct ctagtggtct aggtggtggc ttgggtagcg 10860
tggcagtatt ggagctggag aaacgcagat ggattggaga tttgttttgg agtgacgcca 10920
ttctgtcttg tcaatggatt ggcgaaaaaa gaggcatcaa agatgagtta cacatcattg 10980
aagtgagaac tagggagatg ccagtacttt atttagtatt ttctcagcag ctcaatccat 11040
aaataatttt tggaagacaa caagcagttt cacaaactac ttataagtcc tcaagttcca 11100
aggtaattaa cgtgggtgtc tcattgcctc agagaacaca gcgcagcacg gaaattctac 11160
aagacctgac ggacaggaac atctccgact tcttggtaaa aacgtatcct gctcttataa 11220
gaagcaggta agaagaaatc cttttatgct ttttatcctg gctccctgta gaagatatta 11280
actagggaca gaagataatt ttctctctca atttatgtat gatcagggca gtagattttt 11340 ttcttttta tctgatttga gggccccatt caacataaaa agcaattgag gcacatacaa 11400
gtaaaatgta acttaagatt aattcttttt ttgttgtttg tttgtttgtt tttacattta 11460
gggcaagcag tcttcaccca gctttc 11486

<210> SEQ ID NO 53
<211> LENGTH: 11486
<212> TYPE: DNA
<213> ORGANISM: Artificial Sequence
<220> FEATURE:
<223> OTHER INFORMATION: pCI-Neo-Rho-ABCA4-30-31 c.4539+2001A

<400> SEQUENCE: 53
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa ccccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720
aactagaatg cagtgaaaaa aatgctttat ttgtgaaatt tgtgatgcta ttgctttatt 780
tgtaaccatt ataagctgca ataaacaagt taacaacaac aattgcattc attttatgtt 840

-continued

```
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta attttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
ttttataggt taatgtcatg ataataatgg tttcttagac gtcaggtggc acttttcggg   3180
```

-continued

```
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccaccccat   5580
```

-continued tgacgtcaat gggagtttgt tttggcacca aaatcaacgg gactttccaa aatgtcgtaa 5640
caactgcgat cgcccgcccc gttgacgcaa atgggcggta ggcgtgtacg gtgggaggtc 5700
tatataagca gagctcgttt agtgaaccgt cagatcacta gaagctttat tgcggtagtt 5760
tatcacagtt aaattgctaa cgcagtcagt gcttctgaca caacagtctc gaacttaagc 5820
tgcagtgact ctcttaaggt agccttgcag aagttggtcg tgaggcactg ggcaggtaag 5880
tatcaaggtt acaagacagg tttaaggaga ccaatagaaa ctgggcttgt cgagacagag 5940
aagactcttg cgtttctgat aggcacctat tggtcttact gacatccact ttgcctttct 6000
ctccacaggt gtccactccc agttcaatta cagctcttaa ggctagagta cttaatacga 6060
ctcactatag gctagcctcg agaattccgg aggtcaacaa cgagtctttt gtcatctaca 6120
tgttcgtggt ccacttcacc atccccatga ttatcatctt tttctgctat gggcagctcg 6180
tcttcaccgt caaggaggta cgggccgggg ggtgggcggc ctcacggctc tgagggtcca 6240
gcccccagca tgcatctgcg gctcctgctc cctggaggag ccatatcaca agtttgtaca 6300
aaaaagcagg cttcaaaggg agacaaaacg atccacaagc tagagatggt tattccccag 6360
ccccacacct agtcagtcac aaaaccctag ttttgatatt gcttgagcag aaaccagcct 6420
ccaagagaat aagaagaaag ggcctgggtc taaagaggag gaggaaaggg ttgggcacaa 6480
tttcttatgc ctagggattt gtcagcaact ttgaggctga ttatggaata ttttcttgtc 6540
ttccatgagg gagtacccct gtggcaactc aacaccctgg aagactcctt ctgtgtcccc 6600
aaacatcacc cagctgttcc agaagcagaa atggacacag gtcaaccctt caccatcctg 6660
caggtgcagc accagggaga agctcaccat gctgccagag tgccccgagg gtgccggggg 6720
cctcccgccc ccccaggtac ctgacctcca aacaacgggg ccccaggtct gcctgccaca 6780
gagggactag gggagtccct ggtatctcct gagtctctca caaactaaca tttcaaactg 6840
gcagttgagt aggggactaa accaaactcc ctgcaccctc tgggaggggc tccccacagg 6900
gcgctgtggc tgccaactgg aggaagccac tcaccaaaag cttcattttc caccagatac 6960
ttcctatttg atctagtaga aaaaatgtgt ttaagcacta aaaaaaatta agtcatatgt 7020
gctcattata gaaaaattag aaaacacagg taagtcagaa ggaaaaaaaa tcatcgcttg 7080
gatataaaca cagataatgt ttggtttgca gccacccaaa cagattatat tccaaatatt 7140
gtcttaaaat ctgatttact gcataattta ctaggaacat gcatccatgt caataaatag 7200
acatctgcat cacttttaat atctgtatat tatcccattg tttgaatttc tttttttttt 7260
tttttttttt ttttgagaca gagtctctct ctgtcaccca ggttggagtg cagcggtgtg 7320
atctcggctc actgcaacct ctgcctccca ggttcaattc ttgtgcctca gcccccccga 7380
gtagtgggga ttacaggcat gcaccatcat gcccgcctaa ttttttttggt agttttagta 7440 cagatggggt tttaccatgt tggccaggct ggtgttgaac tcctggcctc aagtgatcta 7500
cccacttctg cctaccagag tgctaggatt acaagcgtca gccactgctc ctggcctaaa 7560
gttactttaa attaactgat ctcccattat tcgccactta ggttttttag ttttcaccat 7620
tataagcaat gctatgatgt acattcaaat ggaaatgtgt ttacacactt attaacagtc 7680
ttaattaaga agctctccat gtgctgtgtc tctaacatct gcaggtatgt acacaaatac 7740
atgcacagcc agcatccatc ttttgcaggg acattaatga tcttggctct gagcagcacc 7800
ctgtcctggg agttctaaag tccagaacag attacagtga gcatctcctg ggggatttag 7860
agacatcaaa gaaggctgtg tccgtggttg ataatgggcc tcccagctga cttgccaggg 7920

```
ctgggcctta gacagccctg tccaatgatt tgtcaatgaa taaactgttc ccaaacaggc   7980
tatgcagttc agtgggaaag cacaggtatg ggacacggag agccccaggt ggactacttg   8040
acctctctga gccttaattt tatcacctgt gaattgggaa taactgctta tttcataata   8100
ttattatgag gatttaatga aatcatgtgg gcaaggaatt atttagaatt agattcaact   8160
caagtgatga caaccccaaa ctaacagcag ataaaacaag acacaacttg tttctcactc   8220
atctaaaagt ctacgtgggt ggtgcacgat gttctattct ctttctcctc cacactaaac   8280
aggcctcagc ctcatcagcc aataaggcag gagctgcctt ccaggcagcg gaatggaaga   8340
aggatgaagc aaaacagagg gcagagtgtg cacatgtgct atgtttaggg aaggttttct   8400
gaagttccca catagtactt ccacttacaa acccaacaaa aaaggctatg gctaaggcag   8460
cagggaggag caaataatgg gagcaactag attttgccac agcacctatc acagtctggt   8520
ttataaatgg ttctaggcca agaacacccg atccctgctc tttttatat tctaaagcat   8580
gtatctttat atttctcaag caatattttc tctctttgaa tcacagctca tctgctgcat   8640
catagggatc ccaaaagaag gacccaagga acttgtctca gtcctctgtg ccccaagagg   8700
aagctttgct tgtttgcttt gctgtcaatg ctgaggactc ctgtggctgc ctccactcaa   8760
aaccctccag catcaggacg tcaaggctgt gatactgtac cctgagctct tggccagggc   8820
gagggagggg aggccaagcc tacctacatg gtgtttcatt tcctaaacga acccttactt   8880
ccacgcggtc tgtccagctt agaaacttat tttcagtagt gttggtcctt ggtccctgga   8940
caaaatgtaa cagccaaagt cctagaaaaa ggcaagccag ttcctgccat tttctttcac   9000
ttctgcattt cctcactatt atacgtgcct tccattggag caaaactgaa tgccacgcat   9060
atgcacagga gctgtgcgcg ctctgtctct ctcactcact ctttttctct ctctctcttt   9120
ctctctcaat ctctctgtct ctatctatct cttactcttt atctctcact ctctcactct   9180
ttctcactct ttctctcaat ctctttctca ttctctctct atctttctct ctctctctct   9240
ttctcacaca cacacactca caaacccaca ctcttattca catctgctca ccctagccac   9300
tcaaacacaa tccctcattc agcctggaat aagtccagag ggcgtgggcc tgattcagag   9360
acaatcagtt gttctcatct gggaaatggg gcaatgtggt catctctagg gaccctccct   9420
gctctaacat tctttgaatg tggtgggtcc tgaggtggaa gcactctgtc cctgacttct   9480
agtatatgtg gagatagggt tacacaaata ttttattggg cagaactttt ataaaacaat   9540
ttatcataag ctatcgcagc cagcagcaat tttccaacc tggattccac caggggagct   9600
tggccggtgt ctgagtgcca ctttcagctt gagaagcagg tgactcagtg aaaagagcaa   9660
ggaggagaca gaggcagatt cagttcctag gccctgggcc acccacctgc aagtttgcag   9720
cccagtcagt gcaagtcagc taactgttct gaacctcagt ttctctgtct gtaaattaag   9780
ctaaaaattc ttctttcaaa gagtgtcagg atgaagtgag atcgtgtatg tagggcattt   9840
aacatagtgc ccgacacaca gggagcattc ggtaggtgcc agctctcctc ctggcaggag   9900
agagagaaac aaggtgaaaa gagtgaatta aagaagagga aagtcaaatg ggaaaacagg   9960
gggaggagat agaaagtgta tgaaaaggaa agaatggtgc gcaataacgg cggtgtaatg  10020
ccaccaaaat cccctcaact acttctgggc agcacccttg acagagtgaa tgcttttatg  10080
agaatgtaag cggaatgtgt tcccagattt gcagtaatat tgccacctgg tggacaaacc  10140
catgcacctt tgaattttcc aaaatatttc gatgaactag cttccagtcc tagatgtatt  10200
ttgaaagtga tttgtaaatt gtaaggaact attcaaattc tttcattaat gtcacaaatc  10260
aactgtgtca tctgtatgcc acccactatt ctgggtgctg ggacacaaac agctcacaaa  10320
```

```
tcaggcaaag tccctgctct caccaaaatg atatcctacg ggggattaca gatacaaata  10380

cgtaaacaga tccatcggga ggaaactctc agatggaaat gagagctatg aagataacac  10440

aacagtacat gacaatacag agtgactgga accaggaaca tttctccgag gaataaaatt  10500

tgaagcgagc catgagaggg tctacaggta gagttcccag gcagagtgaa cagccaagca  10560

caaagctgca ccaggagaga gaggtgctcg ccgagagaca gggaggggag tgtggcaggt  10620

gagctcagag aggggcaggg ccacacacat cggccacatg ggccttggta gtgagtcgag  10680

atttgatccc agggtttatt ggagtggata agtaagcaag gtgactgagg tgctcgggtt  10740

tacattttta tagttcaagc tggctgctgg gtggaaaacg gaagttggca gaccaaggac  10800

agaatcaggc agacccatgt ggaagtttct ctagtggtct aggtggtggc ttgggtagcg  10860

tggcagtatt ggagctggag aaacgcagat ggattggaga tttgttttgg agtgacgcca  10920

ttctgtcttg tcaatggatt ggcgaaaaaa gaggcatcaa agatgagtta cacatcattg  10980

aagtgagaac tagggagatg ccagtacttt atttagtatt ttctcagcag ctcaatccat  11040

aaataatttt tggaagacaa caagcagttt cacaaactac ttataagtcc tcaagttcca  11100

aggtaattaa cgtgggtgtc tcattgcctc agagaacaca gcgcagcacg gaaattctac  11160

aagacctgac ggacaggaac atctccgact tcttggtaaa aacgtatcct gctcttataa  11220

gaagcaggta agaagaaatc cttttatgct ttttatcctg gctccctgta gaagatatta  11280

actagggaca gaagataatt ttctctctca atttatgtat gatcagggca gtagattttt  11340

ttctttttta tctgatttga gggccccatt caacataaaa agcaattgag gcacatacaa  11400

gtaaaatgta acttaagatt aattcttttt ttgttgtttg tttgtttgtt tttacattta  11460

gggcaagcag tcttcaccca gctttc                                        11486
```

```
<210> SEQ ID NO 54
<211> LENGTH: 20
<212> TYPE: DNA
<213> ORGANISM: Artificial Sequence
<220> FEATURE:
<223> OTHER INFORMATION: RT-PCR primer

<400> SEQUENCE: 54

attcgctttg tggtggaact                                                 20


<210> SEQ ID NO 55
<211> LENGTH: 20
<212> TYPE: DNA
<213> ORGANISM: Artificial Sequence
<220> FEATURE:
<223> OTHER INFORMATION: RT-PCT primer

<400> SEQUENCE: 55

actgggacga catggagaag                                                 20


<210> SEQ ID NO 56
<211> LENGTH: 20
<212> TYPE: DNA
<213> ORGANISM: Artificial Sequence
<220> FEATURE:
<223> OTHER INFORMATION: RT-PCR primer

<400> SEQUENCE: 56

aaacatcacc cagctgttcc                                                 20


<210> SEQ ID NO 57
```

<211> LENGTH: 20
<212> TYPE: DNA
<213> ORGANISM: Artificial Sequence
<220> FEATURE:
<223> OTHER INFORMATION: qPCR primer

<400> SEQUENCE: 57
catcctgttc caccacctca 20

<210> SEQ ID NO 58
<211> LENGTH: 20
<212> TYPE: DNA
<213> ORGANISM: Artificial Sequence
<220> FEATURE:
<223> OTHER INFORMATION: qPCR primer

<400> SEQUENCE: 58
gccccactat tctgtcaacg 20

<210> SEQ ID NO 59
<211> LENGTH: 21
<212> TYPE: DNA
<213> ORGANISM: Artificial Sequence
<220> FEATURE:
<223> OTHER INFORMATION: qPCR primer

<400> SEQUENCE: 59
ttgtcttcta ccctgccctc t 21

<210> SEQ ID NO 60
<211> LENGTH: 20
<212> TYPE: DNA
<213> ORGANISM: Artificial Sequence
<220> FEATURE:
<223> OTHER INFORMATION: qPCR primer

<400> SEQUENCE: 60
ttcttccacc agtcccaaag 20

<210> SEQ ID NO 61
<211> LENGTH: 22
<212> TYPE: DNA
<213> ORGANISM: Artificial Sequence
<220> FEATURE:
<223> OTHER INFORMATION: qPCR primer

<400> SEQUENCE: 61
gttcttcatt cactaaggaa gg 22

<210> SEQ ID NO 62
<211> LENGTH: 20
<212> TYPE: DNA
<213> ORGANISM: Artificial Sequence
<220> FEATURE:
<223> OTHER INFORMATION: qPCR primer

<400> SEQUENCE: 62
gtggtcactg catccgtctt 20

<210> SEQ ID NO 63
<211> LENGTH: 20
<212> TYPE: DNA
<213> ORGANISM: Artificial Sequence
<220> FEATURE:
<223> OTHER INFORMATION: qPCR primer

<400> SEQUENCE: 63
accattggta ttggcgtctc 20

<210> SEQ ID NO 64
<211> LENGTH: 20
<212> TYPE: DNA
<213> ORGANISM: Artificial Sequence
<220> FEATURE:
<223> OTHER INFORMATION: qPCR primer

<400> SEQUENCE: 64
acaccaagtt ctcggaggag 20

<210> SEQ ID NO 65
<211> LENGTH: 20
<212> TYPE: DNA
<213> ORGANISM: Artificial Sequence
<220> FEATURE:
<223> OTHER INFORMATION: qPCR primer

<400> SEQUENCE: 65
gctagtctcc aagcgacgaa 20

<210> SEQ ID NO 66
<211> LENGTH: 20
<212> TYPE: DNA
<213> ORGANISM: Artificial Sequence
<220> FEATURE:
<223> OTHER INFORMATION: RT-PCR primer

<400> SEQUENCE: 66
gtcagacagg ccgatgtttt 20

<210> SEQ ID NO 67
<211> LENGTH: 20
<212> TYPE: DNA
<213> ORGANISM: Artificial Sequence
<220> FEATURE:
<223> OTHER INFORMATION: RT-PCR primeR

<400> SEQUENCE: 67
tctcagctgt ggtggtgaag 20

<210> SEQ ID NO 68
<211> LENGTH: 21
<212> TYPE: DNA
<213> ORGANISM: Artificial Sequence
<220> FEATURE:
<223> OTHER INFORMATION: RT-PCR primer

<400> SEQUENCE: 68
gaagtcggag atgttcctgt c 21

<210> SEQ ID NO 69
<211> LENGTH: 20
<212> TYPE: DNA
<213> ORGANISM: Artificial Sequence
<220> FEATURE:
<223> OTHER INFORMATION: qPCR primer

<400> SEQUENCE: 69
ctgtgtcctc caacatggct 20

<210> SEQ ID NO 70
<211> LENGTH: 20
<212> TYPE: DNA

<213> ORGANISM: Artificial Sequence
<220> FEATURE:
<223> OTHER INFORMATION: qPCR primer

<400> SEQUENCE: 70
cttcagagcc acctcctcac 20

<210> SEQ ID NO 71
<211> LENGTH: 21
<212> TYPE: DNA
<213> ORGANISM: Artificial Sequence
<220> FEATURE:
<223> OTHER INFORMATION: qPCR primer

<400> SEQUENCE: 71
gaacaaggga tggagggttt t 21

<210> SEQ ID NO 72
<211> LENGTH: 20
<212> TYPE: DNA
<213> ORGANISM: Artificial Sequence
<220> FEATURE:
<223> OTHER INFORMATION: qPCR primer

<400> SEQUENCE: 72
ttgctccaca ttggaaggtt 20

<210> SEQ ID NO 73
<211> LENGTH: 22
<212> TYPE: DNA
<213> ORGANISM: Artificial Sequence
<220> FEATURE:
<223> OTHER INFORMATION: qPCR primer

<400> SEQUENCE: 73
caagagcatc attgaacttc ac 22

<210> SEQ ID NO 74
<211> LENGTH: 20
<212> TYPE: DNA
<213> ORGANISM: Artificial Sequence
<220> FEATURE:
<223> OTHER INFORMATION: qPCR primer

<400> SEQUENCE: 74
acggtctctg ctaggtcagc 20

<210> SEQ ID NO 75
<211> LENGTH: 20
<212> TYPE: DNA
<213> ORGANISM: Artificial Sequence
<220> FEATURE:
<223> OTHER INFORMATION: qPCR primer

<400> SEQUENCE: 75
ggagagaggc acaatgaagc 20

<210> SEQ ID NO 76
<211> LENGTH: 20
<212> TYPE: DNA
<213> ORGANISM: Artificial Sequence
<220> FEATURE:
<223> OTHER INFORMATION: qPCR primer

<400> SEQUENCE: 76
acttggcgta gatgctctgg 20

<210> SEQ ID NO 77
<211> LENGTH: 20
<212> TYPE: DNA
<213> ORGANISM: Artificial Sequence
<220> FEATURE:
<223> OTHER INFORMATION: qPCR primer

<400> SEQUENCE: 77
gcaagaagcc tctccttgaa 20

<210> SEQ ID NO 78

<400> SEQUENCE: 78

000

<210> SEQ ID NO 79

<400> SEQUENCE: 79

000

<210> SEQ ID NO 80
<211> LENGTH: 162
<212> TYPE: DNA
<213> ORGANISM: Artificial Sequence
<220> FEATURE:
<223> OTHER INFORMATION: Pseudoexon 6-7 (162)

<400> SEQUENCE: 80
gatcagtgat tccatcagtt ttgaaacatg aagcatgaag tcaaacagga catgaccttg 60
gtttccagaa aaccagatgt tcacatcagt ctctggagct tggaggcagc acacctgggg 120
acttccacat cccctgccga ggtggcaaaa gcaggagcag tg 162

<210> SEQ ID NO 81
<211> LENGTH: 262
<212> TYPE: DNA
<213> ORGANISM: Artificial Sequence
<220> FEATURE:
<223> OTHER INFORMATION: Pseudoexon 6-7 (162) larger target + flanking
sequences (+50 nt)

<400> SEQUENCE: 81
gaaaaccact gtctttacac ttagaactca gtcctacatg actcctctag gatcagtgat 60
tccatcagtt ttgaaacatg aagcatgaag tcaaacagga catgaccttg gtttccagaa 120
aaccagatgt tcacatcagt ctctggagct tggaggcagc acacctgggg acttccacat 180
cccctgccga ggtggcaaaa gcaggagcag tggtgagttc acatgggctg gggtttcctg 240
aacactgctg gcaattggag aa 262

<210> SEQ ID NO 82
<211> LENGTH: 202
<212> TYPE: DNA
<213> ORGANISM: Artificial Sequence
<220> FEATURE:
<223> OTHER INFORMATION: Pseudoexon 6-7 (162) larger target + flanking
sequences (+20 nt)

<400> SEQUENCE: 82
gtcctacatg actcctctag gatcagtgat tccatcagtt ttgaaacatg aagcatgaag 60
tcaaacagga catgaccttg gtttccagaa aaccagatgt tcacatcagt ctctggagct 120

```
tggaggcagc acacctgggg acttccacat cccctgccga ggtggcaaaa gcaggagcag    180

tggtgagttc acatgggctg gg                                              202


<210> SEQ ID NO 83
<211> LENGTH: 40
<212> TYPE: DNA
<213> ORGANISM: Artificial Sequence
<220> FEATURE:
<223> OTHER INFORMATION: AON-1 Pseudoexon 6-7 (162) target site and
      flanking sequences (+10 nt)

<400> SEQUENCE: 83

catgactcct ctaggatcag tgattccatc agttttgaaa                            40


<210> SEQ ID NO 84
<211> LENGTH: 30
<212> TYPE: DNA
<213> ORGANISM: Artificial Sequence
<220> FEATURE:
<223> OTHER INFORMATION: AON-1 Pseudoexon 6-7 (162) target site and
      flanking sequences (+5 nt)

<400> SEQUENCE: 84

ctcctctagg atcagtgatt ccatcagttt                                       30


<210> SEQ ID NO 85
<211> LENGTH: 20
<212> TYPE: RNA
<213> ORGANISM: Artificial Sequence
<220> FEATURE:
<223> OTHER INFORMATION: AON-1 Pseudoexon 6-7 (162)

<400> SEQUENCE: 85

gauggaauca cugauccuag                                                  20


<210> SEQ ID NO 86
<211> LENGTH: 40
<212> TYPE: DNA
<213> ORGANISM: Artificial Sequence
<220> FEATURE:
<223> OTHER INFORMATION: AON-2 Pseudoexon 6-7 (162) target site and
      flanking sequences (+10 nt)

<400> SEQUENCE: 86

aaccagatgt tcacatcagt ctctggagct tggaggcagc                            40


<210> SEQ ID NO 87
<211> LENGTH: 30
<212> TYPE: DNA
<213> ORGANISM: Artificial Sequence
<220> FEATURE:
<223> OTHER INFORMATION: AON-2 Pseudoexon 6-7 (162) target site and
      flanking sequences (+5 nt)

<400> SEQUENCE: 87

gatgttcaca tcagtctctg gagcttggag                                       30


<210> SEQ ID NO 88
<211> LENGTH: 20
<212> TYPE: RNA
<213> ORGANISM: Artificial Sequence
<220> FEATURE:
<223> OTHER INFORMATION: AON-2 Pseudoexon 6-7 (162)

<400> SEQUENCE: 88

agcuccagag acugauguga                                                  20
```

<210> SEQ ID NO 89
<211> LENGTH: 37
<212> TYPE: DNA
<213> ORGANISM: Artificial Sequence
<220> FEATURE:
<223> OTHER INFORMATION: AON-3 Pseudoexon 6-7 (162) target site and flanking sequences (+10 nt)

<400> SEQUENCE: 89
ggtggcaaaa gcaggagcag tggtgagttc acatggg 37

<210> SEQ ID NO 90
<211> LENGTH: 27
<212> TYPE: DNA
<213> ORGANISM: Artificial Sequence
<220> FEATURE:
<223> OTHER INFORMATION: AON-3 Pseudoexon 6-7 (162) target site and flanking sequences (+5 nt)

<400> SEQUENCE: 90
caaaagcagg agcagtggtg agttcac 27

<210> SEQ ID NO 91
<211> LENGTH: 17
<212> TYPE: RNA
<213> ORGANISM: Artificial Sequence
<220> FEATURE:
<223> OTHER INFORMATION: AON-3 Pseudoexon 6-7 (162)

<400> SEQUENCE: 91
cucaccacug cuccugc 17

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 141
<212> TYPE: DNA
<213> ORGANISM: Artificial Sequence
<220> FEATURE:
<223> OTHER INFORMATION: Pseudoexon 7-8 (141)

<400> SEQUENCE: 100
tatccccatc ttggtgggac aacagaaccc aagaactggc ttaacagtaa aatattttct 60
gcatttgccc aaggacacat tcccaacgaa ttcaaataaa ggagactaga agaagagagg 120
ctatactaca gtgctctagg g 141

<210> SEQ ID NO 101
<211> LENGTH: 241
<212> TYPE: DNA
<213> ORGANISM: Artificial Sequence
<220> FEATURE:
<223> OTHER INFORMATION: Pseudoexon 7-8 (141) larger target + flanking sequences (+50 nt

<400> SEQUENCE: 101
tacaacagaa tcattcccca atcattttat ttccctcttt ttctccccag tatccccatc 60
ttggtgggac aacagaaccc aagaactggc ttaacagtaa aatattttct gcatttgccc 120
aaggacacat tcccaacgaa ttcaaataaa ggagactaga agaagagagg ctatactaca 180
gtgctctagg ggtcactctg tgatttgttg ttgttgttgt tgttgttttg agacggagta 240
t 241

<210> SEQ ID NO 102
<211> LENGTH: 181
<212> TYPE: DNA
<213> ORGANISM: Artificial Sequence
<220> FEATURE:
<223> OTHER INFORMATION: Pseudoexon 7-8 (141) larger target + flanking sequences (+20 nt)

<400> SEQUENCE: 102
ttccctcttt ttctccccag tatccccatc ttggtgggac aacagaaccc aagaactggc 60
ttaacagtaa aatattttct gcatttgccc aaggacacat tcccaacgaa ttcaaataaa 120
ggagactaga agaagagagg ctatactaca gtgctctagg ggtcactctg tgatttgttg 180
t 181

<210> SEQ ID NO 103
<211> LENGTH: 40
<212> TYPE: DNA
<213> ORGANISM: Artificial Sequence
<220> FEATURE:
<223> OTHER INFORMATION: AON-1 Pseudoexon 7-8 (141) target site and flanking sequences (+10 nt)

<400> SEQUENCE: 103
ttttctcccc agtatcccca tcttggtggg acaacagaac 40

<210> SEQ ID NO 104
<211> LENGTH: 30
<212> TYPE: DNA
<213> ORGANISM: Artificial Sequence
<220> FEATURE:
<223> OTHER INFORMATION: AON-1 Pseudoexon 7-8 (141) target site and flanking sequences (+5 nt)

<400> SEQUENCE: 104
tccccagtat ccccatcttg gtgggacaac 30

<210> SEQ ID NO 105
<211> LENGTH: 20
<212> TYPE: RNA
<213> ORGANISM: Artificial Sequence
<220> FEATURE:
<223> OTHER INFORMATION: AON-1 Pseudoexon 7-8 (141)

<400> SEQUENCE: 105
cccaccaaga uggggauacu 20

<210> SEQ ID NO 106
<211> LENGTH: 40
<212> TYPE: DNA
<213> ORGANISM: Artificial Sequence
<220> FEATURE:
<223> OTHER INFORMATION: AON-2 Pseudoexon 7-8 (141) target site and flanking sequences (+10 nt)

<400> SEQUENCE: 106
gtatccccat cttggtggga caacagaacc caagaactgg 40

<210> SEQ ID NO 107
<211> LENGTH: 30
<212> TYPE: DNA
<213> ORGANISM: Artificial Sequence
<220> FEATURE:
<223> OTHER INFORMATION: AON-2 Pseudoexon 7-8 (141) target site and flanking sequences (+5 nt)

<400> SEQUENCE: 107
cccatcttgg tgggacaaca gaacccaaga 30

<210> SEQ ID NO 108
<211> LENGTH: 20
<212> TYPE: RNA
<213> ORGANISM: Artificial Sequence
<220> FEATURE:
<223> OTHER INFORMATION: AON-2 Pseudoexon 7-8 (141)

<400> SEQUENCE: 108
gguucuguug ucccaccaag 20

<210> SEQ ID NO 109
<211> LENGTH: 40
<212> TYPE: DNA
<213> ORGANISM: Artificial Sequence
<220> FEATURE:
<223> OTHER INFORMATION: AON-3 Pseudoexon 7-8 (141) target site and flanking sequences (+10 nt)

<400> SEQUENCE: 109
acagtgctct aggggtcact ctgtgatttg ttgttgttgt 40

<210> SEQ ID NO 110
<211> LENGTH: 30
<212> TYPE: DNA
<213> ORGANISM: Artificial Sequence
<220> FEATURE:
<223> OTHER INFORMATION: AON-3 Pseudoexon 7-8 (141) target site and
flanking sequences (+5 nt)

<400> SEQUENCE: 110
gctctagggg tcactctgtg atttgttgtt 30

<210> SEQ ID NO 111
<211> LENGTH: 20
<212> TYPE: RNA
<213> ORGANISM: Artificial Sequence
<220> FEATURE:
<223> OTHER INFORMATION: AON-3 Pseudoexon 7-8 (141)

<400> SEQUENCE: 111
caaaucacag acugaccccu 20

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120
<211> LENGTH: 56
<212> TYPE: DNA
<213> ORGANISM: Artificial Sequence
<220> FEATURE:
<223> OTHER INFORMATION: Pseudoexon 7-8 (56)

<400> SEQUENCE: 120
acggagtatt gctcagtcgc ccaggctgga gtgcagtggc acgatgtcta ctcact 56

<210> SEQ ID NO 121
<211> LENGTH: 156
<212> TYPE: DNA
<213> ORGANISM: Artificial Sequence
<220> FEATURE:
<223> OTHER INFORMATION: Pseudoexon 7-8 (56) larger target + flanking
sequences (+50 nt)

<400> SEQUENCE: 121
gctctagggg tcactctgtg atttgttgtt gttgttgttg ttgttttgag acggagtatt 60
gctcagtcgc ccaggctgga gtgcagtggc acgatgtcta ctcactgtaa gctctgcccc 120
ccaggttcac gccattctcc tgcctcagcc tcccga 156

<210> SEQ ID NO 122
<211> LENGTH: 96
<212> TYPE: DNA
<213> ORGANISM: Artificial Sequence
<220> FEATURE:
<223> OTHER INFORMATION: Pseudoexon 7-8 (56) larger target + flanking
sequences (+20 nt)

<400> SEQUENCE: 122
gttgttgttg ttgttttgag acggagtatt gctcagtcgc ccaggctgga gtgcagtggc 60
acgatgtcta ctcactgtaa gctctgcccc ccaggt 96

<210> SEQ ID NO 123
<211> LENGTH: 39
<212> TYPE: DNA
<213> ORGANISM: Artificial Sequence
<220> FEATURE:
<223> OTHER INFORMATION: AON-1 Pseudoexon 7-8 (56) target site and
flanking sequences (+10 nt]

<400> SEQUENCE: 123
gttgttttga gacggagtat tgctcagtcg cccaggctg 39

<210> SEQ ID NO 124
<211> LENGTH: 29
<212> TYPE: DNA
<213> ORGANISM: Artificial Sequence
<220> FEATURE:
<223> OTHER INFORMATION: AON-1 Pseudoexon 7-8 (56) target site and
flanking sequences (+5 nt]

<400> SEQUENCE: 124
tttgagacgg agtattgctc agtcgccca 29

<210> SEQ ID NO 125
<211> LENGTH: 19
<212> TYPE: RNA

-continued

<213> ORGANISM: Artificial Sequence
<220> FEATURE:
<223> OTHER INFORMATION: AON-1 Pseudoexon 7-8 (56)

<400> SEQUENCE: 125
gacugagcaa uacuccguc 19

<210> SEQ ID NO 126
<211> LENGTH: 39
<212> TYPE: DNA
<213> ORGANISM: Artificial Sequence
<220> FEATURE:
<223> OTHER INFORMATION: AON-2 Pseudoexon 7-8 (56) target site and flanking sequences (+10 nt)

<400> SEQUENCE: 126
ctacagtgct ctaggggtca ctctgtgatt tgttgttgt 39

<210> SEQ ID NO 127
<211> LENGTH: 29
<212> TYPE: DNA
<213> ORGANISM: Artificial Sequence
<220> FEATURE:
<223> OTHER INFORMATION: AON-2 Pseudoexon 7-8 (56) target site and flanking sequences (+5 nt)

<400> SEQUENCE: 127
gtgctctagg ggtcactctg tgatttgtt 29

<210> SEQ ID NO 128
<211> LENGTH: 19
<212> TYPE: RNA
<213> ORGANISM: Artificial Sequence
<220> FEATURE:
<223> OTHER INFORMATION: AON-2 Pseudoexon 7-8 (56)

<400> SEQUENCE: 128
aucacagagu gaccccuag 19

<210> SEQ ID NO 129
<211> LENGTH: 39
<212> TYPE: DNA
<213> ORGANISM: Artificial Sequence
<220> FEATURE:
<223> OTHER INFORMATION: AON-3 Pseudoexon 7-8 (56) target site and flanking sequences (+10 nt)

<400> SEQUENCE: 129
ttgttgtttt gagacggagt attgctcagt cgcccaggc 39

<210> SEQ ID NO 130
<211> LENGTH: 29
<212> TYPE: DNA
<213> ORGANISM: Artificial Sequence
<220> FEATURE:
<223> OTHER INFORMATION: AON-3 Pseudoexon 7-8 (56) target site and flanking sequences (+5 nt)

<400> SEQUENCE: 130
gttttgagac ggagtattgc tcagtcgcc 29

<210> SEQ ID NO 131
<211> LENGTH: 19
<212> TYPE: RNA
<213> ORGANISM: Artificial Sequence
<220> FEATURE:
<223> OTHER INFORMATION: AON-3 Pseudoexon 7-8 (56)

<400> SEQUENCE: 131
cugagcaaua cuccgucug 19

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140
<211> LENGTH: 134
<212> TYPE: DNA
<213> ORGANISM: Artificial Sequence
<220> FEATURE:
<223> OTHER INFORMATION: Pseudoexon 13-14 (134)

<400> SEQUENCE: 140
gtctggttcc tgggagccct ggaataatgc agccccttcc ctaactaaca tttccatgat 60
gtatgctcaa tgacaaggca gaggaatgtg ttggatgagc tcaggacctg cctccctgga 120
cactcccatc ccag 134

<210> SEQ ID NO 141

<211> LENGTH: 234
<212> TYPE: DNA
<213> ORGANISM: Artificial Sequence
<220> FEATURE:
<223> OTHER INFORMATION: Pseudoexon 13-14 (134) larger target + flanking sequences (+50 nt)

<400> SEQUENCE: 141
cccaatgatt gccacatcag cattcatttt ggactctgta tggccagtag gtctggttcc 60
tgggagccct ggaataatgc agccccttcc ctaactaaca tttccatgat gtatgctcaa 120
tgacaaggca gaggaatgtg ttggatgagc tcaggacctg cctccctgga cactcccatc 180
ccaggcctgt atatctgttg accaggaata agccaagcaa gcagcctact gttt 234

<210> SEQ ID NO 142
<211> LENGTH: 174
<212> TYPE: DNA
<213> ORGANISM: Artificial Sequence
<220> FEATURE:
<223> OTHER INFORMATION: Pseudoexon 13-14 (134) larger target + flanking sequences (+20 nt)

<400> SEQUENCE: 142
ggactctgta tggccagtag gtctggttcc tgggagccct ggaataatgc agccccttcc 60
ctaactaaca tttccatgat gtatgctcaa tgacaaggca gaggaatgtg ttggatgagc 120
tcaggacctg cctccctgga cactcccatc ccaggcctgt atatctgttg acca 174

<210> SEQ ID NO 143
<211> LENGTH: 39
<212> TYPE: DNA
<213> ORGANISM: Artificial Sequence
<220> FEATURE:
<223> OTHER INFORMATION: AON-1 Pseudoexon 13-14 (134) target site and flanking sequences (+10 nt)

<400> SEQUENCE: 143
gtatggccag taggtctggt tcctgggagc cctggaata 39

<210> SEQ ID NO 144
<211> LENGTH: 29
<212> TYPE: DNA
<213> ORGANISM: Artificial Sequence
<220> FEATURE:
<223> OTHER INFORMATION: AON-1 Pseudoexon 13-14 (134) target site and flanking sequences (+5 nt)

<400> SEQUENCE: 144
gccagtaggt ctggttcctg ggagccctg 29

<210> SEQ ID NO 145
<211> LENGTH: 19
<212> TYPE: RNA
<213> ORGANISM: Artificial Sequence
<220> FEATURE:
<223> OTHER INFORMATION: AON-1 Pseudoexon 13-14 (134)

<400> SEQUENCE: 145
cucccaggaa ccagaccua 19

<210> SEQ ID NO 146
<211> LENGTH: 40
<212> TYPE: DNA
<213> ORGANISM: Artificial Sequence
<220> FEATURE:
<223> OTHER INFORMATION: AON-2 Pseudoexon 13-14 (134) target site and

```
            flanking sequences (+10 nt)

<400> SEQUENCE: 146

tgacaaggca gaggaatgtg ttggatgagc tcaggacctg                              40

<210> SEQ ID NO 147
<211> LENGTH: 30
<212> TYPE: DNA
<213> ORGANISM: Artificial Sequence
<220> FEATURE:
<223> OTHER INFORMATION: AON-2 Pseudoexon 13-14 (134) target site and
      flanking sequences (+5 nt)

<400> SEQUENCE: 147

aggcagagga atgtgttgga tgagctcagg                                         30

<210> SEQ ID NO 148
<211> LENGTH: 20
<212> TYPE: RNA
<213> ORGANISM: Artificial Sequence
<220> FEATURE:
<223> OTHER INFORMATION: AON-2 Pseudoexon 13-14 (134)

<400> SEQUENCE: 148

gcucauccaa cacauuccuc                                                    20

<210> SEQ ID NO 149
<211> LENGTH: 37
<212> TYPE: DNA
<213> ORGANISM: Artificial Sequence
<220> FEATURE:
<223> OTHER INFORMATION: AON-3 Pseudoexon 13-14 (134) target site and
      flanking sequences (+10 nt]

<400> SEQUENCE: 149

tgcctccctg gacactccca tcccaggcct gtatatc                                 37

<210> SEQ ID NO 150
<211> LENGTH: 27
<212> TYPE: DNA
<213> ORGANISM: Artificial Sequence
<220> FEATURE:
<223> OTHER INFORMATION: AON-3 Pseudoexon 13-14 (134) target site and
      flanking sequences (+5 nt)

<400> SEQUENCE: 150

ccctggacac tcccatccca ggcctgt                                            27

<210> SEQ ID NO 151
<211> LENGTH: 17
<212> TYPE: RNA
<213> ORGANISM: Artificial Sequence
<220> FEATURE:
<223> OTHER INFORMATION: AON-3 Pseudoexon 13-14 (134)

<400> SEQUENCE: 151

ccugggaugg gaguguc                                                       17

<210> SEQ ID NO 152

<400> SEQUENCE: 152

000

<210> SEQ ID NO 153
```

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160
<211> LENGTH: 68
<212> TYPE: DNA
<213> ORGANISM: Artificial Sequence
<220> FEATURE:
<223> OTHER INFORMATION: Pseudoexon 30-31 (68)

<400> SEQUENCE: 160
ggacattaat gatcttggct ctgagcagca ccctgtcctg ggagttctaa agtccagaac 60
agattaca 68

<210> SEQ ID NO 161
<211> LENGTH: 168
<212> TYPE: DNA
<213> ORGANISM: Artificial Sequence
<220> FEATURE:
<223> OTHER INFORMATION: Pseudoexon 30-31 (68) larger target + flanking sequences (+50 nt)

<400> SEQUENCE: 161
ctgcaggtat gtacacaaat acatgcacag ccagcatcca tcttttgcag ggacattaat 60
gatcttggct ctgagcagca ccctgtcctg ggagttctaa agtccagaac agattacagt 120
gagcatctcc tgggggattt agagacatca aagaaggctg tgtccgtg 168

<210> SEQ ID NO 162

-continued

<211> LENGTH: 108
<212> TYPE: DNA
<213> ORGANISM: Artificial Sequence
<220> FEATURE:
<223> OTHER INFORMATION: Pseudoexon 30-31 (68) larger target + flanking
sequences (+20 nt)

<400> SEQUENCE: 162
ccagcatcca tcttttgcag ggacattaat gatcttggct ctgagcagca ccctgtcctg 60
ggagttctaa agtccagaac agattacagt gagcatctcc tgggggat 108

<210> SEQ ID NO 163
<211> LENGTH: 38
<212> TYPE: DNA
<213> ORGANISM: Artificial Sequence
<220> FEATURE:
<223> OTHER INFORMATION: AON-1 Pseudoexon 30-31 (68) target site and
flanking sequences (+10 nt)

<400> SEQUENCE: 163
gggagttcta aagtccagaa cagattacag tgagcatc 38

<210> SEQ ID NO 164
<211> LENGTH: 28
<212> TYPE: DNA
<213> ORGANISM: Artificial Sequence
<220> FEATURE:
<223> OTHER INFORMATION: AON-1 Pseudoexon 30-31 (68) target site and
flanking sequences (+5 nt]

<400> SEQUENCE: 164
ttctaaagtc cagaacagat tacagtga 28

<210> SEQ ID NO 165
<211> LENGTH: 18
<212> TYPE: RNA
<213> ORGANISM: Artificial Sequence
<220> FEATURE:
<223> OTHER INFORMATION: AON-1 Pseudoexon 30-31 (68)

<400> SEQUENCE: 165
guaaucuguu cuggacuu 18

<210> SEQ ID NO 166
<211> LENGTH: 38
<212> TYPE: DNA
<213> ORGANISM: Artificial Sequence
<220> FEATURE:
<223> OTHER INFORMATION: AON-2 Pseudoexon 30-31 (68) target site and
flanking sequences (+10 nt]

<400> SEQUENCE: 166
tgagcagcac cctgtcctgg gagttctaaa gtccagaa 38

<210> SEQ ID NO 167
<211> LENGTH: 28
<212> TYPE: DNA
<213> ORGANISM: Artificial Sequence
<220> FEATURE:
<223> OTHER INFORMATION: AON-2 Pseudoexon 30-31 (68) target site and
flanking sequences (+5 nt)

<400> SEQUENCE: 167
agcaccctgt cctgggagtt ctaaagtc 28

<210> SEQ ID NO 168

<211> LENGTH: 18
<212> TYPE: RNA
<213> ORGANISM: Artificial Sequence
<220> FEATURE:
<223> OTHER INFORMATION: AON-2 Pseudoexon 30-31 (68)

<400> SEQUENCE: 168
uagaacuccc aggacagg 18

<210> SEQ ID NO 169
<211> LENGTH: 38
<212> TYPE: DNA
<213> ORGANISM: Artificial Sequence
<220> FEATURE:
<223> OTHER INFORMATION: AON-3 Pseudoexon 30-31 (68) target site and flanking sequences (+10 nt]

<400> SEQUENCE: 169
tacagtgagc atctcctggg ggatttagag acatcaaa 38

<210> SEQ ID NO 170
<211> LENGTH: 28
<212> TYPE: DNA
<213> ORGANISM: Artificial Sequence
<220> FEATURE:
<223> OTHER INFORMATION: AON-3 Pseudoexon 30-31 (68) target site and flanking sequences (+5 nt)

<400> SEQUENCE: 170
tgagcatctc ctgggggatt tagagaca 28

<210> SEQ ID NO 171
<211> LENGTH: 18
<212> TYPE: RNA
<213> ORGANISM: Artificial Sequence
<220> FEATURE:
<223> OTHER INFORMATION: AON-3 Pseudoexon 30-31 (68)

<400> SEQUENCE: 171
cuaaaucccc caggagau 18

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180
<211> LENGTH: 345
<212> TYPE: DNA
<213> ORGANISM: Artificial Sequence
<220> FEATURE:
<223> OTHER INFORMATION: Pseudoexon 30-31 (345)

<400> SEQUENCE: 180
ctcatctgct gcatcatagg gatcccaaaa gaaggaccca aggaacttgt ctcagtcctc 60
tgtgccccaa gaggaagctt tgcttgtttg ctttgctgtc aatgctgagg gctcctgtgg 120
ctgcctccac tcaaaaccct ccagcatcag gacgtcaagg ctgtgatact gtaccctgag 180
ctcttggcca gggcgaggga ggggaggcca agcctaccta catggtgttt catttcctaa 240
acgaaccctt acttccacgc ggtctgtcca gcttagaaac ttattttcag tagtgttggt 300
ccttggtccc tggacaaaat gtaacagcca aagtcctaga aaaag 345

<210> SEQ ID NO 181
<211> LENGTH: 385
<212> TYPE: DNA
<213> ORGANISM: Artificial Sequence
<220> FEATURE:
<223> OTHER INFORMATION: Pseudoexon 30-31 (345) larger target + flanking sequences (+20 nt]

<400> SEQUENCE: 181
tttctctctt tgaatcacag ctcatctgct gcatcatagg gatcccaaaa gaaggaccca 60
aggaacttgt ctcagtcctc tgtgccccaa gaggaagctt tgcttgtttg ctttgctgtc 120
aatgctgagg gctcctgtgg ctgcctccac tcaaaaccct ccagcatcag gacgtcaagg 180
ctgtgatact gtaccctgag ctcttggcca gggcgaggga ggggaggcca agcctaccta 240
catggtgttt catttcctaa acgaaccctt acttccacgc ggtctgtcca gcttagaaac 300
ttattttcag tagtgttggt ccttggtccc tggacaaaat gtaacagcca aagtcctaga 360
aaaaggcaag ccagttcctg ccatt 385

<210> SEQ ID NO 182
<211> LENGTH: 39
<212> TYPE: DNA
<213> ORGANISM: Artificial Sequence
<220> FEATURE:
<223> OTHER INFORMATION: AON-1 Pseudoexon 30-31 (345) target site and flanking sequences (+10 nt)

<400> SEQUENCE: 182
gctttgctgt caatgctgag ggctcctgtg gctgcctcc 39

<210> SEQ ID NO 183
<211> LENGTH: 29
<212> TYPE: DNA
<213> ORGANISM: Artificial Sequence
<220> FEATURE:
<223> OTHER INFORMATION: AON-1 Pseudoexon 30-31 (345) target site and
flanking sequences (+5 nt)

<400> SEQUENCE: 183
gctgtcaatg ctgagggctc ctgtggctg 29

<210> SEQ ID NO 184
<211> LENGTH: 19
<212> TYPE: RNA
<213> ORGANISM: Artificial Sequence
<220> FEATURE:
<223> OTHER INFORMATION: AON-1 Pseudoexon 30-31 (345)

<400> SEQUENCE: 184
acaggagucc ucagcauug 19

<210> SEQ ID NO 185
<211> LENGTH: 39
<212> TYPE: DNA
<213> ORGANISM: Artificial Sequence
<220> FEATURE:
<223> OTHER INFORMATION: AON-2 Pseudoexon 30-31 (345) target site and
flanking sequences (+10 nt)

<400> SEQUENCE: 185
tagtgttggt ccttggtccc tggacaaaat gtaacagcc 39

<210> SEQ ID NO 186
<211> LENGTH: 29
<212> TYPE: DNA
<213> ORGANISM: Artificial Sequence
<220> FEATURE:
<223> OTHER INFORMATION: AON-2 Pseudoexon 30-31 (345) target site and
flanking sequences (+5 nt)

<400> SEQUENCE: 186
ttggtccttg gtccctggac aaaatgtaa 29

<210> SEQ ID NO 187
<211> LENGTH: 19
<212> TYPE: RNA
<213> ORGANISM: Artificial Sequence
<220> FEATURE:
<223> OTHER INFORMATION: AON-2 Pseudoexon 30-31 (345)

<400> SEQUENCE: 187
uuuuguccag ggaccaagg 19

<210> SEQ ID NO 188
<211> LENGTH: 39
<212> TYPE: DNA
<213> ORGANISM: Artificial Sequence
<220> FEATURE:
<223> OTHER INFORMATION: AON-3 Pseudoexon 30-31 (345) target site and
flanking sequences (+10 nt)

<400> SEQUENCE: 188
gtccttggtc cctggacaaa atgtaacagc caaagtcct 39

<210> SEQ ID NO 189
<211> LENGTH: 29
<212> TYPE: DNA
<213> ORGANISM: Artificial Sequence
<220> FEATURE:
<223> OTHER INFORMATION: AON-3 Pseudoexon 30-31 (345) target site and
flanking sequences (+5 nt)

<400> SEQUENCE: 189
tggtccctgg acaaaatgta acagccaaa 29

<210> SEQ ID NO 190
<211> LENGTH: 19
<212> TYPE: RNA
<213> ORGANISM: Artificial Sequence
<220> FEATURE:
<223> OTHER INFORMATION: AON-3 Pseudoexon 30-31 (345)

<400> SEQUENCE: 190
cuguuacauu uuguccagg 19

<210> SEQ ID NO 191
<211> LENGTH: 39
<212> TYPE: DNA
<213> ORGANISM: Artificial Sequence
<220> FEATURE:
<223> OTHER INFORMATION: AON-4 Pseudoexon 30-31 (345) target site and
flanking sequences (+10 nt)

<400> SEQUENCE: 191
aaggaacttg tctcagtcct ctgtgcccca agaggaagc 39

<210> SEQ ID NO 192
<211> LENGTH: 29
<212> TYPE: DNA
<213> ORGANISM: Artificial Sequence
<220> FEATURE:
<223> OTHER INFORMATION: AON-4 Pseudoexon 30-31 (345) target site and
flanking sequences (+5 nt)

<400> SEQUENCE: 192
acttgtctca gtcctctgtg ccccaagag 29

<210> SEQ ID NO 193
<211> LENGTH: 19
<212> TYPE: RNA
<213> ORGANISM: Artificial Sequence
<220> FEATURE:
<223> OTHER INFORMATION: AON-4 Pseudoexon 30-31 (345)

<400> SEQUENCE: 193
ggggcacaga ggacugaga 19

<210> SEQ ID NO 194
<211> LENGTH: 42
<212> TYPE: DNA
<213> ORGANISM: Artificial Sequence
<220> FEATURE:
<223> OTHER INFORMATION: AON-5 Pseudoexon 30-31 (345) target site and
flanking sequences (+10 nt]

<400> SEQUENCE: 194
atctttatat ttctcaagca atattttctc tctttgaatc ac 42

<210> SEQ ID NO 195
<211> LENGTH: 32
<212> TYPE: DNA
<213> ORGANISM: Artificial Sequence
<220> FEATURE:
<223> OTHER INFORMATION: AON-5 Pseudoexon 30-31 (345) target site and
flanking sequences (+5 nt]

<400> SEQUENCE: 195
tatatttctc aagcaatatt ttctctcttt ga 32

<210> SEQ ID NO 196
<211> LENGTH: 22
<212> TYPE: RNA
<213> ORGANISM: Artificial Sequence
<220> FEATURE:
<223> OTHER INFORMATION: AON-5 Pseudoexon 30-31 (345)

<400> SEQUENCE: 196
gagagaaaau auugcuugag aa 22

<210> SEQ ID NO 197
<211> LENGTH: 40
<212> TYPE: DNA
<213> ORGANISM: Artificial Sequence
<220> FEATURE:
<223> OTHER INFORMATION: AON-6 Pseudoexon 30-31 (345) target site and
flanking sequences (+10 nt)

<400> SEQUENCE: 197
ttttctctct ttgaatcaca gctcatctgc tgcatcatag 40

<210> SEQ ID NO 198
<211> LENGTH: 30
<212> TYPE: DNA
<213> ORGANISM: Artificial Sequence
<220> FEATURE:
<223> OTHER INFORMATION: AON-6 Pseudoexon 30-31 (345) target site and
flanking sequences (+5 nt)

<400> SEQUENCE: 198
tctctttgaa tcacagctca tctgctgcat 30

<210> SEQ ID NO 199
<211> LENGTH: 20
<212> TYPE: RNA
<213> ORGANISM: Artificial Sequence
<220> FEATURE:
<223> OTHER INFORMATION: AON-6 Pseudoexon 30-31 (345)

<400> SEQUENCE: 199
gcagaugagc ugugauucaa 20

<210> SEQ ID NO 200
<211> LENGTH: 41
<212> TYPE: DNA
<213> ORGANISM: Artificial Sequence
<220> FEATURE:
<223> OTHER INFORMATION: AON-7 Pseudoexon 30-31 (345) target site and
flanking sequences (+10 nt)

<400> SEQUENCE: 200
ctttgaatca cagctcatct gctgcatcat agggatccca a 41

<210> SEQ ID NO 201
<211> LENGTH: 31

<212> TYPE: DNA
<213> ORGANISM: Artificial Sequence
<220> FEATURE:
<223> OTHER INFORMATION: AON-7 Pseudoexon 30-31 (345) target site and
flanking sequences (+5 nt)

<400> SEQUENCE: 201
aatcacagct catctgctgc atcataggga t 31

<210> SEQ ID NO 202
<211> LENGTH: 21
<212> TYPE: RNA
<213> ORGANISM: Artificial Sequence
<220> FEATURE:
<223> OTHER INFORMATION: AON-7 Pseudoexon 30-31 (345]

<400> SEQUENCE: 202
uaugaugcag cagaugagcu g 21

<210> SEQ ID NO 203
<211> LENGTH: 40
<212> TYPE: DNA
<213> ORGANISM: Artificial Sequence
<220> FEATURE:
<223> OTHER INFORMATION: AON-8 Pseudoexon 30-31 (345) target site and
flanking sequences (+10 nt)

<400> SEQUENCE: 203
cagctcatct gctgcatcat agggatccca aaagaaggac 40

<210> SEQ ID NO 204
<211> LENGTH: 30
<212> TYPE: DNA
<213> ORGANISM: Artificial Sequence
<220> FEATURE:
<223> OTHER INFORMATION: AON-8 Pseudoexon 30-31 (345) target site and
flanking sequences (+5 nt)

<400> SEQUENCE: 204
catctgctgc atcataggga tcccaaaaga 30

<210> SEQ ID NO 205
<211> LENGTH: 20
<212> TYPE: RNA
<213> ORGANISM: Artificial Sequence
<220> FEATURE:
<223> OTHER INFORMATION: AON-8 Pseudoexon 30-31 (345)

<400> SEQUENCE: 205
ugggaucccu augaugcagc 20

<210> SEQ ID NO 206
<211> LENGTH: 40
<212> TYPE: DNA
<213> ORGANISM: Artificial Sequence
<220> FEATURE:
<223> OTHER INFORMATION: AON-9 Pseudoexon 30-31 (345) target site and
flanking sequences (+10 nt)

<400> SEQUENCE: 206
aaggacccaa ggaacttgtc tcagtcctct gtgccccaag 40

<210> SEQ ID NO 207
<211> LENGTH: 30
<212> TYPE: DNA
<213> ORGANISM: Artificial Sequence
<220> FEATURE:

<223> OTHER INFORMATION: AON-9 Pseudoexon 30-31 (345) target site and
      flanking sequences (+5 nt)

<400> SEQUENCE: 207
cccaaggaac ttgtctcagt cctctgtgcc 30

<210> SEQ ID NO 208
<211> LENGTH: 20
<212> TYPE: RNA
<213> ORGANISM: Artificial Sequence
<220> FEATURE:
<223> OTHER INFORMATION: AON-9 Pseudoexon 30-31 (345)

<400> SEQUENCE: 208
agaggacuga gacaaguucc 20

<210> SEQ ID NO 209
<211> LENGTH: 40
<212> TYPE: DNA
<213> ORGANISM: Artificial Sequence
<220> FEATURE:
<223> OTHER INFORMATION: AON-10 Pseudoexon 30-31 (345) target site and
      flanking sequences (+10 nt)

<400> SEQUENCE: 209
gtctcagtcc tctgtgcccc aagaggaagc tttgcttgtt 40

<210> SEQ ID NO 210
<211> LENGTH: 30
<212> TYPE: DNA
<213> ORGANISM: Artificial Sequence
<220> FEATURE:
<223> OTHER INFORMATION: AON-10 Pseudoexon 30-31 (345) target site and
      flanking sequences (+5 nt)

<400> SEQUENCE: 210
agtcctctgt gccccaagag gaagctttgc 30

<210> SEQ ID NO 211
<211> LENGTH: 20
<212> TYPE: RNA
<213> ORGANISM: Artificial Sequence
<220> FEATURE:
<223> OTHER INFORMATION: AON-10 Pseudoexon 30-31 (345)

<400> SEQUENCE: 211
gcuuccucuu ggggcacaga 20

<210> SEQ ID NO 212
<211> LENGTH: 38
<212> TYPE: DNA
<213> ORGANISM: Artificial Sequence
<220> FEATURE:
<223> OTHER INFORMATION: AON-11 Pseudoexon 30-31 (345) target site and
      flanking sequences (+10 nt]

<400> SEQUENCE: 212
cttgtttgct ttgctgtcaa tgctgagggc tcctgtgg 38

<210> SEQ ID NO 213
<211> LENGTH: 28
<212> TYPE: DNA
<213> ORGANISM: Artificial Sequence
<220> FEATURE:
<223> OTHER INFORMATION: AON-11 Pseudoexon 30-31 (345) target site and
      flanking sequences (+5 nt)

<400> SEQUENCE: 213
ttgctttgct gtcaatgctg agggctcc 28

<210> SEQ ID NO 214
<211> LENGTH: 18
<212> TYPE: RNA
<213> ORGANISM: Artificial Sequence
<220> FEATURE:
<223> OTHER INFORMATION: AON-11 Pseudoexon 30-31 (345)

<400> SEQUENCE: 214
ccucagcauu gacagcaa 18

<210> SEQ ID NO 215
<211> LENGTH: 39
<212> TYPE: DNA
<213> ORGANISM: Artificial Sequence
<220> FEATURE:
<223> OTHER INFORMATION: AON-12 Pseudoexon 30-31 (345) target site and flanking sequences (+10 nt)

<400> SEQUENCE: 215
gctttgctgt caatgctgag ggctcctgtg gctgcctcc 39

<210> SEQ ID NO 216
<211> LENGTH: 29
<212> TYPE: DNA
<213> ORGANISM: Artificial Sequence
<220> FEATURE:
<223> OTHER INFORMATION: AON-12 Pseudoexon 30-31 (345) target site and flanking sequences (+5 nt)

<400> SEQUENCE: 216
gctgtcaatg ctgagggctc ctgtggctg 29

<210> SEQ ID NO 217
<211> LENGTH: 19
<212> TYPE: RNA
<213> ORGANISM: Artificial Sequence
<220> FEATURE:
<223> OTHER INFORMATION: AON-12 Pseudoexon 30-31 (345)

<400> SEQUENCE: 217
acaggagccc ucagcauug 19

<210> SEQ ID NO 218
<211> LENGTH: 38
<212> TYPE: DNA
<213> ORGANISM: Artificial Sequence
<220> FEATURE:
<223> OTHER INFORMATION: AON-13 Pseudoexon 30-31 (345) target site and flanking sequences (+10 nt)

<400> SEQUENCE: 218
atgctgaggg ctcctgtggc tgcctccact caaaaccc 38

<210> SEQ ID NO 219
<211> LENGTH: 28
<212> TYPE: DNA
<213> ORGANISM: Artificial Sequence
<220> FEATURE:
<223> OTHER INFORMATION: AON-13 Pseudoexon 30-31 (345) target site and flanking sequences (+5 nt)

<400> SEQUENCE: 219
gagggctcct gtggctgcct ccactcaa 28

<210> SEQ ID NO 220
<211> LENGTH: 18
<212> TYPE: RNA
<213> ORGANISM: Artificial Sequence
<220> FEATURE:
<223> OTHER INFORMATION: AON-13 Pseudoexon 30-31 (345)

<400> SEQUENCE: 220
uggaggcagc cacaggag 18

<210> SEQ ID NO 221
<211> LENGTH: 41
<212> TYPE: DNA
<213> ORGANISM: Artificial Sequence
<220> FEATURE:
<223> OTHER INFORMATION: AON-14 Pseudoexon 30-31 (345) target site and flanking sequences (+10 nt)

<400> SEQUENCE: 221
tggctgcctc cactcaaaac cctccagcat caggacgtca a 41

<210> SEQ ID NO 222
<211> LENGTH: 31
<212> TYPE: DNA
<213> ORGANISM: Artificial Sequence
<220> FEATURE:
<223> OTHER INFORMATION: AON-14 Pseudoexon 30-31 (345) target site and flanking sequences (+5 nt)

<400> SEQUENCE: 222
gcctccactc aaaaccctcc agcatcagga c 31

<210> SEQ ID NO 223
<211> LENGTH: 21
<212> TYPE: RNA
<213> ORGANISM: Artificial Sequence
<220> FEATURE:
<223> OTHER INFORMATION: AON-14 Pseudoexon 30-31 (345)

<400> SEQUENCE: 223
gaugcuggag gguuuugagu g 21

<210> SEQ ID NO 224
<211> LENGTH: 41
<212> TYPE: DNA
<213> ORGANISM: Artificial Sequence
<220> FEATURE:
<223> OTHER INFORMATION: AON-15 Pseudoexon 30-31 (345) target site and flanking sequences (+10 nt)

<400> SEQUENCE: 224
tggctgcctc cactcaaaac cctccagcat caggacgtca a 41

<210> SEQ ID NO 225
<211> LENGTH: 31
<212> TYPE: DNA
<213> ORGANISM: Artificial Sequence
<220> FEATURE:
<223> OTHER INFORMATION: AON-15 Pseudoexon 30-31 (345) target site and flanking sequences (+5 nt)

<400> SEQUENCE: 225
gcctccactc aaaaccctcc agcatcagga c 31

<210> SEQ ID NO 226

<211> LENGTH: 21
<212> TYPE: RNA
<213> ORGANISM: Artificial Sequence
<220> FEATURE:
<223> OTHER INFORMATION: AON-15 Pseudoexon 30-31 (345)

<400> SEQUENCE: 226
gaugcuggag aguuuugagu g 21

<210> SEQ ID NO 227
<211> LENGTH: 39
<212> TYPE: DNA
<213> ORGANISM: Artificial Sequence
<220> FEATURE:
<223> OTHER INFORMATION: AON-16 Pseudoexon 30-31 (345) target site and flanking sequences (+10 nt)

<400> SEQUENCE: 227
aaaaccctcc agcatcagga cgtcaaggct gtgatactg 39

<210> SEQ ID NO 228
<211> LENGTH: 29
<212> TYPE: DNA
<213> ORGANISM: Artificial Sequence
<220> FEATURE:
<223> OTHER INFORMATION: AON-16 Pseudoexon 30-31 (345) target site and flanking sequences (+5 nt):

<400> SEQUENCE: 228
cctccagcat caggacgtca aggctgtga 29

<210> SEQ ID NO 229
<211> LENGTH: 19
<212> TYPE: RNA
<213> ORGANISM: Artificial Sequence
<220> FEATURE:
<223> OTHER INFORMATION: AON-16 Pseudoexon 30-31 (345)

<400> SEQUENCE: 229
gccuugacgu ccugaugcu 19

<210> SEQ ID NO 230
<211> LENGTH: 40
<212> TYPE: DNA
<213> ORGANISM: Artificial Sequence
<220> FEATURE:
<223> OTHER INFORMATION: AON-17 Pseudoexon 30-31 (345) target site and flanking sequences (+10 nt)

<400> SEQUENCE: 230
ggctgtgata ctgtaccctg agctcttggc cagggcgagg 40

<210> SEQ ID NO 231
<211> LENGTH: 30
<212> TYPE: DNA
<213> ORGANISM: Artificial Sequence
<220> FEATURE:
<223> OTHER INFORMATION: AON-17 Pseudoexon 30-31 (345) target site and flanking sequences (+5 nt)

<400> SEQUENCE: 231
tgatactgta ccctgagctc ttggccaggg 30

<210> SEQ ID NO 232
<211> LENGTH: 20
<212> TYPE: RNA
<213> ORGANISM: Artificial Sequence
<220> FEATURE:
<223> OTHER INFORMATION: AON-17 Pseudoexon 30-31 (345)

<400> SEQUENCE: 232
gccaagagcu caggguacag 20

<210> SEQ ID NO 233
<211> LENGTH: 38
<212> TYPE: DNA
<213> ORGANISM: Artificial Sequence
<220> FEATURE:
<223> OTHER INFORMATION: AON-18 Pseudoexon 30-31 (345) target site and flanking sequences (+10 nt)

<400> SEQUENCE: 233
tggccagggc gagggagggg aggccaagcc tacctaca 38

<210> SEQ ID NO 234
<211> LENGTH: 28
<212> TYPE: DNA
<213> ORGANISM: Artificial Sequence
<220> FEATURE:
<223> OTHER INFORMATION: AON-18 Pseudoexon 30-31 (345) target site and flanking sequences (+5 nt)

<400> SEQUENCE: 234
agggcgaggg aggggaggcc aagcctac 28

<210> SEQ ID NO 235
<211> LENGTH: 18
<212> TYPE: RNA
<213> ORGANISM: Artificial Sequence
<220> FEATURE:
<223> OTHER INFORMATION: AON-18 Pseudoexon 30-31 (345)

<400> SEQUENCE: 235
cuuggccucc ccucccuc 18

<210> SEQ ID NO 236
<211> LENGTH: 38
<212> TYPE: DNA
<213> ORGANISM: Artificial Sequence
<220> FEATURE:
<223> OTHER INFORMATION: AON-19 Pseudoexon 30-31 (345) target site and flanking sequences (+10 nt)

<400> SEQUENCE: 236
gggaggccaa gcctacctac atggtgtttc atttccta 38

<210> SEQ ID NO 237
<211> LENGTH: 28
<212> TYPE: DNA
<213> ORGANISM: Artificial Sequence
<220> FEATURE:
<223> OTHER INFORMATION: AON-19 Pseudoexon 30-31 (345) target site and flanking sequences (+5 nt]

<400> SEQUENCE: 237
gccaagccta cctacatggt gtttcatt 28

<210> SEQ ID NO 238
<211> LENGTH: 18
<212> TYPE: RNA
<213> ORGANISM: Artificial Sequence
<220> FEATURE:
<223> OTHER INFORMATION: AON-19 Pseudoexon 30-31 (345)

<400> SEQUENCE: 238
aacaccaugu agguaggc 18

<210> SEQ ID NO 239
<211> LENGTH: 42
<212> TYPE: DNA
<213> ORGANISM: Artificial Sequence
<220> FEATURE:
<223> OTHER INFORMATION: AON-20 Pseudoexon 30-31 (345) target site and
flanking sequences (+10 nt)

<400> SEQUENCE: 239
agcctaccta catggtgttt catttcctaa acgaaccctt ac 42

<210> SEQ ID NO 240
<211> LENGTH: 32
<212> TYPE: DNA
<213> ORGANISM: Artificial Sequence
<220> FEATURE:
<223> OTHER INFORMATION: AON-20 Pseudoexon 30-31 (345) target site and
flanking sequences (+5 nt)

<400> SEQUENCE: 240
acctacatgg tgtttcattt cctaaacgaa cc 32

<210> SEQ ID NO 241
<211> LENGTH: 22
<212> TYPE: RNA
<213> ORGANISM: Artificial Sequence
<220> FEATURE:
<223> OTHER INFORMATION: AON-20 Pseudoexon 30-31 (345)

<400> SEQUENCE: 241
guuuaggaaa ugaaacacca ug 22

<210> SEQ ID NO 242
<211> LENGTH: 38
<212> TYPE: DNA
<213> ORGANISM: Artificial Sequence
<220> FEATURE:
<223> OTHER INFORMATION: AON-21 Pseudoexon 30-31 (345) target site and
flanking sequences (+10 nt)

<400> SEQUENCE: 242
ctaaacgaac ccttacttcc acgcggtctg tccagctt 38

<210> SEQ ID NO 243
<211> LENGTH: 28
<212> TYPE: DNA
<213> ORGANISM: Artificial Sequence
<220> FEATURE:
<223> OTHER INFORMATION: AON-21 Pseudoexon 30-31 (345) target site and
flanking sequences (+5 nt]

<400> SEQUENCE: 243
cgaaccctta cttccacgcg gtctgtcc 28

<210> SEQ ID NO 244
<211> LENGTH: 18
<212> TYPE: RNA
<213> ORGANISM: Artificial Sequence
<220> FEATURE:
<223> OTHER INFORMATION: AON-21 Pseudoexon 30-31 (345)

<400> SEQUENCE: 244
gaccgcgugg aaguaagg 18

<210> SEQ ID NO 245
<211> LENGTH: 41
<212> TYPE: DNA
<213> ORGANISM: Artificial Sequence
<220> FEATURE:
<223> OTHER INFORMATION: AON-22 Pseudoexon 30-31 (345) target site and
flanking sequences (+10 nt)

<400> SEQUENCE: 245
tccacgcggt ctgtccagct tagaaactta ttttcagtag t 41

<210> SEQ ID NO 246
<211> LENGTH: 31
<212> TYPE: DNA
<213> ORGANISM: Artificial Sequence
<220> FEATURE:
<223> OTHER INFORMATION: AON-22 Pseudoexon 30-31 (345) target site and
flanking sequences (+5 nt)

<400> SEQUENCE: 246
gcggtctgtc cagcttagaa acttattttc a 31

<210> SEQ ID NO 247
<211> LENGTH: 21
<212> TYPE: RNA
<213> ORGANISM: Artificial Sequence
<220> FEATURE:
<223> OTHER INFORMATION: AON-22 Pseudoexon 30-31 (345)

<400> SEQUENCE: 247
auaaguuucu aagcuggaca g 21

<210> SEQ ID NO 248
<211> LENGTH: 40
<212> TYPE: DNA
<213> ORGANISM: Artificial Sequence
<220> FEATURE:
<223> OTHER INFORMATION: AON-23 Pseudoexon 30-31 (345) target site and
flanking sequences (+10 nt)

<400> SEQUENCE: 248
cttattttca gtagtgttgg tccttggtcc ctggacaaaa 40

<210> SEQ ID NO 249
<211> LENGTH: 30
<212> TYPE: DNA
<213> ORGANISM: Artificial Sequence
<220> FEATURE:
<223> OTHER INFORMATION: AON-23 Pseudoexon 30-31 (345) target site and
flanking sequences (+5 nt)

<400> SEQUENCE: 249
tttcagtagt gttggtcctt ggtccctgga 30

<210> SEQ ID NO 250
<211> LENGTH: 20
<212> TYPE: RNA
<213> ORGANISM: Artificial Sequence
<220> FEATURE:
<223> OTHER INFORMATION: AON-23 Pseudoexon 30-31 (345)

<400> SEQUENCE: 250
ggaccaagga ccaacacuac 20

<210> SEQ ID NO 251

<211> LENGTH: 41
<212> TYPE: DNA
<213> ORGANISM: Artificial Sequence
<220> FEATURE:
<223> OTHER INFORMATION: AON-24 Pseudoexon 30-31 (345) target site and
flanking sequences (+10 nt)

<400> SEQUENCE: 251
gtccttggtc cctggacaaa atgtaacagc caaagtccta g 41

<210> SEQ ID NO 252
<211> LENGTH: 31
<212> TYPE: DNA
<213> ORGANISM: Artificial Sequence
<220> FEATURE:
<223> OTHER INFORMATION: AON-24 Pseudoexon 30-31 (345) target site and
flanking sequences (+5 nt)

<400> SEQUENCE: 252
tggtccctgg acaaaatgta acagccaaag t 31

<210> SEQ ID NO 253
<211> LENGTH: 21
<212> TYPE: RNA
<213> ORGANISM: Artificial Sequence
<220> FEATURE:
<223> OTHER INFORMATION: AON-24 Pseudoexon 30-31 (345)

<400> SEQUENCE: 253
ggcuguuaca uuuuguccag g 21

<210> SEQ ID NO 254
<211> LENGTH: 40
<212> TYPE: DNA
<213> ORGANISM: Artificial Sequence
<220> FEATURE:
<223> OTHER INFORMATION: AON-25 Pseudoexon 30-31 (345) target site and
flanking sequences (+10 nt)

<400> SEQUENCE: 254
gtcctagaaa aaggcaagcc agttcctgcc attttctttc 40

<210> SEQ ID NO 255
<211> LENGTH: 30
<212> TYPE: DNA
<213> ORGANISM: Artificial Sequence
<220> FEATURE:
<223> OTHER INFORMATION: AON-25 Pseudoexon 30-31 (345) target site and
flanking sequences (+5 nt)

<400> SEQUENCE: 255
agaaaaaggc aagccagttc ctgccatttt 30

<210> SEQ ID NO 256
<211> LENGTH: 20
<212> TYPE: RNA
<213> ORGANISM: Artificial Sequence
<220> FEATURE:
<223> OTHER INFORMATION: AON-25 Pseudoexon 30-31 (345)

<400> SEQUENCE: 256
ggcaggaacu ggcuugccuu 20

<210> SEQ ID NO 257
<211> LENGTH: 42
<212> TYPE: DNA
<213> ORGANISM: Artificial Sequence

```
<220> FEATURE:
<223> OTHER INFORMATION: AON-26 Pseudoexon 30-31 (345) target site and
      flanking sequences (+10 nt)

<400> SEQUENCE: 257

caagccagtt cctgccattt tctttcactt ctgcatttcc tc                              42

<210> SEQ ID NO 258
<211> LENGTH: 32
<212> TYPE: DNA
<213> ORGANISM: Artificial Sequence
<220> FEATURE:
<223> OTHER INFORMATION: AON-26 Pseudoexon 30-31 (345) target site and
      flanking sequences (+5 nt)

<400> SEQUENCE: 258

cagttcctgc cattttcttt cacttctgca tt                                        32

<210> SEQ ID NO 259
<211> LENGTH: 22
<212> TYPE: RNA
<213> ORGANISM: Artificial Sequence
<220> FEATURE:
<223> OTHER INFORMATION: AON-26 Pseudoexon 30-31 (345)

<400> SEQUENCE: 259

agaagugaaa gaaaauggca gg                                                   22

<210> SEQ ID NO 260
<211> LENGTH: 188
<212> TYPE: DNA
<213> ORGANISM: Artificial Sequence
<220> FEATURE:
<223> OTHER INFORMATION: Pseudoexon 36-37 (188)

<400> SEQUENCE: 260

tgagacgctg gcttctctca ctcccaactc atttatctac cggacctata cacctgaaca          60

gtgcccaact ctgccaccat cccctcccca tgtggatgcc gtcctctccc tgctccagct         120

gcctctgctg catgcaggtc ctcctcgttc tgctctggct ctgataccct gcaccagatc         180

agcctcct                                                                 188

<210> SEQ ID NO 261
<211> LENGTH: 288
<212> TYPE: DNA
<213> ORGANISM: Artificial Sequence
<220> FEATURE:
<223> OTHER INFORMATION: Pseudoexon 36-37 (188) larger target + flanking
      sequences (+50 nt)

<400> SEQUENCE: 261

ctcattctag ttttttttct ttccacatct gtaactccct tctccaacag tgagacgctg          60

gcttctctca ctcccaactc atttatctac cggacctata cacctgaaca gtgcccaact         120

ctgccaccat cccctcccca tgtggatgcc gtcctctccc tgctccagct gcctctgctg         180

catgcaggtc ctcctcgttc tgctctggct ctgataccct gcaccagatc agcctcctgt         240

aaggatatct ttctcatccc gttgaggcct ccacacccca cggcaggt                      288

<210> SEQ ID NO 262
<211> LENGTH: 228
<212> TYPE: DNA
<213> ORGANISM: Artificial Sequence
<220> FEATURE:
<223> OTHER INFORMATION: Pseudoexon 36-37 (188) larger target + flanking
```

sequences (+20 nt)

<400> SEQUENCE: 262
gtaactccct tctccaacag tgagacgctg gcttctctca ctcccaactc atttatctac 60
cggacctata cacctgaaca gtgcccaact ctgccaccat cccctcccca tgtggatgcc 120
gtcctctccc tgctccagct gcctctgctg catgcaggtc ctcctcgttc tgctctggct 180
ctgataccct gcaccagatc agcctcctgt aaggatatct ttctcatc 228

<210> SEQ ID NO 263
<211> LENGTH: 38
<212> TYPE: DNA
<213> ORGANISM: Artificial Sequence
<220> FEATURE:
<223> OTHER INFORMATION: AON-1 Pseudoexon 36-37 (188) target site and flanking sequences (+10 nt)

<400> SEQUENCE: 263
ctatacacct gaacagtgcc caactctgcc accatccc 38

<210> SEQ ID NO 264
<211> LENGTH: 28
<212> TYPE: DNA
<213> ORGANISM: Artificial Sequence
<220> FEATURE:
<223> OTHER INFORMATION: AON-1 Pseudoexon 36-37 (188) target site and flanking sequences (+5 nt)

<400> SEQUENCE: 264
cacctgaaca gtgcccaact ctgccacc 28

<210> SEQ ID NO 265
<211> LENGTH: 18
<212> TYPE: RNA
<213> ORGANISM: Artificial Sequence
<220> FEATURE:
<223> OTHER INFORMATION: AON-1 Pseudoexon 36-37 (188)

<400> SEQUENCE: 265
cagaguuggg cacuguuc 18

<210> SEQ ID NO 266
<211> LENGTH: 37
<212> TYPE: DNA
<213> ORGANISM: Artificial Sequence
<220> FEATURE:
<223> OTHER INFORMATION: AON-2 Pseudoexon 36-37 (188) target site and flanking sequences (+10 nt)

<400> SEQUENCE: 266
gctctgatac cctgcaccag atcagcctcc tgtaagg 37

<210> SEQ ID NO 267
<211> LENGTH: 27
<212> TYPE: DNA
<213> ORGANISM: Artificial Sequence
<220> FEATURE:
<223> OTHER INFORMATION: AON-2 Pseudoexon 36-37 (188) target site and flanking sequences (+5 nt)

<400> SEQUENCE: 267
gataccctgc accagatcag cctcctg 27

<210> SEQ ID NO 268
<211> LENGTH: 17

<212> TYPE: RNA
<213> ORGANISM: Artificial Sequence
<220> FEATURE:
<223> OTHER INFORMATION: AON-2 Pseudoexon 36-37 (188)

<400> SEQUENCE: 268
ggcugaucug gugcagg 17

<210> SEQ ID NO 269
<211> LENGTH: 39
<212> TYPE: DNA
<213> ORGANISM: Artificial Sequence
<220> FEATURE:
<223> OTHER INFORMATION: AON-3 Pseudoexon 36-37 (188) target site and flanking sequences (+10 nt)

<400> SEQUENCE: 269
taccctgcac cagatcagcc tcctgtaagg atatctttc 39

<210> SEQ ID NO 270
<211> LENGTH: 29
<212> TYPE: DNA
<213> ORGANISM: Artificial Sequence
<220> FEATURE:
<223> OTHER INFORMATION: AON-3 Pseudoexon 36-37 (188) target site and flanking sequences (+5 nt)

<400> SEQUENCE: 270
tgcaccagat cagcctcctg taaggatat 29

<210> SEQ ID NO 271
<211> LENGTH: 19
<212> TYPE: RNA
<213> ORGANISM: Artificial Sequence
<220> FEATURE:
<223> OTHER INFORMATION: AON-3 Pseudoexon 36-37 (188)

<400> SEQUENCE: 271
cuuacaggag gcugaucug 19

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280
<211> LENGTH: 19
<212> TYPE: RNA
<213> ORGANISM: Artificial Sequence
<220> FEATURE:
<223> OTHER INFORMATION: SON1 (c.4539+2001G>A, sense version of AON1)

<400> SEQUENCE: 280
caaugcugag gacuccugu 19

<210> SEQ ID NO 281
<211> LENGTH: 19
<212> TYPE: RNA
<213> ORGANISM: Artificial Sequence
<220> FEATURE:
<223> OTHER INFORMATION: SON2 (c.4539+2001G>A, sense version of AON4)

<400> SEQUENCE: 281
ucucaguccu cugugcccc 19

<210> SEQ ID NO 282
<211> LENGTH: 20
<212> TYPE: RNA
<213> ORGANISM: Artificial Sequence
<220> FEATURE:
<223> OTHER INFORMATION: SON3 (c.1937+435C>G, sense version of AON2)

<400> SEQUENCE: 282
gaggaaugug uuggaugagc 20

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290
<211> LENGTH: 16272
<212> TYPE: DNA
<213> ORGANISM: Artificial Sequence
<220> FEATURE:
<223> OTHER INFORMATION: pCI-Neo-Rho-ABCA4-intron6-intron7 wild type

<400> SEQUENCE: 290
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720
aactagaatg cagtgaaaaa aatgctttat ttgtgaaatt tgtgatgcta ttgctttatt 780
tgtaaccatt ataagctgca ataaacaagt taacaacaac aattgcattc attttatgtt 840
tcaggttcag ggggagatgt gggaggtttt ttaaagcaag taaaacctct acaaatgtgg 900
taaaatccga taaggatcga tccgggctgg cgtaatagcg aagaggcccg caccgatcgc 960
ccttcccaac agttgcgcag cctgaatggc gaatggacgc gccctgtagc ggcgcattaa 1020
gcgcggcggg tgtggtggtt acgcgcagcg tgaccgctac acttgccagc gccctagcgc 1080
ccgctccttt cgctttcttc ccttcctttc tcgccacgtt cgccggcttt ccccgtcaag 1140
ctctaaatcg gggctccct ttagggttcc gatttagtgc tttacggcac ctcgacccca 1200
aaaaacttga ttagggtgat ggttcacgta gtgggccatc gccctgatag acggtttttc 1260
gccctttgac gttggagtcc acgttcttta atagtggact cttgttccaa actggaacaa 1320
cactcaaccc tatctcggtc tattcttttg atttataagg gattttgccg atttcggcct 1380
attggttaaa aaatgagctg atttaacaaa aatttaacgc gaattttaac aaaatattaa 1440
cgcttacaat ttcctgatgc ggtattttct ccttacgcat ctgtgcggta tttcacaccg 1500
catacgcgga tctgcgcagc accatggcct gaaataacct ctgaaagagg aacttggtta 1560
ggtaccttct gaggcggaaa gaaccagctg tggaatgtgt gtcagttagg gtgtggaaag 1620
tccccaggct ccccagcagg cagaagtatg caaagcatgc atctcaatta gtcagcaacc 1680
aggtgtggaa agtccccagg ctccccagca ggcagaagta tgcaaagcat gcatctcaat 1740
tagtcagcaa ccatagtccc gcccctaact ccgcccatcc cgcccctaac tccgcccagt 1800
tccgcccatt ctccgcccca tggctgacta atttttttta tttatgcaga ggccgaggcc 1860
gcctcggcct ctgagctatt ccagaagtag tgaggaggct tttttggagg cctaggcttt 1920
tgcaaaaagc ttgattcttc tgacacaaca gtctcgaact taaggctaga gccaccatga 1980
ttgaacaaga tggattgcac gcaggttctc cggccgcttg ggtggagagg ctattcggct 2040
atgactgggc acaacagaca atcggctgct ctgatgccgc cgtgttccgg ctgtcagcgc 2100
aggggcgccc ggttcttttt gtcaagaccg acctgtccgg tgccctgaat gaactgcagg 2160
acgaggcagc gcggctatcg tggctggcca cgacgggcgt tccttgcgca gctgtgctcg 2220
acgttgtcac tgaagcggga agggactggc tgctattggg cgaagtgccg gggcaggatc 2280
tcctgtcatc tcaccttgct cctgccgaga aagtatccat catggctgat gcaatgcggc 2340
ggctgcatac gcttgatccg gctacctgcc cattcgacca ccaagcgaaa catcgcatcg 2400
agcgagcacg tactcggatg gaagccggtc ttgtcgatca ggatgatctg gacgaagagc 2460
atcaggggct cgcgccagcc gaactgttcg ccaggctcaa ggcgcgcatg cccgacggcg 2520
aggatctcgt cgtgacccat ggcgatgcct gcttgccgaa tatcatggtg gaaaatggcc 2580
gcttttctgg attcatcgac tgtggccggc tgggtgtggc ggaccgctat caggacatag 2640
cgttggctac ccgtgatatt gctgaagagc ttggcggcga atgggctgac cgcttcctcg 2700
tgctttacgg tatcgccgct cccgattcgc agcgcatcgc cttctatcgc cttcttgacg 2760
agttcttctg agcgggactc tggggttcga aatgaccgac caagcgacgc ccaacctgcc 2820
atcacgatgg ccgcaataaa atatctttat tttcattaca tctgtgtgtt ggttttttgt 2880
gtgaatcgat agcgataagg atccgcgtat ggtgcactct cagtacaatc tgctctgatg 2940
ccgcatagtt aagccagccc cgacacccgc caacacccgc tgacgcgccc tgacgggctt 3000
gtctgctccc ggcatccgct tacagacaag ctgtgaccgt ctccgggagc tgcatgtgtc 3060
agaggttttc accgtcatca ccgaaacgcg cgagacgaaa gggcctcgtg atacgcctat 3120
ttttataggt taatgtcatg ataataatgg tttcttagac gtcaggtggc acttttcggg 3180
gaaatgtgcg cggaacccct atttgtttat ttttctaaat acattcaaat atgtatccgc 3240
tcatgagaca ataaccctga taaatgcttc aataatattg aaaaaggaag agtatgagta 3300
ttcaacattt ccgtgtcgcc cttattccct tttttgcggc attttgcctt cctgtttttg 3360
ctcacccaga aacgctggtg aaagtaaaag atgctgaaga tcagttgggt gcacgagtgg 3420
gttacatcga actggatctc aacagcggta agatccttga gagttttcgc cccgaagaac 3480
gttttccaat gatgagcact tttaaagttc tgctatgtgg cgcggtatta tcccgtattg 3540

-continued acgccgggca agagcaactc ggtcgccgca tacactattc tcagaatgac ttggttgagt 3600
actcaccagt cacagaaaag catcttacgg atggcatgac agtaagagaa ttatgcagtg 3660
ctgccataac catgagtgat aacactgcgg ccaacttact tctgacaacg atcggaggac 3720
cgaaggagct aaccgctttt ttgcacaaca tgggggatca tgtaactcgc cttgatcgtt 3780
gggaaccgga gctgaatgaa gccataccaa acgacgagcg tgacaccacg atgcctgtag 3840
caatggcaac aacgttgcgc aaactattaa ctggcgaact acttactcta gcttcccggc 3900
aacaattaat agactggatg gaggcggata aagttgcagg accacttctg cgctcggccc 3960
ttccggctgg ctggtttatt gctgataaat ctggagccgg tgagcgtggg tctcgcggta 4020
tcattgcagc actggggcca gatggtaagc cctcccgtat cgtagttatc tacacgacgg 4080
ggagtcaggc aactatggat gaacgaaata gacagatcgc tgagataggt gcctcactga 4140
ttaagcattg gtaactgtca gaccaagttt actcatatat actttagatt gatttaaaac 4200
ttcattttta atttaaaagg atctaggtga agatcctttt tgataatctc atgaccaaaa 4260
tcccttaacg tgagttttcg ttccactgag cgtcagaccc cgtagaaaag atcaaaggat 4320
cttcttgaga tccttttttt ctgcgcgtaa tctgctgctt gcaaacaaaa aaaccaccgc 4380
taccagcggt ggtttgtttg ccggatcaag agctaccaac tctttttccg aaggtaactg 4440
gcttcagcag agcgcagata ccaaatactg ttcttctagt gtagccgtag ttaggccacc 4500
acttcaagaa ctctgtagca ccgcctacat acctcgctct gctaatcctg ttaccagtgg 4560
ctgctgccag tggcgataag tcgtgtctta ccgggttgga ctcaagacga tagttaccgg 4620
ataaggcgca gcggtcgggc tgaacggggg gttcgtgcac acagcccagc ttggagcgaa 4680
cgacctacac cgaactgaga tacctacagc gtgagctatg agaaagcgcc acgcttcccg 4740
aagggagaaa ggcggacagg tatccggtaa gcggcagggt cggaacagga gagcgcacga 4800
gggagcttcc agggggaaac gcctggtatc tttatagtcc tgtcgggttt cgccacctct 4860
gacttgagcg tcgatttttg tgatgctcgt caggggggcg gagcctatgg aaaaacgcca 4920
gcaacgcggc ctttttacgg ttcctggcct tttgctggcc ttttgctcac atggctcgac 4980
agatcttcaa tattggccat tagccatatt attcattggt tatatagcat aaatcaatat 5040
tggctattgg ccattgcata cgttgtatct atatcataat atgtacattt atattggctc 5100
atgtccaata tgaccgccat gttggcattg attattgact agttattaat agtaatcaat 5160
tacggggtca ttagttcata gcccatatat ggagttccgc gttacataac ttacggtaaa 5220
tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460
tacttggcag tacatctacg tattagtcat cgctattacc atggtgatgc ggttttggca 5520
gtacaccaat gggcgtggat agcggtttga ctcacgggga tttccaagtc tccaccccat 5580
tgacgtcaat gggagtttgt tttggcacca aaatcaacgg gactttccaa aatgtcgtaa 5640
caactgcgat cgcccgcccc gttgacgcaa atgggcggta ggcgtgtacg gtgggaggtc 5700
tatataagca gagctcgttt agtgaaccgt cagatcacta gaagctttat tgcggtagtt 5760
tatcacagtt aaattgctaa cgcagtcagt gcttctgaca caacagtctc gaacttaagc 5820
tgcagtgact ctcttaaggt agccttgcag aagttggtcg tgaggcactg ggcaggtaag 5880
tatcaaggtt acaagacagg tttaaggaga ccaatagaaa ctgggcttgt cgagacagag 5940
aagactcttg cgtttctgat aggcacctat tggtcttact gacatccact ttgcctttct 6000
ctccacaggt gtccactccc agttcaatta cagctcttaa ggctagagta cttaatacga 6060
ctcactatag gctagcctcg agaattccgg aggtcaacaa cgagtctttt gtcatctaca 6120
tgttcgtggt ccacttcacc atccccatga ttatcatctt tttctgctat gggcagctcg 6180
tcttcaccgt caaggaggta cgggccgggg ggtgggcggc ctcacggctc tgagggtcca 6240
gcccccagca tgcatctgcg gctcctgctc cctggaggag ccatatcaca agtttgtaca 6300
aaaaagcagg cttcgagacc gtttgacatg tcccccaacc ccccagtgat tgagtctgaa 6360
ttctccactg atgacgcatt tcctagcact cagggtgtcc cctcctggtt gccccctcac 6420
cactgaagcc cgcttcctcc cttttcattt gatgcttaac aactgtcagt ttgcaagaaa 6480
catgcttcaa atccacattc tcccagttgc ctagcaacaa cttccctccc ggataaatgt 6540
gggtttcctg tagctcagcc caggactgaa cacagcagca cacacttctg tccactgctt 6600
caactgcttt tcacctctgg tctgcatgcc ttcaagactg cagctcatcc ctcccttcag 6660
aaccttccat agcctgcaga ggccatgtct gccccaaaaa gacacattga acctgaggct 6720
acttatttac ccttgtgtta ggtatatcct caacttagaa attaatactg tttccagatt 6780
gtcttctttg aatcacagaa agtaaaacaa caaaacattc aatgcttaag acatttcatg 6840
tgcggttggg tgacatctgt ttgatgaaca catttgatcc aaagcatcag aaatactatg 6900
ccaacaagac tttttaggag gtgataaaca tgtctgttct accttaagaa aaaaatatta 6960
cacagtccca agggagagac atggttttga tcccagacaa cccaagcaga gacctcttag 7020
ggccggaatc atcttggctg ctgcctagga ccttatatca atttcttaag cacaggatca 7080
aggcctaaag gccccttaga ctgacctcag ttagtagagg cagatccctt cacagcctta 7140
tcttccttag aggtctagtc tgaccttgaa cttcggctgg cagtgctgtc agttgtgatg 7200
tgtgacatgg aagagttatt tgttacttgg aaaattaaga gaacttattt ggcataggaa 7260
attgtgtgtg tgtgtgtgtg tgtgtgtgtg tgtgtgtgtg tgtgtgtgtg agatgatgtt 7320
tgccattttg atctgtgact ttttttccca gaaatagttt ctcagttcca ttccaactaa 7380
acttacagtc tcttccggtt ctttgacaga aacaattcat gtgaatttga acagataata 7440
gggaaggggg aaccaaaaga agaggagagc cctgggaaag ttattttata atttatggca 7500
acctcagtca ggcaactgtg aacaggtaca tatggagggc tccctcggga ctaggcagta 7560
ttcagagatg taaggtgtga ggaccggacc ctcatcattt accattccca ctaaaaagag 7620
ctgggaagga aattgtagct gtagcaccag gcacgtaact ggagcttagt aactatttgg 7680
tgaaggaata ttattaaatt attaacaaga tggaaaaaag ggtattaacc acacaaaaat 7740
acatctcaag ctattgtttc tctgttccct ttcccccaaa ttcctagtct tgctcttatc 7800
tggctgtctc tctagtcact ctttcttgct gactctcttc acgttccttt ctccacctgg 7860
aattcctggg ccctcccctt ttactgacag acactgtcct cactctcaca gtcatcagtt 7920
tgtctcttta caaacctcag ctcaagtgtc acttccccgt ccccaggtga aactgactgc 7980
tccctccctg taagtcacca tgatgactgc tatatatagc cctcatggaa cctaaaacct 8040
caacagacac agtctctttc ctactctgtt atagtttatt tactcattaa ttaccacaac 8100
acgtattatt gagcacctac tgtgtaccat gcccagaaga taaaagacaa acaaaataaa 8160
acctattcct atgcttaatg agtttacagt ctagtggaga gatagataca ttaaaaaata 8220
acagcaaacc aaaataaaag tggtaaataa atgcactgag aaagacagga atagctagga 8280

-continued

```
ggggcaccta atccctaggg aaggaaagct ggaagagcat ggtgatgggg gaagaaggct   8340
ttctggagaa ggtgaggtag tttgaaatga gttgactctg gccagtaggg gtagagtgag   8400
aatggggtga gacagggtgg gttggtcatt ttgatccatt agtcctcaaa gtgataggac   8460
tagtggctaa ggactgcagg ctttacagaa gcctacaaaa ctatttgaga tttgaagttt   8520
ttttttttt ttaattggct ccaaaagaaa atgaaaaaac tttagaatta taatgaatga   8580
atattaaatg aatatttaag gaaggtaatt ttattcaact tcattgttaa atttagttaa   8640
aacaagccct tgagtttcat tcaacactgt tttatcatac cgttgatgag agaaaacaaa   8700
actgattcct ggccagggcc actgtcagcg tggggtttgc acatctttcc catgtctgct   8760
tgggttagct ccaggtactc ctgtttcccc cacatcccca agatgtgccc attagtggaa   8820
acggtgtgtc tgcatgattc caacgtgagt gagtgtgggt gtgggagtga gtgcccctgc   8880
catgggaggg catcctgtcc aggttagatt cctaccttgt gccctgagct gctgggatgg   8940
aatccagcca cccatgactc tgaactgaaa taattgggtg aataattatc ttacttttta   9000
attaatcttt gaaaatgtat gtatagttca catgtatttc aatatttaat attagaagta   9060
ttttagtctt tattttgaag tttggtgatt tattgtaacc agaaacaagc tatagaaact   9120
taattttggg ccaagtgcag tggctcacac ctataatccc agcattttgg gaggccgagg   9180
cagacgcatc acttgaggtc cggagttcaa gatcagcctg gccaacatgg taaaaccctg   9240
tctctactaa aaaatacaaa aattagccag atgtggtggg cacctgtagt cccagctact   9300
tgggtggctg aagcaggaga atcacttgaa cccgggaggc ggagcagtga gcagagatcg   9360
tgccactgca ctcccaccta ggcgacagtg tgacactcca tctcaaaaaa aaaaaaaaat   9420
agaaaagaaa gaaacttaat tctggtttat atcaattagc ctgtggtaaa attggtttca   9480
ttatagccat ttcacttagt tgaagtttcc aataacctgt ggatgaatta agtgaggatt   9540
tactatattc ataaaatctt aaattccaaa gcctgtttgc agttcaggtt tttccacttt   9600
acaaacactt ctaagtattc acaatgattg cttaaaattc ataccagata aatcattaaa   9660
taagttgttc aaagtcaaat aatttcataa gtaaaaatta ggagctttta gaaaactata   9720
cctacataga cctagaccta tagatagaca gagatctgaa tagatatgga cacagatgct   9780
ttccaaagtg ttcatgtgat gtgtggtgga gtttcaagac cagagtgtgc ctggggcctg   9840
cagaagtaaa ggagagggga tggagagaag attgtccaca tggccatggg caatctccca   9900
cccacactca agtgaggaag acaggaaaca aattcagaaa gaagagaaaa taatcaaaac   9960
tgatgggagc ttgtgactga tttacttatg cgcagcctcc ctggagacat gagtgtggct  10020
gttccttagg ttgtgcctct gggctcctac cccctcttag atgccttcct attatctagg  10080
acctggttgc tttttgtctg catagcttct ttggattcca gtctttgatg ccagcttcct  10140
cctaaagtag cctttcagat gtcccttggt taccctctgc tatctaaggg ctcatcctac  10200
cccacactca ttcccagcac caatttctgg atctccaggc tggagattta gacaatggga  10260
tgggaagaac ccatgatggg tcccagacag aaagtggtgc cagccacaga aagggcacac  10320
aggcacagaa gttggtttgg ggtaagacga tgtggtcagt tcagaacacg ctggatctag  10380
gcagatgccc agcagacagt tggatatgta agtctgaagc tctggggaga ggtctaggtt  10440
ggaggtacag atttagaagt catcaacaaa aaggtagcag attaaatgat aaaggaaatg  10500
agactatccg gggagtgtgc agagtgagag gagcaaggga ggcccttggg aacctcagca  10560
cttcagggga aggtagaggt acagttgctg gtgggaaagg cagagaagta gcaaagcaaa  10620
ccaggcaaaa gcagtgtcac agacgaccag ggaggaaaag gacatgatca aaatgttgag  10680
```

aaaagcagag aggtttgaaa atacaagaag caaaaatgtc cactagactt aaaaaccagg 10740
agaaaactgg ggggttcttg ataaagcatc ttagtaggat ggtgagggta gaagccaggg 10800
aagtgttggt gaggaagtga agtcactgat tacggactat gcttaaaaga atgtgggaat 10860
gaagggtgga agagagaaat tagactgtag ctagggagac ataagcgatc agaggtagat 10920
tctttctctc ctgtgggaga atcttgcacg tatacacagc atgacgacag tgatggaagg 10980
gctggcgaag cctcagggag actcttggag gtaaacccca tgaagggagg actttgtttc 11040
attcactgcc gtgtccccag cacctggcac aatagcagac actcaataca tatttgtcaa 11100
atgtgggatt ttatcattta gaaactgcac ctggctgtga gtaacaaaag tcagagaaac 11160
cgtgggtttc atttttctcc ccaggcagag tctggagctg ggtcctccaa gaggggtttg 11220
gagcaccaca ggtttcctca agacccccag gctgccctgt gtttccctcc ttcatcccca 11280
gcatatgcct gtcatctggt gacctccaaa cacctgtgct gcctcctcca gcacatccat 11340
gttgcaggca gggaccaggc aaagggcaga ggggcctact tcaaaagacc atttccagaa 11400
accccatcct atgacttctc ctggtgtctt ggttaccatt gtgccatagg ctcaccctgt 11460
atgcatggga ggctgggcca ggcattatga cttttagcaa tattgcatag ataagcatca 11520
atctttgtca ctgtgacgaa gcctagtcac tcagtgctag gcaaggttaa tggaatgggt 11580
tggtgtgtgc attattcttg aggtctttct tatgcttcat gttatacatt tattaggacg 11640
tttaggcaac agggggataa aaatgaagag gagatgcatg ctatgatctg aatgtttgca 11700
tcctccccaa aattcatatg ttgaaatctt catccccaag atgatggcat taggaggtgg 11760
ggcctttcgg aggcaattag gtcatgactg ggattagtgc ccttgtaaaa ccccagaaag 11820
ccagcttgcc gcttccacca tatgaagaca cagagagaag atgccatcta cgaatcagga 11880
aatgagcccg caccatgcaa taaacctgct ggagccttga tcttagactt cccagctgcc 11940
agatctgtgg gaaatagatt tctgttgttt acccagctta tggtattttg ttgtagcagc 12000
cagagtgaac taagacagtg ctgatctcgt attcttggag ggaaccctta gtctttaggg 12060
aaagcaaagc caccatttgg ggcagggtgt tctccaagtg ctgccacata tgctgatgtg 12120
gttaaactgc aaactatggt aaaaatgtgg aggtctgtgg aattgtcaat caggaaaaag 12180
atataaaaag aagttaaagt cttcgtgctt ctggaaggat atgtgccaaa ttgttaacat 12240
tgattatcct tgggtagaga tgtggggaag tttgcagaga cagttttgcc ttgtacttta 12300
tataagtaaa cagctactac ttcgttgtct taaaaaaaaa aaacagccta tgtgctcttc 12360
atgtgactca gaactaccta ggcaatacga ttaattgaat tagtaaaatt gagtgattat 12420
gaattttcag gaagtcatta atttaccact tctttattac atccacttct aacaggactt 12480
caatataggg gaatttgact tcaagataaa aagaccaaat ttatttaccc ttttaaaaaa 12540
agacaactta aaagcagact tgtcttacag aaccttcctt agttggacat cgatgagtgt 12600
acagaaaatg caatggataa aaagcttggt gatacaaaga taaaaagtgg ggtcctgtcc 12660
ttaatgaaca taccatttca tggagtatca ggtgtataaa caattataat caatctgctt 12720
gttattctga taagatcatt tactcacaca tcaaatactg agtgcccacc acatgcccag 12780
catacctaga agtcatccag tatgatttct gtctacatgg agcatagagt cttacagggg 12840
agatagatga caagtaaaca ccagaataat taccaatggt gaagagcaca aggaaggaaa 12900
cagaactcct aaagagagcg tggctgggca ggggtgagca agaggcatag aaaaaggggc 12960
atctaaatct acttgggagg aagctgtttc tcacataggt catcatgtta ggaatgagac 13020

-continued

```
ttgagggatg agtagaagtt tgccaggcaa agaaggaatg ggggggaata gagagcagag  13080
ctaggggcag gagacagctg acgtgtgagc agacataaaa agaagtccac tgtggcagca  13140
gagaagcagg agagaaggca agtgagggag ccaggcacca gctcacagag gtcatgtgtg  13200
tcaaaacgta gtaatggcct tctcttctgg agacagtagg gagccatgga agatgtttga  13260
gcagggaaag cgacatgact ggattggcct gttgggtaac tcagaccaca atgcattgga  13320
agggaggggg ctagaggcaa ggggactggc aagaaggcca gtcctttttc tatgcctatt  13380
ttgatgaaat attctagaag ggaagtgaac aaaggtagtc ctagagagga agaacaaaac  13440
agataggata cttccttagt atttgctcat tcgacaattt atttttgcat atacactaaa  13500
accttttta ttattaaaac gttttattgt aggaaaaaag tatgaaagta gagtgaataa  13560
taaaatgagc tcccatggat ctatcaccca gcttcaacta ttatcaatat ttggctgttc  13620
ttgttttaac tgttctccac cttttttcc tgaagttttt ttgaagcaaa tcacagacaa  13680
catatcattt caccatatgt acttccctct gtatctctaa catgtaagaa cttgttttaa  13740
caaaatcacc atgctatgat catacccaac aaaatttatc ataatgtctt aataatacct  13800
aatacccatt tcatgtccac tttcccccaa ttgctacagc tggtttgttc agatcagaat  13860
caaaatccac ctgtggccat tttactgcta tgtctctcag gtctcttttc atctctaata  13920
atctcagggg agacaggagg gaggacgggc aggacttggg gctaacttgc ttatcgacac  13980
acagttttgc ctacttgctt cctcccttca cacccactct tcttctcagc cccacccttg  14040
tatggaaaaa acagaaatta aagtgctttg cccagcaccc actgaagcta tttcgaagga  14100
gtttgaagag tactcccggc aagacaaatg cctcggtcca gtgctcaggt caaagagggg  14160
agacgcttct cagtgatgtg gtgtcaatag cagcttagtt gttctttcct ctggaaaatt  14220
ctacccatct gctttgtaac tcccatacct aacaaggcct tttatttcac aattagaaaa  14280
taagcctgaa atatgaatgc tgcctgagtg tacctacatt tattctagag tttcagggtc  14340
aaaaagaata caaggacctc tgcatctaca gccaagagga gaggggcaaa gacacacagc  14400
tacaaatgag aacctggctg gtcaaagcct aactccacct gtttgtcagc actgatgcaa  14460
gttaggtcag cccaatgatc atttaggaga actgtgctgg caaataaaaa gcagaggctt  14520
ttggtcccca gatacttgga tgagaattac aagtccagct ggttaaaagg cacatgccca  14580
gtgctcactt cacacctact caggaagcac acttgagttg gaaaaccact gtctttacac  14640
ttagaactca gtcctacatg actcctctag gatcagtgat tccatcagtt ttgaaacatg  14700
aagcatgaag tcaaacagga catgaccttg gtttccagaa aaccagatgt tcacatcagt  14760
ctctggagct tggaggcagc acacctgggg acttccacat cccctgccga ggtggcaaaa  14820
gcaggagcag tggtgagttc acatgggctg gggtttcctg aacactgctg gcaattggag  14880
aatctgcaag ggaacttctc cgactcctac cagcagctgc tttaaaataa aggtgatgta  14940
gctggtcaaa tcctccatga gagagcagtg ttgaatggag gaagagacac aacctgtctg  15000
aaaatggcac aaaggaagaa agatgtaaac aatgacgaga agactgcagt gtctacaaag  15060
ctccgaggtg aacagatggg caccccaggc ccgcagcact tccttcagtc tctgccagct  15120
gcactctgtt ttccttcctc caggaatctt gtttggtgtc actaaaacag caattagaat  15180
cactttgaaa tagtgatagt atttaatata actatgaaac tatctgtgat tgacaagtgc  15240
agcaaggagt cttggaatga gagcctttat tttttcaatt aaataaaaga gttttttgtt  15300
tctaaaagta atcttgcaga aaagatcctg cgatcagaaa gaaggagggg gggagttttc  15360
aaacatatag gagatcagac tgtgcctatg tgtgtatata cctacaaaca tatatatatt  15420
```

-continued taaaaaattg ttttactgtc aattacagct tcccacactc ctagacagcc gttctcaagg 15480
tatcaatctg agatcttggg gaggaatatt atctgatatg tcaccaagaa ttcaagaggt 15540
gagtagcctg atggtagtaa ttataatttc attatgtctt tccaccattt accccactta 15600
tgtcaaataa tttaattgta tttcaaacct gttcaaggaa aagtacattt gatctttcca 15660
tctagcaatt tcaaagcacc tgttcacatc ccaaattatc tgtgctctta agtaagaggc 15720
agaaagaaag gaaccaccct tctgatttca catcaaaaaa gaaatgccac tggcaataag 15780
caacttgcct ggtgtggcat aaatcatcag aagacttaca gttgaatcta agtcttttca 15840
gtactgaggt ggttcattat tctgttacag tcttaaaatt cacataaata tatactgcca 15900
ataataatag catacacctt tatagcttac aggcactctt cttctaagtg ttttacctat 15960
gttggcttat ttcatcataa agaaaacaat ggacttttgt gttgttttgt aaaaagatgc 16020
gcacatttta attaacatct gattgcacaa gtctcctccc atatagaaat ggattcttcc 16080
acgcaataga taagaggtgc tggggatatg atgatgaaca cacagatttg gtcatgaccc 16140
tgtgggaaag agagatggga aaaaaacaat tctcttcaag tgtgatgagt gttacgaaag 16200
ggagggaaaa gttgaaacag gttttttcc aaacttttct ccctccatta ttcgcagctg 16260
cacccagctt tc 16272

<210> SEQ ID NO 291
<211> LENGTH: 16272
<212> TYPE: DNA
<213> ORGANISM: Artificial Sequence
<220> FEATURE:
<223> OTHER INFORMATION: pCI-Neo-Rho-ABCA4-intron6-intron7 c.769-784T

<400> SEQUENCE: 291
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720
aactagaatg cagtgaaaaa aatgctttat ttgtgaaatt tgtgatgcta ttgctttatt 780
tgtaaccatt ataagctgca ataaacaagt taacaacaac aattgcattc attttatgtt 840
tcaggttcag ggggagatgt gggaggtttt ttaaagcaag taaaacctct acaaatgtgg 900
taaaatccga taaggatcga tccgggctgg cgtaatagcg aagaggcccg caccgatcgc 960
ccttcccaac agttgcgcag cctgaatggc gaatggacgc gccctgtagc ggcgcattaa 1020
gcgcggcggg tgtggtggtt acgcgcagcg tgaccgctac acttgccagc gccctagcgc 1080
ccgctccttt cgctttcttc ccttcctttc tcgccacgtt cgccggcttt ccccgtcaag 1140

-continued ctctaaatcg ggggctccct ttagggttcc gatttagtgc tttacggcac ctcgacccca 1200
aaaaacttga ttagggtgat ggttcacgta gtgggccatc gccctgatag acggtttttc 1260
gccctttgac gttggagtcc acgttcttta atagtggact cttgttccaa actggaacaa 1320
cactcaaccc tatctcggtc tattcttttg atttataagg gattttgccg atttcggcct 1380
attggttaaa aaatgagctg atttaacaaa aatttaacgc gaattttaac aaaatattaa 1440
cgcttacaat ttcctgatgc ggtattttct ccttacgcat ctgtgcggta tttcacaccg 1500
catacgcgga tctgcgcagc accatggcct gaaataacct ctgaaagagg aacttggtta 1560
ggtaccttct gaggcggaaa gaaccagctg tggaatgtgt gtcagttagg gtgtggaaag 1620
tccccaggct ccccagcagg cagaagtatg caaagcatgc atctcaatta gtcagcaacc 1680
aggtgtggaa agtccccagg ctccccagca ggcagaagta tgcaaagcat gcatctcaat 1740
tagtcagcaa ccatagtccc gcccctaact ccgcccatcc cgcccctaac tccgcccagt 1800
tccgcccatt ctccgcccca tggctgacta atttttttta tttatgcaga ggccgaggcc 1860
gcctcggcct ctgagctatt ccagaagtag tgaggaggct tttttggagg cctaggcttt 1920
tgcaaaaagc ttgattcttc tgacacaaca gtctcgaact taaggctaga gccaccatga 1980
ttgaacaaga tggattgcac gcaggttctc cggccgcttg ggtggagagg ctattcggct 2040
atgactgggc acaacagaca atcggctgct ctgatgccgc cgtgttccgg ctgtcagcgc 2100
aggggcgccc ggttcttttt gtcaagaccg acctgtccgg tgccctgaat gaactgcagg 2160
acgaggcagc gcggctatcg tggctggcca cgacgggcgt tccttgcgca gctgtgctcg 2220
acgttgtcac tgaagcggga agggactggc tgctattggg cgaagtgccg gggcaggatc 2280
tcctgtcatc tcaccttgct cctgccgaga aagtatccat catggctgat gcaatgcggc 2340
ggctgcatac gcttgatccg gctacctgcc cattcgacca ccaagcgaaa catcgcatcg 2400
agcgagcacg tactcggatg gaagccggtc ttgtcgatca ggatgatctg gacgaagagc 2460
atcaggggct cgcgccagcc gaactgttcg ccaggctcaa ggcgcgcatg cccgacggcg 2520
aggatctcgt cgtgacccat ggcgatgcct gcttgccgaa tatcatggtg gaaaatggcc 2580
gcttttctgg attcatcgac tgtggccggc tgggtgtggc ggaccgctat caggacatag 2640
cgttggctac ccgtgatatt gctgaagagc ttggcggcga atgggctgac cgcttcctcg 2700
tgctttacgg tatcgccgct cccgattcgc agcgcatcgc cttctatcgc cttcttgacg 2760
agttcttctg agcgggactc tggggttcga aatgaccgac caagcgacgc ccaacctgcc 2820
atcacgatgg ccgcaataaa atatctttat tttcattaca tctgtgtgtt ggttttttgt 2880
gtgaatcgat agcgataagg atccgcgtat ggtgcactct cagtacaatc tgctctgatg 2940
ccgcatagtt aagccagccc cgacacccgc caacacccgc tgacgcgccc tgacgggctt 3000
gtctgctccc ggcatccgct tacagacaag ctgtgaccgt ctccgggagc tgcatgtgtc 3060
agaggttttc accgtcatca ccgaaacgcg cgagacgaaa gggcctcgtg atacgcctat 3120
ttttataggt taatgtcatg ataataatgg tttcttagac gtcaggtggc acttttcggg 3180
gaaatgtgcg cggaacccct atttgtttat ttttctaaat acattcaaat atgtatccgc 3240
tcatgagaca ataaccctga taaatgcttc aataatattg aaaaaggaag agtatgagta 3300
ttcaacattt ccgtgtcgcc cttattccct tttttgcggc attttgcctt cctgtttttg 3360
ctcacccaga aacgctggtg aaagtaaaag atgctgaaga tcagttgggt gcacgagtgg 3420
gttacatcga actggatctc aacagcggta agatccttga gagttttcgc cccgaagaac 3480
gttttccaat gatgagcact tttaaagttc tgctatgtgg cgcggtatta tcccgtattg 3540
acgccgggca agagcaactc ggtcgccgca tacactattc tcagaatgac ttggttgagt 3600
actcaccagt cacagaaaag catcttacgg atggcatgac agtaagagaa ttatgcagtg 3660
ctgccataac catgagtgat aacactgcgg ccaacttact tctgacaacg atcggaggac 3720
cgaaggagct aaccgctttt ttgcacaaca tgggggatca tgtaactcgc cttgatcgtt 3780
gggaaccgga gctgaatgaa gccataccaa acgacgagcg tgacaccacg atgcctgtag 3840
caatggcaac aacgttgcgc aaactattaa ctggcgaact acttactcta gcttcccggc 3900
aacaattaat agactggatg gaggcggata aagttgcagg accacttctg cgctcggccc 3960
ttccggctgg ctggtttatt gctgataaat ctggagccgg tgagcgtggg tctcgcggta 4020
tcattgcagc actggggcca gatggtaagc cctcccgtat cgtagttatc tacacgacgg 4080
ggagtcaggc aactatggat gaacgaaata gacagatcgc tgagataggt gcctcactga 4140
ttaagcattg gtaactgtca gaccaagttt actcatatat actttagatt gatttaaaac 4200
ttcattttta atttaaaagg atctaggtga agatcctttt tgataatctc atgaccaaaa 4260
tcccttaacg tgagttttcg ttccactgag cgtcagaccc cgtagaaaag atcaaaggat 4320
cttcttgaga tcettttttt ctgcgcgtaa tctgctgctt gcaaacaaaa aaaccaccgc 4380
taccagcggt ggtttgtttg ccggatcaag agctaccaac tctttttccg aaggtaactg 4440
gcttcagcag agcgcagata ccaaatactg ttcttctagt gtagccgtag ttaggccacc 4500
acttcaagaa ctctgtagca ccgcctacat acctcgctct gctaatcctg ttaccagtgg 4560
ctgctgccag tggcgataag tcgtgtctta ccgggttgga ctcaagacga tagttaccgg 4620
ataaggcgca gcggtcgggc tgaacggggg gttcgtgcac acagcccagc ttggagcgaa 4680
cgacctacac cgaactgaga tacctacagc gtgagctatg agaaagcgcc acgcttcccg 4740
aagggagaaa ggcggacagg tatccggtaa gcggcagggt cggaacagga gagcgcacga 4800
gggagcttcc agggggaaac gcctggtatc tttatagtcc tgtcgggttt cgccacctct 4860
gacttgagcg tcgatttttg tgatgctcgt caggggggcg gagcctatgg aaaaacgcca 4920
gcaacgcggc ctttttacgg ttcctggcct tttgctggcc ttttgctcac atggctcgac 4980
agatcttcaa tattggccat tagccatatt attcattggt tatatagcat aaatcaatat 5040
tggctattgg ccattgcata cgttgtatct atatcataat atgtacattt atattggctc 5100
atgtccaata tgaccgccat gttggcattg attattgact agttattaat agtaatcaat 5160
tacggggtca ttagttcata gcccatatat ggagttccgc gttacataac ttacggtaaa 5220
tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460
tacttggcag tacatctacg tattagtcat cgctattacc atggtgatgc ggttttggca 5520
gtacaccaat gggcgtggat agcggtttga ctcacgggga tttccaagtc tccaccccat 5580
tgacgtcaat gggagtttgt tttggcacca aaatcaacgg gactttccaa aatgtcgtaa 5640
caactgcgat cgcccgcccc gttgacgcaa atgggcggta ggcgtgtacg gtgggaggtc 5700
tatataagca gagctcgttt agtgaaccgt cagatcacta gaagctttat tgcggtagtt 5760
tatcacagtt aaattgctaa cgcagtcagt gcttctgaca caacagtctc gaacttaagc 5820
tgcagtgact ctcttaaggt agccttgcag aagttggtcg tgaggcactg ggcaggtaag 5880

-continued

```
tatcaaggtt acaagacagg tttaaggaga ccaatagaaa ctgggcttgt cgagacagag   5940

aagactcttg cgtttctgat aggcacctat tggtcttact gacatccact ttgcctttct   6000

ctccacaggt gtccactccc agttcaatta cagctcttaa ggctagagta cttaatacga   6060

ctcactatag gctagcctcg agaattccgg aggtcaacaa cgagtctttt gtcatctaca   6120

tgttcgtggt ccacttcacc atccccatga ttatcatctt tttctgctat gggcagctcg   6180

tcttcaccgt caaggaggta cgggccgggg ggtgggcggc ctcacggctc tgagggtcca   6240

gcccccagca tgcatctgcg gctcctgctc cctggaggag ccatatcaca agtttgtaca   6300

aaaaagcagg cttcgagacc gtttgacatg tcccccaacc ccccagtgat tgagtctgaa   6360

ttctccactg atgacgcatt tcctagcact cagggtgtcc cctcctggtt gccccctcac   6420

cactgaagcc cgcttcctcc cttttcattt gatgcttaac aactgtcagt ttgcaagaaa   6480

catgcttcaa atccacattc tcccagttgc ctagcaacaa cttccctccc ggataaatgt   6540

gggtttcctg tagctcagcc caggactgaa cacagcagca cacacttctg tccactgctt   6600

caactgcttt tcacctctgg tctgcatgcc ttcaagactg cagctcatcc ctcccttcag   6660

aaccttccat agcctgcaga ggccatgtct gccccaaaaa gacacattga acctgaggct   6720

acttatttac ccttgtgtta ggtatatcct caacttagaa attaatactg tttccagatt   6780

gtcttctttg aatcacagaa agtaaaacaa caaaacattc aatgcttaag acatttcatg   6840

tgcggttggg tgacatctgt ttgatgaaca catttgatcc aaagcatcag aaatactatg   6900

ccaacaagac tttttaggag gtgataaaca tgtctgttct accttaagaa aaaaatatta   6960

cacagtccca agggagagac atggttttga tcccagacaa cccaagcaga gacctcttag   7020

ggccggaatc atcttggctg ctgcctagga ccttatatca atttcttaag cacaggatca   7080

aggcctaaag gcccccttaga ctgacctcag ttagtagagg cagatccctt cacagcctta   7140

tcttccttag aggtctagtc tgaccttgaa cttcggctgg cagtgctgtc agttgtgatg   7200

tgtgacatgg aagagttatt tgttacttgg aaaattaaga gaacttattt ggcataggaa   7260

attgtgtgtg tgtgtgtgtg tgtgtgtgtg tgtgtgtgtg tgtgtgtgtg agatgatgtt   7320

tgccattttg atctgtgact tttttttcca gaaatagttt ctcagttcca ttccaactaa   7380

acttacagtc tcttccggtt ctttgacaga aacaattcat gtgaatttga acagataata   7440

gggaaggggg aaccaaaaga agaggagagc cctgggaaag ttatttttata atttatggca   7500

acctcagtca ggcaactgtg aacaggtaca tatggagggc tccctcggga ctaggcagta   7560

ttcagagatg taaggtgtga ggaccggacc ctcatcattt accattccca ctaaaaagag   7620

ctgggaagga aattgtagct gtagcaccag gcacgtaact ggagcttagt aactatttgg   7680

tgaaggaata ttattaaatt attaacaaga tggaaaaaag ggtattaacc acacaaaaat   7740

acatctcaag ctattgtttc tctgttccct ttcccccaaa ttcctagtct tgctcttatc   7800

tggctgtctc tctagtcact ctttcttgct gactctcttc acgttccttt ctccacctgg   7860

aattcctggg ccctcccctt ttactgacag acactgtcct cactctcaca gtcatcagtt   7920

tgtctcttta caaacctcag ctcaagtgtc acttccccgt ccccaggtga aactgactgc   7980

tccctccctg taagtcacca tgatgactgc tatatatagc cctcatggaa cctaaaacct   8040

caacagacac agtctctttc ctactctgtt atagtttatt tactcattaa ttaccacaac   8100

acgtattatt gagcacctac tgtgtaccat gcccagaaga taaaagacaa acaaaataaa   8160

acctattcct atgcttaatg agtttacagt ctagtggaga gatagataca ttaaaaaata   8220

acagcaaacc aaaataaaag tggtaaataa atgcactgag aaagacagga atagctagga   8280
```

ggggcaccta atccctaggg aaggaaagct ggaagagcat ggtgatgggg gaagaaggct 8340
ttctggagaa ggtgaggtag tttgaaatga gttgactctg gccagtaggg gtagagtgag 8400
aatggggtga gacagggtgg gttggtcatt ttgatccatt agtcctcaaa gtgataggac 8460
tagtggctaa ggactgcagg ctttacagaa gcctacaaaa ctatttgaga tttgaagttt 8520
tttttttttt ttaattggct ccaaaagaaa atgaaaaaac tttagaatta taatgaatga 8580
atattaaatg aatatttaag gaaggtaatt ttattcaact tcattgttaa atttagttaa 8640
aacaagccct tgagtttcat tcaacactgt tttatcatac cgttgatgag agaaaacaaa 8700
actgattcct ggccagggcc actgtcagcg tggggtttgc acatctttcc catgtctgct 8760
tgggttagct ccaggtactc ctgtttcccc cacatcccca agatgtgccc attagtggaa 8820
acggtgtgtc tgcatgattc caacgtgagt gagtgtgggt gtgggagtga gtgcccctgc 8880
catgggaggg catcctgtcc aggttagatt cctaccttgt gccctgagct gctgggatgg 8940
aatccagcca cccatgactc tgaactgaaa taattgggtg aataattatc ttacttttta 9000
attaatcttt gaaaatgtat gtatagttca catgtatttc aatatttaat attagaagta 9060
ttttagtctt tattttgaag tttggtgatt tattgtaacc agaaacaagc tatagaaact 9120
taattttggg ccaagtgcag tggctcacac ctataatccc agcattttgg gaggccgagg 9180
cagacgcatc acttgaggtc cggagttcaa gatcagcctg gccaacatgg taaaaccctg 9240
tctctactaa aaaatacaaa aattagccag atgtggtggg cacctgtagt cccagctact 9300
tgggtggctg aagcaggaga atcacttgaa cccgggaggc ggagcagtga gcagagatcg 9360
tgccactgca ctcccaccta ggcgacagtg tgacactcca tctcaaaaaa aaaaaaaaat 9420
agaaaagaaa gaaacttaat tctggtttat atcaattagc ctgtggtaaa attggtttca 9480
ttatagccat ttcacttagt tgaagtttcc aataacctgt ggatgaatta agtgaggatt 9540
tactatattc ataaaatctt aaattccaaa gcctgtttgc agttcaggtt tttccacttt 9600
acaaacactt ctaagtattc acaatgattg cttaaaattc ataccagata aatcattaaa 9660
taagttgttc aaagtcaaat aatttcataa gtaaaaatta ggagctttta gaaaactata 9720
cctacataga cctagaccta tagatagaca gagatctgaa tagatatgga cacagatgct 9780
ttccaaagtg ttcatgtgat gtgtggtgga gtttcaagac cagagtgtgc ctggggcctg 9840
cagaagtaaa ggagagggga tggagagaag attgtccaca tggccatggg caatctccca 9900
cccacactca agtgaggaag acaggaaaca aattcagaaa gaagagaaaa taatcaaaac 9960
tgatgggagc ttgtgactga tttacttatg cgcagcctcc ctggagacat gagtgtggct 10020
gttccttagg ttgtgcctct gggctcctac cccctcttag atgccttcct attatctagg 10080
acctggttgc tttttgtctg catagcttct ttggattcca gtctttgatg ccagcttcct 10140
cctaaagtag cctttcagat gtcccttggt taccctctgc tatctaaggg ctcatcctac 10200
cccacactca ttcccagcac caatttctgg atctccaggc tggagattta gacaatggga 10260
tgggaagaac ccatgatggg tcccagacag aaagtggtgc cagccacaga aagggcacac 10320
aggcacagaa gttggtttgg ggtaagacga tgtggtcagt tcagaacacg ctggatctag 10380
gcagatgccc agcagacagt tggatatgta agtctgaagc tctggggaga ggtctaggtt 10440
ggaggtacag atttagaagt catcaacaaa aaggtagcag attaaatgat aaaggaaatg 10500
agactatccg gggagtgtgc agagtgagag gagcaaggga ggcccttggg aacctcagca 10560
cttcagggga aggtagaggt acagttgctg gtgggaaagg cagagaagta gcaaagcaaa 10620

-continued ccaggcaaaa gcagtgtcac agacgaccag ggaggaaaag gacatgatca aaatgttgag 10680
aaaagcagag aggtttgaaa atacaagaag caaaaatgtc cactagactt aaaaaccagg 10740
agaaaactgg ggggttcttg ataaagcatc ttagtaggat ggtgagggta gaagccaggg 10800
aagtgttggt gaggaagtga agtcactgat tacggactat gcttaaaaga atgtgggaat 10860
gaagggtgga agagagaaat tagactgtag ctagggagac ataagcgatc agaggtagat 10920
tctttctctc ctgtgggaga atcttgcacg tatacacagc atgacgacag tgatggaagg 10980
gctggcgaag cctcagggag actcttggag gtaaacccca tgaagggagg actttgtttc 11040
attcactgcc gtgtccccag cacctggcac aatagcagac actcaataca tatttgtcaa 11100
atgtgggatt ttatcattta gaaactgcac ctggctgtga gtaacaaaag tcagagaaac 11160
cgtgggtttc atttttctcc ccaggcagag tctggagctg ggtcctccaa gaggggtttg 11220
gagcaccaca ggtttcctca agacccccag gctgccctgt gtttccctcc ttcatcccca 11280
gcatatgcct gtcatctggt gacctccaaa cacctgtgct gcctcctcca gcacatccat 11340
gttgcaggca gggaccaggc aaagggcaga ggggcctact tcaaaagacc atttccagaa 11400
accccatcct atgacttctc ctggtgtctt ggttaccatt gtgccatagg ctcaccctgt 11460
atgcatggga ggctgggcca ggcattatga cttttagcaa tattgcatag ataagcatca 11520
atctttgtca ctgtgacgaa gcctagtcac tcagtgctag gcaaggttaa tggaatgggt 11580
tggtgtgtgc attattcttg aggtctttct tatgcttcat gttatacatt tattaggacg 11640
tttaggcaac agggggataa aaatgaagag gagatgcatg ctatgatctg aatgtttgca 11700
tcctccccaa aattcatatg ttgaaatctt catccccaag atgatggcat taggaggtgg 11760
ggcctttcgg aggcaattag gtcatgactg ggattagtgc ccttgtaaaa ccccagaaag 11820
ccagcttgcc gcttccacca tatgaagaca cagagagaag atgccatcta cgaatcagga 11880
aatgagcccg caccatgcaa taaacctgct ggagccttga tcttagactt cccagctgcc 11940
agatctgtgg gaaatagatt tctgttgttt acccagctta tggtattttg ttgtagcagc 12000
cagagtgaac taagacagtg ctgatctcgt attcttggag ggaaccctta gtctttaggg 12060
aaagcaaagc caccatttgg ggcagggtgt tctccaagtg ctgccacata tgctgatgtg 12120
gttaaactgc aaactatggt aaaaatgtgg aggtctgtgg aattgtcaat caggaaaaag 12180
atataaaaag aagttaaagt cttcgtgctt ctggaaggat atgtgccaaa ttgttaacat 12240
tgattatcct tgggtagaga tgtggggaag tttgcagaga cagttttgcc ttgtacttta 12300
tataagtaaa cagctactac ttcgttgtct taaaaaaaaa aaacagccta tgtgctcttc 12360
atgtgactca gaactaccta ggcaatacga ttaattgaat tagtaaaatt gagtgattat 12420
gaattttcag gaagtcatta atttaccact tctttattac atccacttct aacaggactt 12480
caatataggg gaatttgact tcaagataaa aagaccaaat ttatttaccc ttttaaaaaa 12540
agacaactta aaagcagact tgtcttacag aaccttcctt agttggacat cgatgagtgt 12600
acagaaaatg caatggataa aaagcttggt gatacaaaga taaaaagtgg ggtcctgtcc 12660
ttaatgaaca taccatttca tggagtatca ggtgtataaa caattataat caatctgctt 12720
gttattctga taagatcatt tactcacaca tcaaatactg agtgcccacc acatgcccag 12780
catacctaga agtcatccag tatgatttct gtctacatgg agcatagagt cttacagggg 12840
agatagatga caagtaaaca ccagaataat taccaatggt gaagagcaca aggaaggaaa 12900
cagaactcct aaagagagcg tggctgggca ggggtgagca agaggcatag aaaaaggggc 12960
atctaaatct acttgggagg aagctgtttc tcacataggt catcatgtta ggaatgagac 13020

```
ttgagggatg agtagaagtt tgccaggcaa agaaggaatg ggggggaata gagagcagag  13080
ctaggggcag gagacagctg acgtgtgagc agacataaaa agaagtccac tgtggcagca  13140
gagaagcagg agagaaggca agtgagggag ccaggcacca gctcacagag gtcatgtgtg  13200
tcaaaacgta gtaatggcct tctcttctgg agacagtagg gagccatgga agatgtttga  13260
gcagggaaag cgacatgact ggattggcct gttgggtaac tcagaccaca atgcattgga  13320
agggaggggg ctagaggcaa ggggactggc aagaaggcca gtcctttttc tatgcctatt  13380
ttgatgaaat attctagaag ggaagtgaac aaaggtagtc ctagagagga agaacaaaac  13440
agataggata cttccttagt atttgctcat tcgacaattt atttttgcat atacactaaa  13500
accttttttta ttattaaaac gttttattgt aggaaaaaag tatgaaagta gagtgaataa  13560
taaaatgagc tcccatggat ctatcaccca gcttcaacta ttatcaatat ttggctgttc  13620
ttgttttaac tgttctccac ctttttttcc tgaagttttt ttgaagcaaa tcacagacaa  13680
catatcattt caccatatgt acttccctct gtatctctaa catgtaagaa cttgttttaa  13740
caaaatcacc atgctatgat catacccaac aaaatttatc ataatgtctt aataatacct  13800
aatacccatt tcatgtccac tttcccccaa ttgctacagc tggtttgttc agatcagaat  13860
caaaatccac ctgtggccat tttactgcta tgtctctcag gtctcttttc atctctaata  13920
atctcagggg agacaggagg gaggacgggc aggacttggg gctaacttgc ttatcgacac  13980
acagttttgc ctacttgctt cctcccttca cacccactct tcttctcagc cccacccttg  14040
tatggaaaaa acagaaatta aagtgctttg cccagcaccc actgaagcta tttcgaagga  14100
gtttgaagag tactcccggc aagacaaatg cctcggtcca gtgctcaggt caaagagggg  14160
agacgcttct cagtgatgtg gtgtcaatag cagcttagtt gttctttcct ctggaaaatt  14220
ctacccatct gctttgtaac tcccatacct aacaaggcct tttatttcac aattagaaaa  14280
taagcctgaa atatgaatgc tgcctgagtg tacctacatt tattctagag tttcagggtc  14340
aaaaagaata caaggacctc tgcatctaca gccaagagga gaggggcaaa gacacacagc  14400
tacaaatgag aacctggctg gtcaaagcct aactccacct gtttgtcagc actgatgcaa  14460
gttaggtcag cccaatgatc atttaggaga actgtgctgg caaataaaaa gcagaggctt  14520
ttggtcccca gatacttgga tgagaattac aagtccagct ggttaaaagg cacatgccca  14580
gtgctcactt cacacctact caggaagcac acttgagttg gaaaaccact gtctttacac  14640
ttagaactca gtcctacatg actcttctag gatcagtgat tccatcagtt ttgaaacatg  14700
aagcatgaag tcaaacagga catgaccttg gtttccagaa aaccagatgt tcacatcagt  14760
ctctggagct tggaggcagc acacctgggg acttccacat cccctgccga ggtggcaaaa  14820
gcaggagcag tggtgagttc acatgggctg ggtttcctg aacactgctg gcaattggag  14880
aatctgcaag ggaacttctc cgactcctac cagcagctgc tttaaaataa aggtgatgta  14940
gctggtcaaa tcctccatga gagagcagtg ttgaatggag gaagagacac aacctgtctg  15000
aaaatggcac aaaggaagaa agatgtaaac aatgacgaga agactgcagt gtctacaaag  15060
ctccgaggtg aacagatggg caccccaggc ccgcagcact tccttcagtc tctgccagct  15120
gcactctgtt ttccttcctc caggaatctt gtttggtgtc actaaaacag caattagaat  15180
cactttgaaa tagtgatagt atttaatata actatgaaac tatctgtgat tgacaagtgc  15240
agcaaggagt cttggaatga gagcctttat tttttcaatt aaataaaaga gttttttgtt  15300
tctaaaagta atcttgcaga aaagatcctg cgatcagaaa gaaggagggg gggagttttc  15360
```

-continued

```
aaacatatag gagatcagac tgtgcctatg tgtgtatata cctacaaaca tatatatatt  15420

taaaaaattg ttttactgtc aattacagct tcccacactc ctagacagcc gttctcaagg  15480

tatcaatctg agatcttggg gaggaatatt atctgatatg tcaccaagaa ttcaagaggt  15540

gagtagcctg atggtagtaa ttataatttc attatgtctt tccaccattt accccactta  15600

tgtcaaataa tttaattgta tttcaaacct gttcaaggaa aagtacattt gatctttcca  15660

tctagcaatt tcaaagcacc tgttcacatc ccaaattatc tgtgctctta agtaagaggc  15720

agaaagaaag gaaccaccct tctgatttca catcaaaaaa gaaatgccac tggcaataag  15780

caacttgcct ggtgtggcat aaatcatcag aagacttaca gttgaatcta agtcttttca  15840

gtactgaggt ggttcattat tctgttacag tcttaaaatt cacataaata tatactgcca  15900

ataataatag catacacctt tatagcttac aggcactctt cttctaagtg ttttacctat  15960

gttggcttat ttcatcataa agaaaacaat ggacttttgt gttgttttgt aaaaagatgc  16020

gcacatttta attaacatct gattgcacaa gtctcctccc atatagaaat ggattcttcc  16080

acgcaataga taagaggtgc tggggatatg atgatgaaca cacagatttg gtcatgaccc  16140

tgtgggaaag agagatggga aaaaaacaat tctcttcaag tgtgatgagt gttacgaaag  16200

ggagggaaaa gttgaaacag gtttttttcc aaacttttct ccctccatta ttcgcagctg  16260

cacccagctt tc                                                      16272
```

```
<210> SEQ ID NO 292
<211> LENGTH: 13221
<212> TYPE: DNA
<213> ORGANISM: Artificial Sequence
<220> FEATURE:
<223> OTHER INFORMATION: pCI-Neo-Rho-ABCA4-intron6-intron11 wild type

<400> SEQUENCE: 292

ttgtacaaag tggtgatctt gtacaaagtg gtgatgagag gtacctccga ggggtaaaca     60

gttgggtaaa cagtctctga agtcagctct gccattttct agctgtatgg ccctgggcaa    120

gtcaatttcc ttctctgtgc tttggtttcc tcatccatag aaaggtagaa agggcaaaac    180

accaaactct tggattacaa gagataattt acagaacacc cttggcacac agagggcacc    240

atgaaatgtc acgggtgaca cagccccctt gtgctcagtc cctggcatct ctaggggtga    300

ggagcgtctg cctagcaggt tcccaccagg aagctggatt tgagtggatg gggcgctgga    360

atcgtgaggg gcagaagcag gcaaagggtc ggggcgaacc tcactaacgt gccagttcca    420

agcacactgt gggcagccct ggccctgact caagcctctt gccttccagt tccggaactg    480

catgctcacc accatctgct gcggcaagaa cccactgggt gacgatgagg cctctgctac    540

cgtgtccaag acggagacga gccaggtggc cccggcctaa gacctgccta ggactctgtg    600

gccgactata ggcgtctccc atcccctaca cctgtcgacc cgggcggccg cttcccttta    660

gtgagggtta atgcttcgag cagacatgat aagatacatt gatgagtttg gacaaaccac    720

aactagaatg cagtgaaaaa aatgctttat ttgtgaaatt tgtgatgcta ttgctttatt    780

tgtaaccatt ataagctgca ataaacaagt taacaacaac aattgcattc attttatgtt    840

tcaggttcag ggggagatgt gggaggtttt ttaaagcaag taaaacctct acaaatgtgg    900

taaaatccga taaggatcga tccgggctgg cgtaatagcg aagaggcccg caccgatcgc    960

ccttcccaac agttgcgcag cctgaatggc gaatggacgc gccctgtagc ggcgcattaa   1020

gcgcggcggg tgtggtggtt acgcgcagcg tgaccgctac acttgccagc gccctagcgc   1080

ccgctccttt cgctttcttc ccttcctttc tcgccacgtt cgccggcttt ccccgtcaag   1140
```

```
ctctaaatcg ggggctccct ttagggttcc gatttagtgc tttacggcac ctcgacccca   1200

aaaaacttga ttagggtgat ggttcacgta gtgggccatc gccctgatag acggtttttc   1260

gccctttgac gttggagtcc acgttcttta atagtggact cttgttccaa actggaacaa   1320

cactcaaccc tatctcggtc tattcttttg atttataagg gattttgccg atttcggcct   1380

attggttaaa aaatgagctg atttaacaaa aatttaacgc gaattttaac aaaatattaa   1440

cgcttacaat ttcctgatgc ggtattttct ccttacgcat ctgtgcggta tttcacaccg   1500

catacgcgga tctgcgcagc accatggcct gaaataacct ctgaaagagg aacttggtta   1560

ggtaccttct gaggcggaaa gaaccagctg tggaatgtgt gtcagttagg gtgtggaaag   1620

tccccaggct ccccagcagg cagaagtatg caaagcatgc atctcaatta gtcagcaacc   1680

aggtgtggaa agtccccagg ctccccagca ggcagaagta tgcaaagcat gcatctcaat   1740

tagtcagcaa ccatagtccc gcccctaact ccgcccatcc cgcccctaac tccgcccagt   1800

tccgcccatt ctccgcccca tggctgacta atttttttta tttatgcaga ggccgaggcc   1860

gcctcggcct ctgagctatt ccagaagtag tgaggaggct tttttggagg cctaggcttt   1920

tgcaaaaagc ttgattcttc tgacacaaca gtctcgaact taaggctaga gccaccatga   1980

ttgaacaaga tggattgcac gcaggttctc cggccgcttg ggtggagagg ctattcggct   2040

atgactgggc acaacagaca atcggctgct ctgatgccgc cgtgttccgg ctgtcagcgc   2100

aggggcgccc ggttcttttt gtcaagaccg acctgtccgg tgccctgaat gaactgcagg   2160

acgaggcagc gcggctatcg tggctggcca cgacgggcgt tccttgcgca gctgtgctcg   2220

acgttgtcac tgaagcggga agggactggc tgctattggg cgaagtgccg gggcaggatc   2280

tcctgtcatc tcaccttgct cctgccgaga aagtatccat catggctgat gcaatgcggc   2340

ggctgcatac gcttgatccg gctacctgcc cattcgacca ccaagcgaaa catcgcatcg   2400

agcgagcacg tactcggatg gaagccggtc ttgtcgatca ggatgatctg gacgaagagc   2460

atcaggggct cgcgccagcc gaactgttcg ccaggctcaa ggcgcgcatg cccgacggcg   2520

aggatctcgt cgtgacccat ggcgatgcct gcttgccgaa tatcatggtg gaaaatggcc   2580

gcttttctgg attcatcgac tgtggccggc tgggtgtggc ggaccgctat caggacatag   2640

cgttggctac ccgtgatatt gctgaagagc ttggcggcga atgggctgac cgcttcctcg   2700

tgctttacgg tatcgccgct cccgattcgc agcgcatcgc cttctatcgc cttcttgacg   2760

agttcttctg agcgggactc tggggttcga aatgaccgac caagcgacgc ccaacctgcc   2820

atcacgatgg ccgcaataaa atatctttat tttcattaca tctgtgtgtt ggttttttgt   2880

gtgaatcgat agcgataagg atccgcgtat ggtgcactct cagtacaatc tgctctgatg   2940

ccgcatagtt aagccagccc cgacacccgc caacacccgc tgacgcgccc tgacgggctt   3000

gtctgctccc ggcatccgct tacagacaag ctgtgaccgt ctccgggagc tgcatgtgtc   3060

agaggttttc accgtcatca ccgaaacgcg cgagacgaaa gggcctcgtg atacgcctat   3120

ttttataggt taatgtcatg ataataatgg tttcttagac gtcaggtggc acttttcggg   3180

gaaatgtgcg cggaacccct atttgtttat ttttctaaat acattcaaat atgtatccgc   3240

tcatgagaca ataaccctga taaatgcttc aataatattg aaaaaggaag agtatgagta   3300

ttcaacattt ccgtgtcgcc cttattccct tttttgcggc attttgcctt cctgtttttg   3360

ctcacccaga aacgctggtg aaagtaaaag atgctgaaga tcagttgggt gcacgagtgg   3420

gttacatcga actggatctc aacagcggta agatccttga gagttttcgc cccgaagaac   3480
```

-continued gttttccaat gatgagcact tttaaagttc tgctatgtgg cgcggtatta tcccgtattg 3540
acgccgggca agagcaactc ggtcgccgca tacactattc tcagaatgac ttggttgagt 3600
actcaccagt cacagaaaag catcttacgg atggcatgac agtaagagaa ttatgcagtg 3660
ctgccataac catgagtgat aacactgcgg ccaacttact tctgacaacg atcggaggac 3720
cgaaggagct aaccgctttt ttgcacaaca tgggggatca tgtaactcgc cttgatcgtt 3780
gggaaccgga gctgaatgaa gccataccaa acgacgagcg tgacaccacg atgcctgtag 3840
caatggcaac aacgttgcgc aaactattaa ctggcgaact acttactcta gcttcccggc 3900
aacaattaat agactggatg gaggcggata aagttgcagg accacttctg cgctcggccc 3960
ttccggctgg ctggtttatt gctgataaat ctggagccgg tgagcgtggg tctcgcggta 4020
tcattgcagc actggggcca gatggtaagc cctcccgtat cgtagttatc tacacgacgg 4080
ggagtcaggc aactatggat gaacgaaata gacagatcgc tgagataggt gcctcactga 4140
ttaagcattg gtaactgtca gaccaagttt actcatatat actttagatt gatttaaaac 4200
ttcattttta atttaaaagg atctaggtga agatcctttt tgataatctc atgaccaaaa 4260
tcccttaacg tgagttttcg ttccactgag cgtcagaccc cgtagaaaag atcaaaggat 4320
cttcttgaga tccttttttt ctgcgcgtaa tctgctgctt gcaaacaaaa aaaccaccgc 4380
taccagcggt ggtttgtttg ccggatcaag agctaccaac tctttttccg aaggtaactg 4440
gcttcagcag agcgcagata ccaaatactg ttcttctagt gtagccgtag ttaggccacc 4500
acttcaagaa ctctgtagca ccgcctacat acctcgctct gctaatcctg ttaccagtgg 4560
ctgctgccag tggcgataag tcgtgtctta ccgggttgga ctcaagacga tagttaccgg 4620
ataaggcgca gcggtcgggc tgaacggggg gttcgtgcac acagcccagc ttggagcgaa 4680
cgacctacac cgaactgaga tacctacagc gtgagctatg agaaagcgcc acgcttcccg 4740
aagggagaaa ggcggacagg tatccggtaa gcggcagggt cggaacagga gagcgcacga 4800
gggagcttcc agggggaaac gcctggtatc tttatagtcc tgtcgggttt cgccacctct 4860
gacttgagcg tcgatttttg tgatgctcgt caggggggcg gagcctatgg aaaaacgcca 4920
gcaacgcggc ctttttacgg ttcctggcct tttgctggcc ttttgctcac atggctcgac 4980
agatcttcaa tattggccat tagccatatt attcattggt tatatagcat aaatcaatat 5040
tggctattgg ccattgcata cgttgtatct atatcataat atgtacattt atattggctc 5100
atgtccaata tgaccgccat gttggcattg attattgact agttattaat agtaatcaat 5160
tacggggtca ttagttcata gcccatatat ggagttccgc gttacataac ttacggtaaa 5220
tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460
tacttggcag tacatctacg tattagtcat cgctattacc atggtgatgc ggttttggca 5520
gtacaccaat gggcgtggat agcggtttga ctcacgggga tttccaagtc tccaccccat 5580
tgacgtcaat gggagtttgt tttggcacca aaatcaacgg gactttccaa aatgtcgtaa 5640
caactgcgat cgcccgcccc gttgacgcaa atgggcggta ggcgtgtacg gtgggaggtc 5700
tatataagca gagctcgttt agtgaaccgt cagatcacta gaagctttat tgcggtagtt 5760
tatcacagtt aaattgctaa cgcagtcagt gcttctgaca caacagtctc gaacttaagc 5820
tgcagtgact ctcttaaggt agccttgcag aagttggtcg tgaggcactg ggcaggtaag 5880
tatcaaggtt acaagacagg tttaaggaga ccaatagaaa ctgggcttgt cgagacagag 5940
aagactcttg cgtttctgat aggcacctat tggtcttact gacatccact ttgccttttct 6000
ctccacaggt gtccactccc agttcaatta cagctcttaa ggctagagta cttaatacga 6060
ctcactatag gctagcctcg agaattccgg aggtcaacaa cgagtctttt gtcatctaca 6120
tgttcgtggt ccacttcacc atccccatga ttatcatctt tttctgctat gggcagctcg 6180
tcttcaccgt caaggaggta cgggccgggg ggtgggcggc ctcacggctc tgagggtcca 6240
gcccccagca tgcatctgcg gctcctgctc cctggaggag ccatatcaca agtttgtaca 6300
aaaaagcagg cttcaacact gctggcaatt ggagaatctg caagggaact tctccgactc 6360
ctaccagcag ctgctttaaa ataaaggtga tgtagctggt caaatcctcc atgagagagc 6420
agtgttgaat ggaggaagag acacaacctg tctgaaaatg gcacaaagga agaaagatgt 6480
aaacaatgac gagaagactg cagtgtctac aaagctccga ggtgaacaga tgggcacccc 6540
aggcccgcag cacttccttc agtctctgcc agctgcactc tgttttcctt cctccaggaa 6600
tcttgtttgg tgtcactaaa acagcaatta gaatcacttt gaaatagtga tagtatttaa 6660
tataactatg aaactatctg tgattgacaa gtgcagcaag gagtcttgga atgagagcct 6720
ttattttttc aattaaataa aagagttttt tgtttctaaa agtaatcttg cagaaaagat 6780
cctgcgatca gaaagaagga ggggggggagt tttcaaacat ataggagatc agactgtgcc 6840
tatgtgtgta tatacctaca aacatatata tatttaaaaa attgttttac tgtcaattac 6900
agcttcccac actcctagac agccgttctc aaggtatcaa tctgagatct tggggaggaa 6960
tattatctga tatgtcacca agaattcaag aggtgagtag cctgatggta gtaattataa 7020
tttcattatg tctttccacc atttacccca cttatgtcaa ataatttaat tgtatttcaa 7080
acctgttcaa ggaaaagtac atttgatctt tccatctagc aatttcaaag cacctgttca 7140
catcccaaat tatctgtgct cttaagtaag aggcagaaag aaaggaacca cccttctgat 7200
ttcacatcaa aaaagaaatg ccactggcaa taagcaactt gcctggtgtg gcataaatca 7260
tcagaagact tacagttgaa tctaagtctt ttcagtactg aggtggttca ttattctgtt 7320
acagtcttaa aattcacata aatatatact gccaataata atagcataca cctttatagc 7380
ttacaggcac tcttcttcta agtgttttac ctatgttggc ttatttcatc ataaagaaaa 7440
caatggactt ttgtgttgtt ttgtaaaaag atgcgcacat tttaattaac atctgattgc 7500
acaagtctcc tcccatatag aaatggattc ttccacgcaa tagataagag gtgctgggga 7560
tatgatgatg aacacacaga tttggtcatg accctgtggg aaagagagat gggaaaaaaa 7620
caattctctt caagtgtgat gagtgttacg aaagggaggg aaaagttgaa acaggttttt 7680
ttccaaactt ttctccctcc attattcgca gctgacttgg gctccaccaa cctggaaaac 7740
tgcatggttg gaatctgtct ttataaaacg catctcaacc tgggccgagt atgcacactg 7800
atgtgggaaa gttagagaag agcccattgt actaatgctc acctgctaca gtgggagtct 7860
ctgttaaaca gtcttttctt catagcatta aaaaaattta tatcactaca ataaggttga 7920
aattgataga gaatgtacaa acaatcccca aagtatatca acactcttag ttctgagtag 7980
aagttccaga aggcttcttg actgtctaga tagcaagtct aatcatttgt gaactaagtt 8040
aaagcagaag gcccagttta tatgaattgg tattacacca tttgacctga gaacagcccc 8100
ttcatctctg agtgctttga ctaaatgagc aacataataa tagtaataac cccttacaag 8160
atgtcataag actcactgtt gttgaagcaa tttgagattt tgactttatt gaagcataga 8220

-continued tggtgattat aggcatgact cactgtgtgg attctccctg ggctcatcag tttcagaggg 8280
caagtgttgg catgtggaca aagagaggga tgacacgtaa acatggctta ttgcaatggg 8340
gaaatatttt cagtctcact gattgaatcc taatggtttt ataaattccc cagtaccact 8400
gaaagcaaag caagtaatca ggtgtgtttt aggaataaaa gcagcattat tttaatttcg 8460
tattttcccc taaagcaaag ccaaatggca ttatgggagc caagctactg gcagctccac 8520
cagccttctc ctgagttctc ggcattacag atctaccctc aaaggatgag gccagcaagc 8580
accacagggt gcccacatgg agaagagaag gccaccaacc tcctcttagc tggcacagaa 8640
ttgaaaaagt gtttttccag gaatggatac ttcatctgtt ctgtatttgc tagaatttta 8700
aaacgcacac acagacacac acaggcgtgc acacacacac gcacacacac acgagaaaac 8760
cacaaaccac acatttcaag gaaatggaag aattcattgg taaaattaag ctaataagat 8820
tattttccaa atataagaaa ctaaatttta gactatttag ccaaagaaat ttgctctgat 8880
cttgcttttc tacaacagaa tcattcccca atcattttat ttccctcttt ttctccccag 8940
tatccccatc ttggtgggac aacagaaccc aagaactggc ttaacagtaa aatatttttct 9000 gcatttgccc aaggacacat tcccaacgaa ttcaaataaa ggagactaga agaagagagg 9060
ctatactaca gtgctctagg ggtcactctg tgatttgttg ttgttgttgt tgttgttttg 9120
agacggagta ttgctcagtc gcccaggctg gagtgcagtg gcacgatgtc tactcactgt 9180
aagctctgcc ccccaggttc acgccattct cctgcctcag cctcccgaat agctgggagt 9240
acaggggccc gccaccatgt ccggctaatt tttttgtatt tttaatagag acggggtttc 9300
accatgttcg ccaggatggt ctcgatctcc tgacctcgtg atccgcccgc ctcggcctcc 9360
caaagtgcta ggattacagg catgagccac tgcgcccggc cactctgtga ttttctttaa 9420
ggctcatcct agtattctcc tagtccctaa gtagatggca gtaggttttg tttttttgttt 9480 ttcgcagctg gattaaggat tgctgagaat atatggatgt tttcttttaa atgtggaagt 9540
caaaccaaac gttggagcat tggcctcaca gcagattatg actctagctg ccttaaaata 9600
acctgaagac tttgccttgc cctagtttat ccatcggccg agtatgcagg acttgctgtg 9660
ggtgaccagg cccctcatgc agaatggtgg tccagagacc tttacaaagc tgatgggcat 9720
cctgtctgac ctcctgtgtg gctaccccga gggaggtggc tctcgggtgc tctccttcaa 9780
ctggtatgaa gacaataact ataaggcctt tctggggatt gactccacaa ggaaggatcc 9840
tatctattct tatgacagaa gaacaagtaa gttttctgag tcctgcttat aaattggcct 9900
ctcatgttgg ttaagttgat ggtttaacac ttctaggtga aaccaaacct ggggttgcat 9960
ctgtcttgtc ttgctgagtg gccttaggta aagagacttc tcccagaaag tccacttccc 10020
cttgcagaaa gggggcattg cttataagca attctggaca tgaaccacag aaagaactga 10080
ggcccacttg gaaagggaac agaggggcca tttcccactg atgtaattga actagggcta 10140
agttcaagag gaagagaatg atccgcaagg aagcaaccca gagttccagg tgaagctcag 10200
gtcagaaggg ccctggcaag taaacacggc tgtgggatgc ttttacaaac acaatatcgt 10260
gaaaatctat gtgtgtagta ctgaattaca ttccaaatgg caaattcctg gcaaatcatc 10320
ttccccacct ttcactattt tttttttttt ggtcttctat ggggtaaagg aggatggggt 10380
ggggaagaaa tgtaactggc tgcccctcta gttaaaaact gaaaagaggc agcaagggac 10440
atgccaaaag tagttggact ctaagatagc tacacacaac aaagcagcta agcagctaat 10500
tgaagggaaa ttactgaggc tcaagctgag attccaagcg ggggccttgt ttggcctctc 10560
agtccctttc atctgagaaa ggcctcagtt cctagcagta atcagaggca ggcttctcag 10620
cctccttctc ctaaagcaga ataaaccaca gggcaagtcg catcctttgt ttctctgatg 10680
aggccattac tgagagtcac tgtggcattt tgctactaat gatgagcttg ttattggtgg 10740
ggtacagcct attaatttag gttattcatc aaatcctcca gcatggagtt gaatgagaca 10800
tgtgatgtgg atacactaat gactatattg agttacaagc aatggggagt ttctgtaaaa 10860
tctgtccctt gtctcctggc agcatccttt tgtaatgcat tgatccagag cctggagtca 10920
aatcctttaa ccaaaatcgc ttggagggcg gcaaagcctt tgctgatggg aaaaatcctg 10980
tacactcctg attcacctgc agcacgaagg atactgaaga atgtaagatc ccagctgggc 11040
ttgccttgtg taccctggac ctcccagaag tgtgtgtgtg tgtgtgtgtg tgtgagagag 11100
atgtgccttc ctggtagcac atctcatgtt tgttttttgc taagtggact cttgcgtttc 11160
ctcccccatc cacagtcatc actggaatgc tttgcttcag tgcccctgcc tgggccctcc 11220
cctctctact gcagcctaca atgaggtttt ctttcccatt gcttgaatta tatccctaat 11280
ggaagggttc acaattctct gaatcctggc tactcagata aagacaggga ggaagggagg 11340
aagggtattt tctcccaggg ggtccaaatc tagctttaac gagggaggtt ctgagaaaat 11400
aatatcatca atattacatg gacttctgag atactaagaa attagattct gtcagcccag 11460
gaagttggga gatggtgaat tgttctggga aatagcaata gactgagaaa ataaaaacac 11520
ttccttgaaa agcctttccc taacactaag tgataggggc agaaaagaca caaccaaaag 11580
ttctctctca cttttctctc tgttcgtgtc tctgtcttga tctctgtctg gttttaggcc 11640
aactcaactt ttgaagaact ggaacacgtt aggaagttgg tcaaagcctg ggaagaagta 11700
gggccccaga tctggtactt ctttgacaac agcacacaga tgaacatgat cagagtaagg 11760
ggggttggag gatggggagg ggaggggagg aggaagcggt gggggcaaga aagttccact 11820
tgtttccttt tcccaggaaa gagttaatcg ctattggagt tagatcaaaa tacaacaagc 11880
aggccccaaa ggccttcatt ccaagcagtc accaagtggg gtcactgact ttggatgaga 11940
aatatgtttc ttgaattctg ggagaagtct aaaagctgcc acaagaccag tggcttcctg 12000
gagtttccta cttttatgaa ttcactcaag ggcctcaaat tcaaagaggc atctccccaa 12060
ggggccagct ctgtaactcc aaagatggtg gaatgtgttt gtctggtctc attttcagct 12120
ttgcaaaatg aagacaagag ttctatatat cagggacact caaaagaaaa caaaaaatatc 12180
cataagcaaa agaaagcttt ttatacacca tattcaatga cccccatctg gcccctcctt 12240
tgcccctaca catcttccct ctattctaga gacccatgga cttggggaaa tgggatatag 12300
ataggtatgt ttcatagtgg aacaagctca ccagctcttc agggagcctt agcatctcta 12360
tcctcaatca ctaaaaatta gaaatggctg aagaacaaga ccaaagatcc tatggaattt 12420
ctaagcagag cagtgactgt atttcttctt cccaaggata ccctggggaa cccaacagta 12480
aaagactttt tgaataggca gcttggtgaa gaaggtatta ctgctgaagc catcctaaac 12540
ttcctctaca agggccctcg ggaaagccag gctgacgaca tggccaactt cgactggagg 12600
gacatattta acatcactga tcgcaccctc cgcctggtca atcaatacct ggaggtaagg 12660
ggctgcaagc cccacagtgg gccccttgaa gatagcccca tgagtggggc cagagctccc 12720
ttagcaagtc aagtggtctt gaatttaagc tttcattttc cccactgaag aaacaagaat 12780
ccctacatcc cctgtacagt tctcattctc taacagctta tccatactta aaacttatct 12840
atgctgaaaa cggtttcctc ttcacatctc ctacttctca tgctgggcac ctcctcctgt 12900
agccccccttt aagcatctgt gtctgtcctc aaccctcttc tgtctgacat tgcttgagtg 12960
gccatctatg gccagtgtcc cctcaacccc acagtccatt gcttgctgga cactcctgcc 13020
ctcaagttct acaagcacat cagcctcaac atgtcccctc caaaaactgt atgttctcct 13080
tgcccataga acatatcctt ctcctatatt tcctatccta attaacgtcc tcagcatttg 13140
cccgaattct caagtgaggg atttcagggt catccctaat tttccttctt caccctccac 13200
acagtagctc acccagcttt c 13221

<210> SEQ ID NO 293
<211> LENGTH: 13221
<212> TYPE: DNA
<213> ORGANISM: Artificial Sequence
<220> FEATURE:
<223> OTHER INFORMATION: pCI-Neo-Rho-ABCA4-intron6-intron11 c.859-540

<400> SEQUENCE: 293
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720
aactagaatg cagtgaaaaa aatgctttat ttgtgaaatt tgtgatgcta ttgctttatt 780
tgtaaccatt ataagctgca ataaacaagt taacaacaac aattgcattc attttatgtt 840
tcaggttcag ggggagatgt gggaggtttt ttaaagcaag taaaacctct acaaatgtgg 900
taaaatccga taaggatcga tccgggctgg cgtaatagcg aagaggcccg caccgatcgc 960
ccttcccaac agttgcgcag cctgaatggc gaatggacgc gccctgtagc ggcgcattaa 1020
gcgcggcggg tgtggtggtt acgcgcagcg tgaccgctac acttgccagc gccctagcgc 1080
ccgctccttt cgctttcttc ccttcctttc tcgccacgtt cgccggcttt ccccgtcaag 1140
ctctaaatcg ggggctccct ttagggttcc gatttagtgc tttacggcac ctcgacccca 1200
aaaaacttga ttagggtgat ggttcacgta gtgggccatc gccctgatag acggtttttc 1260
gccctttgac gttggagtcc acgttcttta atagtggact cttgttccaa actggaacaa 1320
cactcaaccc tatctcggtc tattcttttg atttataagg gattttgccg atttcggcct 1380
attggttaaa aaatgagctg atttaacaaa aatttaacgc gaattttaac aaaatattaa 1440
cgcttacaat ttcctgatgc ggtattttct ccttacgcat ctgtgcggta tttcacaccg 1500
catacgcgga tctgcgcagc accatggcct gaaataacct ctgaaagagg aacttggtta 1560
ggtaccttct gaggcggaaa gaaccagctg tggaatgtgt gtcagttagg gtgtggaaag 1620
tccccaggct ccccagcagg cagaagtatg caaagcatgc atctcaatta gtcagcaacc 1680
aggtgtggaa agtccccagg ctccccagca ggcagaagta tgcaaagcat gcatctcaat 1740
tagtcagcaa ccatagtccc gcccctaact ccgcccatcc cgcccctaac tccgcccagt 1800

-continued tccgcccatt ctccgcccca tggctgacta atttttttta tttatgcaga ggccgaggcc 1860
gcctcggcct ctgagctatt ccagaagtag tgaggaggct tttttggagg cctaggcttt 1920
tgcaaaaagc ttgattcttc tgacacaaca gtctcgaact taaggctaga gccaccatga 1980
ttgaacaaga tggattgcac gcaggttctc cggccgcttg ggtggagagg ctattcggct 2040
atgactgggc acaacagaca atcggctgct ctgatgccgc cgtgttccgg ctgtcagcgc 2100
aggggcgccc ggttcttttt gtcaagaccg acctgtccgg tgccctgaat gaactgcagg 2160
acgaggcagc gcggctatcg tggctggcca cgacgggcgt tccttgcgca gctgtgctcg 2220
acgttgtcac tgaagcggga agggactggc tgctattggg cgaagtgccg gggcaggatc 2280
tcctgtcatc tcaccttgct cctgccgaga aagtatccat catggctgat gcaatgcggc 2340
ggctgcatac gcttgatccg gctacctgcc cattcgacca ccaagcgaaa catcgcatcg 2400
agcgagcacg tactcggatg gaagccggtc ttgtcgatca ggatgatctg gacgaagagc 2460
atcaggggct cgcgccagcc gaactgttcg ccaggctcaa ggcgcgcatg cccgacggcg 2520
aggatctcgt cgtgacccat ggcgatgcct gcttgccgaa tatcatggtg gaaaatggcc 2580
gcttttctgg attcatcgac tgtggccggc tgggtgtggc ggaccgctat caggacatag 2640
cgttggctac ccgtgatatt gctgaagagc ttggcggcga atgggctgac cgcttcctcg 2700
tgctttacgg tatcgccgct cccgattcgc agcgcatcgc cttctatcgc cttcttgacg 2760
agttcttctg agcgggactc tggggttcga aatgaccgac caagcgacgc ccaacctgcc 2820
atcacgatgg ccgcaataaa atatctttat tttcattaca tctgtgtgtt ggttttttgt 2880
gtgaatcgat agcgataagg atccgcgtat ggtgcactct cagtacaatc tgctctgatg 2940
ccgcatagtt aagccagccc cgacacccgc caacacccgc tgacgcgccc tgacgggctt 3000
gtctgctccc ggcatccgct tacagacaag ctgtgaccgt ctccgggagc tgcatgtgtc 3060
agaggttttc accgtcatca ccgaaacgcg cgagacgaaa gggcctcgtg atacgcctat 3120
ttttataggt taatgtcatg ataataatgg tttcttagac gtcaggtggc acttttcggg 3180
gaaatgtgcg cggaacccct atttgtttat ttttctaaat acattcaaat atgtatccgc 3240
tcatgagaca ataaccctga taaatgcttc aataatattg aaaaaggaag agtatgagta 3300
ttcaacattt ccgtgtcgcc cttattccct tttttgcggc attttgcctt cctgtttttg 3360
ctcacccaga aacgctggtg aaagtaaaag atgctgaaga tcagttgggt gcacgagtgg 3420
gttacatcga actggatctc aacagcggta agatccttga gagttttcgc cccgaagaac 3480
gttttccaat gatgagcact tttaaagttc tgctatgtgg cgcggtatta tcccgtattg 3540
acgccgggca agagcaactc ggtcgccgca tacactattc tcagaatgac ttggttgagt 3600
actcaccagt cacagaaaag catcttacgg atggcatgac agtaagagaa ttatgcagtg 3660
ctgccataac catgagtgat aacactgcgg ccaacttact tctgacaacg atcggaggac 3720
cgaaggagct aaccgctttt ttgcacaaca tgggggatca tgtaactcgc cttgatcgtt 3780
gggaaccgga gctgaatgaa gccataccaa acgacgagcg tgacaccacg atgcctgtag 3840
caatggcaac aacgttgcgc aaactattaa ctggcgaact acttactcta gcttcccggc 3900
aacaattaat agactggatg gaggcggata aagttgcagg accacttctg cgctcggccc 3960
ttccggctgg ctggtttatt gctgataaat ctggagccgg tgagcgtggg tctcgcggta 4020
tcattgcagc actggggcca gatggtaagc cctcccgtat cgtagttatc tacacgacgg 4080
ggagtcaggc aactatggat gaacgaaata gacagatcgc tgagataggt gcctcactga 4140
ttaagcattg gtaactgtca gaccaagttt actcatatat actttagatt gatttaaaac 4200
ttcattttta atttaaaagg atctaggtga agatcctttt tgataatctc atgaccaaaa 4260
tcccttaacg tgagttttcg ttccactgag cgtcagaccc cgtagaaaag atcaaaggat 4320
cttcttgaga tccttttttt ctgcgcgtaa tctgctgctt gcaaacaaaa aaaccaccgc 4380
taccagcggt ggtttgtttg ccggatcaag agctaccaac tctttttccg aaggtaactg 4440
gcttcagcag agcgcagata ccaaatactg ttcttctagt gtagccgtag ttaggccacc 4500
acttcaagaa ctctgtagca ccgcctacat acctcgctct gctaatcctg ttaccagtgg 4560
ctgctgccag tggcgataag tcgtgtctta ccgggttgga ctcaagacga tagttaccgg 4620
ataaggcgca gcggtcgggc tgaacggggg gttcgtgcac acagcccagc ttggagcgaa 4680
cgacctacac cgaactgaga tacctacagc gtgagctatg agaaagcgcc acgcttcccg 4740
aagggagaaa ggcggacagg tatccggtaa gcggcagggt cggaacagga gagcgcacga 4800
gggagcttcc agggggaaac gcctggtatc tttatagtcc tgtcgggttt cgccacctct 4860
gacttgagcg tcgatttttg tgatgctcgt caggggggcg gagcctatgg aaaaacgcca 4920
gcaacgcggc ctttttacgg ttcctggcct tttgctggcc ttttgctcac atggctcgac 4980
agatcttcaa tattggccat tagccatatt attcattggt tatatagcat aaatcaatat 5040
tggctattgg ccattgcata cgttgtatct atatcataat atgtacattt atattggctc 5100
atgtccaata tgaccgccat gttggcattg attattgact agttattaat agtaatcaat 5160
tacggggtca ttagttcata gcccatatat ggagttccgc gttacataac ttacggtaaa 5220
tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460
tacttggcag tacatctacg tattagtcat cgctattacc atggtgatgc ggttttggca 5520
gtacaccaat gggcgtggat agcggtttga ctcacgggga tttccaagtc tccaccccat 5580
tgacgtcaat gggagtttgt tttggcacca aaatcaacgg gactttccaa aatgtcgtaa 5640
caactgcgat cgcccgcccc gttgacgcaa atgggcggta ggcgtgtacg gtgggaggtc 5700
tatataagca gagctcgttt agtgaaccgt cagatcacta gaagctttat tgcggtagtt 5760
tatcacagtt aaattgctaa cgcagtcagt gcttctgaca caacagtctc gaacttaagc 5820
tgcagtgact ctcttaaggt agccttgcag aagttggtcg tgaggcactg ggcaggtaag 5880
tatcaaggtt acaagacagg tttaaggaga ccaatagaaa ctgggcttgt cgagacagag 5940
aagactcttg cgtttctgat aggcacctat tggtcttact gacatccact ttgcctttct 6000
ctccacaggt gtccactccc agttcaatta cagctcttaa ggctagagta cttaatacga 6060
ctcactatag gctagcctcg agaattccgg aggtcaacaa cgagtctttt gtcatctaca 6120
tgttcgtggt ccacttcacc atccccatga ttatcatctt tttctgctat gggcagctcg 6180
tcttcaccgt caaggaggta cgggccgggg ggtgggcggc ctcacggctc tgagggtcca 6240
gcccccagca tgcatctgcg gctcctgctc cctggaggag ccatatcaca agtttgtaca 6300
aaaaagcagg cttcaacact gctggcaatt ggagaatctg caagggaact tctccgactc 6360
ctaccagcag ctgctttaaa ataaaggtga tgtagctggt caaatcctcc atgagagagc 6420
agtgttgaat ggaggaagag acacaacctg tctgaaaatg gcacaaagga agaaagatgt 6480
aaacaatgac gagaagactg cagtgtctac aaagctccga ggtgaacaga tgggcacccc 6540

```
aggcccgcag cacttccttc agtctctgcc agctgcactc tgttttcctt cctccaggaa   6600
tcttgtttgg tgtcactaaa acagcaatta gaatcacttt gaaatagtga tagtatttaa   6660
tataactatg aaactatctg tgattgacaa gtgcagcaag gagtcttgga atgagagcct   6720
ttattttttc aattaaataa aagagttttt tgtttctaaa agtaatcttg cagaaaagat   6780
cctgcgatca gaaagaagga ggggggagt tttcaaacat ataggagatc agactgtgcc    6840
tatgtgtgta tatacctaca aacatatata tatttaaaaa attgttttac tgtcaattac   6900
agcttcccac actcctagac agccgttctc aaggtatcaa tctgagatct tggggaggaa   6960
tattatctga tatgtcacca agaattcaag aggtgagtag cctgatggta gtaattataa   7020
tttcattatg tctttccacc atttacccca cttatgtcaa ataatttaat tgtatttcaa   7080
acctgttcaa ggaaaagtac atttgatctt tccatctagc aatttcaaag cacctgttca   7140
catcccaaat tatctgtgct cttaagtaag aggcagaaag aaaggaacca cccttctgat   7200
ttcacatcaa aaaagaaatg ccactggcaa taagcaactt gcctggtgtg gcataaatca   7260
tcagaagact tacagttgaa tctaagtctt ttcagtactg aggtggttca ttattctgtt   7320
acagtcttaa aattcacata aatatatact gccaataata atagcataca cctttatagc   7380
ttacaggcac tcttcttcta agtgttttac ctatgttggc ttatttcatc ataaagaaaa   7440
caatggactt ttgtgttgtt ttgtaaaaag atgcgcacat tttaattaac atctgattgc   7500
acaagtctcc tcccatatag aaatggattc ttccacgcaa tagataagag gtgctgggga   7560
tatgatgatg aacacacaga tttggtcatg accctgtggg aaagagagat gggaaaaaaa   7620
caattctctt caagtgtgat gagtgttacg aaagggaggg aaaagttgaa acaggttttt   7680
ttccaaactt ttctccctcc attattcgca gctgacttgg gctccaccaa cctggaaaac   7740
tgcatggttg gaatctgtct ttataaaacg catctcaacc tgggccgagt atgcacactg   7800
atgtgggaaa gttagagaag agcccattgt actaatgctc acctgctaca gtgggagtct   7860
ctgttaaaca gtcttttctt catagcatta aaaaaattta tatcactaca ataaggttga   7920
aattgataga gaatgtacaa acaatcccca aagtatatca acactcttag ttctgagtag   7980
aagttccaga aggcttcttg actgtctaga tagcaagtct aatcatttgt gaactaagtt   8040
aaagcagaag gcccagttta tatgaattgg tattacacca tttgacctga gaacagcccc   8100
ttcatctctg agtgctttga ctaaatgagc aacataataa tagtaataac cccttacaag   8160
atgtcataag actcactgtt gttgaagcaa tttgagattt tgactttatt gaagcataga   8220
tggtgattat aggcatgact cactgtgtgg attctccctg ggctcatcag tttcagaggg   8280
caagtgttgg catgtggaca aagagaggga tgacacgtaa acatggctta ttgcaatggg   8340
gaaatatttt cagtctcact gattgaatcc taatggtttt ataaattccc cagtaccact   8400
gaaagcaaag caagtaatca ggtgtgtttt aggaataaaa gcagcattat tttaatttcg   8460
tattttcccc taaagcaaag ccaaatggca ttatgggagc caagctactg gcagctccac   8520
cagccttctc ctgagttctc ggcattacag atctaccctc aaaggatgag gccagcaagc   8580
accacagggt gcccacatgg agaagagaag gccaccaacc tcctcttagc tggcacagaa   8640
ttgaaaaagt gtttttccag gaatggatac ttcatctgtt ctgtatttgc tagaatttta   8700
aaacgcacac acagacacac acaggcgtgc acacacacac gcacacacac acgagaaaac   8760
cacaaaccac acatttcaag gaaatggaag aattcattgg taaaattaag ctaataagat   8820
tattttccaa atataagaaa ctaaatttta gactatttag ccaaagaaat ttgctctgat   8880
```

-continued

```
cttgcttttc tacaacagaa tcattcccca atcattttat ttccctcttt ttctccccag   8940
tatccccatc ttggtgggac aacagaaccc aagaactggc ttaacagtaa aatattttct   9000
gcatttgccc aaggacacat tcccaacgaa ttcaaataaa ggagactaga agaagagagg   9060
ctatactaca gtgctctagg ggtcagtctg tgatttgttg ttgttgttgt tgttgttttg   9120
agacggagta ttgctcagtc gcccaggctg gagtgcagtg gcacgatgtc tactcactgt   9180
aagctctgcc ccccaggttc acgccattct cctgcctcag cctcccgaat agctgggagt   9240
acaggggccc gccaccatgt ccggctaatt tttttgtatt tttaatagag acggggtttc   9300
accatgttcg ccaggatggt ctcgatctcc tgacctcgtg atccgcccgc ctcggcctcc   9360
caaagtgcta ggattacagg catgagccac tgcgcccggc cactctgtga ttttctttaa   9420
ggctcatcct agtattctcc tagtccctaa gtagatggca gtaggttttg tttttttgttt   9480
ttcgcagctg gattaaggat tgctgagaat atatggatgt tttcttttaa atgtggaagt   9540
caaaccaaac gttggagcat tggcctcaca gcagattatg actctagctg ccttaaaata   9600
acctgaagac tttgccttgc cctagtttat ccatcggccg agtatgcagg acttgctgtg   9660
ggtgaccagg cccctcatgc agaatggtgg tccagagacc tttacaaagc tgatgggcat   9720
cctgtctgac ctcctgtgtg gctaccccga gggaggtggc tctcgggtgc tctccttcaa   9780
ctggtatgaa gacaataact ataaggcctt tctggggatt gactccacaa ggaaggatcc   9840
tatctattct tatgacagaa gaacaagtaa gttttctgag tcctgcttat aaattggcct   9900
ctcatgttgg ttaagttgat ggtttaacac ttctaggtga aaccaaacct ggggttgcat   9960
ctgtcttgtc ttgctgagtg gccttaggta aagagacttc tcccagaaag tccacttccc  10020
cttgcagaaa gggggcattg cttataagca attctggaca tgaaccacag aaagaactga  10080
ggcccacttg gaaagggaac agaggggcca tttcccactg atgtaattga actagggcta  10140
agttcaagag gaagagaatg atccgcaagg aagcaaccca gagttccagg tgaagctcag  10200
gtcagaaggg ccctggcaag taaacacggc tgtgggatgc ttttacaaac acaatatcgt  10260
gaaaatctat gtgtgtagta ctgaattaca ttccaaatgg caaattcctg gcaaatcatc  10320
ttccccacct ttcactattt tttttttttt ggtcttctat ggggtaaagg aggatggggt  10380
ggggaagaaa tgtaactggc tgcccctcta gttaaaaact gaaaagaggc agcaagggac  10440
atgccaaaag tagttggact ctaagatagc tacacacaac aaagcagcta agcagctaat  10500
tgaagggaaa ttactgaggc tcaagctgag attccaagcg ggggccttgt ttggcctctc  10560
agtccctttc atctgagaaa ggcctcagtt cctagcagta atcagaggca ggcttctcag  10620
cctccttctc ctaaagcaga ataaaccaca gggcaagtcg catcctttgt ttctctgatg  10680
aggccattac tgagagtcac tgtggcattt tgctactaat gatgagcttg ttattggtgg  10740
ggtacagcct attaatttag gttattcatc aaatcctcca gcatggagtt gaatgagaca  10800
tgtgatgtgg atacactaat gactatattg agttacaagc aatggggagt ttctgtaaaa  10860
tctgtccctt gtctcctggc agcatccttt tgtaatgcat tgatccagag cctggagtca  10920
aatcctttaa ccaaaatcgc ttggagggcg gcaaagcctt tgctgatggg aaaaatcctg  10980
tacactcctg attcacctgc agcacgaagg atactgaaga atgtaagatc ccagctgggc  11040
ttgccttgtg taccctggac ctcccagaag tgtgtgtgtg tgtgtgtgtg tgtgagagag  11100
atgtgccttc ctggtagcac atctcatgtt tgttttttgc taagtggact cttgcgtttc  11160
ctcccccatc cacagtcatc actggaatgc tttgcttcag tgcccctgcc tgggccctcc  11220
cctctctact gcagcctaca atgaggtttt ctttcccatt gcttgaatta tatccctaat  11280
```

```
ggaagggttc acaattctct gaatcctggc tactcagata aagacaggga ggaagggagg  11340
aagggtattt tctcccaggg ggtccaaatc tagctttaac gagggaggtt ctgagaaaat  11400
aatatcatca atattacatg gacttctgag atactaagaa attagattct gtcagcccag  11460
gaagttggga gatggtgaat tgttctggga aatagcaata gactgagaaa ataaaaacac  11520
ttccttgaaa agcctttccc taacactaag tgataggggc agaaaagaca caaccaaaag  11580
ttctctctca cttttctctc tgttcgtgtc tctgtcttga tctctgtctg gttttaggcc  11640
aactcaactt ttgaagaact ggaacacgtt aggaagttgg tcaaagcctg ggaagaagta  11700
gggccccaga tctggtactt ctttgacaac agcacacaga tgaacatgat cagagtaagg  11760
ggggttggag gatggggagg ggaggggagg aggaagcggt gggggcaaga aagttccact  11820
tgtttccttt tcccaggaaa gagttaatcg ctattggagt tagatcaaaa tacaacaagc  11880
aggccccaaa ggccttcatt ccaagcagtc accaagtggg gtcactgact ttggatgaga  11940
aatatgtttc ttgaattctg ggagaagtct aaaagctgcc acaagaccag tggcttcctg  12000
gagtttccta cttttatgaa ttcactcaag ggcctcaaat tcaaagaggc atctccccaa  12060
ggggccagct ctgtaactcc aaagatggtg gaatgtgttt gtctggtctc attttcagct  12120
ttgcaaaatg aagacaagag ttctatatat cagggacact caaaagaaaa caaaaatatc  12180
cataagcaaa agaaagcttt ttatacacca tattcaatga cccccatctg gcccctcctt  12240
tgcccctaca catcttccct ctattctaga gacccatgga cttggggaaa tgggatatag  12300
ataggtatgt ttcatagtgg aacaagctca ccagctcttc agggagcctt agcatctcta  12360
tcctcaatca ctaaaaatta gaaatggctg aagaacaaga ccaaagatcc tatggaattt  12420
ctaagcagag cagtgactgt atttcttctt cccaaggata ccctggggaa cccaacagta  12480
aaagactttt tgaataggca gcttggtgaa gaaggtatta ctgctgaagc catcctaaac  12540
ttcctctaca agggccctcg ggaaagccag gctgacgaca tggccaactt cgactggagg  12600
gacatattta acatcactga tcgcaccctc cgcctggtca atcaatacct ggaggtaagg  12660
ggctgcaagc cccacagtgg gccccttgaa gatagcccca tgagtggggc cagagctccc  12720
ttagcaagtc aagtggtctt gaatttaagc tttcattttc cccactgaag aaacaagaat  12780
ccctacatcc cctgtacagt tctcattctc taacagctta tccatactta aaacttatct  12840
atgctgaaaa cggtttcctc ttcacatctc ctacttctca tgctgggcac ctcctcctgt  12900
agccccccttt aagcatctgt gtctgtcctc aaccctcttc tgtctgacat tgcttgagtg  12960
gccatctatg gccagtgtcc cctcaacccc acagtccatt gcttgctgga cactcctgcc  13020
ctcaagttct acaagcacat cagcctcaac atgtcccctc caaaaactgt atgttctcct  13080
tgcccataga acatatcctt ctcctatatt tcctatccta attaacgtcc tcagcatttg  13140
cccgaattct caagtgaggg atttcagggt catccctaat tttccttctt caccctccac  13200
acagtagctc acccagcttt c                                           13221
```

<210> SEQ ID NO 294
<211> LENGTH: 13221
<212> TYPE: DNA
<213> ORGANISM: Artificial Sequence
<220> FEATURE:
<223> OTHER INFORMATION: pCI-Neo-Rho-ABCA4-intron6-intron11 c.859-506C

<400> SEQUENCE: 294

```
ttgtacaaag tggtgatctt gtacaaagtg gtgatgagag gtacctccga ggggtaaaca     60
```

-continued

```
gttgggtaaa cagtctctga agtcagctct gccattttct agctgtatgg ccctgggcaa    120
gtcaatttcc ttctctgtgc tttggtttcc tcatccatag aaaggtagaa agggcaaaac    180
accaaactct tggattacaa gagataattt acagaacacc cttggcacac agagggcacc    240
atgaaatgtc acgggtgaca cagccccctt gtgctcagtc cctggcatct ctaggggtga    300
ggagcgtctg cctagcaggt tcccaccagg aagctggatt tgagtggatg gggcgctgga    360
atcgtgaggg gcagaagcag gcaaagggtc ggggcgaacc tcactaacgt gccagttcca    420
agcacactgt gggcagccct ggccctgact caagcctctt gccttccagt tccggaactg    480
catgctcacc accatctgct gcggcaagaa cccactgggt gacgatgagg cctctgctac    540
cgtgtccaag acggagacga gccaggtggc cccggcctaa gacctgccta ggactctgtg    600
gccgactata ggcgtctccc atcccctaca cctgtcgacc cgggcggccg cttcccttta    660
gtgagggtta atgcttcgag cagacatgat aagatacatt gatgagtttg gacaaaccac    720
aactagaatg cagtgaaaaa aatgctttat ttgtgaaatt tgtgatgcta ttgctttatt    780
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta atttttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
```

-continued

```
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
ttttataggt taatgtcatg ataataatgg tttcttagac gtcaggtggc acttttcggg   3180
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
```

-continued

```
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttcaacact gctggcaatt ggagaatctg caagggaact tctccgactc   6360
ctaccagcag ctgctttaaa ataaaggtga tgtagctggt caaatcctcc atgagagagc   6420
agtgttgaat ggaggaagag acacaacctg tctgaaaatg gcacaaagga agaaagatgt   6480
aaacaatgac gagaagactg cagtgtctac aaagctccga ggtgaacaga tgggcacccc   6540
aggcccgcag cacttccttc agtctctgcc agctgcactc tgttttcctt cctccaggaa   6600
tcttgtttgg tgtcactaaa acagcaatta gaatcacttt gaaatagtga tagtatttaa   6660
tataactatg aaactatctg tgattgacaa gtgcagcaag gagtcttgga atgagagcct   6720
ttattttttc aattaaataa aagagttttt tgtttctaaa agtaatcttg cagaaaagat   6780
cctgcgatca gaaagaagga ggggggggagt tttcaaacat ataggagatc agactgtgcc   6840
tatgtgtgta tatacctaca aacatatata tatttaaaaa attgttttac tgtcaattac   6900
agcttcccac actcctagac agccgttctc aaggtatcaa tctgagatct tggggaggaa   6960
tattatctga tatgtcacca agaattcaag aggtgagtag cctgatggta gtaattataa   7020
tttcattatg tctttccacc atttacccca cttatgtcaa ataatttaat tgtatttcaa   7080
acctgttcaa ggaaaagtac atttgatctt tccatctagc aatttcaaag cacctgttca   7140
catcccaaat tatctgtgct cttaagtaag aggcagaaag aaaggaacca cccttctgat   7200
```

-continued

```
ttcacatcaa aaaagaaatg ccactggcaa taagcaactt gcctggtgtg gcataaatca   7260
tcagaagact tacagttgaa tctaagtctt ttcagtactg aggtggttca ttattctgtt   7320
acagtcttaa aattcacata aatatatact gccaataata atagcataca cctttatagc   7380
ttacaggcac tcttcttcta agtgttttac ctatgttggc ttatttcatc ataaagaaaa   7440
caatggactt ttgtgttgtt ttgtaaaaag atgcgcacat tttaattaac atctgattgc   7500
acaagtctcc tcccatatag aaatggattc ttccacgcaa tagataagag gtgctgggga   7560
tatgatgatg aacacacaga tttggtcatg accctgtggg aaagagagat gggaaaaaaa   7620
caattctctt caagtgtgat gagtgttacg aaagggaggg aaaagttgaa acaggttttt   7680
ttccaaactt ttctccctcc attattcgca gctgacttgg gctccaccaa cctggaaaac   7740
tgcatggttg gaatctgtct ttataaaacg catctcaacc tgggccgagt atgcacactg   7800
atgtgggaaa gttagagaag agcccattgt actaatgctc acctgctaca gtgggagtct   7860
ctgttaaaca gtcttttctt catagcatta aaaaaattta tatcactaca ataaggttga   7920
aattgataga gaatgtacaa acaatcccca aagtatatca acactcttag ttctgagtag   7980
aagttccaga aggcttcttg actgtctaga tagcaagtct aatcatttgt gaactaagtt   8040
aaagcagaag gcccagttta tatgaattgg tattacacca tttgacctga gaacagcccc   8100
ttcatctctg agtgctttga ctaaatgagc aacataataa tagtaataac cccttacaag   8160
atgtcataag actcactgtt gttgaagcaa tttgagattt tgactttatt gaagcataga   8220
tggtgattat aggcatgact cactgtgtgg attctccctg ggctcatcag tttcagaggg   8280
caagtgttgg catgtggaca aagagaggga tgacacgtaa acatggctta ttgcaatggg   8340
gaaatatttt cagtctcact gattgaatcc taatggtttt ataaattccc cagtaccact   8400
gaaagcaaag caagtaatca ggtgtgtttt aggaataaaa gcagcattat tttaatttcg   8460
tattttcccc taaagcaaag ccaaatggca ttatgggagc caagctactg gcagctccac   8520
cagccttctc ctgagttctc ggcattacag atctaccctc aaaggatgag gccagcaagc   8580
accacagggt gcccacatgg agaagagaag gccaccaacc tcctcttagc tggcacagaa   8640
ttgaaaaagt gtttttccag gaatggatac ttcatctgtt ctgtatttgc tagaatttta   8700
aaacgcacac acagacacac acaggcgtgc acacacacac gcacacacac acgagaaaac   8760
cacaaaccac acatttcaag gaaatggaag aattcattgg taaaattaag ctaataagat   8820
tattttccaa atataagaaa ctaaatttta gactatttag ccaaagaaat ttgctctgat   8880
cttgcttttc tacaacagaa tcattcccca atcattttat ttccctcttt ttctccccag   8940
tatccccatc ttggtgggac aacagaaccc aagaactggc ttaacagtaa aatattttct   9000
gcatttgccc aaggacacat tcccaacgaa ttcaaataaa ggagactaga agaagagagg   9060
ctatactaca gtgctctagg ggtcactctg tgatttgttg ttgttgttgt tgttgttttc   9120
agacggagta ttgctcagtc gcccaggctg gagtgcagtg gcacgatgtc tactcactgt   9180
aagctctgcc ccccaggttc acgccattct cctgcctcag cctcccgaat agctgggagt   9240
acaggggccc gccaccatgt ccggctaatt tttttgtatt tttaatagag acggggtttc   9300
accatgttcg ccaggatggt ctcgatctcc tgacctcgtg atccgcccgc ctcggcctcc   9360
caaagtgcta ggattacagg catgagccac tgcgcccggc cactctgtga ttttctttaa   9420
ggctcatcct agtattctcc tagtccctaa gtagatggca gtaggttttg tttttttgttt  9480
ttcgcagctg gattaaggat tgctgagaat atatggatgt tttcttttaa atgtggaagt   9540
```

-continued caaaccaaac gttggagcat tggcctcaca gcagattatg actctagctg ccttaaaata 9600
acctgaagac tttgccttgc cctagtttat ccatcggccg agtatgcagg acttgctgtg 9660
ggtgaccagg cccctcatgc agaatggtgg tccagagacc tttacaaagc tgatgggcat 9720
cctgtctgac ctcctgtgtg gctaccccga gggaggtggc tctcgggtgc tctccttcaa 9780
ctggtatgaa gacaataact ataaggcctt tctggggatt gactccacaa ggaaggatcc 9840
tatctattct tatgacagaa gaacaagtaa gttttctgag tcctgcttat aaattggcct 9900
ctcatgttgg ttaagttgat ggtttaacac ttctaggtga aaccaaacct ggggttgcat 9960
ctgtcttgtc ttgctgagtg gccttaggta aagagacttc tcccagaaag tccacttccc 10020
cttgcagaaa gggggcattg cttataagca attctggaca tgaaccacag aaagaactga 10080
ggcccacttg gaaagggaac agaggggcca tttcccactg atgtaattga actagggcta 10140
agttcaagag gaagagaatg atccgcaagg aagcaaccca gagttccagg tgaagctcag 10200
gtcagaaggg ccctggcaag taaacacggc tgtgggatgc ttttacaaac acaatatcgt 10260
gaaaatctat gtgtgtagta ctgaattaca ttccaaatgg caaattcctg gcaaatcatc 10320
ttccccacct ttcactattt tttttttttt ggtcttctat ggggtaaagg aggatggggt 10380
ggggaagaaa tgtaactggc tgcccctcta gttaaaaact gaaaagaggc agcaagggac 10440
atgccaaaag tagttggact ctaagatagc tacacacaac aaagcagcta agcagctaat 10500
tgaagggaaa ttactgaggc tcaagctgag attccaagcg gggccttgt ttggcctctc 10560
agtccctttc atctgagaaa ggcctcagtt cctagcagta atcagaggca ggcttctcag 10620
cctccttctc ctaaagcaga ataaaccaca gggcaagtcg catcctttgt ttctctgatg 10680
aggccattac tgagagtcac tgtggcattt tgctactaat gatgagcttg ttattggtgg 10740
ggtacagcct attaatttag gttattcatc aaatcctcca gcatggagtt gaatgagaca 10800
tgtgatgtgg atacactaat gactatattg agttacaagc aatggggagt ttctgtaaaa 10860
tctgtccctt gtctcctggc agcatccttt tgtaatgcat tgatccagag cctggagtca 10920
aatcctttaa ccaaaatcgc ttggagggcg gcaaagcctt tgctgatggg aaaaatcctg 10980
tacactcctg attcacctgc agcacgaagg atactgaaga atgtaagatc ccagctgggc 11040
ttgccttgtg taccctggac ctcccagaag tgtgtgtgtg tgtgtgtgtg tgtgagagag 11100
atgtgccttc ctggtagcac atctcatgtt tgttttttgc taagtggact cttgcgtttc 11160
ctcccccatc cacagtcatc actggaatgc tttgcttcag tgcccctgcc tgggccctcc 11220
cctctctact gcagcctaca atgaggtttt ctttcccatt gcttgaatta tatccctaat 11280
ggaagggttc acaattctct gaatcctggc tactcagata aagacaggga ggaagggagg 11340
aagggtattt tctcccaggg ggtccaaatc tagctttaac gagggaggtt ctgagaaaat 11400
aatatcatca atattacatg gacttctgag atactaagaa attagattct gtcagcccag 11460
gaagttggga gatggtgaat tgttctggga aatagcaata gactgagaaa ataaaaacac 11520
ttccttgaaa agcctttccc taacactaag tgataggggc agaaaagaca caaccaaaag 11580
ttctctctca cttttctctc tgttcgtgtc tctgtcttga tctctgtctg gttttaggcc 11640
aactcaactt ttgaagaact ggaacacgtt aggaagttgg tcaaagcctg ggaagaagta 11700
gggccccaga tctggtactt ctttgacaac agcacacaga tgaacatgat cagagtaagg 11760
ggggttggag gatggggagg ggaggggagg aggaagcggt gggggcaaga aagttccact 11820
tgtttccttt tcccaggaaa gagttaatcg ctattggagt tagatcaaaa tacaacaagc 11880
aggccccaaa ggccttcatt ccaagcagtc accaagtggg gtcactgact ttggatgaga 11940
aatatgtttc ttgaattctg ggagaagtct aaaagctgcc acaagaccag tggcttcctg 12000
gagtttccta cttttatgaa ttcactcaag ggcctcaaat tcaaagaggc atctccccaa 12060
ggggccagct ctgtaactcc aaagatggtg gaatgtgttt gtctggtctc attttcagct 12120
ttgcaaaatg aagacaagag ttctatatat cagggacact caaaagaaaa caaaaatatc 12180
cataagcaaa agaaaagcttt ttatacacca tattcaatga cccccatctg gcccctcctt 12240
tgcccctaca catcttccct ctattctaga gacccatgga cttggggaaa tgggatatag 12300
ataggtatgt ttcatagtgg aacaagctca ccagctcttc agggagcctt agcatctcta 12360
tcctcaatca ctaaaaatta gaaatggctg aagaacaaga ccaaagatcc tatggaattt 12420
ctaagcagag cagtgactgt atttcttctt cccaaggata ccctggggaa cccaacagta 12480
aaagactttt tgaataggca gcttggtgaa gaaggtatta ctgctgaagc catcctaaac 12540
ttcctctaca agggccctcg ggaaagccag gctgacgaca tggccaactt cgactggagg 12600
gacatattta acatcactga tcgcaccctc cgcctggtca atcaatacct ggaggtaagg 12660
ggctgcaagc cccacagtgg gccccttgaa gatagcccca tgagtggggc cagagctccc 12720
ttagcaagtc aagtggtctt gaatttaagc tttcattttc cccactgaag aaacaagaat 12780
ccctacatcc cctgtacagt tctcattctc taacagctta tccatactta aaacttatct 12840
atgctgaaaa cggtttcctc ttcacatctc ctacttctca tgctgggcac ctcctcctgt 12900 agccccctttt aagcatctgt gtctgtcctc aaccctcttc tgtctgacat tgcttgagtg 12960
gccatctatg gccagtgtcc cctcaacccc acagtccatt gcttgctgga cactcctgcc 13020
ctcaagttct acaagcacat cagcctcaac atgtcccctc caaaaactgt atgttctcct 13080
tgcccataga acatatcctt ctcctatatt tcctatccta attaacgtcc tcagcatttg 13140
cccgaattct caagtgaggg atttcagggt catccctaat tttccttctt caccctccac 13200
acagtagctc acccagcttt c 13221

<210> SEQ ID NO 295
<211> LENGTH: 14138
<212> TYPE: DNA
<213> ORGANISM: Artificial Sequence
<220> FEATURE:
<223> OTHER INFORMATION: pCI-Neo-Rho-ABCA4-intron11-intron15 wild type

<400> SEQUENCE: 295
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720

-continued

```
aactagaatg cagtgaaaaa aatgctttat ttgtgaaatt tgtgatgcta ttgctttatt    780
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta atttttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggtttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
```

ttttataggt taatgtcatg ataataatgg tttcttagac gtcaggtggc acttttcggg 3180
gaaatgtgcg cggaacccct atttgtttat ttttctaaat acattcaaat atgtatccgc 3240
tcatgagaca ataaccctga taaatgcttc aataatattg aaaaaggaag agtatgagta 3300
ttcaacattt ccgtgtcgcc cttattccct tttttgcggc attttgcctt cctgtttttg 3360
ctcacccaga aacgctggtg aaagtaaaag atgctgaaga tcagttgggt gcacgagtgg 3420
gttacatcga actggatctc aacagcggta agatccttga gagttttcgc cccgaagaac 3480
gttttccaat gatgagcact tttaaagttc tgctatgtgg cgcggtatta tcccgtattg 3540
acgccgggca agagcaactc ggtcgccgca tacactattc tcagaatgac ttggttgagt 3600
actcaccagt cacagaaaag catcttacgg atggcatgac agtaagagaa ttatgcagtg 3660
ctgccataac catgagtgat aacactgcgg ccaacttact tctgacaacg atcggaggac 3720
cgaaggagct aaccgctttt ttgcacaaca tgggggatca tgtaactcgc cttgatcgtt 3780
gggaaccgga gctgaatgaa gccataccaa acgacgagcg tgacaccacg atgcctgtag 3840
caatggcaac aacgttgcgc aaactattaa ctggcgaact acttactcta gcttcccggc 3900
aacaattaat agactggatg gaggcggata aagttgcagg accacttctg cgctcggccc 3960
ttccggctgg ctggtttatt gctgataaat ctggagccgg tgagcgtggg tctcgcggta 4020
tcattgcagc actggggcca gatggtaagc cctcccgtat cgtagttatc tacacgacgg 4080
ggagtcaggc aactatggat gaacgaaata gacagatcgc tgagataggt gcctcactga 4140
ttaagcattg gtaactgtca gaccaagttt actcatatat actttagatt gatttaaaac 4200
ttcattttta atttaaaagg atctaggtga agatcctttt tgataatctc atgaccaaaa 4260
tcccttaacg tgagttttcg ttccactgag cgtcagaccc cgtagaaaag atcaaaggat 4320
cttcttgaga tcctttttt ctgcgcgtaa tctgctgctt gcaaacaaaa aaaccaccgc 4380
taccagcggt ggtttgtttg ccggatcaag agctaccaac tctttttccg aaggtaactg 4440
gcttcagcag agcgcagata ccaaatactg ttcttctagt gtagccgtag ttaggccacc 4500
acttcaagaa ctctgtagca ccgcctacat acctcgctct gctaatcctg ttaccagtgg 4560
ctgctgccag tggcgataag tcgtgtctta ccgggttgga ctcaagacga tagttaccgg 4620
ataaggcgca gcggtcgggc tgaacggggg gttcgtgcac acagcccagc ttggagcgaa 4680
cgacctacac cgaactgaga tacctacagc gtgagctatg agaaagcgcc acgcttcccg 4740
aagggagaaa ggcggacagg tatccggtaa gcggcagggt cggaacagga gagcgcacga 4800
gggagcttcc agggggaaac gcctggtatc tttatagtcc tgtcgggttt cgccacctct 4860
gacttgagcg tcgatttttg tgatgctcgt caggggggcg gagcctatgg aaaaacgcca 4920
gcaacgcggc ctttttacgg ttcctggcct tttgctggcc ttttgctcac atggctcgac 4980
agatcttcaa tattggccat tagccatatt attcattggt tatatagcat aaatcaatat 5040
tggctattgg ccattgcata cgttgtatct atatcataat atgtacattt atattggctc 5100
atgtccaata tgaccgccat gttggcattg attattgact agttattaat agtaatcaat 5160
tacggggtca ttagttcata gcccatatat ggagttccgc gttacataac ttacggtaaa 5220
tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460

-continued

```
tacttggcag tacatctacg tattagtcat cgctattacc atggtgatgc ggttttggca   5520

gtacaccaat gggcgtggat agcggtttga ctcacgggga tttccaagtc tccaccccat   5580

tgacgtcaat gggagtttgt tttggcacca aaatcaacgg gactttccaa aatgtcgtaa   5640

caactgcgat cgcccgcccc gttgacgcaa atgggcggta ggcgtgtacg gtgggaggtc   5700

tatataagca gagctcgttt agtgaaccgt cagatcacta gaagctttat tgcggtagtt   5760

tatcacagtt aaattgctaa cgcagtcagt gcttctgaca caacagtctc gaacttaagc   5820

tgcagtgact ctcttaaggt agccttgcag aagttggtcg tgaggcactg ggcaggtaag   5880

tatcaaggtt acaagacagg tttaaggaga ccaatagaaa ctgggcttgt cgagacagag   5940

aagactcttg cgtttctgat aggcacctat tggtcttact gacatccact ttgcctttct   6000

ctccacaggt gtccactccc agttcaatta cagctcttaa ggctagagta cttaatacga   6060

ctcactatag gctagcctcg agaattccgg aggtcaacaa cgagtctttt gtcatctaca   6120

tgttcgtggt ccacttcacc atccccatga ttatcatctt tttctgctat gggcagctcg   6180

tcttcaccgt caaggaggta cgggccgggg ggtgggcggc ctcacggctc tgagggtcca   6240

gcccccagca tgcatctgcg gctcctgctc cctggaggag ccatatcaca agtttgtaca   6300

aaaaagcagg cttctcttcc tccttgctct tccctcagct ggccatcctg tgtgtttgga   6360

gagagccaga aaggttcaag gctaggaatg tttctctctc tctttaaagc tctttaatcg   6420

tcaggctttc tgatcttcaa agcaggctgt agccagtgtg accccactcc ctcgcctccc   6480

catgctggag agtaaaagcc tggagtattt ttgtcatttt gaagacttgc atatttggac   6540

agccttggac atctggaaag tgtggtcctc actagctctg cagggataag agcacgtcag   6600

cacttccaag ctctctggcg cccctacatc tggacacgtt gaaaaattaa caccagactc   6660

tggagttaag caaacattaa gtttataggc ctccttgcat ttgaccattt cctgggacag   6720

cagcccttat cctgtgactt tctgtgtgta gagttgagtc tttgcagttg gtcctcctca   6780

cactctctca actttgtgac tctctgcagt gcttggtcct ggataagttt gaaagctaca   6840

atgatgaaac tcagctcacc caacgtgccc tctctctact ggaggaaaac atgttctggg   6900

ccggagtggt attccctgac atgtatccct ggaccagctc tctaccaccc cacgtgaagt   6960

ataagatccg aatggacata gacgtggtgg agaaaaccaa taagattaaa gacaggtgat   7020

gtttcaggaa gggctcgctg catttctcca aagtcagtgg gaaattacat ttggtagaga   7080

gaaagggatt gagactggac tcataaatca ataaaattaa gttaaataag aaaaaataag   7140

atattttata aagctcaaca aagagtcctt gaatgaaagc aattacagag tcacattgtg   7200

gctaatattc aaaactgaga tttaaactga ggactaggaa atagaattgg atccttttga   7260

agcgtttagg agaaagattt taagagaatg agttccgagt caccctgtgg tcgggaggtg   7320

tgagtgagct atccaagccc gttcccatcc tttgtccctc tgtgtcttct caggtattgg   7380

gattctggtc ccagagctga tcccgtggaa gatttccggt acatctgggg cgggtttgcc   7440

tatctgcagg acatggttga acaggggatc acaaggagcc aggtgcaggc ggaggctcca   7500

gttggaatct acctccagca gatgccctac ccctgcttcg tggacgattc gtgagtctga   7560

agttcgcgat cctcctccat gacacgctaa tgggggtgct ggagtgggct ggggtgggct   7620

gggggtgccc tcaaggcttc catgtcttta gagagagccc cagggaccag agccaaattg   7680

gagagcatgg agctctgact gaggaacctg cttctcccaa gctccaggca ggcacagatg   7740

agtcagtgca gtggtgggaa agggaaaaga gttgatgttg tagctggaaa agggaagggg   7800

aaaattaaag caaggaaagt gaggctgggg gaggggacaa attccccact atgtagtatg   7860
```

-continued

```
tttggtatgt ggaagggttc tggtcagaat gtttgcccaa tgattgccac atcagcattc   7920
attttggact ctgtatggcc agtaggtctg gttcctggga gccctggaat aatgcagccc   7980
cttccctaac taacatttcc atgatgtatg ctcaatgaca aggcagagga atgtgttgga   8040
tgagctcagg acctgcctcc ctggacactc ccatcccagg cctgtatatc tgttgaccag   8100
gaataagcca agcaagcagc ctactgtttg actgaatatg gatttggggg gtggtagaga   8160
aagggccggg gtggagggtt gggaggctca tttgtcatta tagatggggt cagacacact   8220
accaaaacag cagcagagat ctacaattga gttcacctaa aactcagtgt ggacacagga   8280
aaccctcttt taataactgt ccaatgggtt ttccagcctc agctctacag aaaacttgag   8340
ataacagtgg ccagtctgca gttagtttgg gttcggacaa taggcagagc tgggaaatgg   8400
agccaggggc gaaagcccag gtccacttta ggatcaggac gggagtggct ggtggggaag   8460
tgaggtgggt gtggggaggc aatagggagc tgggtcattt ggtatgggag agtcctctgg   8520
tggctagtcc cagaagtgca tgctttacga acatatgctt ctctccctag ggccaccttg   8580
agtgaaaccc tcccatgctg gaattgggcc ctttcagtga caacacacaa cagttttcaa   8640
tagataataa tcccaagggc tttactagca catgaaacac agggaaaacg tgtaaagttc   8700
acaagaaagt cgttccagtg tatcaaatct atcctgtttg ccaggtggat ataccagggt   8760
ctcctccacc tgtgcatggc tggtggtggg tccagtggct gttggataac tgatgtattg   8820
atggatcatt cgccttctga aagtgccaaa ctgattagtt attttgtgtg tctttttgtg   8880
taactagggt ttgaccttcc agggcagact gtgctggggc ggctgacccc ttggggagcc   8940
aagttattgc tcttaccacc accacttgcc cttgtcagtc ctccaccctc ttgggtttca   9000
gtgtcagcat gtagctgtct actcagatcc catccacatc atcaagtctg cagtttttc    9060
cttgcaaggc cttacaggga agatctttga catagaggat ataattttat tgacacattt   9120
tacttgcaga gcattcaccc gggctaacca gaaagccagc actctgctat aaacaaaaaa   9180
taatgcttca gggctaacat ggaatgtgtt aaaagattcc agcccattaa atgtccaggg   9240
gaggttttcc tgttttcctt tccctccatc tgggctttgt tctcaacaca ttcattcaac   9300
aaacatttat tctgcctcta ccaggtacag agcactctac tattctgctt ctctcctttt   9360
gctttagttt catgatcatc ctgaaccgct gtttccctat cttcatggtg ctggcatgga   9420
tctactctgt ctccatgact gtgaagagca tcgtcttgga gaaggagttg cgactgaagg   9480
agaccttgaa aaatcagggt gtctccaatg cagtgatttg gtgtacctgg ttcctggaca   9540
gcttctccat catgtcgatg agcatcttcc tcctgacgat attcatcatg gtaagccaaa   9600
tggagaaggc ccagaaaatc ttgaatactt tggttccttt ccccttttcct cctgttcatg  9660
tgcctggatt agtcatgtgg ccaccaagga gagcgtgaca tctagcttcc cagcccttcc   9720
ttttagccaa cgtgggagac actcaaagag acgaaatctc ctgaaggagc cactgtatca   9780
cagcatcctc ccatctccca cttcctgccc aggggtccat ggtccacaca gacttcccag   9840
tcccattccg tgaccatctg gagaagctgc tattagcaga gccctgcaca gggtgatagt   9900
gtaattaaag tggtcttctc tttccaaaca cagaaaaaat cagttcaggg agtgttttcc   9960
tgggcttaca attttaacta ctggctagag ttgaaatggg gaaagccttt tgccttttca   10020
gtagcagtag gggaggagat ctggattatt tacttatcat catcatggtc acctcctaca   10080
tggcttcacc aaaaaacatt ctgctgcctg aaaaagctcc aacacctctc tctcttttaa   10140
aggatggaat ttggagtcca tccttcctca gtgataagga gtttttatag ccacaggcag   10200
```

-continued

```
catctattgg tctgtcctct gcaaacttgc aactcctctg agagctagac ttggaaatga  10260
aacattattt tgcaatgcgc tgctatcctt catttttagc tcctccaccg tagatgatag  10320
tttgtacttg ttaaatgata aggatataaa tttaggtcat tttttatatt ttattgggtg  10380
gaatttggta taatttttag acttcaggct ttacaggctc ctgagatgga ctgattgagc  10440
ttgttctact tcttccccat catgatagga agtgctgtac cacactaggc agtgtgtgta  10500
gtgaccacag actggctgag tgtctcccat cccatgctgg cccatatctg gtacccacct  10560
gatccacaaa tgttccatca gatcctgttc aaacaacaca tctccagtta agccaaatct  10620
tgccctttct ccttacggta aaatgtacta aatctgaagg ttttgtcttt ttaatgttgc  10680
tccatgatcc agtgatctgt ggccttggtt atgctctgtg ctagagtcct aacaagacaa  10740
atgctaaggt agaggtcatt ctgctcaaac aacctgaccc cacctggatg tgggcttaca  10800
tttgcaaagg gcaccaaagt tctaagagat gaggggagga gctgagcccc ttgtccttat  10860
ctaggtttcc cttgttcttt cccatccctc agtctgcttc ttttcccagt accaacatgt  10920
ttgtgtcctc agaattaaag gagtaaaaat gtgtaaacat ctgactagca acagccatga  10980
gattttgcct ggcttgttga taagcagcat tgagatctgc cctcctaaga atgggccatt  11040
aggtcttcaa agcttttacg atgtgaggta aagaatgttc accaggagtt tcatgcacaa  11100
aagggtttct ctttgtggga actagaacat tgttccagtg atgacggaaa cagggctttc  11160
cataccaaaa cagggttttc ctttgaatga ctctcccacc tttcccttgt ctcttcctcc  11220
ccacctcaac aacacaggaa agaagctgga agcagggaca atgggaaggt ccctttgtta  11280
ctcgagctat tagaaacaaa aagaaaagtg gccatctgag gaagccacag ctggtgaaac  11340
tgtagggtca cagagtgaat tacacctctg gcttaagtca gtgaaaagtc ctagaagttt  11400
gtggtcctag aagtcctaaa agtttatggg actttgtttt gagcaaggat aagaaattga  11460
tttcaggctg ggcgtggtgg ctcacgcctg taaccctaat actttgggag acagaggcag  11520
gtggatcact tcaggtcagg agttccagag cagtctggcc aacatggcga aaccctgcct  11580
ctcctaaaaa tacaaaaatt agccaggtgc ggtggcacat gcctgtagtc ccggctactc  11640
aggagactga gcaaggagaa tcccttgaac ccaggaggtg gaggtctcag tgagctgata  11700
tcatatcact gcactctagc ctgggcaaca gagcaagact ctgtctaaaa aaataaataa  11760
ataaaaaaga aattgatttc attcttctga gaactgcaac aactacctta aagtgattcc  11820
atccaaaacc cacatgttca gccatggact tgcttttatg gagctgcgtg tgggtgacac  11880
acaaaatcag gagctctgag tcctaattta gacttttatt tagatttcct caaatttggg  11940
ttccagttaa gcgtgggtct cttctgtgcc ccgctcccct ttgccatttg ttttatctgt  12000
tcttcagtct gttctgtcag tacccacagg caggagagca gaaaggagaa atggcagcca  12060
cagcagacaa atggcacatt cgttccactc agctctcgca tgcccatcac agatacagct  12120
cattggtctc ttttctatga gaggaagcca gagctccagg gaactactgc caactgatca  12180
gaactcattt aggacatgga cctatttgtt cctttatgtt cctgggaaga gcacaggatg  12240
aattctatgt actcatttac gtgttcagag agtaaagtgc ctcataggat gcctccagca  12300
aaagataacc aagaaggtct aatacctttg acaatctcag tttatcctat agtgtaattg  12360
gatagcagtt cccctagcaa aagttgctag tttggtccta ttttctacat agccaaagtg  12420
attgattcat tggttaatgt gaaagttact gagtactgcc agcaggttct aggaaatata  12480
tttgtgtgat attcatggat ggggaggatc aatccacttc caagtgattt ggattaatta  12540
ctggtatttt cacctgtgtg ggtagcaaac ctcagaaaat caagtataga tgacggcata  12600
```

ggacaggcca ggccccaggc aaaatgttga agctcctctg gagttccctc ccatctccct 12660
cttttgtttt ccatatacct ggtttatcca gggccctgga gatgctccaa gaccccctac 12720
ccaggtcttc ctcccttgtc ccagctatat ttctccatat taccactctt ctcaccgagg 12780
atttgcttac ttaacacata ataaatacta ttaaaagaga aacttaggca cattaaaatg 12840
ttagagttga ttccagcaaa cagtgattca caggaggctc cagatcacaa gtggttcagg 12900
gccccactga ggggtaggga agcaagacaa agaaaaacaa agcaaatatt tgattggttc 12960
aagtggaaag tccctgatta caggttagtg ggcagtttgt gattagttaa gtttctctaa 13020
gttgggtttt ggtttgctga tgtaggaaca cagaatgctg gggccgtttc aacctaatgg 13080
tctcccaatt aattttttta acattactga tgactgttag gagtctaatg tgctactcct 13140
cccagggaaa atggcattcc taggattaaa ggaactcagc acatggagtg tgcgtagaaa 13200
tttagacact aactgcaggc tggtgggaga gagcccttta gggcagaatg agaaggcgtc 13260
cggccaaggg caggagttac tgacgcatgg cctcttggtt tcagcatgga agaatcctac 13320
attacagcga cccattcatc ctcttcctgt tcttgttggc tttctccact gccaccatca 13380
tgctgtgctt tctgctcagc accttcttct ccaaggccag tctggcagca gcctgtagtg 13440
gtgtcatcta tttcaccctc tacctgccac acatcctgtg cttcgcctgg caggaccgca 13500
tgaccgctga gctgaagaag gctgtggtga ggcccttggg ctggcccctg tcctacaaca 13560
cgtttccttg gaagggtccg tagcagtcct ggaggcccag cctgccctct gaggggggtcc 13620 actttgcctt tgacctaagg ttaaaaagtt cacgtgaggc taaaatgtac aggggcaaaa 13680
gtgggagcag tcctcacccc gagcgatgca acagtgactc ctcaccacgc ctgcttgatt 13740
catctgccct ggaaagtcat taaaaaacca gttcaactca tgggtccctt tatttactca 13800
caagagagag ccagcagccc atttcactag ttttcctttc ctactctttg agaagaatca 13860
gaagggaggg agcttgccac tttactatct gtctaaagag atgtttccat taattaaagg 13920
tttttgtttt gcttcaaaaa aacttgaatt ggagtatttc cacaagtatc tttaacatgc 13980
tctaccaatg tttgcagaaa gaagtgcaga aatgagactg tccacagagt caggctcgct 14040
ggccaggaga ggactcccga agctgacttc tgatggcctg agaaacttcc tagttcacaa 14100
ttcccagacc cagacaaaga gcactgcacc cagctttc 14138

<210> SEQ ID NO 296
<211> LENGTH: 14138
<212> TYPE: DNA
<213> ORGANISM: Artificial Sequence
<220> FEATURE:
<223> OTHER INFORMATION: pCI-Neo-Rho-ABCA4-intron11-intron15 c.1937+435G

<400> SEQUENCE: 296
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg gggcgctgga 360
atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720
aactagaatg cagtgaaaaa aatgctttat ttgtgaaatt tgtgatgcta ttgctttatt 780
tgtaaccatt ataagctgca ataaacaagt taacaacaac aattgcattc attttatgtt 840
tcaggttcag ggggagatgt gggaggtttt ttaaagcaag taaaacctct acaaatgtgg 900
taaaatccga taaggatcga tccgggctgg cgtaatagcg aagaggcccg caccgatcgc 960
ccttcccaac agttgcgcag cctgaatggc gaatggacgc gccctgtagc ggcgcattaa 1020
gcgcggcggg tgtggtggtt acgcgcagcg tgaccgctac acttgccagc gccctagcgc 1080
ccgctccttt cgctttcttc ccttcctttc tcgccacgtt cgccggcttt ccccgtcaag 1140
ctctaaatcg ggggctccct ttagggttcc gatttagtgc tttacggcac ctcgacccca 1200
aaaaacttga ttagggtgat ggttcacgta gtgggccatc gccctgatag acggtttttc 1260
gccctttgac gttggagtcc acgttcttta atagtggact cttgttccaa actggaacaa 1320
cactcaaccc tatctcggtc tattcttttg atttataagg gattttgccg atttcggcct 1380
attggttaaa aaatgagctg atttaacaaa aatttaacgc gaattttaac aaaatattaa 1440
cgcttacaat ttcctgatgc ggtattttct ccttacgcat ctgtgcggta tttcacaccg 1500
catacgcgga tctgcgcagc accatggcct gaaataacct ctgaaagagg aacttggtta 1560
ggtaccttct gaggcggaaa gaaccagctg tggaatgtgt gtcagttagg gtgtggaaag 1620
tccccaggct ccccagcagg cagaagtatg caaagcatgc atctcaatta gtcagcaacc 1680
aggtgtggaa agtccccagg ctccccagca ggcagaagta tgcaaagcat gcatctcaat 1740
tagtcagcaa ccatagtccc gcccctaact ccgcccatcc cgcccctaac tccgcccagt 1800
tccgcccatt ctccgcccca tggctgacta attttttta tttatgcaga ggccgaggcc 1860
gcctcggcct ctgagctatt ccagaagtag tgaggaggct tttttggagg cctaggcttt 1920
tgcaaaaagc ttgattcttc tgacacaaca gtctcgaact taaggctaga gccaccatga 1980
ttgaacaaga tggattgcac gcaggttctc cggccgcttg ggtggagagg ctattcggct 2040
atgactgggc acaacagaca atcggctgct ctgatgccgc cgtgttccgg ctgtcagcgc 2100
aggggcgccc ggttcttttt gtcaagaccg acctgtccgg tgccctgaat gaactgcagg 2160
acgaggcagc gcggctatcg tggctggcca cgacgggcgt tccttgcgca gctgtgctcg 2220
acgttgtcac tgaagcggga agggactggc tgctattggg cgaagtgccg gggcaggatc 2280
tcctgtcatc tcaccttgct cctgccgaga aagtatccat catggctgat gcaatgcggc 2340
ggctgcatac gcttgatccg gctacctgcc cattcgacca ccaagcgaaa catcgcatcg 2400
agcgagcacg tactcggatg gaagccggtc ttgtcgatca ggatgatctg gacgaagagc 2460
atcaggggct cgcgccagcc gaactgttcg ccaggctcaa ggcgcgcatg cccgacggcg 2520
aggatctcgt cgtgacccat ggcgatgcct gcttgccgaa tatcatggtg gaaaatggcc 2580
gcttttctgg attcatcgac tgtggccggc tgggtgtggc ggaccgctat caggacatag 2640
cgttggctac ccgtgatatt gctgaagagc ttggcggcga atgggctgac cgcttcctcg 2700
tgctttacgg tatcgccgct cccgattcgc agcgcatcgc cttctatcgc cttcttgacg 2760
agttcttctg agcgggactc tggggttcga aatgaccgac caagcgacgc ccaacctgcc 2820
atcacgatgg ccgcaataaa atatctttat tttcattaca tctgtgtgtt ggttttttgt 2880

-continued

```
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
ttttataggt taatgtcatg ataataatgg tttcttagac gtcaggtggc acttttcggg   3180
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
```

-continued

```
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttctcttcc tccttgctct tccctcagct ggccatcctg tgtgtttgga   6360
gagagccaga aaggttcaag gctaggaatg tttctctctc tctttaaagc tctttaatcg   6420
tcaggctttc tgatcttcaa agcaggctgt agccagtgtg accccactcc ctcgcctccc   6480
catgctggag agtaaaagcc tggagtattt ttgtcatttt gaagacttgc atatttggac   6540
agccttggac atctggaaag tgtggtcctc actagctctg cagggataag agcacgtcag   6600
cacttccaag ctctctggcg cccctacatc tggacacgtt gaaaaattaa caccagactc   6660
tggagttaag caaacattaa gtttataggc ctccttgcat ttgaccattt cctgggacag   6720
cagcccttat cctgtgactt tctgtgtgta gagttgagtc tttgcagttg gtcctcctca   6780
cactctctca actttgtgac tctctgcagt gcttggtcct ggataagttt gaaagctaca   6840
atgatgaaac tcagctcacc caacgtgccc tctctctact ggaggaaaac atgttctggg   6900
ccggagtggt attccctgac atgtatccct ggaccagctc tctaccaccc cacgtgaagt   6960
ataagatccg aatggacata gacgtggtgg agaaaaccaa taagattaaa gacaggtgat   7020
gtttcaggaa gggctcgctg catttctcca aagtcagtgg gaaattacat ttggtagaga   7080
gaaagggatt gagactggac tcataaatca ataaaattaa gttaaataag aaaaaataag   7140
atattttata aagctcaaca aagagtcctt gaatgaaagc aattacagag tcacattgtg   7200
gctaatattc aaaactgaga tttaaactga ggactaggaa atagaattgg atcctttga    7260
agcgtttagg agaaagattt taagagaatg agttccgagt caccctgtgg tcgggaggtg   7320
tgagtgagct atccaagccc gttcccatcc tttgtccctc tgtgtcttct caggtattgg   7380
gattctggtc ccagagctga tcccgtggaa gatttccggt acatctgggg cgggtttgcc   7440
tatctgcagg acatggttga acaggggatc acaaggagcc aggtgcaggc ggaggctcca   7500
gttggaatct acctccagca gatgccctac ccctgcttcg tggacgattc gtgagtctga   7560
agttcgcgat cctcctccat gacacgctaa tgggggtgct ggagtgggct ggggtgggct   7620
```

-continued

```
gggggtgccc tcaaggcttc catgtcttta gagagagccc cagggaccag agccaaattg   7680
gagagcatgg agctctgact gaggaacctg cttctcccaa gctccaggca ggcacagatg   7740
agtcagtgca gtggtgggaa agggaaaaga gttgatgttg tagctggaaa agggaagggg   7800
aaaattaaag caaggaaagt gaggctgggg gaggggacaa attccccact atgtagtatg   7860
tttggtatgt ggaagggttc tggtcagaat gtttgcccaa tgattgccac atcagcattc   7920
attttggact ctgtatggcc agtaggtctg gttcctggga gccctggaat aatgcagccc   7980
cttcgctaac taacatttcc atgatgtatg ctcaatgaca aggcagagga atgtgttgga   8040
tgagctcagg acctgcctcc ctggacactc ccatcccagg cctgtatatc tgttgaccag   8100
gaataagcca agcaagcagc ctactgtttg actgaatatg gatttggggg gtggtagaga   8160
aagggccggg gtggagggtt gggaggctca tttgtcatta tagatggggt cagacacact   8220
accaaaacag cagcagagat ctacaattga gttcacctaa aactcagtgt ggacacagga   8280
aaccctcttt taataactgt ccaatgggtt ttccagcctc agctctacag aaaacttgag   8340
ataacagtgg ccagtctgca gttagtttgg gttcggacaa taggcagagc tgggaaatgg   8400
agccaggggc gaaagcccag gtccacttta ggatcaggac gggagtggct ggtggggaag   8460
tgaggtgggt gtggggaggc aatagggagc tgggtcattt ggtatgggag agtcctctgg   8520
tggctagtcc cagaagtgca tgctttacga acatatgctt ctctccctag ggccaccttg   8580
agtgaaaccc tcccatgctg gaattgggcc ctttcagtga caacacacaa cagttttcaa   8640
tagataataa tcccaagggc tttactagca catgaaacac agggaaaacg tgtaaagttc   8700
acaagaaagt cgttccagtg tatcaaatct atcctgtttg ccaggtggat ataccagggt   8760
ctcctccacc tgtgcatggc tggtggtggg tccagtggct gttggataac tgatgtattg   8820
atggatcatt cgccttctga aagtgccaaa ctgattagtt attttgtgtg tctttttgtg   8880
taactagggt ttgaccttcc agggcagact gtgctggggc ggctgacccc ttggggagcc   8940
aagttattgc tcttaccacc accacttgcc cttgtcagtc ctccaccctc ttgggtttca   9000
gtgtcagcat gtagctgtct actcagatcc catccacatc atcaagtctg cagttttttc   9060
cttgcaaggc cttacaggga agatctttga catagaggat ataattttat tgacacattt   9120
tacttgcaga gcattcaccc gggctaacca gaaagccagc actctgctat aaacaaaaaa   9180
taatgcttca gggctaacat ggaatgtgtt aaaagattcc agcccattaa atgtccaggg   9240
gaggttttcc tgttttcctt tccctccatc tgggctttgt tctcaacaca ttcattcaac   9300
aaacatttat tctgcctcta ccaggtacag agcactctac tattctgctt ctctcctttt   9360
gctttagttt catgatcatc ctgaaccgct gtttccctat cttcatggtg ctggcatgga   9420
tctactctgt ctccatgact gtgaagagca tcgtcttgga gaaggagttg cgactgaagg   9480
agaccttgaa aaatcagggt gtctccaatg cagtgatttg gtgtacctgg ttcctggaca   9540
gcttctccat catgtcgatg agcatcttcc tcctgacgat attcatcatg gtaagccaaa   9600
tggagaaggc ccagaaaatc ttgaatactt tggttccttt ccccttttcct cctgttcatg   9660
tgcctggatt agtcatgtgg ccaccaagga gagcgtgaca tctagcttcc cagcccttcc   9720
ttttagccaa cgtgggagac actcaaagag acgaaatctc ctgaaggagc cactgtatca   9780
cagcatcctc ccatctccca cttcctgccc aggggtccat ggtccacaca gacttcccag   9840
tcccattccg tgaccatctg gagaagctgc tattagcaga gccctgcaca gggtgatagt   9900
gtaattaaag tggtcttctc tttccaaaca cagaaaaaat cagttcaggg agtgttttcc   9960
```

```
tgggcttaca attttaacta ctggctagag ttgaaatggg gaaagccttt tgccttttca  10020
gtagcagtag gggaggagat ctggattatt tacttatcat catcatggtc acctcctaca  10080
tggcttcacc aaaaaacatt ctgctgcctg aaaaagctcc aacacctctc tctcttttaa  10140
aggatggaat ttggagtcca tccttcctca gtgataagga gtttttatag ccacaggcag  10200
catctattgg tctgtcctct gcaaacttgc aactcctctg agagctagac ttggaaatga  10260
aacattattt tgcaatgcgc tgctatcctt catttttagc tcctccaccg tagatgatag  10320
tttgtacttg ttaaatgata aggatataaa tttaggtcat tttttatatt ttattgggtg  10380
gaatttggta taatttttag acttcaggct ttacaggctc ctgagatgga ctgattgagc  10440
ttgttctact tcttccccat catgatagga agtgctgtac cacactaggc agtgtgtgta  10500
gtgaccacag actggctgag tgtctcccat cccatgctgg cccatatctg gtacccacct  10560
gatccacaaa tgttccatca gatcctgttc aaacaacaca tctccagtta agccaaatct  10620
tgccctttct ccttacggta aaatgtacta aatctgaagg ttttgtcttt ttaatgttgc  10680
tccatgatcc agtgatctgt ggccttggtt atgctctgtg ctagagtcct aacaagacaa  10740
atgctaaggt agaggtcatt ctgctcaaac aacctgaccc cacctggatg tgggcttaca  10800
tttgcaaagg gcaccaaagt tctaagagat gaggggagga gctgagcccc ttgtccttat  10860
ctaggtttcc cttgttcttt cccatccctc agtctgcttc ttttcccagt accaacatgt  10920
ttgtgtcctc agaattaaag gagtaaaaat gtgtaaacat ctgactagca acagccatga  10980
gattttgcct ggcttgttga taagcagcat tgagatctgc cctcctaaga atgggccatt  11040
aggtcttcaa agcttttacg atgtgaggta aagaatgttc accaggagtt tcatgcacaa  11100
aagggtttct ctttgtggga actagaacat tgttccagtg atgacggaaa cagggctttc  11160
cataccaaaa cagggttttc ctttgaatga ctctcccacc tttcccttgt ctcttcctcc  11220
ccacctcaac aacacaggaa agaagctgga agcagggaca atgggaaggt ccctttgtta  11280
ctcgagctat tagaaacaaa aagaaaagtg gccatctgag gaagccacag ctggtgaaac  11340
tgtagggtca cagagtgaat tacacctctg gcttaagtca gtgaaaagtc ctagaagttt  11400
gtggtcctag aagtcctaaa agtttatggg actttgtttt gagcaaggat aagaaattga  11460
tttcaggctg ggcgtggtgg ctcacgcctg taaccctaat actttgggag acagaggcag  11520
gtggatcact tcaggtcagg agttccagag cagtctggcc aacatggcga aaccctgcct  11580
ctcctaaaaa tacaaaaatt agccaggtgc ggtggcacat gcctgtagtc ccggctactc  11640
aggagactga gcaaggagaa tcccttgaac ccaggaggtg gaggtctcag tgagctgata  11700
tcatatcact gcactctagc ctgggcaaca gagcaagact ctgtctaaaa aaataaataa  11760
ataaaaaaga aattgatttc attcttctga gaactgcaac aactacctta aagtgattcc  11820
atccaaaacc cacatgttca gccatggact tgcttttatg gagctgcgtg tgggtgacac  11880
acaaaatcag gagctctgag tcctaattta gacttttatt tagatttcct caaatttggg  11940
ttccagttaa gcgtgggtct cttctgtgcc ccgctcccct ttgccatttg ttttatctgt  12000
tcttcagtct gttctgtcag tacccacagg caggagagca gaaaggagaa atggcagcca  12060
cagcagacaa atggcacatt cgttccactc agctctcgca tgcccatcac agatacagct  12120
cattggtctc ttttctatga gaggaagcca gagctccagg gaactactgc caactgatca  12180
gaactcattt aggacatgga cctatttgtt cctttatgtt cctgggaaga gcacaggatg  12240
aattctatgt actcatttac gtgttcagag agtaaagtgc ctcataggat gcctccagca  12300
aaagataacc aagaaggtct aataccttttg acaatctcag tttatcctat agtgtaattg  12360
```

gatagcagtt cccctagcaa aagttgctag tttggtccta ttttctacat agccaaagtg 12420
attgattcat tggttaatgt gaaagttact gagtactgcc agcaggttct aggaaatata 12480
tttgtgtgat attcatggat ggggaggatc aatccacttc caagtgattt ggattaatta 12540
ctggtatttt cacctgtgtg ggtagcaaac ctcagaaaat caagtataga tgacggcata 12600
ggacaggcca ggccccaggc aaaatgttga agctcctctg gagttccctc ccatctccct 12660
cttttgtttt ccatatacct ggtttatcca gggccctgga gatgctccaa gaccccctac 12720
ccaggtcttc ctcccttgtc ccagctatat ttctccatat taccactctt ctcaccgagg 12780
atttgcttac ttaacacata ataaatacta ttaaaagaga aacttaggca cattaaaatg 12840
ttagagttga ttccagcaaa cagtgattca caggaggctc cagatcacaa gtggttcagg 12900
gccccactga ggggtaggga agcaagacaa agaaaaacaa agcaaatatt tgattggttc 12960
aagtggaaag tccctgatta caggttagtg ggcagtttgt gattagttaa gtttctctaa 13020
gttgggtttt ggtttgctga tgtaggaaca cagaatgctg gggccgtttc aacctaatgg 13080
tctcccaatt aattttttta acattactga tgactgttag gagtctaatg tgctactcct 13140
cccagggaaa atggcattcc taggattaaa ggaactcagc acatggagtg tgcgtagaaa 13200
tttagacact aactgcaggc tggtgggaga gagcccttta gggcagaatg agaaggcgtc 13260
cggccaaggg caggagttac tgacgcatgg cctcttggtt tcagcatgga agaatcctac 13320
attacagcga cccattcatc ctcttcctgt tcttgttggc tttctccact gccaccatca 13380
tgctgtgctt tctgctcagc accttcttct ccaaggccag tctggcagca gcctgtagtg 13440
gtgtcatcta tttcaccctc tacctgccac acatcctgtg cttcgcctgg caggaccgca 13500
tgaccgctga gctgaagaag gctgtggtga ggcccttggg ctggcccctg tcctacaaca 13560
cgtttccttg gaagggtccg tagcagtcct ggaggcccag cctgccctct gagggggtcc 13620
actttgcctt tgacctaagg ttaaaaagtt cacgtgaggc taaaatgtac aggggcaaaa 13680
gtgggagcag tcctcacccc gagcgatgca acagtgactc ctcaccacgc ctgcttgatt 13740
catctgccct ggaaagtcat taaaaaacca gttcaactca tgggtccctt tatttactca 13800
caagagagag ccagcagccc atttcactag ttttcctttc ctactctttg agaagaatca 13860
gaagggaggg agcttgccac tttactatct gtctaaagag atgtttccat taattaaagg 13920
tttttgtttt gcttcaaaaa aacttgaatt ggagtatttc cacaagtatc tttaacatgc 13980
tctaccaatg tttgcagaaa gaagtgcaga aatgagactg tccacagagt caggctcgct 14040
ggccaggaga ggactcccga agctgacttc tgatggcctg agaaacttcc tagttcacaa 14100
ttcccagacc cagacaaaga gcactgcacc cagctttc 14138

<210> SEQ ID NO 297
<211> LENGTH: 13638
<212> TYPE: DNA
<213> ORGANISM: Artificial Sequence
<220> FEATURE:
<223> OTHER INFORMATION: pCI-Neo-Rho-ABCA4-intron29-intron32 wild type

<400> SEQUENCE: 297
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240

-continued

```
atgaaatgtc acgggtgaca cagccccctt gtgctcagtc cctggcatct ctaggggtga    300
ggagcgtctg cctagcaggt tcccaccagg aagctggatt tgagtggatg gggcgctgga    360
atcgtgaggg gcagaagcag gcaaagggtc ggggcgaacc tcactaacgt gccagttcca    420
agcacactgt gggcagccct ggccctgact caagcctctt gccttccagt tccggaactg    480
catgctcacc accatctgct gcggcaagaa cccactgggt gacgatgagg cctctgctac    540
cgtgtccaag acggagacga gccaggtggc cccggcctaa gacctgccta ggactctgtg    600
gccgactata ggcgtctccc atcccctaca cctgtcgacc cgggcggccg cttcccttta    660
gtgagggtta atgcttcgag cagacatgat aagatacatt gatgagtttg gacaaaccac    720
aactagaatg cagtgaaaaa aatgctttat ttgtgaaatt tgtgatgcta ttgctttatt    780
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta atttttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
```

-continued

```
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
ttttataggt taatgtcatg ataataatgg tttcttagac gtcaggtggc acttttcggg   3180
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
```

-continued

```
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttccccact caatcctgct ctgctggtca cttccatgtc tctgaccagc   6360
actcccccaa cctctccttc cacacttgtg tgcagggaca ttcactacct cctaggaagc   6420
ccccacacca ctggacagct ctatatttct cagcatagaa gttctatgtt gagttgacag   6480
atgattcccc ataacttatt tgaaaggcct ctgagcaggg agggagggaa atagggttat   6540
gctattgtgt gattgggcct tgaatggcgt gagtgacaca gtggccagta ctttgtgata   6600
gttgtgagtc tggagaaggg agttagcgaa ggccattgac atccaccagg aatcctaaaa   6660
gttcaatata attttaactt ttctccctca gtctttttca aagctgtcaa taaggaccaa   6720
aacagactaa tttcaaattc ctcttctggt tgctgtgtct ctcaacagct agagctgcta   6780
ggaataaaaa gggagacaaa acgatccaca agctagagat ggttattccc cagccccaca   6840
cctagtcagt cacaaaaccc tagttttgat attgcttgag cagaaaccag cctccaagag   6900
aataagaaga aagggcctgg gtctaaagag gaggaggaaa gggttgggca caatttctta   6960
tgcctaggga tttgtcagca actttgaggc tgattatgga atatttttctt gtcttccatg  7020
agggagtacc cctgtggcaa ctcaacaccc tggaagactc cttctgtgtc cccaaacatc   7080
acccagctgt tccagaagca gaaatggaca caggtcaacc cttcaccatc ctgcaggtgc   7140
agcaccaggg agaagctcac catgctgcca gagtgccccg agggtgccgg gggcctcccg   7200
cccccccagg tacctgacct ccaaacaacg gggccccagg tctgcctgcc acagagggac   7260
taggggagtc cctggtatct cctgagtctc tcacaaacta acatttcaaa ctggcagttg   7320
agtaggggac taaaccaaac tccctgcacc ctctgggagg ggctccccac agggcgctgt   7380
```

-continued

```
ggctgccaac tggaggaagc cactcaccaa aagcttcatt ttccaccaga tacttcctat   7440
ttgatctagt agaaaaaatg tgtttaagca ctaaaaaaaa ttaagtcata tgtgctcatt   7500
atagaaaaat tagaaaacac aggtaagtca gaaggaaaaa aaatcatcgc ttggatataa   7560
acacagataa tgtttggttt gcagccaccc aaacagatta tattccaaat attgtcttaa   7620
aatctgattt actgcataat ttactaggaa catgcatcca tgtcaataaa tagacatctg   7680
catcactttt aatatctgta tattatccca ttgtttgaat ttcttttttt ttttttttt    7740
tttttttgag acagagtctc tctctgtcac ccaggttgga gtgcagcggt gtgatctcgg   7800
ctcactgcaa cctctgcctc ccaggttcaa ttcttgtgcc tcagcccccc cgagtagtgg   7860
ggattacagg catgcaccat catgcccgcc taattttttt ggtagtttta gtacagatgg   7920
ggttttacca tgttggccag gctggtgttg aactcctggc ctcaagtgat ctacccactt   7980
ctgcctacca gagtgctagg attacaagcg tcagccactg ctcctggcct aaagttactt   8040
taaattaact gatctcccat tattcgccac ttaggttttt tagttttcac cattataagc   8100
aatgctatga tgtacattca aatggaaatg tgtttacaca cttattaaca gtcttaatta   8160
agaagctctc catgtgctgt gtctctaaca tctgcaggta tgtacacaaa tacatgcaca   8220
gccagcatcc atcttttgca gggacattaa tgatcttggc tctgagcagc accctgtcct   8280
gggagttcta aagtccagaa cagattacag tgagcatctc ctgggggatt tagagacatc   8340
aaagaaggct gtgtccgtgg ttgataatgg gcctcccagc tgacttgcca gggctgggcc   8400
ttagacagcc ctgtccaatg atttgtcaat gaataaactg ttcccaaaca ggctatgcag   8460
ttcagtggga aagcacaggt atgggacacg gagagcccca ggtggactac ttgacctctc   8520
tgagccttaa ttttatcacc tgtgaattgg gaataactgc ttatttcata atattattat   8580
gaggatttaa tgaaatcatg tgggcaagga attatttaga attagattca actcaagtga   8640
tgacaacccc aaactaacag cagataaaac aagacacaac ttgtttctca ctcatctaaa   8700
agtctacgtg ggtggtgcac gatgttctat tctctttctc ctccacacta aacaggcctc   8760
agcctcatca gccaataagg caggagctgc cttccaggca gcggaatgga agaaggatga   8820
agcaaaacag agggcagagt gtgcacatgt gctatgttta gggaaggttt tctgaagttc   8880
ccacatagta cttccactta caaacccaac aaaaaaggct atggctaagg cagcagggag   8940
gagcaaataa tgggagcaac tagattttgc cacagcacct atcacagtct ggtttataaa   9000
tggttctagg ccaagaacac ccgatccctg ctctttttta tattctaaag catgtatctt   9060
tatatttctc aagcaatatt ttctctcttt gaatcacagc tcatctgctg catcataggg   9120
atcccaaaag aaggacccaa ggaacttgtc tcagtcctct gtgccccaag aggaagcttt   9180
gcttgtttgc tttgctgtca atgctgaggg ctcctgtggc tgcctccact caaaaccctc   9240
cagcatcagg acgtcaaggc tgtgatactg taccctgagc tcttggccag ggcgagggag   9300
gggaggccaa gcctacctac atggtgtttc atttcctaaa cgaaccctta cttccacgcg   9360
gtctgtccag cttagaaact tattttcagt agtgttggtc cttggtccct ggacaaaatg   9420
taacagccaa agtcctagaa aaaggcaagc cagttcctgc cattttcttt cacttctgca   9480
tttcctcact attatacgtg ccttccattg gagcaaaact gaatgccacg catatgcaca   9540
ggagctgtgc gcgctctgtc tctctcactc actctttttc tctctctctc tttctctctc   9600
aatctctctg tctctatcta tctcttactc tttatctctc actctctcac tctttctcac   9660
tctttctctc aatctctttc tcattctctc tctatctttc tctctctctc tctttctcac   9720
```

-continued acacacacac tcacaaaccc acactcttat tcacatctgc tcaccctagc cactcaaaca 9780
caatccctca ttcagcctgg aataagtcca gagggcgtgg gcctgattca gagacaatca 9840
gttgttctca tctgggaaat ggggcaatgt ggtcatctct agggaccctc cctgctctaa 9900
cattctttga atgtggtggg tcctgaggtg gaagcactct gtccctgact tctagtatat 9960
gtggagatag ggttacacaa atattttatt gggcagaact tttataaaac aatttatcat 10020
aagctatcgc agccagcagc aatttttcca acctggattc caccagggga gcttggccgg 10080
tgtctgagtg ccactttcag cttgagaagc aggtgactca gtgaaaagag caaggaggag 10140
acagaggcag attcagttcc taggccctgg gccacccacc tgcaagtttg cagcccagtc 10200
agtgcaagtc agctaactgt tctgaacctc agtttctctg tctgtaaatt aagctaaaaa 10260
ttcttctttc aaagagtgtc aggatgaagt gagatcgtgt atgtagggca tttaacatag 10320
tgcccgacac acagggagca ttcggtaggt gccagctctc ctcctggcag gagagagaga 10380
aacaaggtga aaagagtgaa ttaaagaaga ggaaagtcaa atgggaaaac agggggagga 10440
gatagaaagt gtatgaaaag gaaagaatgg tgcgcaataa cggcggtgta atgccaccaa 10500
aatcccctca actacttctg ggcagcaccc ttgacagagt gaatgctttt atgagaatgt 10560
aagcggaatg tgttcccaga tttgcagtaa tattgccacc tggtggacaa acccatgcac 10620
ctttgaattt tccaaaatat ttcgatgaac tagcttccag tcctagatgt attttgaaag 10680
tgatttgtaa attgtaagga actattcaaa ttctttcatt aatgtcacaa atcaactgtg 10740
tcatctgtat gccacccact attctgggtg ctggggacac aacagctcac aaatcaggca 10800
aagtccctgc tctcaccaaa atgatatcct acgggggatt acagatacaa atacgtaaac 10860
agatccatcg ggaggaaact ctcagatgga aatgagagct atgaagataa cacaacagta 10920
catgacaata cagagtgact ggaaccagga acatttctcc gaggaataaa atttgaagcg 10980
agccatgaga gggtctacag gtagagttcc caggcagagt gaacagccaa gcacaaagct 11040
gcaccaggag agagaggtgc tcgccgagag acagggaggg gagtgtggca ggtgagctca 11100
gagaggggca gggccacaca catcggccac atgggccttg gtagtgagtc gagatttgat 11160
cccagggttt attggagtgg ataagtaagc aaggtgactg aggtgctcgg gtttacattt 11220
ttatagttca agctggctgc tgggtggaaa acggaagttg gcagaccaag gacagaatca 11280
ggcagaccca tgtggaagtt tctctagtgg tctaggtggt ggcttgggta gcgtggcagt 11340
attggagctg gagaaacgca gatggattgg agatttgttt tggagtgacg ccattctgtc 11400
ttgtcaatgg attggcgaaa aaagaggcat caaagatgag ttacacatca ttgaagtgag 11460
aactagggag atgccagtac tttatttagt attttctcag cagctcaatc cataaataat 11520
ttttggaaga caacaagcag tttcacaaac tacttataag tcctcaagtt ccaaggtaat 11580
taacgtgggt gtctcattgc ctcagagaac acagcgcagc acggaaattc tacaagacct 11640
gacggacagg aacatctccg acttcttggt aaaaacgtat cctgctctta taagaagcag 11700
gtaagaagaa atccttttat gctttttatc ctggctccct gtagaagata ttaactaggg 11760
acagaagata attttctctc tcaatttatg tatgatcagg gcagtagatt tttttctttt 11820
ttatctgatt tgagggcccc attcaacata aaaagcaatt gaggcacata caagtaaaat 11880
gtaacttaag attaattctt tttttgttgt ttgtttgttt gtttttacat ttagggcaag 11940
cagtcttaaa ttttaaccca cgtattatta aaagttatat cagaagacca tagaagttat 12000
tcaaaaatgc agccacatat tttaactagt taaaagagag agtaaaaatt tggagggagg 12060
tggaggagta taggggaaaa ggtagaagaa aaagagaaaa taagtaagtg gcaaaaaaga 12120

```
gaaaggaaaa agatagggtg ggaaagaggc agcgggacag tgtctgagtc cagcacacgc  12180

cagggcgagc caggtcaact gcagctgtca tattctaact gtgaattatc atctttgatc  12240

actgcccttt gagatgccaa tgaacttttc aagaaatatc tagttctctt ggctctccag  12300

ctgttcttat cagccccatc caggatggaa cagctttggc agcccgtatc agaacaagca  12360

gcttgacagg ggcatgccat gccaggagag aggatcctaa ggaagcgtgg tccagtccgc  12420

acaggctctg gggctttaag ataaaacctc ctgtctaact ttagtaggac tttctgttgc  12480

ttcacctgcc agagccctga acgagggata aattgactta attaactaga acacactgca  12540

aatggtgaaa gcatttagca aaacaaagaa tgccatccaa gccccaaaat aaaagcagaa  12600

taaatagaat gcaataaaca gcaaccatcc caaactgagt tctcagcagc aaatctccag  12660

tatgaaattt tggattttgt gcgtgtgtgc ttaaaggtgg atgacaatga cagttcatgg  12720

gattgagctc tggggtccag agttggcatc tgttcatttc ccattttgtc attttaccct  12780

tgattgactg aatgtcagtg ccttaacttt gggctgtgga gtgagtcgga actcccccga  12840

ggtgtgcagg tggttgttag agtctcattt ttgcagggtg gaagacagga gggctgcagc  12900

cttcattcca cactgacatg gtcattgccg tgtgttctgg gtccagatca ggcatattga  12960

cctgacatat gacctgacaa caggaccact cagaaagtcc agcatgcggg atatgatttg  13020

gagagccagt gggggaaatc ataggtcctt tctctgcatg tgtattcagg caatgtccca  13080

gggctgggcg gcttccgcat tgcttggata tcggaaaatg caaaaatgcc cctgaagact  13140

gagacttcag tcttcaaaat gaatgtttgg gaaagaaagt taacggcact gctgtacttg  13200

tggtattcat tgcattattt tattttggct ttcagcttaa agagcaaatt ctgggtcaat  13260

gaacagaggt aagaaactat ttttatcaga attaaaatct cagattgatt cattgttgaa  13320

ataattgcac acttttaaaa ggcacacctc acagccatga ggaggggctg ttctgtaggt  13380

gctcaggaag tcacaagaca cgtcctgaag aatatgtggc tagggacatc ccagactcag  13440

aagacactca gtggtgcctc ttcttggagg acataagtgg gggtggcatt ccctgatgtg  13500

gcgtttcaga gcattctcac ccaaaaaaag cttctaaaac ctccaagtat ataacagttt  13560

ataatactcc aacaagaggg ccttgtagcc taaacccggg acactccttg gcccattcct  13620

tttaagcacc cagctttc                                                13638
```

<210> SEQ ID NO 298
<211> LENGTH: 13638
<212> TYPE: DNA
<213> ORGANISM: Artificial Sequence
<220> FEATURE:
<223> OTHER INFORMATION: pCI-Neo-Rho-ABCA4-intron29-intron32
c.4539+1100G

<400> SEQUENCE: 298

```
ttgtacaaag tggtgatctt gtacaaagtg gtgatgagag gtacctccga ggggtaaaca     60

gttgggtaaa cagtctctga agtcagctct gccattttct agctgtatgg ccctgggcaa    120

gtcaatttcc ttctctgtgc tttggtttcc tcatccatag aaaggtagaa agggcaaaac    180

accaaactct tggattacaa gagataattt acagaacacc cttggcacac agagggcacc    240

atgaaatgtc acgggtgaca cagccccctt gtgctcagtc cctggcatct ctaggggtga    300

ggagcgtctg cctagcaggt tcccaccagg aagctggatt tgagtggatg gggcgctgga    360

atcgtgaggg gcagaagcag gcaaagggtc ggggcgaacc tcactaacgt gccagttcca    420

agcacactgt gggcagccct ggccctgact caagcctctt gccttccagt tccggaactg    480
```

-continued

```
catgctcacc accatctgct gcggcaagaa cccactgggt gacgatgagg cctctgctac    540
cgtgtccaag acggagacga gccaggtggc cccggcctaa gacctgccta ggactctgtg    600
gccgactata ggcgtctccc atcccctaca cctgtcgacc cgggcggccg cttcccttta    660
gtgagggtta atgcttcgag cagacatgat aagatacatt gatgagtttg gacaaaccac    720
aactagaatg cagtgaaaaa aatgctttat ttgtgaaatt tgtgatgcta ttgctttatt    780
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta attttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
```

-continued

```
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
ttttataggt taatgtcatg ataataatgg tttcttagac gtcaggtggc acttttcggg   3180
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
```

tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460
tacttggcag tacatctacg tattagtcat cgctattacc atggtgatgc ggttttggca 5520
gtacaccaat gggcgtggat agcggtttga ctcacgggga tttccaagtc tccaccccat 5580
tgacgtcaat gggagtttgt tttggcacca aaatcaacgg gactttccaa aatgtcgtaa 5640
caactgcgat cgcccgcccc gttgacgcaa atgggcggta ggcgtgtacg gtgggaggtc 5700
tatataagca gagctcgttt agtgaaccgt cagatcacta gaagctttat tgcggtagtt 5760
tatcacagtt aaattgctaa cgcagtcagt gcttctgaca caacagtctc gaacttaagc 5820
tgcagtgact ctcttaaggt agccttgcag aagttggtcg tgaggcactg ggcaggtaag 5880
tatcaaggtt acaagacagg tttaaggaga ccaatagaaa ctgggcttgt cgagacagag 5940
aagactcttg cgtttctgat aggcacctat tggtcttact gacatccact ttgcctttct 6000
ctccacaggt gtccactccc agttcaatta cagctcttaa ggctagagta cttaatacga 6060
ctcactatag gctagcctcg agaattccgg aggtcaacaa cgagtctttt gtcatctaca 6120
tgttcgtggt ccacttcacc atccccatga ttatcatctt tttctgctat gggcagctcg 6180
tcttcaccgt caaggaggta cgggccgggg ggtgggcggc ctcacggctc tgagggtcca 6240
gcccccagca tgcatctgcg gctcctgctc cctggaggag ccatatcaca agtttgtaca 6300
aaaaagcagg cttccccact caatcctgct ctgctggtca cttccatgtc tctgaccagc 6360
actcccccaa cctctccttc cacacttgtg tgcagggaca ttcactacct cctaggaagc 6420
ccccacacca ctggacagct ctatatttct cagcatagaa gttctatgtt gagttgacag 6480
atgattcccc ataacttatt tgaaaggcct ctgagcaggg agggagggaa atagggttat 6540
gctattgtgt gattgggcct tgaatggcgt gagtgacaca gtggccagta ctttgtgata 6600
gttgtgagtc tggagaaggg agttagcgaa ggccattgac atccaccagg aatcctaaaa 6660
gttcaatata attttaactt ttctccctca gtctttttca aagctgtcaa taaggaccaa 6720
aacagactaa tttcaaattc ctcttctggt tgctgtgtct ctcaacagct agagctgcta 6780
ggaataaaaa gggagacaaa acgatccaca agctagagat ggttattccc cagccccaca 6840
cctagtcagt cacaaaaccc tagttttgat attgcttgag cagaaaccag cctccaagag 6900
aataagaaga aagggcctgg gtctaaagag gaggaggaaa gggttgggca caatttctta 6960
tgcctaggga tttgtcagca actttgaggc tgattatgga atattttctt gtcttccatg 7020
agggagtacc cctgtggcaa ctcaacaccc tggaagactc cttctgtgtc cccaaacatc 7080
acccagctgt tccagaagca gaaatggaca caggtcaacc cttcaccatc ctgcaggtgc 7140
agcaccaggg agaagctcac catgctgcca gagtgccccg agggtgccgg gggcctcccg 7200 ccccccagg tacctgacct ccaaacaacg gggccccagg tctgcctgcc acagagggac 7260
taggggagtc cctggtatct cctgagtctc tcacaaacta acatttcaaa ctggcagttg 7320
agtaggggac taaaccaaac tccctgcacc ctctgggagg ggctccccac agggcgctgt 7380
ggctgccaac tggaggaagc cactcaccaa aagcttcatt ttccaccaga tacttcctat 7440
ttgatctagt agaaaaaatg tgtttaagca ctaaaaaaaa ttaagtcata tgtgctcatt 7500
atagaaaaat tagaaaacac aggtaagtca gaaggaaaaa aaatcatcgc ttggatataa 7560

-continued acacagataa tgtttggttt gcagccaccc aaacagatta tattccaaat attgtcttaa 7620
aatctgattt actgcataat ttactaggaa catgcatcca tgtcaataaa tagacatctg 7680
catcactttt aatatctgta tattatccca ttgtttgaat ttcttttttt tttttttttt 7740
tttttttgag acagagtctc tctctgtcac ccaggttgga gtgcagcggt gtgatctcgg 7800
ctcactgcaa cctctgcctc ccaggttcaa ttcttgtgcc tcagcccccc cgagtagtgg 7860
ggattacagg catgcaccat catgcccgcc taattttttt ggtagtttta gtacagatgg 7920
ggttttacca tgttggccag gctggtgttg aactcctggc ctcaagtgat ctacccactt 7980
ctgcctacca gagtgctagg attacaagcg tcagccactg ctcctggcct aaagttactt 8040
taaattaact gatctcccat tattcgccac ttaggttttt tagttttcac cattataagc 8100
aatgctatga tgtacattca aatggaaatg tgtttacaca cttattaaca gtcttaatta 8160
agaagctctc catgtgctgt gtctctaaca tctgcaggta tgtacacaaa tacatgcaca 8220
gccagcatcc atcttttgca gggacattaa tgatcttggc tctgagcagc accctgtcct 8280
gggagttcta aagtccagaa cagattacgg tgagcatctc ctgggggatt tagagacatc 8340
aaagaaggct gtgtccgtgg ttgataatgg gcctcccagc tgacttgcca gggctgggcc 8400
ttagacagcc ctgtccaatg atttgtcaat gaataaactg ttcccaaaca ggctatgcag 8460
ttcagtggga aagcacaggt atgggacacg gagagcccca ggtggactac ttgacctctc 8520
tgagccttaa ttttatcacc tgtgaattgg gaataactgc ttatttcata atattattat 8580
gaggatttaa tgaaatcatg tgggcaagga attatttaga attagattca actcaagtga 8640
tgacaacccc aaactaacag cagataaaac aagacacaac ttgtttctca ctcatctaaa 8700
agtctacgtg ggtggtgcac gatgttctat tctctttctc ctccacacta aacaggcctc 8760
agcctcatca gccaataagg caggagctgc cttccaggca gcggaatgga agaaggatga 8820
agcaaaacag agggcagagt gtgcacatgt gctatgttta gggaaggttt tctgaagttc 8880
ccacatagta cttccactta caaacccaac aaaaaaggct atggctaagg cagcagggag 8940
gagcaaataa tgggagcaac tagattttgc cacagcacct atcacagtct ggtttataaa 9000
tggttctagg ccaagaacac ccgatccctg ctctttttta tattctaaag catgtatctt 9060
tatatttctc aagcaatatt ttctctcttt gaatcacagc tcatctgctg catcataggg 9120
atcccaaaag aaggacccaa ggaacttgtc tcagtcctct gtgccccaag aggaagcttt 9180
gcttgtttgc tttgctgtca atgctgaggg ctcctgtggc tgcctccact caaaaccctc 9240
cagcatcagg acgtcaaggc tgtgatactg taccctgagc tcttggccag ggcgagggag 9300
gggaggccaa gcctacctac atggtgtttc atttcctaaa cgaaccctta cttccacgcg 9360
gtctgtccag cttagaaact tattttcagt agtgttggtc cttggtccct ggacaaaatg 9420
taacagccaa agtcctagaa aaaggcaagc cagttcctgc cattttcttt cacttctgca 9480
tttcctcact attatacgtg ccttccattg gagcaaaact gaatgccacg catatgcaca 9540
ggagctgtgc gcgctctgtc tctctcactc actctttttc tctctctctc tttctctctc 9600
aatctctctg tctctatcta tctcttactc tttatctctc actctctcac tctttctcac 9660
tctttctctc aatctctttc tcattctctc tctatctttc tctctctctc tctttctcac 9720
acacacacac tcacaaaccc acactcttat tcacatctgc tcaccctagc cactcaaaca 9780
caatccctca ttcagcctgg aataagtcca gagggcgtgg gcctgattca gagacaatca 9840
gttgttctca tctgggaaat ggggcaatgt ggtcatctct agggaccctc cctgctctaa 9900
cattctttga atgtggtggg tcctgaggtg gaagcactct gtccctgact tctagtatat 9960

```
gtggagatag ggttacacaa atattttatt gggcagaact tttataaaac aatttatcat  10020
aagctatcgc agccagcagc aatttttcca acctggattc caccagggga gcttggccgg  10080
tgtctgagtg ccactttcag cttgagaagc aggtgactca gtgaaaagag caaggaggag  10140
acagaggcag attcagttcc taggccctgg gccacccacc tgcaagtttg cagcccagtc  10200
agtgcaagtc agctaactgt tctgaacctc agtttctctg tctgtaaatt aagctaaaaa  10260
ttcttctttc aaagagtgtc aggatgaagt gagatcgtgt atgtagggca tttaacatag  10320
tgcccgacac acagggagca ttcggtaggt gccagctctc ctcctggcag gagagagaga  10380
aacaaggtga aaagagtgaa ttaaagaaga ggaaagtcaa atgggaaaac agggggagga  10440
gatagaaagt gtatgaaaag gaaagaatgg tgcgcaataa cggcggtgta atgccaccaa  10500
aatcccctca actacttctg ggcagcaccc ttgacagagt gaatgctttt atgagaatgt  10560
aagcggaatg tgttcccaga tttgcagtaa tattgccacc tggtggacaa acccatgcac  10620
ctttgaattt tccaaaatat ttcgatgaac tagcttccag tcctagatgt attttgaaag  10680
tgatttgtaa attgtaagga actattcaaa ttctttcatt aatgtcacaa atcaactgtg  10740
tcatctgtat gccacccact attctgggtg ctggggacac aacagctcac aaatcaggca  10800
aagtccctgc tctcaccaaa atgatatcct acgggggatt acagatacaa atacgtaaac  10860
agatccatcg ggaggaaact ctcagatgga aatgagagct atgaagataa cacaacagta  10920
catgacaata cagagtgact ggaaccagga acatttctcc gaggaataaa atttgaagcg  10980
agccatgaga gggtctacag gtagagttcc caggcagagt gaacagccaa gcacaaagct  11040
gcaccaggag agagaggtgc tcgccgagag acagggaggg gagtgtggca ggtgagctca  11100
gagaggggca gggccacaca catcggccac atgggccttg gtagtgagtc gagatttgat  11160
cccagggttt attggagtgg ataagtaagc aaggtgactg aggtgctcgg gtttacattt  11220
ttatagttca agctggctgc tgggtggaaa acggaagttg gcagaccaag gacagaatca  11280
ggcagaccca tgtggaagtt tctctagtgg tctaggtggt ggcttgggta gcgtggcagt  11340
attggagctg gagaaacgca gatggattgg agatttgttt tggagtgacg ccattctgtc  11400
ttgtcaatgg attggcgaaa aaagaggcat caaagatgag ttacacatca ttgaagtgag  11460
aactagggag atgccagtac tttatttagt attttctcag cagctcaatc cataaataat  11520
ttttggaaga caacaagcag tttcacaaac tacttataag tcctcaagtt ccaaggtaat  11580
taacgtgggt gtctcattgc ctcagagaac acagcgcagc acggaaattc tacaagacct  11640
gacggacagg aacatctccg acttcttggt aaaaacgtat cctgctctta taagaagcag  11700
gtaagaagaa atccttttat gctttttatc ctggctccct gtagaagata ttaactaggg  11760
acagaagata attttctctc tcaatttatg tatgatcagg gcagtagatt tttttctttt  11820
ttatctgatt tgagggcccc attcaacata aaaagcaatt gaggcacata caagtaaaat  11880
gtaacttaag attaattctt tttttgttgt ttgtttgttt gtttttacat ttagggcaag  11940
cagtcttaaa ttttaaccca cgtattatta aaagttatat cagaagacca tagaagttat  12000
tcaaaaatgc agccacatat tttaactagt taaaagagag agtaaaaatt tggagggagg  12060
tggaggagta taggggaaaa ggtagaagaa aaagagaaaa taagtaagtg gcaaaaaaga  12120
gaaaggaaaa agatagggtg ggaaagaggc agcgggacag tgtctgagtc cagcacacgc  12180
cagggcgagc caggtcaact gcagctgtca tattctaact gtgaattatc atctttgatc  12240
actgcccttt gagatgccaa tgaacttttc aagaaatatc tagttctctt ggctctccag  12300
```

```
ctgttcttat cagccccatc caggatggaa cagctttggc agcccgtatc agaacaagca  12360

gcttgacagg ggcatgccat gccaggagag aggatcctaa ggaagcgtgg tccagtccgc  12420

acaggctctg gggctttaag ataaaacctc ctgtctaact ttagtaggac tttctgttgc  12480

ttcacctgcc agagccctga acgagggata aattgactta attaactaga acacactgca  12540

aatggtgaaa gcatttagca aaacaaagaa tgccatccaa gccccaaaat aaaagcagaa  12600

taaatagaat gcaataaaca gcaaccatcc caaactgagt tctcagcagc aaatctccag  12660

tatgaaattt tggattttgt gcgtgtgtgc ttaaaggtgg atgacaatga cagttcatgg  12720

gattgagctc tggggtccag agttggcatc tgttcatttc ccattttgtc attttaccct  12780

tgattgactg aatgtcagtg ccttaacttt gggctgtgga gtgagtcgga actcccccga  12840

ggtgtgcagg tggttgttag agtctcattt ttgcagggtg gaagacagga gggctgcagc  12900

cttcattcca cactgacatg gtcattgccg tgtgttctgg gtccagatca ggcatattga  12960

cctgacatat gacctgacaa caggaccact cagaaagtcc agcatgcggg atatgatttg  13020

gagagccagt gggggaaatc ataggtcctt tctctgcatg tgtattcagg caatgtccca  13080

gggctgggcg gcttccgcat tgcttggata tcggaaaatg caaaaatgcc cctgaagact  13140

gagacttcag tcttcaaaat gaatgtttgg gaaagaaagt taacggcact gctgtacttg  13200

tggtattcat tgcattattt tattttggct ttcagcttaa agagcaaatt ctgggtcaat  13260

gaacagaggt aagaaactat ttttatcaga attaaaatct cagattgatt cattgttgaa  13320

ataattgcac acttttaaaa ggcacacctc acagccatga ggaggggctg ttctgtaggt  13380

gctcaggaag tcacaagaca cgtcctgaag aatatgtggc tagggacatc ccagactcag  13440

aagacactca gtggtgcctc ttcttggagg acataagtgg gggtggcatt ccctgatgtg  13500

gcgtttcaga gcattctcac ccaaaaaaag cttctaaaac ctccaagtat ataacagttt  13560

ataatactcc aacaagaggg ccttgtagcc taaacccggg acactccttg gcccattcct  13620

tttaagcacc cagctttc                                                13638
```

<210> SEQ ID NO 299
<211> LENGTH: 13638
<212> TYPE: DNA
<213> ORGANISM: Artificial Sequence
<220> FEATURE:
<223> OTHER INFORMATION: pCI-Neo-Rho-ABCA4-intron29-intron32
c.4539+1106T

<400> SEQUENCE: 299

```
ttgtacaaag tggtgatctt gtacaaagtg gtgatgagag gtacctccga ggggtaaaca     60

gttgggtaaa cagtctctga agtcagctct gccattttct agctgtatgg ccctgggcaa    120

gtcaatttcc ttctctgtgc tttggtttcc tcatccatag aaaggtagaa agggcaaaac    180

accaaactct tggattacaa gagataattt acagaacacc cttggcacac agagggcacc    240

atgaaatgtc acgggtgaca cagccccctt gtgctcagtc cctggcatct ctaggggtga    300

ggagcgtctg cctagcaggt tcccaccagg aagctggatt tgagtggatg gggcgctgga    360

atcgtgaggg gcagaagcag gcaaagggtc ggggcgaacc tcactaacgt gccagttcca    420

agcacactgt gggcagccct ggccctgact caagcctctt gccttccagt tccggaactg    480

catgctcacc accatctgct gcggcaagaa cccactgggt gacgatgagg cctctgctac    540

cgtgtccaag acggagacga gccaggtggc ccccggccta gacctgccta ggactctgtg    600

gccgactata ggcgtctccc atcccctaca cctgtcgacc cgggcggccg cttcccttta    660
```

```
gtgagggtta atgcttcgag cagacatgat aagatacatt gatgagtttg gacaaaccac    720
aactagaatg cagtgaaaaa aatgctttat ttgtgaaatt tgtgatgcta ttgctttatt    780
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta atttttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
```

agaggttttc accgtcatca ccgaaacgcg cgagacgaaa gggcctcgtg atacgcctat 3120
ttttataggt taatgtcatg ataataatgg tttcttagac gtcaggtggc acttttcggg 3180
gaaatgtgcg cggaacccct atttgtttat ttttctaaat acattcaaat atgtatccgc 3240
tcatgagaca ataaccctga taaatgcttc aataatattg aaaaaggaag agtatgagta 3300
ttcaacattt ccgtgtcgcc cttattccct tttttgcggc attttgcctt cctgtttttg 3360
ctcacccaga aacgctggtg aaagtaaaag atgctgaaga tcagttgggt gcacgagtgg 3420
gttacatcga actggatctc aacagcggta agatccttga gagttttcgc cccgaagaac 3480
gttttccaat gatgagcact tttaaagttc tgctatgtgg cgcggtatta tcccgtattg 3540
acgccgggca agagcaactc ggtcgccgca tacactattc tcagaatgac ttggttgagt 3600
actcaccagt cacagaaaag catcttacgg atggcatgac agtaagagaa ttatgcagtg 3660
ctgccataac catgagtgat aacactgcgg ccaacttact tctgacaacg atcggaggac 3720
cgaaggagct aaccgctttt ttgcacaaca tgggggatca tgtaactcgc cttgatcgtt 3780
gggaaccgga gctgaatgaa gccataccaa acgacgagcg tgacaccacg atgcctgtag 3840
caatggcaac aacgttgcgc aaactattaa ctggcgaact acttactcta gcttcccggc 3900
aacaattaat agactggatg gaggcggata aagttgcagg accacttctg cgctcggccc 3960
ttccggctgg ctggtttatt gctgataaat ctggagccgg tgagcgtggg tctcgcggta 4020
tcattgcagc actggggcca gatggtaagc cctcccgtat cgtagttatc tacacgacgg 4080
ggagtcaggc aactatggat gaacgaaata gacagatcgc tgagataggt gcctcactga 4140
ttaagcattg gtaactgtca gaccaagttt actcatatat actttagatt gatttaaaac 4200
ttcattttta atttaaaagg atctaggtga agatcctttt tgataatctc atgaccaaaa 4260
tcccttaacg tgagttttcg ttccactgag cgtcagaccc cgtagaaaag atcaaaggat 4320
cttcttgaga tccttttttt ctgcgcgtaa tctgctgctt gcaaacaaaa aaaccaccgc 4380
taccagcggt ggtttgtttg ccggatcaag agctaccaac tctttttccg aaggtaactg 4440
gcttcagcag agcgcagata ccaaatactg ttcttctagt gtagccgtag ttaggccacc 4500
acttcaagaa ctctgtagca ccgcctacat acctcgctct gctaatcctg ttaccagtgg 4560
ctgctgccag tggcgataag tcgtgtctta ccgggttgga ctcaagacga tagttaccgg 4620
ataaggcgca gcggtcgggc tgaacggggg gttcgtgcac acagcccagc ttggagcgaa 4680
cgacctacac cgaactgaga tacctacagc gtgagctatg agaaagcgcc acgcttcccg 4740
aagggagaaa ggcggacagg tatccggtaa gcggcagggt cggaacagga gagcgcacga 4800
gggagcttcc agggggaaac gcctggtatc tttatagtcc tgtcgggttt cgccacctct 4860
gacttgagcg tcgatttttg tgatgctcgt caggggggcg gagcctatgg aaaaacgcca 4920
gcaacgcggc ctttttacgg ttcctggcct tttgctggcc ttttgctcac atggctcgac 4980
agatcttcaa tattggccat tagccatatt attcattggt tatatagcat aaatcaatat 5040
tggctattgg ccattgcata cgttgtatct atatcataat atgtacattt atattggctc 5100
atgtccaata tgaccgccat gttggcattg attattgact agttattaat agtaatcaat 5160
tacggggtca ttagttcata gcccatatat ggagttccgc gttacataac ttacggtaaa 5220
tggcccgcct ggctgaccgc ccaacgaccc ccgcccattg acgtcaataa tgacgtatgt 5280
tcccatagta acgccaatag ggactttcca ttgacgtcaa tgggtggagt atttacggta 5340
aactgcccac ttggcagtac atcaagtgta tcatatgcca agtccgcccc ctattgacgt 5400
caatgacggt aaatggcccg cctggcatta tgcccagtac atgaccttac gggactttcc 5460
tacttggcag tacatctacg tattagtcat cgctattacc atggtgatgc ggttttggca 5520
gtacaccaat gggcgtggat agcggtttga ctcacgggga tttccaagtc tccaccccat 5580
tgacgtcaat gggagtttgt tttggcacca aaatcaacgg gactttccaa aatgtcgtaa 5640
caactgcgat cgcccgcccc gttgacgcaa atgggcggta ggcgtgtacg gtgggaggtc 5700
tatataagca gagctcgttt agtgaaccgt cagatcacta gaagctttat tgcggtagtt 5760
tatcacagtt aaattgctaa cgcagtcagt gcttctgaca caacagtctc gaacttaagc 5820
tgcagtgact ctcttaaggt agccttgcag aagttggtcg tgaggcactg ggcaggtaag 5880
tatcaaggtt acaagacagg tttaaggaga ccaatagaaa ctgggcttgt cgagacagag 5940
aagactcttg cgtttctgat aggcacctat tggtcttact gacatccact ttgcctttct 6000
ctccacaggt gtccactccc agttcaatta cagctcttaa ggctagagta cttaatacga 6060
ctcactatag gctagcctcg agaattccgg aggtcaacaa cgagtctttt gtcatctaca 6120
tgttcgtggt ccacttcacc atccccatga ttatcatctt tttctgctat gggcagctcg 6180
tcttcaccgt caaggaggta cgggccgggg ggtgggcggc ctcacggctc tgagggtcca 6240
gcccccagca tgcatctgcg gctcctgctc cctggaggag ccatatcaca agtttgtaca 6300
aaaaagcagg cttccccact caatcctgct ctgctggtca cttccatgtc tctgaccagc 6360
actcccccaa cctctccttc cacacttgtg tgcagggaca ttcactacct cctaggaagc 6420
ccccacacca ctggacagct ctatatttct cagcatagaa gttctatgtt gagttgacag 6480
atgattcccc ataacttatt tgaaaggcct ctgagcaggg agggagggaa atagggttat 6540
gctattgtgt gattgggcct tgaatggcgt gagtgacaca gtggccagta ctttgtgata 6600
gttgtgagtc tggagaaggg agttagcgaa ggccattgac atccaccagg aatcctaaaa 6660
gttcaatata attttaactt ttctccctca gtctttttca aagctgtcaa taaggaccaa 6720
aacagactaa tttcaaattc ctcttctggt tgctgtgtct ctcaacagct agagctgcta 6780
ggaataaaaa gggagacaaa acgatccaca agctagagat ggttattccc cagccccaca 6840
cctagtcagt cacaaaaccc tagttttgat attgcttgag cagaaaccag cctccaagag 6900
aataagaaga aagggcctgg gtctaaagag gaggaggaaa gggttgggca caatttctta 6960
tgcctaggga tttgtcagca actttgaggc tgattatgga atatttttctt gtcttccatg 7020
agggagtacc cctgtggcaa ctcaacaccc tggaagactc cttctgtgtc cccaaacatc 7080
acccagctgt tccagaagca gaaatggaca caggtcaacc cttcaccatc ctgcaggtgc 7140
agcaccaggg agaagctcac catgctgcca gagtgccccg agggtgccgg gggcctcccg 7200
cccccccagg tacctgacct ccaaacaacg gggccccagg tctgcctgcc acagagggac 7260
taggggagtc cctggtatct cctgagtctc tcacaaacta acatttcaaa ctggcagttg 7320
agtaggggac taaaccaaac tccctgcacc ctctgggagg ggctccccac agggcgctgt 7380
ggctgccaac tggaggaagc cactcaccaa aagcttcatt ttccaccaga tacttcctat 7440
ttgatctagt agaaaaaatg tgtttaagca ctaaaaaaaa ttaagtcata tgtgctcatt 7500
atagaaaaat tagaaaacac aggtaagtca gaaggaaaaa aaatcatcgc ttggatataa 7560
acacagataa tgtttggttt gcagccaccc aaacagatta tattccaaat attgtcttaa 7620
aatctgattt actgcataat ttactaggaa catgcatcca tgtcaataaa tagacatctg 7680
catcactttt aatatctgta tattatccca ttgtttgaat ttcttttttt ttttttttt 7740
tttttttgag acagagtctc tctctgtcac ccaggttgga gtgcagcggt gtgatctcgg 7800
ctcactgcaa cctctgcctc ccaggttcaa ttcttgtgcc tcagcccccc cgagtagtgg 7860
ggattacagg catgcaccat catgcccgcc taattttttt ggtagtttta gtacagatgg 7920
ggttttacca tgttggccag gctggtgttg aactcctggc ctcaagtgat ctacccactt 7980
ctgcctacca gagtgctagg attacaagcg tcagccactg ctcctggcct aaagttactt 8040
taaattaact gatctcccat tattcgccac ttaggttttt tagttttcac cattataagc 8100
aatgctatga tgtacattca aatggaaatg tgtttacaca cttattaaca gtcttaatta 8160
agaagctctc catgtgctgt gtctctaaca tctgcaggta tgtacacaaa tacatgcaca 8220
gccagcatcc atcttttgca gggacattaa tgatcttggc tctgagcagc accctgtcct 8280
gggagttcta aagtccagaa cagattacag tgagtatctc ctgggggatt tagagacatc 8340
aaagaaggct gtgtccgtgg ttgataatgg gcctcccagc tgacttgcca gggctgggcc 8400
ttagacagcc ctgtccaatg atttgtcaat gaataaactg ttcccaaaca ggctatgcag 8460
ttcagtggga aagcacaggt atgggacacg gagagcccca ggtggactac ttgacctctc 8520
tgagccttaa ttttatcacc tgtgaattgg gaataactgc ttatttcata atattattat 8580
gaggatttaa tgaaatcatg tgggcaagga attatttaga attagattca actcaagtga 8640
tgacaacccc aaactaacag cagataaaac aagacacaac ttgtttctca ctcatctaaa 8700
agtctacgtg ggtggtgcac gatgttctat tctctttctc ctccacacta aacaggcctc 8760
agcctcatca gccaataagg caggagctgc cttccaggca gcggaatgga agaaggatga 8820
agcaaaacag agggcagagt gtgcacatgt gctatgttta gggaaggttt tctgaagttc 8880
ccacatagta cttccactta caaacccaac aaaaaaggct atggctaagg cagcagggag 8940
gagcaaataa tgggagcaac tagattttgc cacagcacct atcacagtct ggtttataaa 9000
tggttctagg ccaagaacac ccgatccctg ctcttttta tattctaaag catgtatctt 9060
tatatttctc aagcaatatt ttctctcttt gaatcacagc tcatctgctg catcataggg 9120
atcccaaaag aaggacccaa ggaacttgtc tcagtcctct gtgccccaag aggaagcttt 9180
gcttgtttgc tttgctgtca atgctgaggg ctcctgtggc tgcctccact caaaaccctc 9240
cagcatcagg acgtcaaggc tgtgatactg taccctgagc tcttggccag ggcgagggag 9300
gggaggccaa gcctacctac atggtgtttc atttcctaaa cgaaccctta cttccacgcg 9360
gtctgtccag cttagaaact tattttcagt agtgttggtc cttggtccct ggacaaaatg 9420
taacagccaa agtcctagaa aaaggcaagc cagttcctgc cattttcttt cacttctgca 9480
tttcctcact attatacgtg ccttccattg gagcaaaact gaatgccacg catatgcaca 9540
ggagctgtgc gcgctctgtc tctctcactc actctttttc tctctctctc tttctctctc 9600
aatctctctg tctctatcta tctcttactc tttatctctc actctctcac tctttctcac 9660
tctttctctc aatctctttc tcattctctc tctatctttc tctctctctc tctttctcac 9720
acacacacac tcacaaaccc acactcttat tcacatctgc tcaccctagc cactcaaaca 9780
caatccctca ttcagcctgg aataagtcca gagggcgtgg gcctgattca gagacaatca 9840
gttgttctca tctgggaaat ggggcaatgt ggtcatctct agggaccctc cctgctctaa 9900
cattctttga atgtggtggg tcctgaggtg gaagcactct gtccctgact tctagtatat 9960
gtggagatag ggttacacaa atattttatt gggcagaact tttataaaac aatttatcat 10020
aagctatcgc agccagcagc aatttttcca acctggattc caccagggga gcttggccgg 10080
tgtctgagtg ccactttcag cttgagaagc aggtgactca gtgaaaagag caaggaggag 10140

-continued

```
acagaggcag attcagttcc taggccctgg gccacccacc tgcaagtttg cagcccagtc  10200
agtgcaagtc agctaactgt tctgaacctc agtttctctg tctgtaaatt aagctaaaaa  10260
ttcttctttc aaagagtgtc aggatgaagt gagatcgtgt atgtagggca tttaacatag  10320
tgcccgacac acagggagca ttcggtaggt gccagctctc ctcctggcag gagagagaga  10380
aacaaggtga aaagagtgaa ttaaagaaga ggaaagtcaa atgggaaaac agggggagga  10440
gatagaaagt gtatgaaaag gaaagaatgg tgcgcaataa cggcggtgta atgccaccaa  10500
aatcccctca actacttctg ggcagcaccc ttgacagagt gaatgctttt atgagaatgt  10560
aagcggaatg tgttcccaga tttgcagtaa tattgccacc tggtggacaa acccatgcac  10620
ctttgaattt tccaaaatat ttcgatgaac tagcttccag tcctagatgt attttgaaag  10680
tgatttgtaa attgtaagga actattcaaa ttctttcatt aatgtcacaa atcaactgtg  10740
tcatctgtat gccacccact attctgggtg ctggggacac aacagctcac aaatcaggca  10800
aagtccctgc tctcaccaaa atgatatcct acgggggatt acagatacaa atacgtaaac  10860
agatccatcg ggaggaaact ctcagatgga aatgagagct atgaagataa cacaacagta  10920
catgacaata cagagtgact ggaaccagga acatttctcc gaggaataaa atttgaagcg  10980
agccatgaga gggtctacag gtagagttcc caggcagagt gaacagccaa gcacaaagct  11040
gcaccaggag agagaggtgc tcgccgagag acagggaggg gagtgtggca ggtgagctca  11100
gagaggggca gggccacaca catcggccac atgggccttg gtagtgagtc gagatttgat  11160
cccagggttt attggagtgg ataagtaagc aaggtgactg aggtgctcgg gtttacattt  11220
ttatagttca agctggctgc tgggtggaaa acggaagttg gcagaccaag gacagaatca  11280
ggcagaccca tgtggaagtt tctctagtgg tctaggtggt ggcttgggta gcgtggcagt  11340
attggagctg gagaaacgca gatggattgg agatttgttt tggagtgacg ccattctgtc  11400
ttgtcaatgg attggcgaaa aaagaggcat caaagatgag ttacacatca ttgaagtgag  11460
aactagggag atgccagtac tttatttagt attttctcag cagctcaatc cataaataat  11520
ttttggaaga caacaagcag tttcacaaac tacttataag tcctcaagtt ccaaggtaat  11580
taacgtgggt gtctcattgc ctcagagaac acagcgcagc acggaaattc tacaagacct  11640
gacggacagg aacatctccg acttcttggt aaaaacgtat cctgctctta taagaagcag  11700
gtaagaagaa atccttttat gctttttatc ctggctccct gtagaagata ttaactaggg  11760
acagaagata attttctctc tcaatttatg tatgatcagg gcagtagatt tttttctttt  11820
ttatctgatt tgagggcccc attcaacata aaaagcaatt gaggcacata caagtaaaat  11880
gtaacttaag attaattctt tttttgttgt ttgtttgttt gtttttacat ttagggcaag  11940
cagtcttaaa ttttaaccca cgtattatta aaagttatat cagaagacca tagaagttat  12000
tcaaaaatgc agccacatat tttaactagt taaaagagag agtaaaaatt tggagggagg  12060
tggaggagta taggggaaaa ggtagaagaa aaagagaaaa taagtaagtg gcaaaaaaga  12120
gaaaggaaaa agatagggtg ggaaagaggc agcgggacag tgtctgagtc cagcacacgc  12180
cagggcgagc caggtcaact gcagctgtca tattctaact gtgaattatc atctttgatc  12240
actgcccttt gagatgccaa tgaacttttc aagaaatatc tagttctctt ggctctccag  12300
ctgttcttat cagccccatc caggatggaa cagctttggc agcccgtatc agaacaagca  12360
gcttgacagg ggcatgccat gccaggagag aggatcctaa ggaagcgtgg tccagtccgc  12420
acaggctctg gggctttaag ataaaacctc ctgtctaact ttagtaggac tttctgttgc  12480
ttcacctgcc agagccctga acgagggata aattgactta attaactaga acacactgca  12540
```

aatggtgaaa gcatttagca aaacaaagaa tgccatccaa gccccaaaat aaaagcagaa 12600
taaatagaat gcaataaaca gcaaccatcc caaactgagt tctcagcagc aaatctccag 12660
tatgaaattt tggattttgt gcgtgtgtgc ttaaaggtgg atgacaatga cagttcatgg 12720
gattgagctc tggggtccag agttggcatc tgttcatttc ccattttgtc attttaccct 12780
tgattgactg aatgtcagtg ccttaacttt gggctgtgga gtgagtcgga actcccccga 12840
ggtgtgcagg tggttgttag agtctcattt ttgcagggtg gaagacagga gggctgcagc 12900
cttcattcca cactgacatg gtcattgccg tgtgttctgg gtccagatca ggcatattga 12960
cctgacatat gacctgacaa caggaccact cagaaagtcc agcatgcggg atatgatttg 13020
gagagccagt gggggaaatc ataggtcctt tctctgcatg tgtattcagg caatgtccca 13080
gggctgggcg gcttccgcat tgcttggata tcggaaaatg caaaaatgcc cctgaagact 13140
gagacttcag tcttcaaaat gaatgtttgg gaaagaaagt taacggcact gctgtacttg 13200
tggtattcat tgcattattt tattttggct ttcagcttaa agagcaaatt ctgggtcaat 13260
gaacagaggt aagaaactat ttttatcaga attaaaatct cagattgatt cattgttgaa 13320
ataattgcac acttttaaaa ggcacacctc acagccatga ggaggggctg ttctgtaggt 13380
gctcaggaag tcacaagaca cgtcctgaag aatatgtggc tagggacatc ccagactcag 13440
aagacactca gtggtgcctc ttcttggagg acataagtgg gggtggcatt ccctgatgtg 13500
gcgtttcaga gcattctcac ccaaaaaaag cttctaaaac ctccaagtat ataacagttt 13560
ataatactcc aacaagaggg ccttgtagcc taaacccggg acactccttg gcccattcct 13620
tttaagcacc cagctttc 13638

<210> SEQ ID NO 300
<211> LENGTH: 14728
<212> TYPE: DNA
<213> ORGANISM: Artificial Sequence
<220> FEATURE:
<223> OTHER INFORMATION: pCI-Neo-Rho-ABCA4-intron31-intron37 wild type

<400> SEQUENCE: 300
ttgtacaaag tggtgatctt gtacaaagtg gtgatgagag gtacctccga ggggtaaaca 60
gttgggtaaa cagtctctga agtcagctct gccattttct agctgtatgg ccctgggcaa 120
gtcaatttcc ttctctgtgc tttggtttcc tcatccatag aaaggtagaa agggcaaaac 180
accaaactct tggattacaa gagataattt acagaacacc cttggcacac agagggcacc 240
atgaaatgtc acgggtgaca cagccccctt gtgctcagtc cctggcatct ctaggggtga 300
ggagcgtctg cctagcaggt tcccaccagg aagctggatt tgagtggatg ggcgctgga 360 atcgtgaggg gcagaagcag gcaaagggtc ggggcgaacc tcactaacgt gccagttcca 420
agcacactgt gggcagccct ggccctgact caagcctctt gccttccagt tccggaactg 480
catgctcacc accatctgct gcggcaagaa cccactgggt gacgatgagg cctctgctac 540
cgtgtccaag acggagacga gccaggtggc cccggcctaa gacctgccta ggactctgtg 600
gccgactata ggcgtctccc atcccctaca cctgtcgacc cgggcggccg cttcccttta 660
gtgagggtta atgcttcgag cagacatgat aagatacatt gatgagtttg gacaaaccac 720
aactagaatg cagtgaaaaa aatgctttat ttgtgaaatt tgtgatgcta ttgctttatt 780
tgtaaccatt ataagctgca ataaacaagt taacaacaac aattgcattc attttatgtt 840
tcaggttcag ggggagatgt gggaggtttt ttaaagcaag taaaacctct acaaatgtgg 900

-continued taaaatccga taaggatcga tccgggctgg cgtaatagcg aagaggcccg caccgatcgc 960
ccttcccaac agttgcgcag cctgaatggc gaatggacgc gccctgtagc ggcgcattaa 1020
gcgcggcggg tgtggtggtt acgcgcagcg tgaccgctac acttgccagc gccctagcgc 1080
ccgctccttt cgctttcttc ccttcctttc tcgccacgtt cgccggcttt ccccgtcaag 1140
ctctaaatcg ggggctccct ttagggttcc gatttagtgc tttacggcac ctcgacccca 1200
aaaaacttga ttagggtgat ggttcacgta gtgggccatc gccctgatag acggtttttc 1260
gccctttgac gttggagtcc acgttcttta atagtggact cttgttccaa actggaacaa 1320
cactcaaccc tatctcggtc tattcttttg atttataagg gattttgccg atttcggcct 1380
attggttaaa aaatgagctg atttaacaaa aatttaacgc gaattttaac aaaatattaa 1440
cgcttacaat ttcctgatgc ggtattttct ccttacgcat ctgtgcggta tttcacaccg 1500
catacgcgga tctgcgcagc accatggcct gaaataacct ctgaaagagg aacttggtta 1560
ggtaccttct gaggcggaaa gaaccagctg tggaatgtgt gtcagttagg gtgtggaaag 1620
tccccaggct ccccagcagg cagaagtatg caaagcatgc atctcaatta gtcagcaacc 1680
aggtgtggaa agtccccagg ctccccagca ggcagaagta tgcaaagcat gcatctcaat 1740
tagtcagcaa ccatagtccc gcccctaact ccgcccatcc cgcccctaac tccgcccagt 1800
tccgcccatt ctccgcccca tggctgacta attttttta tttatgcaga ggccgaggcc 1860
gcctcggcct ctgagctatt ccagaagtag tgaggaggct tttttggagg cctaggcttt 1920
tgcaaaaagc ttgattcttc tgacacaaca gtctcgaact taaggctaga gccaccatga 1980
ttgaacaaga tggattgcac gcaggttctc cggccgcttg ggtggagagg ctattcggct 2040
atgactgggc acaacagaca atcggctgct ctgatgccgc cgtgttccgg ctgtcagcgc 2100
aggggcgccc ggttcttttt gtcaagaccg acctgtccgg tgccctgaat gaactgcagg 2160
acgaggcagc gcggctatcg tggctggcca cgacgggcgt tccttgcgca gctgtgctcg 2220
acgttgtcac tgaagcggga agggactggc tgctattggg cgaagtgccg gggcaggatc 2280
tcctgtcatc tcaccttgct cctgccgaga aagtatccat catggctgat gcaatgcggc 2340
ggctgcatac gcttgatccg gctacctgcc cattcgacca ccaagcgaaa catcgcatcg 2400
agcgagcacg tactcggatg gaagccggtc ttgtcgatca ggatgatctg gacgaagagc 2460
atcaggggct cgcgccagcc gaactgttcg ccaggctcaa ggcgcgcatg cccgacggcg 2520
aggatctcgt cgtgacccat ggcgatgcct gcttgccgaa tatcatggtg gaaaatggcc 2580
gcttttctgg attcatcgac tgtggccggc tgggtgtggc ggaccgctat caggacatag 2640
cgttggctac ccgtgatatt gctgaagagc ttggcggcga atgggctgac cgcttcctcg 2700
tgctttacgg tatcgccgct cccgattcgc agcgcatcgc cttctatcgc cttcttgacg 2760
agttcttctg agcgggactc tggggttcga aatgaccgac caagcgacgc ccaacctgcc 2820
atcacgatgg ccgcaataaa atatctttat tttcattaca tctgtgtgtt ggtttttgt 2880 gtgaatcgat agcgataagg atccgcgtat ggtgcactct cagtacaatc tgctctgatg 2940
ccgcatagtt aagccagccc cgacacccgc caacacccgc tgacgcgccc tgacgggctt 3000
gtctgctccc ggcatccgct tacagacaag ctgtgaccgt ctccgggagc tgcatgtgtc 3060
agaggttttc accgtcatca ccgaaacgcg cgagacgaaa gggcctcgtg atacgcctat 3120
ttttataggt taatgtcatg ataataatgg tttcttagac gtcaggtggc acttttcggg 3180
gaaatgtgcg cggaacccct atttgtttat ttttctaaat acattcaaat atgtatccgc 3240
tcatgagaca ataaccctga taaatgcttc aataatattg aaaaaggaag agtatgagta 3300

```
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
```

-continued

```
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttcagcaac catcccaaac tgagttctca gcagcaaatc tccagtatga   6360
aattttggat tttgtgcgtg tgtgcttaaa ggtggatgac aatgacagtt catgggattg   6420
agctctgggg tccagagttg gcatctgttc atttcccatt ttgtcatttt acccttgatt   6480
gactgaatgt cagtgcctta actttgggct gtggagtgag tcggaactcc cccgaggtgt   6540
gcaggtggtt gttagagtct catttttgca gggtggaaga caggagggct gcagccttca   6600
ttccacactg acatggtcat tgccgtgtgt tctgggtcca gatcaggcat attgacctga   6660
catatgacct gacaacagga ccactcagaa agtccagcat gcgggatatg atttggagag   6720
ccagtggggg aaatcatagg tcctttctct gcatgtgtat tcaggcaatg tcccagggct   6780
gggcggcttc cgcattgctt ggatatcgga aaatgcaaaa atgcccctga agactgagac   6840
ttcagtcttc aaaatgaatg tttgggaaag aaagttaacg gcactgctgt acttgtggta   6900
ttcattgcat tattttattt tggctttcag cttaaagagc aaattctggg tcaatgaaca   6960
gaggtaagaa actattttta tcagaattaa aatctcagat tgattcattg ttgaaataat   7020
tgcacacttt taaaaggcac acctcacagc catgaggagg ggctgttctg taggtgctca   7080
ggaagtcaca agacacgtcc tgaagaatat gtggctaggg acatcccaga ctcagaagac   7140
actcagtggt gcctcttctt ggaggacata agtgggggtg gcattccctg atgtggcgtt   7200
tcagagcatt ctcacccaaa aaaagcttct aaaacctcca agtatataac agtttataat   7260
actccaacaa gagggccttg tagcctaaac ccgggacact ccttggccca ttccttttaa   7320
gcttcaggga gtgtgggcca gccccagact caccccattc ctgaggcatc ctggaggttg   7380
aaatatttcc agaggtttag aacctcacca agtgggactc taggagcctg ctgcctccca   7440
gcctccctca ggaactgcac ctccagaaca ggtgcggggc tgacatgtat gtgctttcct   7500
gggcagattc tagaccgtac acatgaaatc tggctttcag gattgctctc cagagggacc   7560
tgtggggcct cggctgagac agagagtagg agtgaggcag tgattcaagg ccctgagaaa   7620
gagctcctcc tctgcttggt ataaccagct aattcattct gttctgttga ctttggcttc   7680
tgccctgcct ttgaagggtt tgaggccagg gagtgatgca ctcagactgg tgtttccaca   7740
cagtcacttc agacttccag ggcagtacag gagatagatc ccagggccag tgaagaagca   7800
gagcacaagt ccaggcagga gaggctaagg gcctccctga acaggtgtga ggcacagaag   7860
ccccgagagg tagggatgac aggatgaaga tgggtcctgt gctgctagaa gtacctgcaa   7920
agcacagagg tggcacagaa aaggagtcct tggctgggat gggaggagat gacatgtgac   7980
atgtgaaaga ggacctggag ttggctcgat gctcccaaaa gggaaaggtg ccgaggggag   8040
```

-continued

```
ctagcagcca tgcaaaggca gagacatgca ggcagtctgg gccatgagga gctctggaag   8100
tgactcgata tgtccagaat aggccactcc agggaagggc tgaggaagga tgaagttgga   8160
gaggggcaca gaccagatgc agaagggcct cagaggccag gatgagggtt tggactcctt   8220
cctggaggca gcagcagtgg gaaaagagtt aaaagctggt ttgtaaagtg gagccatgtt   8280
gctcgctggt ccaggcaatt cccccgaaag ttcatgtttc cctacaaaac ccgagagagc   8340
tactagtagg cgtgaagttc gtggccctgg tctgaggatt tcctgtttcc ttgtcaggta   8400
tggaggaatt tccattggag gaaagctccc agtcgtcccc atcacggggg aagcacttgt   8460
tgggttttta agcgaccttg gccggatcat gaatgtgagc ggggtatgta aacagactgg   8520
agatttgagt aggatttttg acttgcttaa ctaccatgaa tgagaaactc tcatgagtga   8580
taacaggaaa aaaaaattaa aaccgtcttg tttgtttgtt tacatggttt ttagggccct   8640
atcactagag aggcctctaa agaaatacct gatttcctta aacatctaga aactgaagac   8700
aacattaagg tacttgacct atgtataatc tgctctggag ctaaaaattt acctgagctg   8760
gttattttat ttttactttc ctaccttcat taaattccat ccctcctcct gctgaaatct   8820
agcaaggaat gtcttccagc taccaaaccc ttcctgcttc tcaaatttcc tttccttcac   8880
tgatttctgc tttaactagc tgttagtgca gcgtctcaga tgtcctctcc accctctagg   8940
tgtggtttaa taacaaaggc tggcatgccc tggtcagctt tctcaatgtg gcccacaacg   9000
ccatcttacg ggccagcctg cctaaggaca ggagccccga ggagtatgga atcaccgtca   9060
ttagccaacc cctgaacctg accaaggagc agctctcaga gattacagtg taagccacca   9120
cagccccagc ctcaccactt tcttgtcacc ttctccactc tttgaacatc ctgagaggat   9180
tctcaccacc gcgaagtgct gatttggatg gtaatgctgt ttagtcaggc acatatgaac   9240
atccgacttt caaataagtg cctcacactt cacataccag acctcttggt cattctttct   9300
ccccaacatt tatgtggcaa gtaagtttac atttggttcc attccctttt ggcttttgat   9360
agcaagttgc tcctggagct tatacaatta ttatctttgc tatgtgcaaa gcagctgcca   9420
ggaactggca aagttcagta aacctttcag ctccctcgga gtaattatct tagattccag   9480
gaatttcctc agaagagcat actttggaga tgtcgacaga gctttgctac cctcaagctg   9540
aggctcttct tgcacagttt cagccagtgg agacagtggc cttgtgcgtt ttgtagtatg   9600
ttcactctat ttgaggccta catggaggag gggttggtag gagcaccttt gttagtgcaa   9660
acttcagcaa cgttgtgggg tcctgatttt actatcctag cacacgctga gtgccagtga   9720
acatgcccag ggtcatccac taaaacctgg gccttggctc cttggtgtct tcctctggac   9780
accctagggc cctagactgt cctctgttaa ttctcactca gccacacttt cgtgtgtctc   9840
cttccagtca tttgttctaa gcttactacg tgtatggatg atatgatctg tagttttatc   9900
aaggtagtga ctaccacata ggataccttt gtggaaatta gtaaaaatgc tcttttctgc   9960
aggtggacac tgtcccatgc caggggttat ggcttgtaca taaagttcag gctggcttta  10020
gccccaactt acccctcagc cagatgcctt ctatttgtcc gaggaaagaa taaatagagc  10080
caagtccctg tacaacttgc ctgccctctt ttcacttaaa tttacatcat gaacatttcc  10140
ttgtgttacg atgtacttct tgaaaatgtg atttaacaag atgattatta acaaaagata  10200
aatctcacag accgtatgtc tgtcaacata gaaaattcaa gagactctat agacagatta  10260
ttagagctaa tgagagcatt gcagtacata agattaatat aaacatctat ttctatacac  10320
cataaaaata attagagaat ataataaaaa gaaaggttgt ctagaaatat tcacatgaaa  10380
```

-continued tagaaaggca acccgcaaat acccatttaa ccttggtcca tatggattaa gacagtttag 10440
tggagtgaca gcttcaaggt agagaagagg aacctggagg ccacacctgg gcgggtgtaa 10500
ggccttccca aagcctgact ttgtatcttc tcctccttct gctcttccct cttcatcgcc 10560
ctctccctgt gtctctggcc ctgctgcagg ctgaccactt cagtggatgc tgtggttgcc 10620
atctgcgtga ttttctccat gtccttcgtc ccagccagct ttgtccttta tttgatccag 10680
gagcgggtga acaaatccaa gcacctccag tttatcagtg gagtgagccc caccacctac 10740
tgggtgacca acttcctctg ggacatcgta agtgtcagtt tacagcgcct ccctcccctc 10800
cgtgggccca aggtggagct tgtgtgtgct ctgaaggacc agaccaagag gggaggggtt 10860
ctcacggtgc cagggctgct gaaaggcact gggccaaggg ccttgtgtat ctgctgtccc 10920
ttgacatctt ctcagaaagg cacagaacta ggagcccgaa gctaggaaag gctgtggggt 10980
gcagcttaac aactggtgaa cgggggctct ctatgtcctg cactgagggg tcttctgacc 11040
catcaaataa tcactgcacc gcaggcatga gtctggcctt cctggcatca gtctggcgct 11100
gagaaggtaa tatgaagggg tctttcaccc caagtcccct tctcaaatcc tgccccacct 11160
tcaaaagggt aaaggtaaaa ctttccctgt ggtagggtca ccagataaat acaggacacc 11220
cagttaaatt taatttcaga tgatgaataa tttttagtat aagcatatgc tacttcaaat 11280
attgcacagg acatatctac actaaaaaaa aaaaaaaaaa aaaaaaaaac ctggttgttt 11340
atctgaaact caaatttcac taggcatcct agatttttat ttgccaaatc tggcaacccc 11400
agccagtggc caaaataata agaccttcac ttattagatt aaccaccgct acagggaaaa 11460
atgaagaaaa aatatttatt aaatcaatag cacactacca ccttcctgac aaccaaggtt 11520
ggtgggggta gggaggggtc aggatagcgt accctattac aggctgcagg gtcaaaggaa 11580
ttggtagtaa aggcctagtt ataatgtaac agggatcatt atgacatcaa ccccaattta 11640
ttctaggtgt cttgagtagt aaaatctcaa cattttaaga ccaacatgag cctccatttc 11700
atgtgatgat aagatatacc aactgatgga gaccaacaca aatgaccttc tcatccatgg 11760
ttttttaaaa tgatggtgaa tattggaatt cctgaagata tgatttctat cttactcagc 11820
ttagtaagca gctatcactt aacaatacaa aaccagagat tatcagtagc aactaaatta 11880
tttcctctct cttctgtcta cacgaggaaa cactcataaa tgcacgggga ggaggtcaga 11940
acctgaaagc ctttctttgg ataagagcat caactgcagg taccacattg gccctgtgat 12000
gctaatataa aaggagctag gcccaccggt accgaaaagt tacttagaaa agtgcggagg 12060
cttttaattt tacttttttt aaaagataag aaatagaatt tacacacttg gggctggccc 12120
acgtgtttct gtgtgtgtgt atgtgtgcac gcacgcgcgt gtgcgcttac agggatctct 12180
gagcctatgg agagagatgt agctaggata gagtggacat ctgaggtggg aggtgatact 12240
agctggcagt ccaatgaagg ggtagaagat ggtaggcatc atgttagcag gctttctgat 12300
gctccagaat tttaaagctg gcctggaatc tcacctccgc gatccatcat tttggaactt 12360
aggaccacca ttagccagtg gcaaaaaaaa agttgaatga aggaacaaac aattattgct 12420
tatgtaattc acttagcaca tatatgatgt tttaaattct tatatgtgtc atctattttt 12480
ctttacttta aaattttgca acagttacag acttatggaa aagtcacaag tacagttgaa 12540
accttttttt cttagtcatt tgaaagtaac ttctcagcaa gatgcccctt ctcatttatt 12600
tctctcttcc tgtctctctc tctcacaccc ctcagcacgt ccgatgtata cttcctacaa 12660
acgaggatac accccataca accacaacac aaactgtcaa catgaggaaa ccagcactga 12720
tgtgtcatca ccacctaatc ctcacacccc actcctcttt cgcccattgc cccagtgatg 12780
tctttcagaa aaaaggatct agctcagaat catgcatgac atttgattgt gctgtttctt 12840
tagtctcgtt cagcctggaa gagttccaca gtcttttgtt aacactcatg gtcttgacac 12900
tttgaggact gcaggctggt tattttgcag aatgtccctt ggtctgagct tgtctgaggt 12960
ttcctcttgc ccaggttgag ggtgtgcatc ttggcagcag tatcagcaaa cagatgctgt 13020
gttctcactg catcctatca ggtggcttct gatttcaatt tgctctgtta ctgatgatgt 13080
tcaattcggt cacttaagaa ggtgtctgct gagcttcttc actgtaaaat tactcttttc 13140
ccctttataa taaatacaaa tttcaggtag aggcacttca aagatatata aatatcctat 13200
tcattataca attttccatt tattcatcca tttatttatc tctgtatgca gtcatggttc 13260
atgtgttaat caatggacta tgatccaaga ctatcattat ttattttgat attcacatta 13320
tccccactgt ggtcagtggg gggccgttga agctggcttc tgtatcgtct tgacttgggt 13380
cctcatgccc ctggacctcc tccatgctca atggcacagc aagatattcc aggctcatcc 13440
ttccattatc cccattccta ccctctcccc aagaagccct ggttcctgcc agtgggaagt 13500
ggccctcaga agccaaggtc tgagtgctag atatgttcat tgcctctgga gcaccattgg 13560
tcccaggcct tctcagtgat agaactaggg aagatatgga tgtacacaca caggtatgca 13620
cacacctcta tctatagttc tctatctacc tatacagtga acactatgag ctctccaaaa 13680
ccaactccac agggctcatt ctagtttttt ttctttccac atctgtaact cccttctcca 13740
acagtgagac gctggcttct ctcactccca actcatttat ctaccggacc tatacacctg 13800
aacagtgccc aactctgcca ccatcccctc cccatgtgga tgccgtcctc tccctgctcc 13860
agctgcctct gctgcatgca ggtcctcctc gttctgctct ggctctgata ccctgcacca 13920
gatcagcctc ctgtaaggat atctttctca tcccgttgag gcctccacac cccacggcag 13980
gttgccccct gaggaagccc gtctctggtt cttgccctgc tcctgatcac catggctcct 14040
cccctaaccc cactgttgcc gtcccctttc tgtgcccagt atagtggctg taggactaaa 14100
ttgtttaaaa agggtatcat tatttatttg agctttgtga agccaagaac taggctttaa 14160
gtttttctga attctgaaga catgcttaga aagaagaatc aacaaaactt tatgaccaaa 14220
tagaaagagt gagagaccag gcagaatttt gtaattgatc ctttcaaaag atacaaacta 14280
aaggttccct tggcagggag gtagggcatg gggtggggta ggaggactag tgacagctta 14340
acatatgttt gccaaccaag aactgtttaa aaagcaagtc gaatcagaat cccagaccct 14400
acgagctgga ggagcctggc cccacccctc attttgcaga gctggcagca ggtctgagag 14460
gttaagtgac ttgctctcct cttctctttc cgagatgaat tattccgtga gtgctgggct 14520
ggtggtgggc atcttcatcg ggtttcagaa gaaagcctac acttctccag aaaaccttcc 14580
tgcccttgtg gcactgctcc tgctgtatgg gtaagccgtt tgggccatta gctaatgcct 14640
ctgaagagaa gcctggtggt gggggtgggg gatcatctcc tgacagaaaa cctgggctgt 14700
cctgtggtgg tagcaccacc cagctttc 14728

<210> SEQ ID NO 301
<211> LENGTH: 14728
<212> TYPE: DNA
<213> ORGANISM: Artificial Sequence
<220> FEATURE:
<223> OTHER INFORMATION: pCI-Neo-Rho-ABCA4-intron31-intron37 c.5197-557T

<400> SEQUENCE: 301
ttgtacaaag tggtgatctt gtacaaagtg gtgatgagag gtacctccga ggggtaaaca 60

-continued

```
gttgggtaaa cagtctctga agtcagctct gccattttct agctgtatgg ccctgggcaa    120
gtcaatttcc ttctctgtgc tttggtttcc tcatccatag aaaggtagaa agggcaaaac    180
accaaactct tggattacaa gagataattt acagaacacc cttggcacac agagggcacc    240
atgaaatgtc acgggtgaca cagccccctt gtgctcagtc cctggcatct ctaggggtga    300
ggagcgtctg cctagcaggt tcccaccagg aagctggatt tgagtggatg gggcgctgga    360
atcgtgaggg gcagaagcag gcaaagggtc ggggcgaacc tcactaacgt gccagttcca    420
agcacactgt gggcagccct ggccctgact caagcctctt gccttccagt tccggaactg    480
catgctcacc accatctgct gcggcaagaa cccactgggt gacgatgagg cctctgctac    540
cgtgtccaag acggagacga gccaggtggc cccggcctaa gacctgccta ggactctgtg    600
gccgactata ggcgtctccc atcccctaca cctgtcgacc cgggcggccg cttcccttta    660
gtgagggtta atgcttcgag cagacatgat aagatacatt gatgagtttg gacaaaccac    720
aactagaatg cagtgaaaaa aatgctttat ttgtgaaatt tgtgatgcta ttgctttatt    780
tgtaaccatt ataagctgca ataaacaagt taacaacaac aattgcattc attttatgtt    840
tcaggttcag ggggagatgt gggaggtttt ttaaagcaag taaaacctct acaaatgtgg    900
taaaatccga taaggatcga tccgggctgg cgtaatagcg aagaggcccg caccgatcgc    960
ccttcccaac agttgcgcag cctgaatggc gaatggacgc gccctgtagc ggcgcattaa   1020
gcgcggcggg tgtggtggtt acgcgcagcg tgaccgctac acttgccagc gccctagcgc   1080
ccgctccttt cgctttcttc ccttcctttc tcgccacgtt cgccggcttt ccccgtcaag   1140
ctctaaatcg ggggctccct ttagggttcc gatttagtgc tttacggcac ctcgacccca   1200
aaaaacttga ttagggtgat ggttcacgta gtgggccatc gccctgatag acggtttttc   1260
gccctttgac gttggagtcc acgttcttta atagtggact cttgttccaa actggaacaa   1320
cactcaaccc tatctcggtc tattcttttg atttataagg gattttgccg atttcggcct   1380
attggttaaa aaatgagctg atttaacaaa aatttaacgc gaattttaac aaaatattaa   1440
cgcttacaat ttcctgatgc ggtattttct ccttacgcat ctgtgcggta tttcacaccg   1500
catacgcgga tctgcgcagc accatggcct gaaataacct ctgaaagagg aacttggtta   1560
ggtaccttct gaggcggaaa gaaccagctg tggaatgtgt gtcagttagg gtgtggaaag   1620
tccccaggct ccccagcagg cagaagtatg caaagcatgc atctcaatta gtcagcaacc   1680
aggtgtggaa agtccccagg ctccccagca ggcagaagta tgcaaagcat gcatctcaat   1740
tagtcagcaa ccatagtccc gcccctaact ccgcccatcc cgcccctaac tccgcccagt   1800
tccgcccatt ctccgcccca tggctgacta attttttta tttatgcaga ggccgaggcc   1860
gcctcggcct ctgagctatt ccagaagtag tgaggaggct tttttggagg cctaggcttt   1920
tgcaaaaagc ttgattcttc tgacacaaca gtctcgaact taaggctaga gccaccatga   1980
ttgaacaaga tggattgcac gcaggttctc cggccgcttg ggtggagagg ctattcggct   2040
atgactgggc acaacagaca atcggctgct ctgatgccgc cgtgttccgg ctgtcagcgc   2100
aggggcgccc ggttcttttt gtcaagaccg acctgtccgg tgccctgaat gaactgcagg   2160
acgaggcagc gcggctatcg tggctggcca cgacgggcgt tccttgcgca gctgtgctcg   2220
acgttgtcac tgaagcggga agggactggc tgctattggg cgaagtgccg gggcaggatc   2280
tcctgtcatc tcaccttgct cctgccgaga aagtatccat catggctgat gcaatgcggc   2340
ggctgcatac gcttgatccg gctacctgcc cattcgacca ccaagcgaaa catcgcatcg   2400
agcgagcacg tactcggatg gaagccggtc ttgtcgatca ggatgatctg gacgaagagc   2460
```

```
atcaggggct cgcgccagcc gaactgttcg ccaggctcaa ggcgcgcatg cccgacggcg   2520
aggatctcgt cgtgacccat ggcgatgcct gcttgccgaa tatcatggtg gaaaatggcc   2580
gcttttctgg attcatcgac tgtggccggc tgggtgtggc ggaccgctat caggacatag   2640
cgttggctac ccgtgatatt gctgaagagc ttggcggcga atgggctgac cgcttcctcg   2700
tgctttacgg tatcgccgct cccgattcgc agcgcatcgc cttctatcgc cttcttgacg   2760
agttcttctg agcgggactc tggggttcga aatgaccgac caagcgacgc ccaacctgcc   2820
atcacgatgg ccgcaataaa atatctttat tttcattaca tctgtgtgtt ggttttttgt   2880
gtgaatcgat agcgataagg atccgcgtat ggtgcactct cagtacaatc tgctctgatg   2940
ccgcatagtt aagccagccc cgacacccgc caacacccgc tgacgcgccc tgacgggctt   3000
gtctgctccc ggcatccgct tacagacaag ctgtgaccgt ctccgggagc tgcatgtgtc   3060
agaggttttc accgtcatca ccgaaacgcg cgagacgaaa gggcctcgtg atacgcctat   3120
ttttataggt taatgtcatg ataataatgg tttcttagac gtcaggtggc acttttcggg   3180
gaaatgtgcg cggaacccct atttgtttat ttttctaaat acattcaaat atgtatccgc   3240
tcatgagaca ataaccctga taaatgcttc aataatattg aaaaaggaag agtatgagta   3300
ttcaacattt ccgtgtcgcc cttattccct tttttgcggc attttgcctt cctgtttttg   3360
ctcacccaga aacgctggtg aaagtaaaag atgctgaaga tcagttgggt gcacgagtgg   3420
gttacatcga actggatctc aacagcggta agatccttga gagttttcgc cccgaagaac   3480
gttttccaat gatgagcact tttaaagttc tgctatgtgg cgcggtatta tcccgtattg   3540
acgccgggca agagcaactc ggtcgccgca tacactattc tcagaatgac ttggttgagt   3600
actcaccagt cacagaaaag catcttacgg atggcatgac agtaagagaa ttatgcagtg   3660
ctgccataac catgagtgat aacactgcgg ccaacttact tctgacaacg atcggaggac   3720
cgaaggagct aaccgctttt ttgcacaaca tgggggatca tgtaactcgc cttgatcgtt   3780
gggaaccgga gctgaatgaa gccataccaa acgacgagcg tgacaccacg atgcctgtag   3840
caatggcaac aacgttgcgc aaactattaa ctggcgaact acttactcta gcttcccggc   3900
aacaattaat agactggatg gaggcggata aagttgcagg accacttctg cgctcggccc   3960
ttccggctgg ctggtttatt gctgataaat ctggagccgg tgagcgtggg tctcgcggta   4020
tcattgcagc actggggcca gatggtaagc cctcccgtat cgtagttatc tacacgacgg   4080
ggagtcaggc aactatggat gaacgaaata gacagatcgc tgagataggt gcctcactga   4140
ttaagcattg gtaactgtca gaccaagttt actcatatat actttagatt gatttaaaac   4200
ttcattttta atttaaaagg atctaggtga agatcctttt tgataatctc atgaccaaaa   4260
tcccttaacg tgagttttcg ttccactgag cgtcagaccc cgtagaaaag atcaaaggat   4320
cttcttgaga tccttttttt ctgcgcgtaa tctgctgctt gcaaacaaaa aaaccaccgc   4380
taccagcggt ggtttgtttg ccggatcaag agctaccaac tctttttccg aaggtaactg   4440
gcttcagcag agcgcagata ccaaatactg ttcttctagt gtagccgtag ttaggccacc   4500
acttcaagaa ctctgtagca ccgcctacat acctcgctct gctaatcctg ttaccagtgg   4560
ctgctgccag tggcgataag tcgtgtctta ccgggttgga ctcaagacga tagttaccgg   4620
ataaggcgca gcggtcgggc tgaacggggg gttcgtgcac acagcccagc ttggagcgaa   4680
cgacctacac cgaactgaga tacctacagc gtgagctatg agaaagcgcc acgcttcccg   4740
aagggagaaa ggcggacagg tatccggtaa gcggcagggt cggaacagga gagcgcacga   4800
```

-continued

```
gggagcttcc agggggaaac gcctggtatc tttatagtcc tgtcgggttt cgccacctct   4860
gacttgagcg tcgatttttg tgatgctcgt caggggggcg gagcctatgg aaaaacgcca   4920
gcaacgcggc ctttttacgg ttcctggcct tttgctggcc ttttgctcac atggctcgac   4980
agatcttcaa tattggccat tagccatatt attcattggt tatatagcat aaatcaatat   5040
tggctattgg ccattgcata cgttgtatct atatcataat atgtacattt atattggctc   5100
atgtccaata tgaccgccat gttggcattg attattgact agttattaat agtaatcaat   5160
tacggggtca ttagttcata gcccatatat ggagttccgc gttacataac ttacggtaaa   5220
tggcccgcct ggctgaccgc ccaacgaccc ccgcccattg acgtcaataa tgacgtatgt   5280
tcccatagta acgccaatag ggactttcca ttgacgtcaa tgggtggagt atttacggta   5340
aactgcccac ttggcagtac atcaagtgta tcatatgcca agtccgcccc ctattgacgt   5400
caatgacggt aaatggcccg cctggcatta tgcccagtac atgaccttac gggactttcc   5460
tacttggcag tacatctacg tattagtcat cgctattacc atggtgatgc ggttttggca   5520
gtacaccaat gggcgtggat agcggtttga ctcacgggga tttccaagtc tccaccccat   5580
tgacgtcaat gggagtttgt tttggcacca aaatcaacgg gactttccaa aatgtcgtaa   5640
caactgcgat cgcccgcccc gttgacgcaa atgggcggta ggcgtgtacg gtgggaggtc   5700
tatataagca gagctcgttt agtgaaccgt cagatcacta gaagctttat tgcggtagtt   5760
tatcacagtt aaattgctaa cgcagtcagt gcttctgaca caacagtctc gaacttaagc   5820
tgcagtgact ctcttaaggt agccttgcag aagttggtcg tgaggcactg ggcaggtaag   5880
tatcaaggtt acaagacagg tttaaggaga ccaatagaaa ctgggcttgt cgagacagag   5940
aagactcttg cgtttctgat aggcacctat tggtcttact gacatccact ttgcctttct   6000
ctccacaggt gtccactccc agttcaatta cagctcttaa ggctagagta cttaatacga   6060
ctcactatag gctagcctcg agaattccgg aggtcaacaa cgagtctttt gtcatctaca   6120
tgttcgtggt ccacttcacc atccccatga ttatcatctt tttctgctat gggcagctcg   6180
tcttcaccgt caaggaggta cgggccgggg ggtgggcggc ctcacggctc tgagggtcca   6240
gcccccagca tgcatctgcg gctcctgctc cctggaggag ccatatcaca agtttgtaca   6300
aaaaagcagg cttcagcaac catcccaaac tgagttctca gcagcaaatc tccagtatga   6360
aattttggat tttgtgcgtg tgtgcttaaa ggtggatgac aatgacagtt catgggattg   6420
agctctgggg tccagagttg gcatctgttc atttcccatt ttgtcatttt acccttgatt   6480
gactgaatgt cagtgcctta actttgggct gtggagtgag tcggaactcc cccgaggtgt   6540
gcaggtggtt gttagagtct catttttgca gggtggaaga caggagggct gcagccttca   6600
ttccacactg acatggtcat tgccgtgtgt tctgggtcca gatcaggcat attgacctga   6660
catatgacct gacaacagga ccactcagaa agtccagcat gcgggatatg atttggagag   6720
ccagtggggg aaatcatagg tcctttctct gcatgtgtat tcaggcaatg tcccagggct   6780
gggcggcttc cgcattgctt ggatatcgga aaatgcaaaa atgcccctga agactgagac   6840
ttcagtcttc aaaatgaatg tttgggaaag aaagttaacg gcactgctgt acttgtggta   6900
ttcattgcat tattttattt tggctttcag cttaaagagc aaattctggg tcaatgaaca   6960
gaggtaagaa actattttta tcagaattaa aatctcagat tgattcattg ttgaaataat   7020
tgcacacttt taaaaggcac acctcacagc catgaggagg ggctgttctg taggtgctca   7080
ggaagtcaca agacacgtcc tgaagaatat gtggctaggg acatcccaga ctcagaagac   7140
actcagtggt gcctcttctt ggaggacata agtgggggtg gcattccctg atgtggcgtt   7200
```

tcagagcatt ctcacccaaa aaaagcttct aaaacctcca agtatataac agtttataat 7260
actccaacaa gagggccttg tagcctaaac ccgggacact ccttggccca ttccttttaa 7320
gcttcaggga gtgtgggcca gccccagact caccccattc ctgaggcatc ctggaggttg 7380
aaatatttcc agaggtttag aacctcacca agtgggactc taggagcctg ctgcctccca 7440
gcctccctca ggaactgcac ctccagaaca ggtgcggggc tgacatgtat gtgctttcct 7500
gggcagattc tagaccgtac acatgaaatc tggctttcag gattgctctc cagagggacc 7560
tgtggggcct cggctgagac agagagtagg agtgaggcag tgattcaagg ccctgagaaa 7620
gagctcctcc tctgcttggt ataaccagct aattcattct gttctgttga ctttggcttc 7680
tgccctgcct ttgaagggtt tgaggccagg gagtgatgca ctcagactgg tgtttccaca 7740
cagtcacttc agacttccag ggcagtacag gagatagatc ccagggccag tgaagaagca 7800
gagcacaagt ccaggcagga gaggctaagg gcctccctga acaggtgtga ggcacagaag 7860
ccccgagagg tagggatgac aggatgaaga tgggtcctgt gctgctagaa gtacctgcaa 7920
agcacagagg tggcacagaa aaggagtcct tggctgggat gggaggagat gacatgtgac 7980
atgtgaaaga ggacctggag ttggctcgat gctcccaaaa gggaaaggtg ccgaggggag 8040
ctagcagcca tgcaaaggca gagacatgca ggcagtctgg gccatgagga gctctggaag 8100
tgactcgata tgtccagaat aggccactcc agggaagggc tgaggaagga tgaagttgga 8160
gaggggcaca gaccagatgc agaagggcct cagaggccag gatgagggtt tggactcctt 8220
cctggaggca gcagcagtgg gaaaagagtt aaaagctggt ttgtaaagtg gagccatgtt 8280
gctcgctggt ccaggcaatt cccccgaaag ttcatgtttc cctacaaaac ccgagagagc 8340
tactagtagg cgtgaagttc gtggccctgg tctgaggatt tcctgtttcc ttgtcaggta 8400
tggaggaatt tccattggag gaaagctccc agtcgtcccc atcacggggg aagcacttgt 8460
tgggttttta agcgaccttg gccggatcat gaatgtgagc ggggtatgta aacagactgg 8520
agatttgagt aggatttttg acttgcttaa ctaccatgaa tgagaaactc tcatgagtga 8580
taacaggaaa aaaaaattaa aaccgtcttg tttgtttgtt tacatggttt ttagggccct 8640
atcactagag aggcctctaa agaaatacct gatttcctta aacatctaga aactgaagac 8700
aacattaagg tacttgacct atgtataatc tgctctggag ctaaaaattt acctgagctg 8760
gttattttat ttttactttc ctaccttcat taaattccat ccctcctcct gctgaaatct 8820
agcaaggaat gtcttccagc taccaaaccc ttcctgcttc tcaaatttcc tttccttcac 8880
tgatttctgc tttaactagc tgttagtgca gcgtctcaga tgtcctctcc accctctagg 8940
tgtggtttaa taacaaaggc tggcatgccc tggtcagctt tctcaatgtg gcccacaacg 9000
ccatcttacg ggccagcctg cctaaggaca ggagccccga ggagtatgga atcaccgtca 9060
ttagccaacc cctgaacctg accaaggagc agctctcaga gattacagtg taagccacca 9120
cagccccagc ctcaccactt tcttgtcacc ttctccactc tttgaacatc ctgagaggat 9180
tctcaccacc gcgaagtgct gatttggatg gtaatgctgt ttagtcaggc acatatgaac 9240
atccgacttt caaataagtg cctcacactt cacataccag acctcttggt cattctttct 9300
ccccaacatt tatgtggcaa gtaagtttac atttggttcc attccctttt ggcttttgat 9360
agcaagttgc tcctggagct tatacaatta ttatctttgc tatgtgcaaa gcagctgcca 9420
ggaactggca aagttcagta aacctttcag ctccctcgga gtaattatct tagattccag 9480
gaatttcctc agaagagcat actttggaga tgtcgacaga gctttgctac cctcaagctg 9540

-continued

```
aggctcttct tgcacagttt cagccagtgg agacagtggc cttgtgcgtt ttgtagtatg   9600
ttcactctat ttgaggccta catggaggag gggttggtag gagcaccttt gttagtgcaa   9660
acttcagcaa cgttgtgggg tcctgatttt actatcctag cacacgctga gtgccagtga   9720
acatgcccag ggtcatccac taaaacctgg gccttggctc cttggtgtct tcctctggac   9780
accctagggc cctagactgt cctctgttaa ttctcactca gccacacttt cgtgtgtctc   9840
cttccagtca tttgttctaa gcttactacg tgtatggatg atatgatctg tagttttatc   9900
aaggtagtga ctaccacata ggataccttt gtggaaatta gtaaaaatgc tcttttctgc   9960
aggtggacac tgtcccatgc caggggttat ggcttgtaca taaagttcag gctggcttta  10020
gccccaactt accectcagc cagatgcctt ctatttgtcc gaggaaagaa taaatagagc  10080
caagtccctg tacaacttgc ctgccctctt ttcacttaaa tttacatcat gaacatttcc  10140
ttgtgttacg atgtacttct tgaaaatgtg atttaacaag atgattatta acaaaagata  10200
aatctcacag accgtatgtc tgtcaacata gaaaattcaa gagactctat agacagatta  10260
ttagagctaa tgagagcatt gcagtacata agattaatat aaacatctat ttctatacac  10320
cataaaaata attagagaat ataataaaaa gaaaggttgt ctagaaatat tcacatgaaa  10380
tagaaaggca acccgcaaat acccatttaa ccttggtcca tatggattaa gacagtttag  10440
tggagtgaca gcttcaaggt agagaagagg aacctggagg ccacacctgg gcgggtgtaa  10500
ggccttccca aagcctgact ttgtatcttc tcctccttct gctcttccct cttcatcgcc  10560
ctctccctgt gtctctggcc ctgctgcagg ctgaccactt cagtggatgc tgtggttgcc  10620
atctgcgtga ttttctccat gtccttcgtc ccagccagct ttgtccttta tttgatccag  10680
gagcgggtga acaaatccaa gcacctccag tttatcagtg gagtgagccc caccacctac  10740
tgggtgacca acttcctctg ggacatcgta agtgtcagtt tacagcgcct ccctcccctc  10800
cgtgggccca aggtggagct tgtgtgtgct ctgaaggacc agaccaagag gggaggggtt  10860
ctcacggtgc cagggctgct gaaaggcact gggccaaggg ccttgtgtat ctgctgtccc  10920
ttgacatctt ctcagaaagg cacagaacta ggagcccgaa gctaggaaag gctgtggggt  10980
gcagcttaac aactggtgaa cgggggctct ctatgtcctg cactgagggg tcttctgacc  11040
catcaaataa tcactgcacc gcaggcatga gtctggcctt cctggcatca gtctggcgct  11100
gagaaggtaa tatgaagggg tctttcaccc caagtcccct tctcaaatcc tgccccacct  11160
tcaaaagggt aaaggtaaaa ctttccctgt ggtagggtca ccagataaat acaggacacc  11220
cagttaaatt taatttcaga tgatgaataa tttttagtat aagcatatgc tacttcaaat  11280
attgcacagg acatatctac actaaaaaaa aaaaaaaaaa aaaaaaaaac ctggttgttt  11340
atctgaaact caaatttcac taggcatcct agatttttat ttgccaaatc tggcaacccc  11400
agccagtggc caaaataata agaccttcac ttattagatt aaccaccgct acagggaaaa  11460
atgaagaaaa aatatttatt aaatcaatag cacactacca ccttcctgac aaccaaggtt  11520
ggtgggggta gggaggggtc aggatagcgt accctattac aggctgcagg gtcaaaggaa  11580
ttggtagtaa aggcctagtt ataatgtaac agggatcatt atgacatcaa ccccaattta  11640
ttctaggtgt cttgagtagt aaaatctcaa cattttaaga ccaacatgag cctccatttc  11700
atgtgatgat aagatatacc aactgatgga gaccaacaca aatgaccttc tcatccatgg  11760
ttttttaaaa tgatggtgaa tattggaatt cctgaagata tgatttctat cttactcagc  11820
ttagtaagca gctatcactt aacaatacaa aaccagagat tatcagtagc aactaaatta  11880
tttcctctct cttctgtcta cacgaggaaa cactcataaa tgcacgggga ggaggtcaga  11940
```

acctgaaagc ctttctttgg ataagagcat caactgcagg taccacattg gccctgtgat 12000
gctaatataa aaggagctag gcccaccggt accgaaaagt tacttagaaa agtgcggagg 12060
cttttaattt tactttttt aaaagataag aaatagaatt tacacacttg gggctggccc 12120
acgtgtttct gtgtgtgtgt atgtgtgcac gcacgcgcgt gtgcgcttac agggatctct 12180
gagcctatgg agagagatgt agctaggata gagtggacat ctgaggtggg aggtgatact 12240
agctggcagt ccaatgaagg ggtagaagat ggtaggcatc atgttagcag gctttctgat 12300
gctccagaat tttaaagctg gcctggaatc tcacctccgc gatccatcat tttggaactt 12360
aggaccacca ttagccagtg gcaaaaaaaa agttgaatga aggaacaaac aattattgct 12420
tatgtaattc acttagcaca tatatgatgt tttaaattct tatatgtgtc atctattttt 12480
ctttacttta aaattttgca acagttacag acttatggaa aagtcacaag tacagttgaa 12540
acctttttt cttagtcatt tgaaagtaac ttctcagcaa gatgcccctt ctcatttatt 12600
tctctcttcc tgtctctctc tctcacaccc ctcagcacgt ccgatgtata cttcctacaa 12660
acgaggatac accccataca accacaacac aaactgtcaa catgaggaaa ccagcactga 12720
tgtgtcatca ccacctaatc ctcacacccc actcctcttt cgcccattgc cccagtgatg 12780
tctttcagaa aaaaggatct agctcagaat catgcatgac atttgattgt gctgtttctt 12840
tagtctcgtt cagcctggaa gagttccaca gtcttttgtt aacactcatg gtcttgacac 12900
tttgaggact gcaggctggt tattttgcag aatgtccctt ggtctgagct tgtctgaggt 12960
ttcctcttgc ccaggttgag ggtgtgcatc ttggcagcag tatcagcaaa cagatgctgt 13020
gttctcactg catcctatca ggtggcttct gatttcaatt tgctctgtta ctgatgatgt 13080
tcaattcggt cacttaagaa ggtgtctgct gagcttcttc actgtaaaat tactcttttc 13140
ccctttataa taaatacaaa tttcaggtag aggcacttca aagatatata aatatcctat 13200
tcattataca attttccatt tattcatcca tttatttatc tctgtatgca gtcatggttc 13260
atgtgttaat caatggacta tgatccaaga ctatcattat ttattttgat attcacatta 13320
tccccactgt ggtcagtggg gggccgttga agctggcttc tgtatcgtct tgacttgggt 13380
cctcatgccc ctggacctcc tccatgctca atggcacagc aagatattcc aggctcatcc 13440
ttccattatc cccattccta ccctctcccc aagaagccct ggttcctgcc agtgggaagt 13500
ggccctcaga agccaaggtc tgagtgctag atatgttcat tgcctctgga gcaccattgg 13560
tcccaggcct tctcagtgat agaactaggg aagatatgga tgtacacaca caggtatgca 13620
cacacctcta tctatagttc tctatctacc tatacagtga acactatgag ctctccaaaa 13680
ccaactccac agggctcatt ctagtttttt ttctttccac atctgtaact cccttctcca 13740
acagtgagac gctggcttct ctcactccca actcatttat ctaccggacc tatacacctg 13800
aacagtgccc aactctgcca ccatcccctc cccatgtgga tgccgtcctc tccctgctcc 13860
agctgcctct gctgcatgca ggtcctcctc gttctgctct ggctctgata ccctgcatca 13920
gatcagcctc ctgtaaggat atctttctca tcccgttgag gcctccacac ccccacggcag 13980
gttgcccccct gaggaagccc gtctctggtt cttgccctgc tcctgatcac catggctcct 14040
cccctaaccc cactgttgcc gtcccctttc tgtgcccagt atagtggctg taggactaaa 14100
ttgtttaaaa agggtatcat tatttatttg agctttgtga agccaagaac taggctttaa 14160
gtttttctga attctgaaga catgcttaga aagaagaatc aacaaaactt tatgaccaaa 14220
tagaaagagt gagagaccag gcagaatttt gtaattgatc ctttcaaaag atacaaacta 14280
aaggttccct tggcagggag gtagggcatg gggtggggta ggaggactag tgacagctta 14340
acatatgttt gccaaccaag aactgtttaa aaagcaagtc gaatcagaat cccagaccct 14400
acgagctgga ggagcctggc cccacccctc attttgcaga gctggcagca ggtctgagag 14460
gttaagtgac ttgctctcct cttctctttc cgagatgaat tattccgtga gtgctgggct 14520
ggtggtgggc atcttcatcg ggtttcagaa gaaagcctac acttctccag aaaaccttcc 14580
tgcccttgtg gcactgctcc tgctgtatgg gtaagccgtt tgggccatta gctaatgcct 14640
ctgaagagaa gcctggtggt gggggtgggg gatcatctcc tgacagaaaa cctgggctgt 14700
cctgtggtgg tagcaccacc cagctttc 14728

<210> SEQ ID NO 302
<211> LENGTH: 20
<212> TYPE: DNA
<213> ORGANISM: Artificial Sequence
<220> FEATURE:
<223> OTHER INFORMATION: PCR primer RHO ex3 fw

<400> SEQUENCE: 302
cggaggtcaa caacgagtct 20

<210> SEQ ID NO 303
<211> LENGTH: 20
<212> TYPE: DNA
<213> ORGANISM: Artificial Sequence
<220> FEATURE:
<223> OTHER INFORMATION: PCR primer ABCA4 ex7 rev

<400> SEQUENCE: 303
acggctgtct aggagtgtgg 20

<210> SEQ ID NO 304
<211> LENGTH: 20
<212> TYPE: DNA
<213> ORGANISM: Artificial Sequence
<220> FEATURE:
<223> OTHER INFORMATION: PCR primer ABCA4 ex7 fw

<400> SEQUENCE: 304
tctgagatct tggggaggaa 20

<210> SEQ ID NO 305
<211> LENGTH: 20
<212> TYPE: DNA
<213> ORGANISM: Artificial Sequence
<220> FEATURE:
<223> OTHER INFORMATION: PCR primer ABCA4 ex8 rev

<400> SEQUENCE: 305
tggagtcaat ccccagaaag 20

<210> SEQ ID NO 306
<211> LENGTH: 20
<212> TYPE: DNA
<213> ORGANISM: Artificial Sequence
<220> FEATURE:
<223> OTHER INFORMATION: ABCA4 ex13 fw

<400> SEQUENCE: 306
gcctatctgc aggacatggt 20

<210> SEQ ID NO 307
<211> LENGTH: 20

-continued

```
<212> TYPE: DNA
<213> ORGANISM: Artificial Sequence
<220> FEATURE:
<223> OTHER INFORMATION: PCR primer ABCA4 ex14 rev

<400> SEQUENCE: 307

cgcaactcct tctccaagac                                               20


<210> SEQ ID NO 308
<211> LENGTH: 20
<212> TYPE: DNA
<213> ORGANISM: Artificial Sequence
<220> FEATURE:
<223> OTHER INFORMATION: PCR primer ABCA4 ex30 fw

<400> SEQUENCE: 308

aaacatcacc cagctgttcc                                               20


<210> SEQ ID NO 309
<211> LENGTH: 21
<212> TYPE: DNA
<213> ORGANISM: Artificial Sequence
<220> FEATURE:
<223> OTHER INFORMATION: PCR primer ABCA4 ex32 rev

<400> SEQUENCE: 309

tcattgaccc agaatttgct c                                             21


<210> SEQ ID NO 310
<211> LENGTH: 21
<212> TYPE: DNA
<213> ORGANISM: Artificial Sequence
<220> FEATURE:
<223> OTHER INFORMATION: PCR primer ABCA4 ex32 fw

<400> SEQUENCE: 310

gcaaattctg ggtcaatgaa c                                             21


<210> SEQ ID NO 311
<211> LENGTH: 20
<212> TYPE: DNA
<213> ORGANISM: Artificial Sequence
<220> FEATURE:
<223> OTHER INFORMATION: PCR primer ABCA4 ex37 rev

<400> SEQUENCE: 311

cccagcactc acggaataat                                               20
```

ANTISENSE OLIGONUCLEOTIDES FOR THE TREATMENT OF STARGARDT DISEASE

FIELD OF THE INVENTION

The present invention relates to the field of medicine. In particular, it relates to novel antisense oligonucleotides that may be used in the treatment, prevention and/or delay of Stargardt disease.

BACKGROUND OF THE INVENTION

Autosomal recessive mutations in ABCA4 cause Stargardt disease, a progressive disorder characterized by central vision loss and often leading to complete blindness. A typical hallmark of Stargardt disease is the presence of many yellow spots (flecks) distributed throughout the fundus of the patients. The ABCA4 gene is comprised of 50 exons and encodes a protein consisting of 2273 amino acids. This protein is expressed in the outer segments of cone and rod photoreceptor cells and plays an important role in the removal of waste products following phototransduction.

Besides STGD1, variants in ABCA4 can also lead to other subtypes of retinal disease ranging from bull's eye maculopathy to autosomal recessive cone-rod dystrophy (arCRD; Cremers et al, 1998; Maugeri et al, 2000) and pan-retinal dystrophies (Cremers et al, 1998; Martinez-Mir et al, 1998; Shroyer et al, 2001; Duncker et al, 2014), depending on the severity of the alleles.

Biallelic ABCA4 variants can be identified in approximately 80% of the cases with STGD1 (Allikmets et al, 1997; Fujinami et al, 2013; Lewis et al, 1999; Maugeri et al, 1999; Rivera et al, 2000; Schulz et al, 2017; Webster et al, 2001; Zernant et al, 2011; Zernant et al, 2017), and 30% of cases with arCRD (Maugeri et al, 2000), after sequencing coding regions and flanking splice sites. In general, individuals with arCRD or pan-retinal dystrophy carry two severe ABCA4 alleles, whereas individuals with STGD1 carry two moderately severe variants or a combination of a mild and a severe variant (Maugeri et al, 1999; van Driel et al, 1998). It has been hypothesized that the majority of the missing ABCA4 variants in STGD1 patients reside in intronic regions of the gene, and indeed, over the last few years, several groups have demonstrated the existence of such deep-intronic variants (Bauwens et al, 2015; Bax et al, 2015; Braun et al, 2013; Lee et al, 2016; Schulz et al, 2017; Zernant et al, 2014). In 2013, Braun and colleagues (Braun et al, 2013) described two variants in intron 30 (c.4539+2001G>A and c.4539+2028C>T, hereafter denoted M1 and M2, respectively) that supposedly could affect ABCA4 pre-mRNA splicing, yet without providing experimental evidence. M2 thus far has been identified in 13 cases (Bauwens et al, 2015; Bax et al, 2015; Braun et al, 2013; Lee et al, 2016; Schulz et al, 2017; Zernant et al, 2014). M1 has been found in 31 cases and interestingly was particularly frequent in the Dutch and Belgian populations (Bauwens et al, 2015; Bax et al, 2015; Braun et al, 2013; Lee et al, 2016; Zernant et al, 2014). In addition, we have identified several additional deep-intronic ABCA4 mutations that all lead to the insertion of pseudoexons, either by activating cryptic acceptor or splice donor sites, or by strengthening ESE motifs that are located inside the pseudoexons. These additional mutations include c.769-784C>T, c.859-540C>G, c.859-506G>C, c.1937+435C>G, c.4539+1100A>G, c.4539+1106C>T, c.5197-557G>T.

Currently, several clinical trials for STGD1 are being conducted, employing different therapeutic strategies (http://www.clinicaltrials.gov): i) gene replacement therapy by delivering the complete ABCA4 cDNA (~6.8 kb) via a lentiviral vector (NCT01367444 and NCT01736592); ii) subretinal transplantation of human embryonic stem cell-derived retinal pigmented epithelium cells (hESC-RPE) (NCT02445612 and NCT02941991) and iii) administration of C20-D3-retinylacetate (NCT02402660). Each of these approaches have their limitations, and so far, no efficacy data have been reported from these clinical trials.

As a considerable amount of the mutations in ABCA4 affects pre-mRNA splicing of ABCA4, they represent an attractive target for antisense oligonucleotide (AON)-based splice modulation therapy. Accordingly, there is an urge to develop AONs for splice modulation of the ABCA4 gene to enable expression of a functional ABCA4 protein in subjects suffering from Stargardt disease.

SUMMARY OF THE INVENTION

The invention provides for an antisense oligonucleotide for redirecting splicing that is:

- complementary or substantially complementary to a polynucleotide with a nucleotide sequence consisting of SEQ ID NO: 10, 161, 30, 81, 101, 121, 141 or SEQ ID NO: 261, or a part thereof;
- preferably complementary or substantially complementary to a polynucleotide with a nucleotide sequence consisting of SEQ ID NO: 162, 181, 82, 102, 122, 142 or SEQ ID NO: 262, or a part thereof;
- more preferably complementary or substantially complementary to a polynucleotide with a nucleotide sequence consisting of SEQ ID NO: 160, 180, 80, 100, 120, 140 or SEQ ID NO: 260, or a part thereof
- more preferably complementary or substantially complementary to a polynucleotide with a nucleotide sequence consisting of SEQ ID NO: 11 or SEQ ID NO: 31, or a part thereof;
- more preferably complementary or substantially complementary to a polynucleotide with a nucleotide sequence consisting of SEQ ID NO: 12 or SEQ ID NO: 32, or a part thereof;
- more preferably complementary or substantially complementary to a polynucleotide with a nucleotide sequence selected from the group consisting of SEQ ID NO: 13, 16, 19, 163, 166, 169, 33, 36, 39, 42, 182, 185, 188, 191, 194, 197, 200, 203, 206, 209, 212, 215, 218, 221, 224, 227, 230, 233, 236, 239, 242, 245, 248, 251, 254, 257, 83, 86, 89, 103, 106, 109, 123, 126, 129, 143, 146, 149, 263, 266 and SEQ ID NO: 269, or a part thereof; and
- more preferably complementary or substantially complementary to a polynucleotide with a nucleotide sequence selected from the group consisting of SEQ ID NO: 14, 17, 20, 164, 167, 170, 34, 37, 40, 43, 183, 186, 189, 192, 195, 198, 201, 204, 207, 210, 213, 216, 219, 222, 225, 228, 231, 234, 237, 240, 243, 246, 249, 252, 255, 258, 84, 87, 90, 104, 107, 110, 124, 127, 130, 144, 147, 150, 264, and SEQ ID NO: 270, or a part thereof.

The invention further provides for an antisense oligonucleotide for redirecting splicing according to any of the preceding claims, wherein said antisense oligonucleotide comprises or consists of a sequence selected from the group consisting of SEQ ID NO: 15, 18, 21, 165, 168, 171, 35, 38, 41, 44, 184, 187, 190, 193, 196, 199, 202, 205, 208, 211, 214, 217, 220, 223, 226, 229, 232, 235, 238, 241, 244, 247, 250, 253, 256, 259, 85, 88, 91, 105, 108, 111, 125, 128, 131, 145, 148, 151, 265, 268 and SEQ ID NO: 271.

The invention further provides for a viral vector expressing an antisense oligonucleotide for redirecting splicing according to the invention when placed under conditions conducive to expression of the exon skipping antisense oligonucleotide.

The invention further provides for a pharmaceutical composition comprising an antisense oligonucleotide for redirecting splicing according to the invention or a viral vector according to the invention and a pharmaceutically acceptable excipient.

The invention further provides for the antisense oligonucleotide for redirecting splicing according to the invention, the vector according to the invention and the composition according to the invention for use as a medicament.

The invention further provides for the antisense oligonucleotide for redirecting splicing according to the invention, the vector according to the invention and the composition according to the invention for use in the treatment an ABCA4-related disease or condition requiring modulating splicing of ABCA4.

The invention further provides for the use of the antisense oligonucleotide for redirecting splicing according to the invention, the vector according to the invention and the composition according to the invention for the preparation of a medicament.

The invention further provides for the use of the antisense oligonucleotide for redirecting splicing according to the invention, the vector according to the invention and the composition according to the invention for treating an ABCA4-related disease or condition requiring modulating splicing of ABCA4.

The invention further provides for a method for modulating splicing of ABCA4 in a cell, said method comprising contacting said cell with an antisense oligonucleotide for redirecting splicing according to the invention, the vector according to the invention and the composition according to the invention.

The invention further provides for a method for the treatment of an ABCA4-related disease or condition requiring modulating splicing of ABCA4 of an individual in need thereof, said method comprising contacting a cell of said individual with an antisense oligonucleotide for redirecting splicing according to the invention, the vector according the invention and the composition according to the invention.

BRIEF DESCRIPTION OF THE FIGURES

FIG. 4B Quantification of the ratio of correctly and aberrantly spliced ABCA4 transcript for each cell line with and without CHX.

FIG. 6B RNA analysis on AON-treated cells. RT-PCR from exon 30 to exon 31 of ABCA4 in control, M1 (c.4539+2001G>A) and M2 (c.4539+2028C>T)-containing photoreceptor precursor cells (PPCs) upon AON delivery. Actin (ACTB) mRNA amplification was used to normalize samples. NT: non-treated and in absence of cycloheximide (CHX); NT+: non-treated in the presence of CHX; A1: AON1; A2: AON2; A3: AON3; A4: AON4; S: SON and MQ: PCR negative control. FIG. 6C Semi-quantification of the ratio of correctly versus aberrantly spliced transcripts in all M1 and M2 samples. FIG. 6D Percentage of correction of each AON compared to the NT+ based on the ratio observed in FIG. 3C. Statistical differences in the efficacy of the AONs for M1 and M2 are indicated with an asterisk (*: $p \leq 0.05$ using Mann-Whitney test).

FIG. 7A1, FIG. 7A2, FIG. 7A3 Gene expression profile of one control and M1/M2-derived induced pluripotent stem cells (iPSCs) compared with the respective parental fibroblast lines.

FIG. 7B1-FIG. 7B2, FIG. 7B3 Gene expression profile of one control and M1/M2-derived photoreceptor precursor cells (PPCs) after one month of differentiation compared with iPSCs. The appearance of PPCs can be deduced by the increase in expression of CRX. The differentiation into photoreceptor-like cells is shown by the increased expression of OPN1SW, OPN1M/LW, RCV1 and ABCA4 compared with the pluripotency gene OCT3/4. The results are shown as the mean±SD. All data were plotted relative to the expression of ACTB.

FIG. 9A Representative electrophoresis picture of an RT-PCR to detect from exon 30 to exon 31 of ABCA4 in patient-derived PPCs. The lower band represents the correct transcript while the upper bands represent the aberrant ones. The aberrant bands were detected after cycloheximide (CHX) treatment, indicating that those transcripts undergo non-sense mediated decay (NMD). Twenty-six different AON molecules were delivered to the cells together, as well as two SON (negative controls named SON1 and SON2). Results were compared to the non-treated cells (NT) in the presence of CHX (+CHX). Actin was used as loading control. MQ states for the negative control of the PCR.

Figure 9A:
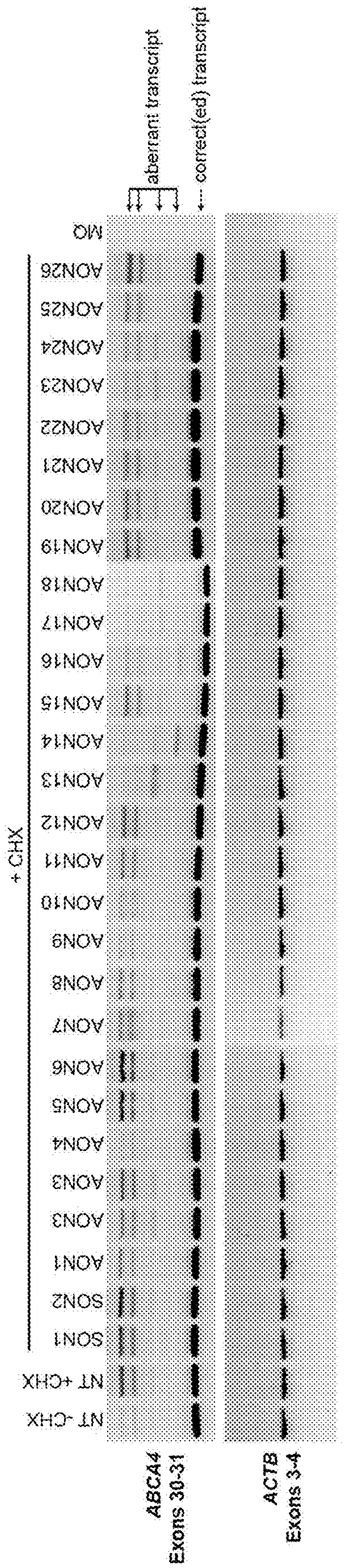
FIG. 9A-9C shows the screening of in total 26 AON sequences for their ability to correct splicing defects caused by the c.4539+2001G>A mutation.
Figure 9B:
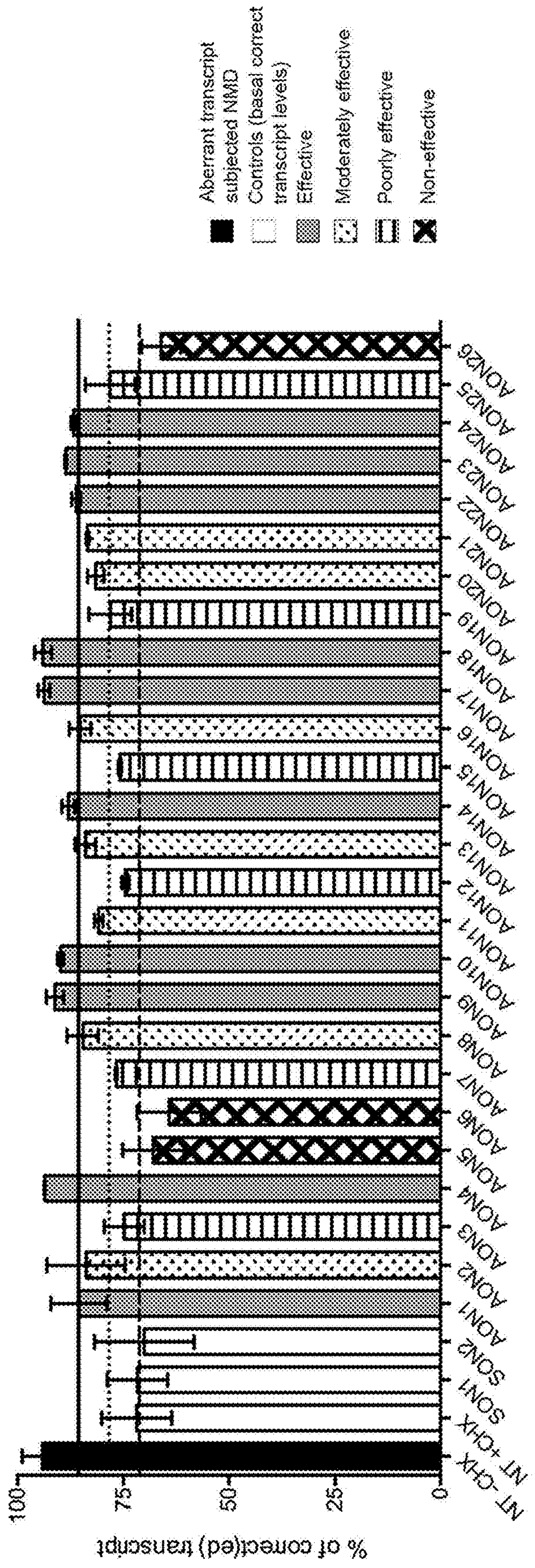
Figure 9C:
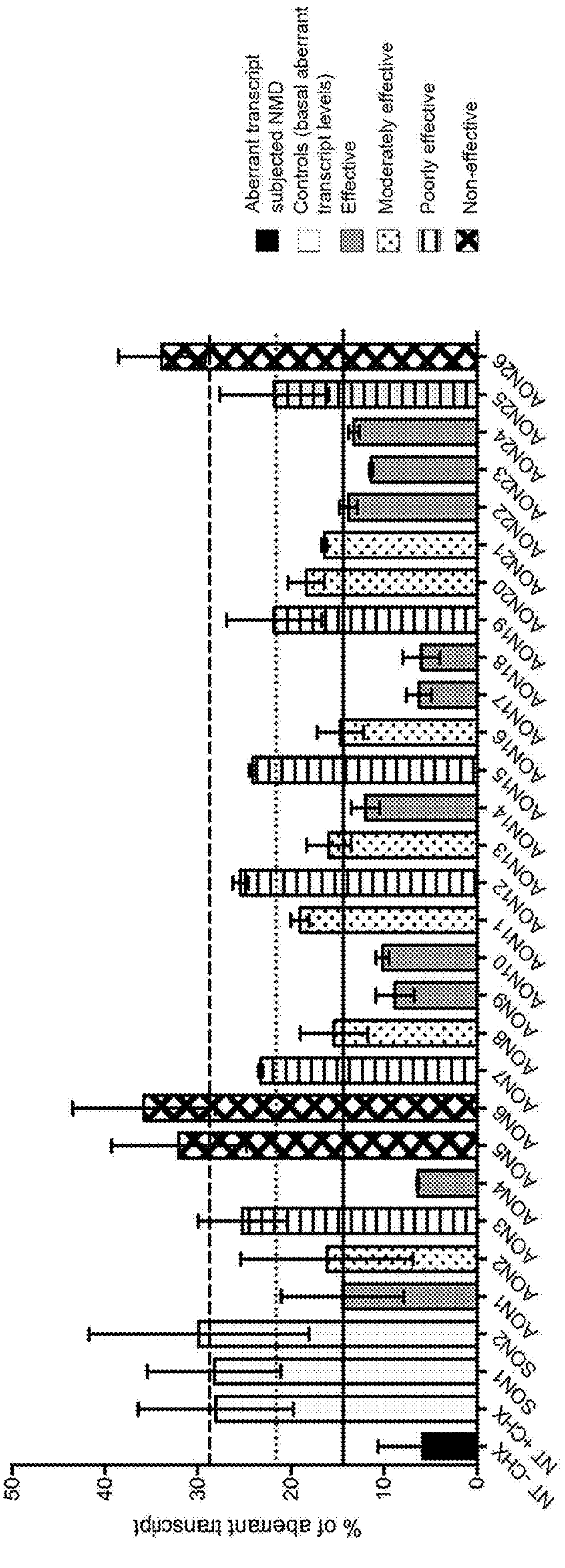
Figure 10A:
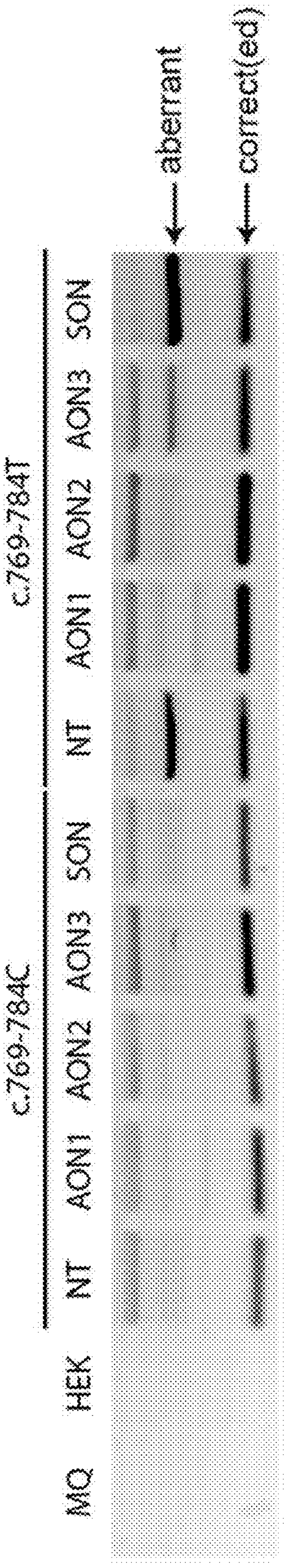
Figure 10B:
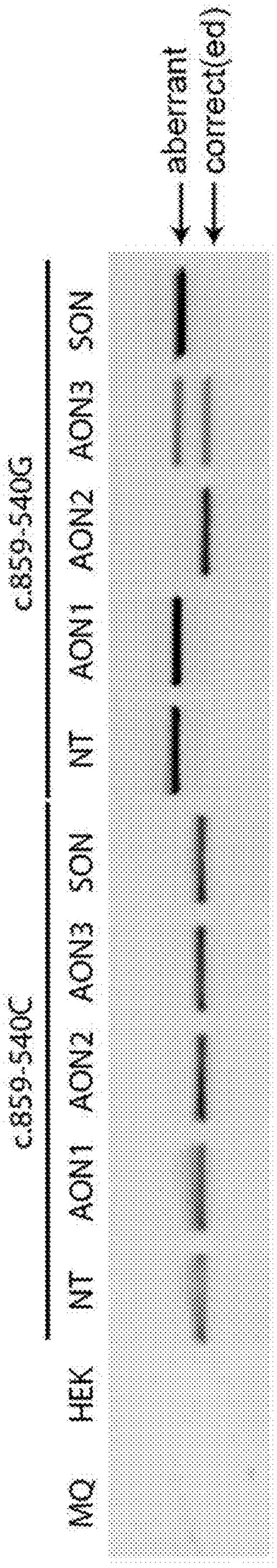
Figure 10C:
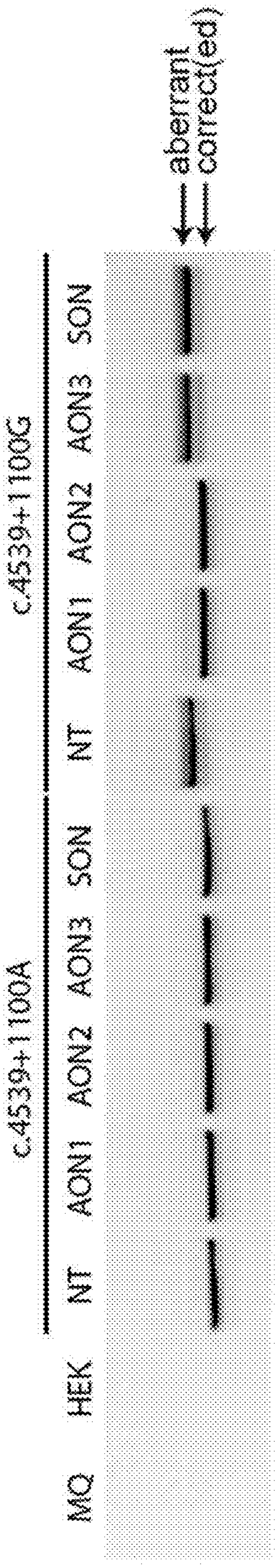
Figure 10D:
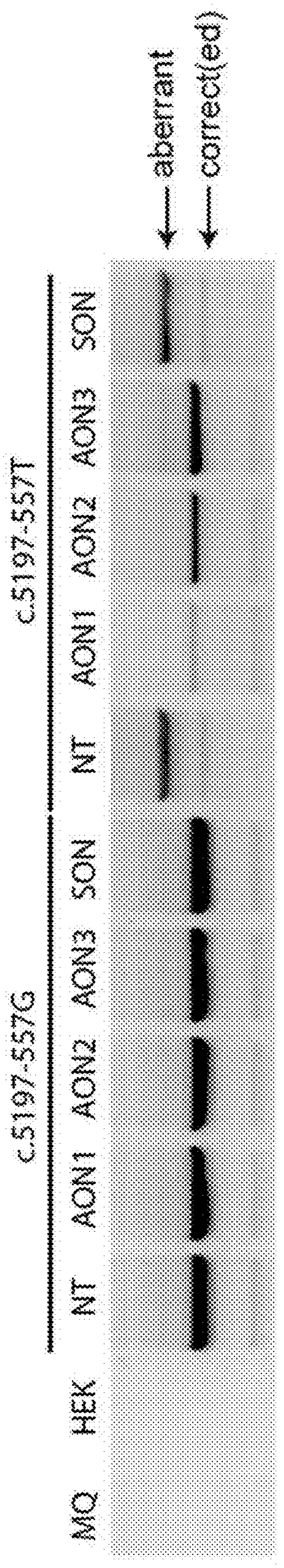
Figure 10E:
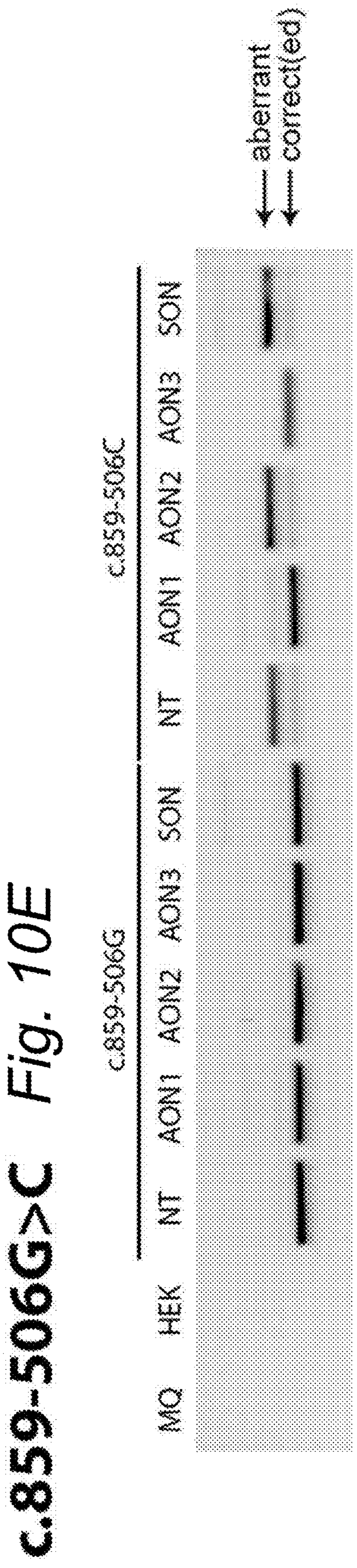
Figure 10F:
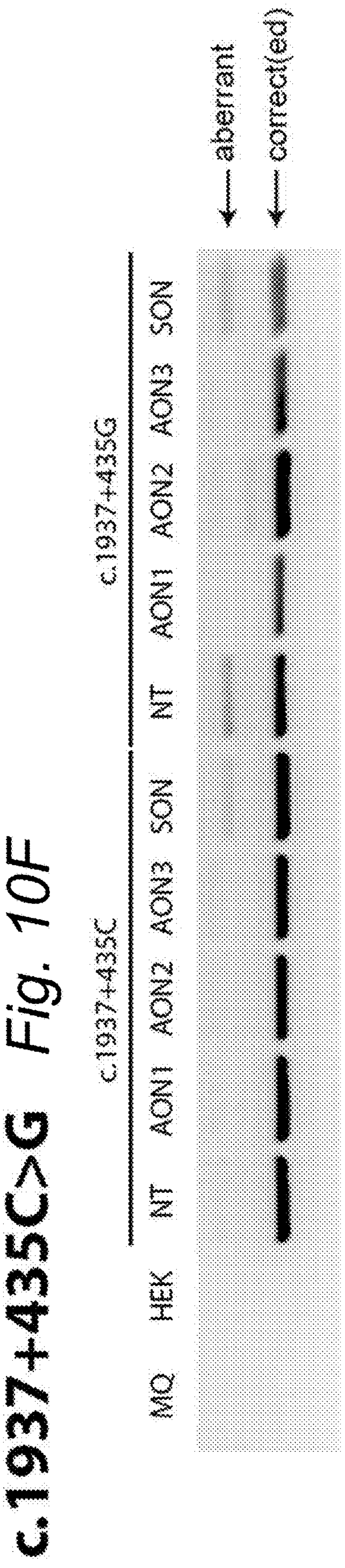
Figure 10G:
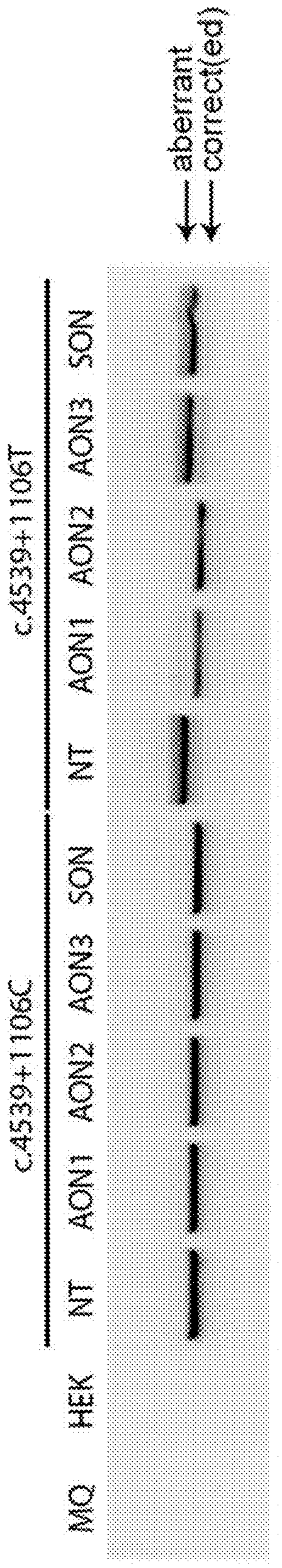

Representation of the percentage of the) FIG. 9B correct(ed) transcripts and the FIG. 9C aberrant transcripts after semi-quantification of two independent replicates. Based on the percentage AON molecules were classified in effective (solid grey), moderately effective (dotted pattern), poorly effective (striped pattern) and non-effective (crossed pattern). Solid, dotted and dashed lines indicate the thresholds to determine the effectiveness of the different AONs. In white are the controls indicating the basal aberrant transcript levels. In black the sample that was not treated with AON and was not subjected to CHX treatment.

FIG. 10A, FIG. 10B, FIG. 10C, FIG. 10D, FIG. 10E, FIG. 10F, FIG. 10G displays the screening of AONs for seven mutations in ABCA4 gene that cause pseudoexon inclusion. Midigenes containing the genomic region were mutagenized to insert the mutation found in humans. Subsequently these midigenes were transfected into HEK293T cells and 24 hours later different AONs were delivered to those cells. Analysis was performed by RT-PCR. For all variants three AONs were designed, and a SON was delivered as a negative control. NT states for non-treated and represents the transfected cells not subjected to AON treatment. HEK lane is an extra negative control consisting on untransfected HEK293T cells.

Description of the sequences

| SEQ ID NO: | Name: |
|---|---|
| 1 | genomic DNA ABCA4 |
| 2 | cDNA ABCA4 |
| 3 | Protein ABCA4 |
| 10 | Pseudoexon 30-31(68) RNA |
| 11 | Pseudoexon 30-31(68) RNA; smaller target |
| 12 | Pseudoexon 30-31 (68) RNA; smaller target (AON area +10) |
| 13 | AON-1 Pseudoexon 30-31 (68) target site and flanking sequences (+10 nt) |
| 14 | AON-1 Pseudoexon 30-31 (68) target site and flanking sequences (+5 nt) |
| 15 | AON-1 Pseudoexon 30-31 (68) |
| 16 | AON-2 Pseudoexon 30-31 (68) target site and flanking sequences (+10 nt) |
| 17 | AON-2 Pseudoexon 30-31 (68) target site and flanking sequences (+5 nt) |
| 18 | AON-2 Pseudoexon 30-31 (68) |
| 19 | AON-3 Pseudoexon 30-31 (68) target site and flanking sequences (+10 nt) |
| 20 | AON-3 Pseudoexon 30-31 (68) target site and flanking sequences (+5 nt) |
| 21 | AON-3 Pseudoexon 30-31 (68) |
| 30 | Pseudoexon 30-31 (345) RNA |
| 31 | Pseudoexon 30-31 (345) RNA; smaller target |
| 32 | Pseudoexon 30-31 (345) RNA; smaller target (AON area +10) |
| 33 | AON-1 Pseudoexon 30-31 (345) target site and flanking sequences (+10 nt) |
| 34 | AON-1 Pseudoexon 30-31 (345) target site and flanking sequences (+5 nt) |
| 35 | AON-1 Pseudoexon 30-31 (345) |
| 36 | AON-2 Pseudoexon 30-31 (345) target site and flanking sequences (+10 nt) |
| 37 | AON-2 Pseudoexon 30-31 (345) target site and flanking sequences (+5 nt) |
| 38 | AON-2 Pseudoexon 30-31 (345) |
| 39 | AON-3 Pseudoexon 30-31 (345) target site and flanking sequences (+10 nt) |
| 40 | AON-3 Pseudoexon 30-31 (345) target site and flanking sequences (+5 nt) |
| 41 | AON-3 Pseudoexon 30-31 (345) |
| 42 | AON-4 Pseudoexon 30-31 (345) target site and flanking sequences (+10 nt) |
| 43 | AON-4 Pseudoexon 30-31 (345) target site and flanking sequences (+5 nt) |
| 44 | AON-4 Pseudoexon 30-31 (345) |
| 45 | SON-1 Pseudoexon 30-31 (345) sense version of SEQ ID NO: 35 |
| 50 | pCI-Neo-Rho-ABCA4-30-31 wild type |
| 51 | pCI-Neo-Rho-ABCA4-30-31 c.4539 + 1100G |
| 52 | pCI-Neo-Rho-ABCA4-30-31 c.4539 + 1106T |
| 53 | pCI-Neo-Rho-ABCA4-30-31 c.4539 + 2001A |
| 54 | ABCA4_ex2 Fw |
| 55 | ACTB_ex3 Fw |
| 56 | ABCA4_ex30 Fw |
| 57 | ABCA4_ex20/21 Fw |
| 58 | CRX Fw |
| 59 | LIN28 Fw |
| 60 | NANOG Fw |
| 61 | OCT4 Fw |
| 62 | OPN1M/LW Fw |
| 63 | OPN1SWFw |
| 64 | RCV1 Fw |
| 65 | SOX2 Fw |
| 66 | ABCA4_ex5 Rv |
| 67 | ACTB_ex4 Rv |
| 68 | ABCA4_ex31 Rv |
| 69 | ABCA4_ex21 Rv |
| 70 | CRX Rv |
| 71 | LIN28 Rv |
| 72 | NANOG Rv |
| 73 | OCT4 Rv |
| 74 | OPN1M/LW Rv |
| 75 | OPN1SW Rv |
| 76 | RCV1 Rv |

-continued

| Description of the sequences | |
|---|---|
| SEQ ID NO: | Name: |
| 77 | SOX2 Rv |
| 80 | Pseudoexon 6-7 (162) |
| 81 | Pseudoexon 6-7 (162) larger target + flanking sequences (+50 nt) |
| 82 | Pseudoexon 6-7 (162) larger target + flanking sequences (+20 nt) |
| 83 | AON-1 Pseudoexon 6-7 (162) target site and flanking sequences (+10 nt) |
| 84 | AON-1 Pseudoexon 6-7 (162) target site and flanking sequences (+5 nt) |
| 85 | AON-1 Pseudoexon 6-7 (162) |
| 86 | AON-2 Pseudoexon 6-7 (162) target site and flanking sequences (+10 nt) |
| 87 | AON-2 Pseudoexon 6-7 (162) target site and flanking sequences (+5 nt) |
| 88 | AON-2 Pseudoexon 6-7 (162) |
| 89 | AON-3 Pseudoexon 6-7 (162) target site and flanking sequences (+10 nt) |
| 90 | AON-3 Pseudoexon 6-7 (162) target site and flanking sequences (+5 nt) |
| 91 | AON-3 Pseudoexon 6-7 (162) |
| 100 | Pseudoexon 7-8 (141) |
| 101 | Pseudoexon 7-8 (141) larger target + flanking sequences (+50 nt) |
| 102 | Pseudoexon 7-8 (141) larger target + flanking sequences (+20 nt) |
| 103 | AON-1 Pseudoexon 7-8 (141) target site and flanking sequences (+10 nt) |
| 104 | AON-1 Pseudoexon 7-8 (141) target site and flanking sequences (+5 nt) |
| 105 | AON-1 Pseudoexon 7-8 (141) |
| 106 | AON-2 Pseudoexon 7-8 (141) target site and flanking sequences (+10 nt) |
| 107 | AON-2 Pseudoexon 7-8 (141) target site and flanking sequences (+5 nt) |
| 108 | AON-2 Pseudoexon 7-8 (141) |
| 109 | AON-3 Pseudoexon 7-8 (141) target site and flanking sequences (+10 nt) |
| 110 | AON-3 Pseudoexon 7-8 (141) target site and flanking sequences (+5 nt) |
| 111 | AON-3 Pseudoexon 7-8 (141) |
| 120 | Pseudoexon 7-8 (56) |
| 121 | Pseudoexon 7-8 (56) larger target + flanking sequences (+50 nt) |
| 122 | Pseudoexon 7-8 (56) larger target + flanking sequences (+20 nt) |
| 123 | AON-1 Pseudoexon 7-8 (56) target site and flanking sequences (+10 nt) |
| 124 | AON-1 Pseudoexon 7-8 (56) target site and flanking sequences (+5 nt) |
| 125 | AON-1 Pseudoexon 7-8 (56) |
| 126 | AON-2 Pseudoexon 7-8 (56) target site and flanking sequences (+10 nt) |
| 127 | AON-2 Pseudoexon 7-8 (56) target site and flanking sequences (+5 nt) |
| 128 | AON-2 Pseudoexon 7-8 (56) |
| 129 | AON-3 Pseudoexon 7-8 (56) target site and flanking sequences (+10 nt) |
| 130 | AON-3 Pseudoexon 7-8 (56) target site and flanking sequences (+5 nt) |
| 131 | AON-3 Pseudoexon 7-8 (56) |
| 140 | Pseudoexon 13-14 (134) |
| 141 | Pseudoexon 13-14 (134) larger target + flanking sequences (+50 nt) |
| 142 | Pseudoexon 13-14 (134) larger target + flanking sequences (+20 nt) |
| 143 | AON-1 Pseudoexon 13-14 (134) target site and flanking seq's (+10 nt) |
| 144 | AON-1 Pseudoexon 13-14 (134) target site and flanking seq's (+5 nt) |
| 145 | AON-1 Pseudoexon 13-14 (134) |
| 146 | AON-2 Pseudoexon 13-14 (134) target site and flanking seq's (+10 nt) |
| 147 | AON-2 Pseudoexon 13-14 (134) target site and flanking seq's (+5 nt) |
| 148 | AON-2 Pseudoexon 13-14 (134) |
| 149 | AON-3 Pseudoexon 13-14 (134) target site and flanking seq's (+10 nt) |
| 150 | AON-3 Pseudoexon 13-14 (134) target site and flanking seq's (+5 nt) |
| 151 | AON-3 Pseudoexon 13-14 (134) |
| 160 | Pseudoexon 30-31 (68) |
| 161 | Pseudoexon 30-31 (68) larger target + flanking sequences (+50 nt) |
| 162 | Pseudoexon 30-31 (68) larger target + flanking sequences (+20 nt) |
| 163 | AON-1 Pseudoexon 30-31 (68) target site and flanking seq's (+10 nt) |
| 164 | AON-1 Pseudoexon 30-31 (68) target site and flanking sequences (+5 nt) |
| 165 | AON-1 Pseudoexon 30-31 (68) |
| 166 | AON-2 Pseudoexon 30-31 (68) target site and flanking seq's (+10 nt) |
| 167 | AON-2 Pseudoexon 30-31 (68) target site and flanking sequences (+5 nt) |
| 168 | AON-2 Pseudoexon 30-31 (68) |
| 169 | AON-3 Pseudoexon 30-31 (68) target site and flanking seq's (+10 nt) |
| 170 | AON-3 Pseudoexon 30-31 (68) target site and flanking sequences (+5 nt) |
| 171 | AON-3 Pseudoexon 30-31 (68) |
| 180 | Pseudoexon 30-31 (345) |
| 181 | Pseudoexon 30-31 (345) larger target + flanking sequences (+20 nt) |
| 182 | AON-1 Pseudoexon 30-31 (345) target site and flanking seq's (+10 nt) |
| 183 | AON-1 Pseudoexon 30-31 (345) target site and flanking seq's (+5 nt) |
| 184 | AON-1 Pseudoexon 30-31 (345) |
| 185 | AON-2 Pseudoexon 30-31 (345) target site and flanking seq's (+10 nt) |
| 186 | AON-2 Pseudoexon 30-31 (345) target site and flanking seq's (+5 nt) |
| 187 | AON-2 Pseudoexon 30-31 (345) |
| 188 | AON-3 Pseudoexon 30-31 (345) target site and flanking seq's (+10 nt) |
| 189 | AON-3 Pseudoexon 30-31 (345) target site and flanking seq's (+5 nt) |
| 190 | AON-3 Pseudoexon 30-31 (345) |
| 191 | AON-4 Pseudoexon 30-31 (345) target site and flanking seq's (+10 nt) |
| 192 | AON-4 Pseudoexon 30-31 (345) target site and flanking seq's (+5 nt) |
| 193 | AON-4 Pseudoexon 30-31 (345) |

-continued

| Description of the sequences | |
|---|---|
| SEQ ID NO: | Name: |
| 194 | AON-5 Pseudoexon 30-31 (345) target site and flanking seq's (+10 nt) |
| 195 | AON-5 Pseudoexon 30-31 (345) target site and flanking seq's (+5 nt) |
| 196 | AON-5 Pseudoexon 30-31 (345) |
| 197 | AON-6 Pseudoexon 30-31 (345) target site and flanking seq's (+10 nt) |
| 198 | AON-6 Pseudoexon 30-31 (345) target site and flanking seq's (+5 nt) |
| 199 | AON-6 Pseudoexon 30-31 (345) |
| 200 | AON-7 Pseudoexon 30-31 (345) target site and flanking seq's (+10 nt) |
| 201 | AON-7 Pseudoexon 30-31 (345) target site and flanking seq's (+5 nt) |
| 202 | AON-7 Pseudoexon 30-31 (345) |
| 203 | AON-8 Pseudoexon 30-31 (345) target site and flanking seq's (+10 nt) |
| 204 | AON-8 Pseudoexon 30-31 (345) target site and flanking seq's (+5 nt) |
| 205 | AON-8 Pseudoexon 30-31 (345) |
| 206 | AON-9 Pseudoexon 30-31 (345) target site and flanking seq's (+10 nt) |
| 207 | AON-9 Pseudoexon 30-31 (345) target site and flanking seq's (+5 nt) |
| 208 | AON-9 Pseudoexon 30-31 (345) |
| 209 | AON-10 Pseudoexon 30-31 (345) target site and flanking seq's (+10 nt) |
| 210 | AON-10 Pseudoexon 30-31 (345) target site and flanking seq's (+5 nt) |
| 211 | AON-10 Pseudoexon 30-31 (345) |
| 212 | AON-11 Pseudoexon 30-31 (345) target site and flanking seq's (+10 nt) |
| 213 | AON-11 Pseudoexon 30-31 (345) target site and flanking seq's (+5 nt) |
| 214 | AON-11 Pseudoexon 30-31 (345) |
| 215 | AON-12 Pseudoexon 30-31 (345) target site and flanking seq's (+10 nt) |
| 216 | AON-12 Pseudoexon 30-31 (345) target site and flanking seq's (+5 nt) |
| 217 | AON-12 Pseudoexon 30-31 (345) |
| 218 | AON-13 Pseudoexon 30-31 (345) target site and flanking seq's (+10 nt) |
| 219 | AON-13 Pseudoexon 30-31 (345) target site and flanking seq's (+5 nt) |
| 220 | AON-13 Pseudoexon 30-31 (345) |
| 221 | AON-14 Pseudoexon 30-31 (345) target site and flanking seq's (+10 nt) |
| 222 | AON-14 Pseudoexon 30-31 (345) target site and flanking seq's (+5 nt) |
| 223 | AON-14 Pseudoexon 30-31 (345) |
| 224 | AON-15 Pseudoexon 30-31 (345) target site and flanking seq's (+10 nt) |
| 225 | AON-15 Pseudoexon 30-31 (345) target site and flanking seq's (+5 nt) |
| 226 | AON-15 Pseudoexon 30-31 (345) |
| 227 | AON-16 Pseudoexon 30-31 (345) target site and flanking seq's (+10 nt) |
| 228 | AON-16 Pseudoexon 30-31 (345) target site and flanking seq's (+5 nt) |
| 229 | AON-16 Pseudoexon 30-31 (345) |
| 230 | AON-17 Pseudoexon 30-31 (345) target site and flanking seq's (+10 nt) |
| 231 | AON-17 Pseudoexon 30-31 (345) target site and flanking seq's (+5 nt) |
| 232 | AON-17 Pseudoexon 30-31 (345) |
| 233 | AON-18 Pseudoexon 30-31 (345) target site and flanking seq's (+10 nt) |
| 234 | AON-18 Pseudoexon 30-31 (345) target site and flanking seq's (+5 nt) |
| 235 | AON-18 Pseudoexon 30-31 (345) |
| 236 | AON-19 Pseudoexon 30-31 (345) target site and flanking seq's (+10 nt) |
| 237 | AON-19 Pseudoexon 30-31 (345) target site and flanking seq's (+5 nt) |
| 238 | AON-19 Pseudoexon 30-31 (345) |
| 239 | AON-20 Pseudoexon 30-31 (345) target site and flanking seq's (+10 nt) |
| 240 | AON-20 Pseudoexon 30-31 (345) target site and flanking seq's (+5 nt) |
| 241 | AON-20 Pseudoexon 30-31 (345) |
| 242 | AON-21 Pseudoexon 30-31 (345) target site and flanking seq's (+10 nt) |
| 243 | AON-21 Pseudoexon 30-31 (345) target site and flanking seq's (+5 nt) |
| 244 | AON-21 Pseudoexon 30-31 (345) |
| 245 | AON-22 Pseudoexon 30-31 (345) target site and flanking seq's (+10 nt) |
| 246 | AON-22 Pseudoexon 30-31 (345) target site and flanking seq's (+5 nt) |
| 247 | AON-22 Pseudoexon 30-31 (345) |
| 248 | AON-23 Pseudoexon 30-31 (345) target site and flanking seq's (+10 nt) |
| 249 | AON-23 Pseudoexon 30-31 (345) target site and flanking seq's (+5 nt) |
| 250 | AON-23 Pseudoexon 30-31 (345) |
| 251 | AON-24 Pseudoexon 30-31 (345) target site and flanking seq's (+10 nt) |
| 252 | AON-24 Pseudoexon 30-31 (345) target site and flanking seq's (+5 nt) |
| 253 | AON-24 Pseudoexon 30-31 (345) |
| 254 | AON-25 Pseudoexon 30-31 (345) target site and flanking seq's (+10 nt) |
| 255 | AON-25 Pseudoexon 30-31 (345) target site and flanking seq's (+5 nt) |
| 256 | AON-25 Pseudoexon 30-31 (345) |
| 257 | AON-26 Pseudoexon 30-31 (345) target site and flanking seq's (+10 nt) |
| 258 | AON-26 Pseudoexon 30-31 (345) target site and flanking seq's (+5 nt) |
| 259 | AON-26 Pseudoexon 30-31 (345) |
| 260 | Pseudoexon 36-37 (188) |
| 261 | Pseudoexon 36-37 (188) larger target + flanking sequences (+50 nt) |
| 262 | Pseudoexon 36-37 (188) larger target + flanking sequences (+20 nt) |
| 263 | AON-1 Pseudoexon 36-37 (188) target site and flanking seq's (+10 nt) |
| 264 | AON-1 Pseudoexon 36-37 (188) target site and flanking seq's (+5 nt) |
| 265 | AON-1 Pseudoexon 36-37 (188) |
| 266 | AON-2 Pseudoexon 36-37 (188) target site and flanking seq's (+10 nt) |
| 267 | AON-2 Pseudoexon 36-37 (188) target site and flanking seq's (+5 nt) |
| 268 | AON-2 Pseudoexon 36-37 (188) |

-continued

| Description of the sequences | |
|---|---|
| SEQ ID NO: | Name: |
| 269 | AON-3 Pseudoexon 36-37 (188) target site and flanking seq's (+10 nt) |
| 270 | AON-3 Pseudoexon 36-37 (188) target site and flanking seq's (+5 nt) |
| 271 | AON-3 Pseudoexon 36-37 (188) |
| 280 | SON-1 (c.4539 + 2001G > A, sense version of AON1 30-31 (345)) |
| 281 | SON-2 (c.4539 + 2001G > A, sense version of AON4 30-31 (345)) |
| 282 | SON-3 (c.1937 + 435C > G, sense version of AON2 13-14 (134)) |
| 290 | pCI-Neo-Rho-ABCA4-intron6-intron7 wild type |
| 291 | pCI-Neo-Rho-ABCA4-intron6-intron7 c.769 − 784T |
| 292 | pCI-Neo-Rho-ABCA4-intron6-intron11 wild type |
| 293 | pCI-Neo-Rho-ABCA4-intron6-intron11 c.859 − 540G |
| 294 | pCI-Neo-Rho-ABCA4-intron6-intron11 c.859 − 506C |
| 295 | pCI-Neo-Rho-ABCA4-intron11-intron15 wild type |
| 296 | pCI-Neo-Rho-ABCA4-intron11-intron15 c.1937 + 435G |
| 297 | pCI-Neo-Rho-ABCA4-intron29-intron32 wild type |
| 298 | pCI-Neo-Rho-ABCA4-intron29-intron32 c.4539 + 1100G |
| 299 | pCI-Neo-Rho-ABCA4-intron29-intron32 c.4539 + 1106T |
| 300 | pCI-Neo-Rho-ABCA4-intron31-intron37 wild type |
| 301 | pCI-Neo-Rho-ABCA4-intron31-intron37 c.5197 − 557T |
| 302 | RHO_ex3 fw |
| 303 | ABCA4_ex7 rev |
| 304 | ABCA4_ex7 fw |
| 305 | ABCA4_ex8 rev |
| 306 | ABCA4_ex13 fw |
| 307 | ABCA4_ex14 rev |
| 308 | ABCA4_ex30 fw |
| 309 | ABCA4_ex32 rev |
| 310 | ABCA4_ex32 fw |
| 311 | ABCA4_ex37 rev |

TABLE 1

Antisense oligonucleotide (AON) characteristics

| Name | SEQ ID NO: | Sequence 5'→3' | Length | % GC | Tm (° C.) |
|---|---|---|---|---|---|
| AON-1 Pseudoexon 30-31 (68) | 15/165 | GUAAUCUGUUCUGGACUU | 18 | 39 | 43.5 |
| AON-2 Pseudoexon 30-31 (68) | 18/168 | UAGAACUCCCAGGACAGG | 18 | 56 | 50.3 |
| AON-3 Pseudoexon 30-31 (68) | 21/171 | CUAAAUCCCCCAGGAGAU | 18 | 50 | 48 |
| AON-1 Pseudoexon 6-7 (162) | 85 | GAUGGAAUCACUGAUCCUAG | 20 | 45 | 49.7 |
| AON-2 Pseudoexon 6-7 (162) | 88 | AGCUCCAGAGACUGAUGUGA | 20 | 50 | 51.8 |
| AON-3 Pseudoexon 6-7 (162) | 91 | CUCACCACUGCUCCUGC | 17 | 65 | 51.9 |
| AON-1 Pseudoexon 7-8 (141) | 105 | CCCACCAAGAUGGGGAUACU | 20 | 55 | 53.8 |
| AON-2 Pseudoexon 7-8 (141) | 108 | GGUUCUGUUGUCCCACCAAG | 20 | 55 | 53.8 |
| AON-3 Pseudoexon 7-8 (141) | 111 | CAAAUCACAGACUGACCCCU | 20 | 50 | 51.8 |

TABLE 1-continued

| Antisense oligonucleotide (AON) characteristics | | | | | |
|---|---|---|---|---|---|
| Name | SEQ ID NO: | Sequence 5'→3' | Length | % GC | Tm (° C.) |
| AON-1 Pseudoexon 7-8 (56) | 125 | GACUGAGCAAUACUCCGUC | 19 | 53 | 51.1 |
| AON-2 Pseudoexon 7-8 (56) | 128 | AUCACAGAGUGACCCCUAG | 19 | 53 | 51.1 |
| AON-3 Pseudoexon 7-8 (56) | 131 | CUGAGCAAUACUCCGUCU<u>G</u> | 19 | 53 | 51.1 |
| AON-1 Pseudoexon 13-14 (134) | 145 | CUCCCAGGAACCAGACCUA | 19 | 58 | 53.2 |
| AON-2 Pseudoexon 13-14 (134) | 148 | GCUCAUCCAACACAUUCCUC | 20 | 50 | 51.8 |
| AON-3 Pseudoexon 13-14 (134) | 151 | CCUGGGAUGGGAGUGUC | 17 | 65 | 51.9 |
| AON-1 Pseudoexon 30-31 (345) | 35/184 | ACAGGAG<u>U</u>CCUCAGCAUUG | 19 | 53 | 51.1 |
| AON-2 Pseudoexon 30-31 (345) | 38/187 | UUUUGUCCAGGGACCAAGG | 19 | 53 | 51.1 |
| AON-3 Pseudoexon 30-31 (345) | 41/190 | CUGUUACAUUUUGUCCAGG | 19 | 42 | 46.8 |
| AON-4 Pseudoexon 30-31 (345) | 44/193 | GGGGCACAGAGGACUGAGA | 19 | 63 | 55.4 |
| AON-5 Pseudoexon 30-31 (345) | 196 | GAGAGAAAAUAUUGCUUGAGAA | 22 | 32 | 47.4 |
| AON-6 Pseudoexon 30-31 (345) | 199 | GCAGAUGAGCUGUGAUUCAA | 20 | 45 | 49.7 |
| AON-7 Pseudoexon 30-31 (345) | 202 | UAUGAUGCAGCAGAUGAGCUG | 21 | 48 | 52.4 |
| AON-8 Pseudoexon 30-31 (345) | 205 | UGGGAUCCCUAUGAUGCAGC | 20 | 55 | 53.8 |
| AON-9 Pseudoexon 30-31 (345) | 208 | AGAGGACUGAGACAAGUUCC | 20 | 50 | 51.8 |
| AON-10 Pseudoexon 30-31 (345) | 211 | GCUUCCUCUUGGGGCACAGA | 20 | 60 | 55.9 |
| AON-11 Pseudoexon 30-31 (345) | 214 | CCUCAGCAUUGACAGCAA | 18 | 50 | 48 |
| AON-12 Pseudoexon 30-31 (345) | 217 | ACAGGAGCCCUCAGCAUUG | 19 | 58 | 53.2 |

TABLE 1-continued

Antisense oligonucleotide (AON) characteristics

| Name | SEQ ID NO: | Sequence 5'→3' | Length | % GC | Tm (° C.) |
|---|---|---|---|---|---|
| AON-13 Pseudoexon 30-31 (345) | 220 | UGGAGGCAGCCACAGGAG | 18 | 67 | 54.9 |
| AON-14 Pseudoexon 30-31 (345) | 223 | GAUGCUGGAGGGUUUUGAGUG | 21 | 52 | 54.4 |
| AON-15 Pseudoexon 30-31 (345) | 226 | GAUGCUGG<u>**A**</u>GAGUUUUGAGUG | 21 | 48 | 52.4 |
| AON-16 Pseudoexon 30-31 (345) | 229 | GCCUUGACGUCCUGAUGCU | 19 | 58 | 53.2 |
| AON-17 Pseudoexon 30-31 (345) | 232 | GCCAAGAGCUCAGGGUACAG | 20 | 60 | 55.9 |
| AON-18 Pseudoexon 30-31 (345) | 235 | CUUGGCCUCCCCUCCCUC | 18 | 72 | 57.2 |
| AON-19 Pseudoexon 30-31 (345) | 238 | AACACCAUGUAGGUAGGC | 18 | 50 | 48 |
| AON-20 Pseudoexon 30-31 (345) | 241 | GUUUAGGAAAUGAAACACCAUG | 22 | 36 | 49.2 |
| AON-21 Pseudoexon 30-31 (345) | 244 | GACCGCGUGGAAGUAAGG | 18 | 61 | 52.6 |
| AON-22 Pseudoexon 30-31 (345) | 247 | AUAAGUUUCUAAGCUGGACAG | 21 | 38 | 48.5 |
| AON-23 Pseudoexon 30-31 (345) | 250 | GGACCAAGGACCAACACUAC | 20 | 55 | 53.8 |
| AON-24 Pseudoexon 30-31 (345) | 253 | GGCUGUUACAUUUUGUCCAGG | 21 | 48 | 52.4 |
| AON-25 Pseudoexon 30-31 (345) | 256 | GGCAGGAACUGGCUUGCCUU | 20 | 60 | 55.9 |
| AON-26 Pseudoexon 30-31 (345) | 259 | AGAAGUGAAAGAAAAUGGCAGG | 22 | 41 | 51.1 |
| AON-1 Pseudoexon 36-37 (188) | 265 | CAGAGUUGGGCACUGUUC | 18 | 56 | 50.3 |
| AON-2 Pseudoexon 36-37 (188) | 268 | GGCUGAUCUGGUGCAGG | 17 | 65 | 51.9 |
| AON-3 Pseudoexon 36-37 (188) | 271 | CUUACAGGAGGCUGAUCUG | 19 | 53 | 51.1 |
| SON-1 Pseudoexon 30-31 (345) | 45/280 | CAAUGCUGAGG<u>**A**</u>CUCCUGU Sense version of AON-1 (SEQ ID NO: 35/184) | 19 | 53 | 51.1 |

TABLE 1-continued

| Antisense oligonucleotide (AON) characteristics | | | | | |
|---|---|---|---|---|---|
| Name | SEQ ID NO: | Sequence 5'→3' | Length | % GC | Tm (° C.) |
| SON-2 Pseudoexon 30-31 (345) | 281 | UCUCAGUCCUCUGUGCCCC Sense version of AON-4 (SEQ ID NO: 44/193) | 19 | 63 | 55.4 |
| SON-3 Pseudoexon 13-14 (134) | 282 | GAGGAAUGUGUUGGAUGAGC Sense version of AON-2 (SEQ ID NO: 148) | 20 | 50 | 51.8 |

Some mutations are located within a pseudoexon (e.g. when the mutation creates an ESE which in turn creates the pseudoexon, the mutation will be part of the pseudoexon) The AONs designed to redirect splicing will have a mismatch in view of the wild-type sequence at the site of the mutation. This is the case for AON's with SEQ ID NO's: 35/184, 131 and 226 and for SON with SEQ ID NO: 45/280; the mutation in view of the wild-type sequence is depicted bold and underlined.

Table 2 describes the characteristics of 26 AONs that were tested for their efficacy to redirect PE inclusion due to the c.4539+2001G>A change. AONs are listed from 5'- to 3'-end of the pseudoexon. Column 2 lists the position relative to the PE. Columns 3 to 6 lists the number of predicted exonic splice enhancer motifs, i.e. SF2, SC35, SRp40 and SRp55 that overlap with the corresponding AON. Column 7 lists the configuration of the RNA at the position of the AONs, i.e. open, closed or a mixed configuration.

TABLE 2

| Additional information on AONs for pseudoexon 30-31 (345) | | | | | | | |
|---|---|---|---|---|---|---|---|
| AON # | Target region | SF2 | SC35 | SRp40 | SRp55 | Type of region | Other comments |
| 5 | intron | 0 | 0 | 1 | 0 | Mixed | |
| 6 | acceptor | 1 | 1 | 1 | 2 | Mixed | |
| 7 | acceptor | 1 | 1 | 2 | 2 | Mixed | |
| 8 | PE | 0 | 2 | 2 | 2 | Mixed | |
| 9 | PE | 0 | 1 | 2 | 0 | Mixed | Partially overlapping with AON4 |
| 4 | PE | 1 | 3 | 3 | 0 | Mixed | |
| 10 | PE | 2 | 3 | 1 | 0 | Mixed | Partially overlapping with AON4 |
| 11 | PE | 1 | 1 | 1 | 1 | Mixed | Partially overlapping with AON1 |
| 1 | PE | 1 | 1 | 2 | 2 | Mixed | c. 4539 + 2001G > A specific |
| 12 | PE | 1 | 1 | 2 | 1 | Mixed | WT version of AON1 |
| 13 | PE | 0 | 2 | 2 | 2 | Mixed | Partially overlapping with AON1 |
| 14 | PE | 1 | 1 | 2 | 1 | Closed/Open | WT version of AON15 |
| 15 | PE | 1 | 1 | 2 | 1 | Closed/Open | c. 4539 + 2028C > T specific |
| 16 | PE | 1 | 0 | 1 | 2 | Mixed | |
| 17 | PE | 0 | 4 | 0 | 0 | Closed/Open | |
| 18 | PE | 1 | 0 | 0 | 0 | Closed/Open | |
| 19 | PE | 0 | 0 | 1 | 2 | Closed/Open | |
| 20 | PE | 0 | 1 | 2 | 1 | Closed/Open | |
| 21 | PE | 1 | 1 | 3 | 1 | Mixed | |
| 22 | PE | 0 | 0 | 0 | 0 | Mixed | |
| 23 | PE | 0 | 2 | 2 | 0 | Mixed | |
| 2 | PE | 1 | 2 | 0 | 0 | Mixed | |
| 3 | PE | 1 | 1 | 2 | 0 | Mixed | |
| 24 | PE | 1 | 1 | 2 | 0 | Mixed | Equal to AON3 but 3 nt longer |
| 25 | Donor site | 0 | 1 | 0 | 0 | Mixed | |
| 26 | Intron | 0 | 2 | 2 | 0 | Mixed | |

DETAILED DESCRIPTION OF THE INVENTION

By definition, AONs are substantially complementary (antisense) to their target, allowing them to bind to the corresponding pre-mRNA molecule, thereby preventing the binding of proteins essential for splicing. Usually, this lack of binding results in the skipping of the targeted exon, as the present inventors have previously shown for the c.2991+1655A>G mutation in CEP290 (Collin et al., 2012; Garanto et al., 2016). In addition, AONs may redirect the splicing machinery towards adjacent splice acceptor or donor sites. This has led the inventors to select ABCA4 mutations that may also be amenable for AON-based splice modulation therapy. These mutations are all deep-intronic variants that create novel splice acceptor, splice donor or exonic splice enhancer binding sites, and result in the inclusion of pseudoexons to the mRNA of the corresponding gene. AONs will be employed to block the recognition of (and thereby induce skipping of) the pseudoexon, thereby fully restoring the wild-type transcript and corresponding protein function. The following mutations have been selected:

- c.769-784C>T. This mutation results in the insertion of a 162-nt pseudoexon in between exons 6 and 7 of ABCA4.
- c.859-540C>G. This mutation results in the insertion of a 141-nt pseudoexon in between exons 7 and 8 of ABCA4.
- c.859-506G>C. This mutation results in the insertion of a 56-nt pseudoexon in between exons 7 and 8 of ABCA4.
- c.1937+435C>G. This mutation results in the insertion of a 134-nt pseudoexon in between exons 13 and 14 of ABCA4.
- c.4539+1100A>G and c.4539+1106C>T. These mutations result in the same insertion of a 68-nt pseudoexon in between exons 30 and 31 of ABCA4 and can thus be treated with the same AONs.
- c.4539+2001G>A and c.4539+2028C>T. These mutations result in the same insertion of a 345-nt pseudoexon in between exons 30 and 31 of ABCA4 and can thus be treated with the same AONs.
- c.5197-557G>T. This mutation results in the insertion of a 188-nt pseudoexon in between exons 36 and 37 of ABCA4.

The inventors have provided AONs to modulate splicing for the mutation classes depicted here above; the terms “modulate splicing” and “redirect splicing” are used herein interchangeably and encompass AON-based splice modulation therapy for the mutations depicted here above.

Accordingly, the present invention provides for an antisense oligonucleotide for redirecting splicing that is:

- complementary or substantially complementary to a polynucleotide with a nucleotide sequence consisting of SEQ ID NO: 10, 161, 30, 81, 101, 121, 141 or SEQ ID NO: 261, or a part thereof;
- preferably complementary or substantially complementary to a polynucleotide with a nucleotide sequence consisting of SEQ ID NO: 162, 181, 82, 102, 122, 142 or SEQ ID NO: 262, or a part thereof;
- more preferably complementary or substantially complementary to a polynucleotide with a nucleotide sequence consisting of SEQ ID NO: 160, 180, 80, 100, 120, 140 or SEQ ID NO: 260, or a part thereof
- more preferably complementary or substantially complementary to a polynucleotide with a nucleotide sequence consisting of SEQ ID NO: 11 or SEQ ID NO: 31, or a part thereof;
- more preferably complementary or substantially complementary to a polynucleotide with a nucleotide sequence consisting of SEQ ID NO: 12 or SEQ ID NO: 32, or a part thereof;
- more preferably complementary or substantially complementary to a polynucleotide with a nucleotide sequence selected from the group consisting of SEQ ID NO: 13, 16, 19, 163, 166, 169, 33, 36, 39, 42, 182, 185, 188, 191, 194, 197, 200, 203, 206, 209, 212, 215, 218, 221, 224, 227, 230, 233, 236, 239, 242, 245, 248, 251, 254, 257, 83, 86, 89, 103, 106, 109, 123, 126, 129, 143, 146, 149, 263, 266 and SEQ ID NO: 269, or a part thereof; and
- more preferably complementary or substantially complementary to a polynucleotide with a nucleotide sequence selected from the group consisting of SEQ ID NO: 14, 17, 20, 164, 167, 170, 34, 37, 40, 43, 183, 186, 189, 192, 195, 198, 201, 204, 207, 210, 213, 216, 219, 222, 225, 228, 231, 234, 237, 240, 243, 246, 249, 252, 255, 258, 84, 87, 90, 104, 107, 110, 124, 127, 130, 144, 147, 150, 264, 268 and SEQ ID NO: 270, or a part thereof.

Herein, there is referred to: “SEQ ID NO: 10, 161, 30, 81, 101, 121, 141 and SEQ ID NO: 261, or a part thereof”. In the context of the invention:

- SEQ ID NO:'s 11, 12, 13, 14, 16, 17, 19, 20, 160, 162, 163, 164, 166, 167, 169 and 170 or a part thereof, are each a preferred part of SEQ ID NO: 10 and 161;
- SEQ ID NO:'s 181, 180, 31, 32, 33, 34, 36, 37, 39, 40, 42, 43, 182, 185, 188, 191, 194, 197, 200, 203, 206, 209, 212, 215, 218, 221, 224, 227, 230, 233, 236, 239, 242, 245, 248, 251, 254, 257, 183, 186, 189, 192, 195, 198, 201, 204, 207, 210, 213, 216, 219, 222, 225, 228, 231, 234, 237, 240, 243, 246, 249, 252, 255 and 258 or a part thereof, are each a preferred part of SEQ ID NO: 30;
- SEQ ID NO:'s 82, 80, 83, 86, 89, 84, 87 and 90 or a part thereof, are each a preferred part of SEQ ID NO: 81;
- SEQ ID NO:'s 102, 100, 103, 106, 109, 104, 107 and 110 or a part thereof, are each a preferred part of SEQ ID NO: 10;
- SEQ ID NO:'s 122, 120, 123, 126, 129, 124, 127 and 130 or a part thereof, are each a preferred part of SEQ ID NO: 121;
- SEQ ID NO:'s 142, 140, 143, 146, 149, 144, 147 and 150 or a part thereof, are each a preferred part of SEQ ID NO: 141;
- SEQ ID NO:'s 262, 260, 263, 266, 269, 264, 267 and 270 or a part thereof, are each a preferred part of SEQ ID NO: 261.

The term exon skipping is herein defined as inducing, producing or increasing production within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules. The term pre-mRNA refers to a non-processed or partly processed precursor mRNA that is synthesized from a DNA template of a cell by transcription, such as in the nucleus.

The term exon retention is herein defined as inducing, producing or increasing production within a cell of a mature mRNA that does retain a particular exon that should be present in the mature mRNA without (aberrant) exon skipping. Exon retention is achieved by providing a cell expressing the pre-mRNA of said mature mRNA with an AON molecule capable of interfering with sequences such as, for example, alternative splice sites upstream or downstream of the regular splice sites. The term "antisense oligonucleotide" or "AON" is understood to refer to an oligonucleotide molecule comprising a nucleotide sequence which is substantially complementary to a target nucleotide sequence in a pre-mRNA molecule, hnRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The terms "antisense oligonucleotide", "AON" and "oligonucleotide" are used interchangeably herein and are understood to refer to an oligonucleotide comprising an antisense sequence. Binding of an AON to its target can easily be assessed by the person skilled in the art using techniques that are known in the field such as the gel mobility shift assay as described in EP1619249. The term "substantially complementary" used in the context of the invention indicates that some mismatches in the antisense sequence are allowed as long as the functionality, i.e. inducing exon skipping or exon retention. Preferably, the complementarity is from 90% to 100%. In general this allows for 1 or 2 mismatches in an AON of 20 nucleotides or 1, 2, 3 or 4 mismatches in an AON of 40 nucleotides, or 1, 2, 3, 4, 5 or 6 mismatches in an AON of 60 nucleotides, etc. Optionally, said AON may further be tested by transfection into retina cells of patients. Skipping of an exon or retention of an exon may be assessed by RT-PCR (such as e.g. described in EP1619249). The complementary regions are preferably designed such that, when combined, they are specific for the exon in the pre-mRNA. Such specificity may be created with various lengths of complementary regions, as this depends on the actual sequences in other (pre-) mRNA molecules in the system.

The risk that the AON will also be able to hybridize to one or more other pre-mRNA molecules decreases with increasing size of the AON. It is clear that AONs comprising mismatches in the region of complementarity but that retain the capacity to hybridize and/or bind to the targeted region (s) in the pre-mRNA, can be used in the invention. However, preferably at least the complementary parts do not comprise such mismatches as AONs lacking mismatches in the complementary part typically have a higher efficiency and a higher specificity than AONs having such mismatches in one or more complementary regions. It is thought, that higher hybridization strengths, (i.e. increasing number of interactions with the opposing strand) are favorable in increasing the efficiency of the process of interfering with the splicing machinery of the system.

The AON according to the invention preferably does not contain a stretch of CpG, more preferably does not contain any CpG. The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an AON according to the invention by detecting the presence of a neutralizing antibody and/or an antibody recognizing said AON using a standard immunoassay known to the skilled person. An inflammatory reaction, type I-like interferon production, IL-12 production and/or an increase in immunogenicity may be assessed by detecting the presence or an increasing amount of a neutralizing antibody or an antibody recognizing said AON using a standard immunoassay. The AON according to the invention furthermore preferably has acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/-cail/biotool/oligo/index) for single stranded RNA using the basic Tm and the nearest neighbor model), and/or the free energy of the AON-target exon complex (using RNA structure version 4.5). If a Tm is too high, the AON is expected to be less specific. An acceptable Tm and free energy depend on the sequence of the AON. Therefore, it is difficult to give preferred ranges for each of these parameters. An acceptable Tm may be ranged between 35 and 70° C. and an acceptable free energy may be ranged between 15 and 45 kcal/mol. The skilled person may therefore first choose an AON as a potential therapeutic compound as binding and/or being complementary to SEQ ID NO: 10, 161, 30, 81, 101, 121, 141 or SEQ ID NO: 261, or a part thereof as defined later herein. The skilled person may check that said AON is able to bind to said sequences as earlier defined herein. Optionally in a second step, he may use the invention to further optimize said AON by checking for the absence of CpG and/or by optimizing its Tm and/or free energy of the AON-target complex. He may try to design an AON wherein few, preferably, no CpG and/or wherein a more acceptable Tm and/or free energy are obtained by choosing a distinct sequence of ABCA4 (including SEQ ID NO: 10, 161, 30, 81, 101, 121, 141 and SEQ ID NO: 261, or a part thereof) to which the AON is complementary. Alternatively, if an AON complementary to a given stretch within SEQ ID NO: 10 or 30, comprises a CpG, and/or does not have an acceptable Tm and/or free energy, the skilled person may improve any of these parameters by decreasing the length of the AON, and/or by choosing a distinct stretch within any of SEQ ID NO: 10, 161, 30, 81, 101, 121, 141 or SEQ ID NO: 261 to which the AON is complementary and/or by altering the chemistry of the AON.

An AON according to the invention is said to induce exon skipping if the skipping percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

An AON according to the invention is said to induce exon retention if the retention percentage as measured by real-time quantitative RT-PCR analysis is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

Preferably, an AON according to the invention comprising a part that is (substantially) complementary to SEQ ID NO: 10, 161, 30, 81, 101, 121, 141 or SEQ ID NO: 261, or a part thereof, or a part thereof, is an AON wherein the (substantially) complementary part is at least 50% of the length of the AON according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an AON according to the invention comprises or consists of a sequence that is complementary or substantially complementary to a part of SEQ ID NO: 10 or 30. As an example, an AON may comprise a sequence that is complementary or substantially complementary to a part of SEQ ID NO: 10 or 30 and comprise additional flanking sequences.

Preferably, an AON according to the invention is an AON wherein the part that is (substantially) complementary to a polynucleotide with a nucleotide sequence consisting of SEQ ID NO: 10 or SEQ ID NO: 30, or a part thereof, comprises at least one ESE (exon splice enhancer) motif, preferably two, three, four or more ESE motifs. ESE motifs are known to the person skilled in the art. Identification and determination of an ESE is preferably performed as in the examples herein. In an embodiment, an AON according to the invention does not comprise an ESE motif.

Preferably, an AON according to the invention is an AON wherein the part that is (substantially) complementary to a polynucleotide with a nucleotide sequence consisting of SEQ ID NO: 10, 161, 30, 81, 101, 121, 141 or SEQ ID NO: 261, or a part thereof, has a length of from about 8 to about 40 nucleotides, such as preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides. Preferably, an AON according to the invention is an AON wherein the part that is (substantially) complementary to a polynucleotide with a nucleotide sequence consisting of SEQ ID NO: 10, 161, 30, 81, 101, 121, 141 or SEQ ID NO: 261, or a part thereof, has a length of from 8 to 40 nucleotides, such as preferably from 10 to 40 nucleotides, more preferably from 14 to 30 nucleotides, more preferably from 16 to 24 nucleotides, such as 16, 17, 18, 19, 20, 21, 22, 23 or 24 nucleotides. Preferably, an AON according to the invention is an AON wherein the part that is (substantially) complementary to a polynucleotide with a nucleotide sequence consisting of SEQ ID NO: 10, 161, 30, 81, 101, 121, 141 or SEQ ID NO: 261, or a part thereof, or a part thereof, has a length of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides and said part that is (substantially) complementary to a polynucleotide with a nucleotide sequence consisting of SEQ ID NO: 10, 161, 30, 81, 101, 121, 141 or SEQ ID NO: 261, or a part thereof, or a part thereof, has a length of at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

Additional sequences the (substantially) complementary part may be used to modify the binding of a protein, such as a splice-promoting factor, to the AON, or to modify a thermodynamic property of the AON, such as to modify target RNA binding affinity.

A preferred AON for redirecting splicing according to the invention has a length of from about 8 to about 100 nucleotides, preferably from about 10 to about 40 nucleotides, more preferably from about 14 to about 30 nucleotides, more preferably from about 16 to 24 nucleotides, such as 16, 17, 18, 19, 20, 21, 22, 23 or 24 nucleotides. A more preferred AON for redirecting splicing according to the invention has a length of from 8 to 100 nucleotides, preferably from 10 to 40 nucleotides, more preferably from 14 to 30 nucleotides, more preferably from 16 to 24 nucleotides, such as 16, 17, 18, 19, 20, 21, 22, 23 or 24 nucleotides. Preferably, an AON according to the invention has a length of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. Preferably, an AON according to the invention has a length of at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides.

In an embodiment, there is provided an AON comprising or consisting of a sequence selected from the group consisting of SEQ ID NO: 15, 18, 21, 165, 168, 171, 35, 38, 41, 44, 184, 187, 190, 193, 196, 199, 202, 205, 208, 211, 214, 217, 220, 223, 226, 229, 232, 235, 238, 241, 244, 247, 250, 253, 256, 259, 85, 88, 91, 105, 108, 111, 125, 128, 131, 145, 148, 151, 265, 268 and SEQ ID NO: 271.

In a preferred embodiment, there is provided an AON comprising or consisting of a sequence selected from the group consisting of SEQ ID NO: 15. The preferred AON comprising SEQ ID NO: 15 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 18. The preferred AON comprising SEQ ID NO: 18 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 21. The preferred AON comprising SEQ ID NO: 21 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 35. The preferred AON comprising SEQ ID NO: 35 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 38. The preferred AON comprising SEQ ID NO: 38 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 41. The preferred AON comprising SEQ ID NO: 41 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 44. The preferred AON comprising SEQ ID NO: 44 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 165. The preferred AON comprising SEQ ID NO: 165 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 168. The preferred AON comprising SEQ ID NO: 168 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 171. The preferred AON comprising SEQ ID NO: 171 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 184. The preferred AON comprising SEQ ID NO: 184 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 187. The preferred AON comprising SEQ ID NO: 187 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 190. The preferred AON comprising SEQ ID NO: 190 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 193. The preferred AON comprising SEQ ID NO: 193 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 196. The preferred AON comprising SEQ ID NO: 196 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 199. The preferred AON comprising SEQ ID NO: 199 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 202. The preferred AON comprising SEQ ID NO: 202 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 205. The preferred AON comprising SEQ ID NO: 205 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 208. The preferred AON comprising SEQ ID NO: 208 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 211 The preferred AON comprising SEQ ID NO: 211 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 214. The preferred AON comprising SEQ ID NO: 214 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 217. The preferred AON comprising SEQ ID NO: 217 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 220. The preferred AON comprising SEQ ID NO: 220 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 223. The preferred AON comprising SEQ ID NO: 223 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 226. The preferred AON comprising SEQ ID NO: 226 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 229. The preferred AON comprising SEQ ID NO: 229 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 232. The preferred AON comprising SEQ ID NO: 232 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 235. The preferred AON comprising SEQ ID NO: 235 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 238. The preferred AON comprising SEQ ID NO: 238 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 241. The preferred AON comprising SEQ ID NO: 241 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 244. The preferred AON comprising SEQ ID NO: 244 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 247. The preferred AON comprising SEQ ID NO: 247 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 250. The preferred AON comprising SEQ ID NO: 250 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 253. The preferred AON comprising SEQ ID NO: 253 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 256. The preferred AON comprising SEQ ID NO: 256 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 259. The preferred AON comprising SEQ ID NO: 259 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 85. The preferred AON comprising SEQ ID NO: 85 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 88. The preferred AON comprising SEQ ID NO: 88 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 91. The preferred AON comprising SEQ ID NO: 91 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 105. The preferred AON comprising SEQ ID NO: 105 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 108. The preferred AON comprising SEQ ID NO: 108 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 111. The preferred AON comprising SEQ ID NO: 111 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 125. The preferred AON comprising SEQ ID NO: 125 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 128. The preferred AON comprising SEQ ID NO: 128 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 131. The preferred AON comprising SEQ ID NO: 131 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 145. The preferred AON comprising SEQ ID NO: 145 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 148. The preferred AON comprising SEQ ID NO: 148 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 151. The preferred AON comprising SEQ ID NO: 151 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 265. The preferred AON comprising SEQ ID NO: 265 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 268. The preferred AON comprising SEQ ID NO: 268 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In a preferred embodiment, there is provided an AON comprising or consisting of a sequence selected from the group consisting of SEQ ID NO: 271. The preferred AON comprising SEQ ID NO: 271 preferably comprises from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

An AON for redirecting splicing according to the invention may comprise one of more RNA residue (ribonucleotide), or one or more DNA residue (deoxyribonucleotide), and/or one or more nucleotide analogues or equivalents, as will be further detailed herein below.

It is preferred that an AON for redirecting splicing according to the invention comprises one or more residues that are modified to increase nuclease resistance, and/or to increase the affinity of the antisense oligonucleotide for the target sequence. Therefore, in a preferred embodiment, the AON comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents.

Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report, demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen et al., 1991). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar, 2005). Since the backbone of a PNA molecule contains no charged phosphate groups, PNA-RNA hybrids are usually more stable than RNA-RNA or RNA-DNA hybrids, respectively (Egholm et al., 1993). A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent according to the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent according to the invention comprises one or more sugar moieties that are mono- or disubstituted at the 2', 3' and/or 5' position such as a —OH; —F; substituted or unsubstituted, linear or branched lower (Cl-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al., 2001). These substitutions render the nucleotide analogue or equivalent RNase H and nuclease resistant and increase the affinity for the target RNA. In another embodiment, a nucleotide analogue or equivalent according to the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an AON to be modified uniformly. In addition, more than one of the aforementioned analogues or equivalents may be incorporated in a single AON or even at a single position within an AON. In certain embodiments, an AON according to the invention has at least two different types of analogues or equivalents. Accordingly, a preferred AON for redirecting splicing according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

It will also be understood by a skilled person that different AON's according to the invention can be combined for efficient therapy. In an embodiment, a combination of at least two AON's according to the invention are used, such as two different AON's according to the invention, three different AON's according to the invention, four different AON's according to the invention, or five AON's according to the invention.

An AON for redirecting splicing according to the invention can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An AON for redirecting splicing according to the invention may be indirectly administrated using suitable means known in the art. It may for example be provided to an individual or a cell, tissue or organ of said individual as such, as a so-called 'naked' AON. It may also be administered in the form of an expression vector wherein the expression vector encodes an RNA transcript comprising the sequence of said AON according to the invention. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an AON for redirecting splicing according to the invention. Accordingly, the invention provides for a viral vector expressing an antisense oligonucleotide for redirecting splicing according to the invention when placed under conditions conducive to expression of the antisense oligonucleotide for redirecting splicing. A cell can be provided with an AON for redirecting splicing according to the invention by plasmid-derived antisense oligonucleotide expression or viral expression provided by adenovirus- or adeno-associated virus-based vectors. Expression may be driven by an RNA polymerase II promoter (Pol II) such as a U7 RNA promoter or an RNA polymerase III (Pol III) promoter, such as a U6 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an AON for redirecting splicing according to the invention. Preferred for the invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts, preferably, in the form of a fusion transcript with an U1 or U7 transcript. Such fusions may be generated as previously described (Gorman et al., 1998).

A preferred expression system for an AON for redirecting splicing according to the invention is an adenovirus associated virus (AAV)-based vector. Single chain and double chain AAV-based vectors have been developed that can be used for prolonged expression of antisense nucleotide sequences for highly efficient redirection of splicing. A preferred AAV-based vector, for instance, comprises an expression cassette that is driven by an RNA polymerase III-promoter (Pol III) or an RNA polymerase II promoter (Pol II). A preferred RNA promoter is, for example, a Pol III U6 RNA promoter, or a Pol II U7 RNA promoter.

The invention accordingly provides for a viral-based vector, comprising a Pol II or a Pol III promoter driven expression cassette for expression of an AON for redirecting splicing according to the invention.

An AAV vector according to the invention is a recombinant AAV vector and refers to an AAV vector comprising part of an AAV genome comprising an encoded AON for redirecting splicing according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. A protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention.

Preferably, a recombinant AAV vector according to the invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the invention comprises a capsid protein shell of AAV serotype 2 and the AAV genome or ITRs present in said vector are derived from AAV serotype 5; such vector is referred to as an AAV 2/5 vector.

More preferably, a recombinant AAV vector according to the invention comprises a capsid protein shell of AAV serotype 2 and the AAV genome or ITRs present in said vector are derived from AAV serotype 8; such vector is referred to as an AAV 2/8 vector.

More preferably, a recombinant AAV vector according to the invention comprises a capsid protein shell of AAV serotype 2 and the AAV genome or ITRs present in said vector are derived from AAV serotype 9; such vector is referred to as an AAV 2/9 vector.

More preferably, a recombinant AAV vector according to the invention comprises a capsid protein shell of AAV serotype 2 and the AAV genome or ITRs present in said vector are derived from AAV serotype 2; such vector is referred to as an AAV 2/2 vector.

A nucleic acid molecule encoding an AON for redirecting splicing according to the invention represented by a nucleic acid sequence of choice is preferably inserted between the AAV genome or ITR sequences as identified above, for example an expression construct comprising an expression regulatory element operably linked to a coding sequence and a 3' termination sequence. "AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art, see e.g. (Chiorini et al., 1999) or U.S. Pat. No. 5,139,941, incorporated herein by reference. The AAV helper functions can be supplied on an AAV helper construct, which may be a plasmid. Introduction of the helper construct into the host cell can occur e.g. by transformation, transfection, or transduction prior to or concurrently with the introduction of the AAV genome present in the AAV vector as identified herein. The AAV helper constructs according to the invention may thus be chosen such that they produce the desired combination of serotypes for the AAV vector's capsid protein shell on the one hand and for the AAV genome present in said AAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

Preferably, an AAV genome as present in a recombinant AAV vector according to the invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

Preferably, an AAV vector according to the invention is constructed and produced according to the method according to Garanto et al., 2016 which is herein incorporated by reference.

A preferred AAV vector according to the invention is an AAV vector, preferably an AAV2/5, AAV2/8, AAV2/9 or AAV2/2 vector, expressing an AON for redirecting splicing according to the invention that is an AON that comprises, or preferably consists of, a sequence that is:

- complementary or substantially complementary to a polynucleotide with a nucleotide sequence consisting of SEQ ID NO: 10, 161, 30, 81, 101, 121, 141 or SEQ ID NO: 261, or a part thereof;
- preferably complementary or substantially complementary to a polynucleotide with a nucleotide sequence consisting of SEQ ID NO: 162, 181, 82, 102, 122, 142 or SEQ ID NO: 262, or a part thereof;
- more preferably complementary or substantially complementary to a polynucleotide with a nucleotide sequence consisting of SEQ ID NO: 160, 180, 80, 100, 120, 140 or SEQ ID NO: 260, or a part thereof
- more preferably complementary or substantially complementary to a polynucleotide with a nucleotide sequence consisting of SEQ ID NO: 11 or SEQ ID NO: 31, or a part thereof;
- more preferably complementary or substantially complementary to a polynucleotide with a nucleotide sequence consisting of SEQ ID NO: 12 or SEQ ID NO: 32, or a part thereof;
- more preferably complementary or substantially complementary to a polynucleotide with a nucleotide sequence selected from the group consisting of SEQ ID NO: 13, 16, 19, 163, 166, 169, 33, 36, 39, 42, 182, 185, 188, 191, 194, 197, 200, 203, 206, 209, 212, 215, 218, 221, 224, 227, 230, 233, 236, 239, 242, 245, 248, 251, 254, 257, 83, 86, 89, 103, 106, 109, 123, 126, 129, 143, 146, 149, 263, 266 and SEQ ID NO: 269, or a part thereof; and more preferably complementary or substantially complementary to a polynucleotide with a nucleotide sequence selected from the group consisting of SEQ ID NO: 14, 17, 20, 164, 167, 170, 34, 37, 40, 43, 183, 186, 189, 192, 195, 198, 201, 204, 207, 210, 213, 216, 219, 222, 225, 228, 231, 234, 237, 240, 243, 246, 249, 252, 255, 258, 84, 87, 90, 104, 107, 110, 124, 127, 130, 144, 147, 150, 264, 268 and SEQ ID NO: 270, or a part thereof.

A further preferred AAV vector according to the invention is an AAV vector, preferably an AAV2/5, AAV2/8, AAV2/9 or AAV2/2 vector, expressing an exon skipping molecule or an exon 12 retention molecule according to the invention that is expressing an AON for redirecting splicing according to the invention that comprises, or preferably consists of, a sequence selected from the group consisting of SEQ ID NO: 15, 18, 21, 165, 168, 171, 35, 38, 41, 44, 184, 187, 190, 193, 196, 199, 202, 205, 208, 211, 214, 217, 220, 223, 226, 229, 232, 235, 238, 241, 244, 247, 250, 253, 256, 259, 85, 88, 91, 105, 108, 111, 125, 128, 131, 145, 148, 151, 265, 268 and SEQ ID NO: 271. Improvements in means for providing an individual or a cell, tissue, organ of said individual with an AON for redirecting splicing according to the invention, are anticipated considering the progress that has already thus far been achieved. Such future improvements may of course be incorporated to achieve the mentioned effect on restructuring of mRNA using a method according to the invention. An AON for redirecting splicing according to the invention can be delivered as such as a 'naked' AON to an individual, a cell, tissue or organ of said individual. When administering an AON for redirecting splicing according to the invention, it is preferred that the molecule is dissolved in a solution that is compatible with the delivery method. Retina cells can be provided with a plasmid for antisense oligonucleotide expression by providing the plasmid in an aqueous solution.

Alternatively, a preferred delivery method for an AON for redirecting splicing or a plasmid for expression of such AON is a viral vector or are nanoparticles. Preferably, viral vectors or nanoparticles are delivered to retina or other relevant cells. Such delivery to retina cells or other relevant cells may be in vivo, in vitro or ex vivo; see e.g. Garanto et al, 2016, which is herein incorporated by reference.

Alternatively, a plasmid can be provided by transfection using known transfection agents. For intravenous, subcutaneous, intramuscular, intrathecal and/or intraventricular administration it is preferred that the solution is a physiological salt solution. Particularly preferred in the invention is the use of an excipient or transfection agents that will aid in delivery of each of the constituents as defined herein to a cell and/or into a cell, preferably a retina cell. Preferred are excipients or transfection agents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self-assembly into particles that can deliver each constitutent as defined herein to a cell, preferably a retina cell. Such excipients have been shown to efficiently deliver an oligonucleotide such as AON's to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N, N, N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such as diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an AON according to the invention, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of ABCA4-related disease or condition. "Prevention, treatment or delay of an ABCA4-related disease or condition" is herein preferably defined as preventing, halting, ceasing the progression of, or reversing partial or complete visual impairment or blindness that is caused by a genetic defect in the ABCA4 gene.

In addition, an AON for redirecting splicing according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an AON for redirecting splicing according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be suitably formulated in one single combination or composition or preparation. Depending on their identity and specific features, the skilled person will know which type of formulation is the most appropriate for each constituent as defined herein. In a preferred embodiment, the invention provides a composition or a preparation which is in the form of a kit of parts comprising an AON for redirecting splicing according to the invention and a further adjunct compound as later defined herein.

If required and/or if desired, an AON for redirecting splicing according to the invention or a vector, preferably a viral vector, according to the invention, expressing an AON for redirecting splicing according to the invention can be incorporated into a pharmaceutically active mixture by adding a pharmaceutically acceptable carrier.

Accordingly, the invention also provides for a composition, preferably a pharmaceutical composition, comprising an AON for redirecting splicing according to the invention, or a viral vector according to the invention and a pharmaceutically acceptable excipient. Such composition may comprise a single AON for redirecting splicing or viral vector according to the invention, but may also comprise multiple, distinct AON's for redirecting splicing or viral vectors according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

A preferred route of administration is through intra-vitreal injection of an aqueous solution or specially adapted formulation for intraocular administration. EP2425 814 discloses an oil in water emulsion especially adapted for intraocular (intravitreal) administration of peptide or nucleic acid drugs. This emulsion is less dense than the vitreous fluid, so that the emulsion floats on top of the vitreous, avoiding that the injected drug impairs vision.

If multiple distinct AON's for redirecting splicing according to the invention are used, the concentration or dose defined herein may refer to the total concentration or dose of all oligonucleotides used or the concentration or dose of each exon skipping molecule used or added. Therefore, in an embodiment, there is provided a composition wherein each or the total amount of AON's for redirecting splicing according to the invention used is dosed in an amount ranged from 0.01 and 20 mg/kg, preferably from 0.05 and 20 mg/kg per eye. A suitable intravitreal dose is provided and comprises between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

A preferred AON for redirecting splicing according to the invention, is for the treatment of an ABCA4-related disease or condition of an individual. In all embodiments of the invention, the term "treatment" is understood to include the prevention and/or delay of the ABCA4-related disease or condition. An individual, which may be treated using an AON for redirecting splicing according to the invention may already have been diagnosed as having an ABCA4-related disease or condition. Alternatively, an individual which may be treated using an AON for redirecting splicing according to the invention may not have yet been diagnosed as having a ABCA4-related disease or condition but may be an individual having an increased risk of developing a ABCA4-related disease or condition in the future given his or her genetic background. A preferred individual is a human being. In all embodiments of the invention, the ABCA4-related disease or condition is preferably Stargardt disease.

Accordingly, the invention further provides for an AON for redirecting splicing according to the invention, or a viral vector according to the invention, or a (pharmaceutical) composition according to the invention for use as a medicament, preferably as a medicament for the treatment of an ABCA4-related disease or condition requiring modulating splicing of ABCA4 and for use as a medicament for the prevention, treatment or delay of an ABCA4-related disease or condition. Each feature of all medical use embodiment herein has earlier been defined herein and is preferably such feature as earlier defined herein.

The invention further provides for, a method of treatment of an ABCA4-related disease or condition requiring modulating splicing of ABCA4, comprising said method comprising contacting a cell of said individual with an AON for redirecting splicing according to the invention, a vector according to the invention or a (pharmaceutical) composition according to the invention. Each feature of all medical use embodiment herein has earlier been defined herein and is preferably such feature as earlier defined herein.

The invention further provides for the use of an AON for redirecting splicing according to the invention, a vector according to the invention or a (pharmaceutical) composition according to the invention for the preparation of a medicament. Each feature of all medical use embodiment herein has earlier been defined herein and is preferably such feature as earlier defined herein.

The invention further provides for the use of an AON for redirecting splicing according to the invention, a vector according to the invention or a (pharmaceutical) composition according to the invention for the preparation of a medicament for the treatment of an ABCA4-related disease or condition requiring modulating splicing of ABCA4. Each feature of all medical use embodiment herein has earlier been defined herein and is preferably such feature as earlier defined herein.

The invention further provides for the use of an AON for redirecting splicing according to the invention, a vector according to the invention or a (pharmaceutical) composition according to the invention for treating an ABCA4 related disease or condition requiring modulating splicing of ABCA4. Each feature of all medical use embodiment herein has earlier been defined herein and is preferably such feature as earlier defined herein.

Treatment in a use or in a method according to the invention is preferably at least once, and preferably lasts at least one week, one month, several months, one year, 2, 3, 4, 5, 6 years or longer, such as life-long. Each AON for redirecting splicing according to the invention or equivalent thereof as defined herein for use according to the invention may be suitable for direct administration to a cell, tissue and/or an organ in vivo of individuals already affected or at risk of developing an ABCA4-related disease or condition, and may be administered directly in vivo, ex vivo or in vitro. The frequency of administration of an AON, composition, compound or adjunct compound according to the invention may depend on several parameters such as the severity of the disease, the age of the patient, the mutation of the patient, the number of AON for redirecting splicing according to the invention (i.e. dose), the formulation of the AON, composition, compound or adjunct compound according to the invention, the route of administration and so forth. The frequency of administration may vary between daily, weekly, at least once in two weeks, or three weeks or four weeks or five weeks or a longer time period.

Dose ranges of an AON, composition, compound or adjunct compound according to the invention are preferably designed on the basis of rising dose studies in clinical trials (in vivo use) for which rigorous protocol requirements exist. An AON according to the invention may be used at a dose which is ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

In a preferred embodiment, a concentration of an oligonucleotide as defined herein, which is ranged from 0.1 nM and 1 μM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nM. If multiple distinct AONs are used, this concentration or dose may refer to the total concentration or dose of the AONs or the concentration or the dose of each AON added.

In a preferred embodiment, a viral vector, preferably an AAV vector as described earlier herein, as delivery vehicle for a molecule according to the invention, is administered in a dose ranging from $1\times10^{9}$-$1\times10^{17}$ virus particles per injection, more preferably from $1\times10^{10}$-$1\times10^{12}$ virus particles per injection.

The ranges of concentration or dose of AONs as depicted above are preferred concentrations or doses for in vivo, in vitro or ex vivo uses. The skilled person will understand that depending on the AONs used, the target cell to be treated, the gene target and its expression levels, the medium used and the transfection and incubation conditions, the concentration or dose of AONs used may further vary and may need to be optimized any further.

An AON for redirecting splicing according to the invention, or a viral vector according to the invention, or a composition according to the invention for use according to the invention may be administered to a cell, tissue and/or an organ in vivo of individuals already affected or at risk of developing a ABCA4-related disease or condition, and may be administered in vivo, ex vivo or in vitro. An AON for redirecting splicing according to the invention, or a viral vector according to the invention, or a composition according to the invention may be directly or indirectly administered to a cell, tissue and/or an organ in vivo of an individual already affected by or at risk of developing a ABCA4-related disease or condition, and may be administered directly or indirectly in vivo, ex vivo or in vitro. As Stargardt disease has a pronounced phenotype in retina cells, it is preferred that said targeted cells are retina cells, it is further preferred that said tissue is the retina and it is further preferred that said organ comprises or consists of the eye.

The invention further provides for a method for modulating splicing of ABCA4 in a cell comprising contacting the cell, preferably a retina cell, with an AON for redirecting splicing according to the invention, or a viral vector according to the invention, or a (pharmaceutical) composition according to the invention. The features of this aspect are preferably those defined earlier herein. Contacting the cell with an AON for redirecting splicing according to the invention, or a viral vector according to the invention, or a composition according to the invention may be performed by any method known by the person skilled in the art. Use of the methods for delivery of AONs for redirecting splicing, viral vectors and compositions as described earlier herein is included. Contacting may be directly or indirectly and may be in vivo, ex vivo or in vitro.

Unless otherwise indicated each embodiment as described herein may be combined with another embodiment as described herein.

Definitions

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 5% of the value. The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

All patent and literature references cited in the present specification are hereby incorporated by reference in their entirety.

Embodiments of the Invention

1. An antisense oligonucleotide for redirecting splicing that is:
   - complementary or substantially complementary to a polynucleotide with a nucleotide sequence consisting of SEQ ID NO: 10 or SEQ ID NO: 30, or a part thereof;
   - preferably complementary or substantially complementary to a polynucleotide with a nucleotide sequence consisting of SEQ ID NO: 11 or SEQ ID NO: 31, or a part thereof;
   - more preferably complementary or substantially complementary to a polynucleotide with a nucleotide sequence consisting of SEQ ID NO: 12 or SEQ ID NO: 32, or a part thereof;
   - more preferably complementary or substantially complementary to a polynucleotide with a nucleotide sequence selected from the group consisting of SEQ ID NO: 13, SEQ ID NO: 16, SEQ ID NO: 19, SEQ ID NO: 33, SEQ ID NO: 36, SEQ ID NO: 39 and SEQ ID NO: 42, or a part thereof; and
   - more preferably complementary or substantially complementary to a polynucleotide with a nucleotide sequence selected from the group consisting of SEQ ID NO: 14, SEQ ID NO: 17, SEQ ID NO: 20, SEQ ID NO: 34, SEQ ID NO: 37, SEQ ID NO: 40 and SEQ ID NO: 43, or a part thereof.

2. An antisense oligonucleotide for redirecting splicing according to embodiment 1, wherein the part that is complementary or substantially complementary to a polynucleotide with a nucleotide sequence consisting of SEQ ID NO: 10 or SEQ ID NO: 30, or a part thereof, has a length of from about 8 to about 40 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides.

3. An antisense oligonucleotide for redirecting splicing according to any of the preceding embodiments that has a length of from about 8 to about 100 nucleotides, preferably from about 10 to about 40 nucleotides, more preferably from about 14 to about 30 nucleotides, more preferably from about 16 to about 24 nucleotides, such as 16, 17, 18, 19, 20, 21, 22, 23 or 24 nucleotides.

4. An antisense oligonucleotide for redirecting splicing according to any of the preceding embodiments, wherein said antisense oligonucleotide comprises or consists of a sequence selected from the group consisting of SEQ ID NO: 15, SEQ ID NO: 18, SEQ ID NO: 21, SEQ ID NO: 35, SEQ ID NO: 38, SEQ ID NO: 41 and SEQ ID NO: 44.

5. An antisense oligonucleotide for redirecting splicing according to any one of the preceding embodiments, comprising at least one ribonucleotide.

6. An antisense oligonucleotide for redirecting splicing according to any one of the preceding embodiments, comprising at least one ESE (exon splice enhancer) motif.

7. An antisense oligonucleotide for redirecting splicing according to any one of the preceding embodiments comprising a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

8. A viral vector expressing an antisense oligonucleotide for redirecting splicing according to any of the preceding embodiments when placed under conditions conducive to expression of the exon skipping antisense oligonucleotide.

9. A pharmaceutical composition comprising an antisense oligonucleotide for redirecting splicing according to any one of embodiments 1-7 or a viral vector according to embodiment 7 and a pharmaceutically acceptable excipient.

10. A pharmaceutical composition according to embodiment 9, wherein the pharmaceutical composition is for intravitreal administration and is dosed in an amount ranged from 0.05 mg and 5 mg of total antisense oligonucleotides for redirecting splicing per eye.

11. A pharmaceutical composition according to embodiment 10, wherein the pharmaceutical composition is for intravitreal administration and is dosed in an amount ranged from 0.1 and 1 mg of total antisense oligonucleotides for redirecting splicing per eye, such as about 0.1, 0.2, 0.3, 0.4, 0.5, 0.6, 0.7, 0.8, 0.9 or 1.0 mg of total antisense oligonucleotides for redirecting splicing per eye.

12. The antisense oligonucleotide for redirecting splicing according to any one of embodiments 1-7, the vector according to embodiment 8 or the composition according to any one of embodiments 9-11 for use as a medicament.

13. The antisense oligonucleotide for redirecting splicing according to any one of embodiments 1-7, the vector according to embodiment 9 or the composition according to any one of embodiments 9-11 for use in the treatment an ABCA4-related disease or condition requiring modulating splicing of ABCA4.

14. Use of the antisense oligonucleotide for redirecting splicing according to any one of embodiments 1-7, the vector according to embodiment 8 or the composition according to any one of embodiments 9-11 for the preparation of a medicament.

15. Use of the antisense oligonucleotide for redirecting splicing according to any one of embodiments 1-6, the vector according to embodiment 7 or the composition according to any one of embodiments 8-10 for the preparation of medicament for treating an ABCA4-related disease or condition requiring modulating splicing of ABCA4.

16. Use of the antisense oligonucleotide for redirecting splicing according to any one of embodiments 1-7, the vector according to embodiment 7 or the composition according to any one of embodiments 9-11 for treating an ABCA4-related disease or condition requiring modulating splicing of ABCA4.

17. A method for modulating splicing of ABCA4 in a cell, said method comprising contacting said cell with an antisense oligonucleotide for redirecting splicing as defined in any one of embodiments 1-7, the vector according to embodiment 7 or the composition according to any one of embodiments 9-11.

18. A method for the treatment of an ABCA4-related disease or condition requiring modulating splicing of ABCA4 of an individual in need thereof, said method comprising contacting a cell of said individual with an antisense oligonucleotide for redirecting splicing as defined in any one of embodiments 1-7, the vector according to embodiment 7 or the composition according to any one of embodiments 9-11.

19. The antisense oligonucleotide for redirecting splicing for use according to embodiment 12 or 13, the use according to embodiment 15 or 16 or the method according to embodiment 18, wherein the ABCA4-related disease or condition is Stargardt disease.

EXAMPLES

Initially, we have assessed the in vitro efficacy of a number of AONs to redirect splice defects due to the c.4539+1100A>G, c.4539+1106C>T and c.4539+2001G>A mutations in ABCA4, in human embryonic kidney (HEK293T) cells. For this, we used minigene constructs, i.e. plasmids that harbour the sequence of a part of the ABCA4 gene, usually the region of interest with or without the mutation, and flanked by at least 500 bp of wild-type ABCA4 sequence on each side. The plasmid also contains the exonic sequences and intron-exon boundaries of exons 3 and 5 of the RHO gene on each side of the ABCA4 sequence, respectively. In this way, the effect of the ABCA4 variant on the splicing of the corresponding exon or pseudo-exons can be readily measured. Later on, we used larger constructs (coined midigenes) to assess the nature of other deep-intronic variants that were discovered, including c.769-784C>T, c.859-540C>G, c.859-506G>C, c.1937+435C>G, c.4539+1100A>G, c.4539+1106C>T and c.5197-557G>T. The generation of these midigenes is described in Sangermano et al. (2018) Finally, in addition to the minigene assays, we also used photoreceptor precursor cells (PPCs) from a patient with compound heterozygous ABCA4 mutations, namely the c.4539+2001G>A mutation together with the c.4892T>C (p.Leu1631Pro) on the other allele, to assess the potential of AONs to rescue the splice defect. PPCs were also used to assess the potential of AONs to rescue splice defects from a patient carrying a complex allele containing c.302+68C>T and c.4539+2028C>T (M2), and the deletion c.6148-698_6670 delinsTGTGCACCTCCCTAG on the other allele (Lee et al. 2016). First, in the Materials and Methods section, the experimental details are described, whereas the results are described and illustrated in the Results section further below.

Materials and Methods

A) Mutations: c.4539+1100A>G & c.4539+1106C>T—Minigenes

Generation of a Minigene for Each Mutation

A minigene was created including part of the intron 29, the complete exon 30, intron 30 and exon 31, and part of intron 31. This genomic region was cloned into a pCI-Neo-Rhodopsin vector using the Gateway System. The resulting vector (coined pCI-Neo-Rho-ABCA4-30-31 wild-type, SEQ ID NO: 50) was used to introduce the c.4539+1100A>G and c.4539+1106C>T mutations by site-directed mutagenesis (new vector was coined pCI-Neo-Rho-ABCA4-c.4539+1100G, SEQ ID NO: 51 and pCI-Neo-Rho-ABCA4-c.4539+1106T, SEQ ID NO: 52). The control and mutated vectors were validated by Sanger sequencing. The minigenes were then transfected in HEK293T cells, which were harvested 48 h post-transfection and were subjected to RT-PCR analysis in order to detect the splicing defect.

AON Design and Testing

The RNA analysis of the HEK293T cells transfected with the minigenes, showed the pre-mRNA splicing defect that consisted of the insertion of a pseudoexon. Using the sequence of this pseudoexon several AONs were designed. Subsequently, AONs were transfected into HEK293T together with the minigenes. To validate the AON efficacy, cells were subjected to RT-PCR analysis. The efficiency of each of the AONs was assessed by delivering identical amounts of minigene and various concentrations of AON and performing RT-PCR analysis afterwards.

RT-PCR Analysis

Total RNA was isolated by using the NucleoSpin RNA Clean-up Kit (catalog no., 740955-50; Macherey-Nagel, Duren, Germany) according to the manufacturers protocol. RNA was quantified and cDNA was synthesized from 1 µg RNA by using the iScript cDNA synthesis kit (catalog no., 1708891; Bio-Rad, Hercules, CA) following the manufacturer's instructions. Finally, the efficacy of the AONs was assessed by performing a PCR from exon 30 to exon 31 or a PCR spanning from exon 29 to 34.

B) Mutation: c.4539+2001G>A—Minigene

Generation of a Minigene

A minigene was created including part of intron 29, the complete exon 30, intron 30 and exon 31, and part of intron 31. This genomic region was cloned into a pCI-Neo-Rhodopsin vector using the Gateway System. The resulting vector (coined pCI-Neo-Rho-ABCA4-30-31 wild type, SEQ ID NO: 50) was used to introduce the c.4539+2001G>A mutation by site-directed mutagenesis (new vector was coined pCI-Neo-Rho-ABCA4-c.4539+2001A, SEQ ID NO: 53). Both control and mutated vectors were validated by Sanger sequencing. The minigenes were then transfected in HEK293T cells, which were harvested 48 h post-transfection and were subjected to RT-PCR analysis in order to detect the splicing defect.

AON Design and Testing

The transfection of minigene pCI-Neo-Rho-ABCA4-c.4539+2001A in HEK293T cells showed the insertion of the pseudoexon. Using the sequence of this pseudoexon, several AONs were designed. AONs were delivered together with the minigene in HEK293T cells. Transfected cells were subjected to RNA analysis.

RNA Analysis

Total RNA was isolated by using the NucleoSpin RNA Clean-up Kit (catalog no., 740955-50; Macherey-Nagel, Duren, Germany) according to the manufacturers protocol. RNA was quantified and cDNA was synthesized from 1 µg RNA by using the iScript cDNA synthesis kit (catalog no., 1708891; Bio-Rad, Hercules, CA) following the manufacturer's instructions. Finally, the efficacy of the AONs was assessed by performing a PCR from exon 30 to exon 31 or a PCR spanning from exon 29 to 34.

C) Mutations: c.4539+2001G>A and c.4539+2028C>T—PPCs Assessment

Generation of Photoreceptor Precursor Cells (PPCs)

Skin biopsies of a patient carrying the c.4539+2001G>A (M1) in a heterozygous manner and of a patient carrying the carrying the c.4539+2028C>T (M2) in a heterozygous state were obtained and fibroblast cell lines were generated. Subsequently, induced pluripotent stem cells (iPSCs) were reprogrammed as described previously (Sangermano et al., 2016), and differentiated to photoreceptor precursor cells (PPCs) using a method adapted from Sangermano et al. (2016) or from Flamier et al. (2016). Differentiated cells were subjected to RT-PCR analysis.

ABCA4 Transcript Analysis

After thirty days of differentiation, control and patient-derived PPCs were harvested. Reverse transcription-PCR (RT-PCR) analysis was performed using primers located in exon 2 (forward) and exon 5 (reverse) or exon 30 (forward) and exon 31 (reverse) of the ABCA4 gene. Actin (ACTB) primers were used as a control. Primer sequences are represented by SEQ ID NOs: 54-77. All reaction mixtures (50 µl) contained 10 µM of each primer pair, Taq DNA Polymerase, 1 U/µl (cat. no. 11647679001. Roche, Basel, Switzerland), 10×PCR buffer without $MgCl_2$, 25 mM $MgCl_2$, 10 mM dNTPs, and 50 ng cDNA. PCR conditions were a first denaturation step of 94° C. for 5 min followed by 35 cycles of melting (94° C. for 30 s), annealing (58° C. for 30 s), and extension (72° C. for 1 min) steps, with a final elongation step of 72° C. for 5 min. PCR products were separated on a 1% (w/v) agarose gel and the resulting bands were excised and purified with the NucleoSpin® Gel & PCR cleanup kit (cat. no. 740609.250, Macherey-Nagel) according to manufacturer's protocol. Finally, 100 ng of the purified PCR product was analyzed via Sanger sequencing, in a 3100 or 3730 DNA Analyzer (Thermo Fisher Scientific).

Antisense Oligonucleotide (AON) Design

The sequence of the PE plus 50 base pairs flanking both sides were analyzed as described previously (Aartsma-Rus et al. 2012). Briefly, the overall RNA structure of the region of interest was analyzed with the mfold software (http://unafold.ma.albany.edu/?q=mfold/RNA-Folding-Form, last accessed 23 Jul. 2017), in order to identify partially open and closed regions. Splice enhancer motifs were determined using ESE finder 3.0 (http://krainer01.cshl.edu/cgi-bin/tools/ESE3/esefinder.cgi?process=home, last accessed 23 Jul. 2017). Special attention was paid to SC35 regions, as it has been demonstrated that there is a positive correlation between the presence of such motifs and the efficacy of AONs (Aartsma-Rus et al. 2012). Initially, this analysis led to the design of four AONs, two that overlap with the highest scoring SC35 motif (AON2 and AON3), one at the 5'-end of the PE (AON4) and one that overlaps with the c.4539+2001G>A mutation (AON1). At a later stage, 22 additional AONs were designed, to find correlations between the efficacy of AONs and their position towards the pseudoexon, their overlap with certain ESE motifs, and their specificity (i.e. whether single nucleotide mismatches could abolish their efficacy). The final AON sequences were also evaluated for the free energy of the molecule alone, the possibility to form dimers, and their interaction with the region of interest. For this, the RNA secondary structure tool (http://rna.urmc.rochester.edu/RNAstructureWeb, last accessed 23 Jul. 2017) was used, employing the RNA secondary structure and bifold prediction tools. We ensured that all AONs had a free energy value above −4 on their own, above −14 as a dimer and between 21 and 28 for the AON-region binding. This was calculated by using the estimated energy of the region of interest minus the energy of the AON bound to the region. All AON sequences had a length of 19 nucleotides with a Tm above 46° C. and a GC content between 40% and 65%. The sequences and properties of the AONs are listed in Table 1; further properties of the AONs for pseudoexon 30-31 (345) are listed in Table 2. AONs were chemically modified by adding a phosphorothioate backbone and a 2-O-methyl sugar modification 2OMe/PS to each nucleotide and were purchased from Eurogentec (Liege, Belgium). AONs were dissolved in PBS 1× (autoclaved twice) to a final concentration of 100 µM. Two sense oligonucleotides (SON-1 [SEQ ID NO: 280] and SON-2 [SEQ ID NO: 281]) were ordered with the same chemistry to be used as a negative control.

AON Treatment

Following differentiation, PPCs were treated with AONs (0.5 and 1 μM) by mixing the naked AONs directly with the culturing medium. After 24 h, cycloheximide (CHX, cat. no. C4859, Sigma Aldrich) was added at a final concentration of 0.1 mg/ml and cells were incubated for another 24 h. Forty-eight hours after AON delivery, cells were harvested, rinsed in PBS and RNA was isolated. cDNA synthesis was performed using 1 μg of RNA, as described above. All reactions were diluted to 20 ng/μl by adding 30 μl of distilled water. For RT-PCR analysis, 80 ng of cDNA was used for all the ABCA4 reactions whereas 40 ng for the ACTB analysis. All reaction mixtures (25 μl) contained 10 μM of each primer pair, Taq DNA Polymerase 1 U/μl (cat. no. 11647679001, Roche), 10×PCR buffer with MgCl2, supplemented with 1 mM MgCl2, 2 μM dNTPs, and 80 or 40 ng cDNA. PCR conditions for ABCA4 fragments from exon 30 to 31 were as follows: 94° C. for 2 min, 35 cycles of 30 s at 94° C., 30 s at 58° C. and 90 s at 72° C., followed by a final step of 2 min at 72° C. For actin amplification, PCR was performed under the same conditions except for an elongation time of 30 s. The entire volume of the ABCA4 PCR products and 10 μl of the actin amplicon were resolved on a 2% (w/v) agarose gel. The resulting bands were analyzed using Sanger sequencing. The ratio between correctly and aberrantly spliced variants was assessed by using Fiji software (Schindelin et al., 2012).

D) Mutations: c.769-784C>T, c.859-540C>G, c.859-506G>C, c.1937+435C>G, c.4539+1100A>G, c.4539+1106C>T and c.5197-557G>T—Midigenes Generation of a Midigene for Each Mutation A midigene was created for each mutation (Sangermano et al. 2018). These midigenes include a considerable fragment of ABCA4 genomic DNA on each side of the corresponding mutations, often encompassing one or more of the flanking exons. This genomic region was cloned into a pCI-Neo-Rhodopsin vector using the Gateway System. The resulting vectors (pCI-Neo-Rho-ABCA4-intron6-intron7 wild type (SEQ ID NO: 290), pCI-Neo-Rho-ABCA4-intron6-intron11 wild type (SEQ ID NO: 292). pCI-Neo-Rho-ABCA4-intron11-intron15 wild type (SEQ ID NO: 295). pCI-Neo-Rho-ABCA4-intron29-intron32 wild type (SEQ ID NO: 297), pCI-Neo-Rho-ABCA4-intron31-intron37 wild type (SEQ ID NO: 300)) were used to introduce the c.769-784C>T, c.859-540C>G, c.859-506G>C, c.1937+435C>G, c.4539+1100A>G, c.4539+1106C>T and c.5197-557G>T mutations to the corresponding vector by site-directed mutagenesis (new vectors were coined pCI-Neo-Rho-ABCA4-intron6-intron7 c.769-784T (SEQ ID NO: 291), pCI-Neo-Rho-ABCA4-intron6-intron11 c.859-540G (SEQ ID NO: 293), pCI-Neo-Rho-ABCA4-intron6-intron11 c.859-506C (SEQ ID NO: 294), pCI-Neo-Rho-ABCA4-intron11-intron15 c.1937+435G (SEQ ID NO: 296), pCI-Neo-Rho-ABCA4-intron29-intron32 c.4539+1100G (SEQ ID NO: 298). pCI-Neo-Rho-ABCA4-intron29-intron32 c.4539+1106T (SEQ ID NO: 299) and pCI-Neo-Rho-ABCA4-intron31-intron37 c.5197-557T (SEQ ID NO: 301)). The control and mutated vectors were validated by Sanger sequencing. The midigenes were then transfected in HEK293T cells, which were harvested 48 h post-transfection and were subjected to RT-PCR analysis in order to detect the splicing defect.

AON Design and Testing

The RNA analysis of the HEK293T cells transfected with the midigenes, showed the pre-mRNA splicing defect that consisted of the insertion of a pseudoexon. Using the sequence of this pseudoexon several AONs were designed. Subsequently, AONs were transfected into HEK293T together with the midigenes. To validate the AON efficacy, cells were subjected to RT-PCR analysis. The efficiency of each of the AONs was assessed by delivering identical amounts of minigene and various concentrations of AON and performing RT-PCR analysis afterwards. For each experiment, one SON was included as a negative control. During the final check, we discovered that AON1 that was designed for the c.859-540C>G mutation was ordered incorrectly, and instead the sequence of AON3 for the c.5197-557G>T mutation was entered and provided. This also affects the interpretation of the results.

RT-PCR Analysis

Total RNA was isolated by using the NucleoSpin RNA Clean-up Kit (catalog no., 740955-50; Macherey-Nagel, Duren, Germany) according to the manufacturers protocol. RNA was quantified and cDNA was synthesized from 1 μg RNA by using the iScript cDNA synthesis kit (catalog no., 1708891; Bio-Rad, Hercules, CA) following the manufacturer's instructions. Finally, the efficacy of the AONs was assessed by performing a PCR using the corresponding ABCA4 primers (SEQ ID NO: 302, Rhodopsin ex3 fw; SEQ ID NO: 303, ABCA4 ex7 rev; SEQ ID NO: 304, ABCA4 ex7 fw; SEQ ID NO: 305, ABCA4 ex8 rev; SEQ ID NO:306, ABCA4 ex13 fw; SEQ ID NO:307, ABCA4 ex14 rev; SEQ ID NO:308, ABCA4 ex30 fw; SEQ ID NO: 309, ABCA4 ex32 rev; SEQ ID NO: 310, ABCA4 ex32 tw; SEQ ID NO: 311, ABCA4 ex37 rev).

Results

A)

Figure 1:
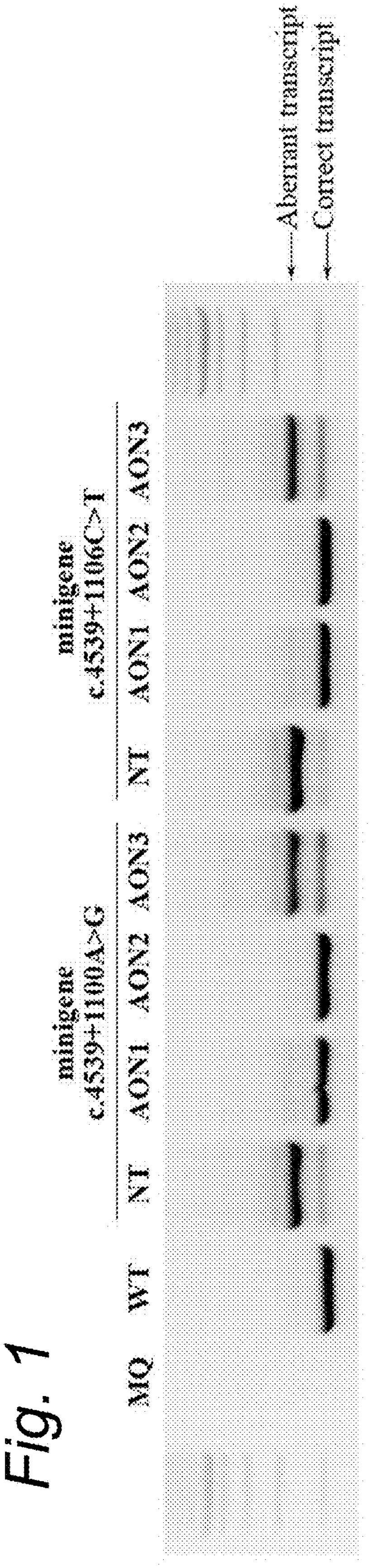
FIG. 1 depicts the results of example A, wherein rescue of splice defects caused by ABCA4 mutation c.4539+1100A>G and c.4539+1106C>T was accomplished by delivery of AONs in a minigene assay.

Minigene constructs harboring the c.4539+1100A>G or the c.4539+1106C>T mutation were transfected into HEK293T cells, together with a construct with the wild type ABCA4 sequence. As depicted in FIG. 1, both mutations result in the insertion of a 86-bp pseudoexon into the transcript (lanes marked with NT), although some remaining wild type transcript was also detected. Transfection of three different AONs showed that for both mutations, the pseudoexon insertion was completely abolished in the presence of AON1 (AON-1 Pseudoexon 30-31(68), SEQ ID NO: 15), and AON2 (AON-2 Pseudoexon 30-31(68), SEQ ID NO: 18), whereas AON3 (AON-3 Pseudoexon 30-31(68), SEQ ID NO: 21) resulted in a partial redirection of splicing events (FIG. 1). These data demonstrate the capability of AONs to redirect the aberrant splicing events due to the c.4539+1100A>G or the c.4539+1106C>T mutations.

B)

Figure 3:
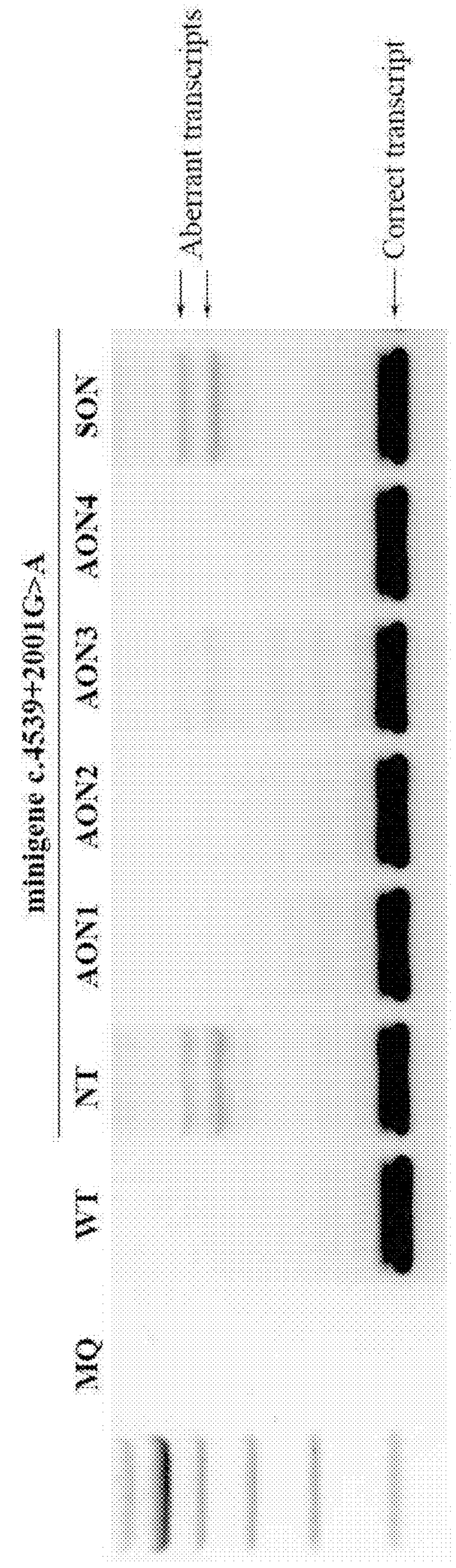
FIG. 3 depicts the results of example B wherein rescue of splice defects caused by ABCA4 mutation c.4539+2001G>A by AONs was accomplished by delivery of AONs in a minigene assay.

A minigene construct harboring the c.4539+2001A>G mutation (A) was transfected into HEK293T cells, together with a construct with the wild type ABCA4 sequence (G). Minigene construct harboring the c.4539+2001G>A mutation were transfected into HEK293T cells, together with a construct with the wild type ABCA4 sequence, RT-PCR analysis using RNA derived from these cells revealed the inclusion of a pseudoexon corresponding to a 345-bp sequence in intron 30, but only when cells were cultured in the presence of cycloheximide (+CHX), an agent regularly used to inhibit nonsense mediated degradation of aberrant transcripts. As shown in FIG. 3, all four AONs (AON1=AON-1 Pseudoexon 30-31(345), SEQ ID NO: 35, AON2=AON-2 Pseudoexon 30-31(345), SEQ ID NO: 38, AON3=AON-3 Pseudoexon 30-31(345), SEQ ID NO: 41, AON4=AON-4 Pseudoexon 30-31(345), SEQ ID NO: 44))

redirected ABCA4 splicing completely, unlike the SON. Using the WT construct (left lane), as expected, only the normal, intact product without pseudoexon was detected. Herein AONs are interchangeably depicted as AON-n and AONn, wherein n is an integer; the AONs may be depicted with "-" or without "-".

C)

Figure 2:
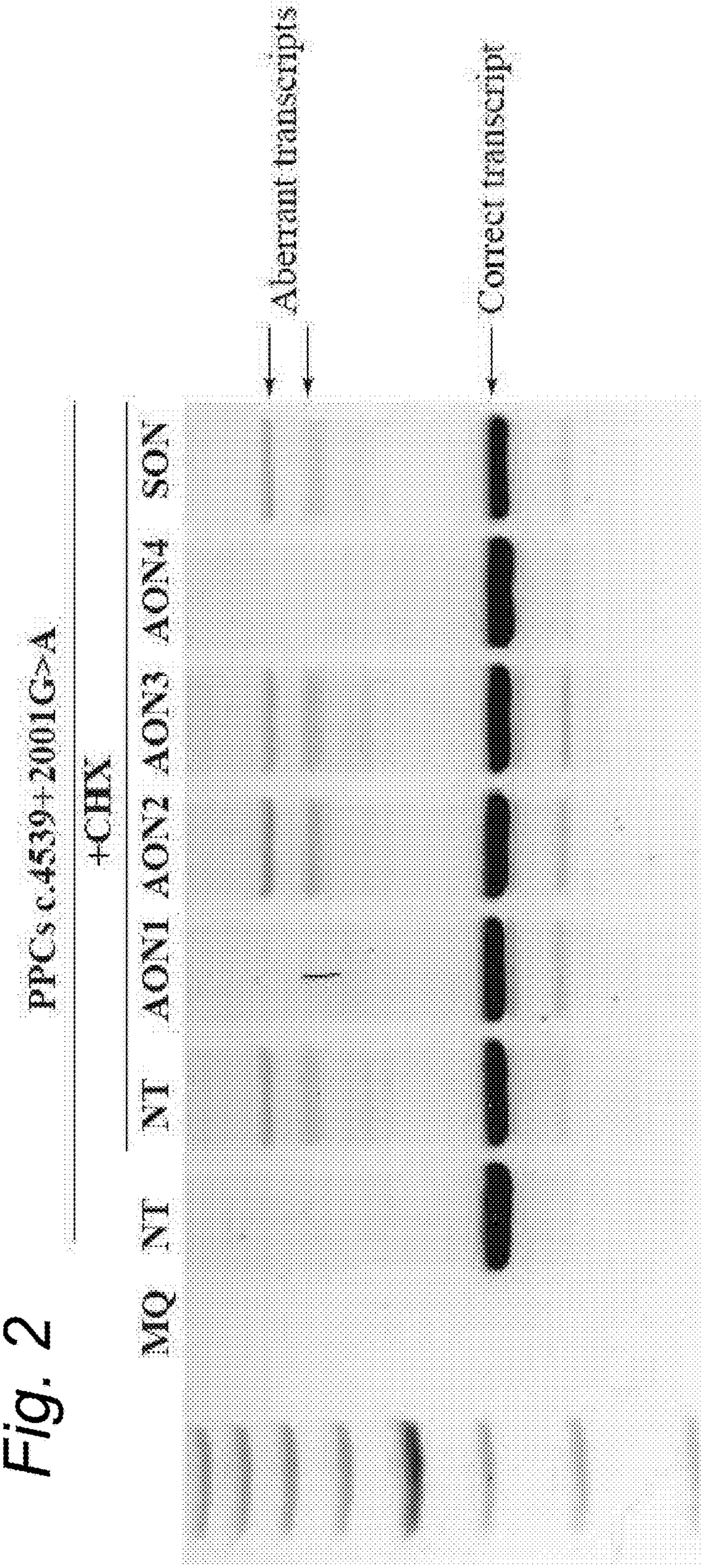
FIG. 2 depicts the results of example C wherein rescue of splice defects caused by ABCA4 mutation c.4539+2001G>A by AONs was accomplished by delivery of AONs to cultured patient-derived photoreceptor precursor cells.

In the photoreceptor precursor cells derived from a patient heterozygously carrying the ABCA4 c.4539+2001G>A (M1) mutation, RT-PCR analysis using RNA derived from these cells revealed the inclusion of a pseudoexon corresponding to a 345-bp sequence in intron 30, but only when cells were cultured in the presence of cycloheximide (+CHX), an agent regularly used to inhibit nonsense mediated degradation of aberrant transcripts. As illustrated in FIG. 2, upon transfection of four different AONs targeting this pseudoexon (AON1=AON-1 Pseudoexon 30-31(345), SEQ ID NO: 35, AON2=AON-2 Pseudoexon 30-31(345), SEQ ID NO: 38, AON3=AON-3 Pseudoexon 30-31(345), SEQ ID NO: 41, AON4=AON-4 Pseudoexon 30-31(345), SEQ ID NO: 44), the pseudoexon insertion completely disappeared after administration of AON1 and AON4. This was not the case for a negative control oligo SON (SEQ ID NO: 45), that has the complementary sequence of AON1, demonstrating that AON1 and AON4 effectively and specifically redirect aberrant splice events caused by the c.4539+2001G>A mutation.

To determine whether variants c.4539+2001G>A (M1) and c.4539+2028C>T (M2) result in aberrant splicing of ABCA4 pre-mRNA, fibroblast cell lines were generated from two unrelated Stargardt disease (STGD1) patients. A STGD1 patient with M1 carried the missense variant c.4892T>C (p.Leu1631Pro) in trans (Webster et al., 2001). A STGD1 patient with M2 carried the deep-intronic variant c.302+68C>T in cis, whereas a deletion c.6148-698_6670 delinsTGTGCACCTCCCTAG (p.?) was present on the other allele. In addition, a fibroblast line from a healthy control was generated. All cells were cultured in the absence and presence of cycloheximide (CHX), a compound used to suppress nonsense-mediated decay of RNA products carrying protein-truncating mutations. RT-PCR analysis with primers located in exons 30 and 31 revealed only one clear product, corresponding to the expected product encompassing exons 30 and 31 (FIG. 4). No aberrantly spliced products were detected in the fibroblasts from the STGD1 patients.

To investigate potentially retina-specific splicing defects caused by the two deep-intronic ABCA4 mutations, control and patient fibroblasts were reprogrammed into induced pluripotent stem cells (iPSCs) via lentiviral transduction of the Yamanaka factors (Takahashi et al., 2006). Quantitative PCR (q-PCR) (FIG. 7) and immunofluorescence analysis (data not shown) validated the pluripotency of the iPSCs. Subsequently, these iPSCs were differentiated for one month into photoreceptor precursor cells (PPCs). We used the protocol described previously by Flamier and colleagues (Flamier et al. 2016) to obtain a relatively homogeneous cone cell population, since the primarily affected cells in STGD1 are the cone photoreceptor cells. Characterization of control and patient-derived PPCs revealed a significantly increased expression of ABCA4, being ~40 times higher in the control PPCs than control iPSCs, but only ~3 times higher in M1- and M2-PPCs compared to M1- and M2-iPSCs. Further characterization of the PPCs revealed that all three cell lines were differentiated towards S-cones, although control PPCs expressed higher amounts of CRX and OPN1SW, compared to M1- and M2-PPCs (FIG. 7B).

Figure 4A:
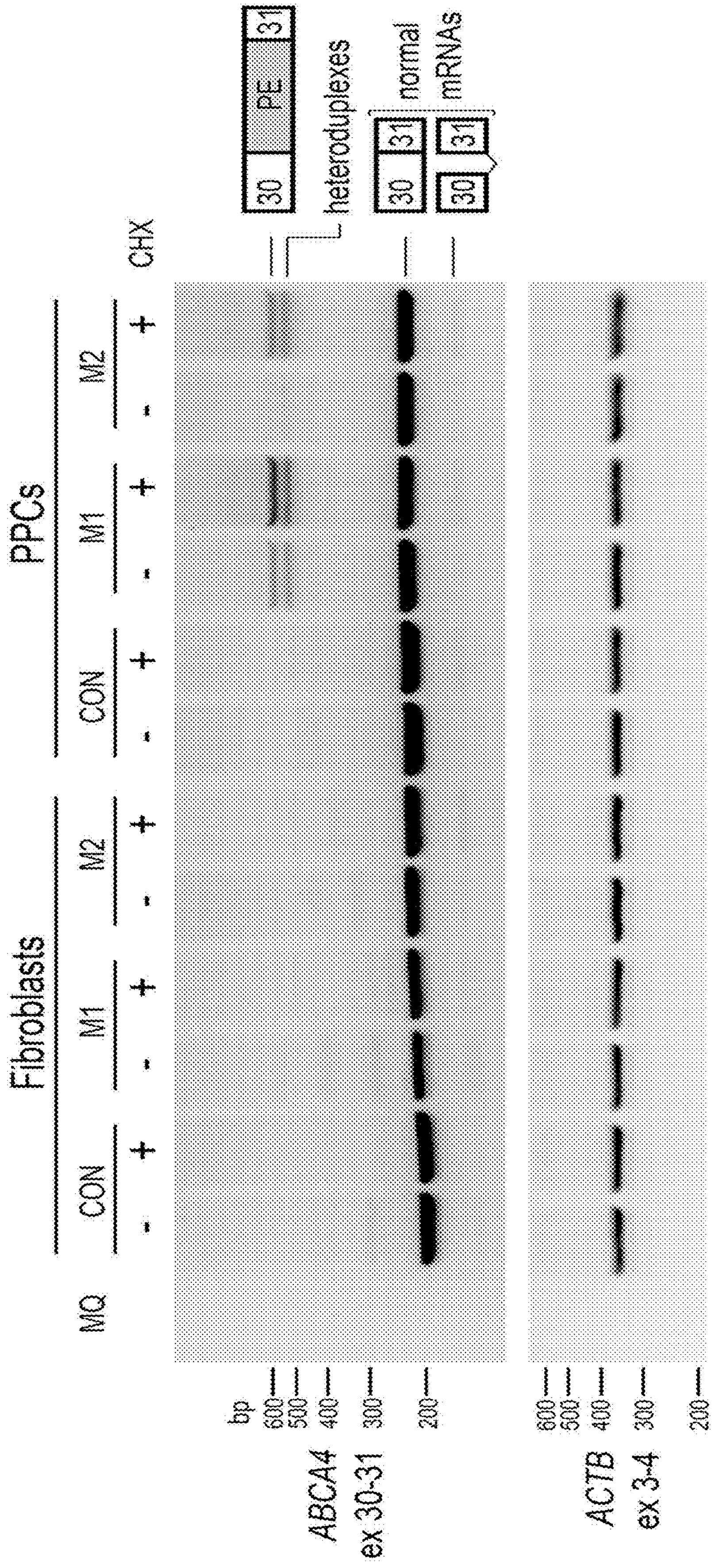
FIG. 4A-4B FIG. 4A depicts the results of example C wherein the splice defects caused by ABCA4 mutations c.4539+2001G>A (M1) and c.4539+2028C>T (M2) are identified. Aberrantly spliced bands were detected, especially after cycloheximide (CHX) treatment (+). Actin (ACTB) RT-PCR was used as a control.
Figure 4B:
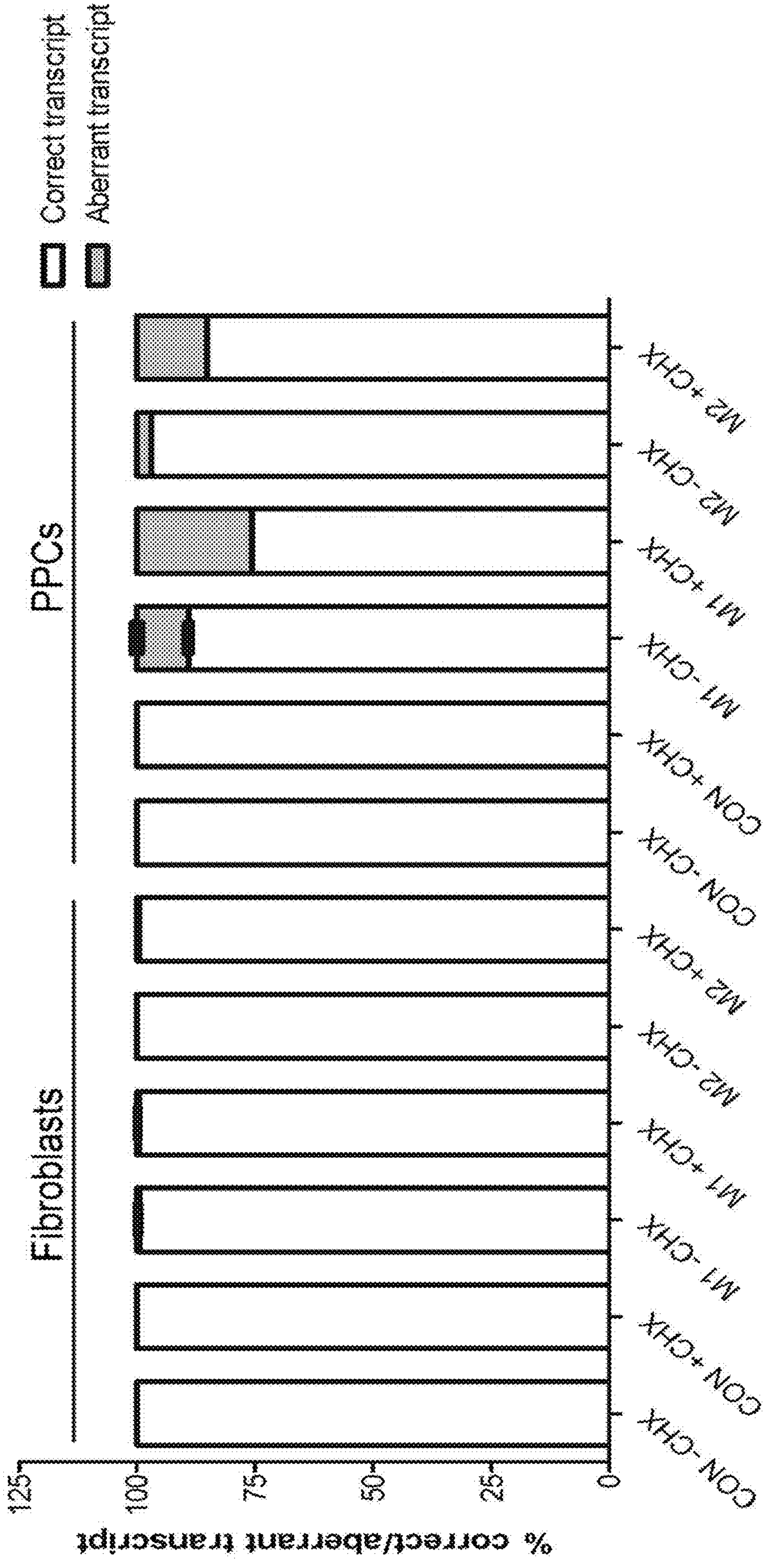
Figure 5:
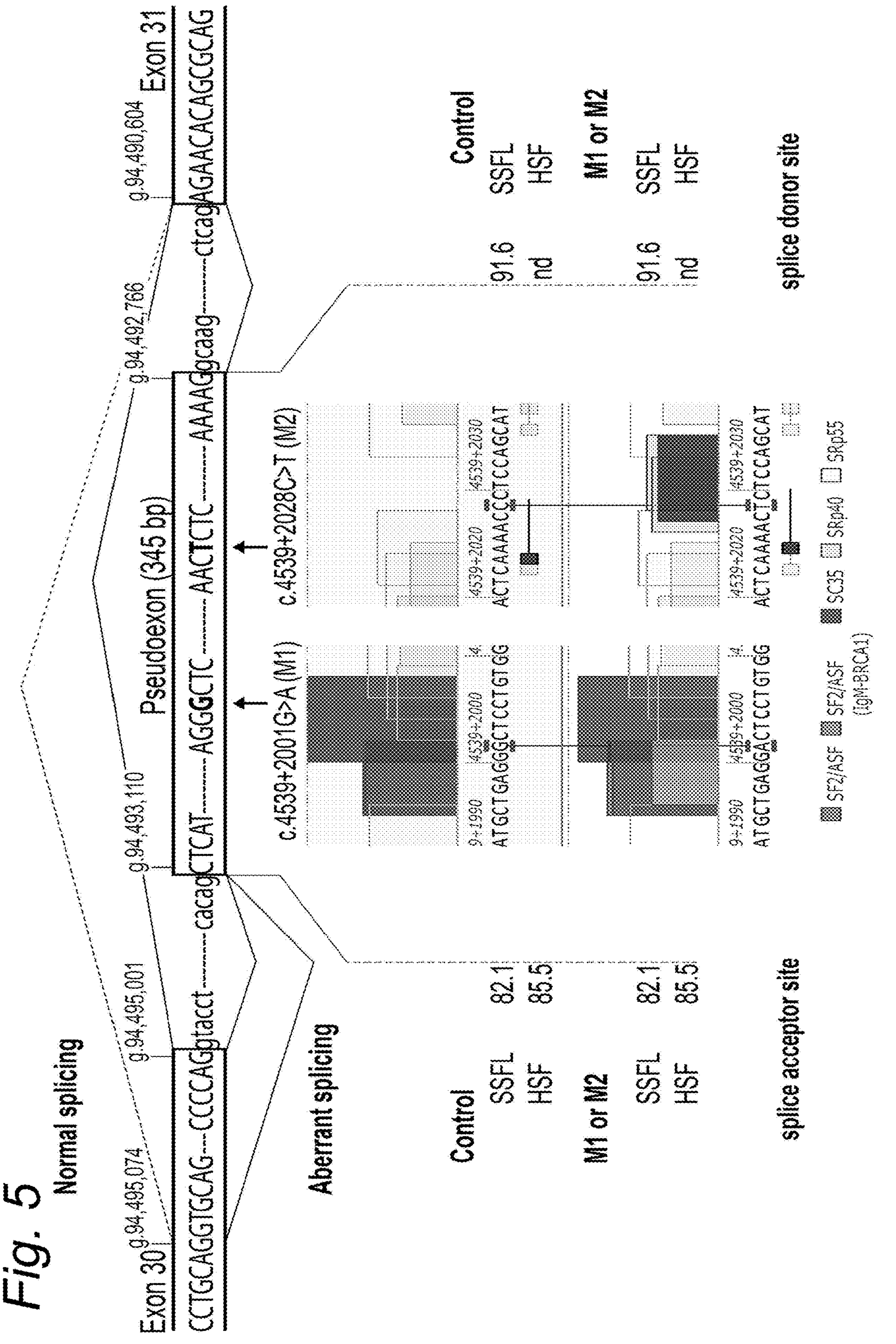
FIG. 5 In silico characterization of the effect caused by deep-intronic variants M1 (c.4539+2001G>A) and M2 (c.4539+2028C>T). The boundaries of the 345-bp pseudoexon with the location of M1 and M2, the genomic positions of the splice sites, the splicing events detected, and the splice site predictions for both acceptor and donor sites are schematically represented. The dotted line represents the splicing from a cryptic splice donor site in exon 30 at position g.94,495,074 (GRCh37/hg19) to the normal splice acceptor site of exon 31 (r.4467_4539del, p.Cys1490Glufs*12). The predicted values of the splice acceptor and donor sites in the control and mutant situations did not show any difference. In the middle panels, the effects of the variants enhancing or creating new ESE motifs are depicted. SSFL: SpliceSite-Finder-like and HSF: Human Splicing Finder.

As ABCA4 was robustly expressed in PPCs, we performed RT-PCR analysis from exon 30 to exon 31 which showed aberrant transcripts in both M1- and M2-derived PPCs upon CHX treatment, but not in control PPCs (FIG. 4A). Semi-quantification of the ratio between correctly and aberrantly spliced variants in the CHX-treated samples revealed that ~25% of ABCA4 transcripts in the patient carrying M1 and ~15% of ABCA4 transcripts in the patient carrying M2 were aberrant (FIG. 4B). A more detailed analysis of all bands by Sanger sequencing revealed a PE of 345 nt containing a premature stop codon (FIG. 5), which is predicted to result in the truncated protein product p.Arg1514Leufs*36. Interestingly, both variants included the same PE in the mRNA transcript upon CHX treatment. Once the sequence was identified, we studied the effect of both variants on splicing. According to all prediction software, neither M1 nor M2 changed the strength of the splice acceptor and donor site (FIG. 5). The splice donor site of the 345-nt PE contains 'GC' as canonical splice site sequence, which is only recognized by the Splice-Site-Finder-Like (SSFL) software. Further in silico predictions showed that M1 increases the strength of an exonic splicing enhancer SF2 site and creates a new SRp55 motif, whereas M2 creates one SC35 and two SRp40 motifs (FIG. 5).

Subsequent in-depth analysis of all the bands observed by RT-PCR revealed that one band contained heteroduplexes of the correctly spliced transcript together with the one containing the PE (FIG. 4). Moreover, an extra faint band lacking the last 73 bp of exon 30 was found in all samples treated with CHX, including the control. A relatively weak splice donor site (Human Splicing Finder (HSF) score: 75.9) explains this alternative transcript that was also detected in the heteroduplex band (FIG. 4). This splice product (r.4467_4539 del, p.Cys1490Glufs*12) was also identified as a result of non-canonical splice site variants at the 'natural' splice donor site of exon 30 (R. Sangermano, M. Khan et al. 2018). Interestingly, this new donor site was previously reported as a splice acceptor site (HSF score: 89.6) creating an isoform lacking the first 114 bp of exon 30 (Gerber et al., 1998).

Figure 8:
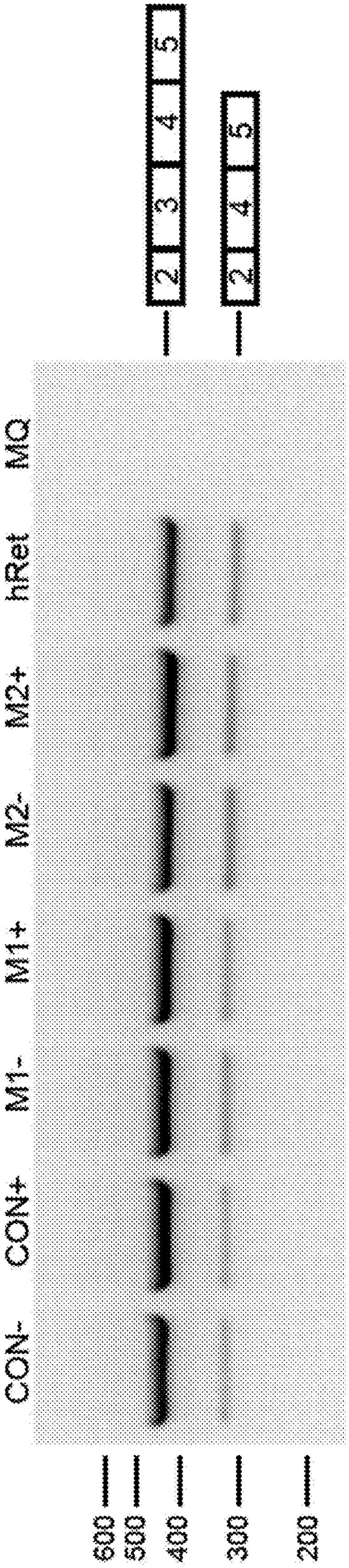
FIG. 8 RT-PCR analysis from exon 2 to exon 5 of ABCA4 in control (CON), M1 (c.4539+2001G>A) and M2 (c.4539+2028C>T) photoreceptor precursor cells in the absence (−) and presence (+) of CHX. Human adult retina RNA was used as a control, while MQ was the negative control of the reaction.

In seven STGD1 cases with M2 in whom this was investigated, c.302+68C>T was found in cis (R. Allikmets, unpublished data; Braun et al., 2013; Lee et al., 2016 and Zernant et al., 2014). To study the contribution of this variant to STGD1 pathology, we performed RT-PCR of mRNA from control PPCs, M1- and M2-PPCs, treated and untreated with CHX, as well as from adult retina mRNA. As shown in FIG. 8, PCR primers located in exons 2 and 5 generated a canonical splice product of 459 nt, as well as a smaller fragment of 317 nt, in all PPCs and in human retina. Validation of the bands by Sanger sequencing revealed that the 317-nt fragment was lacking exon 3 (size: 142 bp). No other splice products were observed, indicating that the c.302+68C>T variant does not result in the activation of cryptic splice sites and/or exonic splice enhancers.

Figure 6A:
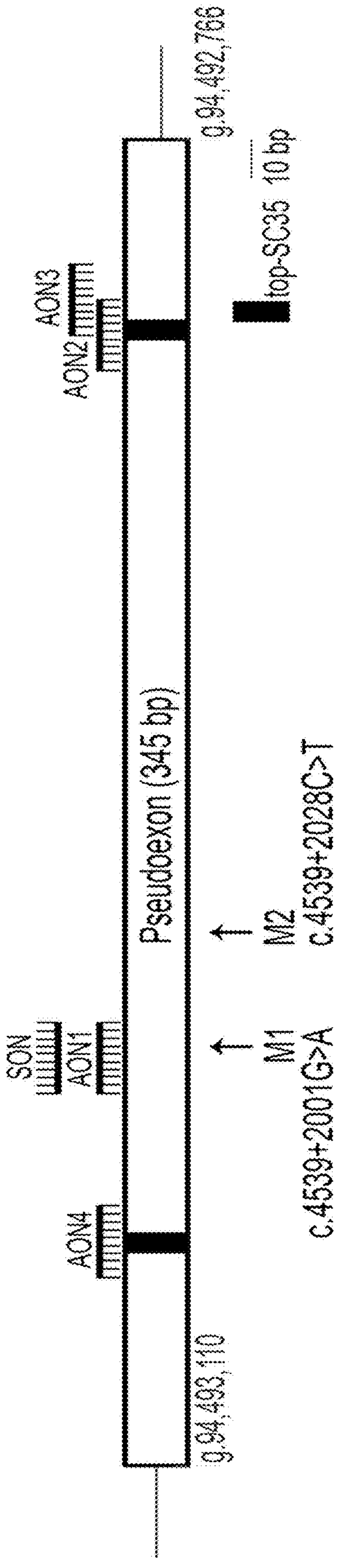
FIG. 6A-6D FIG. 6A Schematic representation of the pseudoexon, indicating the location of the variants, the SC35 motifs with the highest scores and the antisense oligonucleotides (AONs).
Figure 6B:
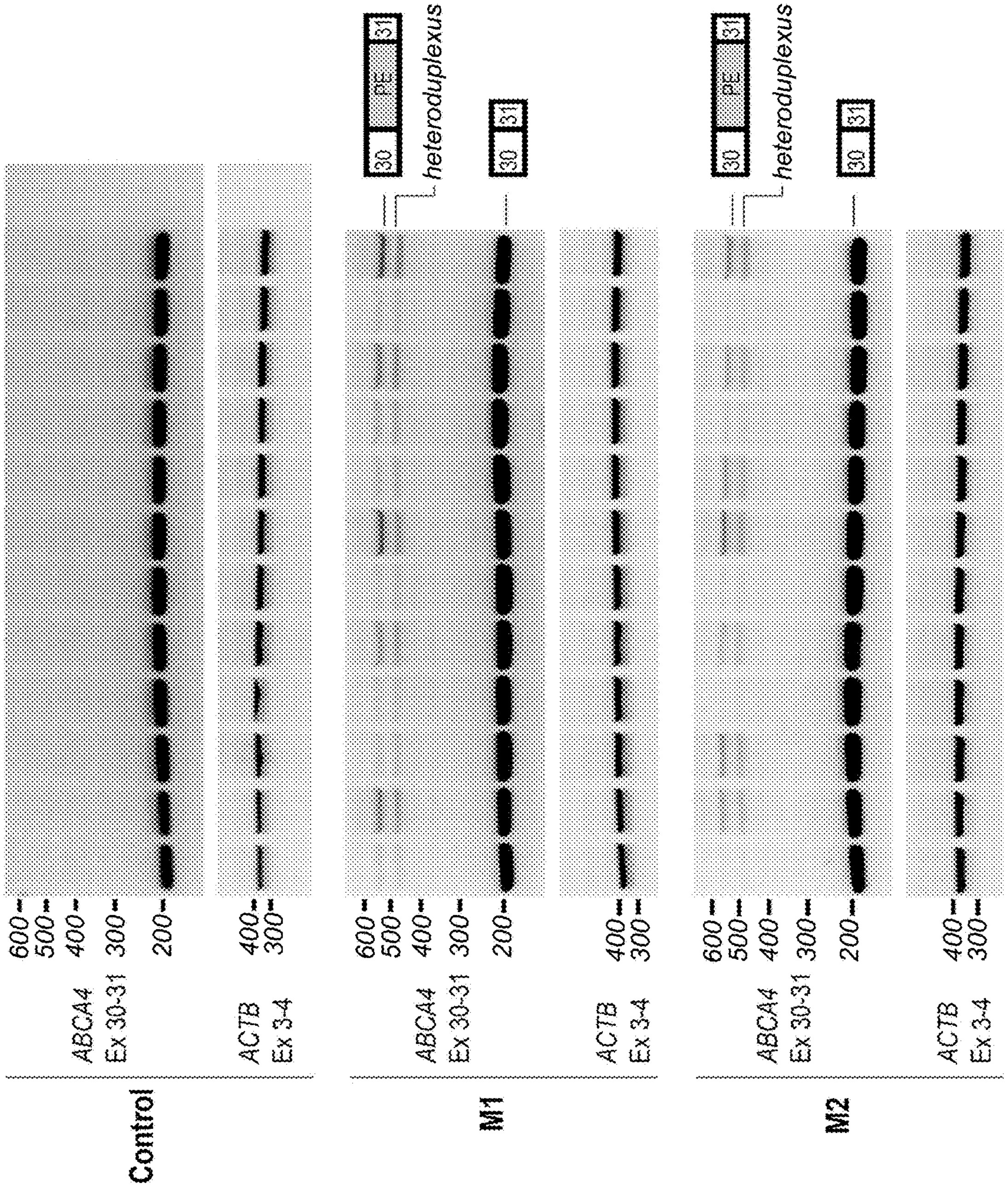
Figure 6C:
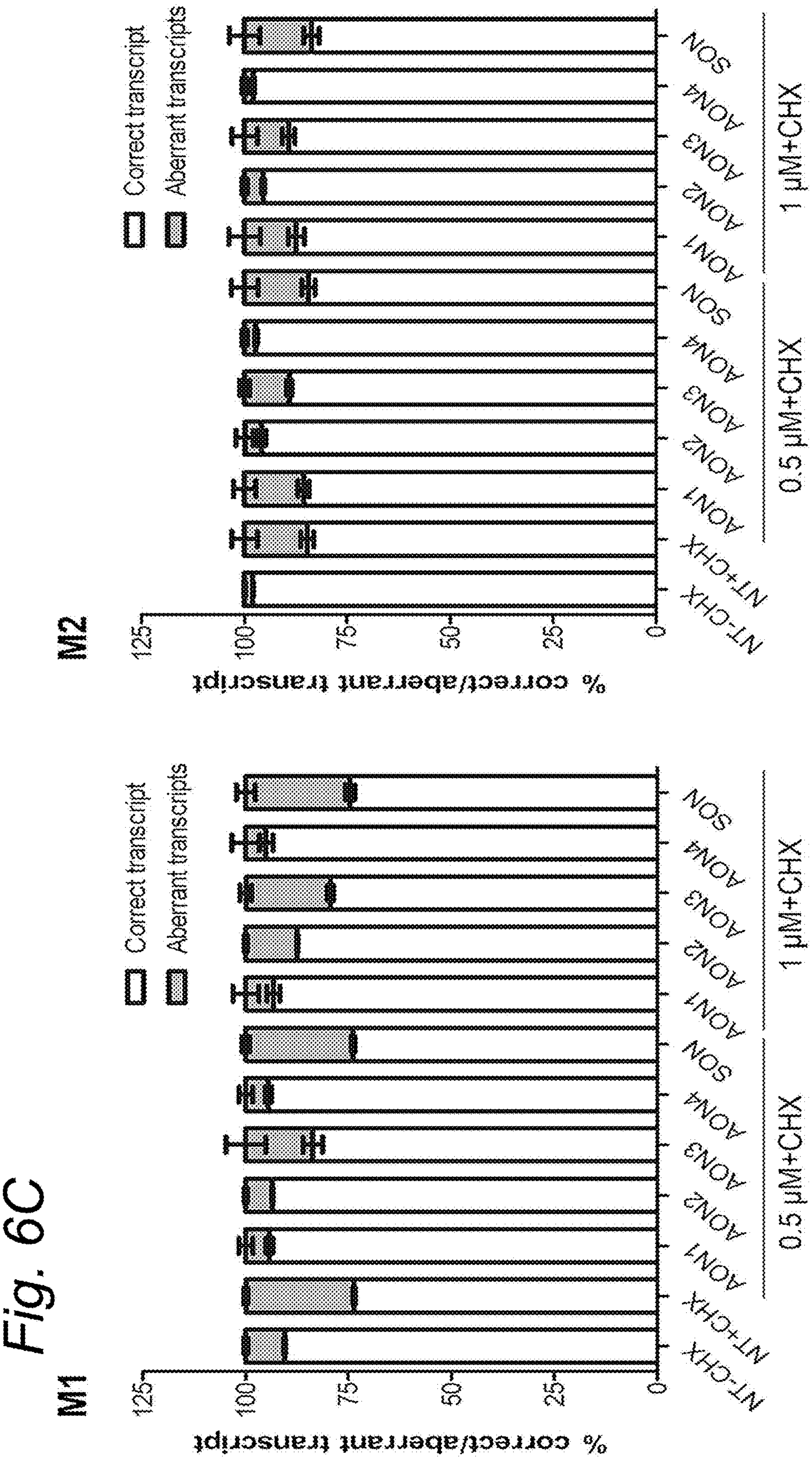
Figure 6D:
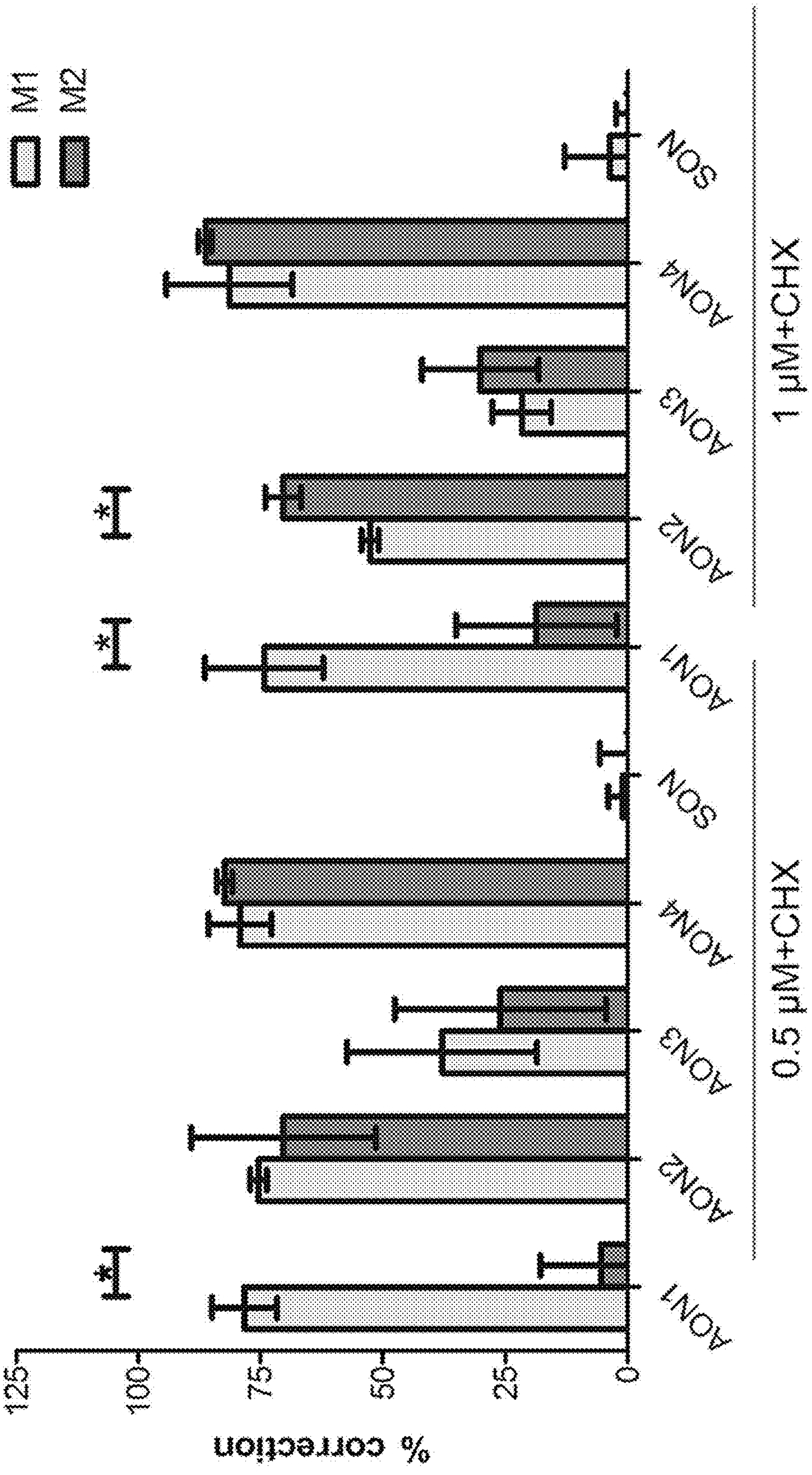

Once the molecular mechanism associated with M1 and M2 variants was elucidated, we aimed to design a therapeutic approach, based on splicing modulation, to skip the PE. An attractive and efficient method is the use of AONs, small RNA molecules that are able to enter the cell, bind to the pre-mRNA and modify the splicing pattern. In order to increase their binding affinity and avoid RNaseH activation (and therefore transcript degradation), we used 2-O-methyl-modified RNA AONs with phosphorothioate (2OMe/PS) backbones, as previously reported (Collin et al., 2012; Garanto et al., 2016; Gerard et al., 2012 and Slijkerman et al., 2016). In total we designed four AONs: two to block the SC35 motif with the highest score located at the 3' end of the PE (AON2, AON3), one to block the second-highest-score SC35 at the 5' of the PE (AON4), and one to block the newly created SRp55 motif due to M1 (AON1; FIG. 6A). In addition, a sense oligonucleotide (SON), complementary to AON1 and containing the same chemical modifications as the other AONs but not able to bind to the pre-mRNA, was designed in the same region. AONs and SON were delivered to −1-month differentiated-PPCs and after 48 h, the RNA was analyzed. As expected, CHX treatment increased the presence of aberrantly spliced transcript in the non-treated cells (FIGS. 6B and 6C). In addition, there were no differences between the non-treated and the SON-treated cells. We have demonstrated that the AONs are efficient in exon skipping. We found that AON4 was efficiently able to produce up to ~75% PE skipping in both cell lines at two different concentrations (FIG. 6D), while AON1 was very efficient in the M1 cell line. AON2 showed variable efficacy, while AON3 was able to redirect splicing both at 0.5 µM and 1 µM (FIGS. 6B, 6C and 6D). One explanation for AON2 and AON3 showing such different behavior despite targeting the same region could be the AON properties (Table 1, Table 2). AON3 compared with AON2 has a low GC content and Tm, which might affect the stability and binding capacity, therefore explaining its low efficiency.

To further expand on our search for the most potent AON to redirect the splice defects caused by the c.4539+2001G>A mutation, we designed and tested 22 additional AONs (AON5-AON26, SEQ ID NO:'s: 196, 199, 202, 205, 208, 211, 214, 217, 220, 223, 226, 229, 232, 235, 238, 241, 244, 247, 250, 253 and 256, respectively), and assessed their capability to redirect ABCA4 splicing by preventing the inclusion of the 345-nt pseudoexon. Previously tested AONs 1-4 (SEQ ID NO:'s 35/184, 38/187, 41/190 and 44/193, respectively) were taken along, as well as two sense oligonucleotides (SON1 [SEQ ID NO: 280] and SON2 [SEQ ID NO: 281]). The results are depicted in FIG. 9. Besides AONs 1 and 4, other effective AONs included AON9, AON10, AON14, AON17, AON18, AON22, AON23 and AON24. Moderately effective AONs include AON2, AON8, AON11, AON13, AON16, AON20 and AON21. Hardly or none effective AONs include AON3, AON5, AON6, AON7, AON12, AON15, AON19, AON25 and AON26. When comparing the properties of these AONs, a number of things become apparent:

i) AONs targeting regions outside the pseudoexon (AON5, AON6, AON7, AON25 and AON26) are not capable of redirecting ABCA4 splicing.
ii) AONs that have a single mismatch to their target are not effective, i.e. AON1 is mutation-specific for c.4539+2001G>A, and does not redirect splicing in a patient with the c.4539+2028C>T mutation (FIG. 6D). Likewise, AON15 is mutation-specific for the pseudoexon with the c.4539+2028C>T change and is not effective in correcting splicing defects due to the c.4539+2001G>A mutation (FIG. 9).
iii) AONs that are effective for redirecting splicing often harbor an SC35 motif (both effective and moderately effective had 1.8 and 1.45 times more SC35 motifs on average when compared to the poorly and non-effective AONs). No big differences were observed for SF2 and SRp40 motifs. For the moderately effective AONs, we detected 4 and 2.6 times enrichment of SRp55 motifs when compared to the effective and the group of poorly effective and non-effective AONs, respectively).
iv) On average there were no differences in the length of the AONs that redirect splicing and those that did not.

However, we did observe that the melting temperature (Tm) was on average 2 and 3 degrees higher in the effective AONs when compared to the moderately effective group and the group comprised of the poorly effective and non-effective AONs.
v) Also on average, both effective and moderately effective AONs showed a percentage of GC content higher than 54%, while the average of the poorly effective or non-effective AONs was below 48%.
vi) We did not observe clear differences between those AONs binding to predicted mixed regions with partially open and partially closed regions to those binding to predicted either closed or open regions.

D)

Midigene constructs harboring the c.769-784C>T, c.859-540C>G, c.859-506G>C, c.1937+435C>G, c.4539+1100A>G, c.4539+1106C>T or c.5197-557G>T mutation were transfected into HEK293T cells, together with a construct with the corresponding wild type ABCA4 sequences. As depicted in FIG. 10, all mutations result in the insertion of a pseudoexon with variable length and to a variable degree (lanes marked with NT). Transfection of three different AONs, as well as one general SON for each mutation, showed that for all mutations, at least one AON was effective in rescuing the pseudoexon insertion associated with this mutation. Specifically, for c.769-784C>T, addition of AON1 and AON2 result in a decrease of the pseudoexon while AON3 partially rescues the splice defect. For c.859-540C>G, AON1 is not effective, AON2 is very effective, while AON3 partially rescues the splice defect. However, during the final check, we discovered that AON1 that was designed for the c.859-540C>G mutation was ordered incorrectly, and instead the sequence of AON3 for the c.5197-557G>T mutation was entered and provided. This also affects the interpretation of the results. Therefore, the negative result found for AON1 is expected because the actual AON that was used is not specific for the corresponding pseudoexon, and therefore should not work. For c.859-506G>C, AON1 and AON3 result in a decrease of the transcript containing the pseudoexon, while AON2 is not effective. For c.1937+435C>G, all three AONs result in a decrease of the ABCA4 transcripts harboring the pseudoexon. For the c.4539+1100A>G and the c.4539+1106C>T mutations, AON1 and AON2 appear to be effective while AON3 clearly is not. Finally, or c.5197-557G>T mutation, all three AONs result in a decrease of the transcripts with the pseudoexon. Together, these data demonstrate the capability of AONs to redirect the aberrant splicing events due to the all deep-intronic ABCA4 mutations tested, with at least one AON for each pseudoexon being effective.

DISCUSSION

In this study, we showed that two neighboring deep-intronic variants in ABCA4, c.4539+2001G>A and c.4539+2028C>T, result in retina-specific inclusion of a 345-nt pseudoexon (PE) in a proportion of ABCA4 transcripts. This PE, which is predicted to lead to protein truncation (p.Arg1514Leufs*36), was found as a low-abundance alternative splice form of ABCA4 when performing deep RNA sequencing of human macula RNA (Braun et al, 2013). RT-PCR product quantification revealed more PE insertion due to M1 than to M2. On the basis of the ocular phenotypes of STGD1 patients carrying M1, and the nature of the variants observed in trans in these patients, M1 was proposed to act as a severe variant (Bauwens et al, 2015; Bax et al, 2015; Braun et al, 2013). In contrast, based on our own observations, and the limited clinical data available for some STGD1 patients carrying M2 (Lee et al, 2016), we hypothesize that M2 acts as a mild to moderately severe variant. We thus would expect that the amount of mutant mRNA in the patient carrying M1, who carries a missense variant in trans, should be equal to the amount of correct product. This is not the case, yet this comparison is difficult, as smaller products amplify more effectively and NMD suppression may be incomplete. The PE insertion due to M2 is less prominent than that for M1, which is in agreement with its less severe character. However, we cannot exclude the possibility that other cis-acting variants missed during locus sequencing (Zernant et al, 2014) act in concert with these intron 30 variants. In addition, cell-type specific mechanisms may play a role, since both patient-derived PPC lines were less well differentiated than the control PPC line, indicating the possibility of a delay in the differentiation. This may have a significant influence on the amount of PE insertion. A clear example of the importance of retinal differentiation for PE recognition was described for the deep-intronic c.2991+1655A>G variant in CEP290. Whereas in lymphoblastoid and fibroblast cells of patients harboring this mutation homozygously, the ratio between correctly and aberrantly spliced CEP290 is ~1:1 (Collin et al, 2012; Garanto et al, 2016; den Hollander et al, 2006), in iPSC-derived photoreceptor cells the amount of aberrantly spliced CEP290 was found to be drastically increased (~1:4 ratio; Parfitt et al; 2016). This study not only revealed insights into why this mutation, despite a ubiquitous expression of CEP290, resulted in a non-syndromic retinal phenotype, but also demonstrated the enormous power of using iPSC-derived retinal cells from patients to study splice defects in a relevant cellular system.

Previous inherited retinal disease (IRD)-associated intronic variants have created new splice acceptor or donor sites that allowed the insertion of a PE (Braun et al, 2013; Bonifert et al, 2016; Webb et al, 2012; van den Hurk et al, 2003; Vache et al, 2012; Rio Frio et al, 2009; Naruto et al, 2015; Mayer et al, 2016; Liguori et al, 2016; den Hollander et al, 2006; Carss et al, 2017). To our knowledge, we are the first to report on the insertion of a PE that is not due to this mechanism but likely because of the creation of new ESE motifs in IRDs. Intronic regions are riddled with pairs of predicted splice acceptor and donor sites that theoretically could flank a PE. Upon the identification of additional PEs that are not activated through the creation of splice sites, it will be possible to determine the sequence motifs that render cryptic PEs into real PEs.

The M1- and M2-associated PE insertions were successfully blocked by several AONs. A M1-specific AON was only effective in the M1-cell line, and even with a doubled AON concentration, AON1 was still unable to correct the splice defect in the M2 cell line. In addition, a M2-specific AON that has a single mismatch to the PE sequence was not effective in a patient with M1. These results highlight the specificity of the sequence and the fact that a single nucleotide mismatch is enough to change the efficacy of an AON. The newly created SRp55 motif may play a crucial role in the detection of the PE. Given the fact that both variants activate the same PE and AON4 is able to skip the PE in both cases, this remains to be further elucidated. One of the limitations of AONs is that they bind to specific sequences and therefore it is not possible to test the same AON in animal models if there is no conserved DNA/RNA region, unless a model is created in which part of the human sequence is inserted at the orthologous position in the animal genome. However, it is already known that the 2OMe/PS chemistry and 2MOE (2-O-Methoxyethyl)/PS are not toxic for the eye as shown in several animal models (Garanto et al, 2016; Gerard et al, 2015; Murray et al, 2015). Furthermore, the first AON commercialized was used to treat the eye condition CMV-retinitis (Fomivirsen approved for CMV retinitis: first antisense drug. AIDS treatment news, 7 (1998). Thus, AON technology seems to be a safe and promising approach to treat eye disorders. Owing to the lack of animal models, the use of iPSC-derived photoreceptors appears to be a suitable alternative, although it still needs to be elucidated whether the function of ABCA4 protein can be restored following treatment of these cells.

In conclusion, by using patient-derived iPSC differentiated into S-cones, we were able to identify the molecular defect due to two recurrent neighboring deep-intronic variants underlying STGD1. The splice defect consisted of the insertion of a 345-nt PE which appears to be tissue-specific and is most likely caused by the presence of newly generated exonic splicing enhancers, instead of by the creation of novel splice sites. Moreover, an AON-based therapeutic approach was designed and tested, showing that one AON was able to redirect the splice defect in both mutated cell lines. Furthermore, a variant-specific AON was very effective against M1 but not M2, indicating that one single nucleotide mismatch can change the AON efficiency drastically. For several other deep-intronic mutations in ABCA4 (i.e. c.769-784C>T, c.859-540C>G, c.859-506G>C, c.1937+435C>G, c.4539+1100A>G, c.4539+1106C>T or c.5197-557G>T) we have shown that all result in the insertion of a pseudoexon. AONs were designed to block the inclusion of these pseudoexon, and for each pseudoexon, at least one AON was capable of significantly decreasing the amount of aberrant ABCA4 transcripts. Overall, these results highlight the potential of AONs as a therapeutic tool for Stargardt disease.

REFERENCES

Aartsma-Rus, A. Overview on AON design. Methods Mol. Biol. 867, 117-129 (2012), doi:10.1007/978-1-61779-767-5_8.

Allikmets, R., Singh, N., Sun, H., Shroyer, N. F., Hutchinson, A., Chidambaram, A., Gerrard, B., Baird, L., Stauffer, D., Peiffer, A., Rattner, A., Smallwood, P., Li, Y., Anderson, K. L., Lewis, R. A., Nathans, J., Leppert, M., Dean, M. & Lupski, J. R. A photoreceptor cell-specific ATP-binding transporter gene (ABCR) is mutated in recessive Stargardt macular dystrophy. *Nat. Genet.* 15, 236-246 (1997), doi:10.1038/ng0397-236.

Bauwens, M., De Zaeytijd, J., Weisschuh, N., Kohl, S., Meire, F., Dahan, K., Depasse, F., De Jaegere, S., De Ravel, T., De Rademaeker, M., Loeys, B., Coppieters, F., Leroy, B. P. & De Baere, E. An augmented ABCA4 screen targeting noncoding regions reveals a deep intronic founder variant in Belgian Stargardt patients. *Hum. Mutat.* 36, 39-42 (2015), doi:10.1002/humu.22716.

Bax, N. M., Sangermano, R., Roosing, S., Thiadens, A. A., Hoefsloot, L. H., van den Born, L. I., Phan, M., Klevering, B. J., Westeneng-van Haaften, C., Braun, T. A., Zonneveld-Vrieling, M. N., de Wijs, I., Mutlu, M., Stone, E. M., den Hollander, A. I., Klaver, C. C., Hoyng, C. B. & Cremers, F. P. M. Heterozygous deep-intronic variants and deletions in ABCA4 in persons with retinal dystrophies and one exonic ABCA4 variant. *Hum. Mutat.* 36, 43-47 (2015), doi:10.1002/humu.22717.

Bonifert, T., Gonzalez Menendez, I., Battke, F., Theurer, Y., Synofzik, M., Schols, L. & Wissinger, B. Antisense oligonucleotide mediated splice correction of a deep intronic mutation in OPA1. *Mol. Ther. Nucleic Acids* 5, e390 (2016), doi:10.1038/mtna.2016.93.

Braun, T. A., Mullins, R. F., Wagner, A. H., Andorf, J. L., Johnston, R. M., Bakall, B. B., Deluca, A. P., Fishman, G. A., Lam, B. L., Weleber, R. G., Cideciyan, A. V., Jacobson, S. G., Sheffield, V. C., Tucker, B. A. & Stone, E. M. Non-exomic and synonymous variants in ABCA4 are an important cause of Stargardt disease. Hum. Mol. Genet. 22, 5136-5145 (2013), doi:10.1093/hmg/ddt367.

Chiorini, J. A., Kim, F., Yang, L., and Kotin, R. M. (1999). Cloning and characterization of adeno-associated virus type 5. Journal of virology 73, 1309-1319.

Collin, R. W., den Hollander, A. I., van der Velde-Visser, S. D., Bennicelli, J., Bennett, J., and Cremers, F. P. (2012). Antisense Oligonucleotide (AON)-based Therapy for Leber Congenital Amaurosis Caused by a Frequent Mutation in CEP290. Molecular therapy Nucleic acids 1, e14.

Cremers, F. P. M., van de Pol, D. J., van Driel, M., den Hollander, A. I., van Haren, F. J., Knoers, N. V., Tijmes, N., Bergen, A. A., Rohrschneider, K., Blankenagel, A., Pinckers, A. J., Deutman, A. F. & Hoyng, C. B. Autosomal recessive retinitis pigmentosa and cone-rod dystrophy caused by splice site mutations in the Stargardt's disease gene ABCR. *Hum. Mol. Gen.* 7, 355-362 (1998).

den Hollander, A. I., Koenekoop, R. K., Yzer, S., Lopez, I., Arends, M. L., Voesenek, K. E., Zonneveld, M. N., Strom, T. M., Meitinger, T., Brunner, H. G., Hoyng, C. B., van den Born, L. I., Rohrschneider, K. & Cremers, F. P. Mutations in the CEP290 (NPHP6) gene are a frequent cause of Leber congenital amaurosis. *Am. J. Hum. Genet.* 79, 556-561 (2006).

Dorn, A., and Kippenberger, S. (2008). Clinical application of CpG-, non-CpG-, and antisense oligodeoxynucleotides as immunomodulators. Current opinion in molecular therapeutics 10, 10-20.

Egholm, M., Buchardt, O., Christensen, L., Behrens, C., Freier, S. M., Driver, D. A., Berg, R. H., Kim, S. K., Norden, B., and Nielsen, P. E. (1993). PNA hybridizes to complementary oligonucleotides obeying the Watson-Crick hydrogen-bonding rules. Nature 365, 566-568.

Flamier, A., Barabino, A. & Bernier, G. Differentiation of human embryonic stem cells into cone photoreceptors. Bio-protocol 6, e1870 (2016), doi:10.21769/BioProtoc.1870

Fujinami, K., Zernant, J., Chana, R. K., Wright, G. A., Tsunoda, K., Ozawa, Y., Tsubota, K., Webster, A. R., Moore, A. T., Allikmets, R. & Michaelides, M. ABCA4 gene screening by next-generation sequencing in a British cohort. *Invest. Ophthalmol. Vis. Sci.* 54, 6662-6674 (2013), doi:10.1167/iovs.13-12570.

Garanto, A., Chung, D. C., Duijkers, L., Corral-Serrano, J. C., Messchaert, M., Xiao, R., Bennett, J., Vandenberghe, L. H., and Collin, R. W. (2016). In vitro and in vivo rescue of aberrant splicing in CEP290-associated LCA by antisense oligonucleotide delivery. Human molecular genetics 25, 2552-2563.

Gerard, X., Perrault, I., Hanein, S., Silva, E., Bigot, K., Defoort-Delhemmes, S., Rio, M., Munnich, A., Scherman, D., Kaplan, J., Kichler, A. & Rozet, J. M. AON-mediated exon skipping restores ciliation in fibroblasts harboring the common Leber congenital amaurosis CEP290 mutation. Mol. Ther. Nucleic Acids 1, e29 (2012), doi:10.1038/mtna.2012.21

Gerard, X., Perrault, I., Munnich, A., Kaplan, J. & Rozet, J. M. Intravitreal injection of splice-switching oligonucleotides to manipulate splicing in retinal cells. *Mol. Ther. Nucleic Acids* 4, e250 (2015), doi:10.1038/mtna.2015.24.

Gerber, S., Rozet, J. M., van de Pol, T. J., Hoyng, C. B., Munnich, A., Blankenagel, A., Kaplan, J. & Cremers, F. P. M. Complete exon-intron structure of the retina-specific ATP binding transporter gene (ABCR) allows the identification of novel mutations underlying Stargardt disease. Genomics 48, 139-142 (1998), doi:10.1006/geno.1997.5164.

Gorman, L., Suter, D., Emerick, V., Schumperli, D., and Kole, R. (1998). Stable alteration of pre-mRNA splicing patterns by modified U7 small nuclear RNAs. Proceedings of the National Academy of Sciences of the United States of America 95, 4929-4934.

Govindaraju, T., and Kumar, V. A. (2005). Backbone-extended pyrrolidine peptide nucleic acids (bepPNA): design, synthesis and DNA/RNA binding studies. Chemical communications, 495-497.

Lee, W., Xie, Y., Zernant, J., Yuan, B., Bearelly, S., Tsang, S. H., Lupski, J. R. & Allikmets, R. Complex inheritance of ABCA4 disease: four mutations in a family with multiple macular phenotypes. Hum. Genet. 135, 9-19 (2016), doi:10.1007/s00439-015-1605-y.

Lewis, R. A., Shroyer, N. F., Singh, N., Allikmets, R., Hutchinson, A., Li, Y., Lupski, J. R., Leppert, M. & Dean, M. Genotype/Phenotype analysis of a photoreceptor-specific ATP-binding cassette transporter gene, ABCR, in Stargardt disease. *Am. J. Hum. Genet.* 64, 422-434 (1999), doi:10.1086/302251.

Martinez-Mir, A., Paloma, E., Allikmets, R., Ayuso, C., del Rio, T., Dean, M., Vilageliu, L., Gonzalez-Duarte, R. & Balcells, S. Retinitis pigmentosa caused by a homozygous mutation in the Stargardt disease gene ABCR. *Nat. Genet.* 18, 11-12 (1998), doi:10.1038/ng0198-11.

Maugeri, A., Klevering, B. J., Rohrschneider, K., Blankenagel, A., Brunner, H. G., Deutman, A. F., Hoyng, C. B. & Cremers, F. P. M. Mutations in the ABCA4 (ABCR) gene are the major cause of autosomal recessive cone-rod dystrophy. *Am. J. Hum. Genet.* 67, 960-966 (2000), doi:10.1086/303079.

Maugeri, A., van Driel, M. A., van de Pol, D. J., Klevering, B. J., van Haren, F. J., Tijmes, N., Bergen, A. A., Rohrschneider, K., Blankenagel, A., Pinckers, A. J., Dahl, N., Brunner, H. G., Deutman, A. F., Hoyng, C. B. & Cremers, F. P. M. The 2588G->C mutation in the ABCR gene is a mild frequent founder mutation in the Western European population and allows the classification of ABCR mutations in patients with Stargardt disease. *Am. J. Hum. Genet.* 64, 1024-1035 (1999).

Morita, K., Hasegawa, C., Kaneko, M., Tsutsumi, S., Sone, J., Ishikawa, T., Imanishi, T., and Koizumi, M. (2001). 2'-O,4'-C-ethylene-bridged nucleic acids (ENA) with nuclease-resistance and high affinity for RNA. Nucleic acids research Supplement, 241-242.

Murray, S. F., Jazayeri, A., Matthes, M. T., Yasumura, D., Yang, H., Peralta, R., Watt, A., Freier, S., Hung, G., Adamson, P. S., Guo, S., Monia, B. P., LaVail, M. M. & McCaleb, M. L. Allele-specific inhibition of rhodopsin with an antisense oligonucleotide slows photoreceptor cell degeneration. *Invest. Ophthalmol. Vis. Sci.* 56, 6362-6375 (2015), doi:10.1167/iovs.15-16400.

Naruto, T., Okamoto, N., Masuda, K., Endo, T., Hatsukawa, Y., Kohmoto, T. & Imoto, I. Deep intronic GPR143 mutation in a Japanese family with ocular albinism. *Sci. Rep.* 5, 11334 (2015), doi:10.1038/srep11334.

Nielsen, P. E., Egholm, M., Berg, R. H., and Buchardt, 0. (1991). Sequence-selective recognition of DNA by strand displacement with a thymine-substituted polyamide. Science 254, 1497-1500.

Parfitt, D. A., Lane, A., Ramsden, C. M., Carr, A. J., Munro, P. M., Jovanovic, K., Schwarz, N., Kanuga, N., Muthiah, M. N., Hull, S., Gallo, J. M., da Cruz, L., Moore, A. T., Hardcastle, A. J., Coffey, P. J. & Cheetham, M. E. Identification and correction of mechanisms underlying inherited blindness in human iPSC-derived optic cups. Cell stem Cell 18, 769-781 (2016), doi:10.1016/j.stem.2016.03.021.

Rio Frio, T., McGee, T. L., Wade, N. M., Iseli, C., Beckmann, J. S., Berson, E. L. & Rivolta, C. A single-base substitution within an intronic repetitive element causes dominant retinitis pigmentosa with reduced penetrance. *Hum. Mutat.* 30, 1340-1347 (2009), doi:10.1002/humu.21071.

Rivera, A., White, K., Stohr, H., Steiner, K., Hemmrich, N., Grimm, T., Jurklies, B., Lorenz, B., Scholl, H. P., Apfelstedt-Sylla, E. & Weber, B. H. A comprehensive survey of sequence variation in the ABCA4 (ABCR) gene in Stargardt disease and age-related macular degeneration. *Am. J. Hum. Genet.* 67, 800-813 (2000), doi:10.1086/303090.

Sangermano, R., Bax, N. M., Bauwens, M., van den Born, L. I., De Baere, E., Garanto, A., Collin, R. W., Goercharn-Ramlal, A. S., den Engelsman-van Dijk, A. H., Rohrschneider, K., et al. (2016). Photoreceptor Progenitor mRNA Analysis Reveals Exon Skipping Resulting from the ABCA4 c.5461-10T->C Mutation in Stargardt Disease. Ophthalmology 123, 1375-1385.

Sangermano R, Khan M, Cornelis S S, Richelle V, Albert S, Elmelik D, Garanto A, Qamar R, Lugtenberg D, van den Born L I, Collin R W J, Cremers F P M. Genome Res (2018), epub ahead of print, doi: 10.1101/gr.226621.117.

Schindelin, J., Arganda-Carreras, I., Frise, E., Kaynig, V., Longair, M., Pietzsch, T., Preibisch, S., Rueden, C., Saalfeld, S., Schmid, B., Tinevez, J. Y., White, D. J., Hartenstein, V., Eliceiri, K., Tomancak, P. & Cardona, A. Fiji: an open-source platform for biological-image analysis. Nat. Methods 9, 676-682 (2012), doi:10.1038/nmeth.2019.

Schulz, H. L., Grassmann, F., Kellner, U., Spital, G., Ruther, K., Jagle, H., Hufendiek, K., Rating, P., Huchzermeyer, C., Baier, M. J., Weber, B. H. & Stohr, H. Mutation spectrum of the ABCA4 gene in 335 Stargardt disease patients from a multicenter German cohort-impact of selected deep intronic variants and common SNPs. *Invest. Ophthalmol. Vis. Sci.* 58, 394-403 (2017), doi:10.1167/iovs.16-19936.

Takahashi, K. & Yamanaka, S. Induction of pluripotent stem cells from mouse embryonic and adult fibroblast cultures by defined factors. Cell 126, 663-676 (2006), doi:10.1016/j.cell.2006.07.024

Vache, C., Besnard, T., le Berre, P., Garcia-Garcia, G., Baux, D., Larrieu, L., Abadie, C., Blanchet, C., Bolz, H. J., Millan, J., Hamel, C., Malcolm, S., Claustres, M. & Roux, A. F. Usher syndrome type 2 caused by activation of an USH2A pseudoexon: implications for diagnosis and therapy. *Hum. Mutat.* 33, 104-108 (2012), doi:10.1002/humu.21634.

van den Hurk, J. A., van de Pol, D. J., Wissinger, B., van Driel, M. A., Hoefsloot, L. H., de Wijs, I. J., van den Born, L. I., Heckenlively, J. R., Brunner, H. G., Zrenner, E., Ropers, H. H. & Cremers, F. P. M. Novel types of mutation in the choroideremia (CHM) gene: a full-length L1 insertion and an intronic mutation activating a cryptic exon. *Hum. Genet.* 113, 268-275 (2003), doi:10.1007/s00439-003-0970-0.

van Driel, M. A., Maugeri, A., Klevering, B. J., Hoyng, C. B. & Cremers, F. P. M. ABCR unites what ophthalmologists divide(s). *Ophthalmic Genet.* 19, 117-122 (1998).

Webb, T. R., Parfitt, D. A., Gardner, J. C., Martinez, A., Bevilacqua, D., Davidson, A. E., Zito, I., Thiselton, D. L., Ressa, J. H., Apergi, M., Schwarz, N., Kanuga, N., Michaelides, M., Cheetham, M. E., Gorin, M. B. & Hardcastle, A. J. Deep intronic mutation in OFD1, identified by targeted genomic next-generation sequencing, causes a severe form of X-linked retinitis pigmentosa (RP23). *Hum. Mol. Genet.* 21, 3647-3654 (2012), doi:10.1093/hmg/dds194.

Webster, A. R., Heon, E., Lotery, A. J., Vandenburgh, K., Casavant, T. L., Oh, K. T., Beck, G., Fishman, G. A., Lam, B. L., Levin, A., Heckenlively, J. R., Jacobson, S. G., Weleber, R. G., Sheffield, V. C. & Stone, E. M. An analysis of allelic variation in the ABCA4 gene. Invest. Ophthal. Vis. Sci. 42, 1179-1189 (2001).

Zernant, J., Lee, W., Collison, F. T., Fishman, G. A., Sergeev, Y. V., Schuerch, K., Sparrow, J. R., Tsang, S. H. & Allikmets, R. Frequent hypomorphic alleles account for a significant fraction of ABCA4 disease and distinguish it from age-related macular degeneration. *J. Med. Genet.* 54, 404-412 (2017), doi:10.1136/jmedgenet-2017-104540.

Zernant, J., Schubert, C., Im, K. M., Burke, T., Brown, C. M., Fishman, G. A., Tsang, S. H., Gouras, P., Dean, M. & Allikmets, R. Analysis of the ABCA4 gene by next-generation sequencing. Invest. Ophthalmol. Vis. Sci. 52, 8479-8487 (2011), doi:10.1167/iovs.11-8182.

Fomivirsen approved for CMV retinitis: first antisense drug. AIDS treatment news, 7 (1998).

The invention claimed is:

1. An antisense oligonucleotide for redirecting splicing that is:

complementary or substantially complementary to a polynucleotide with a nucleotide sequence consisting of SEQ ID NO: 81, and wherein the antisense oligonucleotide comprises a 2'-O alkyl phosphorothioate antisense oligonucleotide, and wherein the antisense oligonucleotide comprises at least one ESE (exon splice enhancer) motif.

2. The antisense oligonucleotide for redirecting splicing according to claim 1, wherein the part that is complementary or substantially complementary to a polynucleotide with a nucleotide sequence consisting of SEQ ID NO: 81, has a length of from about 8 to about 40 nucleotides.

3. The antisense oligonucleotide for redirecting splicing according to claim 1 that has a length of from about 8 to about 100 nucleotides.

4. The antisense oligonucleotide for redirecting splicing according to claim 1, wherein said antisense oligonucleotide comprises a sequence selected from the group consisting of SEQ ID NO: 85, 88, and 91.

5. The antisense oligonucleotide for redirecting splicing according to claim 1, comprising at least one ribonucleotide.

6. A viral vector expressing an antisense oligonucleotide for redirecting splicing according to claim 1 when placed under conditions conducive to expression of the exon skipping antisense oligonucleotide.

7. A pharmaceutical composition comprising an antisense oligonucleotide for redirecting splicing according to claim 1 and a pharmaceutically acceptable excipient.

8. The pharmaceutical composition according to claim 7, wherein the pharmaceutical composition is for intravitreal administration and is dosed in an amount ranged from 0.05 mg and 5 mg of total antisense oligonucleotides for redirecting splicing per eye.

9. The pharmaceutical composition according to claim 8, wherein the pharmaceutical composition is for intravitreal administration and is dosed in an amount ranged from 0.1 and 1 mg of total antisense oligonucleotides for redirecting splicing per eye, such as about 0.1, 0.2, 0.3, 0.4, 0.5, 0.6, 0.7, 0.8, 0.9 or 1.0 mg of total antisense oligonucleotides for redirecting splicing per eye.

10. A method for the treatment of an ABCA4-related disease or condition requiring modulating splicing of ABCA4 of an individual in need thereof, said method comprising contacting a cell of said individual with an antisense oligonucleotide comprising a sequence selected from the group consisting of SEQ ID NO: 85, 88 and 91.

11. The method according to claim 10, wherein the ABCA4-related disease or condition is Stargardt disease.

* * * * *